(12) United States Patent
Moyer et al.

(10) Patent No.: US 7,932,058 B2
(45) Date of Patent: Apr. 26, 2011

(54) RATIONALE, METHODS, AND ASSAYS FOR IDENTIFYING HUMAN AND NON-HUMAN PRIMATE TASTE SPECIFIC GENES AND USE THEREOF IN TASTE MODULATOR AND THERAPEUTIC SCREENING ASSAYS

(75) Inventors: Bryan Moyer, San Diego, CA (US); Albert Zlotnik, San Diego, CA (US); Peter Hevezi, Encinitas, CA (US); Hortensia Soto, San Diego, CA (US); Dalia Kalabat, El Cajon, CA (US); Min Lu, San Diego, CA (US); Na Gao, San Diego, CA (US); Evan Carl White, Fair Oaks, CA (US)

(73) Assignee: Senomyx, Inc., San Diego, CA (US)

( * ) Notice: Subject to any disclaimer, the term of this patent is extended or adjusted under 35 U.S.C. 154(b) by 112 days.

(21) Appl. No.: 12/134,302

(22) Filed: Jun. 6, 2008

(65) Prior Publication Data

US 2009/0208946 A1  Aug. 20, 2009

Related U.S. Application Data

(60) Provisional application No. 60/929,017, filed on Jun. 8, 2007, provisional application No. 60/929,007, filed on Jun. 8, 2007, provisional application No. 60/947,052, filed on Jun. 29, 2007, provisional application No. 60/935,297, filed on Aug. 3, 2007, provisional application No. 60/987,611, filed on Nov. 13, 2007, provisional application No. 60/988,938, filed on Nov. 19, 2007, provisional application No. 60/991,274, filed on Nov. 30, 2007, provisional application No. 60/991,289, filed on Nov. 30, 2007, provisional application No. 60/992,502, filed on Dec. 5, 2007, provisional application No. 60/992,517, filed on Dec. 5, 2007, provisional application No. 61/017,244, filed on Dec. 28, 2007, provisional application No. 61/021,437, filed on Jan. 16, 2008, provisional application No. 61/043,257, filed on Apr. 8, 2008, provisional application No. 61/053,310, filed on May 15, 2008.

(51) Int. Cl.
*C12N 15/10* (2006.01)
*C07K 14/705* (2006.01)

(52) U.S. Cl. ........................................ 435/91.1; 435/7.8

(58) Field of Classification Search ........................ None
See application file for complete search history.

(56) References Cited

U.S. PATENT DOCUMENTS

| | | | |
|---|---|---|---|
| 6,524,798 | B1 | 2/2003 | Goldbard et al. |
| 2005/0037369 | A1 | 2/2005 | Neote et al. |
| 2005/0048586 | A1 | 3/2005 | Zuker et al. |
| 2005/0177886 | A1 | 8/2005 | Margolskee et al. |
| 2005/0221394 | A1 | 10/2005 | Wood et al. |
| 2006/0089306 | A1 | 4/2006 | Wallace et al. |
| 2006/0223117 | A1 | 10/2006 | Moyer et al. |
| 2007/0071757 | A1 | 3/2007 | Yu et al. |
| 2007/0099251 | A1 | 5/2007 | Zhang et al. |

FOREIGN PATENT DOCUMENTS

WO   2007146120 A2   12/2007

OTHER PUBLICATIONS

Li et al., "Expression and localization of amiloride-sensitive sodium channel indicate a role for non-taste cells in taste perception" Proc. Natl. Acad. Sci., vol. 91, No. 5, (1994), pp. 1814-1818.
Supplementary European Search Report dated Jun. 2, 2010 (EP 08 76 8178).

*Primary Examiner* — John D Ulm
(74) *Attorney, Agent, or Firm* — Hunton & Williams LLP

(57) ABSTRACT

This invention relates to novel rationale and methods for identifying human and primate taste-specific genes, including genes involved in salty taste perception, especially human salty taste perception, but also genes involved in sweet, bitter, umami, and sour taste perception, and genes involved in other taste cell or taste receptor related activities such as digestive function and digestive related diseases, taste cell turnover, immunoregulation of the oral and digestive tract, and metabolic regulation such as in diabetes and obesity, the genes identified using these methods, and assays for identifying taste modulators (enhancers or blockers) and potential therapeutics using these genes. These compounds have potential application in modulating (enhancing or blocking) taste perception, especially salty taste perception and as potential therapeutics. In addition, this invention relates to novel methods for identifying taste-specific genes that can be used as markers for different taste cell types, including sweet, bitter, umami, sour, salty, and other taste cells in mammals as well as assays that measure the activity of the sweet, bitter, umami, or sour receptor in the presence of these genes to identify modulators of sweet, bitter, umami, and sour taste and to identify therapeutics especially for treating digestive or metabolic disorders, taste loss, and oral infections. Particularly, the genes identified herein and antibodies or oligos thereto can be used as markers to identify and/or purify specific taste cells e.g., from taste cell suspensions by use of FACS or magnetic bead cell selection or other known cell purification and isolation procedures.

4 Claims, 47 Drawing Sheets

RATIONALE, METHODS, AND ASSAYS FOR IDENTIFYING HUMAN AND NON-HUMAN PRIMATE TASTE SPECIFIC GENES AND USE THEREOF IN TASTE MODULATOR AND THERAPEUTIC SCREENING ASSAYS

RELATED AND PRIORITY PATENT APPLICATIONS

This application relates to earlier filed provisional applications by the present Assignee Senomyx Inc relating to a novel rationale for identifying primate taste specific genes and in particular for identification of the primate salt receptor gene or genes. These provisional applications U.S. Application Ser. No. 60/929,017, filed Jun. 8, 2007; U.S. Application Ser. No. 60/929,007, filed Jun. 8, 2007; U.S. Application Ser. No. 60/947,052, filed Jun. 29, 2007; U.S. Application Ser. No. 60/935,297, filed Aug. 3, 2007; U.S. Application Ser. No. 60/987,611, filed Nov. 13, 2007; U.S. Application Ser. No. 60/988,938, filed Nov. 19, 2007; U.S. Application Ser. No. 60/991,274, filed Nov. 30, 2007; U.S. Application Ser. No. 60/991,289, filed Nov. 30, 2007; U.S. Application Ser. No. 60/992,502, filed Dec. 5, 2007; U.S. Application Ser. No. 60/992,517, filed Dec. 5, 2007; U.S. Application Ser. No. 61/017,244, filed Dec. 28, 2007; US. Application Ser. No. 61/021,437, filed Jan. 16, 2008; US. Application Ser. No. 61/043,257, filed Apr. 8, 2008; and U.S. Application Ser. No. 61/053,310, filed May 15, 2008. In addition, this application relates to, and claims priority to U.S. Ser. No. 11/808,356, filed on Jun. 8, 2007, and to U.S. application Ser. No. 12/134,390 filed on Jun. 6, 2008. All of the afore-mentioned provisional and non-provisional applications are incorporated by reference in their entireties herein.

FIELD OF THE INVENTION

This application generally relates to novel protocols for identifying and functionalizing taste specific genes, especially taste specific genes of primates and non-human primates, which based on their structure, tissue specific expression, cells, where they are expressed in specific tissues and cells therein, and level of expression are predicted to elicit or be involved in one or more taste cell specific functions. As described and shown infra these methods have identified taste specific GPCRs, ion channels, and other transmembrane proteins likely to regulate taste specific cellular activities. In fact, as disclosed in a related application filed on even date claiming benefit of priority to the same provisional and utility applications as the subject application, these methods have already successfully identified a gene which encodes a salty taste receptor in primates including humans, rodents, and likely other vertebrates.

More specifically, the invention relates to novel rationales for identifying and functionalizing human and primate taste specific genes, the taste specific genes identified using these rationale, and specific novel taste cell subsets which express these taste specific genes and the functional characterization of these genes, gene products and novel taste cell subsets and their use as potential taste receptor or therapeutic targets, e.g., salt receptor targets. The genes and gene products identified using these protocols are useful targets in high-throughput screening efforts to identify human salty taste enhancers. These targets are initially identified using a combination of two different techniques, gene chips and a polymerase chain reaction (PCR) screen, resulting in a set of genes which are taste specific and potential taste, e.g., salt or fat taste receptor target genes. First, Affymetrix gene chips containing most all known macaque genes are used to determine which genes are specifically expressed in primate circumvallate at the back of the tongue and fungiform papilla taste cells at the front of the tongue and not lingual epithelial cells isolated by laser capture microdissection. Second, PCR is used to determine which ion channels, from channels we have cataloged in the human/macaque genomes, are specifically expressed in macaque fungiform and/or circumvallate (CV) papilla taste cells but not lingual epithelial cells isolated by laser capture microdissection. Taste-specific expression of genes identified by either approach, are confirmed using an independent histological method such as in situ hybridization or immunohistochemistry, to determine which genes are expressed in taste cells. Using double labeling histological methods, it is determined what novel taste-specific genes are expressed in sweet, bitter, and umami cells that express the taste-specific ion channel TRPM5, sour cells that express the taste-specific ion channel PKD2L1/PKD1L3, or a unique cell type that does not express TRPM5 or PKD2L1/PKD1L3. A taste-specific gene, preferably an ion channel, that is conductive or activated by sodium and is expressed in a TRPM5- and PKD2L1/PKD1L3-negative cell population is a probable candidate for screening efforts to identify the gene(s) that encode mammalian salty taste receptors, as well as specific cell types wherein these salty taste receptor genes are expressed such as in the oral cavity and urinary tract, and also for use in high throughput assays designed to identify enhancers of saltiness in humans. The invention further provides infra in vitro and in vivo strategies for functionalizing the identified taste specific genes, especially those genes identified in unique taste cell subsets also described infra. As described infra and in more detail in the related application cited above, these strategies have already successfully identified a human and non-human primate salty taste receptor and therefore should be effective for functionalizing other taste specific genes such as fat and metallic taste receptors or other taste specific genes involved in ancillary taste cell functions enumerated infra.

In addition, as further described infra, improvements of these methods are also provided which use the combination of real time polymerase chain reaction detection of gene expression and immunochemical assays using taste buds from human post-mortem samples and other methods have been utilized to successfully isolate and identify other unique human taste cell subsets and lineages which in all likelihood are involved in detecting other taste modalities or other taste cell functions.

More specifically, the improved method identifies human taste specific genes by quantitative polymerase chain reaction (PCR). Particularly, the inventors demonstrate taste specific gene expression in humans and primates and have validated the observed specificity of expression by a quantitative method (qPCR or "TaqMan") The identified human taste specific genes (Table 8 infra) (most of which have known primate and other species counterparts) encode multi-span transmembrane proteins and therefore are predicted to include receptors involved in different taste modalities and other functions. (One of the identified human ion channels genes disclosed therein has been confirmed to encode a salty taste receptor.)

Also, in a related aspect this application identifies taste specific genes expressed in humans based on the identification of their counterparts (orthologs) in non-human primates using the disclosed rationales. The inventors predicted that as primates and humans are closely evolutionarily related that gene expression patterns seen in primate taste tissues would correlate to those observed for these genes in human taste tissues. Based on this assumption, taste specific genes shown to be taste specific in primates (including those recited in Tables 1-5 infra) were selected to be validated in human taste buds using non-microarray analysis (TaqMan qPCR).

In another related aspect the invention detects human taste specific genes in human LCM cDNA using LCM from postmortem LC human tissues and a single cDNA amplification step, establishing that human postmortem LCM human tissue can be used to quantify the expression of taste specific genes sung qPCR.

In yet another related aspect the invention establishes that human taste specific genes can be measured by quantitative qPCR (taqMan) and that gene expression profiles of human taste specific genes can be directly measured by TaqMan and the results used to validate previous gene expression data obtained from microarrays and/or in situ hybridization (ISH) from non-human, e.g., macaque taste cell samples.

In an additional aspect the invention provides an improved method for the identification of a set of human and non-human primate taste specific genes which should identify all potential taste receptor and taste modulator genes based on a selection protocol which compares the expression of taste specific genes in cells in the top versus the bottom of the taste bud.

In another related aspect the invention identifies novel human taste-bud specific genes using the successive approaches of gene expression via microarray in primate LCM tongue tissue; top specific gene expression within the taste bud (akin to known taste receptors) and TaqMan quantification of gene expression in human postmortem tissues and have identified new human taste specific genes not described previously as being taste specific.

In another related aspect the invention identifies human taste specific genes expressed in human post-mortem tissues and provides methods for the functionalization of these genes and cells which express these genes or a combination thereof.

In another related aspect the invention provides a method for identifying and categorizing human taste specific genes which are involved in different functions of the taste buds based on measuring their expression by quantitative qPCR or based on where they are expressed in human taste buds.

In another related aspect the invention provides the specific primate and human taste specific genes identified using these methods which are involved in different taste cell functions including taste sensation, taste bud growth and development, control of the lifespan of mature taste bud cells, and the maintenance differentiation and proliferation of taste-bud committed taste stem cells.

Also, the invention provides the specific primate and human taste specific genes identified using these methods and the corresponding gene products as biomarkers of taste-bud committed stem cells.

Also, the invention provides the specific primate and human taste specific genes identified using these methods and the corresponding gene products as biomarkers of different mature taste cell subsets.

Also, the invention provides the specific primate and human taste specific genes identified using these methods and the corresponding gene products in methods which purify, enrich or ablate specific taste cell subsets and taste-bud committed stem cells.

More specifically, this application identifies novel categories of taste specific genes which are tabulated and enumerated infra derived from primates and human taste cell specific sources (See tables 1-8). These genes are expressed in chemosensory or taste cells, e.g. human and non-human primate fungiform or circumvallate macaque taste cells, and taste (e.g., fungiform, circumvallate, foliate, or palate) cells derived from other mammals such as other non-human primates. These genes are referred to by the inventors as "taste-specific" genes because they are strongly expressed in taste cells. These taste-specific genes include genes which are directly or indirectly involved in taste detection and modulation, e.g., salty, umami, sweet, sour, fatty, metallic, or bitter taste transduction as well as including genes which are involved in biological functions not directly related to taste detection such as the modulation of digestion, taste cell turnover, regulation of the immune system, particularly of the oral cavity, and the regulation of metabolism e.g., carbohydrate metabolism, diabetes, obesity, cachexia, detection of food during digestion, et al.

Relating to the foregoing the present invention provides novel sets of genes that are expressed specifically in human and non-human primate (macaque) chemosensory, e.g., macaque fungiform or circumvallate papilla taste cells that are not expressed or are expressed at significantly lower levels in lingual epithelial cells that are useful in screening assays, preferably high throughput screening assays, for identifying compounds that directly or indirectly modulate different taste modalities, e.g., salty, sweet, umami, bitter, sour, fatty, or metallic.

While the identified taste-specific genes include genes which are directly or indirectly involved in taste detection and modulation, e.g., salty, umami, sweet, sour, fatty, metallic, or bitter taste transduction they also include genes which are involved in biological functions not directly related to taste detection such as the modulation of digestion, taste cell turnover, regulation of the immune system, particularly of the oral cavity, and the regulation of metabolism e.g., carbohydrate metabolism, diabetes, obesity, cachexia, detection of food during digestion, et al.

With particular respect to fat or lipid taste detection the present invention further identifies a subgenus of taste specific genes which are predicted to be involved in detecting fats or lipids based on the presence of characteristic lipid or fat binding motifs or based on the classification of these genes. These genes potentially may be used to screen for compounds that enhance or mimic or block fatty taste detection by the taste buds and potentially detection, binding or absorption by gastrointestinal tissues since it is likely that taste receptors which sense fats or lipids may be expressed in the gastrointestinal tissues as has been observed with other types of taste receptors (sweet, umami and bitter). These genes are referred to herein as "fat taste-specific" genes because they are expressed specifically in taste cells and because based on their structure or prior fictionalization as binding to fatty acids or lipids they are predicted to be involved in fat taste detection in human and non-human primates and likely other mammals. Also, these putative fat taste-specific genes include genes that may also play an ancillary role in other taste modalities and the detection or isolation of taste cells involved in other taste modalities such as, e.g., salty, umami, sweet, sour, metallic, or bitter taste transduction. In addition based on their structural characteristics such as characteristic motifs or prior functional characterization as fatty acid or lipid receptors these genes are predicted to possess other non-taste biological functions involving lipid transport and fat metabolism such as gastric motility and gastric peptide secretion.

Further relating to the foregoing the present invention identifies taste specific human and non-human primate (macaque) genes and the corresponding gene products or cells that express same that are useful in screening assays, preferably high throughput screening assays, for identifying compounds that are useful e.g., as therapeutics in the treatment of digestive system disorders such as cancers and autoimmune disorders, for modulating taste cell apoptosis or taste cell turnover, for inducing taste cell regeneration, for affecting the regulation of immunity in the oral cavity, and the regulation of metabolism, e.g., in the treatment of diabetes, obesity, eating disorders, and other metabolic disorders.

Also relating to the foregoing the invention provides a novel set of human and primate (macaque) and human genes which are useful in the identification and/or isolation and/or enrichment of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as cells that aid in food detection, the secretion of hormones or enzymes involved in hunger and digestion, and the like.

Further, the invention relates to the use of these isolated chemosensory or taste cells in screening assays for identifying compounds that modulate taste, as well as in the identification of therapeutics for modulating the immune system, particularly the regulation of the immune homeostasis in the oral cavity, regulation of taste cell apoptosis, turnover or taste cell regeneration and proliferation, regulation of hormones or enzymes involved in digestion and other taste cell functions, treatment of digestive system disorders such as oral or digestive system cancers, autoimmune or inflammatory digestive disorders, treatment of diabetes, obesity, eating disorders, or other metabolic disorders, and the like.

Further relating to the foregoing the present invention provides a novel set of human and primate (macaque) genes and the corresponding gene products or cells that express same that are useful in screening assays, preferably high throughput screening assays, for identifying compounds that are useful e.g., as therapeutics in the treatment or prevention of digestive system disorders involving aberrant lipid and fat metabolism and the co morbidities associated with aberrant fat and lipid intake and metabolism such as obesity, hepatic steatosis, liver cirrhosis, atherosclerosis, hyperglycemia, insulin resistance and hepatic insulin resistance, type 1 and type 2 diabetes, abdominal obesity, cancers that are obesity or diet related, and the like.

Also, the invention relates to the use of such putative taste receptor genes and the corresponding polypeptides and cells which express same such as cancers and autoimmune disorders, in identifying compounds for modulating taste cell apoptosis or taste cell turnover, particularly compounds that modulate or inhibit fat taste cell regeneration and adipocyte differentiation, e.g., for affecting the regulation of metabolism, e.g., in the treatment of diabetes, obesity, fat accumulation, eating disorders, and other metabolic disorders.

Also relating to the foregoing the invention provides a novel set of human and primate (macaque) genes which are useful in identifying, isolating and/or enriching fat taste receptor expressing cells or cell lineages that upon maturation give rise to fat taste receptor cells using the subject genes or probes specific thereto such as nucleic acids or antibodies.

Also, the invention relates to the use of isolated chemosensory, e.g., taste or gastrointestinal, e.g., enteroendocrine cells which express one or more of the genes reported herein the identification and/or isolation and/or enrichment or ablation of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as cells that aid in food detection, the secretion of hormones or enzymes involved in hunger and digestion, and the like.

Further, the invention relates to the use of these isolated chemosensory or taste cells in screening assays for identifying compounds that modulate taste, as well as in the identification of therapeutics for modulating the immune system, regulation of taste cell apoptosis, turnover or taste cell regeneration and proliferation, regulation of hormones or enzymes involved in digestion and other taste cell functions, treatment of digestive system disorders such as digestive system cancers, treatment of diabetes, obesity, eating disorders, or other metabolic disorders, and the like.

The present invention further provides methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

Also the invention relates to the use of markers e.g., antibodies or oligonucleotides, that are specific to one or more of the subject taste specific genes provided herein in mapping regions of the tongue and oral cavity which are involved in specific taste and non-taste specific functions, mapping of cell comprised on specific regions of the gastrointestinal tract and associated organs such as the intestinal epithelium or urinary tract that express specific taste specific genes and which therefore are involved in one or more of the taste cell specific functions disclosed herein, and/or the use of the subject genes and markers specific thereto in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In yet another aspect, this invention relates to assays for identifying a compound having potential in vivo application for modulating human salty or other specific taste. This method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a *Xenopus* oocyte or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8

In a preferred mode, the assay of step (ii) is an electrophysiological assay which uses a sodium sensitive dye, and preferred dyes include membrane potential dyes selected from the group consisting of Molecular Devices Membrane Potential Kit (Cat#R8034), Di-4-ANEPPS (pyridinium, 4-(2-(6-(dibutylamino)-2-naphthalen-yl)ethenyl)-1-(3-sulfopropyl) hydroxide, inner salt, DiSBACC4(2)(bis-(1,2-dibabituric acid)-triethine oxanol), Cc-2-DMPE (Pacific Blue 1,2-di-etradecanoyl-sn-glycerol-3phosphoethanolamine, triethylammonium salt) and SBFI-AM (1,3-benzenedicarboxylic acid, 4,4-[1,4,10-trioxa-7,13-diazacylopentadecane-7,13-diylbis(5-methoxy-6,1,2-benzofurandiyl)}bis-tetrakis {(acetyloxy)methyl}ester (Molecular Probes), more preferably, the sodium sensitive dye is sodium green tetraacetate (Molecular Probes) or Na-sensitive Dye Kit (Molecular Devices). In another preferred mode, the assay of step (ii) is a two electrode voltage clamping assay in *Xenopus* oocytes, or the assay is a patch clamp assay in mammalian cells. Preferably, the assay measures activity by an ion flux assay, including using atomic absorption spectroscopy to detect ion flux.

Alternatively, the assay may use a fluorescence plate reader (FLIPR), or a voltage imaging plate reader (VIPR), which is used to increase ion channel-dependent sodium or fluid absorption. In a preferred embodiment of this method, the activity of the putative salty taste affecting gene is assayed in a frog oocyte electrophysiologically by patch clamping or two electrode voltage clamping, preferably using an automatic imaging instrument, which may be a fluorescence plate reader (FLIPR) or a voltage imaging plate reader (VIPR).

In yet another mode, this invention relates to assays for identifying a compound having potential in vivo application for modulating human sweet, bitter, umami, or sour taste. This method comprises the steps of (i) contacting a cell that expresses a gene in Tables 1-8 with at least one putative enhancer or blocker compound; (ii) assaying sodium conductance, receptor activity or taste gene product function in the presence and absence of said putative enhancer or blocker; and (iii) identifying the compound as a potential enhancer or blocker for sweet, bitter or umami taste based on whether it modulates sodium conductance, the activity of said receptor or taste gene product function.

In a more specific embodiment the present invention relates to assays that screen for activators of TRPM5 or umami (T1R1/T1R3) and/or sweet (T1R2/T1R3) taste receptors preferably those which modulate insulin metabolism and/or the release of a satiety peptide such as GLP-1 (glucagon-like peptide 1), which may be used in treating or preventing metabolic and eating disorders such as in the treatment of one of obesity, diabetes, weight management, fat metabolism, glucose metabolism, insulin metabolism, satiety or other conditions wherein the release of satiety peptides or insulin metabolism is desirably controlled or reduced.

In another specific embodiment the present invention relates to assays using endogenous taste cells, e.g., gastrointestinal cells such as gastro-endocrine or gastro-epithelial cells or cells on the tongue or oral cavity, that screen for compounds which act as activators of TRPM5 or umami (T1R1/T1R3) and/or sweet (T1R2/T1R3) taste receptors, preferably those which modulate insulin metabolism and/or the release of a satiety peptide such as GLP-1 (glucagon-like peptide 1), which activators may be used in treating or preventing metabolic and eating disorders such as in the treatment of one of obesity, diabetes, weight management, fat metabolism, glucose metabolism, insulin metabolism, satiety or other conditions wherein the release of satiety peptides such as GLP-1 (glucagon-like peptide 1) is desirably controlled or reduced.

This invention in a more specific embodiment relates to specific taste specific genes identified infra, e.g., FAM26A, GPR113, MCTP1, TMEM16G, TMEM30B, TMEM44, and TUSC3 that are expressed in chemosensory or more specifically taste cells, e.g., human and primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the invention relates to enriched, isolated or purified taste cell subsets which expresses at least one of FAM26A, MCTP1, TMEM30B, and/or TUSC3 and which further express at least one T1R or T2R or TRPM5 gene and/or which express T1R2/T1R3 or T1R1/T1R3 or T1R3 only. Particularly, the invention provides isolated taste cells that express GPR113 and/or TMEM16G and which isolated taste cells which further expresses at least one of T1R2/T1R3, T1R1/T1R3, T1R3 only, a T2R gene and/or TRPM5.

Also, the invention relates specifically to a method of using a probe specific to a gene or gene product corresponding to the genes to identify and/or isolate and or enrich taste specific cells from non-taste cells in a sample. For example, these methods include a method herein the gene is FAM26A, MCTP1, TMEM30B, and/or TUSC3 and the identified, isolated or enriched cell further expresses T1R1/T1R3, T1R2/T1R3, T1R3 only, a T2R, and/or TRPM5. Also, the invention includes methods wherein the gene is GPR113 and/or TMEM16G and the isolated, identified or enriched cell further expresses at least one of T1R2/T1R3, T1R1/T1R3, T1R3 only, a T2R or TRPM5 and/or wherein said taste cells are human or macaque taste cells. and wherein said isolated taste cells do not express PKD2L1, PKD1L3, or TRPM5 and/or wherein said cells do not express a T1R or a T2R and/or said taste cells express transducin or gustducin.

Also, the invention relates to the use of these identified taste specific genes or an ortholog or variant thereof encoding a protein at least 90% identical thereto in a cell isolation, purification, enrichment, or marking technique that isolates, purifies, enriches and/or marks at least one desired taste cell subtype or lineage contained in a mixed cell population or cell suspension comprising a desired taste cell type or lineage based on the expression or absence of expression of at least one gene contained in Tables 1-8 or an ortholog thereof, or a gene encoding a protein that is at least 90% identical to said gene or an ortholog thereof. Particularly, the invention includes methods wherein the taste cell subtype or taste cell lineage is isolated, purified, enriched, or marked by a method that includes the use of a fluorescence activated cell sorter (FACS) or by the use of labeled magnetic beads and wherein the cell suspension containing the cells may be produced by enzymatic digestion and/or tissue disaggregation of tissues containing taste cells. and methods wherein the desired taste cell subtype or taste cell lineage is isolated, purified, enriched or marked by a method that includes a negative cell selection technique that eliminates at least one non-target taste cell subtype or lineage based on the expression or absence of expression of at least one other taste cell specific gene identified herein. These methods may e.g., use cytotoxic antibodies to specifically kill at least one non-target cell type or lineage. These isolation methods may e.g., result in isolates containing sweet taste cells, umami taste cells, sour, salty, or fat taste cell subtype or lineages, taste stem cells taste cell neurons, or taste immune cells.

Also, the invention relates to methods of using a cell isolated, purified, enriched or marked according to these methods in screens for taste modulatory compounds, or in a method that screens for compounds that induce the differentiation of said enriched, isolated, purified or marked taste stem cells into one or more taste cell lineages or subtypes or taste buds or in a method wherein said taste cell lineages or subtypes are identified based on the expression or absence of expression of at least one the identified taste specific gene identified above. These cells may be used to screen for compounds that modulate at least one of sweet, umami, bitter, sour, fat, salty or metallic taste wherein the gene is GPR113 or TMEM16G or TMEM44 or to screen for compounds that modulate taste cell differentiation or turnover.

Also, the invention relates to these cells or the gene or gene product encoded thereby in assays that screen for compounds that modulate or treat the diseases and conditions involving taste cells previously identified. This in particular relates to GPR113 or the corresponding gene product or cells which express same or an ortholog or variant thereof in assays to identify compounds that modulate taste cell differentiation or taste cell turnover.

Also, the invention relates to isolated immature taste cells and/or taste stem cells that express TMEM44 or GPR113 and the use in an assay for identifying taste modulators, in particular which screens for sweet, umami, bitter, fat, salty, metallic and/or astringent taste modulators. Also, the invention relates to a recombinant cell engineered to co-express T1R3 and GPR113 and optionally TRPM5. Also, the invention embraces an assay for identifying compounds which modulate taste cell differentiation and/or maturation based on whether said compound specifically binds and/or modulates the activity of GPR113.

Also, the invention relates to the use of these cells in assays that screen for compounds that modulate the differentiation and/or maturation of sweet or umami taste cells. Also, the invention provides a method of using GPR113 as a marker to identify, enrich and/or isolate or ablate unique taste cells which express GPR113, TRPM5 and T1R3 wherein said taste cells do not express T1R1, T1R2 and/or a T2R or are immature, e.g., by FACS or magnetic bead cell separation or by use of cytotoxins.

In addition the invention relates to the discovery that TMEM44 and MFSD4 are expressed in unique taste cell type and that these gene are expressed in sensory taste cells that are not sweet, bitter, umami, or sour cells which further expresses another taste-specific gene disclosed herein. Also, the present invention relates to the discovery that expression of TMEM44 and MFSD4 are markers for a unique taste cell type that may correspond to a fat receptor. Further, the invention relates to the discovery that ATP8A1, FAM26B and SLC4A1 are expressed in many TRPM5 cells, suggesting that these genes are expressed in sweet, umami, and bitter taste cells, since TRPM5 is a marker of sweet, bitter, and umami taste cells.

This invention in a more specific embodiment identifies genes infra, e.g., FAM26A, GPR113, MCTP1, TMEM16G, TMEM30B, TMEM44, and TUSC3 that are expressed in chemosensory or more specifically taste cells, e.g., human or primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the present invention relates to the discovery that MFSD4 is expressed in cells that do not express TRPM5 (bitter, sweet, umami) indicating that the expression of this gene is a marker for a unique taste cell type that could correspond to salt, fat, or another taste modality, and, furthermore, that this gene may encode the primary salt or fat receptor.

Also, the invention reveals that the expression pattern of MFSD4 is very similar to TMEM44, indicating that both genes are expressed in the same taste cell type and may be comprised in a heteromeric taste receptor.

Also, the invention relates to the discovery that ATP8A1, FAM26B, and SLC4A11 can be used as markers for sweet, bitter, and umami taste cells or cells expressing TRPM5.

Also, the invention relates to the discovery that ATP8A1, FAM26B, and SLC4A111 and compounds that enhance or inhibit these gene products can selectively modulate taste cell function and responses to tastants including sweet, bitter, and umami.

Also, the invention relates to the discovery based on in situ hybridization results that that TUSC3, ASCL1, FAM26A, FAM26C, IKBKAP, LOC285965, SCNN1D, SLC4A11, SLC26A7, and TMEM30B all are expressed by unique taste cell subsets comprised in primate taste buds and therefore can be used as biomarkers to isolate, enrich, mark or ablate these cells and thereby determine the taste related function of these taste bud cells.

Also, the present invention relates to the discovery that MFSD4 can be used as a marker for a unique, novel taste cell type that does not correspond to sweet, bitter, and umami taste cells. Moreover, the invention relates to the discovery that MFSD4 and compounds that enhance or inhibit this gene product can selectively modulate taste cell function and responses to tastants other than sweet, bitter, and umami, which include salt, fat, and other tastants. Based on the foregoing, the invention relates to the discovery that MFSD4 may correspond to the salt receptor or fat receptor. Also, MFSD4 may be a marker of immature taste cells or developing taste cells.

Related thereto, the present invention also relates to the discovery that MFSD4 and compounds that enhance or inhibit this gene product can selectively modulate taste cell development and/or differentiation of specific taste cell types (i.e. bitter taste cells).

Also, the present invention relates to the discovery that MFSD4 and TMEM44 are expressed in the same unique taste cell type. Also, the present invention relates to the discovery that MFSD4 and TMEM44 may form a complex (heterodimer) to generate a taste receptor for a different taste than sweet, umami, sour or bitter, likely salt or fat. and may be used in screening assays.

Also, the present invention relates to the discovery that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells. and may regulate taste perception or other taste cell function. Moreover, the present invention reveals that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells.

In another embodiment the invention relates to the discovery that ASCL1 also known as MASH is a transcription factor that defines and is a useful marker of sour taste cells as it is selectively expressed in sour taste cells that express PKD1L3 but not in other taste cell types, i.e., it is not expressed in sweet, bitter, or umami cells which express TRPM5. Therefore, the ASCL1 transcription factor may bind to promoter elements in genes involved in sour taste perception. Thus, the invention provides the use thereof in screening the genome for ASCL1 motifs to identify genes in sour cells, including sour receptor genes such as PKD2L1, PKD1L3, or additional genes that may form a complex with PKD2L1/PKD1L3 to generate a sour receptor.

In another embodiment the invention establishes ASCL1 to be a marker of type III taste cells. Type III taste are defined by morphological criteria which include: staining with an intermediate density by electron microscopy and making synaptic contacts with nerve fibers. Thus, the invention reveals that type III taste cells, a cell type previously defined by morphological criteria, correspond to sour taste receptor cells defined by gene expression criteria.

In another embodiment the invention relates to the discovery that other taste receptor cells for sweet, bitter, umami, and salt are likely to express specific transcription factors related thereto that define those cell types. Therefore, the invention provides assays detecting the expression of all transcription factors in the genome in taste cells by PCR and/or histology to determine which taste cell types express which transcription factors.

In another embodiment the invention relaters to the discovery that the ASCL1 transcription factor binds to promoter elements in genes involved in sour taste perception. Thus, the invention encompasses such sequences found in the genome that comprise ASCL1 motifs and the use thereof to identify genes in sour cells, including sour receptor genes such as PKD2L1, PKD1L3, or additional genes that may form a complex with PKD2L1/PKD1L3 to generate a sour receptor.

In another embodiment the invention relates to the discovery that ASCL1 (aka MASH1) is a marker useful for identifying, purifying, and/or isolating or ablating sour taste cells in a mixed cell sample, e.g., derived from the tongue or gastrointestinal or urinary tract.

In a related embodiment the invention provides the use of ASCL1 as a marker of Type III taste cells that correspond to sour taste receptor cells In another embodiment the invention establishes that because ASCL1 defines the sour taste cell lineage it may also control sour taste cell development.

In another embodiment the invention provides the use of ASCL1 transcription factor DNA binding sequences as a probe to identify sour cell genes and sour taste receptor genes that possess related structure such as ASCL1 motifs.

Also, the invention provides the use of these and other taste cell specific transcription factors to define, mark, and/or label taste cell types because each taste cell will express one or more transcription factors that define that taste modality.

The invention further provides the use of these transcription factors that define taste modalities in cell ablation studies to specifically eliminate a specific taste cell or taste modality.

Also, the invention provides ASCL1 or other taste transcriptional gene knockouts which result in transgenic animals possessing altered taste perception and other phenotypic effects, e.g., elimination of sour taste perception or altered urinary or digestive function since ASCL1 may be involved in the metabolic response to pH changes such as excess acidity.

Also, the invention provides the use of these transcription factors that define new taste cell types which can be used in cell ablation studies and in vitro assays to determine what taste modality is lacking as a result of this ablation (i.e. what taste modality is eliminated).

In another embodiment this invention identifies taste-specific genes NALCN, TRPML3 and NKAIN3 which when expressed separately or in combination are predicted to comprise a taste receptor, putatively a salty taste receptor, as these 3 genes are expressed in primate taste cells, are enriched in the top fraction of taste bud cells, and are known to encode sodium channels. In addition the invention relates to the discovery that NALCN is expressed in a unique taste cell subset and is predicted to encode a taste related function. (As noted, TRPML3 has been shown to encode a salty taste receptor).

In a related embodiment the present invention relates to the use of these taste specific ion channel genes as markers which can be used to enrich, identify or isolate salt receptor expressing cells.

In another embodiment the invention relates to assays that identify compounds that modulate the function of the use of NALCN, TRPML3 and/or NKAIN3 and the use of the identified compounds to modulate salty taste perception.

In another embodiment the invention relates to other taste specific genes, i.e., KIT, IKBKAP, LOC285965, and SV2B that are expressed in specific subsets of taste specific cells.

In another embodiment, this invention relates to the discovery that KIT is specifically expressed in TRPM5 and T1R3 taste cells and T1R1 taste cells indicating that the gene can be used as a marker to identify umami taste cells in a mixed cell population and/or may modulate the expression and activity of the umami taste receptor.

In another embodiment, this invention relates to the discovery that IKBKAP and SV2B are specifically expressed in PKD1L3 sour taste receptor cells indicating that these genes can be used as markers to identify sour taste cells and/or modulate taste, especially sour taste.

Also, in another embodiment this invention relates to the discovery that LOC285965 is specifically expressed in TRPM5 and T1R3 taste cell subsets and T1R3 cells lacking T1R1 and T1R2 suggesting that this gene can be used as a marker of these taste cell subsets and/or may associate with or modulate the T1R3 gene and/or encode a taste receptor distant from T1R1/T1R3 or T1R2/T1R3.

Further, in another embodiment the invention relates to the discovery that SV2B is specifically expressed in PKD1L3 cells indicating that this gene can be used as a marker of these specific cell subsets and/or may encode a polypeptide that modulates the activity or expression of the PKD1L3 sour taste receptor.

In addition, in another embodiment the invention relates to the discovery that MFSD4 is expressed in sensory taste cells that are not sweet, bitter, umami, or sour cells and that this gene is expressed in a similar taste cell population as TMEM44.

Also, in another embodiment the invention relates to primate taste specific genes identified in Table 4 found by gene chip analysis which encode transmembrane proteins for ion channels that can conduct sodium, ion transporters, G-protein coupled receptors, or may encode novel multi-transmembrane proteins with no known function which are candidate salty taste receptors.

In another embodiment, the invention relates to the use of compounds that enhance or inhibit IKBKAP and SV2B gene products to selectively modulate taste cell function and responses to sour tastants as well as other functions of the PKD1L3 taste cell population.

In another embodiment, since IKBKAP is mutated in the human disease familial dysautonomia, where taste buds are absent or atrophic and individuals exhibit deficiencies in detection of sweet, bitter, sour, and salty tastants (hypogeusia) the invention related to the discovery that IKBKAP expression in PKD1L3 cells may be important for taste cell development and/or maintenance.

In another embodiment since Botulinum neurotoxin (BoTox) enters neuronal-type cells by interacting with SV2B; the invention relates to the use of BoTox and derivatives to selectively modulate sour taste as well as other functions of the PKD1L3 taste cell population.

In another embodiment since KIT is expressed in umami taste cells the invention relates to the use thereof as a marker of this taste cell type.

In another embodiment the invention relates to the use of KIT and compounds that enhance or inhibit this gene product to selectively modulate taste cell function and responses to umami tastants.

In another embodiment the invention relates to the use of Gleevec (Imatinib), an inhibitor of the KIT tyrosine kinase activity, and other KIT tyrosine kinase inhibitors for selectively inhibiting umami taste.

In another embodiment the invention relates to the discovery that individuals with gain of function mutations in KIT, for example in gastrointestinal stromal tumors (GIST), may have altered umami taste perception.

In another embodiment since LOC285965 is expressed in T1R3 only taste cells similar to GPR113 the invention relates to the use as a marker for a unique, novel taste cell type (T1R3 only cells) that does not correspond to sweet, bitter, and umami taste cells.

In another embodiment the invention relates to the discovery that LOC285965 may correspond to the salt receptor or fat receptor or a receptor for astringency or metallic taste by itself or in combination with GPR113, which is also expressed in T1R3 only cells.

In another embodiment the invention relates to the discovery that LOC285965 may be a coreceptor with T1R3 for specific sweet or umami tastants or other novel tastants such as astringent and metallic tastants.

In another aspect the invention relates to the discovery that compounds that enhance or inhibit LOC285965 can selectively modulate taste function and responses to tastants.

In another embodiment the invention relates to the discovery that LOC285965 may correspond to a marker of immature taste cells that are differentiating into sweet or umami cells.

In another embodiment the invention relates to the discovery that LOC285965 and compounds that enhance or inhibit this gene product can selectively modulate taste cell development and/or differentiation of specific taste cell types (i.e. sweet or umami taste cells).

In another embodiment the invention relates to the discovery that MFSD4 and compounds that enhance or inhibit this gene product can selectively modulate taste cell function and responses to tastants other than sweet, bitter, umami, and sour which include salt, fat, and other tastants.

In another embodiment the invention relates to the discovery that MFSD4 may correspond to the salt receptor or fat receptor.

In another embodiment the invention relates to the discovery that MFSD4 may correspond to a marker of immature taste cells or developing taste cells or support cells.

In another embodiment the invention relates to the use of MFSD4 and compounds that enhance or inhibit this gene product to selectively modulate taste cell development and/or differentiation of specific taste cell types (i.e. bitter taste cells).

In another embodiment the invention relates to the discovery that MFSD4 and TMEM44 are expressed in the same unique taste cell population.

In another embodiment the invention relates to the discovery that MFSD4 and TMEM44 may form a complex (heterodimer) to generate a taste receptor for salt or fat.

In another embodiment the invention relates to the use of the genes listed in Tables 1-8 in assays for candidate salt or fat taste receptors.

BACKGROUND OF THE INVENTION

This invention and the specific rationales for identifying and functionalizing taste specific genes were developed with their initial objective being the identification and functionalization of a gene encoding a salty taste receptor. With respect thereto, epithelial sodium channels (ENaC) are members of the ENaC/degenerin family of ion channels that includes acid-sensing ion channels (ASIC) in mammals, mechanosensitive degenerin channels in worms, and FMRF-amide peptide-gated channels in mollusks (Kellenger, S, and Schild, L. (2002) Physiol. Rev. 82:735-767). ENaC mediates amiloride-sensitive apical membrane $Na^+$ transport across high resistance epithelia in numerous tissues including kidney, colon, and lung and have been well studied and predicted to be involved in salty taste in primates and other species.

ENaC is known to be a heterotrimeric channel comprised of alpha, beta, and gamma subunits or delta, beta, and gamma subunits. Particularly, this heterotrimeric channel has been hypothesized to be involved in human salty taste perception. Previously, assays have been developed by the present assignee using ENaC sequences to identify compounds that modulate the delta beta gamma and alpha beta gamma human ENaC to examine if these compounds will potentially modulate human salty taste perception. Also, these compounds potentially may be used to treat human pathologies involving aberrant ENaC function.

Unlike other mammals, amiloride only slightly reduces the intensity of sodium chloride taste, i.e., by about 15-20% when used at concentrations that specifically modulate ENaC function (Halpern, B. P. (1998) Neuroscience and Behavioral Reviews. 23: 5-47). Experiments conducted by the inventors have shown that amiloride, or the more potent amiloride derivative phenamil did not elicit a significant effect on perceived human salt intensity when tested at levels 300-fold (for amiloride) and 3000-fold (for benzamil) above IC50 values for alpha beta gamma ENaC (equivalent to 10-fold for amiloride and 100-fold for benzamil over IC50 values for delta beta gamma ENaC). Thus, additional non-ENaC genes are likely involved in human salty taste.

In addition, it has been recently reported that taste receptors may be expressed in non-oral tissues, e.g., in the digestive system and potentially other organs such as the kidney. Particularly it has been reported that sweet, umami and bitter taste receptors are expressed in cells other than in the oral cavity such as gastrointestinal cells. (See, e.g., Sternini et al., Amer J Physiol. Gastrointestinal and Liver Physiology, 292: G457-G461, 2007; Mace, O. J. et al, J. Physiology. 10.1113/jphysiol.2007.130906. Published online May 10, 2007). Also, it has been reported by various groups (Margolskee et al., Bezencon et al., Rozengurt et al, and Sternini et al. (2007) (Id)) that bitter and umami taste receptors and other taste signaling molecules such as TRPM5 and gustducin are expressed in specialized cells in the gastrointestinal tract. (See e.g., Margolskee et al., Genes Brain Behavior 2007 (epub March 21); Rozengurt et al., Amer. J. Physiol. Gastroent. Liver Physiol. 291(2):G171-7 (2006); Bezencon et al., Chem Senses 32(1):41-47 (2007)). Margolskee et al. (Id) further reports that the loss of T1R3 or gustducin in rodents resulted in changes in insulin metabolism and the release of satiety peptides such as GLP-1 (glucagon-like peptide 1).

Based on the foregoing, it has been suggested that salty receptors may be expressed in the urinary tract. Taste receptors are purported to be involved in functions not directly related to taste such as digestive functions such as gastric motility, absorption, food detection, metabolism, and immune regulation of the oral or digestive tract and may also affect functions relating to sodium absorption, excretion and transport such as blood pressure and fluid retention.

Therefore, the identification of taste cell specific genes and identifying what specific cells these genes are specifically expressed (including unique taste cell subsets) should facilitate a better understanding of taste and non-taste functions of these taste receptors and should also facilitate the use of these genes, gene products and cells which express same in assays for identifying novel taste modulators and therapeutics, e.g., for treating digestive diseases such as autoimmune, inflammatory and cancers, metabolism, diabetes, eating disorders, obesity, taste cell turnover, hypertension, fluid retention, and immune regulation of the digestive system.

BRIEF DESCRIPTION AND OBJECTS OF THE INVENTION

The invention obviates the problems of the prior art in that it provides novel rationales for identifying and functionalizing primate and human taste specific genes and unique taste cell subsets and further provides novel uses of these taste specific genes, gene products, and modulators of these taste specific genes and cells containing.

This invention in one embodiment relates to the identification of genes that are expressed specifically in chemosensory or taste cells, particularly human and non-human primate (macaque) fungiform or circumvallate papilla cells, and in taste cells (fungiform, circumvallate, foliate, and palate) of other mammals such as humans and other non-human primates. These genes include genes which are directly or indirectly involved in detecting specific taste modalities such as salty, sweet, bitter, umami, sour, fatty and metallic taste and/or in modulating taste intensity and duration.

This invention in another embodiment relates to the identification of genes that are expressed specifically in chemosensory or taste cells, particularly primate (macaque) circumvallate cells and likely in other chemosensory or taste cells and similar cells derived from other mammals such as humans and non-human primates that are involved in other taste cell functions including by way of example taste cell apoptosis or taste cell turnover, taste cell regeneration, digestion, regulation of the immune system in the oral cavity, regulation of carbohydrate or other metabolic functions relating to digestion, food detection, taste cell trafficking, and the like.

The invention in another embodiment further relates to the identification of specific genes or gene products expressed specifically in human and primate (macaque) or other mammalian taste cells that can be used as markers for the identification, isolation, or enrichment of specific taste cell subtypes or taste cell lineages including by way of example sweet, umami, sour, bitter, salty, fatty and metallic taste cells and for isolating taste cells that are involved in non-taste functions such as regulation of immunity, e.g., in the oral cavity, regulation of digestion or metabolism, regulation of taste cell apoptosis, turnover, or taste cell differentiation and proliferation, and regulation of sodium excretion, transport and absorption.

The invention in another embodiment further relates to the use of these taste cell specific genes or gene products or said isolated or enriched taste cell lineages or taste cell types expressing said taste cell specific genes for use in screening assays, e.g. for identifying compounds that elicit of modulate sweet, sour, umami, salty, bitter, fatty or metallic taste as well as the use of these genes, gene products, or isolated or enriched taste cells for the identification of potential therapeutic compounds, e.g., therapeutics for treatment of various digestive system disorders such as ulcerative colitis, Cohn's disease, celiac disease, dyspepsia, cancers of the digestive system, compounds for modulating taste cell turnover or apoptosis or for regulating taste cell differentiation and regeneration e.g., in geriatric subjects or individuals with cancer, or undergoing chemotherapy, or radiation, compounds for modulating or enhancing the immune system of the oral cavity, compounds for the regulation of digestion and metabolism, e.g., compounds that affect the production of digestive fluids, hormones or enzymes such as saliva, stomach and intestinal fluids, GLP-1 (glucagon-like peptide 1), GIP (glucose-dependent insulinotrophic polypeptide), secretin, amylase et al., compounds that affect digestive motility, compounds for treating diabetes, for modulating food detection, and compounds for treating obesity or eating disorders, cachexia, and the like.

This invention in its more specific embodiments relates to novel rationales and methods, and results to date using these rationale and methods for identification and characterization of novel taste-specific genes that based on various parameters constitute salt or other taste modality receptor targets. The targets using these protocols are useful targets in high-throughput screening efforts to identify human salty taste enhancers. These targets are initially identified using two different techniques, gene chips and a polymerase chain reaction (PCR) screen, to identify novel salt receptor target genes. First, Affymetrix gene chips containing most all known macaque genes are used to determine which genes are specifically expressed in primate circumvallate at the back of the tongue and fungiform papilla taste cells at the front of the tongue and not lingual epithelial cells isolated by laser capture microdissection. Second, PCR is used to determine which ion channels, from channels we have cataloged in the human/macaque genomes, are specifically expressed in macaque fungiform and/or circumvallate (CV) papilla taste cells but not lingual epithelial cells isolated by laser capture microdissection. Taste-specific expression of genes identified by either approach, are confirmed using an independent histological method such as in situ hybridization or immunohistochemistry, to determine which genes are expressed in taste cells. Using double labeling histological methods, it is determined what novel taste-specific genes are expressed in sweet, bitter, and umami cells that express the taste-specific ion channel TRPM5, sour cells that express the taste-specific ion channel PKD2L1/PKD1L3, or a unique cell type that does not express TRPM5 or PKD2L1/PKD1L3. A taste-specific gene, preferably an ion channel, that is conductive or activated by sodium and is expressed in a TRPM5- and PKD2L1/PKD1L3-negative cell population is a probable candidate for screening efforts to identify the gene(s) that encode mammalian salty taste receptors, as well as specific cell types wherein these salty taste receptor genes are expressed such as in the oral cavity and urinary tract, and also for use in high throughput assays designed to identify enhancers of saltiness in humans.

In another aspect we describe an improvement of the afore-described methods in the subject application by a method wherein genes expressed in primate taste buds are identified and functionalized using a specific protocol which hinges on where they are expressed and their level of expression in the taste bud. The inventors have developed a rationale wherein they are able to assign gene expression patterns within the primate taste bud (and likely human taste specific genes given the conservation of structure between primate (macaque) and human genes) for all taste bud-specific genes. Specifically, using a comparison of gene expression between the top and bottom sections of the primate taste bud, the inventors have found that they are able to classify genes into one of several functional classes that include taste receptor genes. A subset of genes in this classification is likely to encode taste receptors that include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively (see FIG. 38 and examples infra).

In a related embodiment the invention relates to these categorized taste specific genes. As disclosed infra, gene expression data obtained was queried to obtain three sets of genes. (Appendices 1-3 of this patent application). The first and second sets are genes that are expressed at a higher level in the top or bottom of the primate taste bud relative to the bottom or top respectively. Top-specific genes are listed in Appendix 1 and bottom specific genes are listed in Appendix 2. The third set of genes is expressed at a higher level in the top of the primate taste bud relative to surrounding lingual epithelium samples. These additional taste bud-specific genes are listed in Appendix 3.

Also, in another embodiment this invention describes rationales which are useful for and which have successfully identified human genes which are taste specific and which are predicted to be involved in one or more of the afore-described taste bud related functions. Specifically, these methods include methods which identify human taste specific genes by quantitative polymerase chain reaction (PCR) using taste buds from human postmortem samples. It is an improvement over the primate gene assays since this method provides direct results concerning human taste specific genes which may be functionalized using the described methods.

Also, in another embodiment this invention identifies taste specific genes which should be involved in specific taste cell functions based on where the gene is expressed and levels of expression in the taste bud. These methods are able to classify genes into one of several functional classes that include taste receptor genes. It is an improvement since it provides accurate predictions regarding the taste specific genes which may be functionalized using the described methods.

In another embodiment the invention provides the use of the afore-mentioned improved rationale to demonstrate taste specific gene expression in humans (in addition to primate) and validates the specificity of expression by a quantitative method (qPCR or "TaqMan"). These methods identify the genes contained in the Table 8 infra which all encode multi-span transmembrane proteins, and are predicted to include yet unidentified taste receptors as well as other genes involved in taste modulation including the fat and salt receptor and genes involved in ancillary functions afore-mentioned.

Also, in yet another embodiment the invention identifies unique taste cell subsets which themselves can be used in screens for taste modulatory and therapeutic compounds as described infra, and also further exploits the elucidation of these unique taste cell populations as part of its strategies for identifying salty and other types of taste sensing cells such as fat, metallic, astringent, $CO_2$, et al.

In another embodiment the invention relates to the use of these identified taste specific genes in assays designed to identify therapeutics for the treatment of digestive system disorders such as digestive cancers, autoimmune and inflammatory digestive disorders such as ulcerative colitis, dyspepsia, Cohn's disease, celiac disease, inflammatory bowel syndrome, diverticulitis, et al., for regulating taste cell apoptosis or taste cell turnover, for inducing taste cell regeneration e.g. in geriatrics, cancer patients or individuals undergoing chemotherapy or radiation, for modulating the immune system of the oral cavity, for regulation of digestive mucous and fluids, enzymes or hormones such as GLP-1 (glucagon-like peptide 1), GIP (glucose-dependent insulinotrophic polypeptide), amylase, saliva, stomach acids, intestinal fluids, pepsin, secretin, and the like; for treatment of diabetes, eating disorders, cachexia, and other metabolic disorders involving these genes and/or isolated or enriched taste cells.

In another embodiment the invention relates to the use taste-associated genes and polypeptides in assays to ascertain their role in taste cell development and apoptosis, taste cell regeneration, modulation of transcription factors that modulate taste cell receptor expression, e.g., bitter taste receptors, taste receptor trafficking to and from the apical membrane/taste pore region, regulation of taste cell action potential firing frequency/membrane potential to control the intensity of and/or to modulate specific tastes, neurotransmitter release to afferent nerves that regulate taste intensity or specific tastes, and taste cell signaling to nerve fibers.

In another embodiment the invention relates to the use of these taste-associated genes and polypeptides in assays to ascertain their role in and to identify compounds that specifically bind to or which modulate the activity of these genes which compounds may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

In another embodiment the invention relates to the use of these taste-associated genes and polypeptides in assays to ascertain their role in and to identify compounds that may be used to treat or prevent pathological conditions involving gastrointestinal fluids, mucous, enzymes or hormones involved with digestion or hunger such as gastrin, secretin, pepsin, cholecystokinin, glucose-dependent insulinotrophic polypeptide (GIP), glucagon-like peptide 1 (GLP-1), amylase, ghrelin, leptin and the like. Also these compounds may enhance the production of saliva or other digestive mucous secretions and fluids. These compounds potentially may be used to suppress or induce hunger and/or to modulate digestion in subjects in need thereof.

In another embodiment the invention relates to the use of these taste-associated genes and polypeptides in assays to ascertain their role in and to the use of these genes, gene products, or cells that express same such as but not restricted to taste cells, e.g., gastrointestinal or oral cavity derived cells, in screening assays to identify compounds that bind to or modulate the activity or amount of these genes or gene products compounds which potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

In another embodiment the invention relates to the use of these taste-associated genes and polypeptides in assays to ascertain their role in and in screening assays to identify compounds that bind to or modulate the activity of these genes or gene products which compounds potentially may be used to modulate gastric reflux and diseases or conditions associated therewith such as gastroesophageal reflux disease, heartburn, Barrett's esophagus, and esophagitis.

In another embodiment the invention relates to the use of these taste-associated genes and polypeptides in assays to ascertain their role in and in screening assays to identify compounds that bind to or which modulate the activity of these genes or gene products and which therefore potentially may be used to treat or prevent cancers or malignancies associated with the digestive system such as by way of example cancers of the tongue, and oral cavity such as cancers of the taste buds and salivary gland cancers, stomach, esophagus, small or large intestine, anus or rectum, pancreas, gall bladder, liver, colorectal or colon.

In another embodiment the invention relates to the use of these taste-associated genes and polypeptides in assays to ascertain their role in and in screening assays to identify compounds that bind to or which modulate the activity of genes or gene products which compounds potentially my be use to treat or prevent appetite dysfunction and conditions associated therewith such as obesity, anorexia, bulimia, and cachexia associated therewith.

In another embodiment the invention relates to the use of these taste-associated genes and polypeptides for the isolation or enrichment of specific taste cell lineages or subtypes particularly taste cells derived e.g., from the tongue, oral cavity, or gastrointestinal system, which express one or several of these taste-cell associated genes.

In another embodiment the invention relates to the use of these taste-associated genes and polypeptides in assays to ascertain their role in and in assays to identify compounds that bind to or which modulate the activity of these genes or gene products which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the midabdominal tract or the lower abdominal tract.

In another embodiment the invention relates to the use of these taste-associated genes and polypeptides in assays to ascertain their role in and in screening assays to identify compounds that may be used to treat or prevent pathological conditions involving gastrointestinal hormones, enzymes or fluids involved with digestion or hunger such as saliva, digestive fluids, gastrin, secretin, cholecystokinin, glucose-dependent insulinotrophic polypeptide, glucagon-like peptide 1, amylase, or ghrelin, leptin and the like. These compounds potentially may be used to suppress or induce hunger or to modulate digestion in subjects in need thereof.

In another embodiment the invention relates to the use of these taste-associated genes and polypeptides in assays to ascertain their role in and in screening assays to identify compounds that bind to or modulate the activity of these genes or gene products which compounds potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

In another embodiment the invention relates to the use of these taste-associated genes and polypeptides in assays to ascertain their role in and in screening assays to identify compounds that bind to or modulate the activity of these genes which compounds that potentially may be used to modulate gastric reflux and diseases or conditions associated therewith such as gastroesophageal reflux disease, heartburn, Barrett's esophagus, and esophagitis.

In another embodiment the invention relates to the use of these taste-associated genes and polypeptides in assays to ascertain their role in and in screening assays to identify compounds that bind to or which modulate the activity of these genes and which compounds therefore potentially may be used to treat or prevent cancers or malignancies associated with the digestive system such as by way of example cancers of the salivary glands and taste buds, tongue, oral cavity, stomach, esophagus, small or large intestine, anus, pancreas, gall bladder, liver, colorectal, or colon.

In another embodiment the invention relates to the use of these taste-associated genes and polypeptides in assays to ascertain their role in and in screening assays for identifying compounds that regulate ion transport or ion flux, particularly sodium ions in order to identify therapeutic compounds that may be e.g., used to modulate blood pressure and fluid retention and conditions and diseases involving aberrant sodium absorption, excretion and transport.

In another embodiment the invention relates to the use of these taste-associated genes and polypeptides in assays to ascertain their role in and in screening assays for identifying compounds that regulate selective apoptosis of taste cells, modulation of transcription factors that control taste receptor expression, autocrine/paracrine modulation of taste cell development, taste bud lifetime, screens using genes that result in supertaster phenotypes, compounds that activate taste stem cells, compounds that affect trafficking of taste cell receptors e.g., from the apical membrane/taste pore region, compounds that affect taste intensity by modulating regulation of taste cell action via potential firing frequency/membrane potential, compounds that regulate neurotransmitter release to afferent nerves that control general or specific taste intensity, and autocrine/paracrine modulation of taste receptor function.

In another embodiment the invention relates to the use of these taste-associated genes and polypeptides in assays to ascertain their role in and in screening assays for identifying compounds that affect regeneration of taste cells or taste buds, e.g., in diseased or geriatric individuals or after injury or surgery, subjects undergoing chemotherapy or after injury, compounds for modulating drug-induced dysgeusia, ageusia, taste bud loss, dry mouth or xerostomia as for example found in Sjogren's syndrome, compounds that are useful in maintaining oral hygiene, treating or preventing halitosis, noxious oral microbia such as viruses and bacteria, and the like.

In another embodiment the invention relates to the use of these taste-associated genes and polypeptides in methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example, desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

In another embodiment the invention relates to the use of these taste-associated genes and polypeptides in assays to ascertain their role in and in screening assays to in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In another embodiment the invention relates to, as described in detail infra, a rationale and criteria for a candidate salty taste gene, preferably an ion channel which are:

a) Specific expression in primate (macaque) taste cells, particularly fungiform and/or circumvallate papilla derived taste cells, but also foliate and palate taste cells, and not lingual epithelial cells OR expression at higher levels in taste cells than lingual cells b) Expression in a taste cell by histological methods. Specifically, expression in a unique taste cell type that does not express the sweet, bitter, and umami cell marker TRPM5 or the sour cell marker PKD2L1/PKD1L3. This unique cell type could be a dedicated salt sensing cell.

c) Functional expression as a sodium channel or a sodium-activated receptor with basal, constitutive function (i.e. a fraction of the channel population is open and passing sodium at rest) in heterologous expression systems (such as *Xenopus* oocytes and mammalian cells) or primary neurons (such as dorsal toot ganglia neurons).

Genes fulfilling these criteria will be advanced into high-throughput screening efforts to identify compounds that enhance human salt perception. In addition the taste-specific genes reported herein, e.g., in Tables 1, 2, and 3 supra will be useful in the therapeutic screening assays as afore-mentioned.

Therefore in this patent application we describe screening assays to identify genes putatively involved in salty taste perception as well as taste and other taste-cell mediated activities in general.

In another embodiment the invention relates to a specific rationale that identifies taste-specific genes encoding membrane proteins expressed specifically in taste cells and not lingual cells at higher levels in taste cells than lingual epithelial cells using gene chip and/or PCR methodologies and use same as salt receptor targets in assays to identify salty taste modulators as well as compounds that affect other taste modalities and taste perception and taste-cell related biological and cellular functions and taste cell related phenotypes in general.

In another embodiment the invention relates to a rationale that determines which taste-specific genes are expressed in taste cells and especially in sweet, bitter, and/or umami cells (TRPM5 positive), sour cells (PKD2L1/PKD1L3 positive) or a unique cell type (TRPM5 negative). These unique cell types will likely comprise cells dedicated to salty taste perception.

In another embodiment the invention relates to the use of these taste-associated genes and polypeptides in assays to identify modulators (enhancers) of taste-specific ion channels or taste-specific genes as these compounds may modulate human salty taste perception.

In another embodiment the invention relates to a rationale wherein the inventors describe and are able to assign herein gene expression patterns within the primate taste bud for all taste bud-specific genes. Specifically, using a comparison of gene expression between the top and bottom sections of the primate taste bud, this invention classifies genes into one of several functional classes that include taste receptor genes. A subset of genes in this classification is likely to encode taste receptors that include those for salty taste and other yet to be defined taste specificities. (The rational for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively.)

In another embodiment the invention relates to novel methods for functional characterization of taste bud specific genes based on certain expression criteria. The invention provides three sets of genes which are contained in the Appendices 1-3 to this application identified using this rationale. The first and second sets are genes that are expressed at a higher level in the top or bottom of the primate taste bud relative to the bottom or top respectively. Top-specific genes are listed in Appendix 1 and bottom specific genes are listed in Appendix 2. (Accordingly, these lists contain top enriched and bottom enriched mRNAs). The third set of genes was identified as expressed at a higher level in the top of the primate taste bud relative to surrounding lingual epithelium. This set of taste bud-specific genes was obtained by the identification of taste bud-specific genes by comparing gene expression between whole (top+bottom) taste bud and lingual epithelium LCM samples. These additional taste bud-specific genes are listed in Appendix 3.

In another embodiment the invention relates to the discovery that taste-associated genes and polypeptides are expressed predominantly at the top of the taste buds. In contrast to prior knowledge, our new data clearly indicate that known taste receptor genes are expressed at a higher level in the top fraction of taste buds. It is reasonable to expect other yet to be identified taste receptor genes to be represented in the top-enriched gene list.

In another embodiment the invention relates to the functional characterization of particular "target" taste bud specific genes based on where they are expressed in the taste bud cells. The inventors have discovered based on gene expression profiles of the top and bottom fractions of the taste bud suggest that there are distinct functions for cells in each compartment. Functional classes of genes expressed in the top cells indicate these are mature sensory cells whereas those expressed in the bottom cells indicate these are immature progenitor cells associated with a basement membrane containing cellular environment. Examples of top-specific functional classes include taste receptors, taste-specific signal transduction components and receptors. Examples of bottom-specific functional classes include extracellular matrix components, growth factors and cell cycle-associated proteins.

In another embodiment the invention relates to a comprehensive listing of taste specific genes in the Tables and Appendices of this application. By fractionating the taste bud into top and bottom compartments the inventors have increased the sensitivity of mRNA detection in each compartment by a factor of approximately two and has identified virtually all taste bud specific genes.

In another embodiment the invention relates to a method for identifying genes involved in different functions of the taste bud based on measuring their expression in the top versus bottom of the taste bud.

In another embodiment the invention relates to the use of these taste-associated genes and polypeptides in assays to ascertain their role in and in screening assays to genes identified using the above method where genes involved in taste sensation would be over-expressed in the top part of the taste bud.

In another embodiment the invention relates to the set of genes identified using the above method where genes involved in modulation of taste sensation would be over-expressed in the top part of the taste bud.

In another embodiment the invention relates to a set of genes identified using the above method where genes involves in taste bud growth and development are over-expressed in the bottom part of the taste bud.

In another embodiment the invention relates to the genes identified using the above methods where the genes are involved in control of the lifespan of mature taste bud cells are over-expressed in the top part of the taste bud.

In another embodiment the invention relates to the genes identified using the above methods where genes involved in the maintenance, differentiation and proliferation of taste-bud committed stem cells will be over-expressed at the bottom of the taste bud.

In another embodiment the invention relates to the genes identified using the methods, where the genes represent biomarkers of taste-bud committed stem cells will be over-expressed at the bottom of the taste bud.

In another embodiment the invention relates to the genes identified using the above methods where genes representing biomarkers of different mature taste cell subsets will be over-expressed in the top of the taste bud.

In another embodiment the invention provides a set of genes identified as described above and the use thereof in order to purify, enrich, isolate or label specific taste cell subsets.

In another embodiment the invention provides electrophysiological assays that measure conductance of putative taste ion channels identified herein in the presence and absence of putative enhancers.

In another embodiment the invention identifies enhancers of the subject putative salty taste related ion channels and other taste affecting genes in an oocyte expression system.

In another embodiment the invention relates to the use of these taste-associated genes and polypeptides in patch clamping or two electrode voltage clamping assays using oocytes that express a putative salty taste receptor ion channel for identifying compounds that modulate the activity of this channel and therefore modulate salty taste. These and other objects of the present invention are met by one or more of the embodiments described below.

In another embodiment the invention relates to methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

In another embodiment the invention relates to the use of these taste-associated genes and polypeptides in assays to ascertain their role in and in screening assays to methods of using these genes and gene products as markers e.g., using probes specific thereto such as antibodies or oligonucleotides, i.e., that are specific to one or more of the subject taste specific genes provided herein in mapping regions of the tongue and oral cavity which are involved in specific taste and non-taste specific functions, mapping of cell comprised on specific regions of the gastrointestinal tract and associated organs such as the intestinal epithelium or urinary tract that express specific taste specific genes and which therefore are involved in one or more of the taste cell specific functions disclosed herein, and/or the use of the subject genes and markers specific thereto in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In another specific embodiment the present invention relates to assays using endogenous taste cells, e.g., gastrointestinal cells such as gastro-endocrine or gastro-epithelial cells or cells on the tongue or oral cavity, that screen for compounds which act as activators of TRPM5 or umami (T1R1/T1R3) and/or sweet (T1R2/T1R3) taste receptors, preferably those which modulate insulin metabolism and/or the release of a satiety peptide such as GLP-1 (glucagon-like peptide 1), which activators may be used in treating or preventing metabolic and eating disorders such as in the treatment of one of obesity, diabetes, weight management, fat metabolism, glucose metabolism, insulin metabolism, satiety or other conditions wherein the release of satiety peptides such as GLP-1 (glucagon-like peptide 1) is desirably controlled or reduced.

This invention in a more specific embodiment relates to specific taste specific genes identified infra, e.g., FAM26A, GPR113, MCTP1, TMEM16G, TMEM30B, TMEM44, and TUSC3 that are expressed in chemosensory or more specifically taste cells, e.g., human and primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the invention in another embodiment relates to enriched, isolated or purified taste cell subsets which expresses at least one of FAM26A, MCTP1, TMEM30B, and/or TUSC3 and which further express at least one T1R or T2R or TRPM5 gene and/or which express T1R2/T1R3 or T1R1/T1R3 or T1R3 only. Particularly, the invention provides isolated taste cells that express GPR113 and/or TMEM16G and which isolated taste cells which further expresses at least one of T1R2/T1R3, T1R1/T1R3, T1R3 only, a T2R gene and/or TRPM5.

Also, the invention in another embodiment relates specifically to a method of using a probe specific to a gene or gene product corresponding to the genes to identify and/or isolate and or enrich taste specific cells from non-taste cells in a sample. For example, these methods include a method herein the gene is FAM26A, MCTP1, TMEM30B, and/or TUSC3 and the identified, isolated or enriched cell further expresses T1R1/T1R3, T1R2/T1R3, T1R3 only, a T2R, and/or TRPM5. Also, the invention includes methods wherein the gene is GPR113 and/or TMEM16G and the isolated, identified or enriched cell further expresses at least one of T1R2/T1R3, T1R1/T1R3, T1R3 only, a T2R or TRPM5 and/or wherein said taste cells are human or macaque taste cells. and wherein said isolated taste cells do not express PKD2L1, PKD1L3, or TRPM5 and/or wherein said cells do not express a T1R or a T2R and/or said taste cells express transducin or gustducin.

Also, the invention relates to the use of TUSC3, ASCL1, FAM26A, FAM26C, IKBKAP, LOC285965, SCNN1D, SLC4A11, SLC26A7, and TMEM30B as a biomarker of specific taste cells and the isolated cells which express same as all of these genes are expressed by unique taste cell subsets comprised in primate taste buds and therefore can be used as biomarkers to isolate, enrich, mark or ablate these cells and thereby determine the taste related function of these taste bud cells.

Also, the invention in another embodiment relates to the use of these identified taste specific genes or an ortholog or variant thereof encoding a protein at least 90% identical thereto in a cell isolation, purification, enrichment, or marking technique that isolates, purifies, enriches and/or marks at least one desired taste cell subtype or lineage contained in a mixed cell population or cell suspension comprising a desired taste cell type or lineage based on the expression or absence of expression of at least one gene contained in Tables 1-8 or an ortholog thereof, or a gene encoding a protein that is at least 90% identical to said gene or an ortholog thereof. Particularly, the invention includes methods wherein the taste cell subtype or taste cell lineage is isolated, purified, enriched, or marked by a method that includes the use of a fluorescence activated cell sorter (FACS) or by the use of labeled magnetic beads and wherein the cell suspension containing the cells may be produced by enzymatic digestion and/or tissue disaggregation of tissues containing taste cells. and methods wherein the desired taste cell subtype or taste cell lineage is isolated, purified, enriched or marked by a method that includes a negative cell selection technique that eliminates at least one non-target taste cell subtype or lineage based on the expression or absence of expression of at least one other taste cell specific gene identified herein. These methods may e.g., use cytotoxic antibodies to specifically kill at least one non-target cell type or lineage. These isolation methods may e.g., result in isolates containing sweet taste cells, umami taste cells, sour, salty, or fat taste cell subtype or lineages, taste stem cells taste cell neurons, or taste immune cells.

Also, the invention in another embodiment relates to methods of using a cell isolated, purified, enriched or marked according to these methods in screens for taste modulatory compounds, or in a method that screens for compounds that induce the differentiation of said enriched, isolated, purified or marked taste stem cells into one or more taste cell lineages or subtypes or taste buds or in a method wherein said taste cell lineages or subtypes are identified based on the expression or absence of expression of at least one the identified taste specific gene identified above. These cells may be used to screen for compounds that modulate at least one of sweet, umami, bitter, sour, fat, salty or metallic taste wherein the gene is GPR113 or TMEM16G or TMEM44 or to screen for compounds that modulate taste cell differentiation or turnover.

Also, the invention in another embodiment relates to these cells or the gene or gene product encoded thereby in assays that screen for compounds that modulate or treat the diseases and conditions involving taste cells previously identified. This in particular relates to GPR113 or the corresponding gene product or cells which express same or an ortholog or variant thereof in assays to identify compounds that modulate taste cell differentiation or taste cell turnover.

Also, the invention in another embodiment relates to isolated immature taste cells and/or taste stem cells that express TMEM44 or GPR113 and the use in an assay for identifying taste modulators, in particular which screens for sweet, umami, bitter, fat, salty, metallic and/or astringent taste modulators. Also, the invention relates to a recombinant cell engineered to co-express T1R3 and GPR113 and optionally TRPM5. Also, the invention embraces an assay for identifying compounds which modulate taste cell differentiation and/or maturation based on whether said compound specifically binds and/or modulates the activity of GPR113.

Also, the invention in another embodiment relates to the use of these cells in assays that screen for compounds that modulate the differentiation and/or maturation of sweet or umami taste cells. Also, the invention provides a method of using GPR113 as a marker to identify, enrich and/or isolate or ablate unique taste cells which express GPR113, TRPM5 and T1R3 wherein said taste cells do not express T1R1, T1R2 and/or a T2R or are immature, e.g., by FACS or magnetic bead cell separation or by use of cytotoxins.

In addition the invention in another embodiment relates to the discovery that TMEM44 and MFSD4 are expressed in unique taste cell type and that these gene are expressed in sensory taste cells that are not sweet, bitter, umami, or sour cells which further expresses another taste-specific gene disclosed herein. Also, the present invention relates to the discovery that expression of TMEM44 and MFSD4 are markers for a unique taste cell type that may correspond to a fat receptor. Further, the invention relates to the discovery that ATP8A1, FAM26B and SLC4A11 are expressed in many TRPM5 cells, suggesting that these genes are expressed in sweet, umami, and bitter taste cells, since TRPM5 is a marker of sweet, bitter, and umami taste cells.

This invention in a more specific embodiment identifies genes infra, e.g., FAM26A, GPR113, MCTP1, TMEM16G, TMEM30B, TMEM44, and TUSC3 that are expressed in chemosensory or more specifically taste cells, e.g., human or primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the present invention in another embodiment relates to the discovery that MFSD4 is expressed in cells that do not express TRPM5 (bitter, sweet, umami) indicating that the expression of this gene is a marker for a unique taste cell type e.g., a salt, fat, or another taste modality, and, furthermore, that this gene may encode the primary salt or fat receptor.

Also, the invention in another embodiment reveals that the expression pattern of MFSD4 is very similar to TMEM44, indicating that both genes are expressed in the same taste cell type and may be comprised in a heteromeric taste receptor.

Also, the invention in another embodiment relates to the discovery that ATP8A1, FAM26B, and SLC4A11 can be used as markers for sweet, bitter, and umami taste cells or cells expressing TRPM5.

Also, the invention in another embodiment relates to the discovery that ATP8A1, FAM26B, and SLC4A11 and compounds that enhance or inhibit these gene products can selectively modulate taste cell function and responses to tastants including sweet, bitter, and umami.

Also, the present invention in another embodiment relates to the discovery that MFSD4 can be used as a marker for a unique, novel taste cell type that does not correspond to sweet, bitter, and umami taste cells. Moreover, the invention relates to the discovery that MFSD4 and compounds that enhance or inhibit this gene product can selectively modulate taste cell function and responses to tastants other than sweet, bitter, and umami, which include salt, fat, and other tastants. Based on the foregoing, the invention relates to the discovery that MFSD4 may correspond to the salt receptor or fat receptor. Also, MFSD4 may be a marker of immature taste cells or developing taste cells.

Related thereto, in another embodiment the present invention also relates to the discovery that MFSD4 and compounds that enhance or inhibit this gene product can selectively modulate taste cell development and/or differentiation of specific taste cell types (i.e. bitter taste cells).

Also, the present invention in another embodiment relates to the discovery that MFSD4 and TMEM44 are expressed in the same unique taste cell type. Also, the present invention relates to the discovery that MFSD4 and TMEM44 may form a complex (heterodimer) to generate a taste receptor for a different taste than sweet, umami, sour or bitter, likely salt or fat. and may be used in screening assays.

Also, in another embodiment the present invention relates to the discovery that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells. and may regulate taste perception or other taste cell function. Moreover, the present invention reveals that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells.

In another embodiment the invention relates to the discovery that ASCL1 also known as MASH is a transcription factor that defines and is a useful marker of sour taste cells as it is selectively expressed in sour taste cells that express PKD1L3 but not in other taste cell types, i.e., it is not expressed in sweet, bitter, or umami cells which express TRPM5. Therefore, the ASCL1 transcription factor may bind to promoter elements in genes involved in sour taste perception. Thus, the invention provides the use thereof in screening the genome for ASCL1 motifs to identify genes in sour cells, including sour receptor genes such as PKD2L1, PKD1L3, or additional genes that may form a complex with PKD2L1/PKD1L3 to generate a sour receptor.

In another embodiment the invention establishes ASCL1 to be a marker of type III taste cells. Type III taste are defined by morphological criteria which include: staining with an intermediate density by electron microscopy and making synaptic contacts with nerve fibers. Thus, the invention reveals that type III taste cells, a cell type previously defined by morphological criteria, correspond to sour taste receptor cells defined by gene expression criteria.

In another embodiment the invention relates to the discovery that other taste receptor cells for sweet, bitter, umami, and salt are likely to express specific transcription factors related thereto that define those cell types. Therefore, the invention provides assays detecting the expression of all transcription factors in the genome in taste cells by PCR and/or histology to determine which taste cell types express which transcription factors.

In another embodiment the invention relaters to the discovery that the ASCL1 transcription factor binds to promoter elements in genes involved in sour taste perception. Thus, the invention encompasses such sequences found in the genome that comprise ASCL1 motifs and the use thereof to identify genes in sour cells, including sour receptor genes such as PKD2L1, PKD1L3, or additional genes that may form a complex with PKD2L1/PKD1L3 to generate a sour receptor.

In another embodiment the invention relates to the discovery that ASCL1 (aka MASH1) is a marker useful for identifying, purifying, and/or isolating or ablating sour taste cells in a mixed cell sample, e.g., derived from the tongue or gastrointestinal or urinary tract.

In a related embodiment the invention provides the use of ASCL1 as a marker of Type III taste cells that correspond to sour taste receptor cells In another embodiment the invention establishes that because ASCL1 defines the sour taste cell lineage it may also control sour taste cell development.

In another embodiment the invention provides the use of ASCL1 transcription factor DNA binding sequences as a probe to identify sour cell genes and sour taste receptor genes that possess related structure such as ASCL1 motifs.

Also, in another embodiment the invention provides the use of these and other taste cell specific transcription factors to define, mark, and/or label taste cell types because each taste cell will express one or more transcription factors that define that taste modality.

The invention further provides in another embodiment the use of these transcription factors that define taste modalities in cell ablation studies to specifically eliminate a specific taste cell or taste modality.

Also, in another embodiment the invention provides ASCL1 or other taste transcriptional gene knockouts which result in transgenic animals possessing altered taste perception and other phenotypic effects, e.g., elimination of sour taste perception or altered urinary or digestive function since ASCL1 may be involved in the metabolic response to pH changes such as excess acidity.

Also, t in another embodiment he invention provides the use of these transcription factors that define new taste cell types which can be used in cell ablation studies and in vitro assays to determine what taste modality is lacking as a result of this ablation (i.e. what taste modality is eliminated).

In another embodiment this invention identifies taste-specific genes NALCN, TRPML3 and NKAIN3 which when expressed separately or in combination are predicted to comprise a taste receptor, putatively a salty taste receptor, as these 3 genes are expressed in primate taste cells, are enriched in the top fraction of taste bud cells, and are known to encode sodium channels. In addition the invention relates to the discovery that NALCN is expressed in a unique taste cell subset and is predicted to encode a taste related function. (As noted, TRPML3 has been shown to encode a salty taste receptor).

In a related embodiment the present invention relates to the use of these taste specific ion channel genes as markets which can be used to enrich, identify or isolate salt receptor expressing cells.

In another embodiment the invention relates to assays that identify compounds that modulate the function of the use of NALCN, TRPML3 and/or NKAIN3 and the use of the identified compounds to modulate salty taste perception.

In another embodiment the invention relates to other taste specific genes, i.e., KIT, IKBKAP, LOC285965, and SV2B that are expressed in specific subsets of taste specific cells.

In another embodiment, this invention relates to the discovery that KIT is specifically expressed in TRPM5 and T1R3 taste cells and T1R1 taste cells indicating that the gene can be used as a marker to identify umami taste cells in a mixed cell population and/or may modulate the expression and activity of the umami taste receptor.

In another embodiment, this invention relates to the discovery that IKBKAP and SV2B are specifically expressed in PKD1L3 sour taste receptor cells indicating that these genes can be used as markers to identify sour taste cells and/or modulate taste, especially sour taste.

Also, in another embodiment this invention relates to the discovery that LOC285965 is specifically expressed in TRPM5 and T1R3 taste cell subsets and T1R3 cells lacking T1R1 and T1R2 suggesting that this gene can be used as a marker of these taste cell subsets and/or may associate with or modulate the T1R3 gene and/or encode a taste receptor distant from T1R1/T1R3 or T1R2/T1R3.

Further, in another embodiment the invention relates to the discovery that SV2B is specifically expressed in PKD1L3 cells indicating that this gene can be used as a marker of these specific cell subsets and/or may encode a polypeptide that modulates the activity or expression of the PKD1L3 sour taste receptor.

In addition, in another embodiment the invention relates to the discovery that MFSD4 is expressed in sensory taste cells that are not sweet, bitter, umami, or sour cells and that this gene is expressed in a similar taste cell population as TMEM44.

In another embodiment, the invention relates to the use of compounds that enhance or inhibit IKBKAP and SV2B gene products to selectively modulate taste cell function and responses to sour tastants as well as other functions of the PKD1L3 taste cell population.

In another embodiment, since IKBKAP is mutated in the human disease familial dysautonomia, where taste buds ate absent or atrophic and individuals exhibit deficiencies in detection of sweet, bitter, sour, and salty tastants (hypogeusia) the invention relates to the discovery that IKBKAP expression in PKD1L3 cells may be important for taste cell development and/or maintenance.

In another embodiment since Botulinum neurotoxin (BoTox) enters neuronal-type cells by interacting with SV2B; the invention in another embodiment relates to the use of BoTox and derivatives to selectively modulate sour taste as well as other functions of the PKD1L3 taste cell population.

In another embodiment since KIT is expressed in umami taste cells the invention relates to the use thereof as a marker of this taste cell type.

In another embodiment the invention relates to the use of KIT and compounds that enhance or inhibit this gene product to selectively modulate taste cell function and responses to umami tastants.

In another embodiment the invention relates to the use of Gleevec (Imatinib), an inhibitor of the KIT tyrosine kinase activity, and other KIT tyrosine kinase inhibitors for selectively inhibiting umami taste.

In another embodiment the invention relates to the discovery that individuals with gain of function mutations in KIT, for example in gastrointestinal stromal tumors (GIST), may have altered umami taste perception.

In another embodiment since LOC285965 is expressed in T1R3 only taste cells similar to GPR113 the invention relates to the use as a marker for a unique, novel taste cell type (T1R3 only cells) that does not correspond to sweet, bitter, and umami taste cells.

In another embodiment the invention relates to the discovery that LOC285965 may correspond to the salt receptor or fat receptor or a receptor for astringency or metallic taste by itself or in combination with GPR113, which is also expressed in T1R3 only cells.

Also, the invention relates to the discovery that TUSC3, ASCL1, FAM26A, FAM26C, IKBKAP, LOC285965, SCNN1D, SLC4A11, SLC26A7, and TMEM30B may be used as biomarkers of specific taste cells and the isolated cells which express same as all of these genes are expressed by unique taste cell subsets comprised in primate taste buds and therefore can be used as biomarkers to isolate, enrich, mark or ablate these cells and thereby determine the taste related function of these taste bud cells.

In another embodiment the invention relates to the discovery that LOC285965 may be a coreceptor with T1R3 for specific sweet or umami tastants or other novel tastants such as astringent and metallic tastants.

In another aspect the invention relates to the discovery that compounds that enhance or inhibit LOC285965 can selectively modulate taste function and responses to tastants.

In another embodiment the invention relates to the discovery that LOC285965 may correspond to a marker of immature taste cells that are differentiating into sweet or umami cells.

In another embodiment the invention relates to the discovery that LOC285965 and compounds that enhance or inhibit this gene product can selectively modulate taste cell development and/or differentiation of specific taste cell types (i.e. sweet or umami taste cells).

Moreover, in a related embodiment this invention identifies a novel set of genes, i.e., FAM26A, GPR113, MCTP1, TMEM16G, TMEM30B, TMEM44, TUSC3, ATP8A1, FAM26B, SLC4A11, ASCL1 and MFSD4 and the aforementioned genes that are expressed in chemosensory or more specifically taste cells, e.g., primate fungiform or circumvallate macaque taste cells, and taste (e.g., fungiform, circumvallate, foliate, or palate) cells derived from other mammals such as humans and non-human primates. In some embodiments these genes are expressed in novel taste cells that do not express TRPM5 or PKD2L1/PKD1L3. These genes are referred to herein as "taste-specific" genes because they are strongly expressed in taste cells, preferably a previously unidentified taste cell type that may be involved in fat or salty taste perception. These taste-specific genes include genes which are directly or indirectly involved in taste detection and modulation, e.g., salty, umami, sweet, sour, fatty, metallic, or bitter taste transduction as well as including genes which are involved in biological functions not directly related to taste detection such as the modulation of digestion, taste cell turn-over, regulation of the immune system, particularly of the oral cavity, and the regulation of metabolism e.g., carbohydrate metabolism, diabetes, obesity, cachexia, detection of food during digestion, et al.

In another embodiment the invention relates to the discovery that taste cells in the bottom half of the taste bud are immature.

In another embodiment the invention reveals that taste cells in the top half of the taste bud are mature and express genes for sweet, bitter, umami, and sour taste receptors.

In another embodiment the invention reveals SHH to be a marker of immature and developing taste cells at the bottom of the taste bud.

In another embodiment the invention reveals TMEM44 and MFSD4 to be markers of immature and developing taste cells at the bottom of the taste bud.

In another embodiment the invention reveals a subpopulation of TMEM44 cells may be mature salty taste cells.

In another embodiment the invention suggests that a salt receptor will be expressed in the top taste bud cells, since all other known taste receptors are expressed in the top taste bud cells.

In a related embodiment the invention suggests that a salty taste cell will be present in the top half of the taste bud since all other known professional, mature taste cells are expressed in the top of the taste bud.

In a specific embodiment this invention reveals TMEM44 cells, which comprise about 40% of the taste bud cell population and are located towards the bottom of the taste bud, and have identified that other genes are expressed by these cells or in the bottom of the taste bud including MFSD4 and Sonic Hedgehog (SHH) (a cytokine involved in immature cell differentiation). Based thereon, this invention predicts that cells expressing TMEM44 represent an immature taste cell population that includes stem cells that replenish the taste bud cells every 2-3 weeks in the human and while immature, they may comprise a subset of mature cells that may be responsible for salt sensation.

Also in a specific embodiment this invention reveals that GPR113 cells which represent about 10% of the taste bud cell population, are distinct from sweet, bitter, and umami taste cells, are located in the top of the taste bud, and express T1R3 and TRPM5 but not the G protein alpha subunit gustducin (GNAT3), suggesting that these cells represent a novel taste cell population that detects a novel taste modality such as fat.

Also in a specific embodiment this invention reveals the existence of another cell subset which express TRPM5 and T1R3 and which include sweet cells (which also express T1R2) as well as umami cells (which also express T1R1).

Also in a specific embodiment this invention reveals that bitter (T2R expressing taste cells) express TRPM5 but not T1R3.

Also in a specific embodiment this invention reveals that sweet, bitter, and umami cells express GNAT3 indicating that this gene can be used as a marker of these types of taste cells.

Also in a specific embodiment this invention reveals that PKD2L1 and PKD1L3 cells, (which cells have been previously described to be responsible for sour taste sensation) comprise about 10% of the taste bud cell population located in the top of the taste bud, and are heterogeneous, i.e. there are distinct PKD2L1 and PKD1L3 'single positive' cell populations in addition to a PKD2L1 and PKD1L3 'double positive' cell population suggesting that one of these subsets may represent a salt sensing cell.

Also in a specific embodiment this invention reveals the existence of another subset of taste cells (~8% of the taste bud cell population) that does not express any of the following markers: TMEM44, TRPM5, PKD2L1 or PKD1L3 which in addition or alternatively may represent a salt sensing cells.

More specifically, in a specific embodiment this invention provides a TMEM44 cell ablated non-human animal, e.g., a rodent.

Also, in a specific embodiment the invention provides taste cell suspensions consisting essentially of TMEM44 expressing taste cells.

Also, in a specific embodiment this invention provides a method of using the TMEM44 taste cell ablated animal (rodent) or the TMEM cell suspension for identifying the function of TMEM expressing cells in a taste modality, preferably salt or fat.

Also, in a specific embodiment the invention provides a GPR113 taste cell ablated animal, e.g., a rodent.

Also in a specific embodiment the invention provides taste cell suspensions consisting essentially of GPR113 expressing taste cells.

Also in a specific embodiment the invention provides a method of using the GPR113 taste cell ablated rodent or the GPR113 cell suspension for identifying the function of GPR113 expressing cells in a taste modality, preferably salt or fat.

Also, in a specific embodiment, the invention provides for PKD2L1 and/or PKD1L3 taste cell ablated animals, e.g., rodents.

Also, in a specific embodiment, the invention provides for taste cell suspensions consisting essentially of PKD2L1 and/or PKD1L3 expressing cells.

Also in a specific embodiment the invention reveals that the cells in the bottom half of taste buds are immature whereas taste cells in the top half of the taste bud are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to that of SHH. Thus, TMEM44 cells (which also express MFSD4) are immature and comprise, in part, developing taste cells. Supporting this finding, a small fraction of taste cells expressing TMEM44 also express either TRPM5 (a marker of mature sweet, bitter, and umami cells) or PKD1L3 (a marker of mature sour cells). Cells expressing both TMEM44 and TRPM5 (or PKD1L3) are, therefore, maturing into professional taste cells. By contrast, cells in the top half of the taste bud are mature taste cells, do not express SHH, and express taste receptor genes for the sweet, bitter, umami, and sour taste receptors. Since all mature, professional taste cells and taste receptors are localized to the top half of the taste bud, the salty taste cell and the salty taste receptor should also be present in the top half of the taste bud. Therefore, the invention demonstrates that taste cells in the bottom half of the taste bud are immature.

Also in a specific embodiment the invention demonstrates that taste cells in the top half of the taste bud are mature and express genes for sweet, bitter, umami, and sour taste receptors.

Also in a specific embodiment the invention demonstrates TMEM44 and MFSD4 are markers of immature and developing taste cells at the bottom of the taste bud.

Also the invention reveals a subpopulation of TMEM44 cells may comprise a mature salty taste cell.

SUMMARY OF THE INVENTION

This invention relates in general to novel and improved rationales for identifying (systematically and comprehensively) sets of primate genes which should encompass virtually all primate and human taste specific genes. Thereby, the invention provides a library of genes which will contain all primate and human taste receptors as well as taste specific genes involved in ancillary functions such as those relating to digestion, excretion and sodium ion related functions. These genes and gene products and cells expressing same are useful in screening assays for identifying taste modulators and therapeutics. A further advantage of the invention is that the invention provides methods for categorizing these genes into specific categories which should correlate to function thereby facilitating the number of genes to be functionalized by methods also provided in this application. More specifically, the invention has identified a subgenus of human and primate genes which will contain all taste receptors and taste modulators including those not yet identified. For example, this subgenus contained the salty taste receptor and in all likelihood other taste receptors involved in fat, metallic, $CO_2$, astringent and the like.

Therefore, this invention in its more broad embodiments identifies genes that are expressed in chemosensory, e.g., human and non-human primate (macaque) fungiform and/or circumvallate papilla taste cells, and taste (e.g., fungiform, circumvallate, foliate, or palate) cells derived from other mammals such as humans and non-human primates ("taste specific"). These genes include genes which are directly or indirectly involved in taste detection and taste modulation, e.g., salty, umami, sweet, sour, fatty, metallic, or bitter taste transduction as well as functions not directly related to taste detection and taste modulation such as genes that are involved in the modulation of digestion and the production and composition of digestive fluids, mucous, enzymes and hormones such as saliva, stomach and intestinal fluids, GLP-1 (glucagon-like peptide 1), GIP (glucose-dependent insulinotrophic polypeptide), secretin, pepsin, and the like; genes that are involved in regulation of blood pressure and fluid retention, genes that are involved in taste receptor trafficking, taste cell turnover and taste cell regeneration, genes that are involved in the regulation of the immune system of the oral cavity and gastrointestinal system, genes that are involved in the prevention or onset of gastrointestinal related diseases such as cancers, inflammatory and autoimmune diseases affecting the oral cavity and digestive system, genes that are involved in the regulation of metabolism e.g., carbohydrate metabolism, obesity, eating disorders, genes that are involved in the detection of food during digestion, et al.

Relating to the foregoing the present invention provides genes that are expressed in human and non-human primate (macaque) chemosensory, e.g., primate (macaque) circumvallate and/or fungiform papilla taste cells that are not expressed or are expressed at significantly lower levels in lingual epithelial cells that are useful in screening assays, preferably high throughput screening assays, for identifying compounds that directly or indirectly modulate different taste modalities, e.g., salty, sweet, umami, bitter, sour, fatty, or metallic.

Further relating to the foregoing the present invention provides genes that are useful in screening assays, preferably high throughput screening assays for identifying compounds that are useful as therapeutics in the treatment of digestive system disorders, for modulating taste cell apoptosis or taste cell turnover, for inducing taste cell regeneration, for effecting the regulation of immunity in the oral cavity or digestive system, and the treatment of diabetes, obesity, eating disorders, and other metabolic disorders.

Also relating to the foregoing the invention provides a novel set of genes which are useful in the identification and/or isolation and/or enrichment of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as by aiding in food detection, the secretion of hormones or enzymes involved in hunger and digestion, and the like.

Further, the invention relates to the use of the isolated chemosensory or taste cells in screening assays for identifying compounds that modulate taste, as well as in the identification of therapeutics for modulating the immune system regulation of the oral cavity, taste cell apoptosis turnover, taste cell regeneration, regulation of hormones or enzymes or fluids and mucous involved in digestion and other taste cell functions, treatment of digestive system disorders, treatment of diabetes, obesity, eating disorders, or other metabolic disorders, and the like.

This invention more specifically relates to novel rationale, methods, and assays including electrophysiological assays that identify and characterize novel taste-specific genes, including those that function as salty taste receptors.

It was hypothesized by the inventors (in part based on properties of known taste receptors) that human salty taste may be mediated, in part, by a sodium or other ion channels as well as transporters and GPCRs expressed specifically in taste-cells. Based on this assumption and other criteria provided infra, the invention provides methods for identifying taste-specific genes, including genes that may regulate salty taste, as well as other taste modalities taste cell mediated functions and phenotypes using gene chip and PCR methodologies. The compounds identified and their derivatives that modulate the activity of these target genes potentially can be used as modulators of human salty taste in foods, beverages and medicinals for human consumption. Also, such compounds and their derivatives potentially may be used to treat diseases involving aberrant ion channel function. Further the compounds identified using the genes identified herein and cells which express same are useful in therapeutic screening assays as discussed herein for identifying potential therapeutics that modulate other taste-cell related functions and phenotypes.

In one mode this invention identifies genes expressed in primate taste cells and use of these genes for screening for taste modulators and for identifying and isolating specific taste cell lineages and subtypes. These genes are identified based on their selective expression in primate fungiform papilla taste cells found at the front of the tongue and circumvallate papilla taste cells found at the back of the tongue using gene-chips microarrays from taste receptor cells as compared to non-taste lingual epithelial cells isolated by laser capture microdissection (LCM). Since salt perception is most prevalent at the front of the tongue, a salt receptor gene is likely contained within this set of identified genes.

In another mode, this invention provides a method for identifying a gene encoding a polypeptide involved in taste, preferably salty taste in a mammal. One embodiment of this method comprises the steps of (i) identifying a set of genes including genes which are expressed in macaque taste (fungiform and circumvallate papilla taste cells) but which are not expressed in lingual epithelial cells and/or genes which are expressed in taste cells at substantially higher levels than in lingual cells; (ii) identifying a subset of genes within the set of genes identified in (i) which are selected based on criteria which suggest that they are likely salt receptor candidates, i.e., putative ion channels and/or encode multidomain transmembrane proteins. These genes are then examined to determine whether these genes are expressed or not expressed in taste cells which express umami, sweet or bitter taste receptors (T1Rs or T2Rs) or sour taste receptors (PKD2L1/PKD1L3); and (iii) functionally expressing one or more genes in the subset identified according to (ii) and determining which of these genes function as a sodium responsive ion channel or sodium responsive receptor or transporter and thereby identifying this gene or genes as a putative gene that modulates salty taste. Typically, the taste tissues for this method are derived from human, primate, or rodent sources. In one preferred embodiment of the method, the genes in step (iii) function as sodium responsive ion channels, and more preferably, when the genes are expressed, a fraction of the channel population is open and passing sodium at rest.

In a preferred embodiment, step (i) comprises the use of laser capture microdissection (LCM) to dissect and purify taste tissues from non-taste tissues. In one mode of this embodiment, step (i) comprises RNA amplification of genes from taste cells and lingual cells and the amplified genes are screened against a gene chip containing a sample of genes specific to the particular mammal from which the taste and lingual tissues are obtained, and preferably, the gene chips include a set of annotated human genes. In an alternative mode of this embodiment, step (i) comprises high throughput PCR using primers for each ion channel in a mammalian genome.

In another preferred embodiment, step (ii) is effected by in situ hybridization using antisense RNA probes specific for the set of genes identified in step (i) to determine level of expression in taste versus lingual cells. In an alternative preferred embodiment, step (ii) is effected by use of immunochemical detection using a labeled antibody specific to the protein encoded by gene or genes identified in step (i).

In another embodiment of the method for identifying a gene encoding a polypeptide involved in salty taste perception in a mammal, the method of this invention comprises the steps of (i) identifying a set of macaque genes including genes which are expressed in taste cells but which are not expressed in lingual cells and/or genes which are expressed in taste cells at substantially higher levels than in macaque lingual cells; (ii) identifying a subset of genes within the set of genes identified in (i) which are not expressed in taste cells which express umami, sweet or bitter taste receptors (T1Rs or T2Rs) or sour taste receptors (PKD2L1/PKD1L3); and (iii) determining, in a primary neuron which expresses one or more genes in the subset identified according to (ii), which of said genes functions as a sodium responsive ion channel or sodium responsive receptor or transporter and thereby identifying this gene or genes as a putative gene that modulates salty taste. In one mode of this embodiment, step (iii) comprises contacting the neuron with an antibody which specifically binds the gene and inhibits its function.

Genes identified according to either of the methods described above may be characteristic of cells which do not express TRPM5 and PKD2L1/PKD1L3. In another mode, this invention provides a method to assist in selecting cells which do not express TRPM5 and PKD2L1/PKD1L3 by determining whether a cell expresses a gene identified according to the methods above. Preferably, the gene used in the method of this paragraph is one of the genes listed in Tables 1-3, listing taste-specific genes encoding transmembrane proteins in taste cells. Efforts were focused on transmembrane genes since all known taste receptor genes for sweet, bitter, umami, and sour taste encode transmembrane proteins.

In another aspect this application provides an improvement of the afore-described methods in which genes expressed in primate taste buds are identified and functionalized using the disclosed methods. The inventors have developed a rationale wherein they are able to assign gene expression patterns within the primate taste bud for all taste bud-specific genes. Specifically, using a comparison of gene expression between the top and bottom sections of the primate taste bud, the inventors have found that they are able to classify genes into one of several functional classes that include taste receptor genes. A subset of genes in this classification is likely to encode taste receptors that include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38.

In order to get more information on gene expression in both the top and bottom fractions of the taste bud the inventors isolate the corresponding fractions of primate taste buds using laser capture microdissection (LCM). This technique is described supra and briefly involves excision of specific groups of cells from tissue sections based on morphological distinctions. In the case of taste buds, the inventors are able to readily identify these structures in sections of primate tongue. As exemplified in the supporting experimental example infra, tissue collection was limited to taste buds in circumvallate papillae and then to only taste buds that were sectioned sagittally and at the taste pore. The inventors reasoned that only this type of section would reliably isolate top and bottom fractions. An example of sections used in sample collection is shown in FIG. 39.

The gene expression data obtained was queried to obtain three sets of genes. The first and second sets are genes that are expressed at a higher level in the top or bottom of the primate taste bud relative to the bottom or top respectively. Top-specific genes are listed in Appendix 1 and bottom specific genes are listed in Appendix 2. Accordingly, these lists contain top enriched and bottom enriched mRNAs. The third set of genes was identified as expressed at a higher level in the top of the primate taste bud relative to surrounding lingual epithelium. This set of taste bud-specific genes applications describing the identification of taste bud-specific genes by comparing gene expression between whole (top+bottom) taste bud and lingual epithelium LCM samples. These additional taste bud-specific genes are listed in Appendix 3.

This methodology achieves various advantages and makes certain discoveries including the following:

First, the inventors have found that taste receptor genes are expressed predominantly at the top of the taste bud. In contrast to prior knowledge, the data obtained using these methods clearly indicate that known taste receptor genes are expressed at a higher level in the top fraction of taste buds. It is reasonable to expect yet to be identified taste receptor genes are represented in the genes which are enriched at the top of the taste bud.

Second, the inventive top-versus-bottom gene classification methods allow for the functional classification of genes based on their expression in the cells in the top versus the bottom of the taste bud. Gene expression profiles at the top and bottom fractions of the taste bud suggest distinct functions for cell in each compartment. Functional classes of genes expressed in the top cells indicate that these are mature sensory cells whereas those expressed in the bottom cells indicate that these are immature progenitor cells associated with a basement membrane containing cellular environment. Examples of top-specific functional clauses include taste receptors, taste-specific signal transduction components and receptors. Examples of bottom-specific functional classes include matrix components, growth factors, and cell-cycle-associated proteins.

Third, this methodology allows for the identification of additional taste bud-specific genes. It has been found that by fractionating the taste bud into top and bottom compartments that the inventors have increased the sensitivity of mRNA detection in each compartment by a factor of about 2. This facilitates the identification of other taste specific genes not identified by the prior-described methods. These genes are contained in the Appendices to this patent application.

Therefore, these methods can be used to identify genes involved in different functions of the taste bud based on measuring their expression in the top versus bottom of the taste bud, e.g., where genes over-expressed in the top part of the taste bud. are predicted to be involved in one or more taste sensation, modulation of taste sensation, control of the lifespan of mature taste bud cells or they may be used as biomarkers of different mature taste cell subsets.

By contrast using the inventive rationale genes over-expressed at the bottom of the taste bud are predicted e.g., to be involved in one or more of the maintenance, differentiation and proliferation of taste-bud committed stem cells; or they will represent biomarkers of taste-bud committed stem cells.

In addition, genes expressed specifically in the top or bottom can be using to purify these functionally distinct taste bud cell subsets.

Also, in another aspect this invention describes rationales which are useful and have successfully identified human genes which are taste specific and which are predicted to be involved in one or more of the afore-described taste bud related functions. Specifically, these methods identify human taste specific genes by quantitative polymerase chain reaction (PCR). This also is an improvement of the afore-described methods for identifying taste specific genes, i.e., taste genes expressed in primate taste buds. and more optimally the previous described methods wherein the inventors assign gene expression patterns within the primate taste bud for all taste bud-specific genes; specifically, using a comparison of gene expression between the top and bottom sections of the primate taste bud. and thereby are e able to classify genes into one of several functional classes that include taste receptor genes.

By contrast, the third method demonstrates taste specific gene expression in humans (in addition to primate) and validates the specificity of expression by a quantitative method (qPCR or "TaqMan"). These methods have been used to identify genes contained in the Table 8 infra which all encode multi-span transmembrane proteins, and are predicted to include yet unidentified receptors and other genes involved in taste modulation including the fat and salt receptor and other taste receptors whose function has yet to be defined.

The previous methods which identify primate taste specific genes are useful as primates and humans are closely evolutionary related it is likely that gene expression pattern will also be closely related. Based on this reasonable assumption, taste specific genes identified by these methods (See Tables 1-4) were selected by the subject improved method to be validated in human taste buds using a technology distinct from microarray analysis—TaqMan qPCR.

As disclosed infra, these methods require a source of human taste buds. Human taste buds can be isolated by laser capture microdissection (LCM). This technique has been described supra and involves the excision and isolation of selected cells or groups of cells from tissue sections based on morphological distinctions. In the case of taste buds, these structures can be readily identified in sections of human tongue. In an exemplary embodiment (example 46 infra) tissue collection was limited to taste buds (TB) in circumvallate papillae and, as a control, cells from the adjacent lingual epithelium (LE). FIG. 47 which shows an example of sections used in sample collection, described in more detail in example 46). Essentially, multiple LCM preparations from different human donors are pooled (~4500 cells per sample), RNA extracted and amplified (e.g., by WT-Ovation Pico RNA Amplification System) (NuGEN Technologies, Inc) and analyzed using TaqMan technology to determine specific levels of gene expression in the TB and LE pools.

Thereafter, the expression of the taste-specific genes is quantified by TaqMan in LCM derived cDNA from both LE and TB from the same donors. Exemplary results using this methodology are contained in Table 8 infra. More specifically, gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values>40 are defined as not detectable.

As can be seen from the data in Table 8, for the majority of genes which were identified as being human taste specific genes when assayed using this methodology, expression was not detected in LE samples (CT>40) but was readily detectable in TB samples (CT<35). This is significant outcome as this group of human taste specific genes has not been described before as taste-specific in human tissue.

In contrast to the afore described gene chip and microarray methods, this technique provides yet additional benefits. and discoveries including the following:

Firstly, these methods allow for human taste specific genes to be detected in human LCM cDNA which were not previously known to be taste specific. Particularly, this approach that uses LCM from post-mortem human tissue samples and a single cDNA amplification step, the data obtained to date clearly indicate that postmortem LCM human tissue can be used to quantify the expression of taste specific genes using qPCR.

Secondly, this methodology allows for the expression of human taste specific genes to be reliably and accurately measured by quantitative PCR (TaqMan) providing for the gene expression profiles of taste specific genes as measured by TaqMan. This methodology further validated gene expression data obtained from the previously described methods which used microarrays and/or in situ hybridization (ISH).

Thirdly, these methods have shown to indeed identify human taste bud specific genes which are functional. Particularly, by using the successive approaches of gene expression via microarray in primate LCM tongue tissue; Top-specific gene expression within the taste bud (akin to known taste receptors) and now TaqMan quantification of gene expression in human postmortem tastes tissues, the inventors we identified new human taste specific genes that had not been described previously. (Table 8)

Therefore, these methods allow for identification of human taste specific genes in postmortem tissues, and the identifying of human genes involved in different functions of the taste bud based on measuring their expression by quantitative PCR.

It is anticipated that these human taste specific genes, based on the manner that they were identified, expressed, and categorized are involved in one or more of (i) taste sensation, modulation of taste sensation, regulation of taste bud growth and development, control of the lifespan of mature taste bud cells, and/or are involved in the maintenance, differentiation and proliferation of taste-bud committed stem cells. In addition, genes identified using these methods are biomarkers of taste-bud committed stem cells. or represent biomarkers of different mature taste cell subsets. Therefore, these genes and gene products can be used as a basis in methods which enrich or purify these cell subsets.

In addition, as well as its more generic embodiments this invention further describes certain information and characterization of taste specific genes identified by the rationales described in detail infra. These discoveries are enumerated as follows:

Particularly, the invention describes with respect to the genes infra which are expressed in primate and human taste cell subsets and also describe specific uses of these genes, cells and gene products in taste biology. These genes which are selectively expressed in primate fungiform papilla taste cells at the front of the tongue and circumvallate papilla taste cells at the back of the tongue were identified were identified using the afore-described gene chips/microarray methods by comparing expression in taste receptor cells compared to non-taste lingual epithelial cells isolated by laser capture micro-dissection (LCM). Since salty taste perception is most prevalent at the front of the tongue, taste receptor genes including the salty taste and other taste receptor should be present within this gene set. The genes in Table 6 are expressed in different subsets of primate taste cells and were identified by gene chip analysis and shown to be expressed in subsets of taste cells by in situ hybridization analysis.

The results obtained contained in the examples reveal that FAM26A, MCTP1, TMEM30B, and TUSC3 are expressed in many TRPM5 cells, suggesting that these genes are expressed in sweet, umami, and bitter taste cells, since TRPM5 is a marker of sweet, bitter, and umami taste cells. Also, the results show that GPR113 and TMEM16G are expressed in a subset of TRPM5 cells, suggesting that these genes could be selectively expressed in sweet, umami, or bitter taste cells (or a combination thereof).

Also, these results show that TMEM44 is expressed in cells that do not express TRPM5 (bitter, sweet, umami) or PKD1L3 (sour), indicating that the expression of this gene is a marker for a unique taste cell type that could correspond to salt, fat, or another taste modality, and, furthermore, that this gene may encode the primary salt or fat receptor.

Based on the foregoing, the application teaches that FAM26A, MCTP1, TMEM30B, and TUSC3 can be used as markers for sweet, bitter, and umami taste cells or cells expressing TRPM5. In addition, FAM26A, MCTP1, TMEM30B, and TUSC3 and compounds that enhance or inhibit these gene products can selectively modulate taste cell function and responses to tastants including sweet, bitter, and umami.

In addition, these results indicate that GPR113 and TMEM16G can be used as a marker for sweet, bitter, or umami taste cells or subsets of TRPM5 cells. Also, the results indicate that GPR113 and TMEM16G and compounds that enhance or inhibit these gene products can selectively modulate taste cell function and responses to tastants including sweet, bitter, or umami.

Still further and based thereon this application teaches the use of these that TMEM44 can be used as a marker for a unique, novel taste cell type that does not correspond to sweet, bitter, and umami taste cells and that TMEM44 and compounds that enhance or inhibit this gene product can selectively modulate taste cell function and responses to tastants other than sweet, bitter, and umami, which include salt, fat, and other tastants.

Still further and based thereon this application teaches the use of these that TMEM44 may correspond to a salt receptor or fat receptor, or a marker of immature taste cells or stem cells. Also, TMEM44 and compounds that enhance or inhibit this gene product can selectively modulate taste cell development and/or differentiation of specific taste cell types (i.e. bitter taste cells).

Still further and based thereon this application teaches the use of these gene products and compounds that enhance or inhibit gene products can affect: selective apoptosis of taste cells responding to aversive taste modalities such as bitter and sour cells; modulation of transcription factors that control taste receptor expression; modulation of specific bitter receptor expression to minimize off-tastes of vegetables, children's medicine, and coffee; autocrine/paracrine modulation of taste cell development; prolongation of taste bud lifetime; development of supertasters (rodent model systems) to screen for chemical and biological toxins (terrorism), rancid/spoiled/contaminated food and beverage products; and activation of stem cells to differentiate into defined taste cell types.

Still further this application teaches the use of these gene products as ancillary taste receptors or primary taste receptors including receptors for salt, fat, and other taste modalities including metallic.

Still further this application teaches the use of these gene products and compounds that enhance or inhibit gene products, can modulate the function of any cell expressing a taste receptor, including but not limited to cells in the gastrointestinal tract such as enteroendocrine cells that regulate gastric motility and peptide secretion (e.g. GLP-1: glucagon-like peptide 1; GIP: gastric inhibitory peptide) as well as the other therapeutic applications of taste specific genes and modulators afore-mentioned. These applications include trafficking of taste receptors to and from the apical membrane/taste pore region to enhance or repress general or specific tastes; regulation of taste cell action potential firing frequency/membrane potential to control the intensity of general or specific tastes; regulation of neurotransmitter release to afferent nerve to control the intensity of general or specific tastes; and autocrine/paracrine modulation of taste receptor function; regeneration of taste cells as well as prophylaxis/prevention of taste cell loss following injury, chemotherapy for cancer, radiation therapy for cancer, drug-induced dysgeusia, ageusia, and taste bud loss in the geriatric population; oral hygiene, halitosis, detoxification of noxious substances in oral cavity, and neutralization/elimination of bacteria, viruses, and other immunogens in the saliva/mouth; saliva composition and treatment of dry mouth in conditions of xerostomia and autoimmune disease (Sjogren's syndrome).

Also, this application teaches using double label in situ hybridization histology what specific TRPM5 cell type that GPR113 is expressed in. As disclosed infra in the examples and supporting figure we identify that GPR113 is not expressed in T1R1 umami cells, T1R2 sweet cells, or T2R bitter cells. GPR113 is expressed in a subset of T1R3 cells that do not express T1R1 or T1R2. Thus, GPR113 cells define a new taste cell type of T1R3 only cells.

Therefore, this application teaches the use of GPR113 as a marker for this unique taste cell type that because it is in a unique cell population, is a GPCR (many taste receptors are known to be GPCRs) likely corresponds to a specific taste modality or modulates a specific taste modality such as CO2 sensation, salt, fat, metallic or astringent. Also, GPR113 may associate with T1R3 to form a novel taste receptor for sweet, umami, or other tastants.

Further based on the foregoing, this application teaches the use of GPR113 as a marker to identify and isolate this unique, novel taste cell type (T1R3 only cells) that does not correspond to sweet, bitter, and umami taste cells. and used to identify taste modulators and the aforementioned therapeutic applications of compounds modulating taste specific genes.

Also, the inseminators further identified using the same rationales (gene chip, in situ hybridization analysis) that the genes KIT, IKBKAP, LOC285965, and SV2B are taste specific taste cells and are expressed in the specific primate taste cell subsets (see Table 7 infra). In addition, we show infra that another gene, MFDS4, is expressed in sensory taste cells that are not sweet, umami, bitter or sour cells, suggesting that this gene is expressed in a similar taste cell subset as TMEM44.

Also, in Table 4 the application provides a listing of other primate taste-specific genes also identified by the same rationales. This listing of genes include genes encoding transmembrane proteins such as ion channels (sodium), GPCRs, ion transporters, as well as multi-transmembrane proteins with no function yet assigned. These genes and gene products are also useful in the same therapeutic and taste modulatory screening assays.

Based on the foregoing observations and the information in Table 7, the invention further teaches that since IKBKAP and SV2B are expressed in many PKD1L3 cells, that these genes are likely expressed in sour taste cells, since PKD1L3 is a marker of sour taste cells.

Also, based on the finding that KIT is expressed in cells that express the umami taste receptor component T1R1, the application teaches that KIT is likely expressed in cells responsible for umami taste perception.

Also, based on the finding (as determined by in situ hybridization of primate taste bud cells) that all of TUSC3, ASCL1, FAM26A, FAM26C, IKBKAP, LOC285965, SCNN1D, SLC4A11, SLC26A7, and TMEM30B are expressed by specific taste cell subsets that these genes may be used as biomarkers and that the genes and gene products may be used isolate, mark or ablate these cells and thereby determine the taste related function of these taste bud cells. Based on this same finding the invention further relates to these isolated cells and assays using these cells and genes to identify taste modulators.

Also, based on the finding that LOC285965 is expressed in cells that express TRPM5 and T1R3 but not in cells that express the umami taste receptor component T1R1, or the sweet taste receptor component T1R2; the application teaches that LOC285965 is expressed in the 'T1R3 only' population of taste cells (similar to GPR113).

Also, based on the experimental findings that IKBKAP and SV2B are expressed in PKD1L3 sour taste cells the application teaches that they can be used as markers of this taste cell population.

Also, based on these same experimental findings, the application further teaches that that IKBKAP and SV2B and compounds that enhance or inhibit these gene products can selectively modulate taste cell function and responses to sour tastants as well as other functions of the PKD1L3 taste cell population.

Also, based on these same findings and the fact that IKBKAP is mutated in the human disease familial dysautonomia, where taste buds are absent or atrophic and individuals exhibit deficiencies in detection of sweet, bitter, sour, and salty tastants (hypogeusia), this application teaches that IKBKAP expression in PKD1L3 cells may be important for taste cell development and/or maintenance.

Also, based on these same findings and the fact that Botulinum neurotoxin (BoTox) enters neuronal-type cells by interacting with SV2B; the application also teaches that BoTox may selectively modulate sour taste as well as other functions of the PKD1L3 taste cell population.

Also, based on the findings that KIT is expressed in umami taste cells, this application teaches its use as a marker of this taste cell type.

Also, based on these same findings, the application teaches that KIT and compounds that enhance or inhibit this gene product can selectively modulate taste cell function and responses to umami tastants.

Also, based on these findings and the fact that Gleevec (Imatinib), is an inhibitor of the KIT tyrosine kinase activity, this application teaches that this and other KIT tyrosine kinase inhibitors may selectively inhibit umami taste. Also, these findings suggest that individuals with gain of function mutations in KIT, for example in gastrointestinal stromal tumors (GIST), may have altered umami taste perception.

Also, based on the findings that LOC285965 is expressed in T1R3 only taste cells similar to GPR113, this application teaches that this gene can be used as a marker for a unique, novel taste cell type (T1R3 only cells) that does not correspond to sweet, bitter, and umami taste cells.

Also, based on these findings, the application also teaches that LOC285965 may correspond to the salt receptor or fat receptor or a receptor for astringency or metallic taste by itself or in combination with GPR113.

Also, based on these findings the application teaches that LOC285965 may be a coreceptor with T1R3 for specific sweet or umami tastants or other novel tastants such as astringent and metallic tastants.

Still further, based on these findings the application teaches that compounds that enhance or inhibit LOC285965 can selectively modulate taste function and responses to tastants.

Also, based on these findings the application teaches that LOC285965 may correspond to a marker of immature taste cells that are differentiating into sweet or umami cells.

Also, based on these findings the application teaches that LOC285965 and compounds that enhance or inhibit this gene product can selectively modulate taste cell development and/or differentiation of specific taste cell types (i.e. sweet or umami taste cells).

Also, based on experimental findings the application teaches suggest that MFSD4 and compounds that enhance or inhibit this gene product can selectively modulate taste cell function and responses to tastants other than sweet, bitter, umami, and sour which include salt, fat, and other tastants.

Also, based on experimental findings this application teaches that MFSD4 may correspond to the salt receptor or fat receptor. or may be used as a marker of immature taste cells or developing taste cells or support cells. Still further, these findings suggest that MFSD4 and compounds that enhance or inhibit this gene product can selectively modulate taste cell development and/or differentiation of specific taste cell types (i.e. bitter taste cells).

Also, based on experimental findings that reveal that MFSD4 and TMEM44 are expressed in the same taste cell population the application teaches that this cell may respond to specific tastants and also that MFSD4 and TMEM44 may form a complex (heterodimer) to generate a taste receptor (such as fat, CO2, salt, metallic, or other taste modality).

Also, we describe experimental findings have demonstrated (see results infra in the examples) that the ASCL1 (aka MASH1) transcription factor defines sour taste cells. ASCL1 is expressed in sour taste cells expressing the sour taste receptor gene PKD1L3; ASCL1 is not expressed in sweet, bitter, and umami taste cells expressing TRPM5. ASCL1 was previously reported to be a marker of type III taste cells. Type III taste are defined by morphological criteria which include: staining with an intermediate density by electron microscopy and making synaptic contacts with nerve fibers. Thus, these results demonstrate that type III taste cells, a cell type previously defined by morphological criteria, correspond to sour taste receptor cells defined by gene expression criteria.

This application describes that an application of this finding is that the ASCL1 transcription factor may bind to promoter elements in genes involved in sour taste perception. Thus, the genome could be screened for ASCL1 motifs to identify genes in sour cells, including sour receptor genes such as PKD2L1, PKD1L3, or additional genes that may form a complex with PKD2L1/PKD1 L3 to generate a sour receptor.

Analogously, other taste receptor cells for sweet, bitter, umami, and salt are likely to express specific transcription factors that define those cell types. Therefore, this application teaches that the expression of all transcription factors in the genome can be analyzed in taste cells by PCR and/or histology to determine which taste cell types express which transcription factors.

The application further describes various other practical applications of these discoveries. For example, the ASCL1 (aka MASH1) can be used as a marker of sour taste cells and further identify and allow for the isolation of Type III taste cells which correspond to sour taste receptor cells.

Moreover, it has been determined that ASCL1 defines the sour taste cell lineage and may control sour taste cell development. Therefore, the invention teaches that ASCL1 transcription factor DNA binding sequences can be used to identify sour cell genes and sour taste receptor genes. Also, such transcription factors can be used to define, mark, and/or label taste cell types. With respect thereto, each taste cell will express one or more transcription factors that define that taste modality.

Also, the application teaches the use of the identified transcription factors that define taste modalities such as ASCL1 in cell ablation studies to specifically eliminate a specific taste. Moreover, the application teaches the use of transcription factors that define new taste cell types in cell studies to determine what taste modality is lacking (i.e. what taste can an animal no longer perceive).

Also, as described and supported by data infra, the invention has determined that taste cells expressing the PKD2L1 and PKD1L3 genes, previously implicated in sour taste are heterogeneous and comprise multiple cell populations. In the front of the tongue, in fungiform (FG) papilla there are cells expressing PKD2L1 only, PKD1L3 only, and both PKD2L1 plus PKD1L3. In the back of the tongue, in circumvallate papilla (CV), most cells coexpress PKD2L1 plus PKD1L3, but i addition to this population there is a distinct group of taste cells that express PKD1L3 only and a smaller set of cells that express PKD2L1 only. Previous literature has suggested that cells expressing PKD2L1 (encompassing PKD2L1 and cells coexpresing PKD2L1 plus PKD1L3) responded to sour taste (Huang et al, Nature 2006 Aug. 24; 442(7105):934-8. However, PKD1L3 cells were not previously known and no function has yet been ascribed. Based thereon, the application teaches the use of PKD1L3 cells as candidate basic or salty taste responding cells and that PKD1L3 is involved in a different taste modality, e.g., basic taste perception since the related sour receptor, PKD2L1, responds to acidic taste.

In addition the invention provides experimental findings that the FAM26C gene is expressed in TRPM5 cells (see results infra) and teaches its use as a marker of sweet bitter and umami cells.

Also, based on the experimental findings herein the application teaches that PKD1L3 only taste cells are candidate taste cells, e.g., which modulate basic taste sensation or other taste modalities, and that PKD1L3 is a candidate taste receptor, e.g., basic taste sensation. Also, the application teaches that PKD1L3 may complex with one of the gene products identified herein to form a taste receptor.

Also, based on the experimental findings that FAM26C is expressed in TRPM5 cells, including sweet, bitter, and umami taste cells, the application describes its use as a marker of this taste cell population and FAM26C and use of compounds that enhance or inhibit FAM26C to selectively modulate taste cell function and responses to sweet, bitter, and umami tastants as well as other functions of the TRPM5 taste cell population, including functions of the GPR113 expressing taste cells that are candidate salty taste cells and that coexpress T1R3.

Also, This application provides data shown infra, indicating that taste cells in the bottom of the taste buds are immature whereas cells in the top half are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to SHH. Therefore, this application teaches that TMEM44 cells, (which also express MFSD4) are immature and comprise, in part, developing taste cells. Further supportive of this finding, a small fraction of taste cells expressing TMEM44 also express either TRPM5 (a marker of mature sweet, bitter and umami cells) or PKD1L3 (a marker of mature sour cells). Cells expressing both TMEM44 and TRPM5 (or PKD1L3) are Therefore maturing into professional taste cells. By contrast, cells in the top half of the taste bud are mature taste cells, do not express SHH, and express taste receptor genes for the sweet, bitter, umami, and sour taste receptors. Since all mature, professional taste cells and taste receptors are localized to the top half of the taste bud, the salty taste cell and the salty taste receptor should be found in the top half of the taste bud as well.

Also, this application teaches methods for identifying and assaying the expression of taste specific genes and identifying specific taste receptors and taste cell subsets which have shown that the taste cells in the bottom half of the taste bud are immature, that the taste cells in the top half of the taste bud are mature and express genes for sweet, bitter, umami, and sour taste receptors, that SHH is a marker of immature and developing taste cells at the bottom of the taste bud. and that TMEM44 and MFSD4 are markers of immature and developing taste cells at the bottom of the taste bud.

The application predicts based on these results that a subpopulation of TMEM44 cells may be mature salty taste cells. and that a salt receptor and a salty taste cell will be expressed or comprised in the top taste bud cells, since all other known taste receptors are expressed in the top taste bud cells. This is a reasonable assumption based on the results obtained by the inventors herein, especially since all other known professional, mature taste cells are expressed in the top of the taste bud.

Also, based on experimental findings herein, and further relating to the foregoing, the inventors have gleaned the following information relating to several subsets of taste bud cells we have identified discussed above, including:

With respect to TMEM44 cells, they have found that these cells comprise about 40% of the taste bud cell population and are located towards the bottom of the taste bud. Also, we have identified other genes expressed by these cells or in the bottom of the taste bud including MFSD4 and Sonic Hedgehog (SHH). The latter is a cytokine involved in immature cell differentiation. For this reason, they predict that TMEM44 represents an immature taste cell population that includes stem cells that replenish the taste bud cells every 2-3 weeks in the human. While these cells are immature, they may still contain a subset of mature cells that may be responsible for taste such as salt sensation.

Also, with respect to GPR113 cells, they have discovered that these cells represent about 100% of the taste bud cell population, and are distinct from sweet, bitter, and umami taste cells, and are located in the top of the taste bud. They express T1R3 and TRPM5 but not the G protein alpha subunit gustudin (GNAT3), suggesting that they represent a novel taste cell population that detects a new taste modality such as fat. Other cells that express TRPM5 and T1R3 include sweet cells (also express T1R2) as well as umami cells (also express T1R1). Bitter cells (also express T2Rs) express TRPM5 but not T1R3. In contrast to GPR113 cells, sweet, bitter, and umami cells all express GNAT3.

Also, with respect to PKD2L1 and PKD1L3 cells, reportedly responsible for sour taste sensation, they are found to constitute about 10% of the taste bud cell population and are located in the top of the taste bud. As discussed below, we have observed that these cells are heterogeneous and that there are distinct PKD2L1 and PKD1L3 'single positive' cell populations in addition to a PKD2L1 and PKD1L3 'double positive' cell population. This heterogeneity suggests that one of these subsets could represent a salt sensing cell.

Also, the experimental findings herein suggest that there is another subset of taste cells (~8% of the taste bud cell population) that does not express any of the following markers: TMEM44, TRPM5, PKD2L1 or PKD1L3, which may represent another taste e.g., CO2 or salt sensing cells. As disclosed a primary focus of this invention was the elucidation of the salty taste receptor. These results were successful as TRPML3 gene has been shown to be a salty taste receptor.

The invention further exploits the elucidation of these unique taste cell populations as part of its strategies for identifying salty and other types of taste sensing cells such as fat, metallic, astringent, CO2, et al.

The application provides different methods. For example, one way to identify the salt cell or other taste cell modality population is to use cell ablation. This technique employs diphtheria toxin under the control of a promoter of a gene expressed in one of the taste cell subsets described above to selectively eliminate this taste cell population, while leaving all other taste cell populations intact. Cell ablation has been used successfully in other laboratories to selectively eliminate sweet (T1R2) and sour (PKD2L1) taste cell populations (work of Charles Zuker). Therefore, ablation of the afore-identified taste cell subsets described above and then use nerve recoding and licking/behavior tests will enable evaluating whether the resulting mice still sense a particular type of tastant, e.g., salt, sour, basic, metallic et al. Based thereon, the inventors have made various predictions which will be confirmed or ruled out by the subject functional assays enumerated below:

(1) Assuming that TMEM44 ablated mice do not sense salt but still sense sweet, bitter, umami, and sour, this result would point this population, or a subset of cells within this population, as the salt sensing cell. Alternatively, the resulting mice may lack taste buds and the ability to detect all 5 taste qualities because TMEM44 is expressed in immature cells or may elicit no effect.

(2) Assuming that GPR113 ablated mice cannot sense salt but still sense sweet, bitter, umami, and sour, this result would point to GPR113 expressing cells as the salt sensing cells. (As noted TRPML3 cells have been shown to sense salt, therefore this outcome is not probable. More likely, another taste modality would be affected.)

(3) Assuming that PKD2L1 ablated mice cannot sense salt but still sense sweet, bitter, umami, and sour, this result would point to PKD2L1 expressing cells as the salt sensing cells. (Again, as TRPML3 cells have been shown to sense salt, this outcome is not probable. More likely, another taste modality would potentially be affected.)

(4) Assuming that PKD1L3 ablated mice cannot sense salt but still sense sweet, bitter, umami, and sour. This result would point to PKD1L3 expressing cells as the salt sensing cells. (Again, as TRPML3 cells have been shown to sense salt, this outcome is not probable. More likely, another taste modality would potentially be affected.)

(5) If none of these mice are deficient in salt perception, this suggests that the putative population of taste cells (80%) that do not express any of the aforementioned markers could be the salt sensing cell, or that all or multiple mature taste cell populations are capable of sensing salt.

Another means taught herein in order to identify the salt sensing cell involves generating a single cell suspension from taste buds and then performing single cell analyses with electrophysiology (patch clamping) or calcium imaging coupled with single cell PCR to identify which population(s) responds to sodium.

With respect to the foregoing assays, there are two main models to account for salt sensation in taste buds:

The first model is the labeled line model. In this model, a single cell type is responsible for sensing a given taste quality. This is true for sweet, bitter, umami and sour. In this model, there is a dedicated cell type responsible for salt sensation. As discussed above, and in the related utility application filed on even date, the inventors have narrowed down the list of candidate salt sensing cells and described techniques that have identified TRPML3 as a salt receptor and that TRPML3 expressing cells sense salty taste.

The second model is the across fibre model where there is not a single cell type responsible for salt sensation. Instead, all or multiple cell types sense salt. In this model, a cell surface molecule, such as a receptor or ion channel, expressed in all or multiple mature taste cells would constitute the salt sensor.

The way to distinguish between these two models is to perform cell ablation experiments such as are described above. Ablation experiments in Varitint mice depleted of TRPML3 taste cells indicate that these mice are deficient in their ability to taste salt. These results suggest TRPML3 expressing cells as being responsible for salty taste.

In yet another related aspect of the invention, the inventors teach three primate taste specific genes, TRPML3, NKAIN3 and NALCN, expressed in primate taste cells that were identified as taste specific genes by gene chip analysis, and shown to function as sodium channels in the literature. These genes were identified as being enriched in the top fraction of taste buds along with all other known taste receptor genes. Therefore, these genes were identified as probable candidates for encoding a salty taste receptor. As described in detail, and substantiated by extensive functional data in a related patent application filed on even date as this application, one of these genes, TRPML3 has been shown in functional assays and transgenic animals to be necessary for salty taste perception and to correspond to a salty taste receptor. These ion channel genes, are expressed as follows in the top versus the bottom of taste buds and in taste versus lingual epithelium tissues: NALCN, (aka VGCNL1), top vs. bottom ratio of 7.2, and TB vs. LE ratio of 11.2; TRPML3 (aka MCOLN3) top vs. bottom ratio of 1.6, and TB vs. LE ratio of 10.2; and NKAIN3 (aka FAM77D) which has a top vs. bottom ratio of 1.5, and TB vs. LE ratio of 3.3.

As reported in Cell. 2007 Apr. 20; 129(2):371-83, the neuronal channel NALCN contributes resting sodium permeability and is required for normal respiratory rhythm. Also, Lu et al. describe that NALCN as a sodium leak channel. Further, with respect to TRPML3, J. Biol. Chem. 2007 Oct. 25; [Epub ahead of print] teach that a gain-of-function mutation in TRPML3 causes the mouse varitint-waddler phenotype. Also, Kim et al., describes TRPML3 as a channel permeable to sodium after exposure of the channel to no/low sodium (as in saliva), consistent with a salt receptor. Also, with respect to the NKAIN 3 gene, in Gorokhova et al., Human Mol. Genet. 2007 Oct. 15; 16(20):3394-410. Epub 2007Jul. 2, this gene is reported as a member of a novel family of transmembrane proteins interacting with {beta} subunits of the Na,K-ATPase. Also, Gorokhova et al., describes a *Drosophila* homologue of NKAIN3 as an amiloride-insensitive sodium channel, consistent with a salt receptor. Again, the TRPML3 gene and its functional properties and that it encodes a salty taste receptor and its therapeutic applications are discussed extensively in the utility and PCT patent applications filed on the same date as this application, incorporated by reference in their entireties herein Based on these observations and the experimental data therein and in this application, it was predicted and later confirmed that these 3 genes would include an ion channel that is involved in salty taste (TRPML3) Also, based thereon, this application teaches that NALCN, and NKAIN3 may constitute other salty taste receptors expressed in taste bud cells or may modulate the function of TRPML3 and/or may associate with TRPML3 to produce a functional taste receptor. Based on the foregoing, the application teaches the use of NALCN, and NKAIN3 as markers to identify salty taste receptor cells.

In addition, the application provides additional information in the examples concerning the NALCN taste-specific gene. Particularly, as described in the examples infra, the inventors demonstrated that NALCN is a taste-specific gene by end-point PCR using purified taste buds and lingual epithelial cells isolated by laser capture microdissection. They also found that NALCN is expressed in a novel, unique taste cell type distinct from sweet, bitter, umami, and sour taste cells by immunohistochemistry with a NALCN antibody.

Therefore, since NALCN is a taste-specific gene, is expressed in a novel taste cell type, and has been reported to function as a sodium-channel, the application teaches that NALCN is a candidate salty taste receptor and/or a marker of the salty taste cell population. Since NALCN and TRPML3 are both expressed in novel taste cell types, the application teaches that NALCN and TRPML3 may be co expressed in the same taste cell population. Accordingly, NALCN and TRPML3 may function together in a complex; or NALCN may function independently of TRPML3 as another salty taste receptor. For example, the application teaches that NALCN may function downstream of TRPML3 akin to how TRPM5 functions downstream of sweet, bitter, and umami receptors. In this manner, NALCN would be involved in the signal transduction pathway for salty taste but not constitute the primary salty taste sensory receptor.

This can be determined in mice. Rodents have 3 distinct taste cell types:

Type III cells correspond to sour cells (PKD2L1 positive, SNAP-25 positive);

Type II cells correspond to sweet, bitter, and umami cells (TRPM5-positive, IP3R3 positive); and Type I cells have no defined function.

As shown in the examples infra, the inventors have demonstrated that NALCN is not expressed in IP3R3 cells (Type II) or SNAP-25 cells (Type III) in rodent. Thus, NALCN expression is implicated in Type I cells, and Type I cells are candidate salty taste cells.

However, alternatively, the application teaches that Type I cells may correspond to immature taste cells and if so, would likely be coexpressed with TMEM44/MFSD4 in an immature taste cell population.

Based on the foregoing discoveries, the invention further teaches NALCN as an additional salty (or other taste such as metallic or fat) taste receptor candidate gene or accessory molecule and based thereon the use thereof as a marker to identify these taste cells.

In addition, since NALCN is a sodium ion channel, and is expressed in the top half of taste buds in cells that have an indeterminate taste function, the application teaches that NALCN may control the resting membrane potential and excitability of the taste cells it is expressed in. Related thereto, compounds that enhance or inhibit function of the NALCN channel may regulate the excitability of salty taste cells, i.e., TRPML3 cells.

Based on this modulatory property, the application teaches that compounds that enhance or inhibit function of the NALCN channel may increase and decrease salt perception respectively, e.g., alone or in combination with TRPML3.

In addition, this application teaches that NALCN may associate with TRPML3 to form a salty taste receptor. (Again, as shown in the related applications filed on even date the ablation of TRPML3 expressing taste cells in Varitint mice results in inhibition of salty taste perception in these rodents and in vitro electrophysiological assays using this ion channel have confirmed that it is a functional sodium channels and may be used to identify TRPML3 blockers and enhancers which should modulate salty taste).

Moreover, based on the experimental findings the application teaches that NALCN can be used as a marker of type I taste cells, which likely include salty taste cells. Alternatively, as type I taste cells may function as precursor cells for sweet, bitter, umami and sour taste cells, modulation of NALCN function may control taste cell differentiation and development into mature taste cell types.

In addition, because the application teaches that TMEM44 and MFSD4 are markers of immature taste cells, the application also teaches that NALCN may be expressed in the subset of immature taste cells expressing TMEM44/MFSD4.

Further, because type I taste cells may also function as glial (support) cells, the application teaches that modulation of NALCN function may indirectly control the activity of sweet, bitter, umami, and sour cells and, as a result, sweet, bitter, umami, and sour taste.

Also, the application teaches based on the experimental findings that compounds that enhance or inhibit function of NALCN may increase and decrease salt perception respectively.

In yet another aspect, this invention describes an assay for identifying a compound having potential in vivo application for modulating human salty taste. This method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a Xenopus oocyte or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8.

In a preferred mode, the assay of step (ii) is an electrophysiological assay which uses a sodium sensitive dye, and preferred dyes include membrane potential dyes selected from the group consisting of Molecular Devices Membrane Potential Kit (Cat#R8034), Di-4-ANEPPS (pyridinium, 4-(2-(6-(dibutylamino)-2-naphthalen-yl)ethenyl)-1-(3-sulfopropyl) hydroxide, inner salt, DiSBACC4(2)(bis-(1,2-dibabituric acid)-triethine oxanol), Cc-2-DMPE (Pacific Blue 1,2-dietradecanoyl-sn-glycerol-3phosphoethanolamine, triethylammonium salt) and SBFI-AM (1,3-benzenedicarboxylic acid, 4,4-[1,4,10-trioxa-7,13-diazacylopentadecane-7,13-diylbis(5-methoxy-6,1,2-benzofurandiyl)}bis-tetrakis {(acetyloxy)methyl}ester Molecular Probes), more preferably, the sodium sensitive dye is sodium green tetraacetate (Molecular Probes) or Na-sensitive Dye Kit (Molecular Devices). In another preferred mode, the assay of step (ii) is a two electrode voltage clamping assay in Xenopus oocytes, or the assay is a patch clamp assay in mammalian cells. Preferably, the assay measures activity by an ion flux assay, including using atomic absorption spectroscopy to detect ion flux.

Alternatively, the assay may use a fluorescence plate reader (FLIPR), or a voltage imaging plate reader (VIPR), which is used to increase ion channel-dependent sodium or fluid absorption. In a preferred embodiment of this method, the activity of the putative salty taste affecting gene is assayed in a frog oocyte electrophysiologically by patch clamping or two electrode voltage clamping, preferably using an automatic imaging instrument, which may be a fluorescence plate reader (FLIPR) or a voltage imaging plate reader (VIPR).

In yet another mode, this invention describes an assay for identifying a compound having potential in vivo application for modulating human sweet, bitter, umami, or sour taste. This method comprises the steps of (i) contacting a cell that expresses a gene in Tables 1-8 with at least one putative enhancer or blocker compound; (ii) assaying sodium conductance, receptor activity or taste gene product function in the presence and absence of said putative enhancer or blocker; and (iii) identifying the compound as a potential enhancer or blocker for sweet, bitter or umami taste based on whether it modulates sodium conductance, the activity of said receptor or taste gene product function.

In yet another mode, this invention describes an assay for identifying a compound having potential in vivo application for as a potential therapeutic. This method comprises the steps of (i) contacting a cell that expresses a gene in Tables 1-3 with at least one putative enhancer or blocker compound; (ii) assaying sodium conductance, receptor activity or taste gene product function in the presence and absence of said putative enhancer or blocker; and (iii) identifying the compound as a potential therapeutic that may be used to modulate a taste cell related function or phenotype that does not directly involve taste such a digestive disorder or disease, taste cell or taste bud turnover or regeneration, immune regulation of the oral or digestive system, or treatment of a metabolic disorder such as diabetes, obesity, eating disorder et al., based on whether it modulates sodium conductance, the activity of said receptor or taste gene product function.

In yet another mode the present invention describes using the genes identified herein as markers to identify and/or purify specific taste cells including sweet, bitter, umami, sour, and other cells including stem cells. These methods include positive and negative cell isolation and selection methods and selection and are based on the expression or absence of expression of one or several of the genes contained in Tables 1-3, or an allelic variant or ortholog or gene that hybridizes thereto under stringent hybridization conditions and/or a gene encoding a polypeptide that is at least 80% identical to the polypeptides or orthologs thereof encoded by the genes contained in Table 1-3, moiré preferably at least 90% identical and still more preferably at least 95% identical. In one embodiment, antibodies directed against the proteins encoded by these genes produced by methods well known to those skilled in the art can be used to label cells in a suspension of taste bud cells produced by enzymatic digestion and tissue disaggregation (Herness, M. An exemplary dissociation procedure for mammalian taste buds. is reported in Neuroscience Letters. 106: 60-64, 1989). The separation can be achieved by using a fluorescence activated cell sorter (See e.g., Beavis, A. J. and K. J. Pennline. Biotechniques. 21: 498-503, 1996) or by magnetic beads (See e.g., Jurman, M. E., L. M. Boland, Y. Liu, and G. Yellen. Visual identification of individual transfected cells for electrophysiology using antibody coated beads. Biotechniques. 17: 876-881, 1994). Alternatively, cells belonging to a specific subset can also be purified by negative selection methods, e.g., by eliminating taste bud cells representing other subsets using cytotoxic antibodies against their specific markers produced using methods well known to those skilled in the art) from a cell suspension of taste bud cells.

DETAILS OF THE INVENTION

Figure 1:
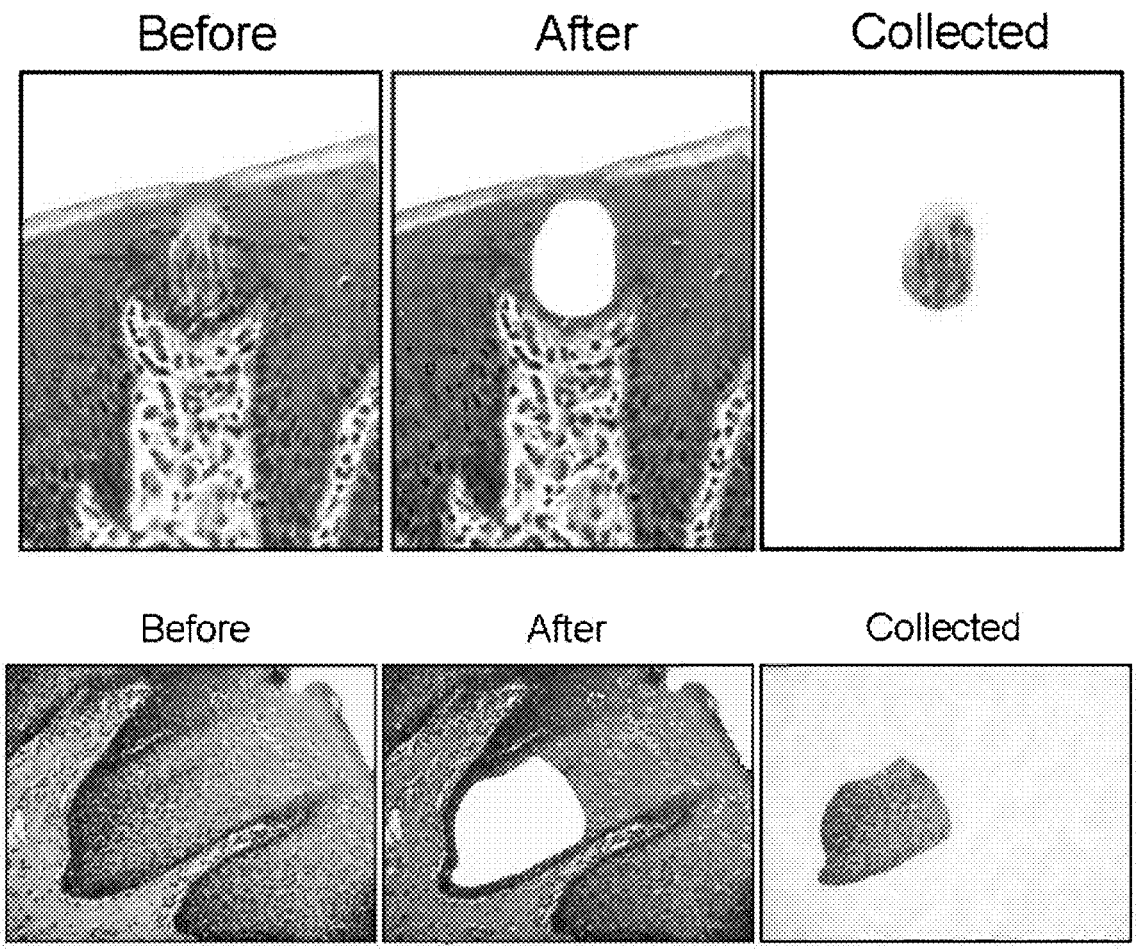
FIG. 1 contains an example of laser capture microdissection (LCM) on primate fungiform (FG) taste tissue (top row) and lingual epithelium (LE) non-taste tissue (bottom row) Top row: Left image shows FG tissue before LCM with a single FG taste bud. Middle image shows FG tissue after LCM where single FG taste bud has been removed. Right image shows collected and isolated FG taste bud used for molecular biology experiments to discover taste-specific genes. Bottom row: Left image shows tissue before LCM with LE from anterior tongue surface. Middle image shows tissue after LCM where a region of LE has been removed. Right image shows collected and isolated LE region used for molecular biology experiments to discover taste-specific genes.

The invention relates to the identification of genes expressed in taste tissues of human and macaque, particularly fungiform and/or circumvallate papilla derived taste cells which are putatively involved in salty taste or other taste modalities or taste in general; or which are involved in taste cell related functions and phenotypes that do not directly involve taste such as taste cell or taste bud regeneration and turnover, immunoregulation of the oral cavity or digestive system, regulation of digestion or metabolism, onset or prevention of digestive system disorders such a cancers, autoimmune diseases, and inflammatory conditions such as IBD, ulcerative colitis, Sjogren's syndrome, celiac disease, Crohn's disease, and the like and the use thereof in screening assays to identify compounds that modulate salty taste perception or other taste modalities or taste in general or for identifying potential therapeutics for use in humans. In particular the invention includes use of the following methodologies, to identify novel taste-specific genes:

1) Laser capture microdissection (LCM) and RNA amplification: In laser capture microdissection, a fine laser beam is used to dissect and purify taste cells from histological sections. This method isolates taste cells, devoid of contaminating lingual epithelial cells and connective tissue, and allows one to perform molecular biology experiments on a highly enriched taste cell population. In parallel, lingual epithelial cells are isolated by LCM and used as a negative control devoid of taste cells. LCM is advantageous to manual or enzymatic dissection of taste papilla because these crude techniques yield a heterogeneous mixture of taste and lingual cells in which taste cells comprise 1-20% of collected material. RNA amplification amplifies total RNAs from taste cells and lingual cells isolated by LCM up to 1 million-fold in a non-biased fashion to generate sufficient genetic material to perform molecular biology studies (gene chips or PCR). We have found that 5,000 taste cells are sufficient for gene chip experiments with macaque taste tissue and greater than 10,000 taste cells are sufficient for PCR experiments with macaque taste tissue.

2) Gene Chips: Gene chips contain most all annotated genes on a small chip. Hybridizing RNA, isolated and amplified from taste and lingual cells, to gene chips can be used to determine which specific genes are expressed in taste cells and not lingual cells and which specific genes are expressed at higher levels in taste cells compared to lingual cells. Gene chips experiments were conducted using paired macaque fungiform (FG) and circumvallate (CV) taste and lingual samples using Affymetrix rhesus macaque genome arrays and analyzed using GeneSpring GX v7.3 software (Agilent Technologies). 5000 fungiform and CV taste and lingual cells were separately isolated by LCM and total RNA was purified for each sample. RNA was then amplified and hybridized to gene chips. Data analyses are performed using two separate algorithms: Affymetrix Microarray Suite 5 (MAS5) which takes into account both perfect match and mismatch probes on gene chips, and robust multi-chip algorithm (RMA) which only takes into account perfect match probes on gene chips. Taste-specific genes encoding transmembrane proteins are identified in this analysis.

3) PCR: High-throughput PCR is performed in 96 well plates using primers specific for ion channels in the human/macaque genome and amplified RNA from human/macaque taste and lingual cells isolated by LCM. Detection of products of the appropriate size in taste cells but not lingual cells and DNA sequencing of PCR products (to confirm gene identity) indicates the ion channel of interest is a taste-specific gene. Prior to high-throughput PCR using primers against ion channels identified in the macaque genome, quality-control PCR reactions are first performed on up to 4 known taste-specific genes and 2 housekeeping genes to ensure that taste and lingual RNAs are of high quality. Four taste-specific genes which may be examined are the G alpha protein gustducin (GNAT3), the sweet receptor components, the ion channel TRPM5 and the enzyme phospholipase beta 2; the two housekeeping genes examined are beta-actin and GAPDH. Specific expression of the taste genes by taste cells but not lingual cells plus expression of the ubiquitous housekeeping genes by both taste and lingual cells indicates high quality RNA material.

PCR products are analyzed on agarose gels to determine if bands of the appropriate size are present in taste cells but not lingual cells. Genes with this expression pattern are putative taste-specific genes. All taste-specific genes were cloned and sequenced to confirm the gene identities.

4) In Situ Hybridization: Antisense RNA probes specific for an individual gene(s) (identified by gene chips or PCR) are hybridized to tissue sections containing taste cells to determine if the mRNA transcript for the gene of interest is expressed in taste cells, specifically in sour, sweet, bitter, and/or umami cells or in a unique cell type that may be involved in salty taste detection. In double labeling in situ hybridization, two different RNA probes are generated to label two different genes, specifically two different taste-specific genes identified by gene chip and/or PCR approaches. Alternatively, one probe can be generated to label a single gene to determine if the gene is expressed in taste cells. For double labeling studies, the first gene is labeled with a FITC probe that generates one color in a fluorescent microscope while the second gene is labeled with a digoxygenin (DIG) probe that generates a different color in a fluorescent microscope. Superimposition of probe 1 and probe 2 reveals if genes are expressed in the same or in different cell types. For example, if a unique ion channel identified by gene chip or PCR approaches colocalizes to cells expressing TRPM5, that unique ion channel is expressed in cells responsible for sweet, bitter, and/or umami taste. By contrast, if a unique ion channel identified by gene chip or PCR approaches does not colocalize to cells expressing TRPM5, that unique ion channel is expressed in a different cell type that may be responsible for salty taste (or another taste modality) and that unique ion channel may be directly involved in sodium detection.

5) Immunohistochemistry: Antibodies specific for an individual protein (whose gene was identified by gene chips or PCR) are applied to tissue sections containing taste cells to determine if the protein of interest is expressed in taste cells, specifically in sour, sweet, bitter, and/or umami cells or in a unique cell type that may be involved in salty taste detection. In double labeling immunohistochemistry, two different antibody probes are used to label two different proteins, specifically two different taste-specific proteins whose genes were identified by gene chip and/or PCR approaches. Alternatively, one antibody probe can be used to label a single protein to determine if the protein is expressed in taste cells. For double labeling studies, the first protein is labeled with an antibody at a very dilute concentration that can only be detected with a sensitive detection method termed tyramide signal amplification (TSA). The second protein is then labeled with another antibody and detected using a non-TSA method. The dilute first antibody cannot be detected by the standard non-TSA method; therefore, two different antibodies from the same species (e.g. rabbit polyclonal antibodies) will not cross-react and, therefore, can be used in double labeling experiments. Superimposition of protein label 1 and protein label 2 reveals if proteins are expressed in the same or in different cell types. For example, if a unique ion channel identified by gene chip or PCR approaches colocalizes to cells expressing TRPM5, that unique ion channel is expressed in cells responsible for sweet, bitter, and/or umami taste. By contrast, if a unique ion channel identified by gene chip or PCR approaches does not colocalize to cells expressing TRPM5, that unique ion channel is expressed in a different cell type that may be responsible for salty taste (or another taste modality) and that unique ion channel may be directly involved in sodium detection.

In particular the present invention preferably uses the following rationale to select potential salty taste receptor or ion channel candidates. It is again emphasized that while this rationale is focused on isolating and functionalizing salty taste receptors because of its inclusive criteria discussed below it likely will identify non-salty taste receptors as well such as fat or metallic taste receptors and genes that encode other functions of taste cells such as discussed above.

First taste buds are isolated using LCM as described above from human or macaque (*Macaca fascicularis*). Macaque genes are on average 90-95% identical to human genes and the macaque is an excellent experimental model for study of human biology including taste. Thus taste genes identified in the macaque will be highly similar to their human orthologs and carry out similar functions to those seen in humans. Using LCM a fine laser beam is used to dissect and purify taste cells from histological sections. This method isolates taste cells devoid of contaminating lingual epithelial cells and connective tissue and allows molecular biology experiments to be effected on a highly enriched taste cell population. In parallel, lingual epithelial cells are isolated by LCM and used as a negative control devoid of taste cells. LCM is advantageous to manual or enzymatic dissection of taste papilla because these crude techniques tend to yield a heterogeneous mixture of taste and lingual cells in which taste cells only comprise about 1-20% of the collected material.

Secondly, RNA isolated from taste and non-taste cells is analyzed using gene chips/microarrays. Gene chips contain most all annotated genes on a small chip. Hybridizing RNA, isolated from taste and lingual cells, to gene chips can be used to determine which specific genes are expressed in taste cells and not lingual cells as well as which specific genes are expressed at higher levels in taste cells compared to lingual cells. In order to identify genes for which probe sets are not functional on gene chips, gene chips were performed on 21 macaque non-taste tissues. Probe sets for genes not yielding data above background levels include both probe sets that do not hybridize efficiently to gene targets as well as probe sets not represented within the panel of 21 macaque tissues. These genes, representing genes not covered by the gene chip approach, are analyzed separately by PCR and/or histology to identify genes, specifically genes encoding transmembrane proteins, which are expressed in taste cells and not lingual cells as well as genes expressed at higher levels in taste cells compared to lingual cells isolated by LCM.

Third, taste-specific genes identified by gene chips and/or PCR are examined by histology using double labeling approaches, With in situ hybridization antisense probes specific for individual genes are hybridized to tissue sections containing taste cells to determine if the mRNA transcript for the gene of interest is expressed in taste cells, specifically in sweet bitter, sour and/or umami taste cells or in a unique cell type that may be involved in salt or other taste modality, e.g., fat taste detection. Using immunohistochemistry antibodies specific for an individual protein (which gene was identified by gene chips) these antibodies are applied to tissue sections containing taste cells to determine if the protein of interest is expressed in taste cells, specifically in sweet, bitter, sour and/or umami cells or in a unique cell type that may be involved in salt or fat taste detection. Genes expressed in taste cells expressing TRPM5, a marker for sweet, bitter, and umami cells, would encode proteins that may modulate sweet, bitter and/or umami taste. Genes expressed in taste cells expressing PKD2L1 or PKD1L3, markers for sour cells, would encode proteins that may modulate sour taste. Genes expressed in taste cells expressing neither TRPM5 nor PKD2L1 or PKD1L3 would encode proteins expressed in a unique cell type that may correspond to a salt or fat cell. Therefore, genes expressed in a unique taste cell type may correspond to a salty taste receptor or a fat taste receptor and may modulate salty or fat taste detection.

Fourth, taste-specific genes expressed in a unique cell type are analyzed by use of functional assays including electrophysiology to determine of gene products expressed in heterologous systems such as HEK293 cells or *Xenopus* oocytes generate sodium-responsive receptors or sodium-conducting ion channels. A salt receptor target should respond to sodium ions at concentrations relevant for human taste (between 20-140 mM sodium).

Fifthly, to ultimately validate the role of a gene as a salt receptor, genes meeting the criteria set forth above are advanced into high-throughput screens to identify enhancers and blockers and these compounds are tested in salty taste tests to determine if they augment or repress salty taste perception. In parallel, mouse knockouts are generated lacking the gene of interest and physiological (nerve recordings) and behavioral (2-bottle preference tests and gustometer tests) experiments are performed to determine if the animals are deficient in or lack salty taste perception.

Therefore, salt receptor candidates will comprise the following criteria: 1) Genes expressed specifically in taste cells or at higher levels in taste cells than lingual cells in gene chip and/or PCR experiments (these are defined as taste-specific genes); 2) Genes expressed in a unique cell type, that does not correspond to sweet, bitter, sour, and/or umami cells by histology; 3) Gene products that generate sodium responsive receptors or sodium channels in electrophysiology or functional experiments; and 4) Enhancers or blockers of gene products modulate salty taste perception and/or mouse knockouts of genes of interest are deficient in or lack salty taste responsiveness.

In a preferred embodiment, step (i) comprises the use of laser capture microdissection (LCM) to dissect and purify taste tissues from non-taste tissues. In one mode of this embodiment, step (i) comprises RNA amplification of genes from taste cells and lingual cells and the amplified genes are screened against a gene chip containing a sample of genes specific to the particular mammal from which the taste and lingual tissues are obtained, and preferably, the gene chips include a set of annotated human genes. In an alternative mode of this embodiment, step (i) comprises high throughput PCR using primers for each ion channel in a mammalian genome.

In another preferred embodiment, step (ii) is effected by in situ hybridization using antisense RNA probes specific for the set of genes identified in step (i) to determine level of expression in taste versus lingual cells. In an alternative preferred embodiment, step (ii) is effected by use of immunochemical detection using a labeled antibody specific to the protein encoded by gene or genes identified in step (i).

In another embodiment of the method for identifying a gene encoding a polypeptide involved in salty taste perception in a mammal, the method of this invention comprises the steps of (i) identifying a set of macaque genes including genes which are expressed in taste cells but which are not expressed in lingual cells and/or genes which are expressed in taste cells at substantially higher levels than in macaque lingual cells; (ii) identifying a subset of genes within the set of genes identified in (i) which are not expressed in taste cells which express umami, sweet or bitter taste receptors (T1Rs or T2Rs) or sour taste receptors (PKD2L1/PKD1L3); and (iii) determining, in a primary neuron which expresses one or more genes in the subset identified according to (ii), which of said genes functions as a sodium responsive ion channel or sodium responsive receptor or transporter and thereby identifying this gene or genes as a putative gene that modulates salty taste. In one mode of this embodiment, step (iii) comprises contacting the neuron with an antibody which specifically binds the gene and inhibits its function.

Genes identified according to either of the methods described above may be characteristic of cells which do not express TRPM5 and PKD2L1/PKD1L3. In another mode, this invention provides a method to assist in selecting cells which do not express TRPM5 and PKD2L1/PKD1L3 by determining whether a cell expresses a gene identified according to the methods above. Preferably, the gene used in the method of this paragraph is one of the genes listed in Tables 1-3, listing taste-specific genes encoding transmembrane proteins in taste cells. Efforts were focused on transmembrane genes since all known taste receptor genes for sweet, bitter, umami, and sour taste encode transmembrane proteins.

In another aspect this application provides an improvement of the afore-described methods in which genes expressed in primate (e.g., macaque) taste buds are identified and functionalized using the disclosed methods. The inventors have developed a rationale wherein they are able to assign gene expression patterns within the primate taste bud for all taste bud-specific genes. Specifically, using a comparison of gene expression between the top and bottom sections of the human or primate taste bud, the inventors have found that they are able to classify genes into one of several functional classes that include taste receptor genes. A subset of genes in this classification is likely to encode all taste receptors and should include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38, described in the examples infra.

Figure 39:
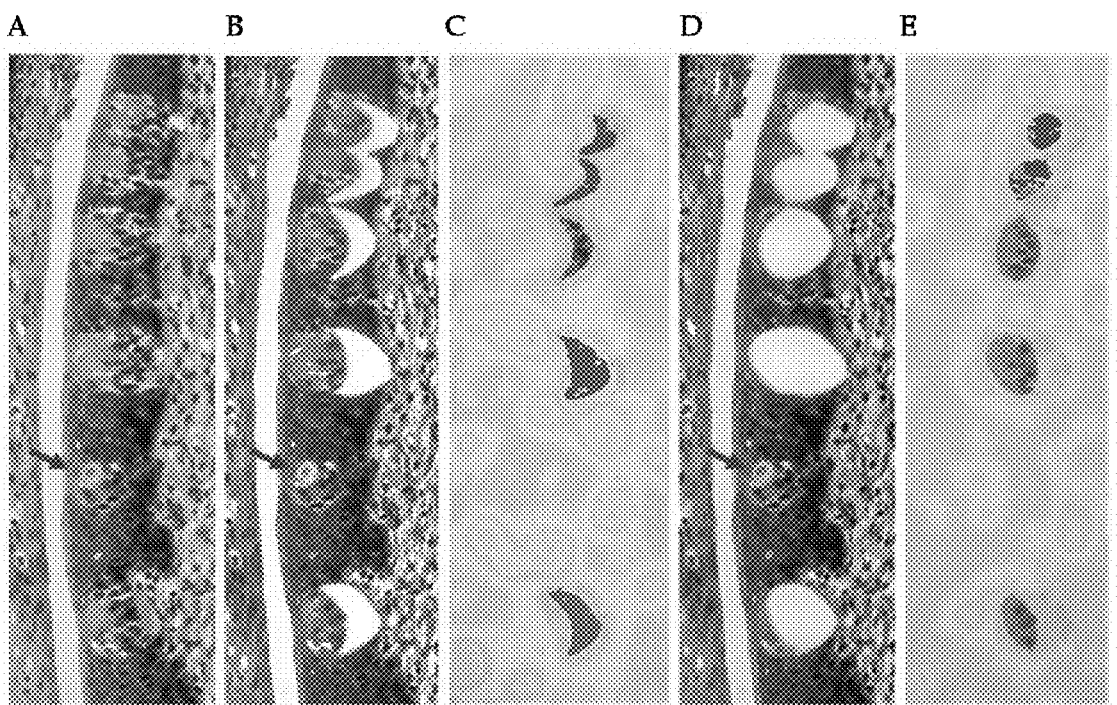
FIG. 39 shows an exemplary experiment showing laser capture microdissection of top and bottom regions of primate taste buds. Panel) contains a methyl blue stained section A of macaque circumvallate taste buds. Panel B shows Section A following excision of bottom fraction of taste buds. Panel C contains the bottom fraction of taste buds. Panel D shows Section A following excision of bottom and top fractions of taste buds. Panel E shows the Top fraction of taste buds. Note, top and bottom fractions were only collected from taste buds exhibiting optimal morphology in section. In the example shown, the taste bud labeled with an arrow was excluded due to suboptimum sectioning or morphology.

In order to get more information on gene expression in both the top and bottom fractions of the taste bud the inventors isolate the corresponding fractions of primate taste buds using laser capture microdissection (LCM). This technique is described supra and briefly involves excision of specific groups of cells from tissue sections based on morphological distinctions. In the case of taste buds, the inventors ate able to readily identify these structures in sections of primate tongue. As exemplified in the supporting experimental example infra, tissue collection was limited to taste buds in circumvallate papillae and then to only taste buds that were sectioned sagittally and at the taste pore. The inventors reasoned that only this type of section would reliably isolate top and bottom fractions. An example of sections used in sample collection is shown in FIG. 39.

The gene expression data obtained is then queried to obtain three sets of genes. The first and second sets are genes that are expressed at a higher level in the top or bottom of the primate taste bud relative to the bottom or top respectively. A third set of genes is identified by comparing gene expression between whole (top+bottom) taste bud and lingual epithelium LCM samples.

This methodology achieves various advantages including the following:

Firstly, the inventors have found that taste receptor genes are expressed predominantly at the top of the taste bud. In contrast to prior knowledge, the data obtained using these methods clearly indicate that known taste receptor genes are expressed at a higher level in the top fraction of taste buds. It is reasonable to expect yet to be identified taste receptor genes are represented in the genes which are enriched at the top of the taste bud.

Secondly, the inventive top-versus-bottom gene classification methods allow for the functional classification of genes based on their expression in the cells in the top versus the bottom of the taste bud. Gene expression profiles at the top and bottom fractions of the taste bud suggest distinct functions for cell in each compartment. Functional classes of genes expressed in the top cells indicate that these are mature sensory cells whereas those expressed in the bottom cells indicate that these are immature progenitor cells associated with a basement membrane containing cellular environment. Examples of top-specific functional clauses include taste receptors, taste-specific signal transduction components and receptors. Examples of bottom-specific functional classes include matrix components, growth factors, and cell-cycle-associated proteins.

Thirdly, this methodology allows for the identification of additional taste bud-specific genes. It has been found that by fractionating the taste bud into top and bottom compartments that the inventors have increased the sensitivity of mRNA detection in each compartment by a factor of about 2. This facilitates the identification of other taste specific genes not identified by the prior-described methods.

Therefore, these methods can be used to identify genes involved in different functions of the taste bud based on measuring their expression in the top versus bottom of the taste bud, e.g., where genes over-expressed in the top part of the taste bud. are predicted to be involved in one or more taste sensation, modulation of taste sensation, control of the lifespan of mature taste bud cells or they may be used as biomarkers of different mature taste cell subsets.

By contrast using the inventive rationale genes over-expressed at the bottom of the taste bud are predicted e.g., to be involved in one or more of the maintenance, differentiation and proliferation of taste-bud committed stem cells; or they will represent biomarkers of taste-bud committed stem cells. n addition, genes expressed specifically in the top or bottom can be using to purify these functionally distinct taste bud cell subsets.

Also, in another aspect this invention describes rationales which are useful and have successfully identified human genes which are taste specific and which are predicted to be involved in one or more of the afore-described taste bud related functions. Specifically, these methods identify human taste specific genes (also identified by the afore-described macaque taste gene selection method) by quantitative polymerase chain reaction (PCR). This is an improvement of the afore-described methods for identifying primate taste specific genes, i.e., taste genes specifically expressed in primate taste buds and may be combined with these method and the previous described method wherein the inventors assign gene expression patterns for genes expressed within the primate taste bud for all taste bud-specific genes; specifically, by comparing taste specific gene expression between the top and bottom sections of the primate taste bud and thereby are able to classify genes into one of several functional classes that include taste receptor genes.

This third method is advantageous as it validates the results of the prior methods (since the identified human taste specific genes are present in those identified as taste specific in the macaque) and also demonstrates similar pattern of taste specific gene expression in humans (in addition to primate) and validates the specificity of expression by a quantitative method (qPCR or "TaqMan").

However, it should be emphasized that the subject methods which identify primate taste specific genes are still very predictive as primates and humans are closely evolutionary related. Therefore, gene expression patterns should also be closely related. Based on this reasonable assumption, taste specific genes identified in the macaque are selected to be validated as being taste specific by assaying the expression thereof in human taste buds using a technology distinct from macroarray analysis—TaqMan qPCR.

These methods similarly require a source of isolated (human) taste buds. Human taste buds can be isolated by laser capture microdissection (LCM). This technique has been described supra and involves the excision and isolation of selected cells or groups of cells from tissue sections based on morphological distinctions. In the case of human taste buds, these structures similarly can be readily identified in sections of human tongue. Essentially, multiple LCM preparations from different human donors are pooled (~4500 cells per sample), RNA extracted and amplified (e.g., by WT-Ovation Pico RNA Amplification System) (NuGEN Technologies, Inc) and analyzed using TaqMan technology to determine specific levels of gene expression in the TB and LE pools.

Thereafter, the expression of the taste-specific genes is quantified by TaqMan in LCM derived cDNA from both LE and TB from the same donors. More specifically, gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values>40 are defined as not detectable.

For the majority of genes which are identified as being human taste specific genes when assayed using this methodology, expression is not detected in LE samples (CT>40) but is readily detectable in TB samples (CT<35). This is significant outcome as this group of human taste specific genes has not been described before as taste-specific in human tissue.

In contrast to the afore described gene chip and microarray methods, this technique provides yet additional benefits. and discoveries including the following:

Firstly, these methods allow for human taste specific genes to be detected in human LCM cDNA which were not previously known to be taste specific. Particularly, this approach that uses LCM from post-mortem human tissue samples and a single cDNA amplification step, the data obtained to date clearly indicate that postmortem LCM human tissue can be used to quantify the expression of taste specific genes using qPCR.

Secondly, this methodology allows for the expression of human taste specific genes to be reliably and accurately measured by quantitative PCR (TaqMan) providing for the gene expression profiles of taste specific genes as measured by TaqMan. This methodology further validates gene expression data obtained from the previously described methods which used microarrays and/or in situ hybridization (ISH).

Thirdly, these methods have shown to indeed identify human taste bud specific genes which are functional. Particularly, by using the successive approaches of gene expression via microarray in primate LCM tongue tissue; Top-specific gene expression within the taste bud (akin to known taste receptors) and now TaqMan quantification of gene expression in human postmortem tastes tissues, the techniques identify human taste specific genes that had not been described previously.

Therefore, these methods allow for identification of human taste specific genes in postmortem tissues, and the identifying of human genes involved in different functions of the taste bud based on measuring their expression by quantitative PCR.

It is anticipated that these human taste specific genes, based on the manner that they were identified, expressed, and categorized are involved in one or more of (i) taste sensation, modulation of taste sensation, regulation of taste bud growth and development, control of the lifespan of mature taste bud cells, and/or are involved in the maintenance, differentiation and proliferation of taste-bud committed stem cells. In addition, genes identified using these methods are biomarkers of taste-bud committed stem cells. or represent biomarkers of different mature taste cell subsets. Therefore, these genes and gene products can be used as a basis in methods which enrich or purify these cell subsets.

Using these rationales, or a combination thereof, the genes contained in Tables 1-8 infra were identified. These Tables are briefly described as follows.

Table 1: This table summarizes primate taste-bud expressed genes that were identified as multi plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions.

Table 2: This table summarizes primate taste-bud expressed genes that were identified as multi plasma membrane proteins with have been functionally characterized but which are potential candidates for salty taste and other taste receptors. In addition this gene set includes genes encoding transmembrane polypeptides involved in other taste cell related functions.

Table 3: This Table contains other fungiform expressed genes and potential taste receptor candidates. This Table of genes was derived after compiling a list of ion channel genes permeable to sodium that were systematically tested for expression in laser capture micro-dissected primate tongue tissue from lingual epithelium and taste buds by end point PCR. Genes that were expressed in fungiform taste buds but not circumvallate taste buds or lingual epithelium were included in this list. Moreover, this list of genes includes other genes which were selected that are likely to encode multi-domain transmembrane proteins included on the macaque oligo array that did not satisfy the inclusion criteria of the systematic array and are not included in the Gene Lists contained in Tables 1 and 2.

Table 4: This table contains additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

Table 5: This table contains additional primate genes previously described as fatty acid receptors or which contain amino acid motifs that are associated with lipid binding. This list of genes includes genes that do not encode multi-transmembrane proteins but which are reported to participate in lipid transport or binding at close to the plasma membrane.

Table 6: This table contains 11 taste-specific genes shown to be expressed in different subsets of primate taste cells. These genes were identified as taste-specific genes by gene chip analysis and shown to be expressed in subsets of taste cells by in situ hybridization analysis as described in the experimental examples and Figures.

Table 7: This table lists 4 other primate taste specific genes identified by the inventive rationales and provides information as to the specific cell types in which these genes are expressed.

Table 8: This table contains a listing of the human taste-specific genes which were quantified by TaqMan in LCM derived cDNA from both LE and TB from the same donors. As noted in Example 46, gene expression was measured in TaqMan as a CT (cycle threshold) value. Briefly the CT value for a given sample was determined by the PCR cycle at which the amount of gene-specific PCR product (as measured by fluorescence) reaches a set value. For highly expressed genes, the threshold is reached early in the PCR run and the CT value is relatively low (<35) while genes with very low or no expression do not reach the threshold before cycle 35. Expression of genes with CT values>40 are defined as not detectable. For the majority of genes listed in Table 8 expression was not detected in LE samples (CT>40) but was readily detectable in TB samples (CT<35).

Therefore, based on the foregoing, the subject invention provides methods for identifying human and other primate taste specific genes, including genes involved in salty taste perception or other taste perception modalities or modulation of taste modalities such as fat, metallic, CO2, sweet, bitter, sour, etc. and the use in screening assays for identifying human salty or other taste enhancers and other taste modulatory compounds and for identifying potential therapeutics that modulate other taste cell related functions and phenotypes including diseases and conditions not directly related to taste transduction.

Particularly, the present invention includes the use of cell-based assays to identify salty taste modulators (enhancers). These compounds have potential application in modulating human salty taste perception. Compounds identified for example in electrophysiological assays and their biologically acceptable derivatives are to be tested in human taste tests using human volunteers to confirm their effect on human salty taste perception. In addition compounds identified as potential therapeutics will be evaluated in appropriate in vitro and in vivo models depending on the nature of the intended application. For example compounds identified as potential therapeutics for diabetes may be evaluated in well known diabetic animal models such the NOD mouse model or BB rat model. Similarly, compounds identified as potential therapeutics for IBD or Crohn's disease may be tested in rodent animal models for IBD or Crohn's disease.

As discussed further infra, the cell-based assays used to identify taste, e.g., salty taste modulatory or therapeutic compounds will preferably comprise high throughput screening platforms to identify compounds that modulate (enhance) the activity of genes involved in salty taste perception using cells that express the genes disclosed herein or combinations thereof. Additionally, these sequences may be modified to introduce silent mutations or mutations having a functional effect such as defined mutations that affect ion (sodium) influx. As noted above, the assays will preferably comprise electrophysiological assays effected in amphibian oocytes or assays using mammalian cells that express a an ion channel according to the invention using fluorescent ion sensitive dyes or membrane potential dyes, e.g., sodium-sensitive dyes. Preferably, compounds that modulate such ion channels are identified by screening using electrophysiological assays effected with oocytes that express an ion channel identified herein (e.g., patch clamping or two electrode voltage clamping).

Still alternatively, compounds that modulate the subject ion channels putatively involved in salty taste may be detected by ion flux assays, e.g., radiolabeled-ion flux assays or atomic absorption spectroscopic coupled ion flux assays. As disclosed supra, these compounds have potential application in modulating human salty taste perception or for modulating other biological processes involving aberrant or normal ion channel function.

The subject cell-based assays use mutant nucleic acid sequences which are expressed in desired cells, preferably oocytes or human cells such as HEK-293 cells, or other human or mammalian cells conventionally used in screens for identifying ion channel or GPCR modulatory compounds. These cells may further be engineered to express other sequences, e.g., other taste GPCRs, i.e., T1Rs or T2Rs such as are described in other patent applications by the present Assignee Senomyx as well as appropriate G proteins. The oocyte system is advantageous as it allows for direct injection of multiple mRNA species, provides for high protein expression and can accommodate the deleterious effects inherent in the overexpression of ion channels. The drawbacks are however that electrophysiological screening using amphibian oocytes is not as amenable to high throughput screening of large numbers of compounds and is not a mammalian system. As noted, the present invention embraces assays using mammalian cells, preferably high throughput assays.

Some ion channels putatively involved in salty taste (ENaC) proteins are known to form heteromeric channels comprised of three subunits, an alpha, beta, and a gamma or delta subunit. The sequences of these respective ENaC subunits are disclosed in an earlier patent application by the present Assignee, U.S. Ser. No. 10/133,573 which is incorporated by reference in its entirety herein. Upon co-expression in a suitable cell these subunits result in a heteromeric channel having cation ion channel activity; in particular it responds to sodium and should similarly respond to lithium ions in cell-based assays such as those which are disclosed herein and in Senomyx's prior application referenced above.

The Senomyx application incorporated by reference provides high throughput screening assays using mammalian cells transfected or seeded into wells or culture plates wherein functional expression in the presence of test compounds is allowed to proceed.

The invention specifically provides methods of screening for modulators, e.g., activators, inhibitors, stimulators, enhancers, etc., of human salty taste or other taste modalities and potential therapeutics that target other taste cell functions or phenotypes using the nucleic acids and proteins, sequences provided herein. Such modulators can affect salty taste or other taste modalities or taste cell related functions and phenotypes, e.g., by modulating transcription, translation, mRNA or protein stability; by altering the interaction of the ion channel with the plasma membrane, or other molecules; or by affecting ion channel protein activity. Compounds are screened, e.g., using high throughput screening (HTS), to identify those compounds that can bind to and/or modulate the activity of a taste receptor or taste ion channel polypeptide or transporter or fragment thereof. In the present invention, proteins are recombinantly expressed in cells, e.g., human cells, or frog oocytes and the modulation of activity is assayed by using any measure of ion channel, receptor or transporter function, such as measurement of the membrane potential, or measures of changes in intracellular sodium or lithium levels. Methods of assaying ion, e.g., cation, channel function include, for example, patch clamp techniques, two electrode voltage clamping, measurement of whole cell currents, and fluorescent imaging techniques that use ion sensitive fluorescent dyes and ion flux assays, e.g., radiolabeled-ion flux assays or ion flux assays.

An enhancer of a gene identified as set forth in the current application can be used for a number of different purposes. For example, it can be included as a flavoring agent to modulate the salty taste of foods, beverages, soups, medicines, and other products for human consumption. Additionally, the invention provides kits for carrying out the herein-disclosed assays.

DEFINITIONS

"Putative taste receptor or ion channel gene" refers to a gene expressed in taste cells that is not expressed in lingual cells or is expressed substantially less in lingual cells that moreover preferably is not expressed in taste cells that express a T1R, T2R, TRPM5, or PKD2L1/PKD1L3 gene.

"Putative salty taste receptor or ion channel gene" refers to a gene specifically expressed in taste cells that is not expressed in lingual cells or is expressed substantially less in lingual cells that moreover preferably is not expressed in taste cells that express a T1R or T2R gene. Preferably this gene will also be an ion channel or a G protein coupled receptor.

"Putative fat or lipid taste receptor or ion channel gene" refers to a gene specifically expressed in taste cells that is not expressed in lingual cells or is expressed substantially less in lingual cells that moreover preferably is not expressed in taste cells that express a T1R or T2R gene. Preferably this gene will also comprise specific motifs characteristic of fatty acid or lipid binding or be predicted to be a fat or lipid associated taste receptor based on its prior identification as encoding a fatty acid binding protein or to possess a structure or homology to another fatty acid binding protein.

"Taste Cell" refers to a cell that when mature expresses at least one receptor, transporter, or ion channel that directly or indirectly regulates or modulates a specific taste modality such as sweet, sour, umami, salty, bitter, fatty, metallic or other taste perception or general taste perception such as taste intensity or the duration of a taste response. Taste cells express mRNA and/or a protein for the gene C6orf15 (chromosome reading frame 15)—also known as STG. This gene has been described as a taste-specific gene (M. Neira et al. Mammalian Genome 12: 60-66, 2001) and is among the macaque taste specific genes reported herein. In addition a mature taste receptor cell typically will express mRNA and/or protein for alpha ENaC. We have data (not shown herein) that reveals that alpha ENaC is expressed in at least sweet, bitter, umami, sour and most likely salty taste cells. Further, a mature taste receptor cell will typically express mRNA and/or protein for cytokeratin 19. This protein is only expressed in mature taste cells and is not found in basal or stem cells. (L. Wong et al. Chemical Senses 19(3): 251-264, 1994). Furthermore, taste cells can be identified by those skilled in the art base on their characteristic morphology. In particular mature taste receptor taste cells are elongated and spindle-shaped. Also, a mature taste receptor cell has the apex of the cell (apical membrane) penetrating into the taste pore thereby gaining access or exposure to saliva. By contrast, an immature taste cell, e.g., a basal cell or stem cell is rounded and is not exposed to the taste pore and saliva. Also, unlike mature taste cells, basal and stem cells tend to be localized towards the base of taste buds.

"Chemosensory cells" are cells that are involved in sensing of chemical stimulants such as tastants and other chemical sensory stimuli such as odorants. Chemosensory cells herein include in particular taste receptor cells and cells comprised in the digestive or urinary tract or other organs that when mature express one or more taste receptors. For example, gastrointestinal chemosensory cells are known which express T1Rs or T2Rs and which cells are likely involved in food sensing, metabolism, digestion, diabetes, food absorption, gastric motility, et al. In addition, cells found in the urinary tract likely express salty taste receptors and are involved in sodium transport, excretion and functions associated therewith such as blood pressure and fluid retention. Further, in the digestive system chemosensory cells that express taste receptors may also express chromogranin A, which is a marker of secretory granules. (C. Sternini, "Taste Receptors in the Gastrointestinal Tract. IV. Functional Implications of Bitter Taste Receptors in Gastrointestinal Chemosensing". American Journal of Physiology, Gastrointestinal and Liver Physiology.", 292:G457-G461, 2007).

"Taste-cell associated gene" or "taste specific gene" herein refers to a gene expressed by a taste cell that is not expressed by lingual cell that is involved in a taste or non-taste related taste cell function or phenotype. Taste cells include cells in the oral cavity that express taste receptors such as the tongue and taste cells in other areas of the body that express taste receptors such as the digestive system and urinary tract. Such genes are contained in Tables 1, 2, 3, 4, 5, 6, 7, and 8. With respect to putative taste receptor or taste modulatory genes, preferably, these genes are expressed more in cells comprised in the top half relative to the bottom half of the taste bud. These genes include genes involved in taste and non-taste related functions such a taste cell turnover, diseases affecting the digestive system or oral cavity, immunoregulation of the oral cavity and/or digestive system, digestive and metabolic functions involving taste cells such a diabetes, obesity, blood pressure, fluid retention et al. In referring to the particular taste specific genes identified herein these genes include the nucleic acid sequences corresponding the Accession Numbers contained in Tables 1, 2, 3, 4, 5, 6, 7, and 8 and contained in the Sequence Listing preceding the claims as well as orthologs thereof and chimeras and variants including allelic variants thereof. In particular such variants include sequences encoding polypeptides that are at least 80% identical, more preferably at least 90% or 95, 96, 97, 98 or 99% identical to the polypeptides encoded by the genes corresponding to the recited Accession numbers or to orthologs thereof, especially human and non-human primate orthologs. In addition, the genes include nucleic acid sequences that hybridize under stringent hybridization conditions to a nucleic acid sequence corresponding to one of the gene sequences corresponding to the gene Accession numbers recited in the Tables and sequence listing herein.

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" is a polypeptide monomer that is an auxiliary subunit of a cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits.

The term "authentic" or wild-type" or "native" nucleic acid sequences refer to the wild-type nucleic acid sequences contained in the Tables and sequence listing herein as well as splice variants and other nucleic acid sequences generally known in the art.

The term "authentic" or "wild-type" or "native" polypeptides refers to the polypeptide encoded by the genes and nucleic acid sequence contained in the Tables and Sequence Listing.

The term "modified enhance receptor nuclear acid sequence" or "optimized nucleic acid sequence" refers to a nucleic acid sequence which contains one or more mutations, particularly those that affect (inhibit or enhance) gene activity in recombinant host cells, and most especially oocytes or human cells such as HEK-293 cells. Particularly, these mutations include those that affect gating by the resultant ion channel containing the mutated subunit sequence. The ion channel may comprise such mutations in one or several of the three subunits that constitute the particular ion channel. The modified nucleic acid sequence for example may contain substitution mutations in one subunit that affect (impair) gating function or defective surface expression. The invention embraces the use of other mutated gene sequences, i.e., splice variants, those containing deletions or additions, chimeras of the subject sequences and the like. Further, the invention may use sequences which may be modified to introduce host cell preferred codons, particularly amphibian or human host cell preferred codons.

The term receptor or ion channel protein or transporter or fragment thereof, or a nucleic acid encoding a particular taste receptor or ion channel or transporter or a fragment thereof according to the invention refers to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by the wild-type nucleic acid or amino acid sequence of the taste protein, e.g., proteins encoded by the gene nucleic acid sequences contained in the Tables and Sequence Listing herein as well as fragments thereof, and conservatively modified variants thereof; (3) polypeptides encoded by nucleic acid sequences which specifically hybridize under stringent hybridization conditions to an anti-sense strand corresponding to a nucleic acid sequence encoding a gene encoded by one of said genes, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a nucleic acid, e.g., those disclosed herein.

A putative salty or other taste specific gene or polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Typically these genes will encode proteins that have ion channel activity, i.e., they are permeable to sodium or lithium.

By "determining the functional effect" or "determining the effect on the cell" is meant assaying the effect of a compound that increases or decreases a parameter that is indirectly or directly under the influence of a taste gene, preferably salty taste gene identified herein e.g., functional, physical, phenotypic, and chemical effects. Such functional effects include, but are not limited to, changes in ion flux, membrane potential, current amplitude, and voltage gating, a as well as other biological effects such as changes in gene expression of any marker genes, and the like. The ion flux can include any ion that passes through the channel, e.g., sodium or lithium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties.

"Inhibitors," "activators," and "modulators" of the subject taste cell expressed polynucleotide and polypeptide sequences are used to refer to activating, inhibitory, or modulating molecules identified using in vitro and in vivo assays of these polynucleotide and polypeptide sequences. Inhibitors are compounds that, e.g., bind to, partially or totally block activity, decrease, prevent, delay activation, inactivate, desensitize, or down regulate the activity or expression of these taste specific proteins, e.g., antagonists. "Activators" are compounds that increase, open, activate, facilitate, enhance activation, sensitize, agonize, or up regulate protein activity. Inhibitors, activators, or modulators also include genetically modified versions of the subject taste cell specific proteins, e.g., versions with altered activity, as well as naturally occurring and synthetic ligands, antagonists, agonists, peptides, cyclic peptides, nucleic acids, antibodies, antisense molecules, siRNA, ribozymes, small organic molecules and the like. Such assays for inhibitors and activators include, e.g., expressing the subject taste cell specific protein in vitro, in cells, cell extracts, or cell membranes, applying putative modulator compounds, and then determining the functional effects on activity, as described above.

Samples or assays comprising the proteins encoded by genes identified herein that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of an ion channel is achieved when the activity value relative to the control is about 80%, preferably 50%, more preferably 25-0%. Activation of an ion channel is achieved when the activity value relative to the control (untreated with activators) is 110%, more preferably 150%, more preferably 200-500% (i.e., two to five fold higher relative to the control), more preferably 1000-3000% or higher.

The term "test compound" or "drug candidate" or "modulator" or grammatical equivalents as used herein describes any molecule, either naturally occurring or synthetic compound, preferably a small molecule, or a protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, siRNA, oligonucleotide, ribozyme, etc., to be tested for the capacity to modulate cold sensation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., a gene or sequence contained in the Tables and Sequence Listing herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nucl. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci., USA 89:10915 (1989)) alignments (B) of 50, expectation (E) of 10, M=5, N=-4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "ammo acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine m; and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the ammo acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of beta.-sheet and .alpha.-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1.×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The term antibody, as used herein, also includes antibody fragments either produced by the modification of whole antibodies, or those synthesized de novo using recombinant DNA methodologies (e.g., single chain Fv), chimeric, humanized or those identified using phage display libraries (see, e.g., McCafferty et al., Nature 348:552-554 (1990)) For preparation of antibodies, e.g., recombinant, monoclonal, or polyclonal antibodies, many technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988) and Harlow & Lane, Using Antibodies, A Laboratory Manual (1999); and Goding, Monoclonal Antibodies: Principles and Practice (2d ed. 1986)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a protein, polymorphic variants, alleles, orthologs, and conservatively modified variants, or splice variants, or portions thereof, can be selected to obtain only those polyclonal antibodies that are specifically immunoreactive with proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999).

Therefore, based on the foregoing, this invention provides in its generic embodiments methods for identifying taste specific genes which may be functionalized using the methods disclosed herein. These techniques have identified all of the genes contained in Tables 1-8 too be taste specific. In addition, as disclosed in the experimental examples this invention further provides specific information and characterization of certain human and primate taste specific genes identified by the rationales described in detail infra and further practical applications of these genes, gene products, and cells which express same as well as modulators of these genes. The more specific aspects of the invention are described as follows and in the examples.

Particularly, the inventors provide lists of genes in Table 6 and 7 infra which are expressed in primate taste cell subsets and describe uses of these genes in taste biology. These genes which are selectively expressed in primate fungiform papilla taste cells at the front of the tongue and circumvallate papilla taste cells at the back of the tongue were identified were identified using the afore-described gene chips/microarray methods by comparing expression in taste receptor cells compared to non-taste lingual epithelial cells isolated by laser capture micro-dissection (LCM). Since salty taste perception is most prevalent at the front of the tongue, taste receptor genes potentially including the salty taste and other taste receptor could be present within this gene set. The genes in Table 6 and Table 7 as reported therein are expressed in different subsets of primate taste cells and were identified by gene chip analysis and shown to be expressed in subsets of taste cells by in situ hybridization analysis.

For example, results contained in the experimental examples and figures referred to therein reveal that FAM26A, MCTP1, TMEM30B, and TUSC3 are expressed in many TRPM5 cells, suggesting that these genes are expressed in sweet, umami, and bitter taste cells, since TRPM5 is a marker of sweet, bitter, and umami taste cells. Also, the results show that GPR113 and TMEM16G are expressed in a subset of TRPM5 cells, suggesting that these genes could be selectively expressed in sweet, umami, or bitter taste cells (or a combination thereof).

Also, the results contained in the experimental examples and figures referred to therein show that TMEM44 is expressed in cells that do not express TRPM5 (bitter, sweet, umami) or PKD1L3 (sour), indicating that the expression of this gene is a marker for a unique taste cell type that could correspond to salt, fat, or another taste modality, and, furthermore, that this gene may encode the primary salt or fat receptor.

Based on the foregoing, this invention contemplates the use of FAM26A, MCTP1, TMEM30B, and TUSC3 as markers alone or in combination with other taste specific genes contained herein for marking, isolating, enriching or ablating sweet, bitter, and umami taste cells or cells expressing TRPM5. In addition, this invention includes the use FAM26A, MCTP1, TMEM30B, and TUSC3 and compounds that enhance or inhibit these gene products in order to selectively modulate taste cell function and responses to tastants including sweet, bitter, and umami.

In addition, the results contained in the experimental examples and figures referred to therein indicate that GPR113 and TMEM16G can be used as a marker for sweet, bitter, or umami taste cells or subsets of TRPM5 cells. Therefore, the invention further describes the use of the use of GPR113 and TMEM16G as markers alone or in combination with other taste specific genes contained herein for marking, isolating, enriching or ablating sweet, bitter, and umami taste cells or cells expressing TRPM5.

In addition, the results contained in the experimental examples and figures referred to therein indicate that GPR113 and TMEM16G and compounds that enhance or inhibit these gene products can selectively modulate taste cell function and responses to tastants including sweet, bitter, or umami. Therefore, the invention further embraces the use of these genes and corresponding polypeptides in assays for identifying sweet, bitter or umami taste modulators.

In addition, based on the finding (as determined by in situ hybridization of primate taste bud cells) that all of TUSC3, ASCL1, FAM26A, FAM26C, IKBKAP, LOC285965, SCNN1D, SLC4A11, SLC26A7, and TMEM30B are expressed by specific taste cell subsets that these genes may be used as biomarkers and that the genes and gene products may be used isolate, mark or ablate these cells and thereby determine the taste related function of these taste bud cells. Based on this same finding the invention further relates to these isolated cells and assays using these cells and genes to identify taste modulators Still further, the results contained in the experimental examples and figures referred to therein indicate that TMEM44 can be used as a marker for a unique, novel taste cell type that does not correspond to sweet, bitter, and umami taste cells and that TMEM44 and compounds that enhance or inhibit this gene product can selectively modulate taste cell function and responses to tastants other than sweet, bitter, and umami, which include salt, fat, and other tastants. Therefore, the invention further includes the use of these genes and their corresponding polypeptides in screening assays for identifying taste modulators.

Still further, the results contained in the experimental examples and figures referred to therein indicate that TMEM44 may correspond to a salt receptor or fat receptor, or a marker of immature taste cells or stem cells. Also, this suggests that TMEM44 and compounds that enhance or inhibit this gene product can selectively modulate taste cell development and/or differentiation of specific taste cell types (i.e. bitter taste cells). Accordingly, the invention embraces the use of these genes and polypeptides in screening assays for identifying compounds that selectively modulate taste cell development and/or differentiation of specific taste cell types (i.e. bitter taste cells).

Still further, based on the experimental data, the invention embraces the use of these gene products and compounds that enhance or inhibit gene products can affect: selective apoptosis of taste cells responding to aversive taste modalities such as bitter and sour cells; modulation of transcription factors that control taste receptor expression; modulation of specific bitter receptor expression to minimize off-tastes of vegetables, children's medicine, and coffee; autocrine/paracrine modulation of taste cell development; prolongation of taste bud lifetime; development of supertasters (rodent model systems) to screen for chemical and biological toxins (terrorism), rancid/spoiled/contaminated food and beverage products; and activation of stem cells to differentiate into defined taste cell types.

In addition, the invention further encompasses the possibility that these gene products can also be ancillary taste receptors or primary taste receptors including receptors for salt, fat, and other taste modalities including metallic. This can be determined by the inventive methods.

Also, based on the experimental results, the invention includes the use of these gene products and compounds that enhance or inhibit gene products to modulate the function of any cell expressing a taste receptor, including but not limited to cells in the gastrointestinal tract such as enteroendocrine cells that regulate gastric motility and peptide secretion (e.g. GLP-1: glucagon-like peptide 1; GIP: gastric inhibitory peptide) as well as the other therapeutic applications of taste specific genes and modulators afore-mentioned. These applications include trafficking of taste receptors to and from the apical membrane/taste pore region to enhance or repress general or specific tastes; regulation of taste cell action potential firing frequency/membrane potential to control the intensity of general or specific tastes; regulation of neurotransmitter release to afferent nerve to control the intensity of general or specific tastes; and autocrine/paracrine modulation of taste receptor function; regeneration of taste cells as well as prophylaxis/prevention of taste cell loss following injury, chemotherapy for cancer, radiation therapy for cancer, drug-induced dysgeusia, ageusia, and taste bud loss in the geriatric population; oral hygiene, halitosis, detoxification of noxious substances in oral cavity, and neutralization/elimination of bacteria, viruses, and other immunogens in the saliva/mouth; saliva composition and treatment of dry mouth in conditions of xerostomia and autoimmune disease (Sjogren's syndrome).

Still further, the results contained in the experimental examples and figures referred to therein indicate by use of double label in situ hybridization histology what specific TRPM5 cell type that GPR113 is expressed in. As disclosed infra we identify that GPR113 is not expressed in T1R1 umami cells, T1R2 sweet cells, or T2R bitter cells. Also, it was found that GPR113 is expressed in a subset of T1R3 cells that do not express T1R1 or T1R2. Thus, GPR113 cells define a new taste cell type of T1R3 only cells. Accordingly, this invention embraces the use of this gene to mark, enrich, isolate or ablate these cells.

Also, based on this discovery the invention provides for the use of GPR113 as a marker for this unique taste cell type that because it is in a unique cell population, is a GPCR (many taste receptors are already known to be GPCRs) and therefore this cell likely corresponds to a specific taste modality for which taste cells have not yet been characterized or modulates a specific taste modality such as $CO_2$ sensation, salt, fat, metallic or astringent. Also, the invention provides for the further possibility that GPR113 may associate with T1R3 to form a novel taste receptor for sweet, umami, or other tastants.

Further, based on the foregoing experimental evidence, this invention provides for the use of GPR113 or the corresponding polypeptide as a marker to identify and isolate this unique, novel taste cell type (T1R3 only cells) that does not correspond to sweet, bitter, and umami taste cells and its use to identify taste modulators as well as the aforementioned therapeutic applications of compounds modulating taste specific polypeptides.

Still further, the results contained in the experimental examples and figures referred to therein indicate that the genes KIT, IKBKAP, LOC285965, and SV2B are taste specific taste genes and are expressed in the specific primate taste cell subsets (see Table 7 infra). In addition, the results contained in the experimental examples and figures referred to therein indicate that another gene, MFDS4 is expressed in sensory taste cells that are not sweet, umami, bitter or sour cells, suggesting that this gene is expressed in a similar taste cell subset as TMEM44. Therefore, the invention includes the use of these genes and corresponding polypeptides in screening assays for taste modulators and therapeutics and as biomarkers of specific, unique taste cell subsets.

Still further, in Tables 1-5 of this application the inventors provide a listing of primate taste-specific genes also identified by the inventive rationales that have been demonstrated to reliably include functional taste specific genes already known. These listing of genes include genes encoding transmembrane proteins such as ion channels (sodium), GPCRs, ion transporters, as well as multi-transmembrane proteins with no function yet assigned. Therefore, the invention further includes functionalizing these genes and assessing their function in taste detection or modulation or ancillary taste cell functions.

Still further, the results contained in the experimental examples and figures referred to therein indicate that IKBKAP and SV2B are expressed in many PKD1L3 cells, and that these genes are likely expressed in sour taste cells, since PKD1L3 is a marker of sour taste cells. Therefore, the invention embraces screening assays to assess the effect of modulators on specific taste modalities including sour, or basic taste or other tastes.

Still further, the results contained in the experimental examples and figures referred to therein indicate that KIT is expressed in cells that express the umami taste receptor component T1R1. This is predicted by the inventors to support a view that KIT is expressed in cells responsible for umami taste perception. Accordingly, KIT may modulate umami taste perception.

Still further, the results contained in the experimental examples and figures referred to therein indicate that LOC285965 is expressed in cells that express TRPM5 and T1R3 but not in cells that express the umami taste receptor component T1R1, or the sweet taste receptor component T1R2. These results suggest that LOC285965 is expressed in the 'T1R3 only' population of taste cells (similar to GPR113).

Still further, the results contained in the experimental examples and figures referred to therein indicate that IKBKAP and SV2B are expressed in PKD1L3 sour taste cells and indicate that they can be used as markers of this taste cell population. Therefore, the invention includes the use thereof to mark, enrich, isolate or ablate these taste cells so that their effect can be assessed in vitro or in vivo.

Still further, the results contained in the experimental examples and figures referred to therein indicate that IKBKAP and SV2B and compounds that enhance or inhibit these gene products can selectively modulate taste cell function and responses to sour tastants as well as other functions of the PKD1L3 taste cell population. Accordingly, this invention includes the use of these genes and gene products in sour taste modulatory or other taste assays.

Still further, the results contained in the experimental examples and figures referred to therein indicate further that since IKBKAP is mutated in the human disease familial dysautonomia, where taste buds are absent or atrophic and individuals exhibit deficiencies in detection of sweet, bitter, sour, and salty tastants (hypogeusia) that IKBKAP expression in PKD1L3 cells may be important for taste cell development and/or maintenance. Accordingly, the invention embraces the use of this gene and gene product in assays to identify compounds that modulate taste cell development and/or maintenance.

Also, these same findings that and the fact that Botulinum neurotoxin (BoTox) enters neuronal-type cells by interacting with SV2B; indicate that BoTox may selectively modulate sour taste as well as other functions of the PKD1L3 taste cell population. Therefore, SV2B modulators identified by the inventive methods may elicit neuronal effects and may be useful in cosmetic applications.

Also, the same aforementioned findings that KIT is expressed in umami taste cells indicate that it can be used as a marker of this taste cell type. Therefore, the invention embraces the use of KIT as a marker of umami cells. Also, because these findings that indicate that KIT and compounds that enhance or inhibit this gene product can selectively modulate taste cell function and responses to umami tastants the invention further embraces the compounds identified and their use in modulating umami gene functions including taste and food sensing.

Also, these same findings and the fact that Gleevec (Imatinib), is an inhibitor of the KIT tyrosine kinase activity, indicate that this and other KIT tyrosine kinase inhibitors may selectively inhibit umami taste. Also, these findings suggest that individuals with gain of function mutations in KIT, for example in gastrointestinal stromal tumors (GIST), may have altered umami taste perception. Therefore, the invention further embraces the use of KIT modulators in treating gastrointestinal cancers and for detecting these conditions.

Still further, the results contained in the experimental examples and figures referred to therein indicate that LOC285965 is expressed in T1R3 only taste cells similar to GPR113 and indicate that this gene is useful as a marker for a unique, novel taste cell type (T1R3 only cells) that does not correspond to sweet, bitter, and umami taste cells.

Still further, the results contained in the experimental examples and figures referred to therein indicate that LOC285965 may correspond to a salt receptor or fat receptor or a receptor for astringency or metallic taste by itself or in combination with GPR113. Therefore, the invention further provides for this possibility.

Still further, the results contained in the experimental examples and figures referred to therein indicate that LOC285965 may be a coreceptor with T1R3 for specific sweet or umami tastants or other novel tastants such as astringent and metallic tastants.

Still further, these same findings suggest that compounds that enhance or inhibit LOC285965 can selectively modulate taste function and responses to tastants. Accordingly, the invention embraces the use of this gene and gene products in screening assays for taste modulators.

Also, these same findings suggest that LOC285965 may correspond to a marker of immature taste cells that are differentiating into sweet or umami cells. Therefore, the invention embraces the use of this gene or polypeptide as a marker of immature taste cells and/or to isolate, enrich or deplete these cells.

Also, these same findings suggest that LOC285965 and compounds that enhance or inhibit this gene product can selectively modulate taste cell development and/or differentiation of specific taste cell types (i.e. sweet or umami taste cells). Therefore, the invention embraces the use of these compounds as sweet or umami or other taste modulators.

Still further, the results contained in the experimental examples and figures referred to therein indicate that MFSD4 and compounds that enhance or inhibit this gene product can selectively modulate taste cell function and responses to tastants other than sweet, bitter, umami, and sour which include salt, fat, and other tastants. Therefore, the invention includes the use of MFSD4 modulators to modulate taste.

Also, these same findings suggest that MFSD4 may correspond to the salt receptor or fat receptor or may be used as a marker of immature taste cells or developing taste cells or support cells. The invention Therefore includes the use of this gene in such usages.

Still further, these findings suggest that MFSD4 and compounds that enhance or inhibit this gene product can selectively modulate taste cell development and/or differentiation of specific taste cell types (i.e. bitter taste cells). Accordingly, the invention embraces the use of modulators of this gene for modulating taste cell development or differentiation.

Also, the data infra reveal that MFSD4 and TMEM44 are expressed in the same taste cell population which may respond to specific tastants. Therefore, the invention includes assays which coexpress these genes in order to identify taste modulators.

Also, the invention embraces the resultant taste receptor wherein MFSD4 and TMEM44 form a complex (heterodimer) to generate a taste receptor (such as fat, CO2, salt, metallic, or other taste modality).

Still further, the results contained in the experimental examples and figures referred to therein indicate that the ASCL1 (aka MASH1) transcription factor defines sour taste cells. ASCL1 is expressed in sour taste cells expressing the sour taste receptor gene PKD1L3; ASCL1 is not expressed in sweet, bitter, and umami taste cells expressing TRPM5. ASCL1 was previously reported to be a marker of type III taste cells. Type III taste are defined by morphological criteria which include: staining with an intermediate density by electron microscopy and making synaptic contacts with nerve fibers. Thus, our results demonstrate that type III taste cells, a cell type previously defined by morphological criteria, correspond to sour taste receptor cells defined by gene expression criteria.

Therefore, an application of this finding is that the ASCL1 transcription factor may bind to promoter elements in genes involved in sour taste perception. Thus, the genome could be screened for ASCL1 motifs to identify genes in sour cells, including sour receptor genes such as PKD2L1, PKD1L3, or additional genes that may form a complex with PKD2L1/PKD1L3 to generate a sour receptor.

Analogously, other taste receptor cells for sweet, bitter, umami, and salt are likely to express specific transcription factors that define those cell types. Therefore, the invention further embraces methods wherein the expression of all transcription factors in the genome is analyzed in taste cells by PCR and/or histology to determine which taste cell types express which transcription factors.

These finding further support other applications of this gene. For example, the invention includes the use of ASCL1 (aka MASH1) as a marker of sour taste cells and further for the isolation of Type III taste cells which correspond to sour taste receptor cells.

Moreover, because it has been determined that ASCL1 defines the sour taste cell lineage and may control sour taste cell development, the invention further provides for ASCL1 transcription factor DNA binding sequences to be used to identify sour cell genes and sour taste receptor genes. Also, the invention includes the use of such transcription factors can be used to define, mark, and/or label taste cell types. With respect thereto, each taste cell will express one or more transcription factors that define that taste modality.

Also, the invention further encompasses the use of the identified transcription factors to define taste modalities and in cell ablation studies to specifically eliminate a specific taste. Moreover, the invention includes the use of these identified transcription factors that define new taste cell types in cell studies to determine what taste modality is lacking (i.e. what taste can an animal no longer perceive).

Also, as described and supported by data infra, this invention also shows that taste cells expressing the PKD2L1 and PKD1L3 genes, previously implicated in sour taste are heterogeneous and comprise multiple cell populations. In the front of the tongue, in fungiform (FG) papilla there are cells expressing PKD2L1 only, PKD1L3 only, and both PKD2L1 plus PKD1L3. By contrast, in the back of the tongue, in circumvallate papilla (CV), most cells coexpress PKD2L1 plus PKD1L3.

Also, the invention reveals that in addition thereto there is a distinct group of taste cells that express PKD1L3 only and a smaller set of cells that express PKD2L1 only. Previous literature has suggested that cells expressing PKD2L1 (encompassing PKD2L1 and cells coexpresing PKD2L1 plus PKD1L3) respond to sour taste (Huang et al, Nature 2006 Aug. 24; 442(7105):934-8.) However, PKD1L3 cells were not previously known and no function has yet been ascribed.

Therefore, the invention further contemplates the use of PKD1L3 cells as candidate basic or salt responding cells and that PKD1L3 is involved in a different (other than sour) taste modality, e.g., basic taste perception since the related sour receptor, PKD2L1, responds to acidic taste.

Still further, the results contained in the experimental examples and figures referred to therein indicate that the FAM26C gene is expressed in TRPM5 cells (see results infra) and therefore can be used as a marker of sweet, bitter and umami cells. Therefore, the invention further includes the use of FAM26C as a marker or to isolate, enrich or purify or ablate specific taste cells including sweet, bitter and umami cells.

Also, based on these same findings the invention includes the possibility that PKD1L3 only taste cells are candidate taste cells, e.g., which modulate basic taste sensation or other taste modalities, and that PKD1L3 is a candidate taste receptor, e.g., basic taste sensation. Also, the invention provides for an embodiment wherein PKD1L3 may complex with one of the gene products identified herein to form a taste receptor.

Also, based on the findings that FAM26C is expressed in TRPM5 cells, including sweet, bitter, and umami taste cells, it can be used as a marker of this taste cell population and FAM26C and compounds that enhance or inhibit FAM26C can selectively modulate taste cell function and responses to sweet, bitter, and umami tastants as well as other functions of the TRPM5 taste cell population, including functions of the TRPM5 taste cells that are candidate salty taste cells and that coexpress T1R3.

Also, as shown infra, this invention reveals that taste cells in the bottom of the taste buds are immature whereas cells in the top half are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to SHH. Therefore, we have predicted that TMEM44 cells, (which also express MFSD4) are immature and comprise, in part, developing taste cells. Supportive of this finding, a small fraction of taste cells expressing TMEM44 also express either TRPM5 (a marker of mature sweet, bitter and umami cells) or PKD1L3 (a marker of mature sour cells). Cells expressing both TMEM44 and TRPM5 (or PKD1L3) are therefore maturing into professional taste cells. By contrast, cells s in the top half of the taste bud are mature taste cells, do not express SHH, and express taste receptor genes for the sweet, bitter, umami, and sour taste receptors. Since all mature, professional taste cells and taste receptors are localized to the top half of the taste bud, the invention further includes methods for recovery of a fraction of taste bud cells that should include virtually all the functional taste cells including the salty taste cells. Particularly, recovery of the cells in the top half of the taste buds should include cells expressing the salty taste receptor.

Therefore, the invention and methods for assaying taste specific genes and identifying specific taste receptors and taste cell subsets have shown that the taste cells in the bottom half of the taste bud are immature, that the taste cells in the top half of the taste bud are mature and express genes for sweet, bitter, umami, and sour taste receptors, and further that SHH can be used as a marker of immature and developing taste cells at the bottom of the taste bud and that TMEM44 and MFSD4 are markers of immature and developing taste cells at the bottom of the taste bud.

It is predicted based on these results that a subpopulation of TMEM44 cells may be mature taste cells corresponding to a yet unidentified taste cell, e.g., metallic, fat, astringent, CO2, and the like and that a corresponding taste receptor and taste cell will be expressed or comprised in the top taste bud cells, since all other known taste receptors are expressed in the top taste bud cells. This is a reasonable assumption based on the results obtained by the inventors herein, especially since all other known professional, mature taste cells are expressed in the top of the taste bud.

More specifically, and further relating to the foregoing, and the results and data in the experimental examples and supporting figures, the inventors have gleaned the following information relating to several subsets of taste bud cells we have identified discussed above, including:

(i) with particular respect to TMEM44 cells, the inventors have found that these cells comprise about 40% of the taste bud cell population and are located towards the bottom of the taste bud. Also, we have identified other genes expressed by these cells or in the bottom of the taste bud including MFSD4 and Sonic Hedgehog (SHH). The latter is a cytokine involved in immature cell differentiation. For this reason, we predict that TMEM44 represents an immature taste cell population that includes stem cells that replenish the taste bud cells every 2-3 weeks in the human. While these cells are immature, they may still contain a subset of mature cells that may be responsible for taste such as salt sensation.

(ii) with particular respect to GPR113 cells, the inventors have discovered that these cells represent about 10% of the taste bud cell population, and are distinct from sweet, bitter, and umami taste cells, and are located in the top of the taste bud. They express T1R3 and TRPM5 but not the G protein alpha subunit gustudin (GNAT3), suggesting that they represent a novel taste cell population that detects a new taste modality such as fat. Other cells that express TRPM5 and T1R3 include sweet cells (also express T1R2) as well as umami cells (also express T1R1). Bitter cells (also express T2Rs) express TRPM5 but not T1R3. In contrast to GPR113 cells, sweet, bitter, and umami cells all express GNAT3.

(iii) with particular respect to PKD2L1 and PKD1L3 cells, reportedly responsible for sour taste sensation, the inventors have found that they comprise about 10% of the taste bud cell population and are located in the top of the taste bud. Also, they have observed that these cells are heterogeneous and that there are distinct PKD2L1 and PKD1L3 'single positive' cell populations in addition to a PKD2L1 and PKD1L3 'double positive' cell population. This heterogeneity suggests that one of these subsets could represent a salt or another type of taste sensing cell.

(iv) with particular respect to other markers, the inventors' results suggest that there is another subset of taste cells (~8% of the taste bud cell population) that does not express any of the following markers: TMEM44, TRPM5, PKD2L1 or PKD1L3, which may represent another taste e.g., CO2 or salt sensing cells. As disclosed while a primary focus of this invention was the elucidation of the salty taste receptor and that these efforts have been successful as the TRPML3 gene has been shown to be a salty taste receptor there may be other salty taste receptors.

The invention further includes the use of these unique taste cell populations as part of its strategies for identifying salty and other types of taste sensing cells such as fat, metallic, astringent, CO2, et al.

Also, the invention further encompasses the use of the genes reported herein as a specific means for confirming the identity of salt and other types of taste cells. In particular, the invention includes the use of the specific taste genes reported herein in methods of cell ablation as a means to identify the specific effect of the selective removal of distinct cell subsets on taste and other ancillary taste related functions already mentioned.

One way to identify the salt cell or other taste cell modality population is to use cell ablation. This technique employs diphtheria toxin under the control of a promoter of a gene expressed in one of the taste cell subsets described above to selectively eliminate this taste cell population, while leaving all other taste cell populations intact. Cell ablation has been used successfully in other laboratories to selectively eliminate sweet (T1R2) and sour (PKD2L1) taste cell populations (work of Charles Zuker). Therefore, ablation of the aforeidentified taste cell subsets described herein and others and these of the resultant ablated animals in assays of function (such as nerve recoding and licking/behavior tests will enable evaluating whether the resulting mice still sense a particular type of tastant, e.g., salt, sour, basic, metallic et al or possess an ancillary taste cell function such as taste cell differentiation, proliferation, et al.

For example, in the case of TMEM44, assuming that TMEM44 ablated mice do not sense salt but still sense sweet, bitter, umami, and sour, this result would point this population, or a subset of cells within this population, as the salt sensing cell. Alternatively, if the resulting mice lack taste buds this would suggest that the mice lose the ability to detect all 5 taste qualities because TMEM44 is expressed in immature cells or cell ablation may elicit no effect.

Alternatively, in the case of GPR113, assuming that GPR113 ablated mice cannot sense salt but still sense sweet, bitter, umami, and sour, this result would point to GPR113 expressing cells as the salt sensing cells. (As noted TRPML3 cells have been shown to sense salt, therefore this outcome is not probable. More likely, another taste modality would be affected.)

Alternatively, in the case of PKD2L1 assuming that PKD2L1 ablated mice cannot sense salt but still sense sweet, bitter, umami, and sour, this result would point to PKD2L1 expressing cells as the salt sensing cells. (Again, as TRPML3 cells have been shown to sense salt, this outcome is not probable. More likely, another taste modality would potentially be affected.)

Still alternatively in the case of PKD1L3, assuming that PKD1L3 ablated mice cannot sense salt but still sense sweet, bitter, umami, and sour, this result would point to PDK1L3 expressing cells as the salt sensing cells. (Again, as TRPML3 cells have been shown to sense salt, this outcome is not probable. More likely, another taste modality would potentially be affected.)

Yet alternatively, if none of these mice are deficient in salt or another taste perception, this suggests that the putative population of taste cells (8%) that do not express any of the aforementioned markers could be the salt or another desired taste cell subset, e.g., a fat or metallic taste sensing cell, or that all or multiple mature taste cell populations are capable of sensing salt.

Another means encompassed by the invention for the use in identifying salt or other types of taste cells and further based on the information provided herein relating to taste specific genes and the identified unique taste cell subsets, and the various genes they express or do not express involves generating a single cell suspension from taste buds and then performing single cell analyses with electrophysiology (patch clamping) or calcium imaging coupled with single cell PCR to identify which population(s) responds to sodium or other ions or molecules.

With respect to the foregoing, there are two main models to account for salt sensation in taste buds:

The first model is the labeled line model. In this model, a single cell type is responsible for sensing a given taste quality. This is true for sweet, bitter, umami and sour. In this model, there is a dedicated cell type responsible for salt sensation. As discussed above, we have narrowed down the list of candidate salt sensing cells and described techniques we would use to identify the salt cell.

The second model is the across fibre model where there is not a single cell type responsible for salt sensation. Instead, all or multiple cell types sense salt. In this model, a cell surface molecule, such as a receptor or ion channel, expressed in all or multiple mature taste cells would constitute the salt sensor.

The way to distinguish between these two models and to determine which is valid is to perform ell ablation experiments such as are described above.

In yet another aspect of the invention, this invention provides three primate taste specific genes expressed specifically in primate taste cells that were identified as taste specific genes by gene chip analysis, and shown to function as sodium channels in the literature. These genes, NALCN, NKAIN3 and TRPML3 were identified as being enriched in the top fraction of taste buds along with all other known taste receptor genes. Therefore, these genes are probable candidates for encoding a salty taste receptor. As described in detail, and substantiated by extensive functional data in a related patent application filed on even date as this application, cells expressing one of these genes, TRPML3 has been shown in functional assays and transgenic animals to be necessary for salty taste perception and to correspond to a salty taste receptor.

These ion channels were selected as probable candidates for the salty taste receptor based on a compilation of the rationales provide herein including the primate microarray/gene chip methods, the top versus bottom gene selection technique (these ion channels are all expressed in the top half of taste buds) and that they are identified in the qPCR methods as being expressed by isolated human taste bud cells. In addition all of these genes were selected as they correspond to previously reported putative sodium channels (but not known to be expressed specifically in taste cells much less to be expressed specifically in the top portion of the taste bud where a salty taste cell would be predicted to be present. The gene expression profiles for these 3 ion channels detected according to the inventive method is as follows:

NALCN, (aka VGCNL1), top vs. bottom ratio of 7.2, and TB vs. LE ratio of 11.2; TRPML3 (aka MCOLN3) top vs. bottom ratio of 1.6, and TB vs. LE ratio of 10.2; and NKAIN3 (aka FAM7D) which has a top vs. bottom ratio of 1.5, and TB vs. LE ratio of 3.3.

There has been information reported about all of these ion channels in the literature. For example, in Cell. 2007 Apr. 20; 129(2):371-83, the neuronal channel NALCN reportedly contributes resting sodium permeability and is required for normal respiratory rhythm. Also, Lu et al., describe that NALCN as a sodium leak channel. Further, in Kim et al., J. Biol. Chem. 2007 Oct. 25; [Epub ahead of print] the authors teach that a gain-of-function mutation in TRPML3 causes the mouse varitint-waddler phenotype. Also, Kim et al., (Id.) describes TRPML3 as a channel permeable to sodium after exposure of the channel to no/low sodium (consistent with saliva), and which was deemed by the inventors to potentially correlate with a putative salt receptor. Also, with respect to the NKAIN 3 gene, in Gorokhova et al., Human Mol. Genet. 2007 Oct. 15; 16(20):3394-410. Epub 2007 Jul. 2, this gene is reported as a member of a novel family of transmembrane proteins interacting with {beta} subunits of the Na,K-ATPase. Also, Gorokhova et al., (Id.) describe a *Drosophila* homologue of NKAIN3 as an amiloride-insensitive sodium channel, which the inventors also concluded would potentially be consistent with a putative salt receptor.

The identification of TRPML3 gene as encoding a polypeptide that is involved in salty taste and evidence that it functions as a salty taste receptor and the therapeutic applications of this gene are discussed extensively in the utility and PCT patent applications filed on the same date as this application, incorporated by reference in their entireties herein, and therefore is not discussed herein. However, this information is relevant as it substantiates the validity of the subject rationales for identifying and functionalizing the identified primate and human taste specific genes.

However, based thereon, NALCN, and NKAIN3 may still constitute other salty taste receptors expressed in taste bud cells and/or may modulate the function of TRPML3 and/or may associate with TRPML3 to produce a functional taste receptor. Based on the foregoing, NALCN, and NKAIN3 may constitute markers to identify salty taste receptor cells.

In addition, the inventors have obtained additional information concerning NALCN taste-specific gene identified by gene chip analysis and which gene was further found to be enriched in the top fraction of taste bud cells (along with all other known taste receptor genes).

Particularly, as described in the examples infra, it was demonstrated that NALCN is a taste-specific gene by end-point PCR using purified taste buds and lingual epithelial cells isolated by laser capture microdissection. It was found that NALCN is expressed in a novel, unique taste cell type distinct from sweet, bitter, umami, and sour taste cells by immunohistochemistry with a NALCN antibody.

Therefore, since NALCN is a taste-specific gene, is expressed in a novel taste cell type, (and has been reported to function as a sodium-channel), NALCN is a candidate salty taste receptor and/or a marker of the salty taste cell population. Since NALCN and TRPML3 are both expressed in novel taste cell types, NALCN and TRPML3 may be coexpressed in the same taste cell population. Accordingly, NALCN and TRPML3 may function together in a complex; or NALCN may function independently of TRPML3 as another salty taste receptor. For example, NALCN may function downstream of TRPML3 akin to how TRPM5 functions downstream of sweet, bitter, and umami receptors. In this manner, NALCN would be involved in the signal transduction pathway for salty taste but not constitute the primary salty taste sensory receptor.

This can be determined in mice. Rodents have 3 distinct taste cell types:

Type III cells correspond to sour cells (PKD2L1 positive, SNAP-25 positive);

Type II cells correspond to sweet, bitter, and umami cells (TRPM5-positive, IP3R3 positive); and Type I cells have no defined function.

As shown in the examples infra, the inventors have demonstrated that NALCN is not expressed in IP3R3 cells (Type II) or SNAP-25 cells (Type III) in rodent. Thus, NALCN expression is implicated in Type I cells, and Type I cells are candidate salty taste cells.

However, alternatively, Type I cells may correspond to immature taste cells and if so, would likely be coexpressed with TMEM44/MFSD4 in an immature taste cell population.

Therefore, based on the foregoing information, the invention further encompasses NALCN as an additional salty (or other taste such as metallic or fat) taste receptor candidate gene and based thereon the use thereof as a marker to identify these taste cells.

In addition, since NALCN is a sodium ion channel, and is expressed in the top half of taste buds in cells that have an indeterminate taste function NALCN may control the resting membrane potential and excitability of the taste cells it is expressed in. Related thereto, compounds that enhance or inhibit function of the NALCN channel may regulate the excitability of salty taste cells, i.e., TRPML3 cells.

Based on this modulatory property, compounds that enhance or inhibit function of the NALCN channel may increase and decrease salt perception respectively, e.g., alone or in combination with TRPML3.

Also, NALCN may associate with TRPML3 to form a salty taste receptor. (As shown in the related application ablation of TRPML3 expressing taste cells in Varitint mice results in inhibition of salty taste perception in these rodents and in vitro electrophysiological assays using this ion channel have confirmed that it is a functional sodium channels and may be used to identify TRPML3 blockers and enhancers which should modulate salty taste).

Moreover, NALCN can be used as a marker of type I taste cells, which likely include salty taste cells. Alternatively, as type I taste cells may function as precursor cells for sweet, bitter, umami and sour taste cells, modulation of NALCN function may control taste cell differentiation and development into mature taste cell types.

In addition, because TMEM44 and MFSD4 are markers of immature taste cells, NALCN may be expressed in the subset of immature taste cells expressing TMEM44/MFSD4.

Further, because type I taste cells may also function as glial (support) cells, modulation of NALCN function may indirectly control the activity of sweet, bitter, umami, and sour cells and, as a result, sweet, bitter, umami, and sour taste.

Also, compounds that enhance or inhibit function of NALCN may increase and decrease salt perception respectively.

In yet another aspect, this invention provides specific assays for identifying a compound having potential in vivo application for modulating human salty taste. One method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a *Xenopus* oocyte or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8 and in the Sequence Listing.

Recombinant Expression of Taste (Salty) Gene Identified Herein

To obtain high level expression of a cloned gene, such as those cDNAs encoding the subject genes, one typically subclones the gene into an expression vector that contains a strong promoter to direct transcription, a transcription/translation terminator, and if for a nucleic acid encoding a protein, a ribosome binding site for translational initiation. Suitable eukaryotic and prokaryotic promoters are well known in the art and described, e.g., in Sambrook et al., and Ausubel et al., supra. For example, bacterial expression systems for expressing the taste specific protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. For example, retroviral expression systems may be used in the present invention. As described infra, the subject putative salty taste affecting genes are preferably expressed in human cells such as HEK-293 cells which are widely used for high throughput screening.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the identified gene and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

The vectors used in the invention may include a regulatable promoter, e.g., tet-regulated systems and the RU-486 system (see, e.g., Gossen & Bujard, Proc. Nat'l Acad. Sci. USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a gene sequence under the direction of the polyhedrin promoter or other strong baculovirus promoters.

The elements that are typically included in expression vectors also include a replicon that functions in the particular host cell. In the case of *E. coli*, the vector may contain a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods may be used to produce bacterial, mammalian, yeast or insect cell lines that express large quantities of the desired taste specific protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the gene.

After the expression vector is introduced into the cells, the transfected cells are cultured under conditions favoring expression of the gene. In some instances, such polypeptides may be recovered from the culture using standard techniques identified below.

Assays for Modulators of Putative Taste Cell Specific Gene Products Identified Herein Modulation of a putative taste cell specific protein, can be assessed using a variety of in vitro and in vivo assays, including cell-based models as described above. Such assays can be used to test for inhibitors and activators of the protein or fragments thereof, and, consequently, inhibitors and activators thereof. Such modulators are potentially useful in medications or as flavorings to modulate salty or other taste modalities or taste in general or for usage as potential therapeutics for modulating a taste cell related function or phenotype involving one or several of the identified taste cell specific genes reported herein.

Assays using cells expressing the subject taste specific proteins, either recombinant or naturally occurring, can be performed using a variety of assays, in vitro, in vivo, and ex vivo, as described herein. To identify molecules capable of modulating activity thereof, assays are performed to detect the effect of various candidate modulators on activity preferably expressed in a cell.

The channel activity of ion channel proteins in particular can be assayed using a variety of assays to measure changes in ion fluxes including patch clamp techniques, measurement of whole cell currents, radiolabeled ion flux assays or a flux assay coupled to atomic absorption spectroscopy, and fluorescence assays using voltage-sensitive dyes or lithium or sodium sensitive dyes (see, e.g., Vestergarrd-Bogind et al., J. Membrane Biol. 88:67-75 (1988); Daniel et al., J. Pharmacol. Meth. 25:185-193 (1991); Hoevinsky et al., J. Membrane Biol. 137:59-70 (1994)). For example, a nucleic acid encoding a protein or homolog thereof can be injected into *Xenopus* oocytes or transfected into mammalian cells, preferably human cells such as HEK-293 cells. Channel activity can then be assessed by measuring changes in membrane polarization, i.e., changes in membrane potential.

A preferred means to obtain electrophysiological measurements is by measuring currents using patch clamp techniques, e.g., the "cell-attached" mode, the "inside-out" mode, and the "whole cell" mode (see, e.g., Ackerman et al., New Engl. J. Med. 336:1575-1595, 1997). Whole cell currents can be determined using standard methodology such as that described by Hamil et al., Pflugers. Archiv. 391:185 (1981).

Channel activity is also conveniently assessed by measuring changes in intracellular ion levels, i.e., sodium or lithium. Such methods are exemplified herein. For example, sodium flux can be measured by assessment of the uptake of radiolabeled sodium or by using suitable fluorescent dyes. In a typical microfluorimetry assay, a dye which undergoes a change in fluorescence upon binding a single sodium ion, is loaded into the cytosol of taste cell specific ion channel-expressing cells. Upon exposure to an agonist, an increase in cytosolic sodium is reflected by a change in fluorescence that occurs when sodium is bound.

The activity of the subject taste cell specific polypeptides can in addition to these preferred methods also be assessed using a variety of other in vitro and in vivo assays to determine functional, chemical, and physical effects, e.g., measuring the binding thereof to other molecules, including peptides, small organic molecules, and lipids; measuring protein and/or RNA levels, or measuring other aspects of the subject polypeptides, e.g., transcription levels, or physiological changes that affects the taste cell specific protein's activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors of KCNB proteins. Modulators thus identified are useful for, e.g., many diagnostic and therapeutic applications.

In Vitro Assays

Assays to identify compounds with modulating activity on the subject genes are preferably performed in vitro. The assays herein preferably use full length protein according to the invention or a variant thereof. This protein can optionally be fused to a heterologous protein to form a chimera. In the assays exemplified herein, cells which express the full-length polypeptide are preferably used in high throughput assays are used to identify compounds that modulate gene function. Alternatively, purified recombinant or naturally occurring protein can be used in the in vitro methods of the invention. In addition to purified protein or fragment thereof, the recombinant or naturally occurring taste cell protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands such as menthol). These in vitro assays include measuring changes in spectroscopic (e.g., fluorescence, absorbance, refractive index), hydrodynamic (e.g., shape), chromatographic, or solubility properties for the protein.

Preferably, a high throughput binding assay is performed in which the protein is contacted with a potential modulator and incubated for a suitable amount of time. A wide variety of modulators can be used, as described below, including small organic molecules, peptides, antibodies, and ligand analogs. A wide variety of assays can be used to identify modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. In such assays the known ligand is bound first, and then the desired compound i.e., putative enhancer is added. After the particular protein is washed, interference with binding, either of the potential modulator or of the known ligand, is determined. Often, either the potential modulator or the known ligand is labeled.

In addition, high throughput functional genomics assays can also be used to identify modulators of cold sensation by identifying compounds that disrupt protein interactions between the taste specific polypeptide and other proteins to which it binds. Such assays can, e.g., monitor changes in cell surface marker expression, changes in intracellular calcium, or changes in membrane currents using either cell lines or primary cells. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the protein encoded by a cDNA according to the invention can be isolated using a yeast two-hybrid system, mammalian two hybrid system, or phage display screen, etc. Targets so identified can be further used as bait in these assays to identify additional components that may interact with the particular ion channel, receptor or transporter protein which members are also targets for drug development (see, e.g., Fields et al., Nature 340:245 (1989); Vasavada et al., Proc. Nat'l Acad. Sci. USA 88:10686 (1991); Fearon et al., Proc. Nat'l Acad. Sci. USA 89:7958 (1992); Dang et al., Mol. Cell. Biol. 11:954 (1991); Chien et al., Proc. Nat'l Acad. Sci. USA 9578 (1991); and U.S. Pat. Nos. 5,283, 173, 5,667,973, 5,468,614, 5,525,490, and 5,637,463).

Cell-Based In Vivo Assays

In preferred embodiments, wild-type and mutant taste cell specific proteins are expressed in a cell, and functional, e.g., physical and chemical or phenotypic, changes are assayed to identify modulators that modulate function or which restore the function of mutant genes, e.g., those having impaired gating function. Cells expressing proteins can also be used in binding assays. Any suitable functional effect can be measured, as described herein. For example, changes in membrane potential, changes in intracellular lithium or sodium levels, and ligand binding are all suitable assays to identify potential modulators using a cell based system. Suitable cells for such cell based assays include both primary cells and recombinant cell lines engineered to express a protein. The subject taste cell specific proteins therefore can be naturally occurring or recombinant. Also, as described above, fragments of these proteins or chimeras with ion channel activity can be used in cell based assays. For example, a transmembrane domain of a ion channel or GPCR or transporter gene according to the invention can be fused to a cytoplasmic domain of a heterologous protein, preferably a heterologous ion channel protein. Such a chimeric protein would have ion channel activity and could be used in cell based assays of the invention. In another embodiment, a domain of the taste cell specific protein, such as the extracellular or cytoplasmic domain, is used in the cell-based assays of the invention.

In another embodiment, cellular polypeptide levels of the particular target taste polypeptide can be determined by measuring the level of protein or mRNA. The level of protein or proteins related to ion channel activation are measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatic ally labeled antibodies, and the like, as described herein.

Alternatively, protein expression can be measured using a reporter gene system. Such a system can be devised using a promoter of the target gene operably linked to a reporter gene such as chloramphenicol acetyltransferase, firefly luciferase, bacterial luciferase, beta-galactosidase and alkaline phosphatase. Furthermore, the protein of interest can be used as an indirect reporter via attachment to a second reporter such as red or green fluorescent protein (see, e.g., Mistili & Spector, Nature Biotechnology 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to signal transduction can be measured. An activated or inhibited ion channel or GPCR or transporter will potentially alter the properties of target enzymes, second messengers, channels, and other effector proteins. The examples include the activation of phospholipase C and other signaling systems. Downstream consequences can also be examined such as generation of diacyl glycerol and IP3 by phospholipase C.

Assays for ion channel activity include cells that are loaded with ion or voltage sensitive dyes to report activity, e.g., by observing sodium influx or intracellular sodium release. Assays for determining activity of such receptors can also use known agonists and antagonists for these receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. Radiolabeled ion flux assays or a flux assay coupled to atomic absorption spectroscopy can also be used.

Animal Models

Animal models also find potential use in screening for modulators of gene activity. Transgenic animal technology results in gene overexpression, whereas siRNA and gene knockout technology results in absent or reduced gene expression following homologous recombination with an appropriate gene targeting vector. The same technology can also be applied to make knock-out cells. When desired, tissue-specific expression or knockout of the target gene may be necessary. Transgenic animals generated by such methods find use as animal models of responses related to the gene target. For example such animals expressing a gene or genes according to the invention may be used to derive supertaster phenotypes such as for use in screening of chemical and biological toxins, rancid/spoiled/contaminated foods, and beverages or for screening for therapeutic compounds that modulate taste stem cell differentiation.

Knock-out cells and transgenic mice can be made by insertion of a marker gene or other heterologous gene into an endogenous gene site in the mouse genome via homologous recombination. Such mice can also be made by substituting an endogenous gene with a mutated version of the target gene, or by mutating an endogenous gene, e.g., by exposure to known mutagens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., Science 244:1288 (1989)). Chimeric targeted mice can be derived according to Hogan et al., Manipulating the Mouse Embryo: A Laboratory Manual (1988) and Teratocarcinomas and Embryonic Stem Cells: A Practical Approach (Robertson, ed., 1987).

Candidate Modulators

The compounds tested as modulators of the putative taste related proteins or other non-taste related functions and phenotypes involving taste cells can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of a protein. Typically, test compounds will be small organic molecules, peptides, lipids, and lipid analogs. In one embodiment, the compound is a menthol analog, either naturally occurring or synthetic.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md.). C. Solid State and Soluble High Throughput Assays.

Additionally soluble assays can be effected using a target taste specific protein, or a cell or tissue expressing a target taste protein disclosed herein, either naturally occurring or recombinant. Still alternatively, solid phase based in vitro assays in a high throughput format can be effected, where the protein or fragment thereof, such as the cytoplasmic domain, is attached to a solid phase substrate. Any one of the assays described herein can be adapted for high throughput screening, e.g., ligand binding, calcium flux, change in membrane potential, etc.

In the high throughput assays of the invention, either soluble or solid state, it is possible to screen several thousand different modulators or ligands in a single day. This methodology can be used for assaying proteins in vitro, or for cell-based or membrane-based assays comprising an protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of, e.g., peptides); Geysen et al., J. Immunol. Meth. 102:259-274 (1987) (describing synthesis of solid phase components on pins); Frank & Doring, Tetrahedron 44:6031-6040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753-759 (1996) (all describing arrays of biopolymers fixed to solid substrates). Non-chemical approaches for fixing tag binders to substrates include other common methods, such as heat, cross-linking by UV radiation, and the like.

Having described the invention supra, the examples provided infra further illustrate some preferred embodiments of the invention. These examples are provided only for purposes of illustration and should not be construed as limiting the subject invention.

Practical Applications of the Invention

Compounds which modulate, preferably enhance the activity of genes identified herein in the Tables have important implications in modulation of human salty taste and potentially other taste modalities or taste in general. In addition these compounds are potentially useful in therapeutic applications involving other taste cell related functions and phenotypes such as taste cell turnover, digestive diseases, digestive function, regulation of metabolism, regulation of immunity in the oral cavity and/or digestive system and the like.

Compounds which activate taste ion channels in taste papillae on the tongue can be used to enhance salt sensation by promoting $Na^+$ transport into taste bud cells. This has obvious consumer applications in improving the taste and palatability of low salt foods and beverages.

In addition the genes and gene products herein can be used as markers for identifying, isolating or enriching specific taste cell types or lineages including sweet, bitter, umami, sour, salt, fat, metallic et al.

Further the genes and gene products specific to taste cells identified herein can be used to identify compounds that modulate apoptosis of taste cells, modulate transcription factors that control taste receptor expression, modulate bitter receptor expression e.g., to alleviate the off-taste of some vegetables, medicines, coffee, and the like; modulate autocrine/paracrine modulation of taste cell development, prolong taste bud lifetime, yield supertaster animal phenotypes for use in screening such as for bioterrorism or animals for use in screening for compounds that induce the activation and differentiation of stem cells into taste cells in vivo.

In addition the subject genes and gene products and cells which express may be used to identify ancillary taste receptors or primary taste receptors such as fat or metallic taste cells.

Also the subject genes, gene products and cells which express same can be used in screens to identify compounds that affect digestive function such s gastric motility, food detection, food absorption or the production of digestive fluids, peptides, hormones or enzymes such as Glucagon Like Peptide-1, Glucose Dependent Insulinotropic polypeptide, pepsin, secretin, amylase, saliva, et al.

Also the subject genes, gene products and cells which express same may be used to screen for compounds that affect trafficking of taste receptors to and from the apical membrane/taste pore region to enhance or repress general or specific tastes, regulation of taste cell action potential firing frequency/membrane potential to control the intensity of general or specific tastes, regulation of neurotransmitter release to afferent nerve to control the intensity of general or specific taste, and autocrine/paracrine modulation of taste receptor function.

Further the subject genes, gene products and cells which express same can be used to identify compounds that regenerate taste cells such as in geriatric individuals or patients with cancer, chemotherapy radiation, injury or surgery affecting taste, drug-induced dysgeusia, ageusia, and for alleviating taste bud loss.

Still further the subject genes and gene products and cells which express same can be used to screen for compounds that affect oral hygiene, halitosis, detoxification of noxious substances in the oral cavity, and neutralization/elimination of bacteria, viruses, and other immunogens in the saliva/mouth or digestive tract.

Yet additionally the subject genes, gene products and cells which express same can be used in screens to identify compounds that affect saliva production and composition and treatment of dry mouth in conditions such as xerostomia and Sjogren's disease, in autoimmune or inflammatory gastrointestinal diseases, IBD, ulcerative colitis, and diverticulitis and cancers affecting the oral cavity and digestive tract.

The following examples were effected using the materials and methods described supra. These examples are put forth so as to provide those of ordinary skill in the art with a complete disclosure and description of how to make and use the subject invention, and are not intended to limit the scope of what is regarded as the invention.

EXAMPLES

Example 1

This experimental example the results of which are contained in FIG. 1 is exemplary of the results obtained with laser capture microdissection (LCM) on primate fungiform (FG) taste tissue (top row) and lingual epithelium (LE) non-taste tissue (bottom row). Shown in the top row, in the left image is FG tissue before LCM with a single FG taste bud. The middle image in FIG. 1 shows FG tissue after LCM where single FG taste bud has been removed. The right image in FIG. 1 shows collected and isolated FG taste bud used for molecular biology experiments to discover taste-specific genes. Shown in the bottom row, in the left image is tissue before LCM with LE from anterior tongue surface. The middle image in the same Figure shows tissue after LCM where a region of LE has been removed. Shown in the right image is the collected and isolated LE region used for molecular biology experiments to discover taste-specific genes.

Example 2

Figure 2:
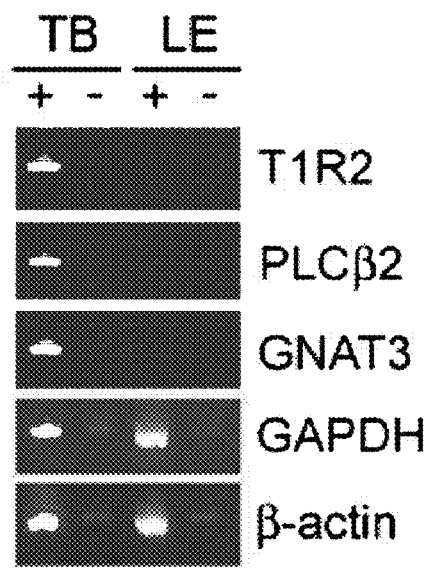
FIG. 2 contains an example of PCR quality control of primate taste and lingual cells collected by LCM. Taste bud cells (TB), but not lingual epithelial cells (LE), specifically express the known taste-specific genes T1R2 (a component of the sweet receptor), PLCbeta2 (an enzyme involved in sweet, bitter, and umami taste detection), and GNAT3 (i.e. gustducin, a G-protein alpha subunit involved in sweet, bitter, and umami taste detection). By contrast, both taste and lingual cells express the ubiquitous housekeeping genes GAPDH and beta-actin, indicating that taste and lingual cell RNA is intact and of high quality. '+' indicates reverse transcription and '−' indicates no reverse transcription was performed.

This experimental example the results of which are contained in FIG. 2 is exemplary of PCR quality control of primate taste and lingual cells collected by LCM. It can be seen therefrom that taste bud cells (TB), but not lingual epithelial cells (LE), specifically express the known taste-specific genes T1R2 (a component of the sweet receptor), PLCbeta2 (an enzyme involved in sweet, bitter, and umami taste detection), and GNAT3 (i.e. gustducin, a G-protein alpha subunit involved in sweet, bitter, and umami taste detection). By contrast, it can be seen that both taste and lingual cells express the ubiquitous housekeeping genes GAPDH and beta-actin, indicating that taste and lingual cell RNA is intact and of high quality. '+' indicates reverse transcription and '−' indicates no reverse transcription was performed.

Example 3

Figure 3:
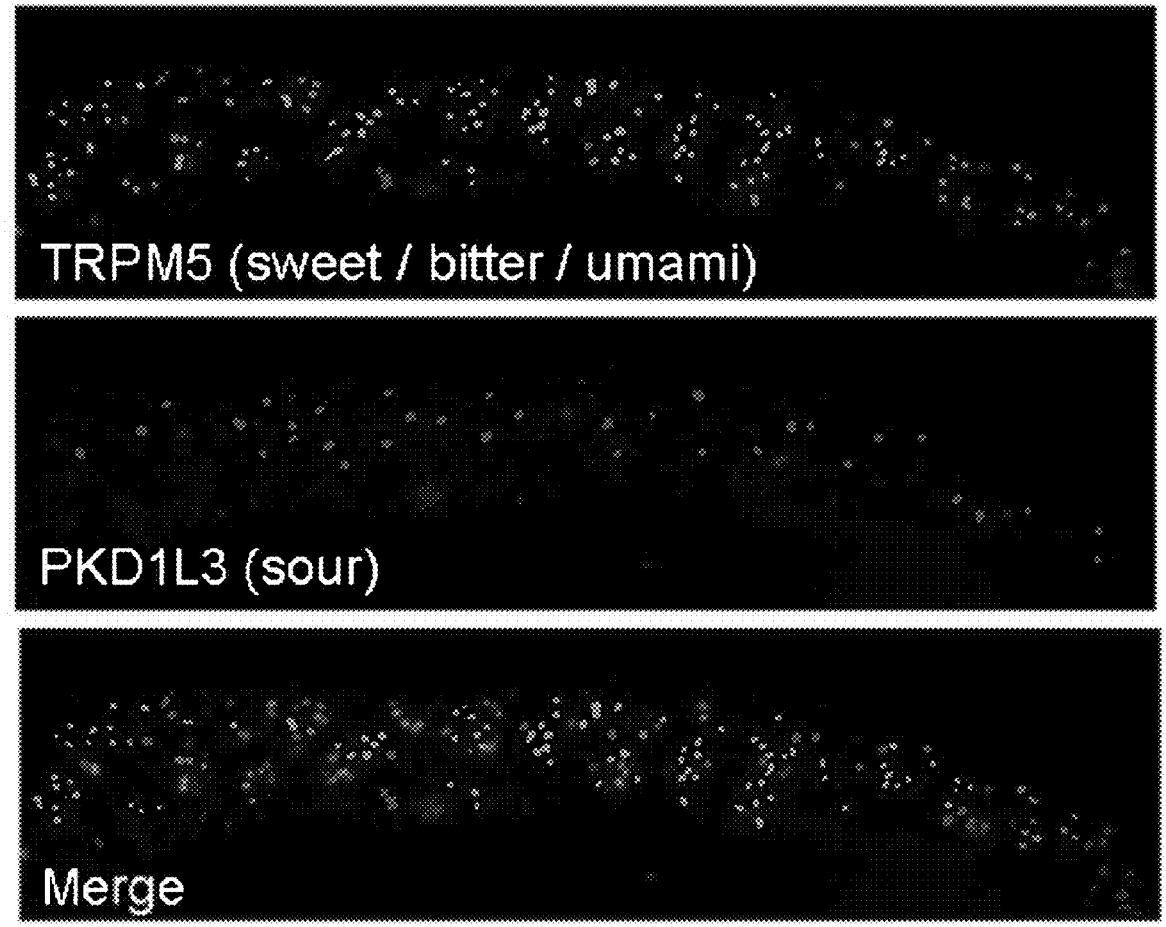
FIG. 3 contains an example of double labeling in situ hybridization illustrating expression of TRPM5 and PKD1L3 in different taste cells in primate circumvallate (CV) taste tissue. TRPM5 (top; green) is not detectable in cells expressing PKD1L3 (middle; red). Overlay of TRPM5 and PKD1L3 signals is depicted in the bottom image. Note that TRPM5 and PKD1L3 signals are present in different taste cells. TRPM5 is expressed in cells responsible for sweet, bitter, and umami taste, whereas PKD1L3 is expressed in cells responsible for sour taste.

This example relates to the experiment contained in FIG. 3. Shown therein is an example of double labeling in situ hybridization illustrating expression of TRPM5 and PKD1L3 in different taste cells in primate circumvallate (CV) taste tissue.

It can be seen that TRPM5 (top; green) is not detectable in cells expressing PKD1L3 (middle; red). The overlay of TRPM5 and PKD1L3 signals is depicted in the bottom image. It can further be seen that TRPM5 and PKD1L3 signals are present in different taste cells. Particularly, TRPM5 is expressed in cells responsible for sweet, bitter, and umami taste, whereas PKD1L3 is expressed in cells responsible for sour taste.

Example 4

Figure 4:
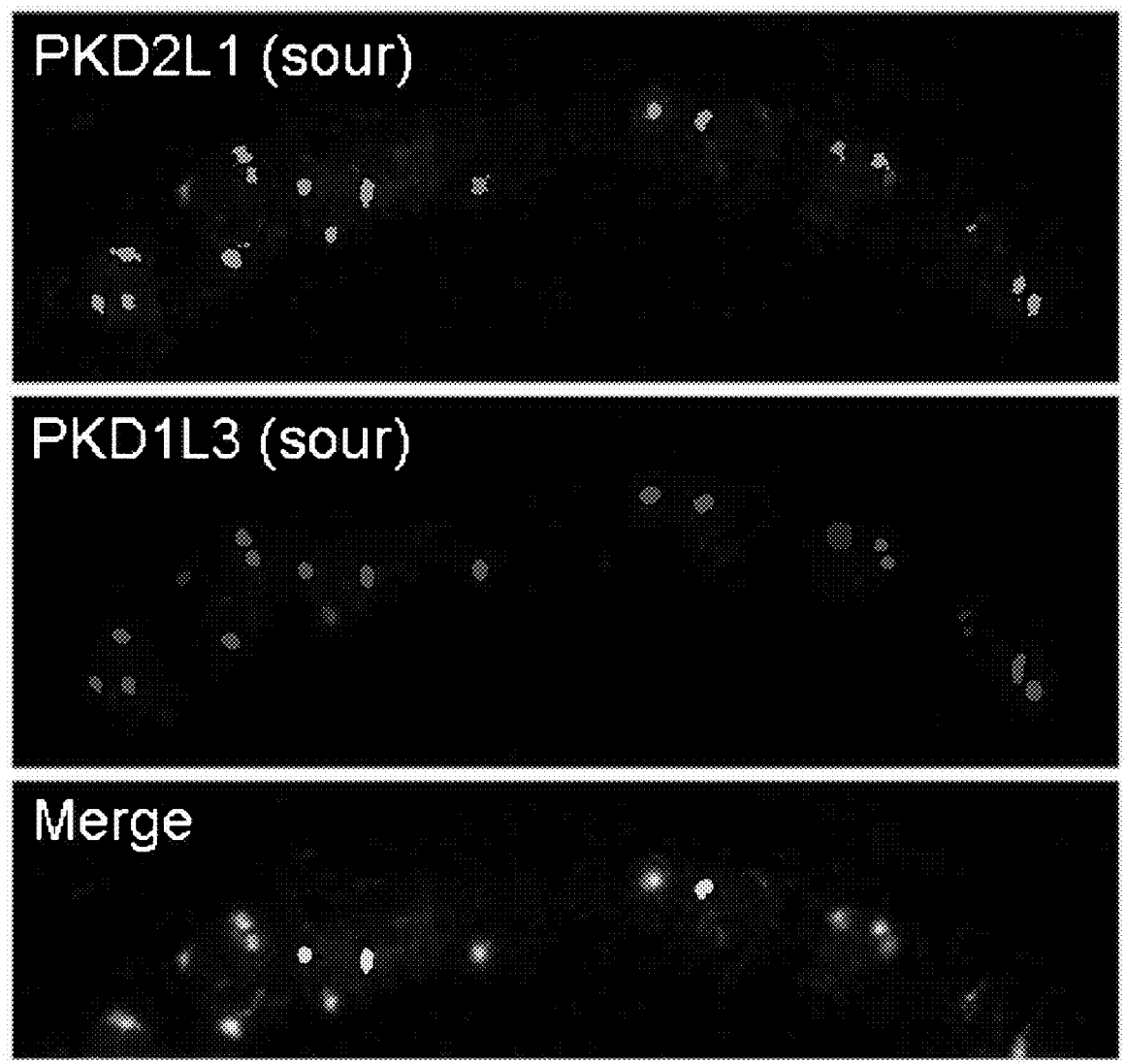
FIG. 4 contains an example of double labeling in situ hybridization illustrating coexpression of PKD2L1 and PKD1L3 in the same taste cells in primate circumvallate (CV) taste tissue. PKD2L1 (top; green) is coexpressed in cells expressing PKD1L3 (middle; red). Overlay of PKD2L1 and PKD1L3 signals is depicted in the bottom image in yellow. Note that both PKD2L1 and PKD1L3 signals are present in the same taste cells. Both PKD2L1 and PKD1L3 are expressed in cells responsible for sour taste.

This example which is contained in FIG. 4 shows a double labeling in situ hybridization illustrating coexpression of PKD2L1 and PKD1L3 in the same taste cells in primate circumvallate (CV) taste tissue. It can be seen therein that PKD2L1 (top; green) is coexpressed in cells expressing PKD1L3 (middle; red). The overlay of PKD2L1 and PKD1L3 signals is depicted in the bottom image in yellow. It can further be seen that both PKD2L1 and PKD1L3 signals are present in the same taste cells. Both PKD2L1 and PKD1L3 are expressed in cells responsible for sour taste.

Example 5

Figure 5:
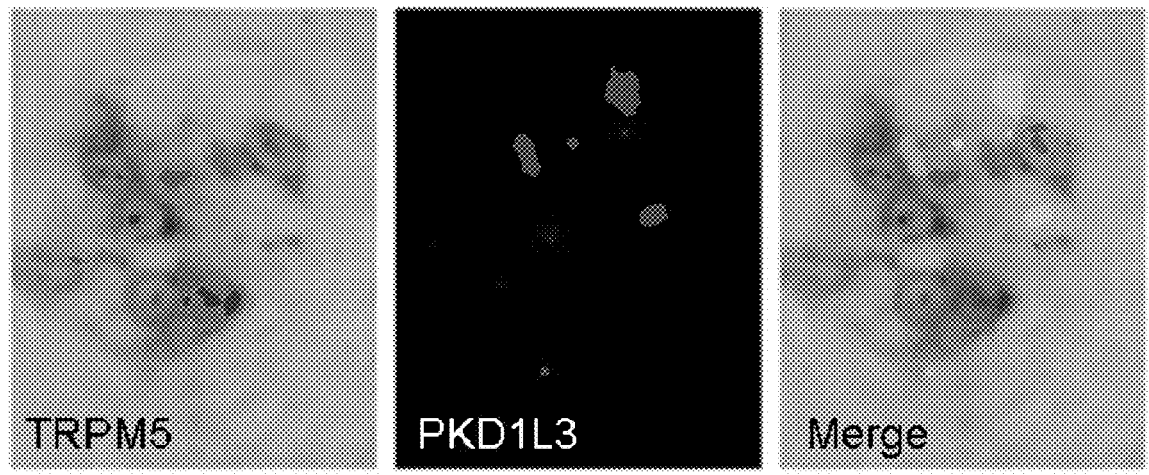
FIG. 5 contains an example of double labeling in situ hybridization illustrating expression of TRPM5 and PKD1L3 in different taste cells in primate fungiform (FG) taste tissue. TRPM5 (left; purple stain) is not detectable in cells expressing PKD1L3 (middle; red). Overlay of TRPM5 and PKD1L3 signals is depicted in the left image. Note that TRPM5 and PKD1L3 signals are present in different taste cells. TRPM5 is expressed in cells responsible for sweet, bitter, and umami taste, whereas PKD1L3 is expressed in cells responsible for sour taste tissue.

This example relates to the experiments contained in FIG. 5. This experiment is an example of double labeling in situ hybridization illustrating expression of TRPM5 and PKD1L3 in different taste cells in primate fungiform (FG) taste tissue. It can be seen therein that TRPM5 (left; purple stain) is not detectable in cells expressing PKD1L3 (middle; red). The overlay of TRPM5 and PKD1L3 signals is depicted in the left image. It can further be seen therein that TRPM5 and PKD1L3 signals are present in different taste cells. Particularly, the Figure shows that TRPM5 is expressed in cells responsible for sweet, bitter, and umami taste, whereas PKD1L3 is expressed in cells responsible for sour taste.

Example 6

Figure 6:
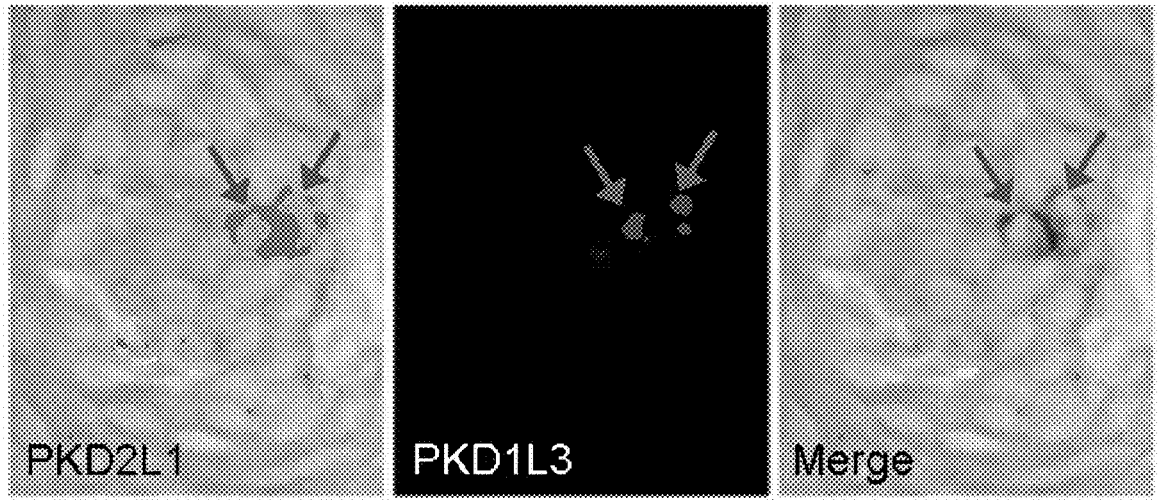
FIG. 6 contains an example of double labeling in situ hybridization illustrating coexpression of PKD2L1 and PKD1L3 in the same taste cells in primate fungiform (FG) taste tissue. PKD2L1 (left; purple stain) is coexpressed in cells expressing PKD1L3 (middle; red). Overlay of PKD2L1 and PKD1L3 signals is depicted in the right image. Note that both PKD2L1 and PKD1L3 signals are present in the same taste cells. Both PKD2L1 and PKD1L3 are expressed in cells responsible for sour taste.

This example relates to the results of a double labeling in situ hybridization experiment contained in FIG. 6. The Figure illustrates the coexpression of PKD2L1 and PKD1L3 in the same taste cells in primate fungiform (FG) taste tissue. It can further be seen that PKD2L1 (left; purple stain) is coexpressed in cells expressing PKD1L3 (middle; red). The overlay of PKD2L1 and PKD1L3 signals is depicted in the right image. The Figure further reveals that that both PKD2L1 and PKD1L3 signals are present in the same taste cells. Both PKD2L1 and PKD1L3 are expressed in cells responsible for sour taste.

Example 7

Figure 7:
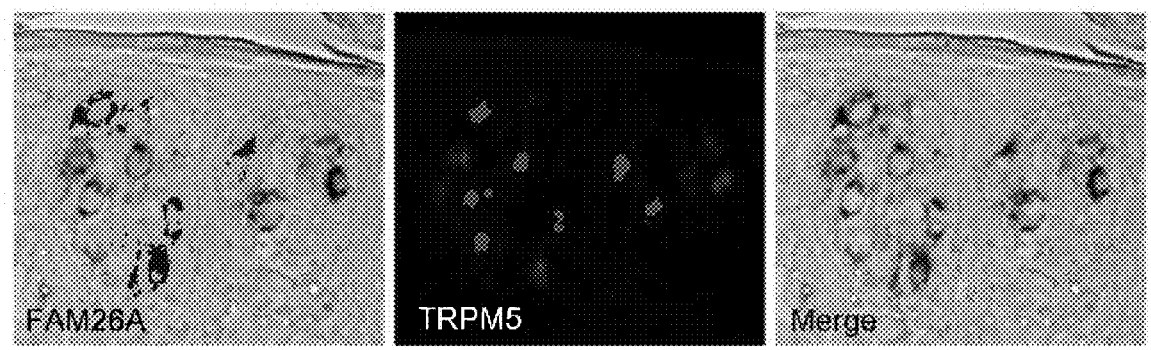
FIG. 7 contains an example of a double labeling hybridization experiment using primate circumvallate papilla. The results in FIG. 7 reveal that FAM26A (purple color; left image) colocalizes with TRPM5 (red; middle image). The results contained in the figure also show that FAM26A cells express TRPM5, a marker of sweet, umami, and bitter taste cells (merged image on the right).

This example relates to the double labeling hybridization experiment contained in FIG. 7. This experiment which again involved double label in situ hybridization of primate circumvallate papilla revealed that FAM26A (purple color; left image) colocalizes with TRPM5 (red; middle image). The results contained in the figure also show that FAM26A cells express TRPM5, a marker of sweet, umami, and bitter taste cells (merged image on the right).

Example 8

Figure 8:
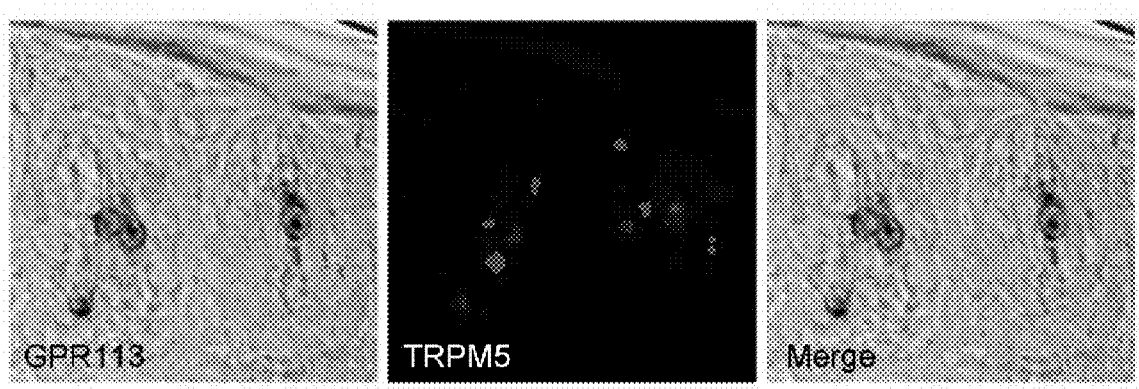
FIG. 8 contains another double label in situ hybridization experiment. This hybridization experiment which again used primate circumvallate papilla revealed that the taste cell specific gene GPR113 (purple color; left image) colocalizes with a subset of TRPM5 cells (red; middle image). It can be seen from the figure that that only a fraction of cells expressing TRPM5, a marker of sweet, umami, and bitter taste cells, also express GPR113 (merged image on the right), but that all GPR113 cells express TRPM5. Two taste buds are shown.

This example relates to the double label in situ hybridization experiment contained in FIG. 8. This hybridization experiment which again used primate circumvallate papilla revealed that the taste cell specific gene GPR113 (purple color; left image) colocalizes with a subset of TRPM5 cells (red; middle image). It can be seen from the figure that that only a fraction of cells expressing TRPM5, a marker of sweet, umami, and bitter taste cells, also express GPR113 (merged image on the right), but that all GPR113 cells express TRPM5. Two taste buds are shown.

Example 9

Figure 9:
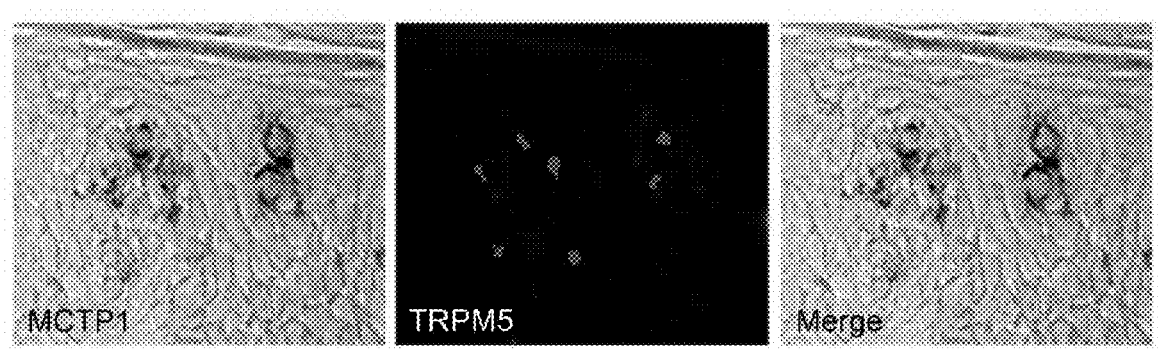
FIG. 9 contains another double hybridization experiment using primate circumvallate papilla cells. The results contained in the Figure reveal that MCTP1 (purple color; left image), a taste cell specific gene, colocalizes with TRPM5 (red; middle image). It can be further seen that MCTP1 cells express TRPM5, a marker of sweet, umami, and bitter taste cells (merged image on the right). Two taste buds are shown in the Figure.

The experiment contained in FIG. 9 is another double hybridization experiment using primate circumvallate papilla cells. The results contained in the Figure reveal that MCTP1 (purple color; left image), a taste cell specific gene, colocalizes with TRPM5 (red; middle image). It can be seen that MCTP1 cells express TRPM5, a marker of sweet, umami, and bitter taste cells (merged image on the right). Two taste buds are shown in the Figure.

Example 10

Figure 10:
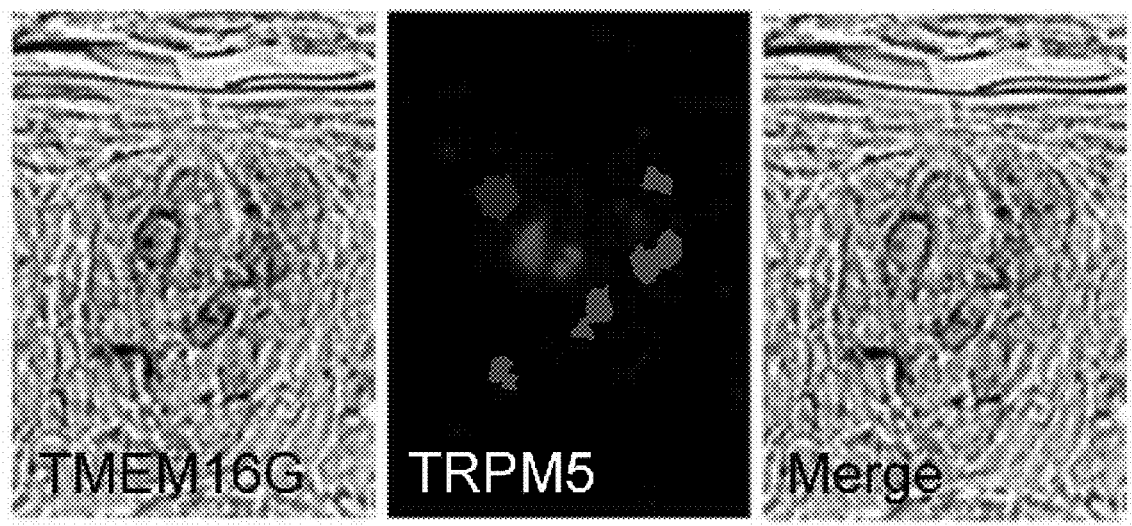
FIG. 10 contains another double label in situ hybridization experiment using primate circumvallate papilla cells. The results in FIG. 10 show that TMEM16G (purple color; left image) colocalizes with a subset of TRPM5 cells (red; middle image). It can also be seen that only a fraction of cells expressing TRPM5, a marker of sweet, umami, and bitter taste cells, also express TMEM16G (merged image on the right), but that all TMEM16G cells express TRPM5.

This example relates to another double label in situ hybridization of primate circumvallate papilla cells. The results in FIG. 10 show that TMEM16G (purple color; left image) colocalizes with a subset of TRPM5 cells (red; middle image). It can also be seen that only a fraction of cells expressing TRPM5, a marker of sweet, umami, and bitter taste cells, also express TMEM16G (merged image on the right), but that all TMEM16G cells express TRPM5.

Example 11

Figure 11:
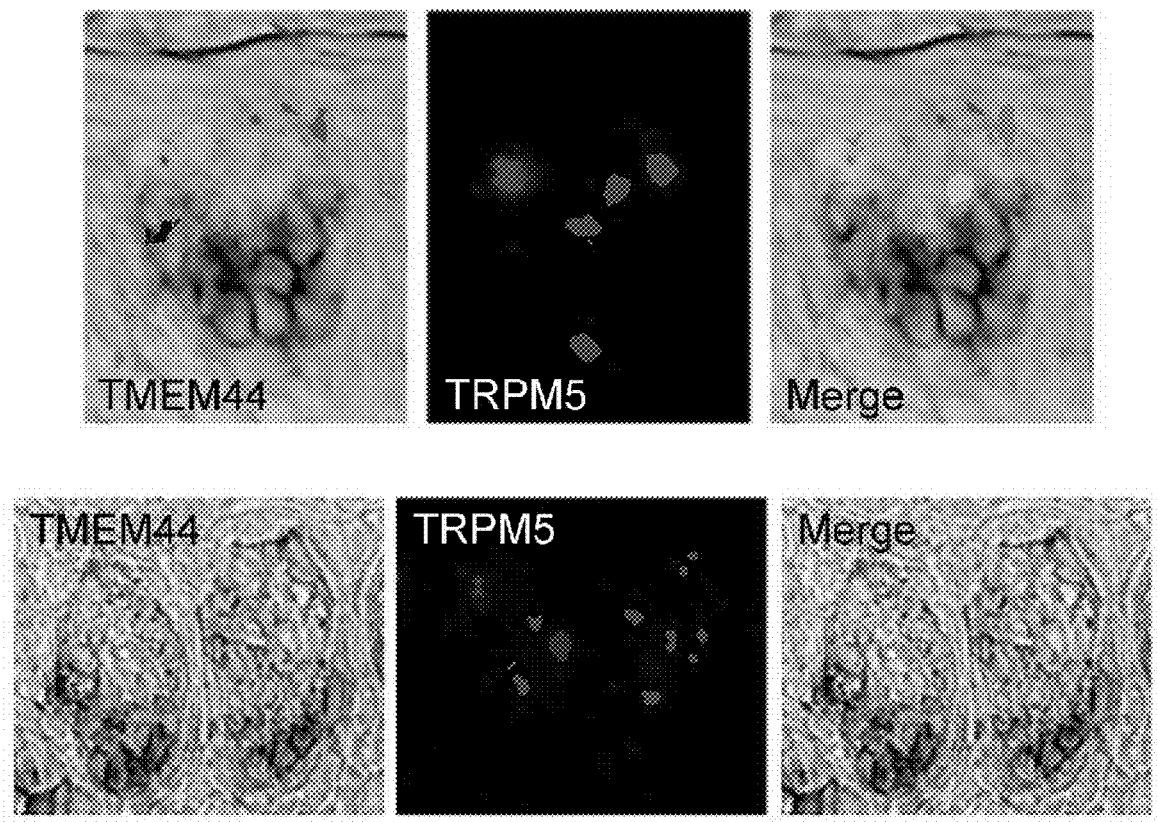
FIG. 11 contains another double label in situ hybridization experiment using primate circumvallate papilla cells. The results contained in FIG. 11 show that TMEM44 (purple color; left image), a taste cell specific gene, does not colocalize with TRPM5 (red; middle image). It can be seen from the results in the figure that TMEM44 cells do not express TRPM5, a marker of sweet, umami, and bitter taste cells (merged image on the right). Two taste buds are shown in the figure.

This example relates to another double label in situ hybridization of primate circumvallate papilla cells. The results contained in FIG. 11 show that TMEM44 (purple color; left image), a taste cell specific gene, does not colocalize with TRPM5 (red; middle image). It can be seen from the results in the figure that TMEM44 cells do not express TRPM5, a marker of sweet, umami, and bitter taste cells (merged image on the right). Two taste buds are shown in the figure.

Example 12

Figure 12:
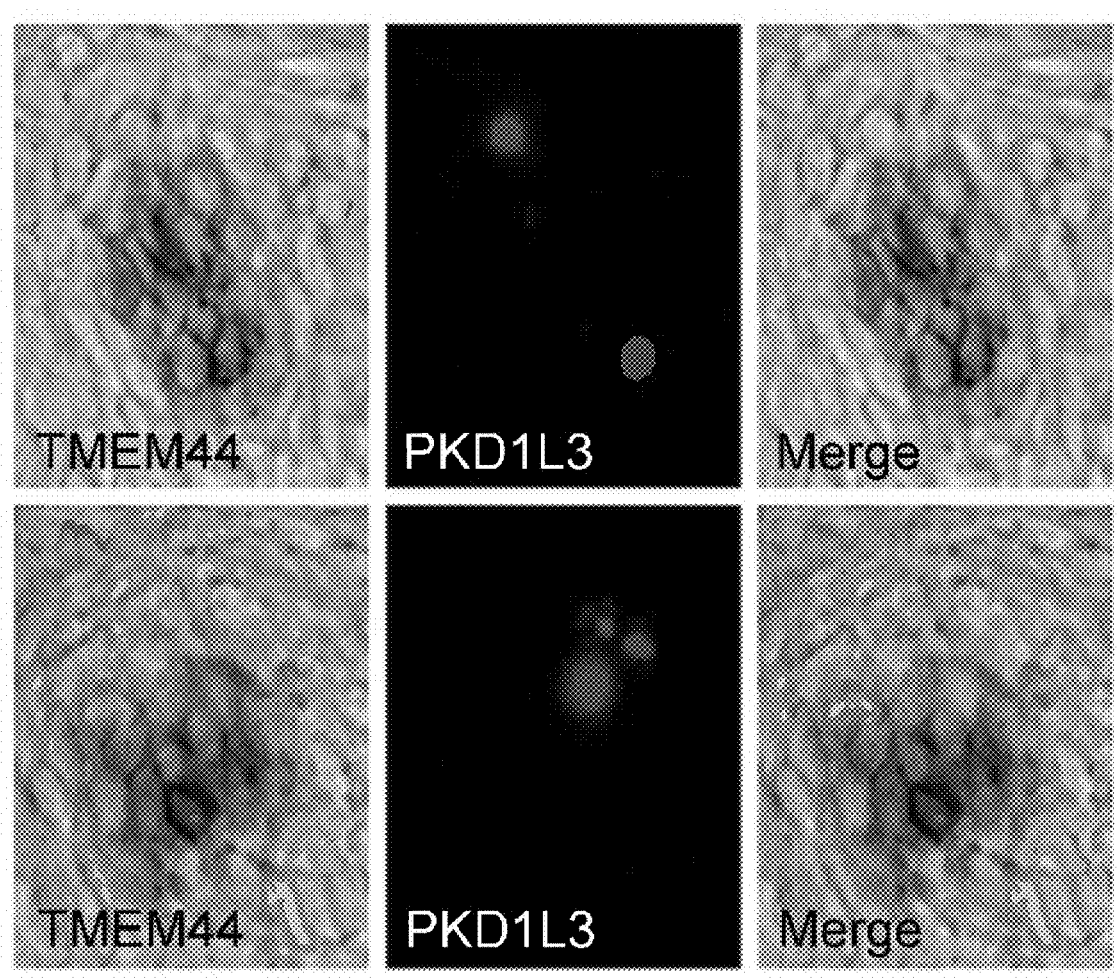
FIG. 12 contains another double label in situ hybridization experiment of primate circumvallate papilla cells. The results contained therein reveal that TMEM44 (purple color; left image) does not colocalize with PKD1L3 (red; middle image). It can also be seen therein that TMEM44 cells do not express PKD1L3, a market of sour taste cells (merged image on the right). Two taste buds are shown.

This example relates to the double label in situ hybridization of primate circumvallate papilla cells contained in FIG. 12. The results contained therein reveal that TMEM44 (purple color; left image) does not colocalize with PKD1L3 (red; middle image). It can also be seen that TMEM44 cells do not express PKD1L3, a marker of sour taste cells (merged image on the right). Two taste buds are shown.

Example 13

Figure 13:
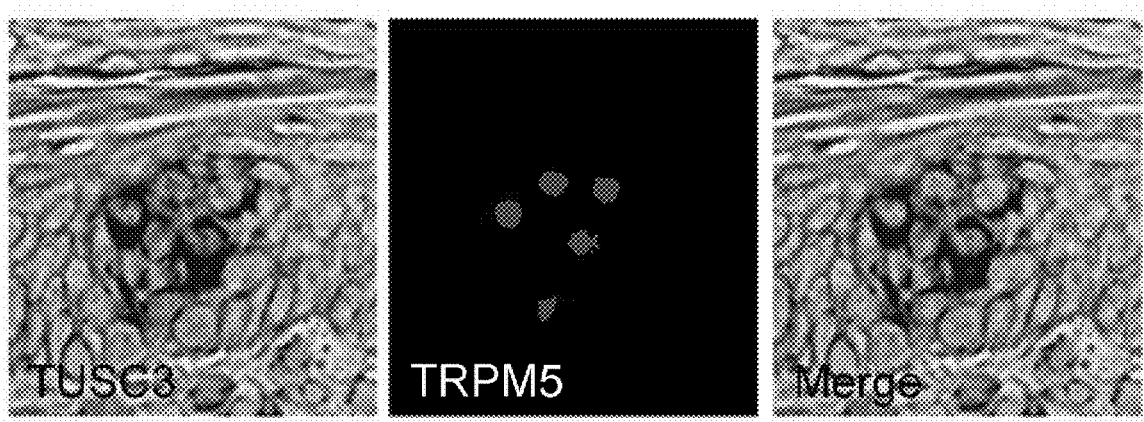
FIG. 13 contains another double label in situ hybridization experiment using primate circumvallate papilla cells. The results which are contained in FIG. 13 show that TUSC3 (purple color; left image), a taste cell specific gene, colocalizes with TRPM5 (red; middle image). It can also be seen that TUSC3 cells express TRPM5, a marker of sweet, umami, and bitter taste cells (merged image on the right).
Figure 14:
FIG. 14 shows that GPR113 is not expressed in T1R1 umami cells. Double label in situ hybridization of primate circumvallate papilla showing that GPR113 (purple color; left image) does not colocalize with T1R1 (red; middle image). Note that GPR113 and T1R1, a marker of umami cells, are in different taste cells (merged image on the right).
Figure 15:
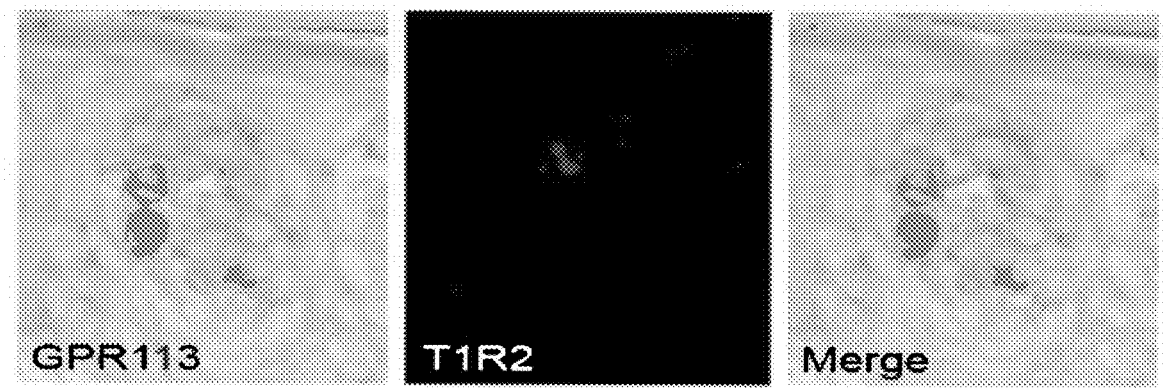
FIG. 15 shows that GPR113 is not expressed in T1R2 sweet cells. Double label in situ hybridization of primate circumvallate papilla showing that GPR113 (purple color; left image) does not colocalize with T1R2 (red; middle image). Note that GPR113 and T1R2, a marker of sweet cells, are in different taste cells (merged image on the right).
Figure 16:
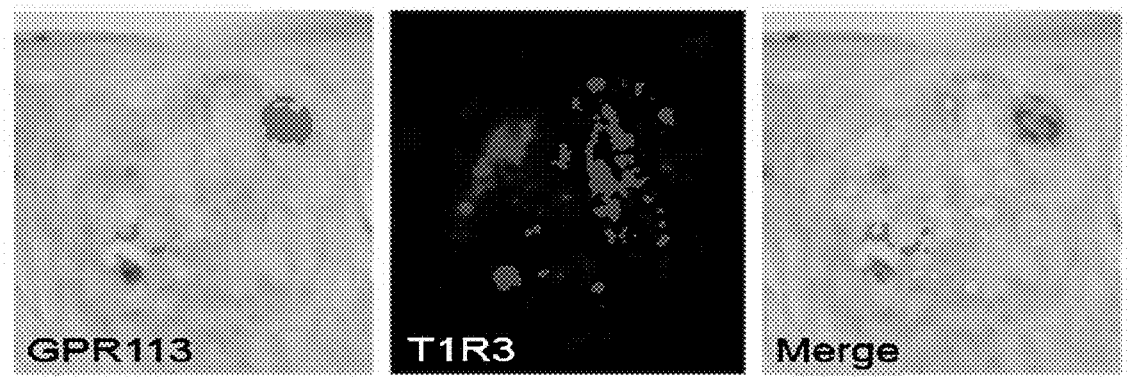
FIG. 16 shows that GPR113 is expressed in a subset of T1R3 cells. Double label in situ hybridization of primate circumvallate papilla showing that GPR113 (purple color; left image) does colocalize with a subset of T1R3 cells (red; middle image). Note that GPR113 is always expressed in cells with T1R3, but that there are T1R3 cells that do not express GPR113 (merged image on the tight). These T1R3 cells that do not express GPR113 likely coexpress either T1R1 or T1R2. The T1R3 only cells are a new population of taste cells that coexpress GPR113.
Figure 17:
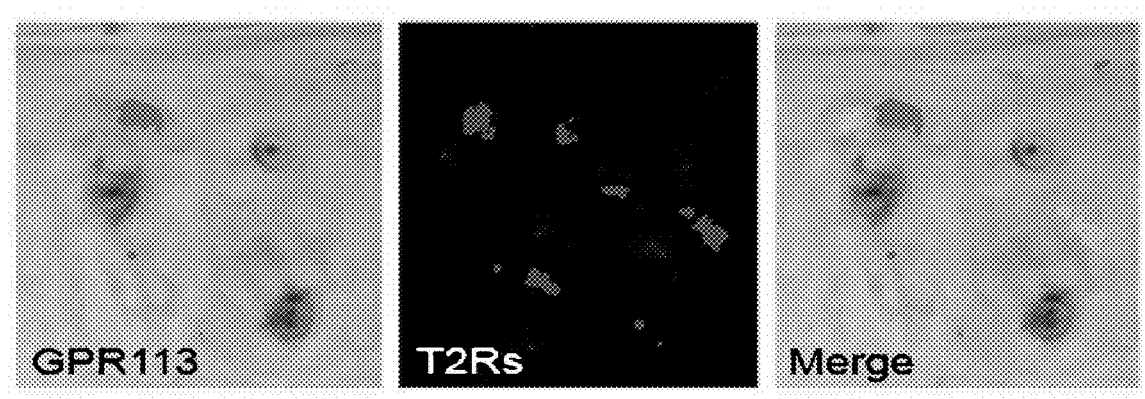
FIG. 17 shows that GPR113 is not expressed in T2R bitter cells. Double label in situ hybridization of primate circumvallate papilla showing that GPR113 (purple color; left image) does not colocalize with T2R (red; middle image). Note that GPR113 and T2R, a marker of bitter cells, are in different taste cells (merged image on the right).
Figure 18:
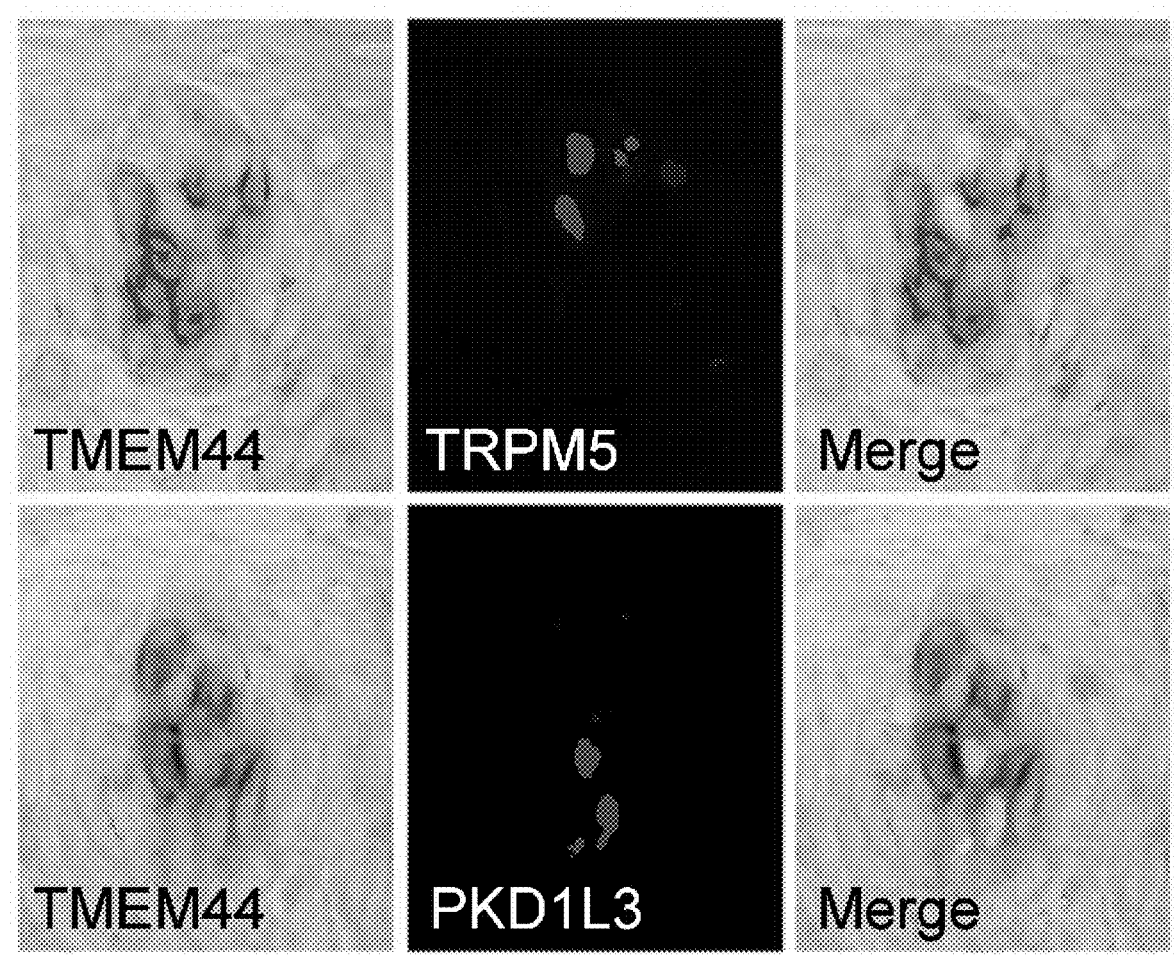
FIG. 18 shows that TMEM44 is not expressed in TRPM5 or PKD1L3 cells in fungiform taste buds. Double label in situ hybridization of primate fungiform papilla from the front of the tongue showing that TMEM44 (blue/purple color; left images) does not colocalize with TRPM5 (red; middle top image) or PKD1L3 (red; middle bottom image). Note that TMEM44 cells do not express TRPM5, a marker of sweet, umami, and bitter taste cells, or PKD1L3, a marker of sour cells, in the merged images on the right.
Figure 19:
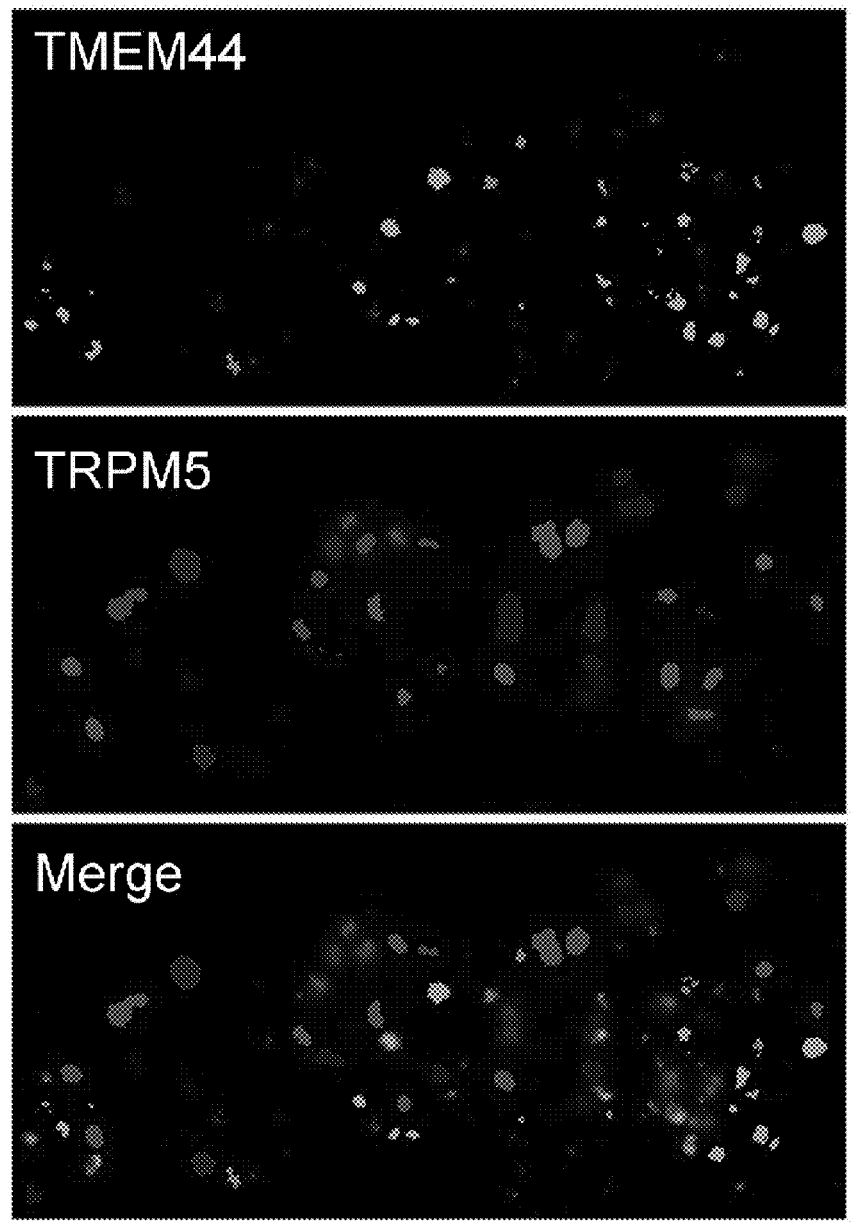
FIG. 19 shows that TMEM44 is not expressed in TRPM5 cells in circumvallate papilla. Double fluorescent label in situ hybridization of primate circumvallate papilla at the back of the tongue showing that TMEM44 (green cells; top image) does not colocalize with TRPM5 (red cells; middle image). Note that TMEM44 cells do not express TRPM5, a marker of sweet, umami, and bitter taste cells (merged image on the bottom).
Figure 20:
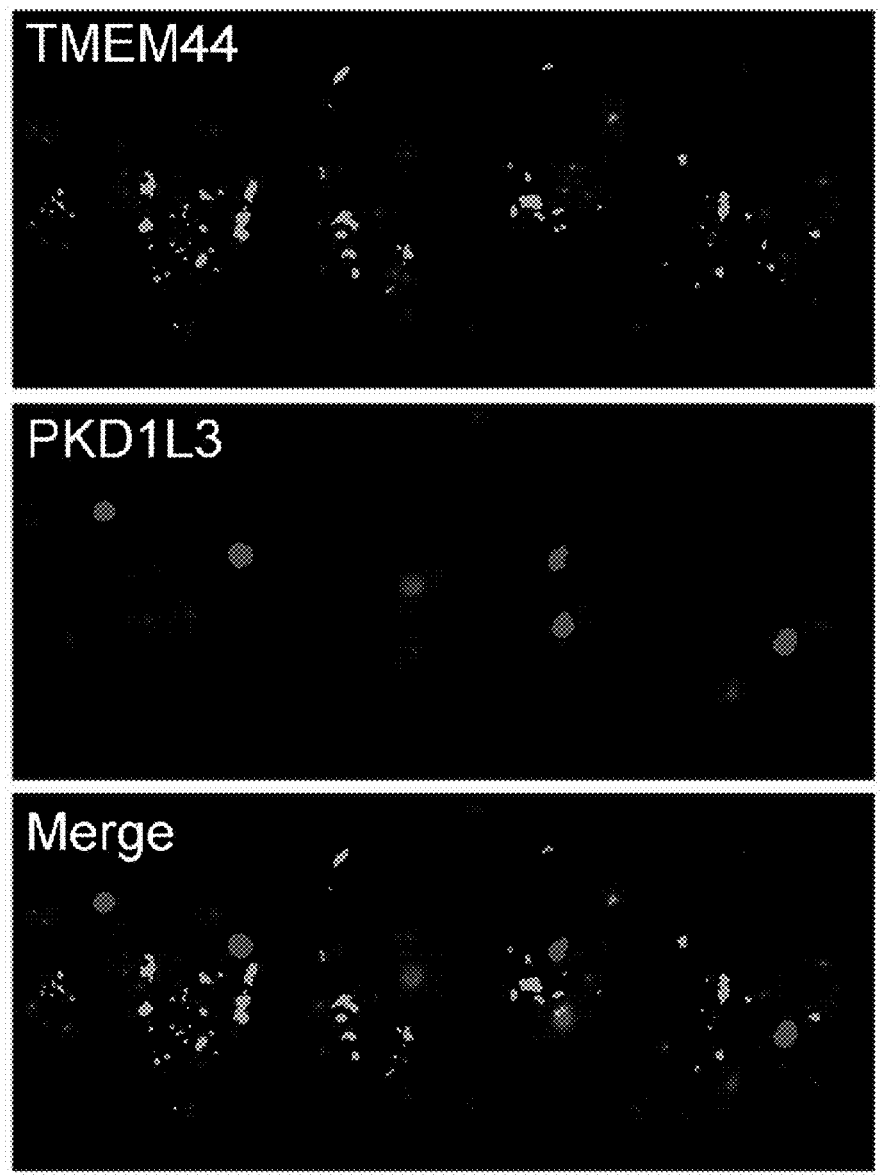
FIG. 20 shows that TMEM44 is not expressed in PKD1L3 cells in circumvallate papilla. Double fluorescent label in situ hybridization of primate circumvallate papilla at the back of the tongue showing that TMEM44 (green cells; top image) does not colocalize with PKD1L3 (red cells; middle image). Note that TMEM44 cells do not express PKD1L3, a marker of sour taste cells (merged image on the bottom).
Figure 21:
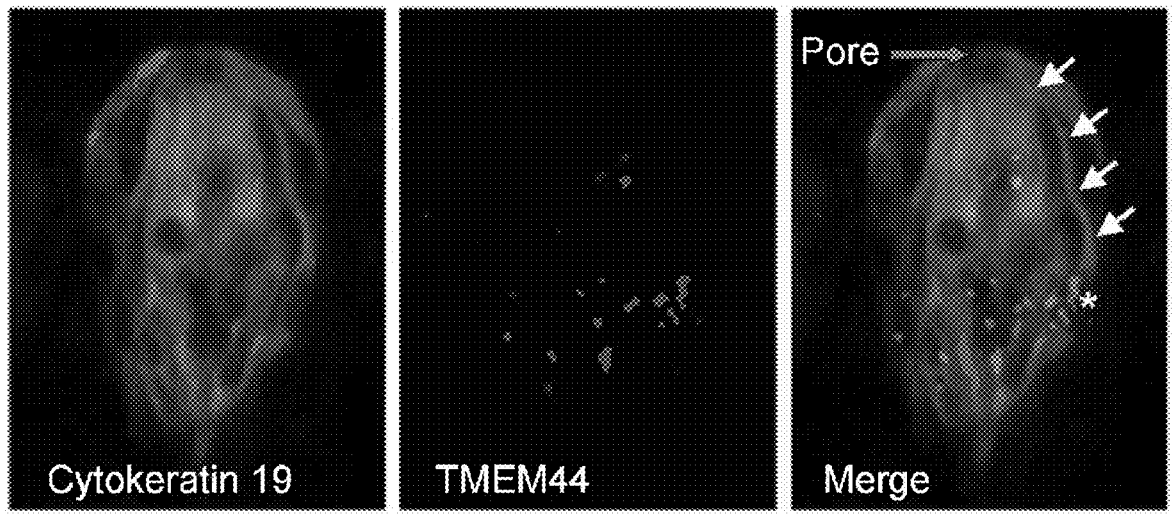
FIG. 21 shows that TMEM44 cells extend processes to the taste pore. Double label histology experiment of primate circumvallate papilla at the back of the tongue. Cytokeratin 19 protein (green; left image) is present in cells expressing TMEM44 RNA (red; middle image). Note that TMEM44 cells extend processes to the taste pore facing the saliva. Asterisk denotes a TMEM44 cell nucleus and white arrows denote the apical process of this same cell extending to the taste pore (merged image on the right). Thus, TMEM44 cells are sensory taste cells that can sample the saliva for tastants. Cytokeratin 19 is a marker of all taste cells.
Figure 22:
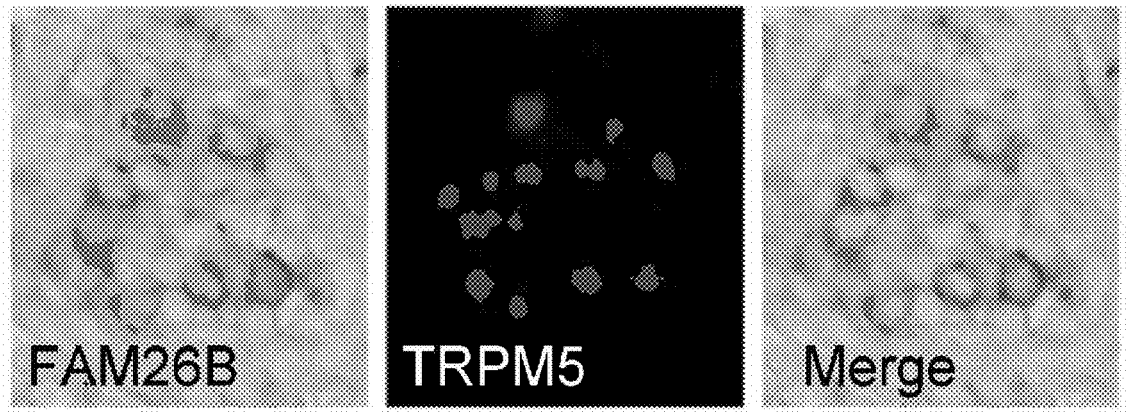
FIG. 22 shows that FAM26B is expressed in TRPM5 cells Double label in situ hybridization of primate circumvallate papilla showing that FAM26B (blue/purple color; left image) colocalizes with TRPM5 (red; middle image). Note that FAM26B cells express TRPM5, a marker of sweet, umami, and bitter taste cells (merged image on the right).
Figure 23:
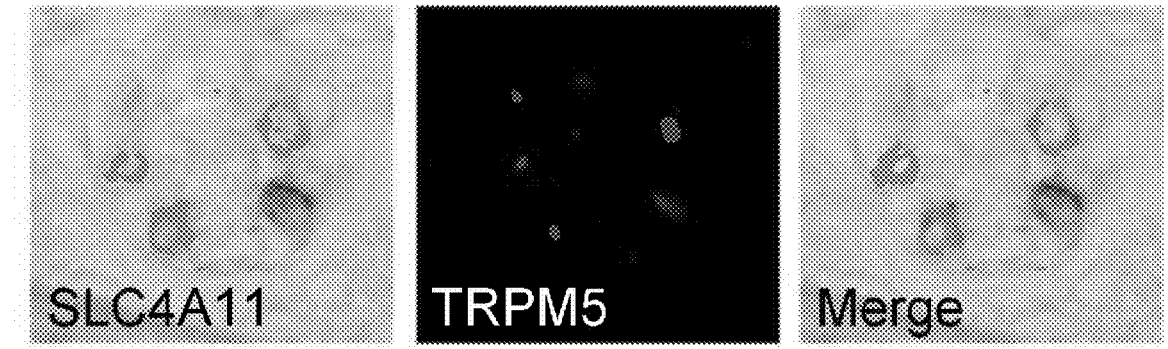
FIG. 23 shows that SLC4A11 is expressed in TRPM5 cells. Double label in situ hybridization of primate circumvallate papilla showing that SLC4A11 (blue/purple color; left image) colocalizes with TRPM5 (red; middle image). Note that SLC4A11 cells express TRPM5, a marker of sweet, umami, and bitter taste cells (merged image on the right).
Figure 24:
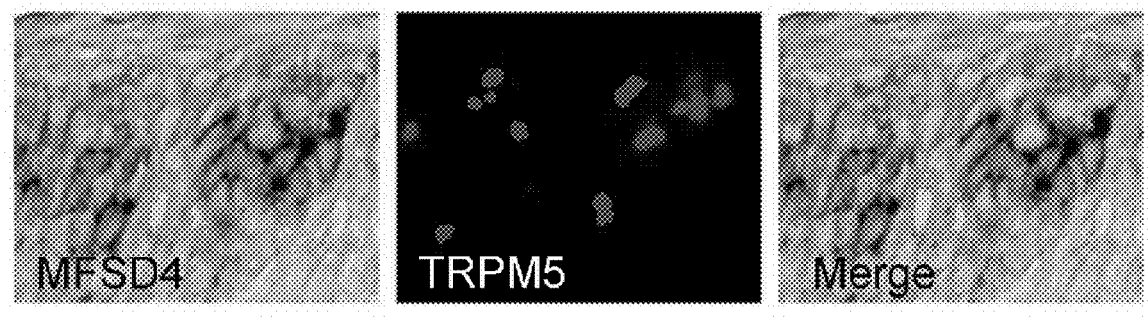
FIG. 24 reveals that MFSD4 is not expressed in TRPM5 cells. Double label in situ hybridization of primate circumvallate papilla showing that MFSD4 (blue/purple color; left image) does not colocalize with TRPM5 (red; middle image). Note that MFSD4 cells do not express TRPM5, a marker of sweet, umami, and bitter taste cells (merged image on the right). Two taste buds are shown.
Figure 25:
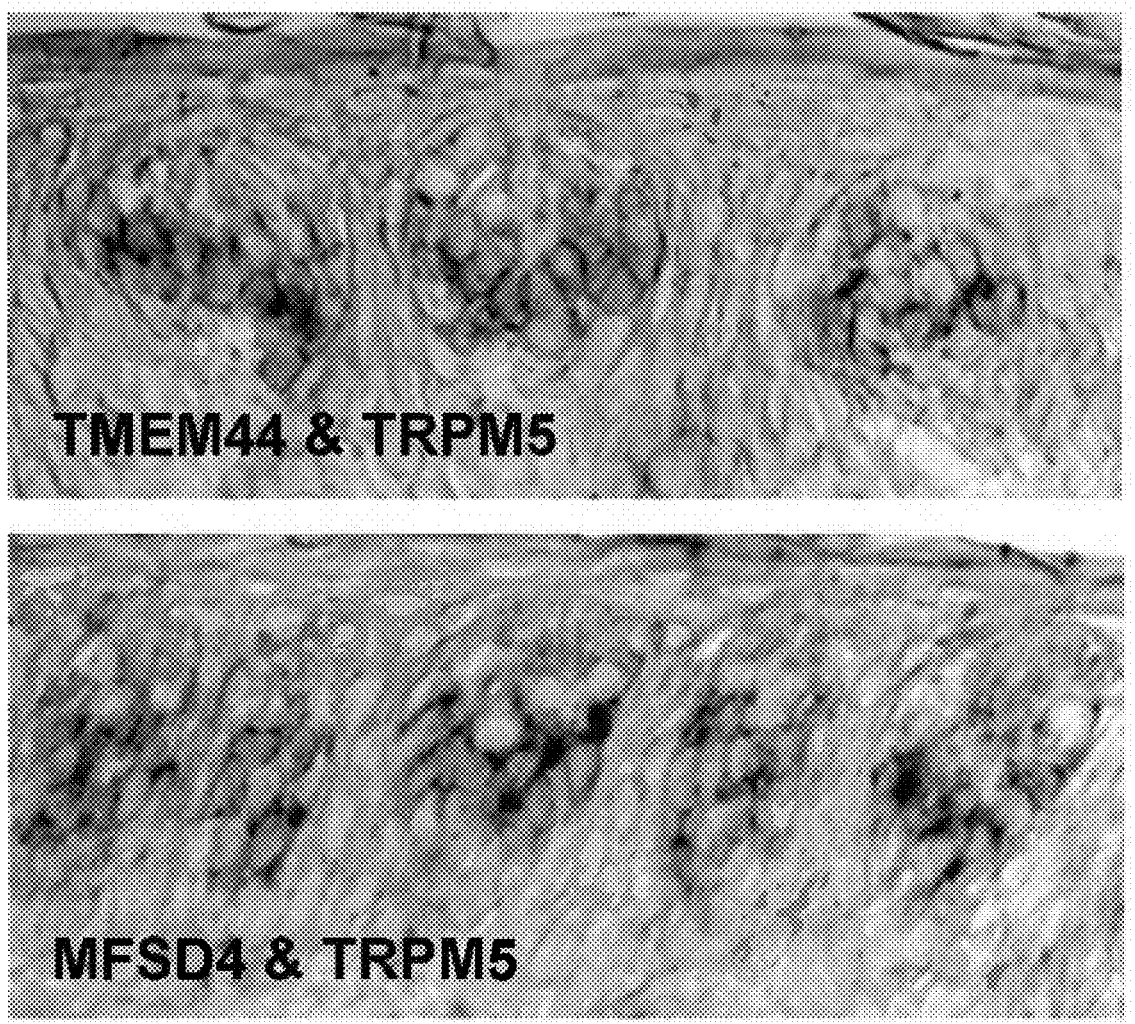
FIG. 25 shows that MFSD4 and TMEM44 are expressed in the same taste cells. Double label in situ hybridization of primate circumvallate papilla showing that MFSD4 and TMEM44 are expressed in the same taste cell population. TMEM44 (top blue/purple color) and MFSD4 (bottom blue/purple color) do not colocalize with TRPM5 (red color top and bottom images) and are expressed in taste cells in the bottom halves of taste buds. The equivalent localization, abundance, and morphology of TMEM44 and MFSD4 taste cells indicates that these cells are identical and that both TMEM44 and MFSD4 genes are expressed in the same taste cell type.

This example relates to another double label in situ hybridization of primate circumvallate papilla cells. The results which are contained in FIG. 13 show that TUSC3 (purple color; left image), a taste cell specific gene, colocalizes with TRPM5 (red; middle image). It can also be seen that TUSC3 cells express TRPM5, a marker of sweet, umami, and bitter taste cells (merged image on the right).

Example 14

This example shows that GPR113 is not expressed in T1R1 umami cells. Double label in situ hybridization of primate circumvallate papilla showing that GPR113 (purple color; left image) does not colocalize with T1R1 (red; middle image). Note that GPR113 and T1R1, a market of umami cells, are in different taste cells (merged image on the right)

Example 15

This example shows that GPR113 is not expressed in T1R2 sweet cells. Double label in situ hybridization of primate circumvallate papilla showing that GPR113 (purple color; left image) does not colocalize with T1R2 (red; middle image). Note that GPR113 and T1R2, a marker of sweet cells, are in different taste cells (merged image on the right).

Example 16

This example shows that GPR113 is expressed in a subset of T1R3 cells. Double label in situ hybridization of primate circumvallate papilla showing that GPR113 (purple color; left image) does colocalize with a subset of T1R3 cells (red; middle image). Note that GPR113 is always expressed in cells with T1R3, but that there are T1R3 cells that do not express GPR113 (merged image on the right). These T1R3 cells that do not express GPR113 likely coexpress either T1R1 or T1R2. The T1R3 only cells are a new population of taste cells that coexpress GPR113.

Example 17

This example shows that GPR113 is not expressed in T2R bitter cells. Double label in situ hybridization of primate circumvallate papilla showing that GPR113 (purple color; left image) does not colocalize with T2R (red; middle image). Note that GPR113 and T2R, a marker of bitter cells, are in different taste cells (merged image on the right).

Example 18

This example contains an experiment that shows that TMEM44 is not expressed in TRPM5 or PKD1L3 cells in fungiform taste buds. Double label in situ hybridization experiments were conducted using primate fungiform papilla from the front of the tongue showing that TMEM44 (blue/purple color; left images) does not colocalize with TRPM5 (red; middle top image) or PKD1L3 (red; middle bottom image). Note that TMEM44 cells do not express TRPM5, a marker of sweet, umami, and bitter taste cells, or PKD1L3, a marker of sour cells, in the merged images on the right.

Example 19

This example contains an experiment that shows that TMEM44 is not expressed in TRPM5 cells in circumvallate papilla. Double fluorescent label in situ hybridization of primate circumvallate papilla at the back of the tongue showing that TMEM44 (green cells; top image) does not colocalize with TRPM5 (red cells; middle image). Note that TMEM44 cells do not express TRPM5, a marker of sweet, umami, and bitter taste cells (merged image on the bottom).

Example 20

This example contains experiments that show that TMEM44 is not expressed in PKD1L3 cells in circumvallate papilla. Double fluorescent label in situ hybridization of primate circumvallate papilla at the back of the tongue showing that TMEM44 (green cells; top image) does not colocalize with PKD1L3 (red cells; middle image). Note that TMEM44 cells do not express PKD1L3, a marker of sour taste cells (merged image on the bottom).

Example 21

This example contains experiments that reveal that TMEM44 cells extend processes to the taste pore. Double label histology experiment of primate circumvallate papilla at the back of the tongue. Cytokeratin 19 protein (green; left image) is present in cells expressing TMEM44 RNA (red; middle image). Note that TMEM44 cells extend processes to the taste pore facing the saliva. Asterisk denotes a TMEM44 cell nucleus and white arrows denote the apical process of this same cell extending to the taste pore (merged image on the right). Thus, TMEM44 cells are sensory taste cells that can sample the saliva for tastants. Cytokeratin 19 is a marker of all taste cells.

Example 22

This example shows that FAM26B is expressed in TRPM5 cells. Double label in situ hybridization of primate circumvallate papilla showing that FAM26B (blue/purple color; left image) colocalizes with TRPM5 (red; middle image). Note that FAM26B cells express TRPM5, a marker of sweet, umami, and bitter taste cells (merged image on the right).

Example 23

This example shows that SLC4A11 is expressed in TRPM5 cells. Double label in situ hybridization of primate circumvallate papilla showing that SLC4A11 (blue/purple color; left image) colocalizes with TRPM5 (red; middle image). Note that SLC4A11 cells express TRPM5, a marker of sweet, umami, and bitter taste cells (merged image on the right).

Example 24

This example shows that MFSD4 is not expressed in TRPM5 cells. Double label in situ hybridization of primate circumvallate papilla showing that MFSD4 (blue/purple color; left image) does not colocalize with TRPM5 (red; middle image). Note that MFSD4 cells do not express TRPM5, a marker of sweet, umami, and bitter taste cells (merged image on the right). Two taste buds are shown.

Example 25

Figure 26:
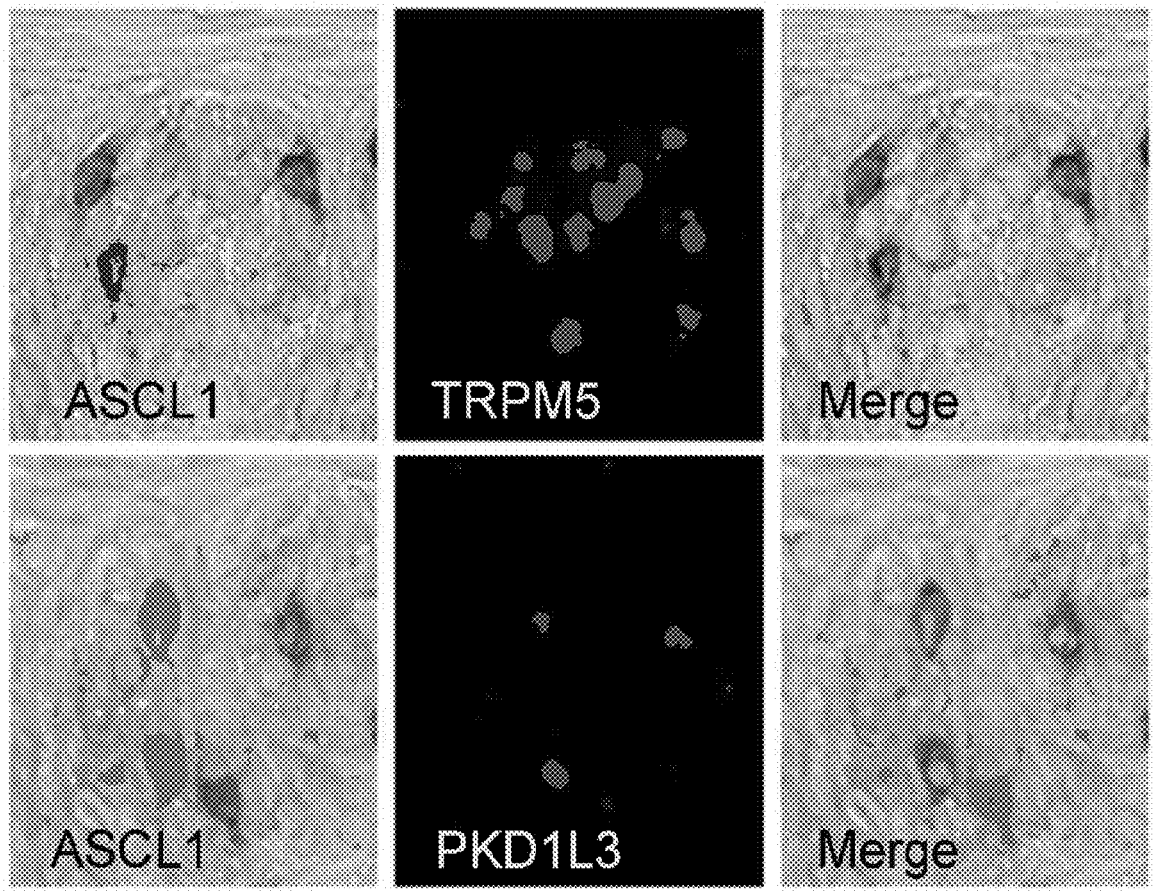
FIG. 26 shows that ASCL1 is expressed in sour taste cells but not sweet, bitter or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.
Figure 27:
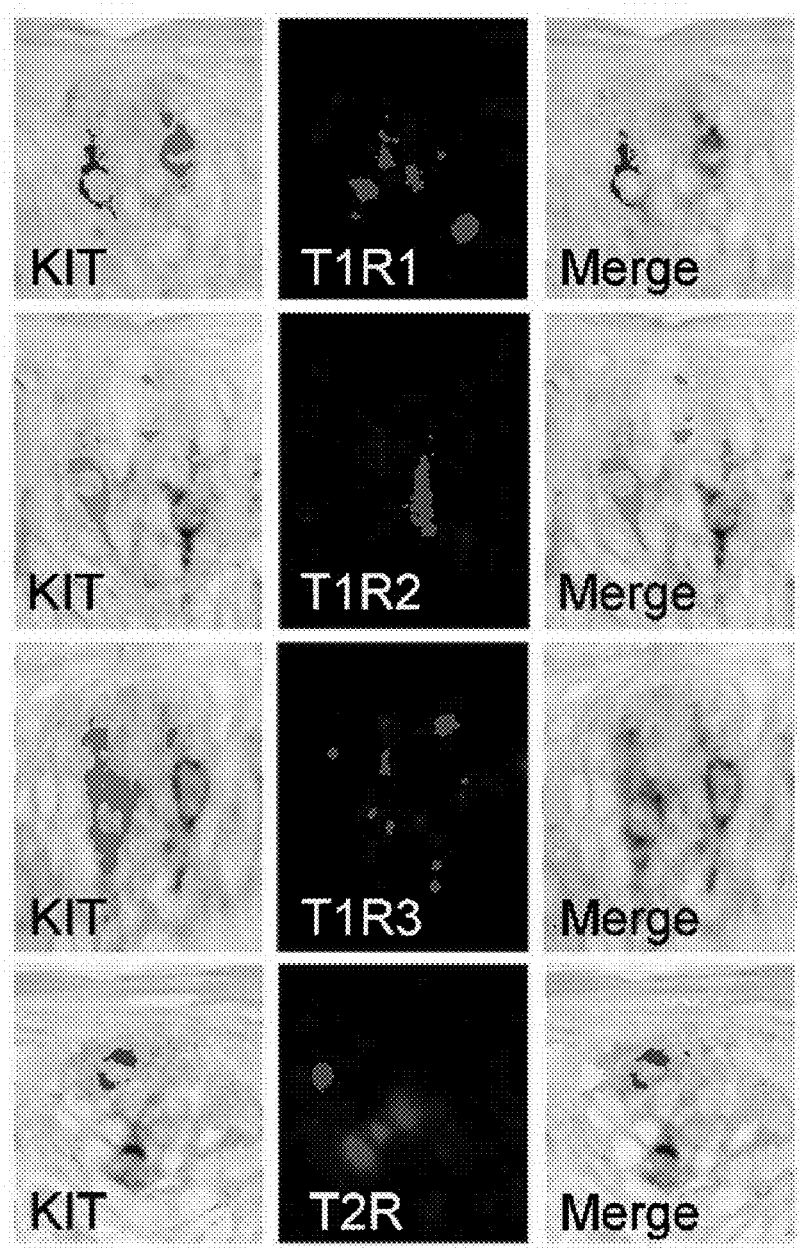
FIG. 27 shows that KIT is expressed in T1R1 umami taste cells. Double label in situ hybridization of primate circumvallate papilla from the back of the tongue showing that KIT (blue/purple color; left images) colocalizes with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that KIT cells express T1R1 and T1R3, markers of umami taste cells, but not T1R2 or T2Rs, markers of sweet and bitter cells respectively, in the merged images on the right.
Figure 28:
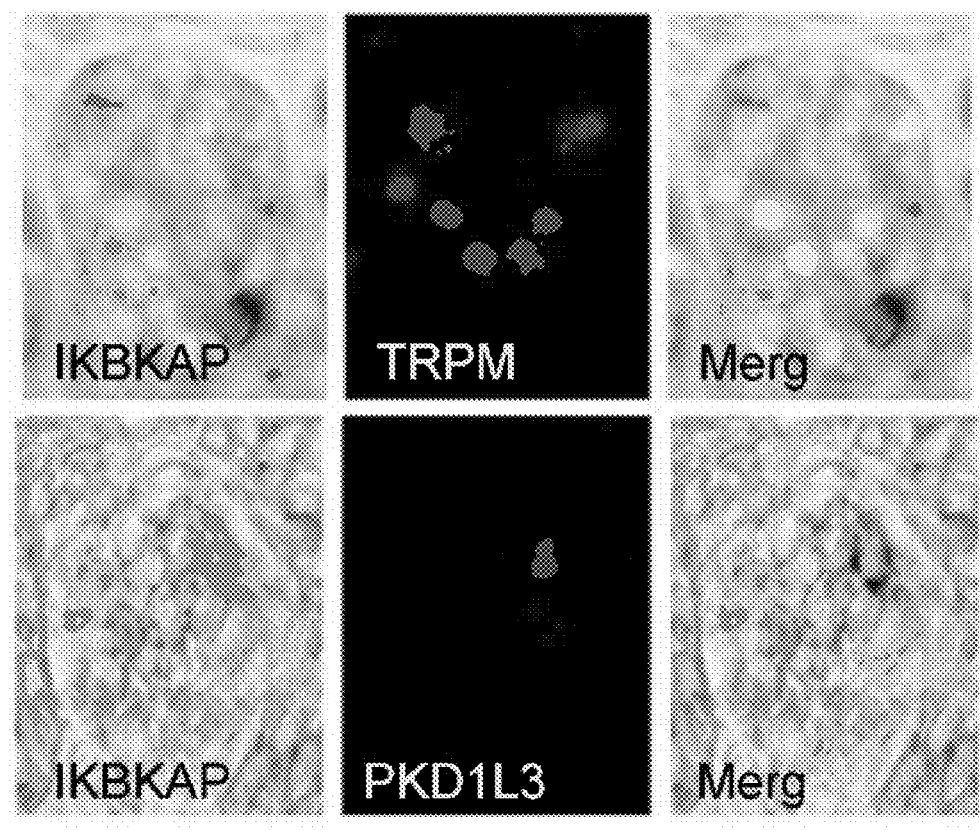
FIG. 28 shows that IKBKAP is expressed in PKD1L3 sour taste cells. Double fluorescent label in situ hybridization of primate circumvallate papilla at the back of the tongue showing that IKBKAP (blue/purple color; left images) does not colocalize with TRPM5 (red; middle image top) but does colocalize with PKD1L3 (red; middle image bottom). Note that IKBKAP cells express PKD1L3, a market of sour taste cells (merge image bottom) but do not express TRPM5, a marker of sweet, umami, and bitter taste cells (merged image top).
Figure 29:
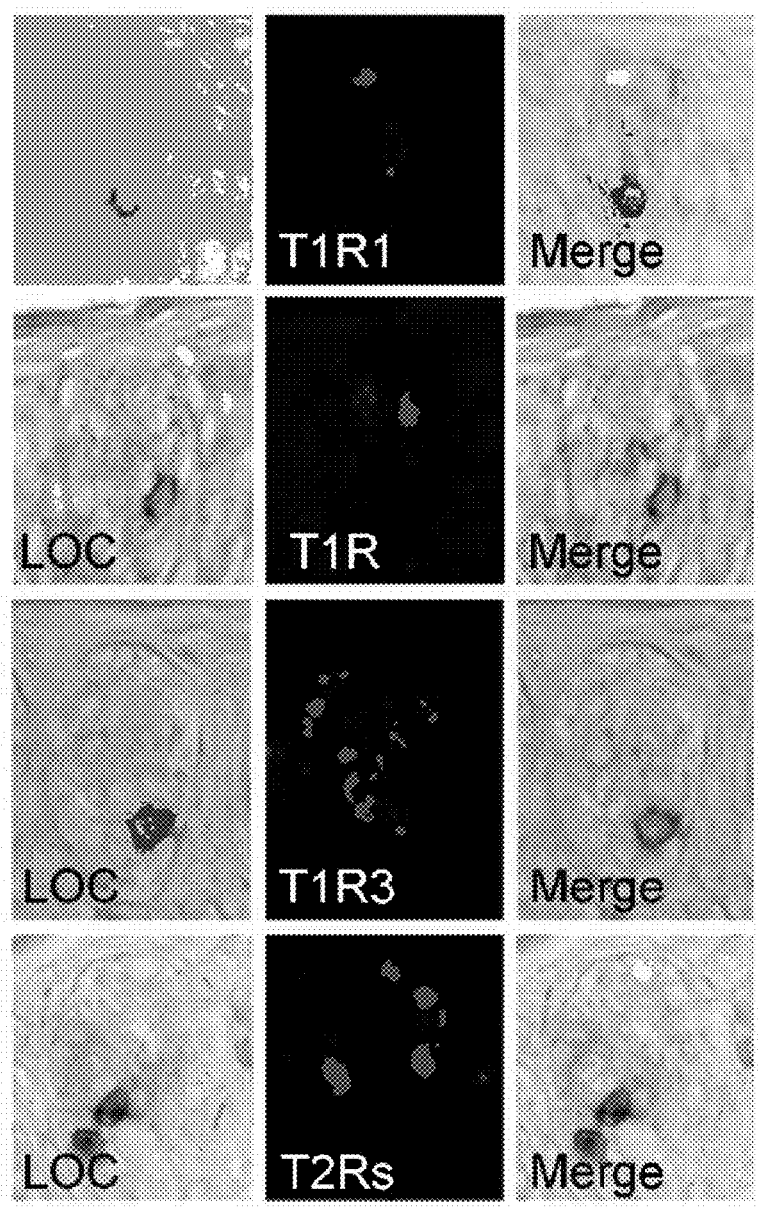
FIG. 29 shows that LOC285965 is expressed in T1R3 only taste cells. Double label in situ hybridization of primate circumvallate papilla from the back of the tongue showing that LOC285965 (blue/purple color; left images) does not colocalize with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that LOC285965 cells express T1R3, but not T1R1, T1R2 or T2Rs, markers of umami, sweet and bitter cells respectively, in the merged images on the right.
Figure 30:
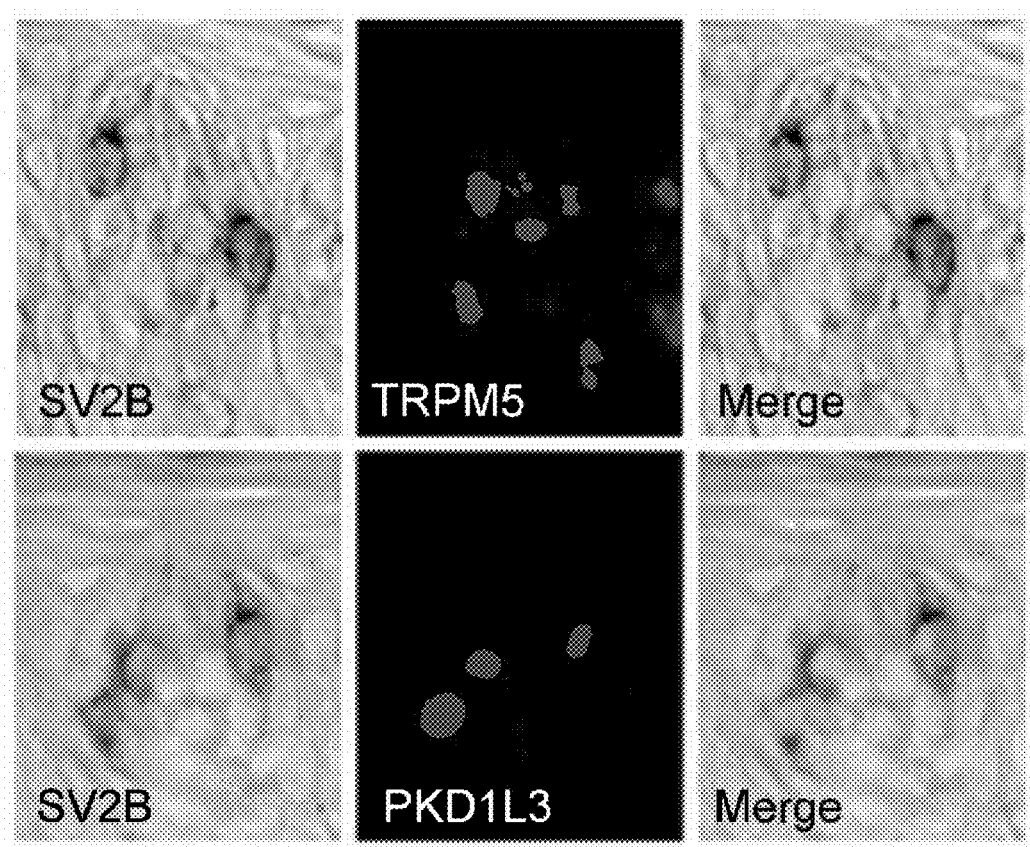
FIG. 30 shows that SV2B is expressed in PKD1L3 sour taste cells. Double fluorescent label in situ hybridization of primate circumvallate papilla at the back of the tongue showing that SV2B (blue/purple color; left images) does not colocalize with TRPM5 (red; middle image top) but does colocalize with PKD1L3 (red; middle image bottom). Note that SV2B cells express PKD1L3, a marker of sour taste cells (merge image bottom) but do not express TRPM5, a marker of sweet, umami, and bitter taste cells (merged image top).
Figure 31:
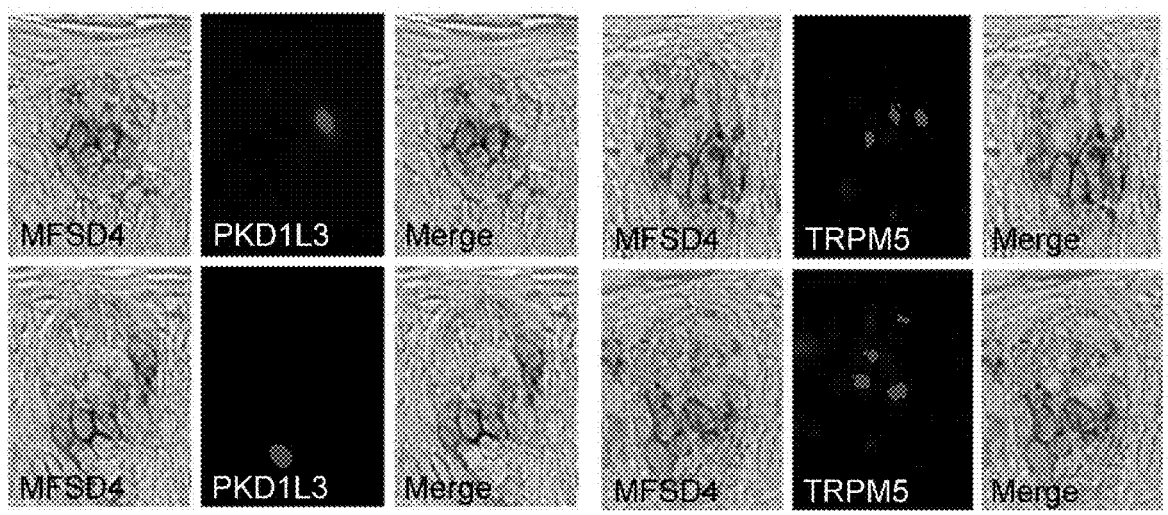
FIG. 31 shows that MFSD4 is expressed in a unique taste cell type. Double label in situ hybridization of primate circumvallate papilla showing that MFSD4 (blue/purple color; left image) does not colocalize with PKD1L3 or TRPM5 (red; middle images) but is expressed in a unique taste cell type. Note that MFSD4 cells do not express PKD1L3, a marker of sour taste cells or TRPM5, a marker of sweet, umami, and bitter taste cells (merged images on the right). Two taste buds each are shown for PKD1L3 & TRPM5 double labels.
Figure 32:
FIG. 32 shows that MFSD4 and TMEM44 are expressed in the same taste cell population. Double label in situ hybridization of primate circumvallate papilla showing that MFSD4 and TMEM44 are expressed in the same taste cell population. MFSD4 (left; green) and TMEM44 (middle; red) signals are present in the same taste cell (right; merged image).

This example shows that MFSD4 and TMEM44 are expressed in the same taste cells. Double label in situ hybridization of primate circumvallate papilla showing that MFSD4 and TMEM44 are expressed in the same taste cell population. TMEM44 (top blue/purple color) and MFSD4 (bottom blue/purple color) do not colocalize with TRPM5 (red color top and bottom images) and are expressed in taste cells in the bottom halves of taste buds. The equivalent localization, abundance, and morphology of TMEM44 and MFSD4 taste cells indicates that these cells are identical and that both TMEM44 and MFSD4 genes are expressed in the same taste cell type FIG. 26 shows that ASCL1 is expressed in sour taste cells but not sweet, bitter, or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.

Example 26

Example 26 shows that ASCL1 is expressed in sour taste cells but not sweet, bitter, or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.

Example 27

KIT is expressed in T1R1 umami taste cells. Double label in situ hybridization of primate circumvallate papilla from the back of the tongue showing that KIT (blue/purple color; left images) colocalizes with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that KIT cells express T1R1 and T1R3, markers of umami taste cells, but not T1R2 or T2Rs, markers of sweet and bitter cells respectively, in the merged images on the right.

Example 28

IKBKAP is expressed in PKD1L3 sour taste cells. Double fluorescent label in situ hybridization of primate circumvallate papilla at the back of the tongue showing that IKBKAP (blue/purple color; left images) does not colocalize with TRPM5 (red; middle image top) but does colocalize with PKD1L3 (red; middle image bottom). Note that IKBKAP cells express PKD1L3, a marker of sour taste cells (merge image bottom) but do not express TRPM5, a marker of sweet, umami, and bitter taste cells (merged image top).

Example 29

This experiment revealed that the taste specific gene LOC285965 is expressed in T1R3 only taste cells. Double label in situ hybridization of primate circumvallate papilla from the back of the tongue showing that LOC285965 (blue/purple color; left images) does not colocalize with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that LOC285965 cells express T1R3, but not T1R1, T1R2 or T2Rs, markers of umami, sweet and bitter cells respectively, in the merged images on the right.

Example 30

This experiment revealed that the taste specific gene SV2B is expressed in PDK1L3 sour taste cells. Double fluorescent label in situ hybridization of primate circumvallate papilla at the back of the tongue showing that SV2B (blue/purple color; left images) does not colocalize with TRPM5 (red; middle image top) but does colocalize with PKD1L3 (red; middle image bottom). Note that SV2B cells express PKD1L3, a marker of sour taste cells (merge image bottom) but do not express TRPM5, a marker of sweet, umami, and bitter taste cells (merged image top).

Example 31

This experiment revealed that the taste specific gene MFSD4 is expressed in a unique taste cell type. Double label in situ hybridization of primate circumvallate papilla showing that MFSD4 (blue/purple color; left image) does not colocalize with PKD1L3 or TRPM5 (red; middle images) but is expressed in a unique taste cell type. Note that MFSD4 cells do not express PKD1L3, a marker of sour taste cells or TRPM5, a marker of sweet, umami, and bitter taste cells (merged images on the right). Two taste buds each are shown for PKD1L3 & TRPM5 double labels.

Example 32

This experiment revealed that the taste specific genes MFSD4 and TMEM44 are expressed in the same taste cell population. Double label in situ hybridization of primate circumvallate papilla showing that MFSD4 and TMEM44 are expressed in the same taste cell population. MFSD4 (left; green) and TMEM44 (middle; red) signals are present in the same taste cells (right; merged image).

Example 33

Figure 33:
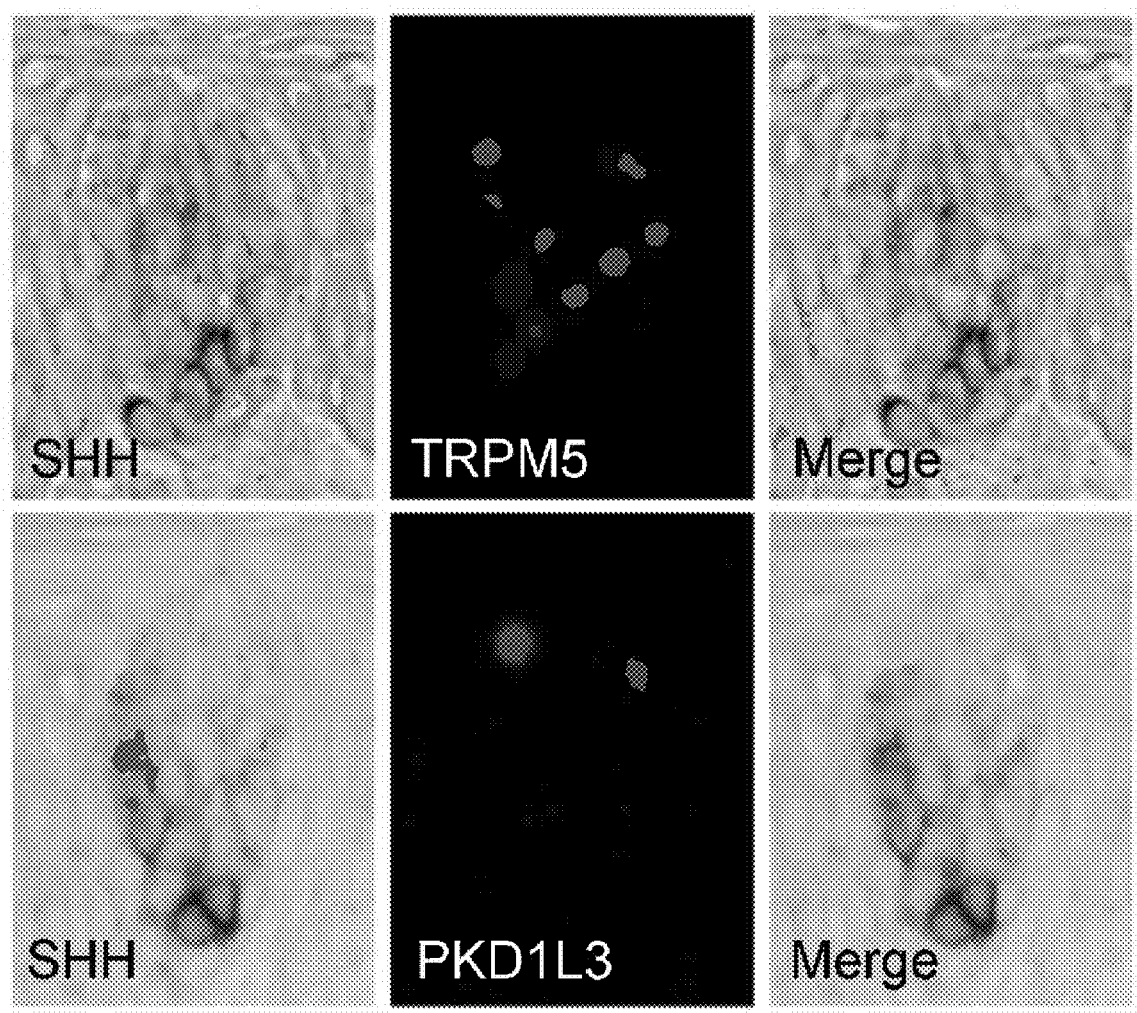
FIG. 33 contains an experiment showing that SHH is expressed in immature taste cells in the bottom of the taste bud. Double in situ hybridization of primate circumvallate papilla at the back of the tongue showing that SHH (blue/purple color; left images) does not colocalize with TRPM5 (red; middle image top) or PKD1L3 (red; middle image bottom). Note that SHH cells do not express TRPM5, a marker of sweet, bitter, and umami taste cells (merge; right image top) or PKD1L3 (merge; right image bottom). Both TRPM5 and PKD1L3 genes are expressed in professional taste cells.

This experiment the results of which are contained in FIG. 33 revealed that SHH is expressed in immature taste cells in the bottom of the taste bud. Double in situ hybridization of primate circumvallate papilla at the back of the tongue showing that SHH (blue/purple color; left images) does not colocalize with TRPM5 (red; middle image top) or PKD1L3 (red; middle image bottom). Note that SHH cells do not express TRPM5, a marker of sweet, bitter, and umami taste cells (merge; right image top) or PKD1L3 (merge; right image bottom). Both TRPM5 and PKD1L3 genes are expressed in professional taste cells.

Example 34

Figure 34:
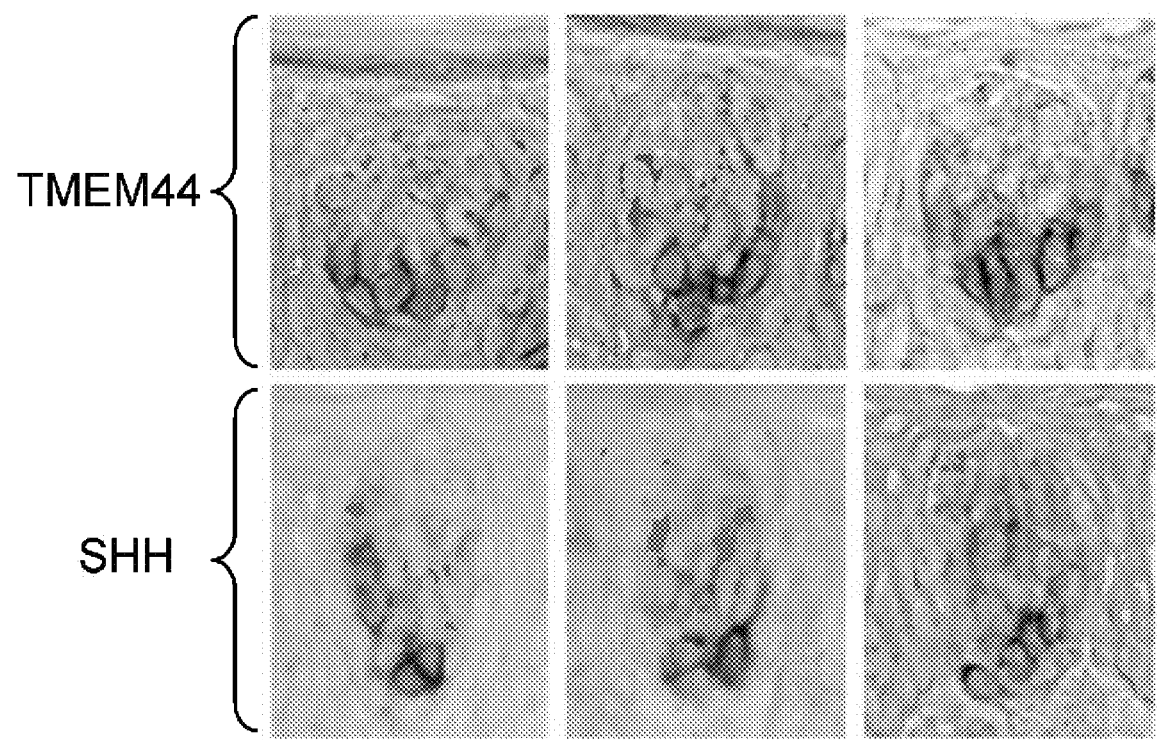
FIG. 34 contains an experiment showing that TMEM44 and SHH are expressed in immature taste cells at the bottom of the taste bud. In situ hybridization of primate circumvallate papilla at the back of the tongue showing that TMEM44 (blue/purple color; top 3 images) is expressed in cells towards the base of the taste bud. A similar expression pattern was observed with SHH (blue/purple color; bottom 3 images). Since SHH is marker of immature, developing taste cells, these data indicate that TMEM44 is expressed in and is a marker of immature taste cells FIG. 35 contains a schematic model of taste cell development. In situ hybridization of primate circumvallate papilla at the back of the tongue showing SHH (blue/purple color) expression at the base of the taste bud and PKD1L3 (red color) expression towards the top of the taste bud. This model indicates a gradient of SHH expression from high levels at the base of the taste bud (immature cells) to low levels at the top of the taste bud (mature cells). As SHH expression levels decrease, expression of taste receptor genes such as TRPM5 and PKD1L3 increase. Thus, an opposite gradient of taste cell maturation exists where taste cells progressively mature and express taste receptor genes as they differentiate from the bottom to the top of the taste bud.

This experiment the results of which are contained in FIG. 34 show that the taste specific genes TMEM44 and SHH are expressed in immature taste cells at the bottom of the taste bud. In situ hybridization of primate circumvallate papilla at the back of the tongue showing that TMEM44 (blue/purple color; top 3 images) is expressed in cells towards the base of the taste bud. A similar expression pattern was observed with SHH (blue/purple color; bottom 3 images). Since SHH is marker of immature, developing taste cells, these data indicate that TMEM44 is expressed in and is a marker of immature taste cells.

Example 35

Figure 35:
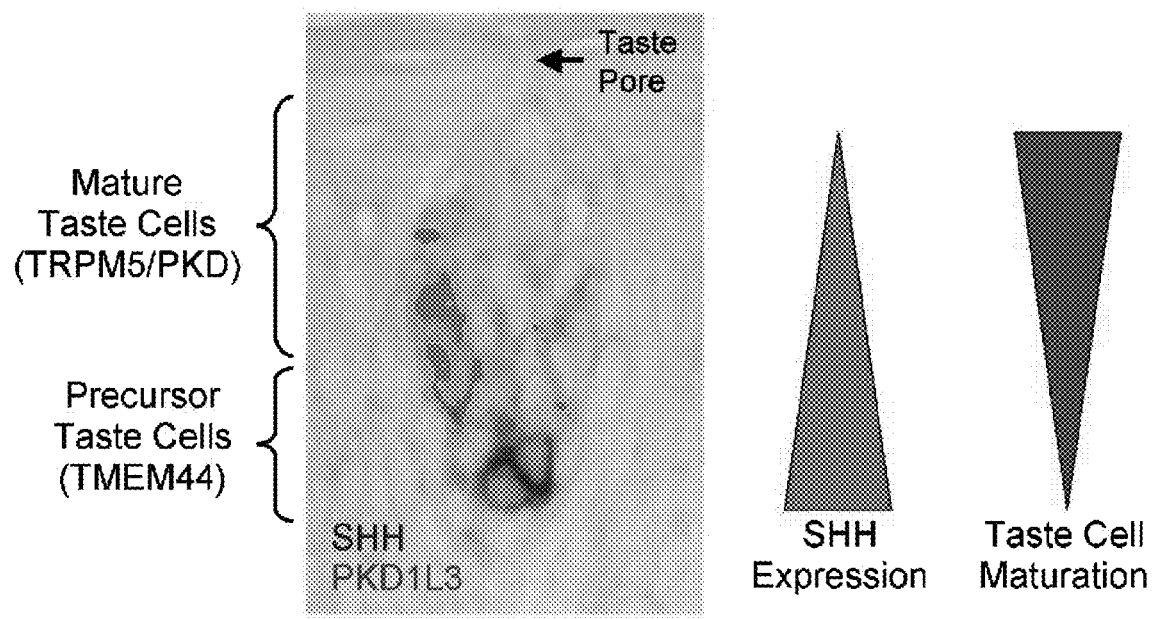

This experiment relates to the experiment in FIG. 35. In situ hybridization of primate circumvallate papilla at the back of the tongue showing SHH (blue/purple color) expression at the base of the taste bud and PKD1L3 (red color) expression towards the top of the taste bud. This figure contains a schematic model of taste cell development which indicates that the is a gradient of SHH expression from high levels at the base of the taste bud (immature cells) to low levels at the top of the taste bud (mature cells). As SHH expression levels decrease, expression of taste receptor genes such as TRPM5 and PKD1L3 increase. Thus, an opposite gradient of taste cell maturation exists where taste cells progressively mature and express taste receptor genes as they differentiate from the bottom to the top of the taste bud.

Example 36

Figure 36:
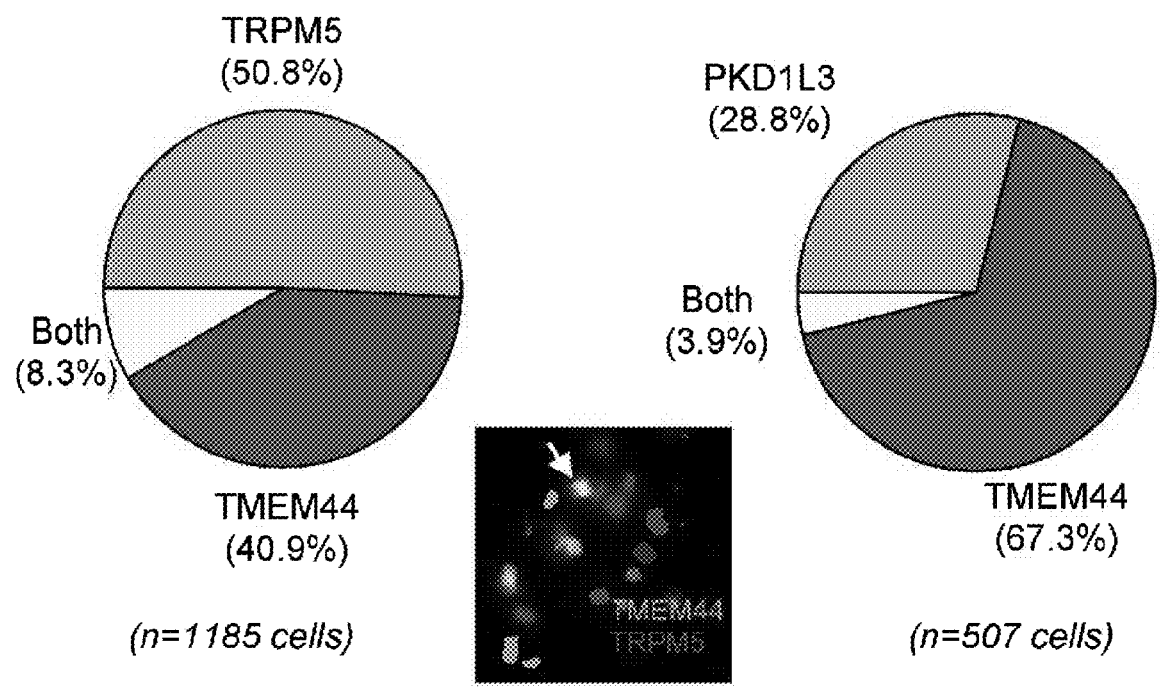
FIG. 36 shows that a small fraction of TMEM44 cells express TRPM5 or PKD1L3 as they differentiate into mature taste cells. Double label in situ hybridization of primate circumvallate papilla was performed using TRPM5 and TMEM44 riboprobes (left pie chart) or PKD1L3 and TMEM44 riboprobes (right pie chart). Taste cells expressing TRPM5 (blue pie region; left pie chart), TMEM44 (magenta graph region; left pie chart), or TRPM5 plus TMEM44 (labeled 'both' and yellow graph region; left pie chart) genes were counted and graphed in pie charts. Taste cells expressing PKD1L3 (blue graph region; right pie chart), TMEM44 (magenta graph region; right pie chart), or TRPM5 plus TMEM44 (labeled 'both' and yellow graph region; right pie chart) genes were counted and graphed in pie charts. Total number of counted cells is listed below each pie chart in parentheses. A small fraction of TMEM44 cells also express TRPM5 or PKD1L3, indicating that these cells are differentiating from an immature state (TMEM44 only) to a mature state (TRPM5 or PKD1L3 only). Inset shows example of CV taste bud labeled with TMEM44 (green) and TRPM5 (red). Note cell indicated with arrow that coexpresses both TMEM44 and TRPM5 (yellow).

This experiment the results of which are contained in FIG. 36 show that a small fraction of TMEM44 cells express TRPM5 or PKD1L3 as they differentiate into mature taste cells. Double label in situ hybridization of primate circumvallate papilla was performed using TRPM5 and TMEM44 riboprobes (left pie chart) or PKD1L3 and TMEM44 riboprobes (right pie chart). Taste cells expressing TRPM5 (blue graph region; left pie chart), TMEM44 (magenta graph region; left pie chart), or TRPM5 plus TMEM44 (labeled 'both' and yellow graph region; left pie chart) genes were counted and graphed in pie charts. Taste cells expressing PKD1L3 (blue graph region; right pie chart), TMEM44 (magenta graph region; right pie chart), or TRPM5 plus TMEM44 (labeled 'both' and yellow graph region; right pie chart) genes were counted and graphed in pie charts. Total number of counted cells is listed below each pie chart in parentheses. A small fraction of TMEM44 cells also express TRPM5 or PKD1L3, indicating that these cells are differentiating from an immature state (TMEM44 only) to a mature state (TRPM5 or PKD1L3 only). Inset shows example of CV taste bud labeled with TMEM44 (green) and TRPM5 (red). Note cell indicated with arrow that coexpresses both TMEM44 and TRPM5 (yellow).

Example 37

Figure 37:
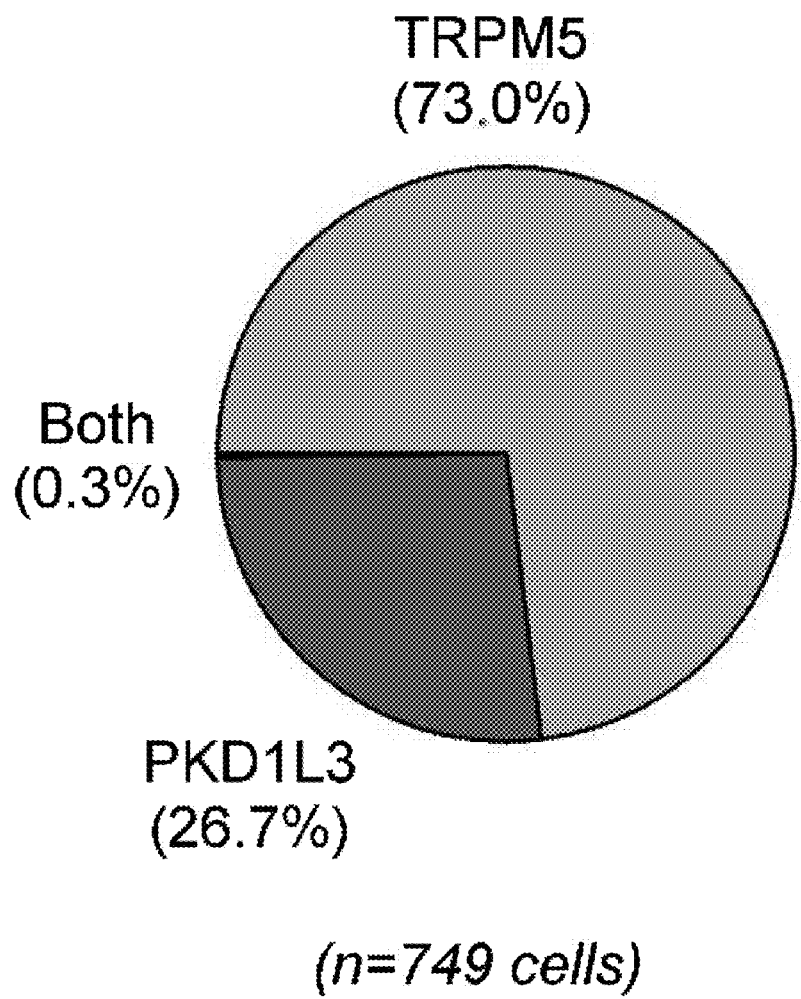
FIG. 37 contains an experiment showing that mature taste cells do not coexpress markers for distinct taste modalities. Double label in situ hybridization of primate circumvallate papilla was performed using TRPM5 and PKD1L3. Taste cells expressing TRPM5 (blue graph region), PKD1L3 (magenta graph region), or TRPM5 plus PKD1L3 (labeled 'both' and yellow graph region which is too small to see any yellow segment due to the near absence of cells within this category) genes were counted and graphed in the pie chart. Total number of counted cells is listed below the pie chart in parentheses.

This experiment the results of which are contained in FIG. 37 reveals that mature taste cells do not coexpress markers for distinct taste modalities. Double label in situ hybridization of primate circumvallate papilla was performed using TRPM5 and PKD1L3. Taste cells expressing TRPM5 (blue graph region), PKD1L3 (magenta graph region), or TRPM5 plus PKD1L3 (labeled 'both' and yellow graph region which is too small to see any yellow segment due to the near absence of cells within this category) genes were counted and graphed in the pie chart. Total number of counted cells is listed below the pie chart in parentheses.

Example 38

Top Versus Bottom Gene Expression in the Taste Buds

The experiments and results herein relate to a systematic method for assigning gene expression patterns within the primate taste bud for taste bud-specific genes. Specifically, using a comparison of gene expression between the top and bottom sections of the primate taste bud, the inventors were able to classify genes into one of several functional classes that include taste receptor genes. A subset of genes in this classification is likely to encode taste receptors that include those for salty taste and other yet to be defined taste specificities.

As explained previously, the rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38.

In order to get more information on gene expression in both the top and bottom fractions of the taste bud we undertook an experiment to isolate the corresponding fractions of primate taste buds using laser capture microdissection (LCM). As described previously, LCM involves the excision and isolation of selected cells or groups of cells from tissue sections based on morphological distinctions. In the case of taste buds, we can readily identify these structures in sections of primate tongue. In this specific example tissue collection was limited to taste buds in circumvallate papillae and then to only taste buds that were sectioned sagittally and at the taste pore. We reasoned it was only from this type of section would we be able to reliably isolate top and bottom fractions. An example of sections used in sample collection is shown in FIG. 39.

Multiple LCM preparations from each of 4 animals were pooled (4 top samples, 4 bottom samples, ~5000 cells per sample) RNA extracted and analyzed using Affymetrix whole genome macaque Gene Chips to obtain global mRNA expression profiles for the top and bottom fractions.

The gene expression data was queried to obtain three sets of genes. The first and second sets are genes that are expressed at a higher level in the top or bottom of the primate taste bud relative to the bottom or top respectively. Top-specific genes were listed in one group of genes, and bottom specific genes are listed in a second group. Accordingly, these lists contain top enriched and bottom enriched mRNAs. The third set of genes was also identified as being expressed at a higher level in the top of the primate taste bud relative to surrounding lingual epithelium.

Figure 38:
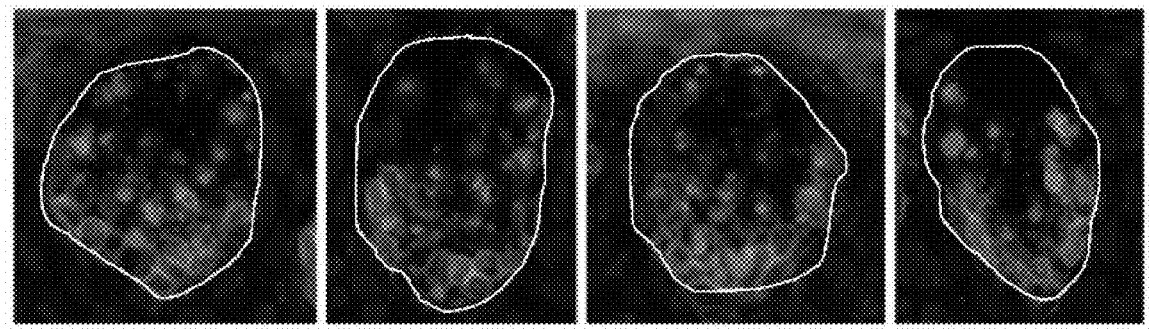
FIG. 38 contains an experiment showing that levels of gene expression define two compartments in primate taste buds. To create this overlay image sagittal sections of primate taste buds were initially stained with DAPI (4',6-diamidino-2-phenylindole) to visualize cell nuclei; blue color. Double label in situ hybridization images of the same sections for TMEM44; green color and TRPM5+PKD1L3; pink color were then added. The overlay image shows that TMEM44 expression is restricted to the bottom third of each of the four taste buds shown and that TRPM5+PKD1L3 expression occurs predominantly in the upper regions of each of the taste buds.

An exemplary experiment validating this methodology is contained in FIG. 38. This experiment contains an experiment showing that levels of gene expression define two compartments in primate taste buds. To create this overlay image sagittal sections of primate taste buds were initially stained with DAPI (4',6-diamidino-2-phenylindole) to visualize cell nuclei; blue color. Double label in situ hybridization images of the same sections for TMEM44; green color and TRPM5+ PKD1L3; pink color were then added. The overlay image shows that TMEM44 expression is restricted to the bottom third of each of the four taste buds shown and that TRPM5+ PKD1L3 expression occurs predominantly in the upper regions of each of the taste buds.

FIG. 39 shows an exemplary experiment showing laser capture microdissection of top and bottom regions of primate taste buds. Panel) contains a methyl blue stained section A of macaque circumvallate taste buds. Panel B shows Section A following excision of bottom fraction of taste buds. Panel C contains the bottom fraction of taste buds. Panel D shows Section A following excision of bottom and top fractions of taste buds. Panel E shows the Top fraction of taste buds. Note, top and bottom fractions were only collected from taste buds exhibiting optimal morphology in section. In the example shown, the taste bud labeled with an arrow was excluded due to suboptimum sectioning or morphology.

The results obtained by the inventors revealed that taste receptor genes are expressed predominantly at the top of the taste bud. In contrast to what has been reported, the data of the inventors suggests that known taste receptor genes are expressed at higher level in the top fraction of the taste buds. Therefore, this technique should allow for other yet to be identified taste receptor genes to be represented in the top-enriched set of genes.

In addition, there is an apparent functional classification that can be made based on top versus bottom taste bud cells.

The gene expression profiles of the top and bottom fractions of the taste bud suggest distinct functions for cells in each compartment. Functional classes of genes represented in the top cells indicate that these are mature sensory cells whereas those expressed in the bottom cells indicate these are immature progenitor cells associated with a basement membrane containing cellular environment. Examples of top specific functional classes include taste receptors, taste-specific signal transduction components and receptors. Examples of bottom-specific functional classes include extracellular metric components, growth factors and cell-cycle associated proteins.

Also, based thereon, these techniques allow for the identification of additional taste bud-specific genes. By fractionating the taste buds into top and bottom compartments the inventors were able to increase the sensitivity of mRNA detection in each compartment by a factor of approximately two. This enables us to identify another set of taste bud specific genes Example 39

Figure 40:
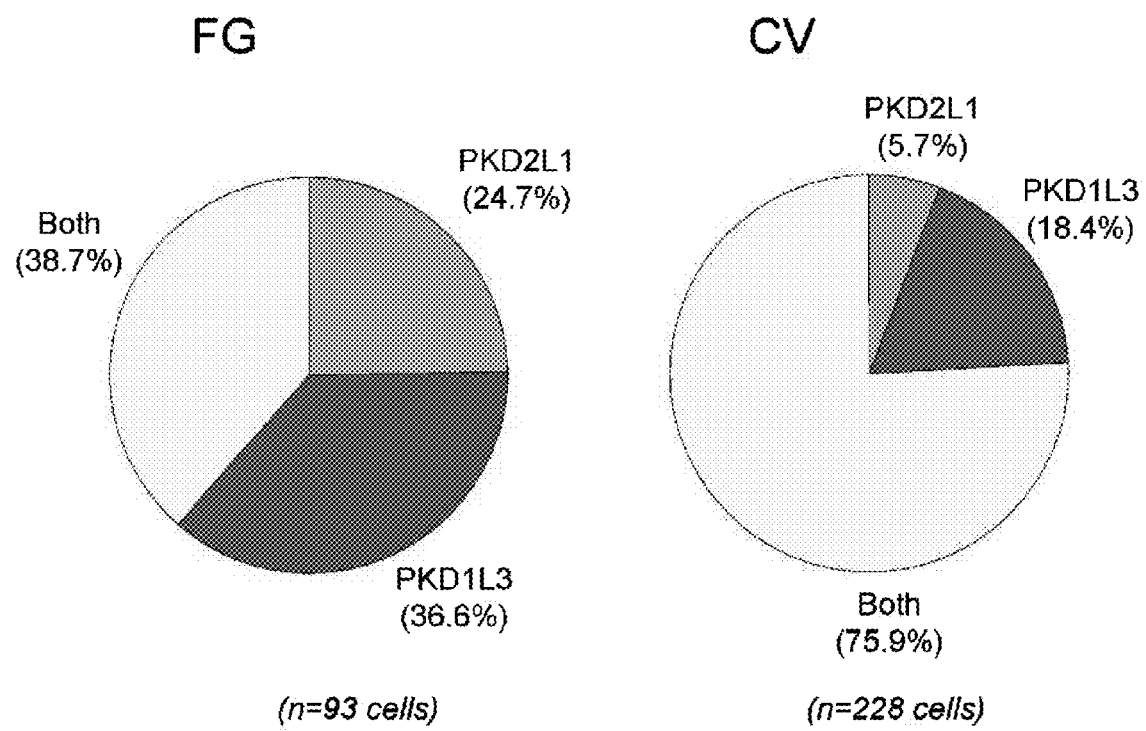
FIG. 40 contains the results of an experiment establishing that distinct cell populations PKD2L1, PKD1L3 and PKD2L1 plus PKD1L3. Double label in situ hybridization of primate fungiform (FG; left) and circumvallate (CV; right) was performed using PKD2L1 and PKD1L3 riboprobes. Taste cells expressing PKD2L1 (blue graph regions), PKD1L3 (magenta graph regions), or PKD2L1 plus PKD1L3 (labeled 'both' and yellow graph regions) genes were counted and graphed in pie charts. Total number of counted cells is listed below each pie chart in parentheses.

This experiment the results of which are contained in FIG. 40 establish that distinct cell populations PKD2L1, PKD1L3 and PKD2L1 plus PKD1L3. Double label in situ hybridization of primate fungiform (FG; left) and circumvallate (CV; right) was performed using PKD2L1 and PKD1L3 riboprobes. Taste cells expressing PKD2L1 (blue graph regions), PKD1L3 (magenta graph regions), or PKD2L1 plus PKD1 L3 (labeled 'both' and yellow graph regions) genes were counted and graphed in pie charts. Total number of counted cells is listed below each pie chart in parentheses.

Example 40

Figure 41:
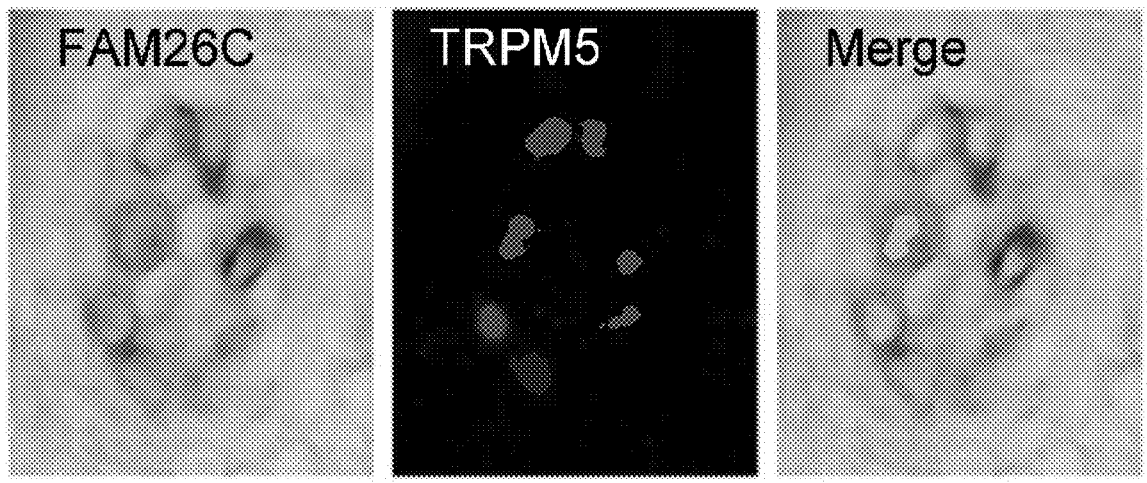
FIG. 41 The experiment in FIG. 41 shows that FAM26C is expressed in TRPM5 taste cells. Therein double in situ hybridization of primate circumvallate papilla at the back of the tongue showing that FAM26C (blue/purple color; left image) colocalizes with TRPM5 (red; middle image). Note that FAM26C cells express TRPM5, a marker of sweet, bitter, and umami taste cells (merge; right image).

This experiment the results of which are contained in FIG. 41 shows that FAM26C is expressed in TRPM5 taste cells. Therein double in situ hybridization of primate circumvallate papilla at the back of the tongue showing that FAM26C (blue/purple color; left image) colocalizes with TRPM5 (red; middle image). Note that FAM26C cells express TRPM5, a marker of sweet, bitter, and umami taste cells (merge; right image).

Example 41

Figure 42:
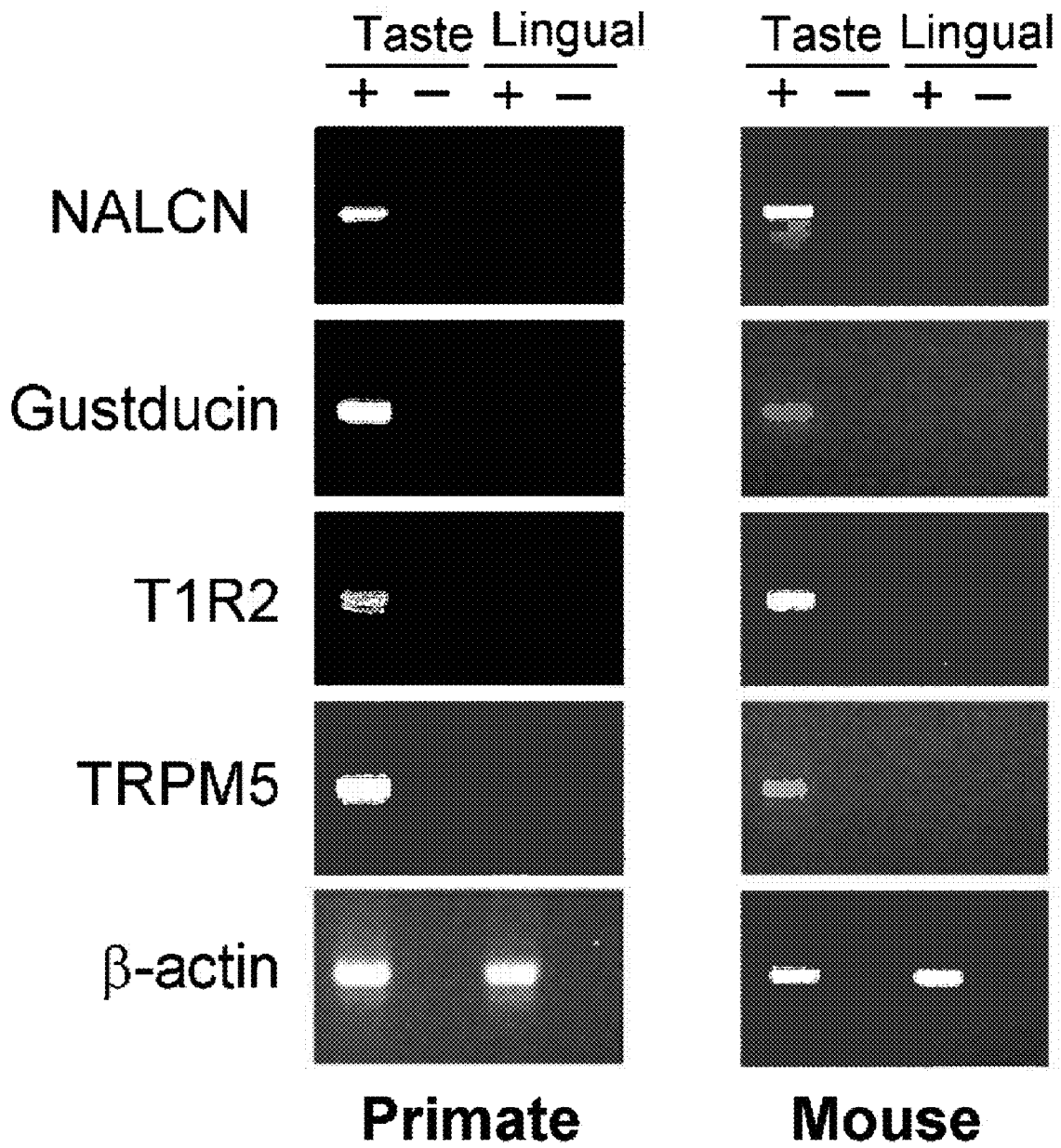
FIG. 42 The experiment in FIG. 42 shows that NALCN is a taste-specific gene. The figure shows end-point PCR experiments on circumvallate taste buds (taste) and lingual epithelial cells (lingual) of non-human primate (left) and mouse (right) isolated by laser-capture microdissection demonstrating that NALCN is a taste-specific gene. NALCN is only expressed in taste cells and is not detectable in lingual cells, similar to the known taste-specific genes gustducin, T1R2, and TRPM5. □-actin is detectable in both taste and lingual samples, indicating that high-quality RNA was present in both samples. '+' indicates that reverse transcription was performed and '−' indicates that no reverse transcription was performed. PCR bands were only observed with reverse transcriptase indicating that PCR products are derived from mRNA and not genomic DNA. PCR products were cloned and sequenced to verify that the bands corresponded to the expected gene products.

This experiment the results of which are contained in FIG. 42 shows that NALCN is a taste-specific gene. The figure shows end-point PCR experiments on circumvallate taste buds (taste) and lingual epithelial cells (lingual) of non-human primate (left) and mouse (right) isolated by laser-capture microdissection demonstrating that NALCN is a taste-specific gene. NALCN is only expressed in taste cells and is not detectable in lingual cells, similar to the known taste-specific genes gustducin, T1R2, and TRPM5. β-actin is detectable in both taste and lingual samples, indicating that high-quality RNA was present in both samples. '+' indicates that reverse transcription was performed and '−' indicates that no reverse transcription was performed. PCR bands were only observed with reverse transcriptase indicating that PCR products are derived from mRNA and not genomic DNA. PCR products were cloned and sequenced to verify that the bands corresponded to the expected gene products.

Example 42

Figure 43:
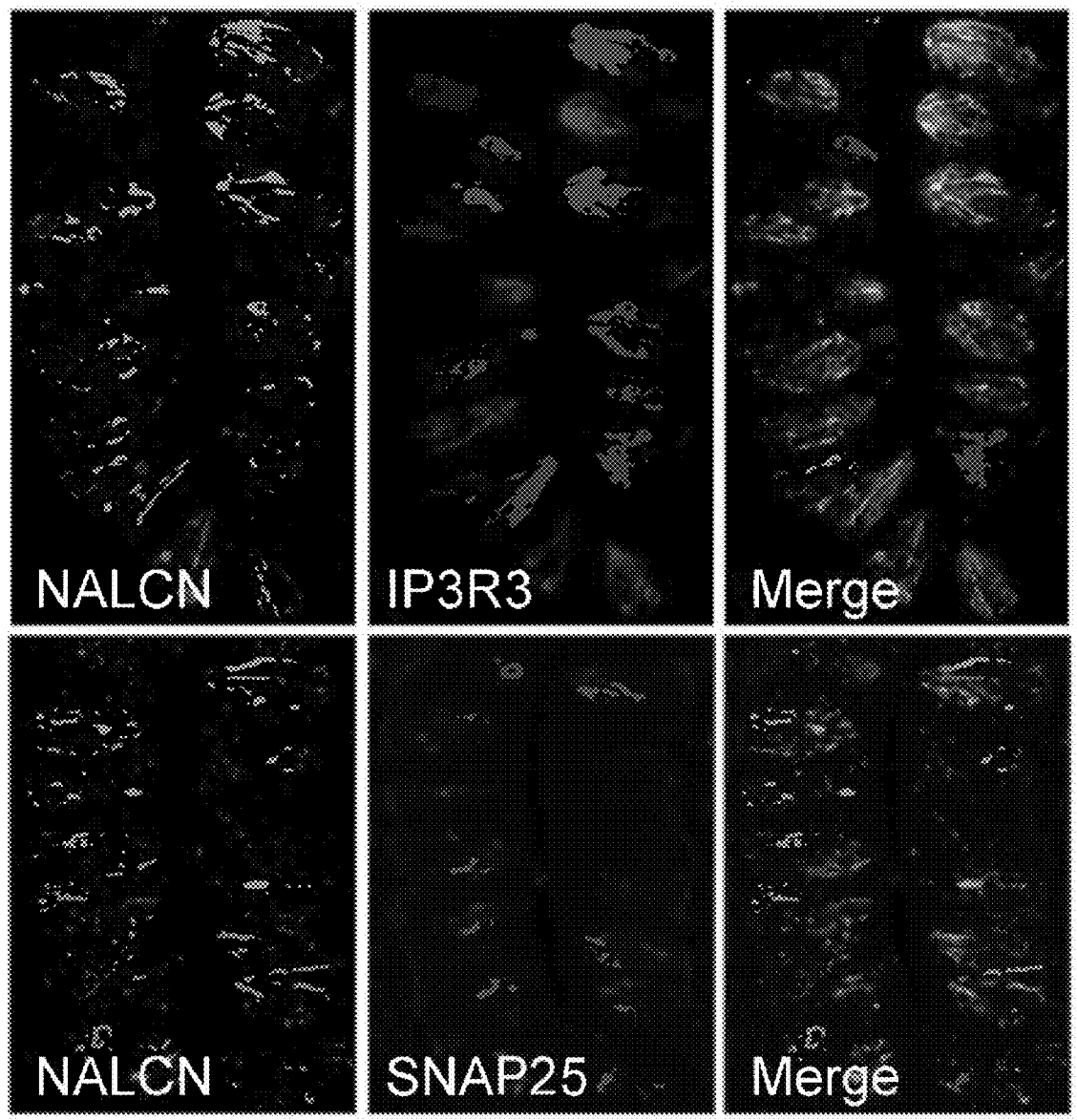
FIG. 43 The experiment in FIG. 43 shows that NALCN is expressed in a unique taste cell type effected at low magnification. Therein is shown a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. Numerous taste buds are shown.

This experiment the results of which are contained in FIG. 43 shows that NALCN is expressed in a unique taste cell type effected at low magnification. Therein is shown a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. Numerous taste buds are shown.

Example 43

Figure 44:
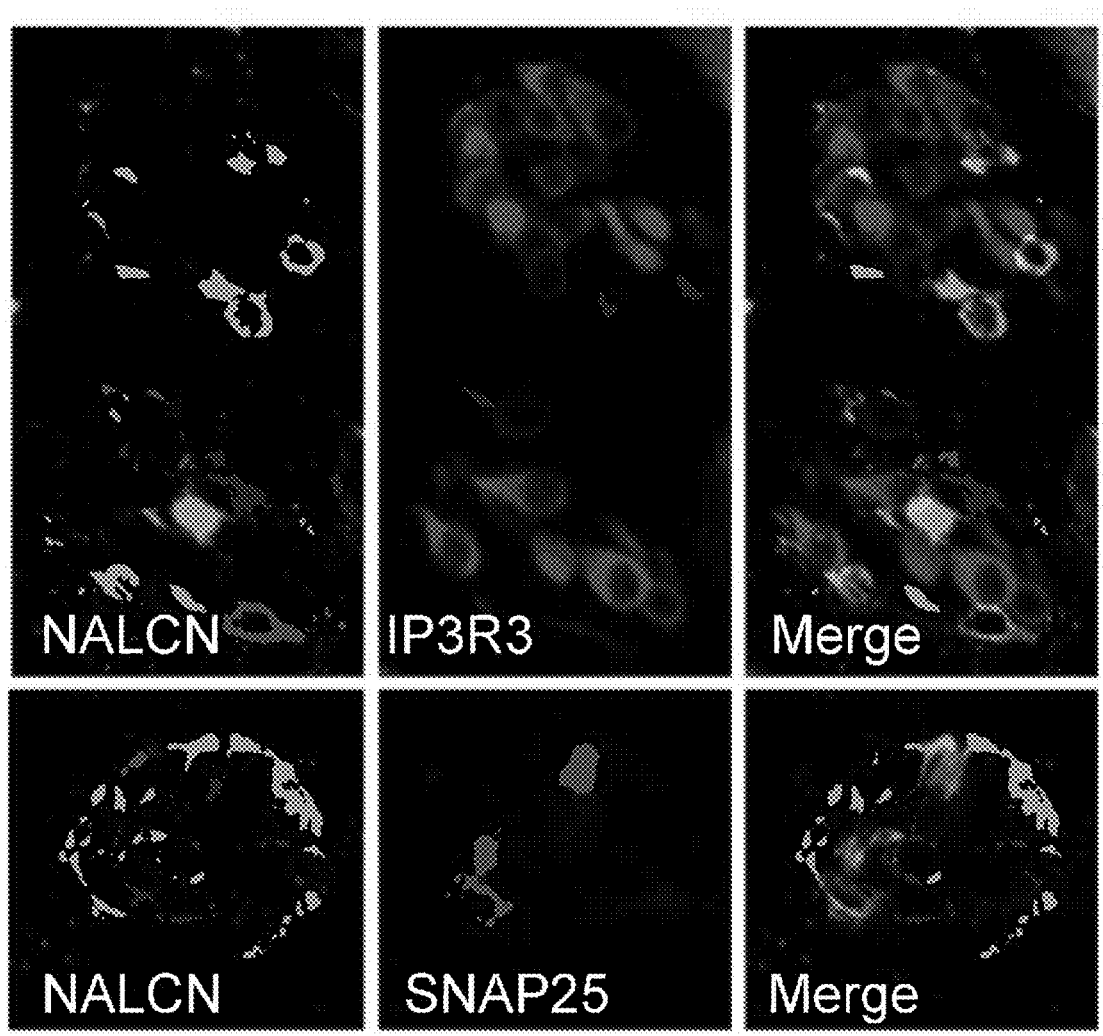
FIG. 44 The experiment in FIG. 44 also shows that NALCN is expressed in a unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. One to two taste buds are shown.

This experiment the results of which are contained in FIG. 44 also shows that NALCN is expressed in a unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. One to two taste buds are shown.

Example 44

Figure 45:
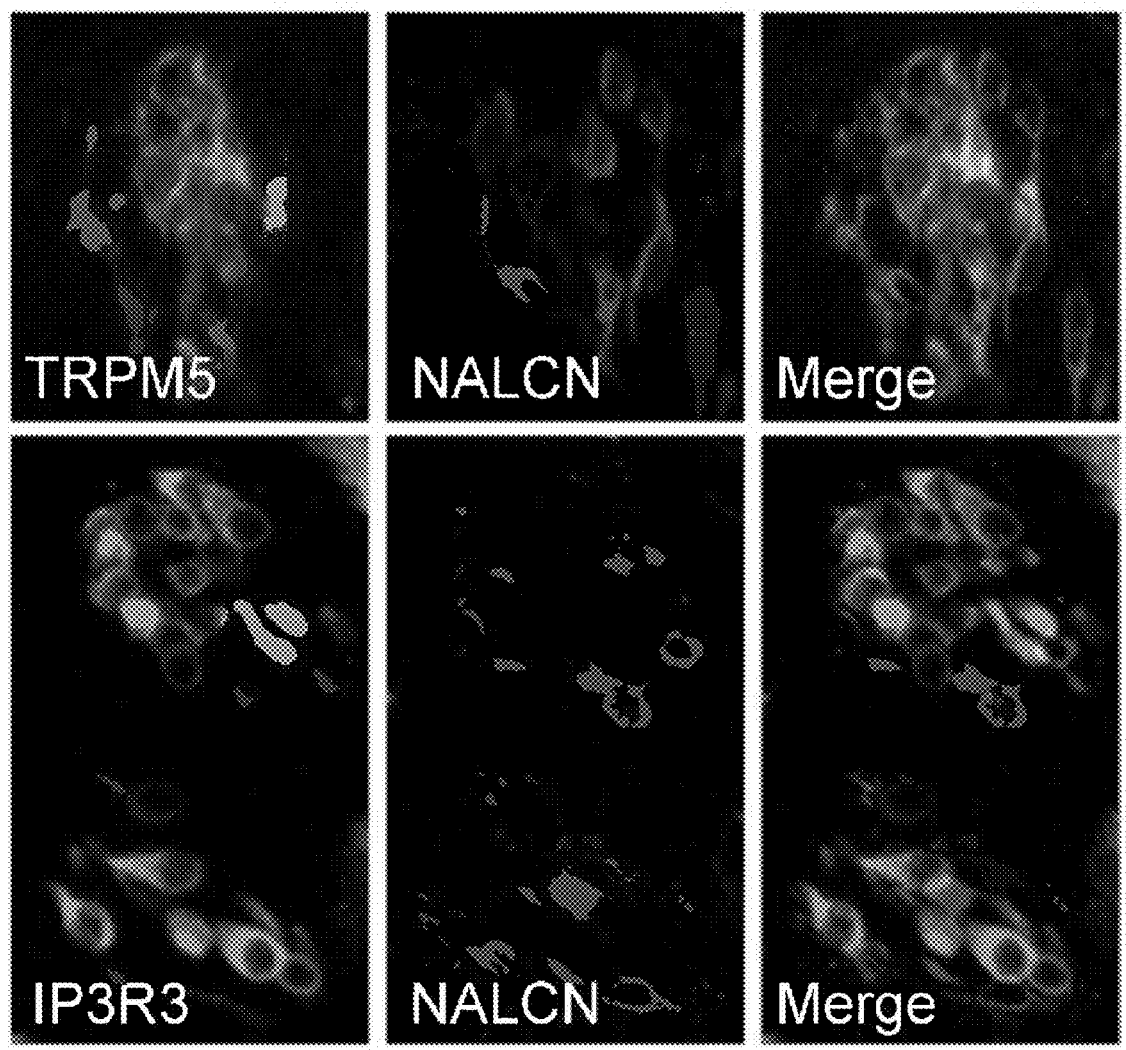
FIG. 45 The experiment in FIG. 45 shows hat NALCN is not expressed in TRPM5 cells. The figure contains a double label immunochemistry of circumvallate papilla from the back of the tongue showing that NALCN (red color, middle images( ) does not colocalize with TRPM5 in non-human primate (green, left image top row) or IP3R3 in rat (green; left image bottom row). Note that red and green stains localize to different cell types in the merged images on the right. Since TRPM5 and IP3R3 mark sweet, bitter, and umami cells, equivalent to type II cells, NALCN is not expressed in type II cells in non-human primate and rat.

This experiment the results of which are contained in FIG. 45 shows that NALCN is not expressed in TRPM5 cells. The figure contains a double label immunochemistry of circumvallate papilla from the back of the tongue showing that NALCN (red color, middle images( ) does not colocalize with TRPM5 in non-human primate (green, left image top row) or IP3R3 in rat (green; left image bottom row). Note that red and green stains localize to different cell types in the merged images on the right. Since TRPM5 and IP3R3 mark sweet, bitter, and umami cells, equivalent to type II cells, NALCN is not expressed in type II cells in non-human primate and rat.

Example 45

Figure 46:
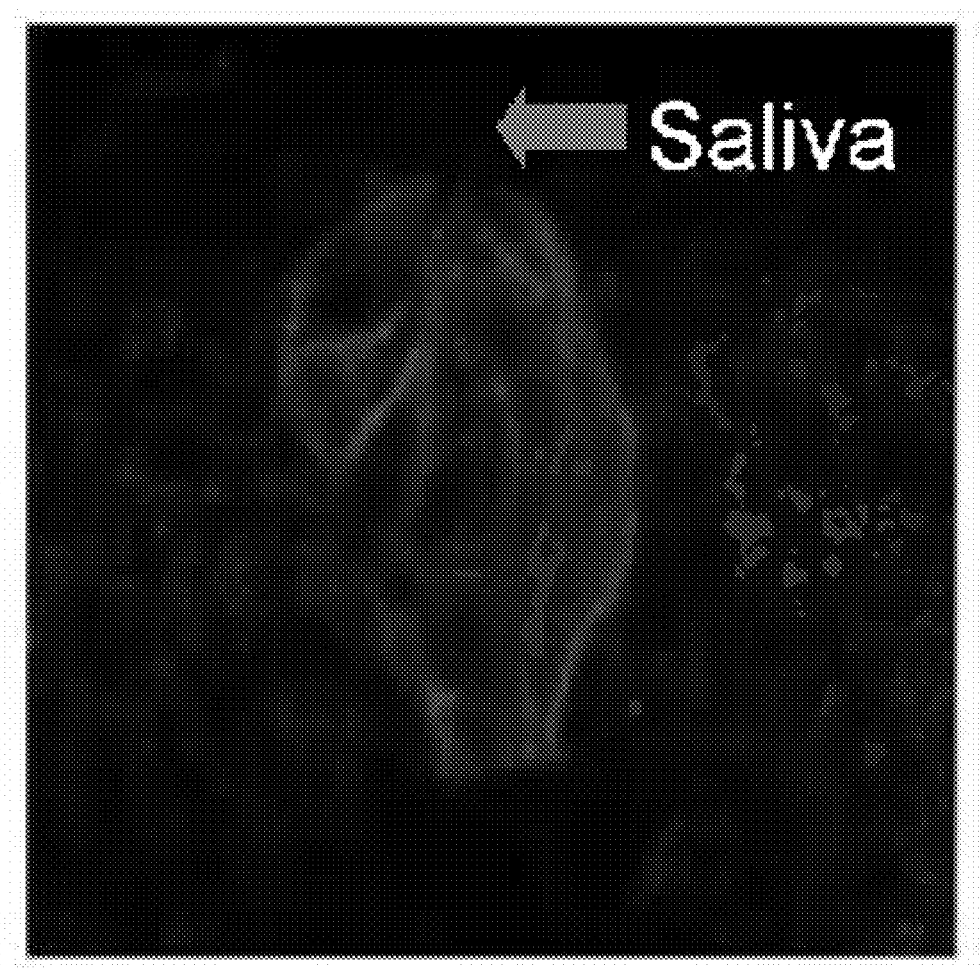
FIG. 46 The experiment in FIG. 46 shows that NALCN is expressed in a subset of fungiform taste cells. Therein single label immunochemistry of fungiform papilla from the front of the tongue of non-human primate showing that NALCN (red color) is expressed in a subset of taste cells. Top of the taste bud, facing saliva, if oriented towards the top in the image is shown (see arrow). unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel. taste cell population. One to two taste buds are shown.

The experiment in FIG. 46 shows that NALCN is expressed in a subset of fungiform taste cells. Therein single label immunochemistry of fungiform papilla from the front of the tongue of non-human primate showing that NALCN (red color) is expressed in a subset of taste cells. Top of the taste bud, facing saliva, if oriented towards the top in the image is shown (see arrow). unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel. taste cell population. One to two taste buds are shown Example 46

Identification of Human Taste Specific Genes by Quantitative PCR

Experiments enabling the identification of human taste specific genes by quantitative polymerase chain reaction (PCR) were also effected. In the previous examples we described genes expressed in primate taste buds and we assigned gene expression patterns within the primate taste bud for all taste bud-specific genes; specifically, using a comparison of gene expression between the top and bottom sections of the primate taste bud. By these methods the inventors were able to classify genes into one of several functional classes that include taste receptor genes. In this example we demonstrate taste specific gene expression in humans (in addition to primate) and have validated the specificity of expression by a quantitative method (qPCR or "TaqMan"). The genes described in Table below, identified by these methods all encode multi-span transmembrane proteins, and it is likely that they include the salt receptor and others taste receptors whose function has yet to be defined.

Figure 47:
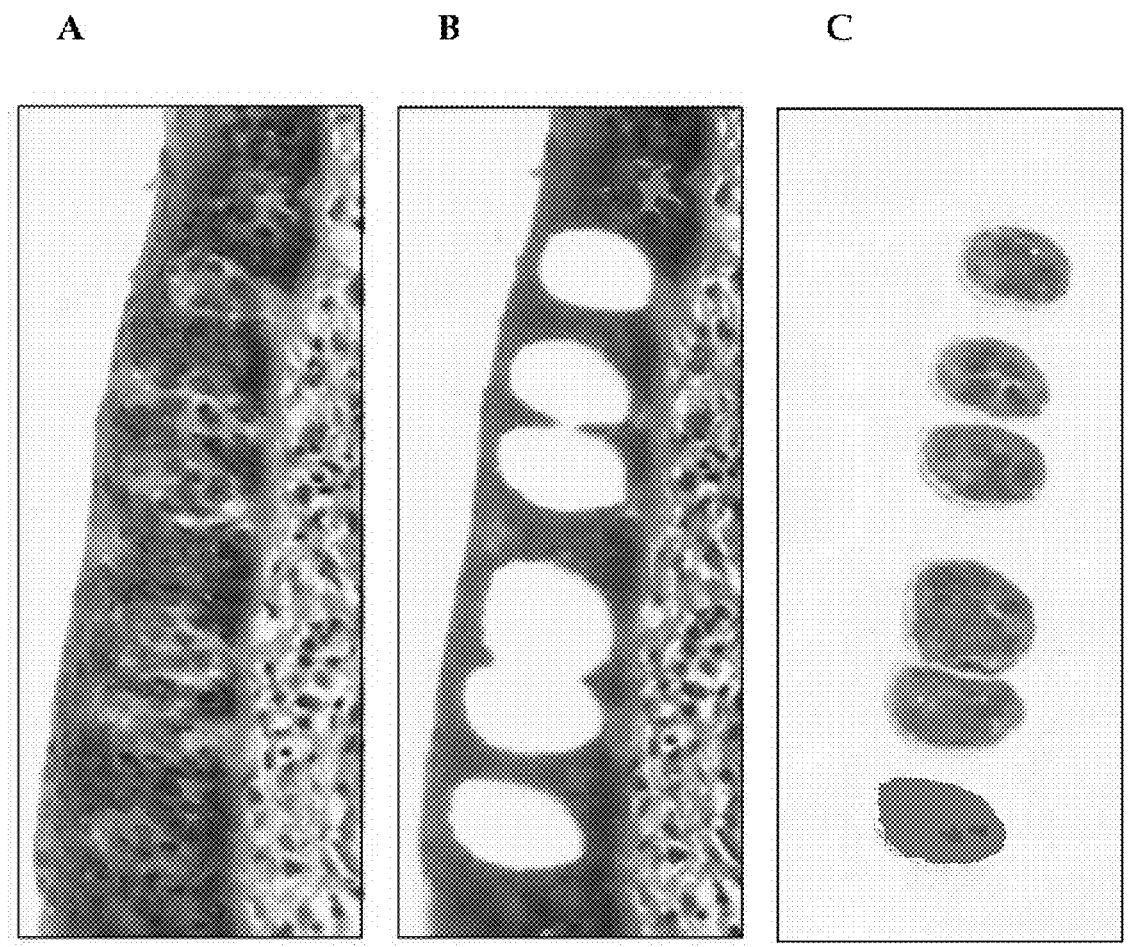
FIG. 47 shows the laser capture microdissection of human taste buds. Panel A shows methyl blue stained section of human circumvallate human taste buds. Panel B shows Section A following excision of taste buds. Panel C contains the captured taste buds.

In these experiments the inventors used human taste bud samples. In order to isolate human taste buds we performed laser capture microdissection (LCM). This technique has been described in detail in the provisional patent applications and incorporated by reference and supra. Briefly, it involves the excision and isolation of selected cells or groups of cells from tissue sections based on morphological distinctions. In the case of taste buds, we can readily identify these structures in sections of human tongue. In this specific example tissue collection was limited to taste buds (TB) in circumvallate papillae and, as a control, cells from the adjacent lingual epithelium (LE). An example of sections used in sample collection is shown in FIG. 47. Multiple LCM preparations from each of 3 human donors were pooled (~4500 cells per sample), RNA extracted and amplified by WT-Ovation Pico RNA Amplification System (NuGEN Technologies, Inc) and analyzed using TaqMan technology to determine specific levels of gene expression in the TB and LE pools.

The expression of the taste-specific genes was quantified by TaqMan in LCM derived cDNA from both LE and TB from the same donors. FIG. 47 shows the laser capture microdissection of human taste buds. Panel A shows methyl blue stained section of human circumvallate human taste buds. Panel B shows Section A following excision of taste buds. Panel C contains the captured taste buds.

A list of the analyzed human genes expressed are contained in Table 8 infra. Gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values>40 are defined as not detectable. For the majority of genes listed in the Table, expression was not detected in LE samples (CT>40) but was readily detectable in TB samples (CT<35).

The group of human taste specific genes contained in Table 8 has not been described before as taste-specific in human tissue.

Therefore, these results show that by using this approach that uses LCM from post-mortem human tissue samples and a single cDNA amplification step, our data clearly indicate that postmortem LCM human tissue can be used to quantify the expression of taste specific genes using qPCR. and that human taste specific genes can be measured by quantitative PCR (TaqMan). Particularly, gene expression profiles of taste specific genes can be measured by TaqMan. This methodology validated gene expression data obtained from microarrays and/or in situ hybridization (ISH). Therefore, by using the successive approaches of gene expression via microarray in primate LCM tongue tissue; top-specific gene expression within the taste bud (akin to known taste receptors) and TaqMan quantification of gene expression in human postmortem tastes tissues, new human taste specific genes that had not been described previously were identified as contained in Table 8.

Additional Results and Tables Listing Taste Specific Genes (Human and Macaque)

The primate taste bud-specific gene list which resulted in the taste-specific genes contained in Tables 1-5 below were generated by the use of specific inclusion criteria. These inclusion criteria used Affymetrix MAS5 normalized data as follows:

Inclusion Criteria
Using Affymetrix MAS5 Normalized Data
FG taste bud mean expression value≧50
FG versus LE expression ratio≧2-fold up
FG versus LE expression ratio p value≦0.05
  [01] 424 probe sets
  [02] Using Affymetrix GC-RMA normalized data
FG taste bud mean expression value≧20
FG versus LE expression ratio≧2-fold up
FG versus LE expression ratio p value≦0.05
  [03] 504 probe sets
  [04] PLUS 3211 probe sets isolated from both data sets
  [05] [TOTAL Number of Primate Taste Bud Specific probe Sets Equals 4139}
  [06] TOTAL Number of Primate Taste Bud Specific Genes Equals 3455

TABLE 1

| Representative Public ID | Representative Public ID: Species | MAS5 LE mean | MAS5 TB mean | MAS5 fold change | MAS5 p value |
|---|---|---|---|---|---|
| XM_001085855 | Mm | 168.1 | 825.8 | 4.9 | 0.0007 |
| XM_001106014 | Mm | 50.9 | 113.9 | 2.2 | 0.0386 |
| XM_001084081 | Mm | 17.1 | 174.9 | 10.2 | 0.0066 |
| XM_001099138 | Mm | 126.8 | 547.4 | 4.3 | 0.0244 |
| XM_001101439 | Mm | 30.3 | 102.6 | 3.4 | 0.0250 |
| XM_001113252 | Mm | 5.0 | 702.3 | 139.3 | 0.0006 |
| XM_001107314 | Mm | 12.3 | 74.2 | 6.0 | 0.0001 |
| XR_014466 | Mm | 185.9 | 584.9 | 3.1 | 0.0056 |
| XR_013101 | Mm | 63.8 | 405.3 | 6.4 | 0.0103 |
| XM_001083619 | Mm | 16.5 | 155.4 | 9.4 | 0.0496 |
| XM_001088479 | Mm | 344.9 | 1388.2 | 4.0 | 0.0043 |
| XM_001088853 | Mm | 44.9 | 102.2 | 2.3 | 0.1992 |
| XM_001085289 | Mm | 416.8 | 2226.5 | 5.3 | 0.0001 |
| XM_001086036 | Mm | 34.3 | 88.7 | 2.6 | 0.0421 |
| XM_001114058 | Mm | 404.5 | 3269.5 | 8.1 | 0.0007 |
| XM_001112907 | Mm | 81.7 | 715.0 | 8.8 | 0.0223 |

TABLE 1-continued

| Representative Public ID | Representative Public ID: Species | MAS5 LE mean | MAS5 TB mean | MAS5 fold change | MAS5 p value |
|---|---|---|---|---|---|
| BV165948 | Mm | 35.9 | 111.9 | 3.1 | 0.0172 |
| BV166168 | Mm | 11.1 | 93.6 | 8.5 | 0.0026 |
| BV166439 | Mm | 11.0 | 75.4 | 6.9 | 0.0016 |
| BV209038 | Mm | 35.5 | 154.1 | 4.3 | 0.0139 |
| BV209579 | Mm | 22.4 | 51.7 | 2.3 | 0.0393 |
| BV209589 | Mm | 18.5 | 109.8 | 5.9 | 0.0340 |
| BV209803 | Mm | 31.9 | 97.2 | 3.0 | 0.0775 |
| BV209934 | Mm | 40.2 | 104.0 | 2.6 | 0.0606 |
| BV210562 | Mm | 626.9 | 1473.7 | 2.4 | 0.0003 |
| BV211039 | Mm | 164.1 | 439.3 | 2.7 | 0.0026 |
| BV445286 | Mm | 51.7 | 493.2 | 9.5 | 0.0039 |
| BV447952 | Mm | 36.9 | 454.5 | 12.3 | 0.0001 |
| BV447979 | Mm | 22.4 | 123.1 | 5.5 | 0.0001 |
| BV448453 | Mm | 36.7 | 184.8 | 5.0 | 0.0333 |
| BV448619 | Mm | 32.7 | 90.3 | 2.8 | 0.0288 |
| BV448731 | Mm | 374.3 | 769.4 | 2.1 | 0.0179 |
| BV448735 | Mm | 20.6 | 1485.7 | 72.2 | 0.0010 |
| BV448827 | Mm | 44.4 | 110.9 | 2.5 | 0.0441 |
| AL833583 | Hs | 31.4 | 267.0 | 8.5 | 0.1140 |
| CB550378 | Mm | 16.2 | 136.4 | 8.4 | 0.0164 |
| CN804030 | Mm | 431.4 | 1060.7 | 2.5 | 0.0387 |
| CO774248 | Mm | 22.4 | 70.6 | 3.1 | 0.0233 |
| NM_000166 | Hs | 19.1 | 64.4 | 3.4 | 0.0466 |
| NM_000335 | Hs | 4.5 | 381.4 | 85.4 | 0.0003 |
| NM_001001666 | Hs | 13.0 | 139.7 | 10.7 | 0.0009 |
| NM_001001994 | Hs | 40.0 | 1037.3 | 25.9 | 0.0003 |
| NM_001002796 | Hs | 3.7 | 2066.5 | 558.9 | 0.0046 |
| NM_001004746 | Hs | 35.3 | 102.1 | 2.9 | 0.0148 |
| NM_001010898 | Hs | 26.8 | 106.7 | 4.0 | 0.0016 |
| NM_001011655 | Hs | 8.2 | 1258.5 | 154.2 | 0.0035 |
| NM_001012302 | Hs | 28.9 | 64.8 | 2.2 | 0.0090 |
| NM_001017970 | Hs | 348.7 | 1779.2 | 5.1 | 0.0000 |
| NM_001025356 | Hs | 43.1 | 175.0 | 4.1 | 0.0071 |
| NM_001033026 | Hs | 90.2 | 180.8 | 2.0 | 0.0091 |
| NM_001037984 | Hs | 134.6 | 263.8 | 2.0 | 0.0032 |
| NM_001040456 | Hs | 46.2 | 155.1 | 3.4 | 0.0019 |
| NM_001042680 | Hs | 28.4 | 59.3 | 2.1 | 0.0495 |
| NM_001046 | Hs | 41.8 | 182.3 | 4.4 | 0.0002 |
| NM_001076674 | Hs | 174.4 | 351.5 | 2.0 | 0.0666 |
| NM_001077241 | Hs | 52.8 | 129.7 | 2.5 | 0.0175 |
| NM_001079669 | Hs | 245.7 | 3971.8 | 16.2 | 0.0000 |
| NM_001425 | Hs | 29.3 | 60.9 | 2.1 | 0.1000 |
| NM_001606 | Hs | 700.5 | 3503.3 | 5.0 | 0.0000 |
| NM_002211 | Hs | 7.1 | 42.6 | 6.0 | 0.0249 |
| NM_003615 | Hs | 8.4 | 413.3 | 48.9 | 0.0034 |
| NM_004099 | Hs | 66.5 | 174.0 | 2.6 | 0.0010 |
| NM_005502 | Hs | 223.5 | 611.5 | 2.7 | 0.0264 |
| NM_005724 | Hs | 321.1 | 666.4 | 2.1 | 0.0048 |
| NM_007213 | Hs | 23.6 | 78.8 | 3.3 | 0.0336 |
| NM_012329 | Hs | 43.0 | 209.1 | 4.9 | 0.0577 |
| NM_014399 | Hs | 2718.3 | 5413.0 | 2.0 | 0.0013 |
| NM_014858 | Hs | 62.8 | 176.7 | 2.8 | 0.0597 |
| NM_014982 | Hs | 18.0 | 86.9 | 4.8 | 0.0493 |
| NM_015205 | Hs | 177.2 | 389.7 | 2.2 | 0.0234 |
| NM_015257 | Hs | 38.7 | 134.4 | 3.5 | 0.0269 |
| NM_015292 | Hs | 986.6 | 2513.0 | 2.5 | 0.0004 |
| NM_015916 | Hs | 5.2 | 152.3 | 29.5 | 0.0057 |
| NM_016127 | Hs | 1915.3 | 3775.3 | 2.0 | 0.0003 |
| NM_016235 | Hs | 27.7 | 584.2 | 21.1 | 0.0007 |
| NM_016475 | Hs | 49.3 | 143.6 | 2.9 | 0.0400 |
| NM_017586 | Hs | 266.0 | 1076.2 | 4.0 | 0.0140 |
| NM_017672 | Hs | 68.9 | 231.9 | 3.4 | 0.0074 |
| NM_017744 | Hs | 81.3 | 202.7 | 2.5 | 0.0061 |
| NM_017799 | Hs | 42.0 | 191.1 | 4.6 | 0.0047 |
| NM_017801 | Hs | 78.5 | 154.7 | 2.0 | 0.0110 |
| NM_017814 | Hs | 33.0 | 100.7 | 3.1 | 0.0049 |
| NM_017849 | Hs | 43.5 | 109.5 | 2.5 | 0.0092 |
| NM_017905 | Hs | 32.5 | 91.7 | 2.8 | 0.0382 |
| NM_017918 | Hs | 48.9 | 232.0 | 4.7 | 0.0012 |
| NM_018056 | Hs | 25.7 | 63.3 | 2.5 | 0.0298 |
| NM_018452 | Hs | 48.4 | 146.0 | 3.0 | 0.0090 |
| NM_018487 | Hs | 8.9 | 924.9 | 103.6 | 0.0004 |
| NM_018502 | Hs | 14.0 | 47.3 | 3.4 | 0.0234 |
| NM_019118 | Hs | 37.5 | 451.0 | 12.0 | 0.0000 |
| NM_020215 | Hs | 12.9 | 108.0 | 8.4 | 0.0112 |
| NM_020448 | Hs | 34.7 | 93.3 | 2.7 | 0.0445 |
| NM_020925 | Hs | 27.9 | 480.2 | 17.2 | 0.0069 |

TABLE 1-continued

| Representative Public ID | Representative Public ID: Species | MAS5 LE mean | MAS5 TB mean | MAS5 fold change | MAS5 p value |
|---|---|---|---|---|---|
| NM_021194 | Hs | 132.0 | 329.5 | 2.5 | 0.0493 |
| NM_021259 | Hs | 20.1 | 115.0 | 5.7 | 0.0178 |
| NM_021637 | Hs | 6.9 | 64.5 | 9.3 | 0.0032 |
| NM_021727 | Hs | 46.6 | 106.0 | 2.3 | 0.0132 |
| NM_022369 | Hs | 8.6 | 131.0 | 15.3 | 0.0940 |
| NM_022458 | Hs | 32.9 | 145.1 | 4.4 | 0.0203 |
| NM_022495 | Hs | 33.1 | 154.8 | 4.7 | 0.0239 |
| NM_023003 | Hs | 16.0 | 157.6 | 9.9 | 0.0175 |
| NM_023943 | Hs | 7.7 | 57.2 | 7.4 | 0.0375 |
| NM_024628 | Hs | 47.5 | 710.7 | 15.0 | 0.0018 |
| NM_024630 | Hs | 71.6 | 386.9 | 5.4 | 0.0159 |
| NM_024956 | Hs | 64.7 | 129.7 | 2.0 | 0.0211 |
| NM_025257 | Hs | 9.7 | 275.1 | 28.2 | 0.0024 |
| NM_030651 | Hs | 7.1 | 183.8 | 25.9 | 0.0053 |
| NM_030923 | Hs | 6.5 | 1801.8 | 276.3 | 0.0004 |
| NM_031442 | Hs | 8.7 | 73.8 | 8.5 | 0.0415 |
| NM_031484 | Hs | 88.3 | 881.7 | 10.0 | 0.0001 |
| NM_032012 | Hs | 390.0 | 1480.2 | 3.8 | 0.0006 |
| NM_032016 | Hs | 135.4 | 961.3 | 7.1 | 0.0023 |
| NM_032295 | Hs | 112.6 | 267.8 | 2.4 | 0.0152 |
| NM_032483 | Hs | 87.0 | 224.8 | 2.6 | 0.0200 |
| NM_032824 | Hs | 90.1 | 335.9 | 3.7 | 0.0563 |
| NM_032826 | Hs | 17.5 | 62.2 | 3.6 | 0.0084 |
| NM_032890 | Hs | 93.4 | 987.6 | 10.6 | 0.0000 |
| NM_033102 | Hs | 7.8 | 125.6 | 16.1 | 0.0202 |
| NM_138346 | Hs | 573.4 | 2006.8 | 3.5 | 0.0001 |
| NM_139075 | Hs | 48.1 | 138.1 | 2.9 | 0.0046 |
| NM_144638 | Hs | 19.8 | 92.2 | 4.6 | 0.0170 |
| NM_144649 | Hs | 21.9 | 52.6 | 2.4 | 0.1617 |
| NM_144686 | Hs | 18.0 | 406.4 | 22.6 | 0.0034 |
| NM_145290 | Hs | 44.9 | 192.8 | 4.3 | 0.1919 |
| NM_152288 | Hs | 353.5 | 1590.1 | 4.5 | 0.0006 |
| NM_152522 | Hs | 357.2 | 514.3 | 1.4 | 0.0595 |
| NM_152588 | Hs | 182.1 | 560.3 | 3.1 | 0.0148 |
| NM_152778 | Hs | 43.7 | 208.5 | 4.8 | 0.0139 |
| NM_153354 | Hs | 38.2 | 118.1 | 3.1 | 0.0523 |
| NM_153365 | Hs | 600.9 | 1850.8 | 3.1 | 0.0027 |
| NM_153704 | Hs | 8.9 | 46.9 | 5.3 | 0.0288 |
| NM_153811 | Hs | 105.8 | 303.3 | 2.9 | 0.0433 |
| NM_173512 | Hs | 10.3 | 77.0 | 7.5 | 0.0169 |
| NM_173653 | Hs | 159.5 | 357.2 | 2.2 | 0.0187 |
| NM_174926 | Hs | 8.2 | 211.1 | 25.9 | 0.0246 |
| NM_175861 | Hs | 15.1 | 74.4 | 4.9 | 0.0146 |
| NM_177964 | Hs | 27.7 | 267.4 | 9.7 | 0.0016 |
| NM_178818 | Hs | 54.5 | 167.8 | 3.1 | 0.0145 |
| NM_181644 | Hs | 63.9 | 520.8 | 8.2 | 0.0095 |
| NM_181787 | Hs | 52.3 | 246.1 | 4.7 | 0.0109 |
| NM_182494 | Hs | 5.4 | 1159.4 | 215.5 | 0.0010 |
| NM_182504 | Hs | 8.4 | 53.3 | 6.4 | 0.0151 |
| NM_182532 | Hs | 4.8 | 74.8 | 15.5 | 0.0180 |
| NM_182547 | Hs | 1722.3 | 3135.0 | 1.8 | 0.0023 |
| NM_198276 | Hs | 35.7 | 127.6 | 3.6 | 0.0226 |
| NM_207351 | Hs | 116.0 | 890.6 | 7.7 | 0.0035 |
| XM_001128552 | Hs | 4.7 | 292.8 | 62.8 | 0.0505 |
| XM_370997 | Hs | 6.3 | 70.5 | 11.2 | 0.0057 |
| XM_927351 | Hs | 5.3 | 1085.9 | 204.3 | 0.0027 |

[08] This table summarizes primate taste-bud expressed genes that were identified as multi-plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions. Representative accession numbers are from primate (i.e. *Macaca mulatta* abbreviated Mm) or humans (i.e. *Homo sapiens* abbreviated Hs).

TABLE 2

| Representative Public ID | Representative Public ID: Species | MAS5 LE mean | MAS5 TB mean | MAS5 fold change | MAS5 p value |
|---|---|---|---|---|---|
| XR_011926 | Mm | 11.4 | 213.4 | 18.7 | 0.0231 |
| XM_001099450 | Mm | 10.2 | 57.8 | 5.7 | 0.0126 |
| XM_001098390 | Mm | 12.8 | 93.4 | 7.3 | 0.0196 |
| XM_001086764 | Mm | 12.5 | 58.0 | 4.6 | 0.0870 |
| XM_001114476 | Mm | 5.3 | 122.9 | 23.1 | 0.0047 |
| XM_001110867 | Mm | 16.0 | 245.0 | 15.3 | 0.0015 |
| R58928 | Mm | 5.6 | 50.6 | 9.0 | 0.0126 |
| XM_001093116 | Mm | 8.8 | 121.0 | 13.7 | 0.0095 |
| XM_001099593 | Mm | 9.4 | 126.9 | 13.6 | 0.0008 |
| XR_010972 | Mm | 9.2 | 547.5 | 59.6 | 0.0005 |
| XM_001084620 | Mm | 4.4 | 1917.8 | 433.3 | 0.0001 |

TABLE 2-continued

| Representative Public ID | Representative Public ID: Species | MAS5 LE mean | MAS5 TB mean | MAS5 fold change | MAS5 p value |
|---|---|---|---|---|---|
| XM_001090982 | Mm | 34.3 | 229.2 | 6.7 | 0.0060 |
| XM_001098500 | Mm | 20.0 | 1366.9 | 68.2 | 0.0022 |
| XM_001088661 | Mm | 12.7 | 70.0 | 5.5 | 0.0327 |
| XM_001097918 | Mm | 367.0 | 1244.3 | 3.4 | 0.0059 |
| XM_001089122 | Mm | 9.9 | 176.2 | 17.8 | 0.0307 |
| XM_001106548 | Mm | 16.7 | 854.3 | 51.2 | 0.0001 |
| BV166050 | Mm | 12.1 | 108.1 | 8.9 | 0.0043 |
| BV166421 | Mm | 10.3 | 2141.3 | 207.1 | 0.0001 |
| BV166428 | Mm | 90.1 | 1287.4 | 14.3 | 0.0010 |
| BV166437 | Mm | 13.5 | 253.1 | 18.7 | 0.0871 |
| BV166724 | Mm | 9.6 | 59.6 | 6.2 | 0.0304 |
| BV166739 | Mm | 150.9 | 719.0 | 4.8 | 0.0002 |
| BV166741 | Mm | 159.5 | 303.8 | 1.9 | 0.0297 |
| BV166749 | Mm | 56.6 | 156.9 | 2.8 | 0.0055 |
| BV166757 | Mm | 212.7 | 1221.6 | 5.7 | 0.0011 |
| BV166818 | Mm | 23.3 | 157.6 | 6.8 | 0.0822 |
| BV208636 | Mm | 25.4 | 584.3 | 23.0 | 0.0013 |
| BV208853 | Mm | 23.0 | 225.5 | 9.8 | 0.0043 |
| BV209086 | Mm | 22.9 | 85.6 | 3.7 | 0.0012 |
| BV209237 | Mm | 26.3 | 1562.2 | 59.5 | 0.0000 |
| BV209238 | Mm | 302.6 | 964.7 | 3.2 | 0.0073 |
| BV209550 | Mm | 5.3 | 2121.2 | 398.1 | 0.0000 |
| BV209574 | Mm | 20.8 | 111.0 | 5.3 | 0.0154 |
| BV210515 | Mm | 100.4 | 202.2 | 2.0 | 0.0022 |
| BV210859 | Mm | 46.9 | 140.8 | 3.0 | 0.0156 |
| BV210983 | Mm | 181.8 | 563.9 | 3.1 | 0.0031 |
| BV447592 | Mm | 12.8 | 1670.7 | 130.7 | 0.0003 |
| BV447751 | Mm | 4.4 | 406.5 | 91.5 | 0.0010 |
| BV448581 | Mm | 50.3 | 159.8 | 3.2 | 0.0422 |
| BV448600 | Mm | 6.9 | 179.2 | 26.1 | 0.0071 |
| AK057677 | Hs | 17.8 | 616.2 | 34.6 | 0.0017 |
| AK095199 | Hs | 6.0 | 189.4 | 31.8 | 0.0313 |
| NM_000068 | Hs | 20.9 | 379.4 | 18.1 | 0.0007 |
| NM_000112 | Hs | 21.3 | 337.8 | 15.9 | 0.0182 |
| NM_000238 | Hs | 8.8 | 427.4 | 48.5 | 0.0019 |
| NM_000617 | Hs | 72.1 | 238.1 | 3.3 | 0.0359 |
| NM_001001396 | Hs | 18.4 | 116.6 | 6.3 | 0.0081 |
| NM_001001787 | Hs | 414.9 | 2580.5 | 6.2 | 0.0006 |
| NM_001008783 | Hs | 1.0 | 114.5 | 117.2 | 0.0196 |
| NM_001017403 | Hs | 4.6 | 265.1 | 57.2 | 0.0086 |
| NM_001020818 | Hs | 484.8 | 1455.0 | 3.0 | 0.0006 |
| NM_001023587 | Hs | 163.3 | 1680.5 | 10.3 | 0.0042 |
| NM_001024938 | Hs | 35.3 | 114.7 | 3.2 | 0.0255 |
| NM_001029858 | Hs | 4.3 | 2244.2 | 523.9 | 0.0033 |
| NM_001076785 | Hs | 6.7 | 128.0 | 19.0 | 0.0178 |
| NM_001106 | Hs | 12.5 | 65.6 | 5.2 | 0.0223 |
| NM_002241 | Hs | 3.2 | 132.8 | 42.1 | 0.0018 |
| NM_002980 | Hs | 35.9 | 156.4 | 4.4 | 0.0119 |
| NM_003043 | Hs | 213.6 | 900.2 | 4.2 | 0.0147 |
| NM_003304 | Hs | 144.8 | 663.9 | 4.6 | 0.0007 |
| NM_003641 | Hs | 33.5 | 327.9 | 9.8 | 0.0086 |
| NM_004616 | Hs | 13.2 | 795.8 | 60.4 | 0.0022 |
| NM_004733 | Hs | 314.5 | 810.9 | 2.6 | 0.0187 |
| NM_004770 | Hs | 1.8 | 305.6 | 173.7 | 0.0098 |
| NM_004974 | Hs | 1.9 | 125.3 | 65.7 | 0.0017 |
| NM_004996 | Hs | 923.5 | 4019.0 | 4.4 | 0.0000 |
| NM_005173 | Hs | 29.8 | 3560.0 | 119.4 | 0.0000 |
| NM_005415 | Hs | 468.3 | 1315.2 | 2.8 | 0.0035 |
| NM_005669 | Hs | 2293.8 | 4587.3 | 2.0 | 0.0009 |
| NM_006054 | Hs | 681.2 | 1701.5 | 2.5 | 0.0035 |
| NM_006435 | Hs | 1431.8 | 4294.5 | 3.0 | 0.0198 |
| NM_006598 | Hs | 71.4 | 673.6 | 9.4 | 0.0021 |
| NM_006608 | Hs | 66.8 | 172.7 | 2.6 | 0.1044 |
| NM_007001 | Hs | 10.3 | 80.3 | 7.8 | 0.0472 |
| NM_012129 | Hs | 303.5 | 542.9 | 1.8 | 0.0154 |
| NM_014220 | Hs | 81.6 | 306.2 | 3.8 | 0.0029 |
| NM_015236 | Hs | 6.2 | 407.8 | 66.3 | 0.0041 |
| NM_016395 | Hs | 25.6 | 100.9 | 3.9 | 0.0407 |
| NM_018144 | Hs | 75.3 | 214.4 | 2.8 | 0.1049 |
| NM_018155 | Hs | 84.9 | 411.3 | 4.8 | 0.0005 |
| NM_020724 | Hs | 5.7 | 44.6 | 7.8 | 0.0120 |
| NM_021095 | Hs | 41.5 | 203.3 | 4.9 | 0.0262 |
| NM_022109 | Hs | 763.0 | 182.3 | 2.4 | 0.0046 |
| NM_022154 | Hs | 20.8 | 552.8 | 26.5 | 0.0087 |
| NM_022754 | Hs | 65.5 | 213.6 | 3.3 | 0.1189 |
| NM_024534 | Hs | 27.0 | 549.1 | 20.3 | 0.1113 |
| NM_030571 | Hs | 373.9 | 735.4 | 2.0 | 0.0062 |
| NM_031462 | Hs | 6.1 | 51.5 | 8.5 | 0.0173 |
| NM_033272 | Hs | 7.0 | 677.5 | 97.3 | 0.0185 |
| NM_052885 | Hs | 13.8 | 64.7 | 4.7 | 0.0270 |
| NM_133329 | Hs | 7.6 | 160.7 | 21.3 | 0.0078 |
| NM_138694 | Hs | 11.9 | 227.0 | 19.0 | 0.0066 |
| NM_144673 | Hs | 19.6 | 288.7 | 14.7 | 0.0004 |
| NM_152264 | Hs | 19.3 | 87.7 | 4.5 | 0.0088 |
| NM_152686 | Hs | 17.7 | 392.4 | 22.2 | 0.0099 |
| NM_153357 | Hs | 9.7 | 84.5 | 8.7 | 0.0578 |
| NM_178276 | Hs | 1442.4 | 2921.0 | 2.0 | 0.0028 |
| NM_178568 | Hs | 9.5 | 48.1 | 5.0 | 0.0462 |
| XM_370711 | Hs | 17.4 | 91.9 | 5.3 | 0.0236 |
| XM_931948 | Hs | 256.3 | 1010.3 | 3.9 | 0.0000 |
| XM_001084141 | Mm | 65.3 | 229.1 | 3.5 | 0.0024 |
| XM_001108664 | Mm | 21.1 | 79.8 | 3.8 | 0.0184 |
| XM_001103706 | Mm | 82.6 | 232.7 | 2.8 | 0.0027 |
| NM_207627 | Hs | 8.1 | 181.4 | 22.3 | 0.0499 |
| XM_001083115 | Mm | 228.6 | 705.3 | 3.1 | 0.0040 |
| XM_001103565 | Mm | 328.5 | 797.1 | 2.4 | 0.0015 |
| BV166047 | Mm | 10.0 | 98.9 | 9.9 | 0.0445 |
| BV166216 | Mm | 5.9 | 218.2 | 37.0 | 0.0000 |
| BV166400 | Mm | 160.3 | 1036.6 | 6.5 | 0.0001 |
| BV166539 | Mm | 111.9 | 1279.1 | 11.4 | 0.0036 |
| BV166725 | Mm | 6.7 | 78.5 | 11.6 | 0.0192 |
| BV208837 | Mm | 41.7 | 209.0 | 5.0 | 0.0010 |
| BV209241 | Mm | 230.8 | 515.4 | 2.2 | 0.0041 |
| BV209592 | Mm | 42.0 | 303.8 | 7.2 | 0.0004 |
| BV445228 | Mm | 42.3 | 136.5 | 3.2 | 0.0530 |
| BV447852 | Mm | 4.0 | 120.0 | 30.2 | 0.0205 |
| NM_018398 | Hs | 5.8 | 273.7 | 46.9 | 0.0294 |
| NM_001035 | Hs | 18.1 | 59.4 | 3.3 | 0.0342 |
| NM_001736 | Hs | 168.9 | 1036.9 | 6.1 | 0.0013 |
| NM_001992 | Hs | 7.0 | 73.7 | 10.6 | 0.0081 |
| NM_004700 | Hs | 5.2 | 114.1 | 22.1 | 0.0005 |
| NM_005845 | Hs | 35.4 | 616.0 | 17.4 | 0.0007 |
| NM_006218 | Hs | 46.6 | 186.2 | 4.0 | 0.0460 |
| NM_012072 | Hs | 12.7 | 110.8 | 8.7 | 0.0448 |
| NM_012319 | Hs | 16.7 | 165.4 | 9.9 | 0.0586 |
| NM_013384 | Hs | 19.1 | 187.2 | 9.8 | 0.0010 |
| NM_013388 | Hs | 40.4 | 79.5 | 2.0 | 0.0281 |
| NM_014331 | Hs | 90.2 | 544.5 | 6.0 | 0.0006 |
| NM_015444 | Hs | 38.1 | 134.1 | 3.5 | 0.1685 |
| NM_017746 | Hs | 24.5 | 54.3 | 2.2 | 0.0858 |
| NM_017839 | Hs | 21.9 | 139.0 | 6.3 | 0.0280 |
| NM_021814 | Hs | 126.4 | 686.9 | 5.4 | 0.0006 |
| NM_022374 | Hs | 777.3 | 1714.3 | 2.2 | 0.0027 |
| NM_022768 | Hs | 10.2 | 95.9 | 9.4 | 0.0320 |
| NM_024809 | Hs | 40.6 | 87.9 | 2.2 | 0.0498 |
| NM_025141 | Hs | 685.7 | 1708.0 | 2.5 | 0.0006 |
| NM_025154 | Hs | 267.0 | 1000.7 | 3.7 | 0.0000 |
| NM_031301 | Hs | 22.8 | 185.8 | 8.1 | 0.0629 |
| NM_032027 | Hs | 288.0 | 667.2 | 2.3 | 0.0548 |
| NM_144991 | Hs | 13.5 | 40.9 | 3.0 | 0.0153 |
| NM_152261 | Hs | 38.0 | 262.7 | 6.9 | 0.0025 |
| NM_152621 | Hs | 54.5 | 367.4 | 6.7 | 0.0128 |
| NM_182589 | Hs | 6.2 | 214.2 | 34.5 | 0.0258 |
| XM_290972 | Hs | 44.3 | 225.5 | 5.1 | 0.0000 |

[010] Table 2 below summarizes primate taste-bud expressed genes that were identified as multitransmembrane domain proteins that have been functionally characterized and which are potential candidates for salty taste and other taste receptors. In addition this gene set includes genes encoding transmembrane polypeptides involved in other taste cell related functions. Representative accession numbers are from primate (i.e. *Macaca mulatta* abbreviated Mm) or humans (i.e. *Homo sapiens* abbreviated Hs).

[011] Table 3:

[012] Fungiform Specific Genes and Other Potential Tate Receptor Candidates

[013] This Table of genes was derived after compiling a list of ion channel genes permeable to sodium that were systematically tested for expression in laser capture micro-dissected primate tongue tissue from lingual epithelium and taste buds by end point PCR. Genes that were expressed in fungiform taste buds but not circumvallate taste buds or lingual epithelium were included in this list. Moreover, this list of genes includes other genes which were selected that are likely to encode multi-domain transmembrane proteins included on the macaque oligo array that did not satisfy the inclusion criteria of the systematic array and are not included in the Gene Lists contained in Tables 1 and 2 supra.

TABLE 3

| RefSeq Transcript ID |
| --- |
| NM_178826 |
| NM_021625 |
| NM_020199 |
| NM_014386 |
| NM_006765 |
| NM_016113 |
| NM_003305 |
| NM_007369 |
| NM_018202 |
| NM_005725 |
| NM_000334 |
| NM_002976 |
| NM_002977 |
| NM_030782 |
| CK232413 |
| NM_005669 |
| NM_001001188 |
| XR_018915 |
| NM_145239 |
| NM_012264 |
| NM_001040151 |
| NM_005727 |
| NM_004621 |
| NM_002420 |
| NM_019841 |
| NM_153835 |
| NM_018653 |
| NM_152487 |
| NM_018022 |
| NM_001040142 |
| NM_000297 |
| NM_001040107 |
| NM_032824 |
| NM_031457 |
| NM_018298 |
| BV445354 |
| XM_001111007 |
| BV444941 |
| AANU01224075; AANU01224076 |

[014] (CLASS 2 Genes) Putative Fatty Taste Gene Receptors

[015] Table 4

TABLE 4

Additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

| Accession number or Unigene cluster | TB vs. LE ratio | TB vs. LE p value |
| --- | --- | --- |
| BC017041 | 4.93 | 0.3961 |
| XM_001094702 | 4.36 | 0.0817 |
| XM_001093133 | 6.08 | 0.3922 |
| NM_020141 | 5.00 | 0.1647 |
| XM_001101699 | 5.16 | 0.0204 |
| XM_001084342 | 11.25 | 0.0894 |
| XM_001097482 | 6.19 | 0.0498 |
| Hs.98728 | 8.99 | 0.0141 |
| Mmu.5446 | 16.62 | 0.1980 |
| XM_001113863 | 18.35 | 0.1654 |
| Hs.568078 | 13.28 | 0.3665 |
| Hs.136017 | 4.93 | 0.0575 |
| XM_001086597 | 6.50 | 0.0156 |
| XM_001103527 | 15.02 | 0.3411 |
| Hs.127196 | 10.66 | 0.2504 |
| Hs.21606 | 11.47 | 0.3328 |
| XM_001083605 | 13.09 | 0.1231 |
| XM_001083934 | 25.63 | 0.3774 |
| XM_001085321 | 5.89 | 0.2483 |
| Hs.88972 | 5.01 | 0.1045 |
| Hs.47068 | 14.48 | 0.0790 |
| XR_010355 | 6.71 | 0.1362 |
| XM_001088824 | 9.47 | 0.0968 |
| NM_198503 | 56.03 | 0.0551 |
| Hs.292453 | 5.45 | 0.2891 |
| XM_001082226 | 1.33 | 0.2803 |
| XM_001115408 | 5.84 | 0.2666 |
| Hs.285976.2.S1 | 6.57 | 0.0156 |
| Hs.306723 | 4.72 | 0.0762 |
| XM_001117492 | 55.50 | 0.0903 |
| XM_001114070 | 4.99 | 0.3147 |
| XM_001083482 | 8.39 | 0.1759 |
| XM_001085289 | 6.53 | 0.0358 |
| XM_001090289 | 5.70 | 0.2157 |
| XM_001099752 | 4.72 | 0.0333 |
| XM_001103706 | 1.53 | 0.6021 |
| XM_001108095 | 10.17 | 0.2344 |
| XM_001099350 | 1.50 | 0.7839 |
| XM_001092868 | 11.47 | 0.0594 |
| XM_001082482 | 5.76 | 0.0990 |
| XM_001087669 | 5.40 | 0.2955 |
| XM_001085445 | 322.37 | 0.1177 |
| XM_001095050 | 23.94 | 0.3918 |
| XM_001090844 | 5.21 | 0.0776 |
| XM_001118514 | 5.56 | 0.0704 |
| XR_011068 | 11.49 | 0.3387 |
| XM_001099407 | 10.13 | 0.1970 |
| XM_001098987 | 226.16 | 0.0153 |
| XR_012702 | 9.67 | 0.3743 |
| XM_001090295 | 10.66 | 0.3814 |
| XM_001101662 | 9.51 | 0.1324 |
| XM_001113146 | 5.38 | 0.2783 |
| XM_001103667 | 5.24 | 0.2633 |
| XM_001106443 | 5.16 | 0.0742 |
| XM_001103701 | 5.23 | 0.0055 |
| Hs.76722 | 7.66 | 0.3632 |
| NM_052832 | 199.81 | 0.0108 |
| XM_001114769 | 13.77 | 0.0748 |
| Mmu.9408 | 5.68 | 0.1025 |
| NM_001032861 | 7.74 | 0.0691 |
| Hs.199243 | 8.99 | 0.3158 |
| XM_001111927 | 2.33 | 0.0255 |
| Hs.255056 | 10.46 | 0.3185 |
| XM_001084483 | 1.78 | 0.3006 |
| XM_001108758 | 0.45 | 0.0553 |
| XM_001084211 | 77.55 | 0.0168 |
| Hs.8116 | 24.11 | 0.2107 |
| Hs.18653 | 21.23 | 0.2566 |
| Hs.35861 | 1.07 | 0.6589 |
| XM_001118212 | 5.53 | 0.1690 |
| XM_001090523 | 29.84 | 0.0230 |

TABLE 4-continued

Additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

| Accession number or Unigene cluster | TB vs. LE ratio | TB vs. LE p value |
|---|---|---|
| XM_001099752 | 16.53 | 0.0181 |
| XM_001108428 | 14.42 | 0.0212 |
| XM_001103909 | 22.02 | 0.0309 |
| Hs.211167 | 7.44 | 0.4008 |
| XM_001083172 | 57.01 | 0.1186 |
| XM_001112011 | 5.33 | 0.0137 |
| Hs.166845 | 9.46 | 0.2667 |
| XM_001111915 | 34.66 | 0.3156 |
| XM_001117478 | 112.45 | 0.0068 |
| Hs.45080 | 11.18 | 0.0012 |

TABLE 5

| Public Transcript ID | Public Transcript ID: Species | MAS5 LE mean | MAS5 TB mean | MAS5 fold change | MAS5 p value |
|---|---|---|---|---|---|
| CO583226 | Mm | 8.5 | 48.0 | 5.7 | 0.0226 |
| CB309123 | Mm | 17.1 | 130.1 | 7.6 | 0.0367 |
| NM_001647 | Hs | 21.9 | 119.7 | 5.5 | 0.0235 |
| NM_016619 | Hs | 22.1 | 1139.3 | 51.6 | 0.0018 |
| NM_207352 | Hs | 91.3 | 405.4 | 4.4 | 0.0245 |
| NM_000229 | Hs | 13.4 | 77.3 | 5.8 | 0.0036 |
| NM_021105 | Hs | 20.6 | 203.8 | 9.9 | 0.0000 |
| NM_004915 | Hs | 17.5 | 139.7 | 8.0 | 0.0811 |
| NM_001017403 | Hs | 4.6 | 265.1 | 57.2 | 0.0086 |
| NM_002899 | Hs | 631.1 | 3718.0 | 5.9 | 0.0001 |
| NM_001153 | Hs | 1778.3 | 3990.5 | 2.2 | 0.0000 |
| NM_017784 | Hs | 144.0 | 348.8 | 2.4 | 0.0002 |
| NM_001077400 | Hs | 16.4 | 197.3 | 12.0 | 0.0050 |
| NM_000253 | Hs | 7.1 | 493.9 | 69.4 | 0.0018 |
| NM_002336 | Hs | 111.3 | 1452.8 | 13.0 | 0.0000 |
| NM_032360 | Hs | 32.8 | 168.5 | 5.1 | 0.0180 |
| NM_001004746 | Hs | 35.3 | 102.1 | 2.9 | 0.0148 |
| NM_006551 | Hs | 10.0 | 78.1 | 7.8 | 0.0191 |
| AB220498 | Mm | 81.7 | 715.0 | 8.8 | 0.0223 |
| XM_001086422 | Mm | 48.4 | 262.8 | 5.4 | 0.0345 |
| NM_014349 | Hs | 24.4 | 98.5 | 4.0 | 0.0054 |
| XM_001100224 | Mm | 173.6 | 525.8 | 3.0 | 0.0411 |
| NM_006684 | Hs | 7.5 | 107.1 | 14.4 | 0.0465 |
| NM_006377 | Hs | 405.4 | 2498.0 | 6.2 | 0.0000 |
| CO583346 | Mm | 160.3 | 1036.6 | 6.5 | 0.0001 |

[018] Table 5 below contains primate genes previously described as fatty acid receptors or which contain amino acid motifs that are associated with lipid binding. This list of genes includes genes that do not encode multi-transmembrane proteins but which are reported to participate in lipid transport or binding at close to the plasma membrane.

TABLE 6

| Gene Name | Cell type gene expressed in |
|---|---|
| FAM26A | Many TRPM5 cells |
| GPR113 | Subset TRPM5 cells |
| MCTP1 | Many TRPM5 cells |
| TMEM16G | Subset TRPM5 cells |
| TMEM30B | Many TRPM5 cells |
| TMEM44 | Many non-TRPM5 and non-PKD1L3 cells |
| TUSC3 | Many TRPM5 cells |
| FAM26C | MANY TRPM5 CELLS |
| FAM26B | Many TRPM5 cells |
| MFSD4 | Many Non-TRPM5 cells |
| ATP8A1 | Many TRPM5 and some non-TRPM5 cells |
| SLC4A11 | Many TRPM5 cells |
| SLC4A7 | Subset TRPM5 cells |

[020] The 11 taste-specific genes contained in Table 6 were shown to be expressed in different subsets of primate taste cells. These genes were identified as taste-specific genes by gene chip analysis and shown to be expressed in subsets of taste cells by in situ hybridization analysis as described in the experimental examples and Figures.

Table 7 below lists 4 other primate taste specific genes identified by the inventive rationales and provides information as to the specific cell types in which these genes are expressed.

TABLE 7

| Gene Name | Cell type gene expressed in |
|---|---|
| KIT | TRPM5 & T1R3 subset; T1R1 umami taste receptor cells |
| IKBKAP | PKD1L3 sour taste receptor cells |
| LOC285965 | TRPM5 & T1R3 subset; T1R3 only cells lacking T1R1 (umami) and T1R2 (sweet) |
| SV2B | PKD1L3 sour taste receptor cells |

[022] Table 8

[023] Table 8 contains a listing of the human taste-specific genes which were quantified by TaqMan in LCM derived cDNA from both LE and TB from the same donors. As noted in Example 46, gene expression was measured in TaqMan as a CT (cycle threshold) value. Briefly the CT value for a given sample was determined by the PCR cycle at which the amount of gene-specific PCR product (as measured by fluorescence) reaches a set value. For highly expressed genes, the threshold is reached early in the PCR run and the CT value is relatively low (<35) while genes with very low or no expression do not reach the threshold before cycle 35. Expression of genes with CT values>40 are defined as not detectable. For the majority of genes listed in Table 8 below, expression was not detected in LE samples (CT>40) but was readily detectable in TB samples (CT<35).

[027] Also these taste specific genes may be used in screening assays to identify compounds that affect taste cell turnover. It is known that taste cells turnover rapidly (about every couple of weeks). Moreover, many conditions including chemotherapy or radiation treatment, as well as old age may negatively affect the ability of taste cells to develop. The result is a diminished sense of taste which may result in a decreased quality of life in cancer

TABLE 8

| Gene Title | Gene Symbol | TB CT value | LE CT value* |
|---|---|---|---|
| solute carrier family 9 (sodium/hydrogen exchanger), member 2 | SLC9A2 | 24.63 | No Ct |
| solute carrier family 44, member 4 | SLC44A4 | 25.2 | No Ct |
| membrane-spanning 4-domains, subfamily A, member 8B | MS4A8B | 25.2 | No Ct |
| tetraspanin 2 | TSPAN2 | 25.79 | No Ct |
| transmembrane protein 38B | TMEM38B | 26.44 | No Ct |
| family with sequence similarity 26, member C | FAM26C | 26.93 | No Ct |
| LR8 protein | LR8 | 28.01 | No Ct |
| leucine-rich repeat-containing G protein-coupled receptor 6 | LGR6 | 28.01 | No Ct |
| G protein-coupled receptor, family C, group 5, member B | GPRC5B | 28.51 | 38.69 |
| solute carrier family 35, member E2 | SLC35E2 | 28.58 | 39.46 |
| G protein-coupled receptor 155 | GPR155 | 28.64 | No Ct |
| LAG1 longevity assurance homolog 2 (S. cerevisiae) | LASS2 | 29.12 | No Ct |
| major facilitator superfamily domain containing 4 | MFSD4 | 29.23 | No Ct |
| transmembrane protein 108 | TMEM108 | 29.28 | No Ct |
| tetraspanin 17 | TSPAN17 | 29.37 | No Ct |
| G protein-coupled receptor 113 | GPR113 | 29.44 | No Ct |
| transmembrane protein 163 | TMEM163 | 29.61 | No Ct |
| Hypothetical protein LOC644139 | LOC644139 | 29.93 | No Ct |
| transmembrane protein 16G | TMEM16G | 30 | No Ct |
| transient receptor potential cation channel, subfamily C, member 1 | TRPC1 | 30.11 | No Ct |
| transmembrane 6 superfamily member 1 | TM6SF1 | 30.13 | 36.8 |
| leucine-rich repeat-containing G protein-coupled receptor 5 | LGR5 | 30.15 | No Ct |
| transmembrane protein 44 | TMEM44 | 30.26 | No Ct |
| family with sequence similarity 26, member A | FAM26A | 30.39 | No Ct |
| Transmembrane protein 118 | TMEM118 | 30.91 | No Ct |
| chromosome 14 open reading frame 135 | C14orf135 | 32.17 | 38.68 |
| solute carrier family 8 (sodium/calcium exchanger), member 1 | SLC8A1 | 32.72 | No Ct |
| brain-specific angiogenesis inhibitor 2 | BAI2 | 32.97 | No Ct |
| hypothetical protein LOC130576 | LOC130576 | 34.03 | No Ct |
| potassium voltage-gated channel, KQT-like subfamily, member 1 | KCNQ1 | 34.26 | No Ct |
| ATPase, Class VI, type 11A | ATP11A | 34.33 | No Ct |
| ATPase, aminophospholipid transporter (APLT), Class I, type 8A, member 1 | ATP8A1 | 34.54 | No Ct |
| chromosome 14 open reading frame 101 | C14orf101 | 35.44 | 38.27 |
| potassium channel, subfamily T, member 2 | KCNT2 | 35.62 | No Ct |
| synaptic vesicle glycoprotein 2B | SV2B | 35.95 | No Ct |

*No Ct = CT value > 40, or, not detectable. See text.

[025] As aforementioned the taste cell specific genes identified herein and the corresponding gene products and cells which express same e.g., endogenous taste or chemosensory cells and recombinant cells including the taste specific genes recited in Tables 1, 2, 3, 4, 5, 6, 7, and 8 and their orthologs, allelic variants, variants possessing at least 90% sequence identity thereto and/or genes which specifically hybridize thereto under hybridization conditions denied supra may be used in assays to identify taste modulatory compounds as well as in therapeutic screening assays.

[026] For example these taste specific genes, polypeptides and cells expressing same can be used to screen for compounds for treatment of digestive system disorders. These disorders include by way of example conditions affecting digestion such as dyspepsia, autoimmune and inflammatory diseases affecting the digestive system such as ulcerative colitis, inflammatory bowel syndrome, Crohn's syndrome, celiac disease, and precancers and cancers that affect the digestive system such as cancers affecting the salivary glands, taste buds, stomach, pancreas, gall bladder, esophagus, small or large intestine, anus or colon.

patients or the elderly. This is particularly pronounced in patients with head and neck cancer, esophageal, stomach, lung, or pancreatic cancers. Additionally, this may evolve along with another condition, cachexia or wasting syndrome that combines to reduce the desire to eat. Lack of proper nutrition is a serious cause of morbidity and mortality in cancer patients. The subject taste specific genes contain genes expressed in stem cells suggesting that they are markers of stem cells that are the precursors of and which evolve into taste cells. These genes or cells which express same can be used to identify signals that accelerate taste cell development. These signals which likely comprise cytokine-like receptors present on taste cells likely mediate taste cell development and can be used in screens to identify compounds that induce taste cell differentiation or proliferation. The ligands therefore potentially may be isolated from saliva and may account for the ability of saliva to influence taste function. For example, patients with Sjogren's syndrome (an autoimmune disease that attacks the salivary glands) exhibit altered taste functions. The subject genes and the study of gene expression in the salivary glands by use of gene arrays will facilitate an understanding of these differentiation mechanisms.

[028] The subject taste cell specific genes and corresponding gene products and cells which express these genes may also be used in order to identify potential therapeutics for modulating the immune system of the oral cavity. The oral cavity is populated by normal flora as is the digestive tract. Alterations in normal flora may give rise to conditions such as gingivitis, halitosis, gastric problems and other infections that may result in tooth decay or tooth loss. Included within the taste cell specific genes identified herein are a number of immune system genes. These genes and the corresponding polypeptides or cells which express same can be used to identify therapeutics for maintaining immune homeostasis in the oral cavity, preventing overgrowth of pathogenic microbia, and for identification of the cell types in the oral cavity that are the key players in maintaining proper oral cavity immunity.

[029] Moreover, the subject taste cell specific genes and the corresponding gene products or cells which express same are useful in screening assays for identifying compounds for treatment of diabetes, eating disorders such as obesity, anorexia, bulimia, and other metabolic disorders. The expression of taste receptors in the digestive system likely represents a comprehensive system that detects food and different types at different places during digestion. Therefore, "sensing" the presence of food or specific types such as carbohydrates, fats, umami foods, salts, should trigger various signals that may regulate the production of molecules that participate in the regulation of digestion such as GIP (glucose-dependent insulinotrophic polypeptide) and GLP-1 (glucagon-like peptide 1) produced by the enteroendocrine cells in the intestine. It is likely that taste receptors on these cells regulate the production of other molecular signals in other cells of the digestive system when triggered. These phenomena may be studied by determining which cells express different receptors and then using gene arrays to study the molecules that these cells produce when activated.

[030] References

[031] All the references cited in this application are incorporated by reference in their entirety herein.

[032] Sequence Listing

>gi|89886487|ref|NM_014848.3|*Homo sapiens* synaptic vesicle glycoprotein 2B (SV2B) (SEQ ID NO:1)

| Probe Set ID | Gene Title | Gene Symbol | Ratio Top verus Bottom | p value Top versus Bottom |
|---|---|---|---|---|
| MmugDNA.12222.1.S1_at | chloride channel, calcium activated, family member 1 | CLCA1 | 28.26 | 0.0794 |
| MmugDNA.18105.1.S1_at | ST8 alpha-N-acetyl-neuraminide alpha-2,8-sialyltransferase 1 | ST8SIA1 | 25.30 | 0.0112 |
| MmugDNA.11091.1.S1_at | — | — | 14.48 | 0.0463 |
| MmugDNA.15011.1.S1_at | toll-like receptor 10 precursor | LOC697980 | 14.47 | 0.0262 |
| MmugDNA.41559.1.S1_at | taste receptor, type 2, member 16 | TAS2R16 | 13.96 | 0.0356 |
| MmugDNA.24584.1.S1_at | hypothetical protein LOC703243 | LOC703243 | 13.55 | 0.0725 |
| MmugDNA.15361.1.S1_at | phosphatidylinositol glycan, class N | LOC699219 | 12.99 | 0.0249 |
| Mmu.10677.1.S1_at | matrix metalloproteinase 7 | MMP7 | 11.87 | 0.0181 |
| MmuSTS.783.1.S1_at | taste receptor T2R7 | LOC717909 | 11.70 | 0.0671 |
| MmugDNA.25181.1.S1_at | 3-hydroxysteroid epimerase | LOC713549 | 11.52 | 0.0396 |
| MmugDNA.9747.1.S1_at | — | — | 11.31 | 0.0934 |
| MmugDNA.10468.1.S1_at | hypothetical protein LOC709833 | LOC709833 | 11.21 | 0.0379 |
| MmugDNA.7746.1.S1_at | Protein FAM3B precursor (Cytokine-like protein 2-21) | LOC722516 | 11.10 | 0.0882 |
| MmugDNA.11368.1.S1_at | proprotein convertase subtilisin/kexin type 2 | PCSK2 | 10.97 | 0.0486 |
| MmugDNA.26966.1.S1_at | — | — | 10.92 | 0.0376 |
| MmugDNA.15380.1.S1_at | taste receptor T2R13 | LOC718046 | 10.82 | 0.0924 |
| MmugDNA.32635.1.S1_at | — | — | 10.78 | 0.0891 |
| MmugDNA.37045.1.S1_at | — | — | 10.61 | 0.0029 |
| MmugDNA.36075.1.S1_at | potassium voltage-gated channel, shaker-related subfamily, member 2 | KCNA2 | 10.45 | 0.0060 |
| MmugDNA.35060.1.S1_at | kinesin-like motor protein C20orf23 | LOC695167 | 10.35 | 0.0420 |
| MmugDNA.13207.1.S1_at | — | — | 10.20 | 0.0665 |
| MmunewRS.875.1.S1_at | neuroligin 4 | NLGN4X | 10.13 | 0.0053 |
| MmugDNA.35863.1.S1_at | zinc finger protein 533 | LOC704204 | 10.10 | 0.0657 |
| MmugDNA.121.1.S1_at | golgi SNAP receptor complex member 2 isoform A | LOC716841 | 10.09 | 0.0493 |
| MmugDNA.38131.1.S1_at | kelch-like 8 | LOC700864 | 9.90 | 0.0023 |
| MmugDNA.41159.1.S1_at | interleukin 17B receptor | IL17RB | 9.77 | 0.0005 |
| MmugDNA.11591.1.S1_s_at | dipeptidase 2 | LOC701570 | 9.73 | 0.0020 |
| MmugDNA.5167.1.S1_at | male sterility domain containing 1 | LOC710740 | 9.37 | 0.0930 |
| MmugDNA.656.1.S1_at | — | — | 9.25 | 0.0001 |
| MmugDNA.7006.1.S1_at | sialyltransferase 7E | LOC705908 | 9.24 | 0.0467 |
| MmugDNA.3684.1.S1_at | G protein-coupled receptor 85 | GPR85 | 9.18 | 0.0664 |
| MmugDNA.1571.1.S1_at | — | — | 9.09 | 0.0263 |
| MmugDNA.24639.1.S1_at | — | — | 9.04 | 0.0042 |
| MmuSTS.906.1.S1_at | taste receptor, type 2, member 14 | LOC718111 | 9.00 | 0.0288 |
| MmugDNA.30874.1.S1_at | transmembrane protein 45B | LOC718735 | 9.00 | 0.0000 |
| MmugDNA.34847.1.S1_at | apoptosis inhibitor 5 | API5 | 8.45 | 0.0755 |
| MmuSTS.778.1.S1_at | Taste receptor type 2 member 49 (T2R49) (T2R56) | TAS2R49 | 8.44 | 0.0007 |
| MmuSTS.2869.1.S1_at | tachykinin 1 isoform alpha precursor | TAC1 | 8.44 | 0.0726 |
| MmugDNA.30525.1.S1_at | FCH and double SH3 domains 1 | — | 8.37 | 0.0258 |
| MmugDNA.42433.1.S1_at | — | — | 8.36 | 0.0058 |
| MmugDNA.10579.1.S1_at | dopamine receptor interacting protein | — | 8.30 | 0.0060 |
| MmugDNA.16546.1.S1_at | CMP-N-acetylneuraminic acid hydroxylase | LOC574186 | 8.25 | 0.0649 |
| MmugDNA.29722.1.S1_at | — | — | 8.18 | 0.0717 |

-continued

| Probe Set ID | Gene Title | Gene Symbol | Ratio Top verus Bottom | p value Top versus Bottom |
|---|---|---|---|---|
| MmuSTS.4056.1.S1_at | Cornifin B (Small proline-rich protein IB) (SPR-IB) (14.9 kDa pancornulin) | LOC717850 | 7.96 | 0.0689 |
| MmugDNA.30502.1.S1_at | NIPA-like domain containing 2 | LOC703585 | 7.94 | 0.0421 |
| MmugDNA.6642.1.S1_at | leprecan-like 1 | LOC704118 | 7.86 | 0.0183 |
| MmugDNA.23279.1.S1_at | transmembrane protein 46 | LOC702501 | 7.85 | 0.0427 |
| MmugDNA.3909.1.S1_at | CG2698-PA | LOC710299 | 7.80 | 0.0116 |
| MmugDNA.39327.1.S1_at | — | — | 7.78 | 0.0960 |
| MmugDNA.3544.1.S1_at | solute carrier family 22 (organic cation transporter), member 15 | LOC710102 | 7.72 | 0.0869 |
| MmugDNA.39807.1.S1_at | protocadherin beta 13 precursor | LOC700999 | 7.71 | 0.0311 |
| MmugDNA.17676.1.S1_at | PXR2b protein | PEX5L | 7.65 | 0.0969 |
| MmugDNA.30327.1.S1_at | — | — | 7.62 | 0.0341 |
| MmugDNA.6455.1.S1_at | F11 receptor | F11R | 7.58 | 0.0487 |
| MmugDNA.3223.1.S1_at | — | — | 7.57 | 0.0247 |
| MmugDNA.11678.1.S1_at | 3(2),5-bisphosphate nucleotidase 1 (Bisphosphate 3-nucleotidase 1) (PAP-inositol-1,4-phosphatase) (PIP) | — | 7.57 | 0.0034 |
| MmugDNA.7247.1.S1_at | nemo-like kinase | NLK | 7.56 | 0.0087 |
| MmugDNA.10209.1.S1_at | PHD finger protein 14 | PHF14 | 7.51 | 0.0000 |
| MmuSTS.3737.1.S1_at | protein tyrosine phosphatase, receptor type, C isoform 1 precursor | LOC712657 | 7.42 | 0.0139 |
| MmuSTS.1381.1.S1_at | basic helix-loop-helix domain containing, class B, 5 | LOC701485 | 7.39 | 0.0378 |
| MmugDNA.20444.1.S1_at | formin 2 | LOC708376 | 7.38 | 0.0999 |
| MmuSTS.1175.1.S1_at | Taste receptor type 2 member 10 (T2R10) (Taste receptor family B member 2) (TRB2) | TAS2R10 | 7.36 | 0.0445 |
| MmuSTS.2644.1.S1_s_at | taste receptor T2R55 | LOC695053 | 7.36 | 0.0182 |
| MmuSTS.3441.1.S1_at | annexin A9 | ANXA9 | 7.32 | 0.0133 |
| MmugDNA.9493.1.S1_at | — | — | 7.30 | 0.0007 |
| MmugDNA.4334.1.S1_at | tyrosine aminotransferase | TAT | 7.18 | 0.0194 |
| MmuSTS.1040.1.S1_at | ST8 alpha-N-acetyl-neuraminide alpha-2,8-sialyltransferase 5 | ST8SIA5 | 7.18 | 0.0759 |
| MmugDNA.25088.1.S1_at | GTP-binding protein Rit2 (Ras-like protein expressed in neurons) (Ras-like without CAAX protein 2) | RIT2 | 7.14 | 0.0292 |
| MmugDNA.689.1.S1_at | hypothetical protein LOC707842 | LOC707842 | 7.11 | 0.0615 |
| MmugDNA.4223.1.S1_at | echinoderm microtubule associated protein like 5 | LOC718818 | 7.08 | 0.0053 |
| MmugDNA.29749.1.S1_at | — | — | 7.02 | 0.0598 |
| MmugDNA.1798.1.S1_at | doublecortin and CaM kinase-like 3 | LOC699654 | 6.99 | 0.0589 |
| MmuSTS.1232.1.S1_at | copine IV | LOC717868 /// LOC719231 | 6.98 | 0.0579 |
| MmuSTS.784.1.S1_at | taste receptor, type 2, member 8 | LOC717924 | 6.95 | 0.0189 |
| MmugDNA.26125.1.S1_at | — | — | 6.94 | 0.0509 |
| MmuSTS.2013.1.S1_at | protocadherin beta 10 | PCDHB10 | 6.92 | 0.0000 |
| MmugDNA.19056.1.S1_at | somatostatin receptor 1 | SSTR1 | 6.90 | 0.0040 |
| MmugDNA.43165.1.S1_at | — | — | 6.88 | 0.0378 |
| MmugDNA.34029.1.S1_at | secernin 1 | SCRN1 | 6.83 | 0.0410 |
| MmugDNA.40941.1.S1_at | — | — | 6.81 | 0.0380 |
| MmugDNA.21034.1.S1_at | — | — | 6.68 | 0.0782 |
| MmugDNA.31223.1.S1_at | protocadherin beta 3 | PCDHB3 | 6.68 | 0.0261 |
| MmugDNA.10620.1.S1_at | Rho GTPase activating protein 18 | LOC711107 | 6.67 | 0.0000 |
| MmugDNA.35495.1.S1_at | — | — | 6.67 | 0.0569 |
| MmugDNA.23300.1.S1_at | KIAA0828 protein | KIAA0828 | 6.65 | 0.0692 |
| MmugDNA.20297.1.S1_at | hypothetical protein LOC705695 | LOC705695 | 6.64 | 0.0273 |
| MmugDNA.43474.1.S1_at | protection of telomeres 1 | POT1 | 6.62 | 0.0587 |
| MmuSTS.1939.1.S1_at | Fibroblast growth factor 11 (FGF-11) (Fibroblast growth factor homologous factor 3) (FHF-3) | FGF11 | 6.61 | 0.0983 |
| MmugDNA.26964.1.S1_at | calponin like transmembrane domain protein | LOC709910 | 6.59 | 0.0179 |
| MmugDNA.33339.1.S1_at | — | — | 6.58 | 0.0179 |
| MmugDNA.32991.1.S1_at | ectonucleotide pyrophosphatase/phosphodiesterase 6 | LOC693950 | 6.54 | 0.0834 |
| MmugDNA.34284.1.S1_at | Sodium channel beta-3 subunit precursor | LOC714673 | 6.52 | 0.0945 |
| MmugDNA.20971.1.S1_at | — | — | 6.49 | 0.0462 |
| MmugDNA.9521.1.S1_at | glutaminyl-peptide cyclotransferase | QPCT | 6.49 | 0.0528 |
| MmuSTS.1179.1.S1_s_at | taste receptor, type 2, member 43 | LOC694161 | 6.47 | 0.0060 |
| MmugDNA.25858.1.S1_at | — | — | 6.47 | 0.0087 |
| MmugDNA.38257.1.S1_at | hypothetical protein LOC701675 | LOC701675 | 6.46 | 0.0506 |
| MmugDNA.41639.1.S1_at | phosphodiesterase 1C, calmodulin-dependent 70 kDa | PDE1C | 6.44 | 0.0007 |
| MmugDNA.33151.1.S1_at | — | — | 6.42 | 0.0253 |
| MmugDNA.1887.1.S1_at | zinc finger protein 395 | LOC698947 | 6.41 | 0.0237 |
| MmuSTS.1713.1.S1_at | WNT1 inducible signaling pathway protein 3 | WISP3 | 6.37 | 0.0601 |
| MmugDNA.8585.1.S1_at | — | — | 6.34 | 0.0451 |
| MmugDNA.17339.1.S1_s_at | leucine rich repeat neuronal 3 | LOC701932 | 6.31 | 0.0171 |
| MmuSTS.527.1.S1_at | platelet-derived growth factor C precursor | — | 6.30 | 0.0362 |
| MmugDNA.15109.1.S1_s_at | — | — | 6.29 | 0.0096 |
| MmugDNA.2733.1.S1_s_at | Fatty acid-binding protein, epidermal (E-FABP) (Psoriasis-associated fatty acid-binding protein homolog) (PA-FABP) | — | 6.23 | 0.0651 |
| MmugDNA.35813.1.S1_at | — | — | 6.23 | 0.0411 |
| MmugDNA.20157.1.S1_at | nel-like 1 precursor | LOC701438 | 6.21 | 0.0389 |
| MmugDNA.39143.1.S1_at | — | — | 6.20 | 0.0333 |
| MmuSTS.2452.1.S1_at | McLeod syndrome-associated, Kell blood group protein | LOC696407 | 6.20 | 0.0099 |

-continued

| Probe Set ID | Gene Title | Gene Symbol | Ratio Top verus Bottom | p value Top versus Bottom |
|---|---|---|---|---|
| MmugDNA.33888.1.S1_at | egl nine homolog 1 | LOC713410 | 6.18 | 0.0609 |
| MmugDNA.7614.1.S1_at | ADP-ribosylation factor-like 6 | LOC696616 | 6.17 | 0.0002 |
| MmuSTS.1330.1.S1_at | dual-specificity tyrosine-(Y)-phosphorylation regulated kinase 2 | DYRK2 | 6.16 | 0.0203 |
| MmuSTS.3090.1.S1_at | latrophilin 3 | LPHN3 | 6.16 | 0.0063 |
| MmugDNA.23556.1.S1_at | — | — | 6.14 | 0.0144 |
| MmuSTS.1177.1.S1_at | taste receptor, type 2, member 39 | TAS2R39 | 6.10 | 0.0094 |
| MmugDNA.14803.1.S1_s_at | Fibroblast growth factor 12 (FGF-12) (Fibroblast growth factor homologous factor 1) (FHF-1) | LOC705813 | 6.05 | 0.0344 |
| Mmu.3466.1.S1_at | — | — | 6.03 | 0.0171 |
| MmugDNA.35142.1.S1_at | — | — | 6.01 | 0.0002 |
| MmuSTS.3438.1.S1_at | ankyrin 2 | ANK2 | 6.01 | 0.0264 |
| MmugDNA.16713.1.S1_at | potassium channel tetramerisation domain containing 4 | LOC701916 | 6.00 | 0.0289 |
| MmugDNA.23811.1.S1_at | sel-1 suppressor of lin-12-like | LOC708651 | 5.97 | 0.0664 |
| MmunewRS.311.1.S1_at | — | — | 5.95 | 0.0419 |
| MmugDNA.2511.1.S1_at | — | — | 5.93 | 0.0561 |
| MmugDNA.5134.1.S1_at | thrombospondin 4 | THBS4 | 5.90 | 0.0003 |
| MmugDNA.27291.1.S1_at | — | — | 5.90 | 0.0192 |
| MmugDNA.35237.1.S1_at | — | — | 5.89 | 0.0799 |
| MmugDNA.29494.1.S1_at | coagulation factor II receptor | F2R | 5.86 | 0.0249 |
| MmugDNA.41193.1.S1_at | phosducin-like 3 | — | 5.86 | 0.0302 |
| MmugDNA.27343.1.S1_s_at | DnaJ (Hsp40) homolog, subfamily C, member 3 | LOC695757 | 5.83 | 0.0649 |
| MmugDNA.8284.1.S1_at | — | — | 5.77 | 0.0007 |
| MmuSTS.909.1.S1_at | taste receptor, type 2, member 50 | LOC693513 | 5.76 | 0.0712 |
| MmuSTS.2673.1.S1_at | calmegin | CLGN | 5.76 | 0.0576 |
| MmugDNA.37138.1.S1_at | Discs large homolog 2 (Postsynaptic density protein PSD-93) (Channel-associated protein of synapse-110) (Chapsyn-110) | LOC704826 | 5.76 | 0.0582 |
| MmugDNA.15905.1.S1_at | — | — | 5.68 | 0.0480 |
| MmugDNA.32064.1.S1_at | butyrophilin-like 8 | BTNL8 | 5.67 | 0.0176 |
| MmugDNA.34572.1.S1_at | decay accelerating factor for complement | LOC714370 | 5.65 | 0.0083 |
| MmugDNA.22059.1.S1_at | integrin alpha 2 | ITGA2 | 5.64 | 0.0227 |
| MmuSTS.861.1.S1_at | CG7231-PB, isoform B | LOC715256 | 5.62 | 0.0968 |
| MmugDNA.29329.1.S1_at | — | — | 5.61 | 0.0108 |
| MmugDNA.14073.1.S1_at | microtubule-associated protein 6 isoform 2 | LOC696223 | 5.60 | 0.0103 |
| MmugDNA.27825.1.S1_at | alpha 4 type IV collagen | COL4A4 | 5.59 | 0.0662 |
| MmugDNA.34698.1.S1_at | ankyrin repeat domain 43 | LOC708755 | 5.57 | 0.0236 |
| MmuSTS.2650.1.S1_at | adenylate kinase 5 isoform 1 | LOC706248 | 5.57 | 0.0477 |
| MmugDNA.21615.1.S1_at | — | — | 5.56 | 0.0504 |
| MmugDNA.18178.1.S1_at | autotaxin | ENPP2 | 5.56 | 0.0036 |
| MmuSTS.1143.1.S1_at | Beta-synuclein | SNCB | 5.53 | 0.0727 |
| MmugDNA.40607.1.S1_at | hypothetical protein LOC717552 | LOC717552 | 5.53 | 0.0701 |
| MmugDNA.18538.1.S1_s_at | serine (or cysteine) proteinase inhibitor, clade I (neuroserpin), member 1 | SERPINI1 | 5.53 | 0.0790 |
| MmugDNA.5368.1.S1_at | — | — | 5.50 | 0.0256 |
| MmugDNA.30317.1.S1_at | Baculoviral IAP repeat-containing protein 4 (Inhibitor of apoptosis protein 3) (X-linked inhibitor of apoptosis protein) (X-linked IAP) (IAP-like protein) (HILP) | LOC698057 | 5.49 | 0.0475 |
| MmugDNA.35810.1.S1_at | adenosine A2b receptor | ADORA2B | 5.48 | 0.0099 |
| MmugDNA.22262.1.S1_at | neurotrypsin precursor | LOC704461 | 5.46 | 0.0150 |
| Mmu.9266.1.S1_x_at | alpha-defensin 3 precursor | LOC574310 | 5.46 | 0.0796 |
| MmugDNA.1819.1.S1_at | chromodomain helicase DNA binding protein 5 | — | 5.44 | 0.0524 |
| MmugDNA.37049.1.S1_at | Dipeptidyl aminopeptidase-like protein 6 (Dipeptidylpeptidase VI) (Dipeptidylpeptidase 6) (Dipeptidyl peptidase IV-like protein) (Dipeptidyl aminopeptidase-related protein) (DPPX) | LOC718148 | 5.42 | 0.0278 |
| MmugDNA.26844.1.S1_at | hypothetical protein LOC716906 | LOC716906 | 5.40 | 0.0620 |
| MmugDNA.40160.1.S1_at | — | — | 5.34 | 0.0828 |
| MmugDNA.13497.1.S1_at | runt-related transcription factor 2 isoform b | LOC703331 | 5.33 | 0.0463 |
| MmugDNA.35702.1.S1_at | ADAMTS-like 1 | ADAMTSL1 | 5.33 | 0.0106 |
| Mmu.335.1.S1_at | carboxypeptidase E | CPE | 5.30 | 0.0493 |
| MmugDNA.13656.1.S1_at | — | — | 5.30 | 0.0030 |
| MmugDNA.22297.1.S1_at | lysozyme | LOC718361 | 5.29 | 0.0804 |
| MmugDNA.28583.1.S1_at | — | — | 5.25 | 0.0006 |
| MmugDNA.18724.1.S1_s_at | UDP-Gal:betaGlcNAc beta 1,4-galactosyltransferase 6 | B4GALT6 | 5.25 | 0.0461 |
| MmugDNA.38162.1.S1_at | — | — | 5.24 | 0.0001 |
| MmugDNA.27108.1.S1_at | matrix metalloproteinase 19 | MMP19 | 5.21 | 0.0313 |
| MmugDNA.24659.1.S1_at | mesothelin isoform 1 preproprotein | LOC698095 | 5.19 | 0.0431 |
| Mmu.11741.1.S1_at | N-ethylmaleimide-sensitive factor | LOC715297 | 5.19 | 0.0035 |
| MmugDNA.1267.1.S1_at | cytochrome P450 3A64 /// Cytochrome P450 3A7 (CYP3A7) (P450-HFLA) | CYP3A64 /// LOC718917 | 5.18 | 0.0847 |
| MmuSTS.3164.1.S1_at | cathepsin C | CTSC | 5.16 | 0.0003 |
| MmugDNA.2042.1.S1_at | dual specificity phosphatase 10 | DUSP10 | 5.16 | 0.0148 |
| MmuSTS.4822.1.S1_at | GATA binding protein 6 | LOC699591 | 5.15 | 0.0204 |
| MmugDNA.28021.1.S1_at | zinc finger and BTB domain containing 10 | LOC704721 | 5.15 | 0.0905 |
| MmugDNA.32990.1.S1_at | protocadherin beta 5 | PCDHB5 | 5.14 | 0.0458 |

-continued

| Probe Set ID | Gene Title | Gene Symbol | Ratio Top verus Bottom | p value Top versus Bottom |
|---|---|---|---|---|
| MmugDNA.27188.1.S1_at | hypothetical protein LOC694387 | LOC694387 | 5.11 | 0.0446 |
| MmugDNA.18606.1.S1_at | — | — | 5.10 | 0.0278 |
| MmugDNA.36968.1.S1_at | microsomal triglyceride transfer protein large subunit | MTTP | 5.07 | 0.0525 |
| MmugDNA.12625.1.S1_at | Ras protein-specific guanine nucleotide-releasing factor 2 | LOC711350 | 5.07 | 0.0298 |
| MmuSTS.597.1.S1_s_at | Hypoxanthine-guanine phosphoribosyltransferase (HGPRT) (HGPRTase) | LOC709186 | 5.07 | 0.0051 |
| MmugDNA.8387.1.S1_at | S-acyl fatty acid synthase thioesterase, medium chain (Thioesterase II) (Thioesterase domain-containing protein 1) | THEDC1 | 5.06 | 0.0290 |
| MmugDNA.19071.1.S1_at | — | — | 5.06 | 0.0453 |
| MmugDNA.1497.1.S1_at | vacuolar protein sorting 13A isoform A | LOC705323 | 5.04 | 0.0367 |
| MmugDNA.26354.1.S1_at | GEM 1 protein | GEM 1 | 5.04 | 0.0011 |
| MmunewRS.58.1.S1_at | — | — | 5.04 | 0.0241 |
| MmuSTS.531.1.S1_at | UDP-GlcNAc:betaGal beta-1,3-N-acetylglucosaminyltransferase 1 | LOC693396 | 5.04 | 0.0968 |
| MmugDNA.38025.1.S1_at | glycoprotein M6B | GPM6B | 5.03 | 0.0248 |
| MmuSTS.1448.1.S1_at | v-yes-1 Yamaguchi sarcoma viral related oncogene homolog | LYN | 5.03 | 0.0807 |
| MmugDNA.1649.1.S1_at | DHHC-containing protein 20 | LOC705802 | 5.02 | 0.0886 |
| MmugDNA.38429.1.S1_at | hypothetical protein LOC698744 | LOC698744 | 5.00 | 0.0001 |
| MmugDNA.3432.1.S1_at | plexin C1 | LOC711320 | 4.99 | 0.0000 |
| MmugDNA.30924.1.S1_at | mothers against decapentaplegic homolog 4 | SMAD4 | 4.97 | 0.0151 |
| MmugDNA.43332.1.S1_at | — | — | 4.96 | 0.0931 |
| MmuSTS.4050.1.S1_at | diacylglycerol kinase, beta | DGKB | 4.95 | 0.0176 |
| MmugDNA.31803.1.S1_at | calcium binding protein 39-like | CAB39L | 4.88 | 0.0227 |
| MmugDNA.42361.1.S1_at | — | — | 4.87 | 0.0521 |
| MmugDNA.36141.1.S1_at | — | — | 4.87 | 0.0504 |
| MmuSTS.2022.1.S1_at | Glutathione-requiring prostaglandin D synthase (Glutathione-dependent PGD synthetase) (Prostaglandin-H2 D-isomerase) (Hematopoietic prostaglandin D synthase) (H-PGDS) | PGDS | 4.87 | 0.0504 |
| MmugDNA.20560.1.S1_at | tripartite motif protein 9 | TRIM9 | 4.86 | 0.0363 |
| MmuSTS.1776.1.S1_at | SATB family member 2 | SATB2 | 4.86 | 0.0000 |
| MmugDNA.17660.1.S1_s_at | ectonucleotide pyrophosphatase/phosphodiesterase 4 (putative function) | LOC703680 | 4.83 | 0.0657 |
| MmugDNA.8441.1.S1_s_at | GalNAc-4-sulfotransferase 2 | LOC703877 | 4.83 | 0.0984 |
| MmugDNA.10568.1.S1_at | — | — | 4.81 | 0.0080 |
| MmugDNA.5130.1.S1_at | neuropilin- and tolloid-like protein 2 precursor | LOC716468 | 4.81 | 0.0436 |
| MmugDNA.10470.1.S1_at | cyclic nucleotide gated channel beta 1 | LOC708851 | 4.80 | 0.0916 |
| MmugDNA.25697.1.S1_at | — | — | 4.80 | 0.0646 |
| MmugDNA.2214.1.S1_at | protocadherin beta 14 | PCDHB14 | 4.79 | 0.0153 |
| MmuSTS.1120.1.S1_s_at | protocadherin alpha 9 | PCDHA9 | 4.78 | 0.0373 |
| MmugDNA.33308.1.S1_at | tetratricopeptide repeat domain 7B | LOC696029 | 4.76 | 0.0022 |
| MmugDNA.9526.1.S1_at | Kelch repeat and BTB domain-containing protein 11 (Kelch domain-containing protein 7B) | KBTBD11 | 4.75 | 0.0031 |
| MmugDNA.42933.1.S1_at | hypothetical protein LOC712344 | LOC712344 | 4.74 | 0.0099 |
| MmugDNA.28339.1.S1_at | c-myc promoter binding protein | LOC709675 | 4.74 | 0.0345 |
| MmugDNA.16977.1.S1_at | — | — | 4.73 | 0.0001 |
| MmugDNA.9216.1.S1_s_at | tripartite motif protein 31 isoform alpha | — | 4.71 | 0.0045 |
| MmugDNA.29917.1.S1_at | — | — | 4.69 | 0.0000 |
| MmugDNA.8704.1.S1_at | stanniocalcin 2 precursor | LOC703900 | 4.69 | 0.0960 |
| MmugDNA.11746.1.S1_at | hypothetical protein LOC716531 | LOC716531 | 4.64 | 0.0001 |
| MmugDNA.7242.1.S1_at | ring finger protein 183 | LOC705679 | 4.63 | 0.0183 |
| MmugDNA.34448.1.S1_at | — | — | 4.62 | 0.0856 |
| MmugDNA.12226.1.S1_at | KIAA1946 | LOC712442 | 4.61 | 0.0021 |
| MmugDNA.16242.1.S1_at | — | — | 4.61 | 0.0284 |
| MmugDNA.42287.1.S1_at | Beta crystallin A2 (Beta-A2-crystallin) | LOC701178 | 4.59 | 0.0674 |
| MmugDNA.13689.1.S1_at | acyl-Coenzyme A oxidase 3, pristanoyl | ACOX3 | 4.58 | 0.0836 |
| MmugDNA.35429.1.S1_at | — | — | 4.58 | 0.0297 |
| MmugDNA.42474.1.S1_at | neural cell adhesion molecule 1 | NCAM1 | 4.58 | 0.0986 |
| MmugDNA.42278.1.S1_at | — | — | 4.58 | 0.0006 |
| MmugDNA.15856.1.S1_at | — | — | 4.57 | 0.0006 |
| MmugDNA.26231.1.S1_at | protein phosphatase 1, regulatory (inhibitor) subunit 14B | — | 4.56 | 0.0040 |
| MmuSTS.1471.1.S1_at | guanylate cyclase activator 1A (retina) | LOC695552 | 4.56 | 0.0712 |
| MmugDNA.38210.1.S1_at | — | — | 4.56 | 0.0013 |
| MmugDNA.8341.1.S1_at | potassium voltage-gated channel, subfamily H, member 7 isoform 2 | LOC702259 | 4.55 | 0.0691 |
| MmugDNA.40476.1.S1_at | CG17660-PA | LOC698581 | 4.55 | 0.0164 |
| MmugDNA.21371.1.S1_at | L1 cell adhesion molecule | L1CAM | 4.54 | 0.0016 |
| MmugDNA.10362.1.S1_at | — | — | 4.54 | 0.0247 |
| MmugDNA.34200.1.S1_at | solute carrier family 16, member 10 | LOC696132 | 4.54 | 0.0008 |
| MmugDNA.10673.1.S1_at | — | — | 4.53 | 0.0098 |
| MmugDNA.34348.1.S1_at | — | — | 4.51 | 0.0776 |
| MmugDNA.14801.1.S1_at | — | — | 4.51 | 0.0800 |
| MmugDNA.16806.1.S1_at | — | — | 4.51 | 0.0104 |
| MmugDNA.26715.1.S1_at | hypothetical protein LOC705319 | LOC705319 | 4.50 | 0.0377 |
| MmugDNA.29516.1.S1_at | Transcribed locus | — | 4.50 | 0.0131 |

| Probe Set ID | Gene Title | Gene Symbol | Ratio Top verus Bottom | p value Top versus Bottom |
|---|---|---|---|---|
| MmugDNA.35871.1.S1_at | alpha-fetoprotein | AFP | 4.49 | 0.0827 |
| MmuSTS.3720.1.S1_at | prostaglandin-endoperoxide synthase 1 | PTGS1 | 4.49 | 0.0550 |
| MmugDNA.13337.1.S1_at | — | — | 4.48 | 0.0825 |
| MmugDNA.42244.1.S1_at | — | — | 4.48 | 0.0930 |
| MmugDNA.21236.1.S1_at | arginine/serine-rich coiled-coil 1 | LOC704232 | 4.47 | 0.0144 |
| MmugDNA.36820.1.S1_at | 1-acylglycerol-3-phosphate O-acyltransferase 5 | AGPAT5 | 4.47 | 0.0076 |
| MmugDNA.37762.1.S1_at | methylenetetrahydrofolate dehydrogenase (NADP+ dependent) 1-like | LOC705222 | 4.47 | 0.0074 |
| MmugDNA.3018.1.S1_at | Corticotropin-lipotropin precursor (Pro-opiomelanocortin) (POMC) | POMC | 4.46 | 0.0858 |
| MmugDNA.30526.1.S1_at | breast cancer membrane protein 11 | LOC714517 | 4.46 | 0.0302 |
| MmuSTS.2215.1.S1_at | carbohydrate (N-acetylglucosamine-6-O) sulfotransferase 2 | LOC713994 | 4.45 | 0.0820 |
| MmuSTS.1144.1.S1_at | Jun dimerization protein p21SNFT | LOC710551 | 4.45 | 0.0023 |
| MmugDNA.33092.1.S1_s_at | alpha-2-glycoprotein 1, zinc | LOC710136 | 4.44 | 0.0971 |
| MmugDNA.34402.1.S1_at | taste receptor, type 1, member 2 | LOC714666 | 4.44 | 0.0587 |
| MmugDNA.583.1.S1_at | phosphatidylinositol transfer protein, cytoplasmic 1 isoform a | LOC718773 | 4.43 | 0.0076 |
| MmugDNA.10551.1.S1_at | Alpha-1,6-mannosyl-glycoprotein 2-beta-N-acetylglucosaminyltransferase (Mannoside acetylglucosaminyltransferase 2) (N-glycosyl-oligosaccharide-glycoprotein N-acetylglucosaminyltransferase II) (Beta-1,2-N-acetylglucosaminyltransferase II) . . . | MGAT2 | 4.42 | 0.0455 |
| MmugDNA.10172.1.S1_at | — | — | 4.42 | 0.0763 |
| MmugDNA.7644.1.S1_at | amyloid beta (A4) precursor-like protein 2 | APLP2 | 4.42 | 0.0771 |
| MmuSTS.4251.1.S1_at | DnaJ (Hsp40) homolog, subfamily B, member 9 | LOC701094 | 4.42 | 0.0012 |
| MmugDNA.30872.1.S1_at | Tescalcin (TSC) | TESC | 4.41 | 0.0018 |
| MmugDNA.16779.1.S1_at | solute carrier organic anion transporter family member 4A1 | SLCO4A1 | 4.41 | 0.0008 |
| MmugDNA.36628.1.S1_at | — | — | 4.39 | 0.0293 |
| MmugDNA.39982.1.S1_at | hydrogen voltage-gated channel 1 | LOC709745 | 4.39 | 0.0378 |
| MmugDNA.12304.1.S1_at | — | — | 4.39 | 0.0926 |
| MmugDNA.22401.1.S1_at | goosecoid | LOC702308 | 4.39 | 0.0452 |
| MmugDNA.3017.1.S1_at | — | — | 4.39 | 0.0176 |
| MmugDNA.40588.1.S1_at | — | — | 4.38 | 0.0736 |
| MmugDNA.9680.1.S1_at | — | — | 4.38 | 0.0521 |
| MmugDNA.27684.1.S1_at | guanine nucleotide binding protein (G protein), alpha 14 | LOC705448 | 4.38 | 0.0003 |
| MmugDNA.24197.1.S1_at | — | — | 4.37 | 0.0840 |
| MmugDNA.28806.1.S1_at | — | — | 4.37 | 0.0872 |
| MmugDNA.21653.1.S1_at | Y17G7B.10b | LOC704285 | 4.37 | 0.0535 |
| MmugDNA.26796.1.S1_at | beta-galactoside alpha-2,6-sialyltransferase II | LOC713552 | 4.37 | 0.0025 |
| MmugDNA.41976.1.S1_s_at | probable nucleolar complex protein 14 | LOC720068 | 4.37 | 0.0973 |
| MmuSTS.63.1.S1_at | hemochromatosis protein | HFE | 4.37 | 0.0581 |
| MmugDNA.17587.1.S1_at | molybdenum cofactor synthesis 3 | MOCS3 | 4.36 | 0.0773 |
| MmugDNA.22799.1.S1_at | — | — | 4.35 | 0.0910 |
| MmugDNA.43244.1.S1_at | — | — | 4.35 | 0.0287 |
| MmugDNA.4726.1.S1_at | — | — | 4.35 | 0.0236 |
| MmugDNA.27474.1.S1_at | NIF3 NGG1 interacting factor 3-like 1 | — | 4.34 | 0.0009 |
| MmuSTS.113.1.S1_at | monogenic, audiogenic seizure susceptibility 1 | LOC697794 | 4.34 | 0.0120 |
| MmugDNA.13225.1.S1_at | — | — | 4.34 | 0.0230 |
| MmugDNA.40434.1.S1_at | ataxin-1 ubiquitin-like interacting protein | LOC714928 | 4.34 | 0.0944 |
| MmuSTS.3087.1.S1_at | RAD50 homolog isoform 1 | LOC710718 | 4.33 | 0.0858 |
| MmugDNA.2856.1.S1_at | — | — | 4.32 | 0.0586 |
| MmugDNA.24690.1.S1_at | — | — | 4.32 | 0.0188 |
| MmugDNA.17638.1.S1_at | — | — | 4.32 | 0.0420 |
| Mmu.4140.1.S1_at | peptidylglycine alpha-amidating monooxygenase isoform b, preproprotein | LOC707733 | 4.31 | 0.0208 |
| MmuSTS.1399.1.S1_at | complement factor B | CFB | 4.31 | 0.0450 |
| MmugDNA.28599.1.S1_at | dedicator of cytokinesis 10 | DOCK10 | 4.30 | 0.0532 |
| MmugDNA.5642.1.S1_at | — | — | 4.28 | 0.0091 |
| MmugDNA.33945.1.S1_at | — | — | 4.28 | 0.0090 |
| MmugDNA.845.1.S1_at | N(4)-(beta-N-acetylglucosaminyl)-L-asparaginase precursor (Glycosylasparaginase) (Aspartylglucosaminidase) (N4-(N-acetyl-beta-glucosaminyl)-L-asparagine amidase) (AGA) | AGA | 4.28 | 0.0049 |
| MmugDNA.14017.1.S1_at | dedicator of cytokinesis 9 | DOCK9 | 4.28 | 0.0381 |
| MmugDNA.1746.1.S1_at | — | — | 4.27 | 0.0148 |
| MmugDNA.7878.1.S1_at | — | — | 4.27 | 0.0396 |
| MmugDNA.42983.1.S1_s_at | tripeptidyl-peptidase I precursor | LOC709838 | 4.27 | 0.0116 |
| MmugDNA.17468.1.S1_at | protocadherin beta 6 | PCDHB6 | 4.27 | 0.0080 |
| MmugDNA.27490.1.S1_at | — | — | 4.26 | 0.0588 |
| MmugDNA.25045.1.S1_at | — | — | 4.26 | 0.0872 |
| MmugDNA.21311.1.S1_at | ankyrin repeat and SOCS box-containing protein 4 | ASB4 | 4.26 | 0.0713 |
| MmugDNA.12780.1.S1_at | BMX non-receptor tyrosine kinase | BMX | 4.26 | 0.0018 |
| MmugDNA.39574.1.S1_at | RWD domain containing 2 | RWDD2 | 4.25 | 0.0242 |
| MmugDNA.23856.1.S1_at | — | — | 4.24 | 0.0588 |
| MmugDNA.10231.1.S1_at | mannosidase, endo-alpha | LOC716710 | 4.24 | 0.0469 |
| MmugDNA.38293.1.S1_at | guiescin Q6 isoform a | LOC718589 | 4.23 | 0.0244 |
| MmugDNA.32049.1.S1_at | transmembrane protein 64 | LOC695826 | 4.23 | 0.0216 |

| Probe Set ID | Gene Title | Gene Symbol | Ratio Top verus Bottom | p value Top versus Bottom |
|---|---|---|---|---|
| MmugDNA.10078.1.S1_at | allantoicase | ALLC | 4.22 | 0.0463 |
| MmugDNA.34409.1.S1_at | — | — | 4.22 | 0.0589 |
| MmugDNA.3676.1.S1_at | — | — | 4.22 | 0.0067 |
| MmugDNA.27799.1.S1_at | hypothetical protein LOC703244 | LOC703244 | 4.20 | 0.0047 |
| MmugDNA.35140.1.S1_at | UDP-glucuronate decarboxylase 1 | LOC718456 | 4.20 | 0.0026 |
| MmugDNA.12308.1.S1_at | — | — | 4.20 | 0.0676 |
| MmugDNA.29177.1.S1_at | DNA polymerase zeta catalytic subunit (Seizure-related protein 4) | LOC703920 | 4.19 | 0.0016 |
| MmugDNA.366.1.S1_at | fucosyltransferase 11 (alpha (1,3) fucosyltransferase) | LOC706552 | 4.19 | 0.0249 |
| MmugDNA.31712.1.S1_at | polypeptide N-acetylgalactosaminyltransferase 6 | GALNT6 | 4.18 | 0.0496 |
| MmuSTS.649.1.S1_at | interleukin 25 isoform 1 precursor | LOC713943 | 4.18 | 0.0789 |
| MmugDNA.41214.1.S1_at | — | — | 4.16 | 0.0827 |
| MmugDNA.28831.1.S1_at | G protein-regulated inducer of neurite outgrowth 1 | LOC697365 | 4.16 | 0.0458 |
| MmugDNA.8787.1.S1_at | Protein C10orf70 | — | 4.15 | 0.0040 |
| MmuSTS.3573.1.S1_at | protocadherin 8 | PCDH8 | 4.15 | 0.0273 |
| MmugDNA.13403.1.S1_at | complement component 5 receptor 1 (C5a ligand) | C5AR1 | 4.14 | 0.0245 |
| MmugDNA.21971.1.S1_at | N-acylsphingosine amidohydrolase (acid ceramidase) 1 preproprotein isoform a | LOC703699 | 4.13 | 0.0000 |
| MmugDNA.17057.1.S1_at | RECK protein precursor | — | 4.13 | 0.0061 |
| MmugDNA.22311.1.S1_at | — | — | 4.12 | 0.0879 |
| MmugDNA.8200.1.S1_at | transglutaminase 7 | LOC712676 | 4.12 | 0.0472 |
| MmugDNA.42341.1.S1_at | rabconnectin-3 beta isoform 2 | LOC695302 | 4.11 | 0.0175 |
| MmugDNA.601.1.S1_at | SPRY domain-containing SOCS box protein SSB-4 | LOC715278 | 4.10 | 0.0041 |
| MmugDNA.27605.1.S1_at | Spir-1 protein isoform 1 | LOC722155 | 4.09 | 0.0878 |
| MmugDNA.17977.1.S1_at | neurexin 1 | NRXN1 | 4.09 | 0.0029 |
| MmugDNA.9585.1.S1_at | histone deacetylase 9 isoform 3 | LOC708314 | 4.08 | 0.0429 |
| MmugDNA.43369.1.S1_at | T-cell immunomodulatory protein | LOC716435 | 4.08 | 0.0209 |
| MmuSTS.2480.1.S1_at | zinc finger protein 287 | LOC695524 | 4.08 | 0.0212 |
| MmugDNA.37092.1.S1_at | down-regulator of transcription 1 (predicted) | DR1 | 4.08 | 0.0606 |
| MmugDNA.30978.1.S1_at | desmoglein 2 | DSG2 | 4.06 | 0.0049 |
| MmuSTS.3837.1.S1_at | solute carrier organic anion transporter family, member 2A1 | SLCO2A1 | 4.05 | 0.0641 |
| MmugDNA.26101.1.S1_at | — | — | 4.04 | 0.0842 |
| MmugDNA.25428.1.S1_at | zinc finger protein 382 | LOC713048 | 4.04 | 0.0143 |
| MmugDNA.4774.1.S1_at | — | — | 4.04 | 0.0319 |
| MmugDNA.30877.1.S1_at | zyg-11 homolog B (C. elegans)-like | LOC715671 | 4.04 | 0.0081 |
| MmugDNA.24520.1.S1_at | synapsin II isoform IIa | LOC695412 | 4.04 | 0.0046 |
| MmugDNA.11034.1.S1_at | — | — | 4.04 | 0.0031 |
| MmugDNA.21096.1.S1_at | zinc finger protein 275 | ZNF275 | 4.03 | 0.0093 |
| MmugDNA.43413.1.S1_at | immunoglobin superfamily, member 21 | LOC701539 | 4.03 | 0.0227 |
| MmugDNA.42897.1.S1_at | hypothetical protein LOC701560 | LOC701560 | 4.03 | 0.0379 |
| MmugDNA.19620.1.S1_at | — | — | 4.02 | 0.0364 |
| MmugDNA.15063.1.S1_s_at | phosphatidate cytidylyltransferase 1 | LOC706649 | 4.02 | 0.0319 |
| MmugDNA.21133.1.S1_at | — | — | 4.01 | 0.0911 |
| MmugDNA.12118.1.S1_at | — | — | 4.00 | 0.0007 |
| MmugDNA.20406.1.S1_at | GLE1-like, RNA export mediator isoform 1 | LOC717474 | 4.00 | 0.0184 |
| MmugDNA.34611.1.S1_at | — | — | 4.00 | 0.0155 |
| MmugDNA.19800.1.S1_at | vang-like 1 | LOC709730 | 3.99 | 0.0971 |
| MmugDNA.6828.1.S1_at | zinc finger protein 233 | LOC713398 | 3.99 | 0.0396 |
| MmugDNA.32366.1.S1_at | — | — | 3.99 | 0.0269 |
| MmugDNA.13572.1.S1_at | — | — | 3.99 | 0.0080 |
| MmugDNA.23433.1.S1_at | — | — | 3.98 | 0.0701 |
| MmugDNA.22715.1.S1_s_at | — | — | 3.98 | 0.0039 |
| MmugDNA.334.1.S1_at | serine (or cysteine) proteinase inhibitor, clade B (ovalbumin), member 2 | SERPINB2 | 3.96 | 0.0921 |
| MmuSTS.1861.1.S1_at | cholinergic receptor, nicotinic, alpha polypeptide 10 | LOC718133 | 3.96 | 0.0531 |
| MmugDNA.28216.1.S1_at | CDC42-binding protein kinase alpha isoform B | LOC697811 | 3.95 | 0.0269 |
| MmugDNA.33930.1.S1_at | LIN-7 homolog A (LIN-7A) (mLin-7) (Mammalian LIN-seven protein 1) (MALS-1) (Vertebrate LIN 7 homolog 1) (Veli-1 protein) | LOC697557 | 3.95 | 0.0069 |
| MmugDNA.2196.1.S1_at | — | — | 3.94 | 0.0044 |
| MmuSTS.1116.1.S1_at | — | — | 3.94 | 0.0137 |
| MmugDNA.29351.1.S1_at | alpha-synuclein isoform NACP140 | LOC706985 | 3.94 | 0.0198 |
| MmugDNA.12808.1.S1_at | hypothetical protein LOC694824 | LOC694824 | 3.94 | 0.0695 |
| MmugDNA.9043.1.S1_at | ADP-ribosylation factor-like 6 interacting protein 2 | LOC710647 | 3.94 | 0.0582 |
| Mmu.937.1.S1_at | hypothetical protein LOC710176 | LOC710176 | 3.94 | 0.0314 |
| MmugDNA.13793.1.S1_at | — | — | 3.93 | 0.0047 |
| MmugDNA.22471.1.S1_at | — | — | 3.93 | 0.0011 |
| MmugDNA.13861.1.S1_at | fatty acid 2-hydroxylase | LOC710403 | 3.92 | 0.0262 |
| MmugDNA.31129.1.S1_at | G protein-coupled receptor, family C, group 5, member B | GPRC5B | 3.92 | 0.0025 |
| MmugDNA.41489.1.S1_at | — | — | 3.91 | 0.0302 |
| MmugDNA.12173.1.S1_at | hypothetical protein LOC695417 | LOC695417 | 3.91 | 0.0320 |
| MmugDNA.37274.1.S1_s_at | secretin receptor | SCTR | 3.91 | 0.0497 |
| MmugDNA.10795.1.S1_at | SVH protein | LOC695210 | 3.90 | 0.0590 |
| MmugDNA.24744.1.S1_at | homeodomain leucine zipper protein | LOC713087 | 3.90 | 0.0347 |
| MmugDNA.39071.1.S1_at | — | — | 3.89 | 0.0087 |
| MmugDNA.818.1.S1_at | — | — | 3.89 | 0.0375 |

| Probe Set ID | Gene Title | Gene Symbol | Ratio Top verus Bottom | p value Top versus Bottom |
|---|---|---|---|---|
| MmugDNA.4556.1.S1_at | Sorting nexin-5 | — | 3.89 | 0.0175 |
| MmugDNA.13966.1.S1_s_at | regulator of G-protein signalling 8 | RGS8 | 3.89 | 0.0312 |
| MmunewRS.597.1.S1_at | Ral GEF with PH domain and SH3 binding motif 2 isoform 2 | LOC717165 | 3.89 | 0.0520 |
| MmuSTS.4601.1.S1_at | interleukin 19 isoform 1 precursor | LOC694806 | 3.89 | 0.0032 |
| MmugDNA.13652.1.S1_at | — | — | 3.87 | 0.0550 |
| MmugDNA.7329.1.S1_s_at | — | — | 3.86 | 0.0750 |
| MmugDNA.40738.1.S1_at | — | — | 3.86 | 0.0007 |
| MmugDNA.2633.1.S1_at | small nuclear RNA activating complex, polypeptide 1, 43 kDa | LOC704797 | 3.86 | 0.0327 |
| MmugDNA.7168.1.S1_at | — | — | 3.86 | 0.0832 |
| MmugDNA.36780.1.S1_at | — | — | 3.85 | 0.0778 |
| Mmu.14893.1.S1_x_at | cytochrome P450 3A64 | CYP3A64 | 3.84 | 0.0771 |
| MmugDNA.19443.1.S1_at | ataxin 2-binding protein 1 isoform 1 | LOC713147 | 3.84 | 0.0099 |
| MmugDNA.30992.1.S1_at | SH3 and multiple ankyrin repeat domains 2 isoform 1 | LOC708192 | 3.84 | 0.0487 |
| MmugDNA.33696.1.S1_at | hyaluronan binding protein 4 | LOC710213 | 3.82 | 0.0699 |
| MmugDNA.20527.1.S1_at | — | — | 3.82 | 0.0945 |
| MmugDNA.9900.1.S1_at | nuclear factor of activated T-cells, cytoplasmic, calcineurin-dependent 2 isoform C | LOC710601 | 3.82 | 0.0643 |
| MmuSTS.3411.1.S1_at | Ribose-phosphate pyrophosphokinase I (Phosphoribosyl pyrophosphate synthetase I) (PRS-I) | LOC702529 | 3.82 | 0.0608 |
| MmugDNA.4816.1.S1_at | hypothetical protein LOC719170 | LOC719170 | 3.81 | 0.0018 |
| MmugDNA.35136.1.S1_at | transmembrane protein 35 | LOC702205 | 3.81 | 0.0773 |
| MmugDNA.25086.1.S1_at | glucosidase, alpha; neutral C | GANC | 3.80 | 0.0077 |
| MmugDNA.1845.1.S1_at | — | — | 3.80 | 0.0967 |
| MmugDNA.29812.1.S1_at | adaptor-related protein complex 3, beta 2 subunit | AP3B2 | 3.79 | 0.0056 |
| MmuSTS.4436.1.S1_at | — | — | 3.79 | 0.0006 |
| MmuSTS.782.1.S1_at | potassium voltage-gated channel, Shab-related subfamily, member 2 | KCNB2 | 3.79 | 0.0129 |
| MmugDNA.3088.1.S1_at | WNK lysine deficient protein kinase 3 | WNK3 | 3.79 | 0.0093 |
| MmuSTS.3509.1.S1_at | Complement component 6 | C6 | 3.78 | 0.0826 |
| MmugDNA.41339.1.S1_at | GTP cyclohydrolase I (GTP-CH-I) | GCH1 | 3.78 | 0.0160 |
| MmugDNA.14784.1.S1_at | — | — | 3.77 | 0.0005 |
| MmugDNA.9742.1.S1_at | — | — | 3.77 | 0.0120 |
| MmugDNA.5664.1.S1_at | — | — | 3.76 | 0.0445 |
| MmugDNA.480.1.S1_at | — | — | 3.75 | 0.0159 |
| MmugDNA.34213.1.S1_at | cDNA sequence BC021395 | LOC709217 | 3.74 | 0.0930 |
| MmugDNA.16508.1.S1_at | — | — | 3.73 | 0.0079 |
| MmugDNA.17649.1.S1_at | Sp3 transcription factor | SP3 | 3.73 | 0.0274 |
| MmugDNA.41644.1.S1_at | spermatogenesis associated 5-like 1 | LOC713376 | 3.72 | 0.0074 |
| MmugDNA.9202.1.S1_at | — | — | 3.72 | 0.0472 |
| MmugDNA.17057.1.S1_s_at | tumor suppressor candidate 3 isoform a | LOC701123 | 3.72 | 0.0011 |
| MmuSTS.56.1.S1_at | hypothetical protein LOC715723 | LOC715723 | 3.72 | 0.0043 |
| MmugDNA.39898.1.S1_at | — | — | 3.71 | 0.0068 |
| MmugDNA.40119.1.S1_s_at | HIV-1 Tat interactive protein 2, 30 kDa | LOC701908 | 3.71 | 0.0078 |
| MmugDNA.27371.1.S1_at | hypothetical protein LOC697751 | LOC697751 | 3.71 | 0.0857 |
| MmugDNA.16327.1.S1_at | pad-1-like | DOPEY2 | 3.70 | 0.0023 |
| MmuSTS.3363.1.S1_at | phosphodiesterase 2A, cGMP-stimulated | PDE2A | 3.70 | 0.0029 |
| MmugDNA.14309.1.S1_at | activated leukocyte cell adhesion molecule | LOC703777 | 3.70 | 0.0030 |
| MmugDNA.24681.1.S1_at | CTAGE family, member 5 | — | 3.70 | 0.0392 |
| MmuSTS.101.1.S1_at | acyl-Coenzyme A oxidase isoform b | LOC705197 | 3.69 | 0.0138 |
| MmugDNA.27013.1.S1_at | — | — | 3.69 | 0.0484 |
| MmugDNA.29538.1.S1_at | — | — | 3.69 | 0.0315 |
| MmugDNA.43028.1.S1_at | — | — | 3.68 | 0.0468 |
| MmugDNA.34314.1.S1_at | synovial sarcoma, X breakpoint 2 interacting protein | SSX2IP | 3.67 | 0.0570 |
| MmugDNA.33133.1.S1_at | hypothetical protein LOC711218 | LOC711218 | 3.67 | 0.0227 |
| MmugDNA.11493.1.S1_at | — | — | 3.67 | 0.0378 |
| MmugDNA.16985.1.S1_at | ets variant gene 1 | ETV1 | 3.67 | 0.0532 |
| MmuSTS.1797.1.S1_at | — | — | 3.67 | 0.0668 |
| MmuSTS.2054.1.S1_at | protein (peptidyl-prolyl cis/trans isomerase) NIMA-interacting, 4 (parvulin) | LOC699273 | 3.67 | 0.0431 |
| MmugDNA.18533.1.S1_at | phospholipase D family, member 5 | LOC706256 | 3.66 | 0.0682 |
| MmuSTS.1511.1.S1_at | RNA binding motif protein 15B | LOC700716 | 3.66 | 0.0181 |
| MmugDNA.15936.1.S1_at | — | — | 3.66 | 0.0183 |
| MmugDNA.29618.1.S1_at | K09A9.6 | LOC712623 | 3.65 | 0.0282 |
| MmugDNA.831.1.S1_at | — | — | 3.65 | 0.0675 |
| MmugDNA.22531.1.S1_s_at | — | — | 3.65 | 0.0988 |
| MmugDNA.6653.1.S1_at | tudor repeat associator with PCTAIRE 2 | PCTAIRE2BP | 3.65 | 0.0018 |
| MmugDNA.25839.1.S1_at | RAD1 homolog isoform 1 | LOC703720 | 3.64 | 0.0444 |
| MmugDNA.6534.1.S1_at | hypothetical protein LOC701296 | LOC701296 | 3.64 | 0.0007 |
| MmugDNA.30983.1.S1_at | — | — | 3.64 | 0.0165 |
| MmugDNA.18313.1.S1_at | arrestin beta 1 isoform A | LOC695250 | 3.64 | 0.0141 |
| MmugDNA.25553.1.S1_at | retinitis pigmentosa GTPase regulator interacting protein 1 | LOC697345 | 3.63 | 0.0105 |
| MmugDNA.31716.1.S1_s_at | molybdenum cofactor sulfurase | LOC715633 | 3.62 | 0.0761 |
| MmugDNA.41201.1.S1_at | — | — | 3.62 | 0.0012 |
| MmugDNA.7740.1.S1_at | — | — | 3.61 | 0.0206 |
| MmugDNA.1555.1.S1_at | C29E4.8 | LOC714698 | 3.61 | 0.0795 |
| MmugDNA.27957.1.S1_at | ganglioside induced differentiation associated protein 2 | LOC714615 | 3.59 | 0.0280 |

| Probe Set ID | Gene Title | Gene Symbol | Ratio Top verus Bottom | p value Top versus Bottom |
|---|---|---|---|---|
| MmugDNA.2255.1.S1_at | phosphatidylinositol-4-phosphate 5-kinase, type I, beta isoform 2 | LOC700538 | 3.59 | 0.0003 |
| MmugDNA.23037.1.S1_at | Ephrin type-B receptor 2 precursor (Tyrosine-protein kinase receptor EPH-3) (Neural kinase) (Nuk receptor tyrosine kinase) (SEK-3) | LOC720107 | 3.59 | 0.0647 |
| MmugDNA.41938.1.S1_at | proline-rich protein PRP2 | LOC702863 | 3.59 | 0.0012 |
| MmugDNA.7947.1.S1_at | — | — | 3.59 | 0.0538 |
| MmugDNA.4820.1.S1_at | Rho GTPase activating protein 6 | ARHGAP6 | 3.59 | 0.0726 |
| MmugDNA.31476.1.S1_at | Ras-related protein Rab-28 (Rab-26) | LOC694111 | 3.58 | 0.0643 |
| MmugDNA.16749.1.S1_at | — | — | 3.58 | 0.0095 |
| MmugDNA.39259.1.S1_at | — | — | 3.57 | 0.0161 |
| MmugDNA.3689.1.S1_at | nuclear factor of kappa light polypeptide gene enhancer in B-cells inhibitor, beta isoform a | LOC694844 | 3.57 | 0.0001 |
| MmugDNA.17315.1.S1_at | — | — | 3.57 | 0.0712 |
| MmugDNA.23019.1.S1_at | — | — | 3.56 | 0.0014 |
| MmugDNA.37589.1.S1_at | Ubiquitin-conjugating enzyme E2S (Ubiquitin-conjugating enzyme E2-24 kDa) (Ubiquitin-protein ligase) (Ubiquitin carrier protein) (E2-EPF5) | — | 3.55 | 0.0112 |
| MmugDNA.17498.1.S1_at | — | — | 3.55 | 0.0024 |
| MmugDNA.13233.1.S1_at | brain expressed X-linked 2 | LOC696048 | 3.55 | 0.0065 |
| MmugDNA.22053.1.S1_at | gamma-glutamyl carboxylase | GGCX | 3.55 | 0.0254 |
| MmugDNA.35529.1.S1_at | PARK2 co-regulated | PACRG | 3.55 | 0.0412 |
| MmugDNA.40108.1.S1_at | hypothetical protein LOC698322 | LOC698322 | 3.54 | 0.0882 |
| Mmu.1639.1.S1_at | solute carrier family 15 (H+/peptide transporter), member 2 | SLC15A2 | 3.54 | 0.0400 |
| MmugDNA.19566.1.S1_at | Type I iodothyronine deiodinase (Type-I 5deiodinase) (DIOI) (Type 1 DI) (5DI) | DIO1 | 3.54 | 0.0037 |
| MmuSTS.106.1.S1_at | Elongation factor 1-delta (EF-1-delta) (Antigen NY-CO-4) | — | 3.54 | 0.0407 |
| MmugDNA.41451.1.S1_s_at | F33H2.6 | LOC710209 | 3.52 | 0.0008 |
| MmugDNA.39857.1.S1_at | hypothetical protein LOC703607 | LOC703607 | 3.52 | 0.0070 |
| MmuSTS.3342.1.S1_at | SET and MYND domain containing 3 | SMYD3 | 3.52 | 0.0919 |
| MmugDNA.31877.1.S1_at | calreticulin 3 | LOC719532 | 3.52 | 0.0899 |
| MmugDNA.13028.1.S1_at | periaxin | LOC707626 | 3.52 | 0.0013 |
| MmugDNA.29176.1.S1_at | MEGF11 protein | LOC714198 | 3.51 | 0.0977 |
| MmuSTS.4142.1.S1_at | — | — | 3.51 | 0.0060 |
| MmugDNA.17878.1.S1_at | CG5359-PA | LOC711098 | 3.51 | 0.0020 |
| MmugDNA.41017.1.S1_at | — | — | 3.50 | 0.0855 |
| MmugDNA.12740.1.S1_at | — | — | 3.49 | 0.0567 |
| MmugDNA.2965.1.S1_at | butyrate-induced transcript 1 | LOC709590 | 3.49 | 0.0306 |
| MmuSTS.4796.1.S1_at | flavin containing monooxygenase 4 | FMO4 | 3.49 | 0.0927 |
| MmuSTS.4569.1.S1_at | MAD, mothers against decapentaplegic homolog 9 | SMAD9 | 3.48 | 0.0297 |
| MmuSTS.3579.1.S1_at | — | — | 3.48 | 0.0321 |
| MmugDNA.29168.1.S1_at | Collagen alpha-1(III) chain precursor | LOC719369 | 3.47 | 0.0245 |
| MmugDNA.24379.1.S1_at | tissue factor pathway inhibitor | TFPI | 3.47 | 0.0251 |
| MmugDNA.6495.1.S1_at | hypothetical protein LOC701956 | LOC701956 | 3.47 | 0.0063 |
| MmugDNA.31684.1.S1_at | Protein C6orf78 homolog | LOC714815 | 3.47 | 0.0341 |
| MmugDNA.8650.1.S1_at | solute carrier family 6, member 17 | LOC701162 | 3.47 | 0.0032 |
| MmuSTS.2222.1.S1_at | synaptic vesicle protein 2B homolog | LOC710980 | 3.46 | 0.0052 |
| MmuSTS.2708.1.S1_at | ADAM metallopeptidase domain 10 | ADAM10 | 3.46 | 0.0615 |
| MmugDNA.4023.1.S1_at | — | — | 3.46 | 0.0005 |
| MmugDNA.3743.1.S1_at | transmembrane and coiled-coil domains 3 | LOC716185 | 3.46 | 0.0184 |
| MmuSTS.3521.1.S1_at | arginyltransferase 1 | ATE1 | 3.45 | 0.0116 |
| MmugDNA.35799.1.S1_at | — | — | 3.45 | 0.0060 |
| MmugDNA.3417.1.S1_at | — | — | 3.45 | 0.0480 |
| MmugDNA.14546.1.S1_at | testis specific, 10 interacting protein | LOC715217 | 3.45 | 0.0517 |
| MmugDNA.41404.1.S1_at | cytoplasmic polyadenylation element binding protein 3 | LOC698133 | 3.45 | 0.0022 |
| MmugDNA.40609.1.S1_at | — | — | 3.45 | 0.0449 |
| MmugDNA.15703.1.S1_at | putative homeodomain transcription factor 1 | PHTF1 | 3.44 | 0.0091 |
| MmugDNA.6582.1.S1_at | hypothetical protein LOC701911 | LOC701911 | 3.44 | 0.0206 |
| MmugDNA.28101.1.S1_at | ST3 beta-galactoside alpha-2,3-sialyltransferase 5 | ST3GAL5 | 3.44 | 0.0116 |
| MmugDNA.41240.1.S1_at | — | — | 3.44 | 0.0124 |
| MmugDNA.8735.1.S1_at | — | — | 3.44 | 0.0204 |
| MmugDNA.14126.1.S1_at | hypothetical protein LOC694536 | LOC694536 | 3.44 | 0.0688 |
| MmugDNA.31606.1.S1_at | — | — | 3.43 | 0.0033 |
| MmugDNA.34884.1.S1_at | CUB and zona pellucida-like domains 1 | LOC706861 | 3.43 | 0.0890 |
| MmugDNA.23074.1.S1_at | plexin A2 | LOC713800 | 3.43 | 0.0004 |
| MmuSTS.1012.1.S1_at | USP6 N-terminal like | USP6NL | 3.43 | 0.0199 |
| MmugDNA.40409.1.S1_at | Y55F3AM.9 | LOC703159 | 3.42 | 0.0256 |
| MmuSTS.3876.1.S1_at | solute carrier family 6 (amino acid transporter), member 14 | SLC6A14 | 3.42 | 0.0305 |
| MmugDNA.38177.1.S1_at | F-box only protein 21 isoform 2 | LOC693647 | 3.41 | 0.0637 |
| MmugDNA.35235.1.S1_at | hypothetical protein LOC710443 | LOC710443 | 3.41 | 0.0899 |
| MmugDNA.19514.1.S1_at | — | — | 3.41 | 0.0487 |
| MmugDNA.25771.1.S1_at | Protein C20orf22 homolog | LOC706758 | 3.41 | 0.0889 |
| MmugDNA.3375.1.S1_at | ankyrin repeat domain 28 | LOC696592 | 3.41 | 0.0355 |
| MmunewRS.255.1.S1_at | — | — | 3.41 | 0.0055 |
| MmugDNA.38350.1.S1_s_at | Potassium channel, subfamily K, member 5 | — | 3.41 | 0.0273 |
| MmugDNA.29156.1.S1_at | cyclin T2 isoform b | LOC708813 | 3.40 | 0.0315 |

-continued

| Probe Set ID | Gene Title | Gene Symbol | Ratio Top verus Bottom | p value Top versus Bottom |
|---|---|---|---|---|
| MmugDNA.1804.1.S1_at | — | — | 3.40 | 0.0046 |
| MmugDNA.13727.1.S1_at | beta-site APP-cleaving enzyme 1 | BACE1 | 3.40 | 0.0104 |
| MmugDNA.36294.1.S1_at | dopa decarboxylase (aromatic L-amino acid decarboxylase) | DDC | 3.40 | 0.0052 |
| MmugDNA.18015.1.S1_at | HLA class II histocompatibility antigen, DM beta chain precursor (MHC class II antigen DMB) | LOC717870 | 3.40 | 0.0951 |
| MmugDNA.10946.1.S1_at | — | — | 3.40 | 0.0129 |
| MmugDNA.35307.1.S1_at | IQ motif containing G | LOC714807 | 3.39 | 0.0051 |
| MmugDNA.40386.1.S1_at | hypothetical protein LOC718008 | LOC718008 | 3.39 | 0.0568 |
| MmuSTS.1442.1.S1_at | — | — | 3.39 | 0.0810 |
| MmugDNA.30491.1.S1_at | neurexin 3 | LOC678699 | 3.39 | 0.0046 |
| MmugDNA.40498.1.S1_at | — | — | 3.38 | 0.0141 |
| MmuSTS.3629.1.S1_at | EMI domain containing 1 | LOC717414 | 3.38 | 0.0283 |
| MmugDNA.42049.1.S1_at | synaptotagmin-like 5 | LOC697915 | 3.38 | 0.0543 |
| MmugDNA.33991.1.S1_at | ELOVL family member 6, elongation of long chain fatty acids (FEN1/Elo2, SUR4/Elo3-like, yeast) | LOC698870 | 3.37 | 0.0453 |
| MmugDNA.30419.1.S1_at | — | — | 3.37 | 0.0108 |
| MmugDNA.38819.1.S1_at | hypothetical protein LOC716712 | LOC716712 | 3.37 | 0.0815 |
| MmugDNA.11736.1.S1_at | — | — | 3.37 | 0.0918 |
| MmugDNA.8760.1.S1_at | — | — | 3.37 | 0.0545 |
| MmugDNA.21748.1.S1_at | FXYD domain containing ion transport regulator 4 | LOC717636 | 3.37 | 0.0147 |
| MmugDNA.40624.1.S1_at | — | — | 3.37 | 0.0144 |
| MmugDNA.34981.1.S1_at | CG17687-PA | LOC716031 | 3.36 | 0.0598 |
| MmugDNA.21769.1.S1_at | transmembrane protein 141 | LOC721687 | 3.36 | 0.0278 |
| MmugDNA.12396.1.S1_at | zinc finger protein 621 | LOC717189 | 3.36 | 0.0150 |
| MmugDNA.35827.1.S1_s_at | glucosaminyl (N-acetyl) transferase 2, l-branching enzyme isoform B | LOC697468 | 3.35 | 0.0492 |
| MmugDNA.31910.1.S1_at | — | — | 3.35 | 0.0987 |
| MmugDNA.39573.1.S1_s_at | — | — | 3.35 | 0.0001 |
| MmugDNA.27074.1.S1_at | hypothetical protein LOC707868 | LOC707868 | 3.35 | 0.0014 |
| MmugDNA.4152.1.S1_at | esophageal cancer related gene 4 protein | LOC713611 | 3.34 | 0.0126 |
| MmugDNA.28574.1.S1_at | zinc finger protein 483 | ZNF483 | 3.34 | 0.0050 |
| MmugDNA.14788.1.S1_at | CG14868-PA | LOC715968 | 3.34 | 0.0385 |
| Mmu.2046.1.S1_at | Hypothetical protein LOC693623 | — | 3.34 | 0.0130 |
| MmugDNA.38470.1.S1_at | hypothetical protein LOC704380 | LOC704380 | 3.33 | 0.0041 |
| MmugDNA.43475.1.S1_at | inositol polyphosphate-4-phosphatase, type 1 | INPP4A | 3.33 | 0.0395 |
| MmugDNA.11863.1.S1_at | receptor expression enhancing protein 1 | LOC697390 | 3.32 | 0.0807 |
| MmugDNA.12356.1.S1_at | peroxin1 | LOC702392 | 3.32 | 0.0067 |
| MmugDNA.34502.1.S1_at | bactericidal/permeability-increasing protein-like 2 | LOC717287 | 3.32 | 0.0813 |
| MmugDNA.28096.1.S1_at | KIAA1799 protein | LOC696830 | 3.32 | 0.0034 |
| MmugDNA.19117.1.S1_at | — | — | 3.32 | 0.0948 |
| MmugDNA.22544.1.S1_at | lysosomal-associated membrane protein 2 | LAMP2 | 3.32 | 0.0120 |
| MmugDNA.2026.1.S1_at | neuraminidase | NEU1 | 3.32 | 0.0176 |
| MmuSTS.2482.1.S1_at | zinc finger protein 3 isoform 2 | LOC719069 | 3.31 | 0.0772 |
| MmugDNA.8202.1.S1_at | — | — | 3.31 | 0.0236 |
| MmugDNA.12374.1.S1_at | 5-nucleotidase, cytosolic III isoform 1 | LOC708743 | 3.31 | 0.0020 |
| MmugDNA.18151.1.S1_at | — | — | 3.31 | 0.0350 |
| MmugDNA.40189.1.S1_at | 3-hydroxy-3-methylglutaryl-Coenzyme A reductase | HMGCR | 3.31 | 0.0110 |
| MmugDNA.43623.1.S1_s_at | disabled homolog 2 | DAB2 | 3.31 | 0.0650 |
| MmugDNA.22195.1.S1_at | prospero-related homeobox 1 | LOC709465 | 3.31 | 0.0373 |
| MmugDNA.12057.1.S1_at | hypothetical protein LOC708157 | LOC708157 | 3.31 | 0.0963 |
| MmugDNA.29604.1.S1_at | — | — | 3.30 | 0.0482 |
| MmugDNA.36778.1.S1_at | ADAMTS-like 3 | LOC712844 | 3.30 | 0.0777 |
| MmugDNA.43352.1.S1_at | chromobox homolog 2 isoform 1 | LOC717462 | 3.30 | 0.0674 |
| MmugDNA.41900.1.S1_at | nudix-type motif 10 | LOC695921 | 3.30 | 0.0511 |
| MmugDNA.5215.1.S1_at | — | — | 3.30 | 0.0039 |
| MmugDNA.3581.1.S1_at | — | — | 3.29 | 0.0050 |
| MmugDNA.42978.1.S1_at | — | — | 3.29 | 0.0052 |
| MmugDNA.11001.1.S1_at | transcription factor-like nuclear regulator | — | 3.29 | 0.0396 |
| MmugDNA.32117.1.S1_at | — | — | 3.28 | 0.0977 |
| MmugDNA.4792.1.S1_at | — | — | 3.28 | 0.0123 |
| MmugDNA.14682.1.S1_at | — | — | 3.28 | 0.0017 |
| MmuSTS.1437.1.S1_at | L-plastin | LCP1 | 3.27 | 0.0624 |
| Mmu.1276.1.S1_at | serine protease inhibitor, Kunitz type, 2 | LOC714755 | 3.27 | 0.0799 |
| MmugDNA.29558.1.S1_at | leucine rich repeat containing 7 | LOC702347 | 3.27 | 0.0047 |
| MmugDNA.36803.1.S1_at | — | — | 3.26 | 0.0986 |
| MmugDNA.37994.1.S1_at | — | — | 3.26 | 0.0694 |
| MmugDNA.37151.1.S1_at | — | — | 3.26 | 0.0730 |
| MmuSTS.2193.1.S1_at | acid sphingomyelinase-like phosphodiesterase 3A | LOC713696 | 3.25 | 0.0359 |
| MmugDNA.15609.1.S1_at | — | — | 3.25 | 0.0134 |
| MmugDNA.34021.1.S1_at | ARP3 actin-related protein 3 homolog | ACTR3 | 3.25 | 0.0910 |
| MmugDNA.13552.1.S1_at | — | — | 3.25 | 0.0538 |
| MmugDNA.14095.1.S1_at | calpain 9 | CAPN9 | 3.25 | 0.0723 |
| MmugDNA.20778.1.S1_at | transcriptional regulator ATRX isoform 2 | LOC705735 | 3.24 | 0.0808 |
| MmuSTS.3264.1.S1_at | norrin | LOC702203 | 3.24 | 0.0996 |
| MmugDNA.21014.1.S1_at | — | — | 3.24 | 0.0033 |
| MmugDNA.26007.1.S1_at | — | — | 3.24 | 0.0467 |

-continued

| Probe Set ID | Gene Title | Gene Symbol | Ratio Top verus Bottom | p value Top versus Bottom |
|---|---|---|---|---|
| Mmu.14792.1.S1_at | solute carrier family 40 (iron-regulated transporter), member 1 | SLC40A1 | 3.24 | 0.0230 |
| MmugDNA.14237.1.S1_at | Dynein heavy chain at 16F CG7092-PA | LOC694115 | 3.24 | 0.0962 |
| MmuSTS.4208.1.S1_at | glucosaminyl (N-acetyl) transferase 3, mucin type | LOC702754 | 3.22 | 0.0016 |
| MmugDNA.19093.1.S1_at | — | — | 3.22 | 0.0397 |
| MmugDNA.8868.1.S1_at | hypothetical protein LOC710705 | LOC710705 | 3.21 | 0.0002 |
| MmugDNA.16163.1.S1_at | — | — | 3.21 | 0.0003 |
| MmugDNA.30042.1.S1_at | CG1 protein (F18) | LOC703003 | 3.21 | 0.0622 |
| MmugDNA.100.1.S1_at | — | — | 3.20 | 0.0940 |
| MmugDNA.10033.1.S1_at | poliovirus receptor | LOC714190 | 3.20 | 0.0577 |
| MmugDNA.26257.1.S1_at | echinoderm microtubule associated protein like 1 isoform b | LOC705977 | 3.20 | 0.0866 |
| MmugDNA.37272.1.S1_at | zinc finger protein 467 | LOC712106 | 3.20 | 0.0577 |
| MmugDNA.30904.1.S1_at | — | — | 3.19 | 0.0072 |
| MmuSTS.772.1.S1_at | cytosolic sialic acid 9-O-acetylesterase homolog | LOC711816 | 3.19 | 0.0375 |
| MmugDNA.1780.1.S1_at | — | — | 3.19 | 0.0140 |
| MmuSTS.1855.1.S1_at | cadherin 2, type 1 preproprotein | LOC711526 | 3.19 | 0.0108 |
| MmugDNA.36726.1.S1_at | NG22 protein | SLC44A4 | 3.18 | 0.0184 |
| MmugDNA.28522.1.S1_at | — | — | 3.18 | 0.0106 |
| MmugDNA.40772.1.S1_at | — | — | 3.18 | 0.0538 |
| MmugDNA.40592.1.S1_at | reticulon 4 receptor-like 1 | LOC720246 | 3.18 | 0.0448 |
| MmugDNA.41621.1.S1_at | F54C1.5a | LOC702261 | 3.18 | 0.0527 |
| MmugDNA.20138.1.S1_at | CXXC finger 6 | LOC707759 | 3.17 | 0.0697 |
| MmugDNA.30196.1.S1_at | — | — | 3.17 | 0.0365 |
| Mmu.16247.1.S1_at | EF hand domain family, member A1 | LOC706065 | 3.17 | 0.0044 |
| MmugDNA.24683.1.S1_at | — | — | 3.17 | 0.0121 |
| MmugDNA.21254.1.S1_at | hypothetical protein LOC695666 | LOC695666 | 3.16 | 0.0344 |
| MmugDNA.30331.1.S1_at | multiple C2-domains with two transmembrane regions 1 isoform S | LOC697733 | 3.16 | 0.0017 |
| MmugDNA.14053.1.S1_at | — | — | 3.16 | 0.0862 |
| MmuSTS.72.1.S1_at | hephaestin isoform a | LOC709879 | 3.15 | 0.0624 |
| Mmu.12852.1.S1_at | Nedd4 family interacting protein 1 | LOC705716 | 3.15 | 0.0181 |
| MmugDNA.21162.1.S1_at | 1D-myo-inositol-trisphosphate 3-kinase B | LOC698185 | 3.15 | 0.0210 |
| MmugDNA.2522.1.S1_at | gamma-aminobutyric acid (GABA) A receptor, beta 3 isoform 2 precursor | GABRB3 | 3.15 | 0.0383 |
| MmugDNA.1070.1.S1_at | — | — | 3.15 | 0.0660 |
| MmugDNA.11921.1.S1_at | CG7071-PA, isoform A | LOC708298 | 3.15 | 0.0754 |
| MmuSTS.2765.1.S1_at | class III alcohol dehydrogenase 5 chi subunit | ADH5 | 3.14 | 0.0011 |
| MmugDNA.40331.1.S1_at | — | — | 3.14 | 0.0007 |
| MmugDNA.25139.1.S1_at | carboxypeptidase D precursor | LOC712407 | 3.14 | 0.0055 |
| MmugDNA.12314.1.S1_at | — | — | 3.14 | 0.0034 |
| MmugDNA.32572.1.S1_at | Fibroblast growth factor 14 (FGF-14) (Fibroblast growth factor homologous factor 4) (FHF-4) | FGF14 | 3.14 | 0.0082 |
| MmugDNA.3590.1.S1_at | — | — | 3.13 | 0.0150 |
| MmugDNA.13879.1.S1_at | mannosidase, alpha, class 2A, member 1 | LOC705480 | 3.13 | 0.0429 |
| MmugDNA.3209.1.S1_at | microfibrillar-associated protein 3-like | MFAP3L | 3.12 | 0.0120 |
| MmugDNA.7233.1.S1_at | — | — | 3.12 | 0.0851 |
| MmugDNA.15955.1.S1_at | TAO kinase 2 | TAOK2 | 3.12 | 0.0021 |
| MmugDNA.38589.1.S1_at | lethal (2) k00619 CG4775-PA | LOC715015 | 3.12 | 0.0309 |
| MmugDNA.546.1.S1_at | alpha glucosidase II alpha subunit isoform 2 | LOC718672 | 3.12 | 0.0262 |
| MmugDNA.41951.1.S1_at | LPS-responsive vesicle trafficking, beach and anchor containing | LOC693823 | 3.12 | 0.0005 |
| MmugDNA.1873.1.S1_at | — | — | 3.11 | 0.0183 |
| MmugDNA.18551.1.S1_at | inositol polyphosphate-5-phosphatase, 75 kDa | INPP5B | 3.11 | 0.0058 |
| MmugDNA.15348.1.S1_at | ERO1-like | ERO1L | 3.10 | 0.0079 |
| MmugDNA.20795.1.S1_at | slit homolog 1 | LOC697716 | 3.10 | 0.0012 |
| MmugDNA.28842.1.S1_at | CKLF-like MARVEL transmembrane domain containing 7 isoform b | LOC704329 | 3.10 | 0.0648 |
| MmugDNA.10278.1.S1_at | slit and trk like 3 protein | LOC700660 | 3.10 | 0.0457 |
| MmugDNA.41181.1.S1_at | — | — | 3.09 | 0.0747 |
| MmugDNA.42278.1.S1_s_at | — | — | 3.09 | 0.0003 |
| Mmu.12401.1.S1_at | SECIS binding protein 2 | LOC697442 | 3.09 | 0.0551 |
| MmugDNA.7049.1.S1_at | — | — | 3.09 | 0.0652 |
| MmugDNA.11735.1.S1_at | — | — | 3.08 | 0.0835 |
| MmugDNA.42396.1.S1_at | germ cell-less | LOC701545 | 3.08 | 0.0538 |
| MmugDNA.26488.1.S1_at | — | — | 3.08 | 0.0363 |
| MmugDNA.2284.1.S1_at | notch 2 preproprotein | LOC713798 | 3.08 | 0.0619 |
| MmugDNA.28250.1.S1_at | — | — | 3.08 | 0.0459 |
| MmugDNA.17056.1.S1_s_at | reticulon 4 receptor precursor | LOC694382 | 3.08 | 0.0373 |
| MmunewRS.972.1.S1_at | glutamate decarboxylase-like 1 | LOC706457 | 3.08 | 0.0098 |
| MmugDNA.11045.1.S1_s_at | microtubule-associated protein 7 | LOC705355 | 3.07 | 0.0015 |
| MmuSTS.1473.1.S1_at | mitogen-activated protein kinase 9 isoform 1 | LOC699736 | 3.07 | 0.0243 |
| MmugDNA.31498.1.S1_at | — | — | 3.07 | 0.0225 |
| MmuSTS.4269.1.S1_at | glutamate receptor, metabotropic 8 | GRM8 | 3.07 | 0.0386 |
| MmugDNA.18449.1.S1_s_at | zinc finger, ZZ type with EF hand domain 1 | — | 3.06 | 0.0534 |
| MmugDNA.11192.1.S1_at | CG8312-PA, isoform A | LOC705659 | 3.06 | 0.0538 |
| MmugDNA.1116.1.S1_at | — | — | 3.06 | 0.0407 |
| MmugDNA.30277.1.S1_at | — | — | 3.06 | 0.0039 |

-continued

| Probe Set ID | Gene Title | Gene Symbol | Ratio Top verus Bottom | p value Top versus Bottom |
|---|---|---|---|---|
| MmugDNA.14729.1.S1_at | CD82 antigen isoform 2 | CD82 | 3.06 | 0.0323 |
| MmugDNA.27419.1.S1_at | actin-related protein 3-beta isoform 1 | LOC715965 | 3.06 | 0.0384 |
| MmuSTS.3981.1.S1_at | SH3-domain GRB2-like 2 | SH3GL2 | 3.05 | 0.0871 |
| MmugDNA.37217.1.S1_at | — | — | 3.05 | 0.0935 |
| MmugDNA.15075.1.S1_at | hypothetical protein LOC716982 | LOC716982 | 3.05 | 0.0080 |
| MmugDNA.16118.1.S1_at | hect domain and RLD 3 | HERC3 | 3.05 | 0.0004 |
| MmunewRS.326.1.S1_at | hypothetical protein LOC717316 | LOC717316 | 3.05 | 0.0589 |
| MmugDNA.9126.1.S1_at | lin-7 homolog C | LIN7C | 3.05 | 0.0998 |
| MmugDNA.10794.1.S1_at | — | — | 3.04 | 0.0857 |
| MmugDNA.32230.1.S1_at | nucleolar protein 1, 120 kDa | — | 3.04 | 0.0954 |
| MmugDNA.37502.1.S1_at | — | — | 3.04 | 0.0417 |
| MmugDNA.17117.1.S1_at | hypothetical protein LOC700172 | LOC700172 | 3.04 | 0.0173 |
| MmugDNA.9078.1.S1_at | zinc finger protein 141 (clone pHZ-44) | ZNF141 | 3.03 | 0.0537 |
| MmugDNA.9853.1.S1_at | arachidonate 5-lipoxygenase | ALOX5 | 3.03 | 0.0808 |
| MmugDNA.22211.1.S1_at | PET112-like | LOC694983 | 3.03 | 0.0437 |
| MmugDNA.26554.1.S1_at | UDP glycosyltransferase 3 family, polypeptide A1 | LOC700115 | 3.03 | 0.0736 |
| MmugDNA.3964.1.S1_at | chromosome 2 open reading frame 30 | LOC716460 | 3.03 | 0.0238 |
| MmugDNA.36028.1.S1_at | — | — | 3.03 | 0.0039 |
| MmugDNA.19859.1.S1_at | hypothetical protein LOC700866 | LOC700866 | 3.03 | 0.0654 |
| MmugDNA.15510.1.S1_s_at | beta-amyloid binding protein precursor | LOC694282 | 3.02 | 0.0002 |
| MmugDNA.16151.1.S1_at | zinc finger protein 567 | LOC713173 | 3.02 | 0.0327 |
| MmugDNA.43512.1.S1_at | Transcribed locus | — | 3.02 | 0.0112 |
| MmuSTS.1643.1.S1_at | transient receptor potential cation channel, subfamily M, member 5 | LOC705070 | 3.02 | 0.0082 |
| MmugDNA.24619.1.S1_at | WD repeat domain 56 | LOC705146 | 3.01 | 0.0331 |
| MmuSTS.3607.1.S1_at | cadherin 11, type 2 preproprotein | LOC708826 | 3.01 | 0.0107 |
| MmugDNA.29541.1.S1_at | — | — | 3.00 | 0.0050 |
| MmugDNA.36083.1.S1_s_at | — | — | 3.00 | 0.0042 |
| MmugDNA.15113.1.S1_at | endoplasmic reticulum oxidoreductin 1-Lbeta | LOC710912 | 3.00 | 0.0927 |
| MmuSTS.2617.1.S1_at | — | — | 3.00 | 0.0676 |
| Mmu.380.1.S1_at | tetratricopeptide repeat domain 27 | LOC707021 | 3.00 | 0.0738 |
| MmuSTS.898.1.S1_at | engulfment and cell motility 1 isoform 1 /// hypothetical protein LOC713462 | LOC705818 /// LOC713462 | 3.00 | 0.0255 |
| MmugDNA.21372.1.S1_at | formin binding protein 3 | PRPF40A | 3.00 | 0.0062 |
| MmugDNA.6394.1.S1_at | microtubule-associated protein tau | MAPT | 3.00 | 0.0052 |
| MmugDNA.10807.1.S1_at | HESB like domain containing 1 | — | 2.99 | 0.0965 |
| MmugDNA.34681.1.S1_at | sortilin-related receptor containing LDLR class A repeats preproprotein | LOC713011 | 2.99 | 0.0129 |
| MmugDNA.6380.1.S1_at | ankylosis, progressive homolog | LOC717689 | 2.99 | 0.0159 |
| MmugDNA.4142.1.S1_at | RAB3B, member RAS oncogene family | LOC712683 | 2.99 | 0.0030 |
| MmugDNA.20373.1.S1_at | galactosylceramidase | GALC | 2.98 | 0.0973 |
| MmugDNA.29366.1.S1_at | Transitional endoplasmic reticulum ATPase (TER ATPase) (15S Mg(2+)-ATPase p97 subunit) (Valosin-containing protein) (VCP) | LOC698707 | 2.98 | 0.0020 |
| MmugDNA.33876.1.S1_s_at | olfactomedin 2 | LOC711336 | 2.98 | 0.0088 |
| MmugDNA.7330.1.S1_at | mannosidase, alpha, class 1C, member 1 | MAN1C1 | 2.98 | 0.0027 |
| MmuSTS.2879.1.S1_at | transforming growth factor, beta receptor III (betaglycan, 300 kDa) | LOC705053 | 2.98 | 0.0240 |
| MmugDNA.39004.1.S1_at | sweet taste receptor T1r isoform b | LOC720987 | 2.98 | 0.0973 |
| MmugDNA.32903.1.S1_at | Protein C9orf116 (Pierce 1) | LOC720855 | 2.97 | 0.0828 |
| MmugDNA.23567.1.S1_at | HMT1 hnRNP methyltransferase-like 6 | PRMT6 | 2.97 | 0.0334 |
| MmugDNA.24770.1.S1_at | hypothetical protein LOC696555 | LOC696555 | 2.97 | 0.0271 |
| MmugDNA.39298.1.S1_at | EGF-like-domain, multiple 5 | MEGF9 | 2.97 | 0.0006 |
| MmugDNA.39357.1.S1_at | — | — | 2.97 | 0.0237 |
| MmugDNA.6683.1.S1_at | — | — | 2.96 | 0.0069 |
| MmugDNA.17131.1.S1_at | — | — | 2.96 | 0.0290 |
| MmuSTS.2496.1.S1_at | zinc finger protein 618 | LOC708866 | 2.95 | 0.0450 |
| MmugDNA.17574.1.S1_at | polycystic kidney disease 2-like 1 | PKD2L1 | 2.95 | 0.0062 |
| MmuSTS.4419.1.S1_at | FXYD domain-containing ion transport regulator 6 | LOC698456 | 2.95 | 0.0109 |
| MmuSTS.546.1.S1_at | membrane associated guanylate kinase, WW and PDZ domain containing 1 isoform a | LOC698092 | 2.95 | 0.0917 |
| MmugDNA.5553.1.S1_at | hypothetical protein LOC695259 | LOC695259 | 2.95 | 0.0337 |
| MmugDNA.1170.1.S1_at | — | — | 2.94 | 0.0216 |
| MmugDNA.39293.1.S1_at | — | — | 2.94 | 0.0220 |
| MmugDNA.36751.1.S1_at | — | — | 2.94 | 0.0034 |
| MmugDNA.2580.1.S1_at | adaptor-related protein complex 3, beta 1 subunit | AP3B1 | 2.94 | 0.0353 |
| MmugDNA.42089.1.S1_at | ectonucleoside triphosphate diphosphohydrolase 3 | ENTPD3 | 2.94 | 0.0140 |
| MmugDNA.5339.1.S1_at | transportin 1 | LOC707195 | 2.94 | 0.0080 |
| MmugDNA.37020.1.S1_at | dedicator of cytokinesis 1 | DOCK1 | 2.94 | 0.0400 |
| MmuSTS.2157.1.S1_at | Scm-like with four mbt domains 1 | LOC694961 | 2.93 | 0.0548 |
| MmuSTS.2057.1.S1_at | phosphoinositide-specific phospholipase C beta 1 isoform a | LOC718387 | 2.93 | 0.0630 |
| MmugDNA.32391.1.S1_at | hepatocellular carcinoma-associated antigen 112 | LOC713786 | 2.93 | 0.0012 |
| MmugDNA.15308.1.S1_s_at | — | — | 2.93 | 0.0128 |
| MmuSTS.1570.1.S1_at | neurobeachin | NBEA | 2.93 | 0.0050 |
| MmugDNA.22319.1.S1_at | histidine triad nucleotide binding protein 3 | LOC712779 | 2.93 | 0.0091 |
| MmugDNA.32797.1.S1_at | CTAGE family, member 5 isoform 1 | LOC699511 | 2.93 | 0.0027 |

| Probe Set ID | Gene Title | Gene Symbol | Ratio Top verus Bottom | p value Top versus Bottom |
|---|---|---|---|---|
| MmugDNA.9436.1.S1_at | — | — | 2.92 | 0.0507 |
| MmugDNA.28664.1.S1_at | guanine nucleotide binding protein, alpha stimulating activity polypeptide 1 isoform c | LOC694289 | 2.92 | 0.0333 |
| MmugDNA.21110.1.S1_at | zinc finger protein 398 isoform 1 | LOC710358 | 2.92 | 0.0141 |
| MmugDNA.5715.1.S1_at | tissue inhibitor of matrix metalloproteinase-1 | TIMP-1 | 2.92 | 0.0113 |
| MmugDNA.13442.1.S1_at | ATPase, aminophospholipid transporter (APLT), class I, type 8A, member 1 | LOC702630 | 2.92 | 0.0030 |
| Mmu.3604.1.S1_s_at | synaptotagmin binding, cytoplasmic RNA interacting protein | LOC700732 | 2.92 | 0.0255 |
| MmugDNA.35867.1.S1_at | fibronectin leucine rich transmembrane protein 3 | FLRT3 | 2.92 | 0.0081 |
| MmugDNA.27436.1.S1_at | — | — | 2.92 | 0.0200 |
| MmugDNA.9183.1.S1_at | Protein NipSnap3B (SNAP1) | NIPSNAP3B | 2.91 | 0.0192 |
| MmugDNA.39239.1.S1_at | TMEM9 domain family, member B /// hypothetical protein LOC719509 | LOC694700 /// LOC708447 /// LOC719509 | 2.91 | 0.0009 |
| MmugDNA.9888.1.S1_at | Tetratricopeptide repeat protein 9 (TPR repeat protein 9) | LOC693495 | 2.91 | 0.0121 |
| MmugDNA.29679.1.S1_at | — | — | 2.91 | 0.0380 |
| MmugDNA.36914.1.S1_at | — | — | 2.90 | 0.0254 |
| MmugDNA.38533.1.S1_at | — | — | 2.90 | 0.0802 |
| MmugDNA.6837.1.S1_at | sorting nexin 13 | SNX13 | 2.89 | 0.0060 |
| MmugDNA.3572.1.S1_at | — | — | 2.89 | 0.0038 |
| MmugDNA.27179.1.S1_at | synapse-associated protein 102 | LOC697179 | 2.89 | 0.0797 |
| MmugDNA.37780.1.S1_at | — | — | 2.89 | 0.0748 |
| MmugDNA.31668.1.S1_at | — | — | 2.89 | 0.0279 |
| MmuSTS.4659.1.S1_at | tumor necrosis factor, alpha-induced protein 3 | TNFAIP3 | 2.89 | 0.0946 |
| MmugDNA.25426.1.S1_at | — | — | 2.89 | 0.0361 |
| MmugDNA.24776.1.S1_at | protein phosphatase 1, regulatory subunit 7 | LOC700574 | 2.89 | 0.0728 |
| MmugDNA.5386.1.S1_at | zinc finger protein 354B | LOC712885 | 2.89 | 0.0369 |
| MmugDNA.21944.1.S1_s_at | holocytochrome c synthase (cytochrome c heme-lyase) | HCCS | 2.89 | 0.0331 |
| MmugDNA.2867.1.S1_at | — | — | 2.88 | 0.0624 |
| MmugDNA.21421.1.S1_at | RAB3A interacting protein isoform alpha 2 | LOC717215 | 2.88 | 0.0107 |
| MmugDNA.3747.1.S1_at | Transmembrane protein 51 | LOC693771 | 2.88 | 0.0127 |
| MmugDNA.26393.1.S1_at | MOCO sulphurase C-terminal domain containing 2 | LOC705543 | 2.88 | 0.0080 |
| MmugDNA.22547.1.S1_at | transcriptional adaptor 2-like | TADA2L | 2.87 | 0.0311 |
| MmugDNA.7154.1.S1_at | kelch repeat and BTB (POZ) domain containing 2 | KBTBD2 | 2.87 | 0.0286 |
| MmugDNA.14782.1.S1_at | CG15120-PA | LOC715522 | 2.87 | 0.0118 |
| MmuSTS.3706.1.S1_at | presenilin 2 | PSEN2 | 2.87 | 0.0715 |
| MmugDNA.15936.1.S1_s_at | — | — | 2.87 | 0.0067 |
| MmugDNA.39373.1.S1_at | putative aminopeptidase Fxna | LOC717415 | 2.87 | 0.0888 |
| MmugDNA.34782.1.S1_at | Keratin, type II cytoskeletal 8 (Cytokeratin-8) (CK-8) (Keratin-8) (K8) | — | 2.87 | 0.0613 |
| MmugDNA.8649.1.S1_at | p300/CBP-associated factor | LOC698283 | 2.87 | 0.0028 |
| MmugDNA.29427.1.S1_at | hypothetical protein LOC702110 | LOC702110 | 2.86 | 0.0045 |
| MmugDNA.26314.1.S1_at | basigin isoform 1 | LOC721068 | 2.86 | 0.0328 |
| MmugDNA.2721.1.S1_s_at | — | — | 2.86 | 0.0111 |
| MmugDNA.27358.1.S1_at | — | — | 2.86 | 0.0056 |
| MmugDNA.15702.1.S1_at | — | — | 2.86 | 0.0184 |
| MmugDNA.43128.1.S1_at | choline kinase alpha isoform a | LOC710564 | 2.86 | 0.0726 |
| MmuSTS.3669.1.S1_at | eyes absent 1 isoform b | LOC694364 | 2.86 | 0.0024 |
| MmugDNA.31695.1.S1_at | Alpha-parvin (Calponin-like integrin-linked kinase-binding protein) (CH-ILKBP) | LOC703481 | 2.85 | 0.0278 |
| MmugDNA.6693.1.S1_at | CG3304-PA, isoform A | LOC708497 | 2.85 | 0.0432 |
| Mmu.3814.1.S1_at | MGC15407-like | LOC677698 | 2.85 | 0.0073 |
| MmugDNA.8146.1.S1_at | ELOVL family member 7, elongation of long chain fatty acids | LOC709866 | 2.85 | 0.0008 |
| MmugDNA.17821.1.S1_at | Protein KIAA1434 | LOC719117 | 2.85 | 0.0623 |
| MmugDNA.34061.1.S1_s_at | glycosyltransferase 28 domain containing 1 | LOC706863 | 2.85 | 0.0030 |
| MmugDNA.43525.1.S1_at | — | — | 2.85 | 0.0870 |
| MmugDNA.11817.1.S1_at | — | — | 2.84 | 0.0015 |
| MmugDNA.10536.1.S1_at | — | — | 2.84 | 0.0255 |
| MmugDNA.20224.1.S1_at | cullin 4B | CUL4B | 2.84 | 0.0531 |
| MmugDNA.21065.1.S1_at | — | — | 2.84 | 0.0726 |
| MmugDNA.11873.1.S1_s_at | NEDD4 family-interacting protein 2 (NEDD4 WW domain-binding protein 5A) (Putative MAPK-activating protein PM04/PM05/PM06/PM07) (Putative NF-kappa-B-activating protein 413) | NDFIP2 | 2.84 | 0.0019 |
| MmugDNA.30250.1.S1_at | multiple coiled-coil GABABR1-binding protein | LOC722750 | 2.84 | 0.0046 |
| MmugDNA.3547.1.S1_at | nuclear receptor binding factor 2 | LOC697756 | 2.84 | 0.0023 |
| MmugDNA.39661.1.S1_at | heparan sulfate 2-O-sulfotransferase 1 | HS2ST1 | 2.84 | 0.0407 |
| MmugDNA.23891.1.S1_at | Derlin-3 (Degradation in endoplasmic reticulum protein 3) (Der1-like protein 3) (DERtrin-3) | DERL3 | 2.84 | 0.0321 |
| MmugDNA.35787.1.S1_at | — | — | 2.83 | 0.0922 |
| MmugDNA.15859.1.S1_at | hypothetical protein LOC709702 | LOC709702 | 2.83 | 0.0784 |
| MmugDNA.906.1.S1_at | tRNA nucleotidyl transferase, CCA-adding, 1 | TRNT1 | 2.83 | 0.0724 |
| MmugDNA.39895.1.S1_at | — | — | 2.83 | 0.0492 |
| MmugDNA.12342.1.S1_at | — | — | 2.83 | 0.0679 |
| MmugDNA.41431.1.S1_at | — | — | 2.83 | 0.0252 |

-continued

| Probe Set ID | Gene Title | Gene Symbol | Ratio Top verus Bottom | p value Top versus Bottom |
|---|---|---|---|---|
| MmugDNA.24761.1.S1_at | — | — | 2.82 | 0.0013 |
| MmugDNA.8211.1.S1_at | — | — | 2.82 | 0.0781 |
| MmugDNA.40614.1.S1_at | — | — | 2.82 | 0.0136 |
| MmugDNA.9573.1.S1_at | — | — | 2.82 | 0.0541 |
| MmugDNA.36144.1.S1_at | G-protein coupled receptor 113 | LOC696215 | 2.82 | 0.0137 |
| MmugDNA.5429.1.S1_at | RNA pseudouridylate synthase domain containing 4 | LOC714162 | 2.82 | 0.0238 |
| MmugDNA.390.1.S1_at | — | — | 2.82 | 0.0224 |
| MmuSTS.1860.1.S1_at | Homeobox protein CDX-1 (Caudal-type homeobox protein 1) | CDX1 | 2.82 | 0.0302 |
| MmugDNA.15649.1.S1_at | — | — | 2.81 | 0.0524 |
| MmugDNA.41609.1.S1_at | golgi apparatus protein 1 | LOC710037 | 2.81 | 0.0682 |
| MmugDNA.39981.1.S1_at | microtubule associated monoxygenase, calponin and LIM domain containing 2 | MICAL2 | 2.81 | 0.0354 |
| MmugDNA.41888.1.S1_at | UDP glycosyltransferase 8 (UDP-galactose ceramide galactosyltransferase) | UGT8 | 2.81 | 0.0002 |
| Mmu.1028.1.S1_at | Tetraspanin-8 (Tspan-8) (Transmembrane 4 superfamily member 3) (Tumor-associated antigen CO-029) | TSPAN8 | 2.80 | 0.0037 |
| MmugDNA.40411.1.S1_at | — | — | 2.80 | 0.0431 |
| MmugDNA.6270.1.S1_at | — | — | 2.80 | 0.0207 |
| MmugDNA.3465.1.S1_at | — | — | 2.80 | 0.0758 |
| MmugDNA.28869.1.S1_s_at | follicular lymphoma variant translocation 1 | LOC700476 | 2.80 | 0.0299 |
| MmugDNA.17877.1.S1_at | — | — | 2.80 | 0.0198 |
| MmugDNA.43133.1.S1_at | Nucleoside diphosphate kinase homolog 5 (NDK-H 5) (NDP kinase homolog 5) (nm23-H5) (Testis-specific nm23 homolog) (Inhibitor of p53-induced apoptosis-beta) (IPIA-beta) | LOC713837 | 2.80 | 0.0119 |
| MmugDNA.38316.1.S1_at | family with sequence similarity 20, member A | LOC718937 | 2.80 | 0.0064 |
| MmugDNA.28033.1.S1_at | SID1 transmembrane family, member 1 | SIDT1 | 2.80 | 0.0014 |
| MmugDNA.29959.1.S1_at | transducin-like enhancer protein 4 | TLE4 | 2.80 | 0.0125 |
| MmugDNA.11210.1.S1_s_at | protocadherin gamma subfamily A, 12 isoform 2 precursor | LOC702071 | 2.79 | 0.0187 |
| MmuSTS.1312.1.S1_at | DnaJ (Hsp40) homolog, subfamily C, member 6 | LOC698682 | 2.79 | 0.0716 |
| MmugDNA.19131.1.S1_at | BTB (POZ) domain containing 4 | BTBD4 | 2.79 | 0.0448 |
| MmugDNA.26541.1.S1_at | fibronectin type III domain containing 4 | LOC702098 | 2.79 | 0.0462 |
| MmugDNA.11140.1.S1_at | notch homolog 5 | LOC694004 | 2.79 | 0.0549 |
| MmugDNA.20304.1.S1_at | modulator of apoptosis 1 | LOC707922 /// LOC708231 | 2.79 | 0.0003 |
| MmugDNA.8309.1.S1_at | — | — | 2.79 | 0.0744 |
| MmugDNA.35571.1.S1_at | transposon-derived Buster3 transposase-like | LOC695905 | 2.79 | 0.0239 |
| MmuSTS.3190.1.S1_at | — | — | 2.78 | 0.0062 |
| MmugDNA.31552.1.S1_at | CG18769-PB, isoform B | LOC698670 | 2.78 | 0.0044 |
| MmugDNA.11968.1.S1_at | — | — | 2.78 | 0.0831 |
| MmugDNA.31850.1.S1_at | START domain containing 4, sterol regulated | LOC706654 | 2.78 | 0.0281 |
| MmugDNA.26580.1.S1_at | TGF beta receptor associated protein-1 | LOC713102 | 2.78 | 0.0062 |
| MmugDNA.39053.1.S1_at | — | — | 2.78 | 0.0250 |
| MmugDNA.13898.1.S1_at | — | — | 2.78 | 0.0892 |
| Mmu.15592.2.S1_at | phosphatidylinositol glycan, class F isoform 1 | LOC714844 | 2.78 | 0.0019 |
| MmugDNA.29438.1.S1_at | — | — | 2.78 | 0.0522 |
| MmugDNA.13438.1.S1_at | CG11670-PA | LOC701685 | 2.77 | 0.0273 |
| MmugDNA.33828.1.S1_at | hypothetical protein LOC693883 | LOC693883 | 2.77 | 0.0613 |
| MmugDNA.12035.1.S1_at | — | — | 2.77 | 0.0187 |
| MmugDNA.28591.1.S1_s_at | taspase 1 | TASP1 | 2.77 | 0.0529 |
| MmugDNA.29219.1.S1_at | — | — | 2.77 | 0.0025 |
| MmugDNA.17221.1.S1_at | hypothetical protein LOC719100 | LOC719100 | 2.77 | 0.0461 |
| Mmu.2523.1.S1_at | legumain | LGMN | 2.76 | 0.0855 |
| MmugDNA.14436.1.S1_at | — | — | 2.76 | 0.0851 |
| MmugDNA.12446.1.S1_at | — | — | 2.76 | 0.0162 |
| MmugDNA.24601.1.S1_at | — | — | 2.76 | 0.0027 |
| MmugDNA.7915.1.S1_at | — | — | 2.76 | 0.0117 |
| MmugDNA.35603.1.S1_at | Sortilin precursor (Neurotensin receptor 3) (NTR3) (NT3) (Glycoprotein 95) (Gp95) (100 kDa NT receptor) | SORT1 | 2.75 | 0.0309 |
| MmugDNA.36573.1.S1_at | CTCL tumor antigen se57-1 | LOC694841 | 2.75 | 0.0207 |
| MmuSTS.2972.1.S1_at | lipase A precursor | LOC695240 | 2.75 | 0.0071 |
| MmuSTS.3122.1.S1_at | myosin VIIA and Rab interacting protein | LOC717173 | 2.74 | 0.0042 |
| MmugDNA.26602.1.S1_at | nuclear factor of activated T-cells, cytosolic component 1 isoform C | LOC698089 | 2.74 | 0.0049 |
| MmuSTS.1119.1.S1_at | secreted modular calcium-binding protein 2 | LOC703155 | 2.74 | 0.0582 |
| MmugDNA.38654.1.S1_at | — | — | 2.74 | 0.0116 |
| MmugDNA.24367.1.S1_at | islet cell autoantigen 1 | LOC695889 | 2.74 | 0.0417 |
| MmugDNA.7470.1.S1_at | — | — | 2.74 | 0.0823 |
| MmugDNA.21317.1.S1_at | spermatid perinuclear RNA-binding protein | LOC695402 | 2.74 | 0.0240 |
| MmugDNA.36894.1.S1_at | dehydrogenase/reductase (SDR family) member 7 | DHRS7 | 2.74 | 0.0004 |
| MmuSTS.3892.1.S1_at | sphingomyelin phosphodiesterase 1, acid lysosomal | SMPD1 | 2.73 | 0.0291 |
| MmuSTS.3004.1.S1_at | mutS homolog 3 | MSH3 | 2.73 | 0.0912 |
| MmugDNA.18199.1.S1_at | unc-13 homolog D | LOC704431 | 2.73 | 0.0133 |
| MmugDNA.32264.1.S1_at | G protein-coupled receptor 126 alpha 2 | LOC706017 | 2.73 | 0.0429 |
| MmuSTS.2507.1.S1_at | GTP binding protein 1 | GTPBP1 | 2.73 | 0.0496 |

-continued

| Probe Set ID | Gene Title | Gene Symbol | Ratio Top verus Bottom | p value Top versus Bottom |
|---|---|---|---|---|
| MmugDNA.22747.1.S1_at | tripartite motif-containing 2 | LOC696517 | 2.73 | 0.0162 |
| MmuSTS.1188.1.S1_at | phospholipid scramblase 1 | LOC713232 | 2.73 | 0.0006 |
| MmugDNA.2003.1.S1_at | — | — | 2.73 | 0.0904 |
| MmugDNA.6213.1.S1_at | — | — | 2.73 | 0.0031 |
| MmugDNA.27564.1.S1_at | Guanine nucleotide-binding protein G(t), alpha-3 subunit (Gustducin alpha-3 chain) | LOC708828 | 2.73 | 0.0162 |
| MmugDNA.33552.1.S1_at | — | — | 2.73 | 0.0364 |
| MmuSTS.2414.1.S1_at | Guanine nucleotide-binding protein alpha-12 subunit (G alpha-12) | LOC699857 | 2.72 | 0.0319 |
| MmugDNA.37242.1.S1_at | serine/threonine kinase 32A | LOC708524 | 2.72 | 0.0499 |
| MmuSTS.2307.1.S1_at | beta isoform of regulatory subunit B55, protein phosphatase 2 | PPP2R2B | 2.72 | 0.0797 |
| MmugDNA.35445.1.S1_at | PHD finger protein 7 isoform 1 | LOC697103 | 2.72 | 0.0380 |
| MmugDNA.31310.1.S1_at | CG13902-PA | LOC699197 | 2.72 | 0.0796 |
| Mmu.13628.1.S1_x_at | FGFR1 oncogene partner 2 | LOC708905 | 2.72 | 0.0287 |
| MmugDNA.34470.1.S1_s_at | hypothetical protein LOC708552 | LOC708552 | 2.71 | 0.0083 |
| MmugDNA.27420.1.S1_at | — | — | 2.71 | 0.0567 |
| MmugDNA.15282.1.S1_at | hypothetical protein LOC711477 | LOC711477 | 2.71 | 0.0018 |
| MmugDNA.12849.1.S1_at | Eukaryotic translation initiation factor 6 (eIF-6) (B4 integrin interactor) (CAB) (p27(BBP)) (B(2)GCN homolog) | ITGB4BP | 2.71 | 0.0280 |
| MmugDNA.14244.1.S1_at | — | — | 2.71 | 0.0049 |
| MmugDNA.25223.1.S1_at | CG31803-PA | LOC701263 | 2.71 | 0.0197 |
| MmugDNA.22504.1.S1_at | — | — | 2.71 | 0.0906 |
| MmuSTS.3220.1.S1_at | v-myb myeloblastosis viral oncogene homolog (avian)-like 1 | MYBL1 | 2.71 | 0.0824 |
| MmugDNA.13093.1.S1_at | hypothetical protein LOC708259 | LOC708259 | 2.71 | 0.0701 |
| MmugDNA.13057.1.S1_at | protease, serine, 36 | LOC714626 | 2.70 | 0.0599 |
| MmugDNA.9375.1.S1_at | — | — | 2.70 | 0.0479 |
| MmuSTS.1294.1.S1_at | RAP1, GTPase activating protein 1 | RAP1GAP | 2.70 | 0.0278 |
| MmugDNA.11685.1.S1_at | poly (ADP-ribose) polymerase family, member 8 | LOC702637 | 2.70 | 0.0995 |
| Mmu.14396.1.S1_at | Glutathione S-transferase A1 (GTH1) (HA subunit 1) (GST-epsilon) (GSTA1-1) (GST class-alpha) | — | 2.70 | 0.0140 |
| MmugDNA.20427.1.S1_at | inosine monophosphate dehydrogenase 1 isoform b | LOC701039 | 2.70 | 0.0686 |
| MmugDNA.26008.1.S1_at | — | — | 2.70 | 0.0015 |
| MmugDNA.24890.1.S1_at | CG4341-PA | LOC698022 | 2.70 | 0.0249 |
| MmuSTS.1767.1.S1_at | N-myc downstream regulated gene 3 | LOC702452 | 2.70 | 0.0887 |
| MmugDNA.28653.1.S1_at | — | — | 2.70 | 0.0331 |
| MmugDNA.11814.1.S1_at | zinc finger protein 322A | LOC701098 | 2.70 | 0.0466 |
| MmugDNA.25299.1.S1_at | Small nuclear ribonucleoprotein Sm D1 (snRNP core protein D1) (Sm-D1) (Sm-D autoantigen) | LOC698965 | 2.70 | 0.0816 |
| MmugDNA.41883.1.S1_at | — | — | 2.70 | 0.0762 |
| MmugDNA.31230.1.S1_at | Fibronectin type-III domain-containing protein 3a | LOC705570 | 2.69 | 0.0370 |
| MmugDNA.42805.1.S1_at | Kinesin-like protein KIF2 | LOC696561 | 2.69 | 0.0624 |
| MmugDNA.26243.1.S1_at | — | — | 2.69 | 0.0404 |
| MmugDNA.27058.1.S1_at | phosphoribosyl pyrophosphate amidotransferase proprotein | LOC694868 | 2.69 | 0.0094 |
| MmugDNA.41943.1.S1_at | — | — | 2.69 | 0.0346 |
| MmugDNA.9762.1.S1_at | — | — | 2.69 | 0.0721 |
| MmugDNA.22290.1.S1_at | brefeldin A-inhibited guanine nucleotide-exchange protein 1 | LOC704359 | 2.69 | 0.0717 |
| MmugDNA.41355.1.S1_at | — | — | 2.68 | 0.0676 |
| MmugDNA.37885.1.S1_at | homer 1 | HOMER1 | 2.68 | 0.0925 |
| MmugDNA.38723.1.S1_at | a disintegrin and metalloprotease domain 28 isoform 1 | LOC710953 | 2.68 | 0.0741 |
| MmugDNA.12874.1.S1_at | — | — | 2.68 | 0.0745 |
| MmugDNA.38436.1.S1_at | hypothetical protein LOC695519 | LOC695519 | 2.68 | 0.0060 |
| MmugDNA.23725.1.S1_at | stress 70 protein chaperone, microsome-associated, 60 kDa | STCH | 2.67 | 0.0479 |
| MmugDNA.18237.1.S1_at | peroxisomal short-chain alcohol dehydrogenase | — | 2.67 | 0.0492 |
| Mmu.7752.1.S1_at | hypothetical protein LOC704532 | LOC704532 | 2.67 | 0.0265 |
| Mmu.7453.1.S1_at | rabaptin, RAB GTPase binding effector protein 1 | LOC711646 | 2.67 | 0.0190 |
| MmugDNA.13154.1.S1_at | — | — | 2.67 | 0.0955 |
| MmugDNA.12949.1.S1_at | — | — | 2.67 | 0.0394 |
| MmuSTS.2807.1.S1_at | solute carrier family 38, member 1 | LOC702135 | 2.67 | 0.0217 |
| MmugDNA.28465.1.S1_at | Transgelin-3 (Neuronal protein NP25) (Neuronal protein 22) (NP22) | TAGLN3 | 2.67 | 0.0651 |
| MmugDNA.29560.1.S1_at | hypothetical protein LOC710681 | LOC710681 | 2.67 | 0.0154 |
| MmugDNA.16975.1.S1_at | — | — | 2.67 | 0.0968 |
| MmugDNA.30208.1.S1_at | — | — | 2.66 | 0.0462 |
| MmugDNA.33379.1.S1_at | — | — | 2.66 | 0.0063 |
| MmugDNA.29425.1.S1_at | B0507.2 | LOC704194 | 2.66 | 0.0105 |
| MmugDNA.28288.1.S1_at | Dual specificity protein phosphatase 3 (Dual specificity protein phosphatase VHR) | DUSP3 | 2.66 | 0.0224 |
| MmugDNA.15303.1.S1_s_at | ninein isoform 5 | LOC709532 | 2.65 | 0.0437 |
| MmugDNA.29050.1.S1_at | — | — | 2.65 | 0.0291 |
| MmunewRS.265.1.S1_at | kin of IRRE like 3 | LOC714534 | 2.65 | 0.0267 |
| MmugDNA.24675.1.S1_at | — | — | 2.65 | 0.0414 |
| MmugDNA.8597.1.S1_at | — | — | 2.65 | 0.0379 |
| MmugDNA.10005.1.S1_at | pre-B-cell leukemia transcription factor interacting protein 1 | LOC717036 | 2.65 | 0.0501 |
| MmugDNA.951.1.S1_at | — | — | 2.65 | 0.0297 |
| MmugDNA.35108.1.S1_at | secretory carrier membrane protein 5 | LOC710454 | 2.64 | 0.0103 |
| MmugDNA.13757.1.S1_at | Placenta-specific gene 8 protein (C15 protein) | PLAC8 | 2.64 | 0.0186 |

-continued

| Probe Set ID | Gene Title | Gene Symbol | Ratio Top verus Bottom | p value Top versus Bottom |
|---|---|---|---|---|
| MmugDNA.30027.1.S1_at | hypothetical protein LOC695033 | LOC695033 | 2.64 | 0.0128 |
| MmugDNA.7760.1.S1_at | — | — | 2.64 | 0.0072 |
| MmugDNA.21589.1.S1_at | protocadherin beta 4 | PCDHB4 | 2.64 | 0.0703 |
| Mmu.9306.1.S1_at | growth factor receptor-bound protein 2 isoform 2 | LOC702041 | 2.63 | 0.0360 |
| MmugDNA.11105.1.S1_at | centaurin, gamma 2 isoform 2 | LOC693652 | 2.63 | 0.0244 |
| MmugDNA.26258.1.S1_at | — | — | 2.63 | 0.0637 |
| Mmu.14771.1.S1_at | calcipressin 1 isoform c | LOC697108 | 2.63 | 0.0245 |
| MmugDNA.30706.1.S1_at | — | — | 2.63 | 0.0016 |
| MmugDNA.37595.1.S1_s_at | mortality factor 4 like 1 isoform b | LOC711357 | 2.63 | 0.0734 |
| MmugDNA.42160.1.S1_at | — | — | 2.63 | 0.0710 |
| MmugDNA.34056.1.S1_at | RAP1 interacting factor 1 | LOC694817 | 2.63 | 0.0344 |
| MmugDNA.40644.1.S1_at | solute carrier family 41 member 1 | LOC696944 | 2.62 | 0.0135 |
| MmugDNA.43211.1.S1_at | IBR domain containing 1 | LOC716647 | 2.62 | 0.0077 |
| MmugDNA.32694.1.S1_at | tumor necrosis factor, alpha-induced protein 8 | LOC700778 | 2.62 | 0.0399 |
| MmugDNA.22014.1.S1_at | golgi autoantigen, golgin subfamily a, 7 | LOC709911 | 2.62 | 0.0044 |
| MmugDNA.32609.1.S1_at | — | — | 2.61 | 0.0756 |
| MmugDNA.28006.1.S1_at | minichromosome maintenance protein domain containing 1 | LOC714711 | 2.61 | 0.0293 |
| MmugDNA.21156.1.S1_at | — | — | 2.61 | 0.0666 |
| MmuSTS.2808.1.S1_s_at | chromobox homolog 3 | — | 2.61 | 0.0714 |
| MmugDNA.14756.1.S1_at | hypothetical protein LOC694136 | LOC694136 | 2.61 | 0.0658 |
| MmuSTS.4364.1.S1_at | sterol O-acyltransferase (acyl-Coenzyme A: cholesterol acyltransferase) 1 | SOAT1 | 2.61 | 0.0632 |
| MmugDNA.34121.1.S1_at | pappalysin 2 | PAPPA2 | 2.60 | 0.0655 |
| MmugDNA.3334.1.S1_at | sidekick homolog 1 | LOC719431 | 2.60 | 0.0565 |
| MmugDNA.14892.1.S1_at | iduronate-2-sulfatase | IDS | 2.60 | 0.0535 |
| MmugDNA.39834.1.S1_s_at | — | — | 2.60 | 0.0269 |
| MmugDNA.16052.1.S1_at | SEC10 protein | EXOC5 | 2.60 | 0.0882 |
| MmugDNA.10569.1.S1_at | Golgin subfamily A member 1 (Golgin-97) | LOC693285 | 2.60 | 0.0126 |
| MmugDNA.10679.1.S1_at | vacuolar H+ ATPase G1 | LOC699522 | 2.60 | 0.0027 |
| MmugDNA.1854.1.S1_at | ankyrin repeat domain 20 family, member A2 | LOC707318 | 2.60 | 0.0773 |
| MmugDNA.23815.1.S1_at | — | — | 2.59 | 0.0204 |
| Mmu.7599.1.S1_at | smooth muscle cell associated protein 5 | LOC706656 | 2.59 | 0.0065 |
| MmugDNA.14931.1.S1_at | syntaxin 7 | LOC701269 | 2.59 | 0.0544 |
| MmugDNA.13732.1.S1_at | — | — | 2.59 | 0.0529 |
| MmugDNA.4660.1.S1_at | — | — | 2.59 | 0.0470 |
| MmugDNA.23822.1.S1_s_at | cell adhesion molecule 1 | CADM1 | 2.59 | 0.0163 |
| MmugDNA.37623.1.S1_at | protein tyrosine phosphatase, receptor type, G precursor | LOC703937 | 2.59 | 0.0246 |
| MmugDNA.32519.1.S1_at | — | — | 2.58 | 0.0279 |
| MmugDNA.13687.1.S1_at | — | — | 2.58 | 0.0779 |
| MmuSTS.4721.1.S1_at | thyroid hormone receptor interactor 11 | LOC697489 | 2.58 | 0.0012 |
| MmugDNA.21480.1.S1_at | — | — | 2.58 | 0.0742 |
| MmugDNA.13466.1.S1_at | activating transcription factor 6 | LOC720056 | 2.58 | 0.0029 |
| MmuSTS.3905.1.S1_at | recoverin | LOC717807 | 2.57 | 0.0728 |
| MmuSTS.1760.1.S1_at | alpha-N-acetylgalactosaminidase | NAGA | 2.57 | 0.0040 |
| MmugDNA.9095.1.S1_at | — | — | 2.57 | 0.0102 |
| MmugDNA.535.1.S1_at | — | — | 2.57 | 0.0131 |
| MmugDNA.22662.1.S1_at | — | — | 2.57 | 0.0151 |
| MmugDNA.42675.1.S1_at | transforming growth factor, beta 2 | LOC707540 | 2.57 | 0.0522 |
| MmugDNA.6958.1.S1_at | — | — | 2.57 | 0.0725 |
| MmugDNA.2631.1.S1_at | Tetraspanin-6 (Tspan-6) (Transmembrane 4 superfamily member 6) (T245 protein) (Tetraspanin TM4-D) (A15 homolog) | LOC703166 | 2.57 | 0.0170 |
| MmugDNA.13189.1.S1_at | CG10233-PA, isoform A | LOC706860 | 2.57 | 0.0238 |
| Mmu.14100.1.S1_at | hypothetical protein LOC716612 | LOC716612 | 2.56 | 0.0589 |
| MmugDNA.37486.1.S1_at | — | — | 2.56 | 0.0030 |
| MmugDNA.6803.1.S1_at | — | — | 2.56 | 0.0676 |
| MmugDNA.20096.1.S1_at | tropomodulin 3 (ubiquitous) | TMOD3 | 2.56 | 0.0158 |
| MmugDNA.4732.1.S1_at | — | — | 2.56 | 0.0239 |
| MmugDNA.3551.1.S1_at | Y73F8A.5 | LOC697670 | 2.56 | 0.0018 |
| MmugDNA.11777.1.S1_at | — | — | 2.56 | 0.0022 |
| MmugDNA.6129.1.S1_at | solute carrier family 25, member 35 | LOC721965 | 2.56 | 0.0343 |
| MmuSTS.1392.1.S1_at | — | — | 2.55 | 0.0039 |
| MmugDNA.33992.1.S1_at | PTPRF interacting protein alpha 1 | PPFIA1 | 2.55 | 0.0925 |
| MmuSTS.1581.1.S1_at | IQ motif containing GTPase activating protein 2 | IQGAP2 | 2.55 | 0.0393 |
| MmugDNA.32972.1.S1_at | — | — | 2.55 | 0.0061 |
| MmuSTS.1848.1.S1_at | resistance to inhibitors of cholinesterase 8B isoform 2 | LOC703061 | 2.55 | 0.0576 |
| MmugDNA.12186.1.S1_at | protein tyrosine phosphatase-like (proline instead of catalytic arginine), member b | — | 2.55 | 0.0353 |
| MmugDNA.10635.1.S1_at | Hypothetical protein LOC717382 | — | 2.54 | 0.0303 |
| MmugDNA.7743.1.S1_at | hypothetical protein LOC694489 | LOC694489 | 2.54 | 0.0909 |
| MmugDNA.22818.1.S1_at | LOC57821 | LOC700803 | 2.54 | 0.0571 |
| MmugDNA.28543.1.S1_at | ubiquitin specific protease 46 | LOC698618 | 2.54 | 0.0001 |
| MmugDNA.7920.1.S1_at | synaptosomal-associated protein 29 | LOC696708 | 2.53 | 0.0316 |
| MmugDNA.41817.1.S1_at | — | — | 2.53 | 0.0047 |
| MmugDNA.33998.1.S1_at | CG9240-PA /// hypothetical protein LOC718215 | LOC696105 /// LOC718215 | 2.53 | 0.0613 |

| Probe Set ID | Gene Title | Gene Symbol | Ratio Top verus Bottom | p value Top versus Bottom |
|---|---|---|---|---|
| MmuSTS.4005.1.S1_at | thrombospondin 2 precursor | LOC708165 | 2.53 | 0.0700 |
| MmugDNA.7442.1.S1_at | NAD(P) dependent steroid dehydrogenase-like | LOC714229 | 2.53 | 0.0286 |
| MmugDNA.37241.1.S1_at | hypothetical protein LOC704834 | LOC704834 | 2.53 | 0.0785 |
| MmugDNA.18544.1.S1_at | MAPK/MAK/MRK overlapping kinase | RAGE | 2.52 | 0.0619 |
| MmugDNA.14567.1.S1_at | CGI-01 protein isoform 1 | LOC704943 | 2.52 | 0.0722 |
| MmugDNA.39392.1.S1_at | Tumor necrosis factor receptor superfamily member 19L precursor (Receptor expressed in lymphoid tissues) | LOC718143 | 2.52 | 0.0339 |
| MmugDNA.36135.1.S1_at | — | | 2.52 | 0.0009 |
| MmugDNA.38008.1.S1_at | asparaginase-like 1 protein | LOC718871 | 2.52 | 0.0079 |
| MmugDNA.894.1.S1_at | — | | 2.52 | 0.0553 |
| MmugDNA.9940.1.S1_s_at | — | | 2.52 | 0.0117 |
| MmugDNA.30902.1.S1_at | zinc finger protein 452 | LOC708122 | 2.52 | 0.0174 |
| MmunewRS.671.1.S1_at | — | | 2.51 | 0.0611 |
| MmugDNA.29345.1.S1_at | Golgi-localized syntaphilin-related protein isoform C | LOC699436 | 2.51 | 0.0454 |
| MmuSTS.1714.1.S1_s_at | muscle-type acylphosphatase 2 | LOC716728 | 2.51 | 0.0007 |
| MmugDNA.17463.1.S1_at | hypothetical protein LOC696917 | LOC696917 | 2.51 | 0.0447 |
| MmuSTS.4655.1.S1_at | 2',5'-oligoadenylate synthetase 1 | OAS1 | 2.51 | 0.0103 |
| MmugDNA.2445.1.S1_at | — | | 2.51 | 0.0229 |
| MmuSTS.2654.1.S1_at | ATP-binding cassette, sub-family A member 3 | LOC696496 | 2.51 | 0.0198 |
| MmugDNA.10791.1.S1_at | Coiled-coil domain-containing protein 11 | LOC700084 | 2.50 | 0.0645 |
| MmugDNA.30349.1.S1_at | Transmembrane protein 33 (DB83 protein) | TMEM33 | 2.50 | 0.0047 |
| MmugDNA.8272.1.S1_at | — | | 2.50 | 0.0928 |
| MmuSTS.3815.1.S1_at | ATPase, H+ transporting, lysosomal accessory protein 1 | ATP6AP1 | 2.50 | 0.0128 |
| MmugDNA.16292.1.S1_at | transmembrane protein 56 | LOC709729 | 2.50 | 0.0116 |
| MmugDNA.33608.1.S1_at | jumonji domain containing 1B | LOC716648 | 2.50 | 0.0832 |
| MmugDNA.20325.1.S1_s_at | Kruppel-like factor 3 (basic) | KLF3 | 2.50 | 0.0533 |
| MmugDNA.36544.1.S1_at | — | | 2.50 | 0.0239 |
| MmugDNA.18568.1.S1_s_at | coiled-coil domain containing 64 | LOC698147 | 2.50 | 0.0156 |
| MmuSTS.1282.1.S1_at | retinoic acid induced 2 | LOC693329 | 2.50 | 0.0020 |
| MmugDNA.16604.1.S1_at | — | | 2.50 | 0.0753 |
| MmugDNA.2019.1.S1_at | — | | 2.50 | 0.0009 |
| MmugDNA.15319.1.S1_at | EH-domain containing 3 | LOC705316 | 2.49 | 0.0546 |
| MmuSTS.3025.1.S1_at | — | | 2.49 | 0.0259 |
| MmugDNA.4609.1.S1_at | sparc/osteonectin, cwcv and kazal-like domains proteoglycan 1 | SPOCK1 | 2.49 | 0.0876 |
| MmugDNA.26967.1.S1_at | ROD1 regulator of differentiation 1 | LOC711210 | 2.49 | 0.0050 |
| MmugDNA.37971.1.S1_at | heat shock 70 kDa protein 4 isoform a | LOC709585 | 2.49 | 0.0242 |
| MmuSTS.3404.1.S1_at | — | | 2.49 | 0.0276 |
| MmugDNA.2456.1.S1_at | CG14185-PA | LOC698952 | 2.49 | 0.0639 |
| Mmu.4703.1.S1_at | — | | 2.49 | 0.0143 |
| MmugDNA.16581.1.S1_at | calponin 3 | LOC709538 | 2.49 | 0.0128 |
| MmugDNA.6.1.S1_at | secretogranin III | LOC694089 | 2.49 | 0.0059 |
| MmuSTS.1273.1.S1_at | doublecortin and CaM kinase-like 1 | LOC722071 | 2.49 | 0.0570 |
| MmugDNA.39606.1.S1_at | DNAJ domain-containing | LOC700339 | 2.48 | 0.0702 |
| MmugDNA.32745.1.S1_at | — | | 2.48 | 0.0016 |
| MmugDNA.5221.1.S1_at | — | | 2.48 | 0.0528 |
| MmugDNA.13152.1.S1_at | — | | 2.48 | 0.0168 |
| MmugDNA.27246.1.S1_s_at | leucine rich repeat containing 16 | LOC694909 | 2.48 | 0.0648 |
| MmuSTS.3254.1.S1_at | semaphorin 3A | LOC708263 | 2.47 | 0.0730 |
| MmugDNA.12122.1.S1_s_at | — | | 2.47 | 0.0389 |
| MmugDNA.29872.1.S1_at | GTPase activating Rap/RanGAP domain-like 1 isoform 1 | LOC695674 | 2.47 | 0.0024 |
| MmugDNA.34800.1.S1_at | — | | 2.47 | 0.0944 |
| MmugDNA.25958.1.S1_at | DEAH (Asp-Glu-Ala-Asp/His) box polypeptide 57 | LOC713523 | 2.47 | 0.0649 |
| MmugDNA.32735.1.S1_at | hypothetical protein LOC702345 | LOC702345 | 2.47 | 0.0058 |
| MmugDNA.17104.1.S1_at | — | | 2.47 | 0.0822 |
| MmugDNA.15497.1.S1_at | Hypothetical protein LOC708044 | | 2.47 | 0.0563 |
| MmugDNA.13708.1.S1_at | — | | 2.47 | 0.0398 |
| MmugDNA.35844.1.S1_at | Protein C10orf57 homolog | LOC701130 | 2.47 | 0.0547 |
| MmugDNA.3000.1.S1_at | signal sequence receptor gamma subunit | LOC706518 | 2.47 | 0.0144 |
| MmugDNA.18159.1.S1_at | bone morphogenetic protein receptor type II | BMPR2 | 2.47 | 0.0575 |
| Mmu.10229.1.S1_at | CD46 molecule, complement regulatory protein | CD46 | 2.47 | 0.0654 |
| MmugDNA.13343.1.S1_at | erythrocyte protein band 4.1-like 1 isoform L | LOC710697 | 2.47 | 0.0020 |
| MmugDNA.32527.1.S1_at | mitogen-activated protein kinase kinase kinase 7 interacting protein 2 | LOC696875 | 2.46 | 0.0710 |
| MmugDNA.8354.1.S1_at | HGFL protein | LOC716694 | 2.46 | 0.0605 |
| MmugDNA.32803.1.S1_at | hypothetical protein LOC717255 | LOC717255 | 2.46 | 0.0654 |
| MmugDNA.25652.1.S1_at | netrin-G1 ligand | LOC698610 | 2.46 | 0.0244 |
| MmugDNA.39872.1.S1_at | parathyroid hormone-responsive B1 isoform 2 | LOC708412 | 2.46 | 0.0721 |
| MmugDNA.13779.1.S1_at | protein kinase C and casein kinase substrate in neurons 3 | LOC713919 | 2.46 | 0.0997 |
| MmugDNA.11262.1.S1_at | — | | 2.46 | 0.0172 |
| MmugDNA.11097.1.S1_at | Ribonuclease K6 precursor (RNase K6) | | 2.46 | 0.0658 |
| MmugDNA.13830.1.S1_at | — | | 2.45 | 0.0381 |
| MmugDNA.20861.1.S1_at | spermatogenesis associated 13 | LOC721468 | 2.45 | 0.0640 |
| MmuSTS.2607.1.S1_at | citrate synthase precursor, isoform a | | 2.45 | 0.0385 |
| MmugDNA.15111.1.S1_at | — | | 2.45 | 0.0528 |
| MmuSTS.2246.1.S1_at | phospholipase C, gamma 2 (phosphatidylinositol-specific) | PLCG2 | 2.45 | 0.0006 |

| Probe Set ID | Gene Title | Gene Symbol | Ratio Top verus Bottom | p value Top versus Bottom |
|---|---|---|---|---|
| MmugDNA.17805.1.S1_at | solute carrier family 9 (sodium/hydrogen exchanger), isoform 2 | LOC712199 | 2.45 | 0.0407 |
| MmugDNA.19536.1.S1_at | — | — | 2.45 | 0.0378 |
| MmugDNA.17107.1.S1_at | mitogen-activated protein kinase 1 | MAPK1 | 2.44 | 0.0344 |
| MmugDNA.24092.1.S1_at | hypothetical protein LOC708570 | LOC708570 | 2.44 | 0.0745 |
| MmugDNA.14738.1.S1_at | TRAF2 and NCK interacting kinase | TNIK | 2.44 | 0.0358 |
| MmugDNA.5147.1.S1_s_at | Kelch repeat and BTB domain-containing protein 4 (BTB and kelch domain-containing protein 4) | LOC711452 | 2.44 | 0.0121 |
| MmugDNA.6438.1.S1_at | nudix (nucleoside diphosphate linked moiety X)-type motif 21 | LOC707828 | 2.44 | 0.0458 |
| MmugDNA.17791.1.S1_at | — | — | 2.44 | 0.0445 |
| MmugDNA.19209.1.S1_s_at | Neutrophil gelatinase-associated lipocalin precursor (NGAL) (p25) (25 kDa alpha-2-microglobulin-related subunit of MMP-9) (Lipocalin-2) (Oncogene 24p3) | LOC697208 | 2.44 | 0.0703 |
| MmugDNA.20574.1.S1_at | v-kit Hardy-Zuckerman 4 feline sarcoma viral oncogene homolog | KIT | 2.44 | 0.0258 |
| MmugDNA.35313.1.S1_at | hypothetical protein LOC704554 /// adenylate cyclase 9 | ADCY9 /// LOC704554 | 2.44 | 0.0330 |
| MmugDNA.20823.1.S1_at | — | — | 2.43 | 0.0067 |
| MmugDNA.42796.1.S1_at | inositol 1,3,4,5,6-pentakisphosphate 2-kinase | LOC705937 | 2.43 | 0.0129 |
| MmugDNA.17764.1.S1_at | CG6678-PA | LOC715524 | 2.43 | 0.0114 |
| MmugDNA.43422.1.S1_at | postsynaptic protein CRIPT | LOC714949 | 2.43 | 0.0240 |
| MmugDNA.34136.1.S1_at | Normal mucosa of esophagus-specific gene 1 protein | LOC713440 | 2.43 | 0.0780 |
| MmugDNA.30592.1.S1_at | transmembrane 9 superfamily member 2 | TM9SF2 | 2.43 | 0.0017 |
| MmugDNA.27400.1.S1_at | mannosyl (alpha-1,3-)-glycoprotein beta-1,4-N-acetylglucosaminyltransferase, isoenzyme A | LOC708094 | 2.43 | 0.0393 |
| MmuSTS.4839.1.S1_at | golgi phosphoprotein 2 | LOC715029 | 2.43 | 0.0064 |
| Mmu.8934.1.S1_at | Alpha- and gamma-adaptin-binding protein p34 | LOC711436 | 2.43 | 0.0144 |
| MmugDNA.2329.1.S1_at | — | — | 2.43 | 0.0587 |
| MmugDNA.17344.1.S1_at | neurotrophin 3 | NTF3 | 2.42 | 0.0822 |
| MmugDNA.36340.1.S1_at | — | — | 2.42 | 0.0398 |
| MmugDNA.21012.1.S1_at | rabphilin 3A-like (without C2 domains) | — | 2.42 | 0.0932 |
| MmugDNA.17438.1.S1_at | — | — | 2.42 | 0.0767 |
| MmuSTS.1305.1.S1_at | disrupted in renal carcinoma 2 | LOC715135 | 2.42 | 0.0004 |
| MmuSTS.664.1.S1_at | caspase 7 isoform delta | LOC697633 | 2.42 | 0.0130 |
| MmugDNA.26043.1.S1_at | Ataxin-7-like protein 1 | LOC698666 | 2.41 | 0.0286 |
| MmugDNA.33509.1.S1_at | CG11178-PB, isoform B | LOC693868 | 2.41 | 0.0659 |
| MmugDNA.6922.1.S1_at | — | — | 2.41 | 0.0385 |
| MmugDNA.31513.1.S1_at | ubiquitin specific protease 38 | LOC700235 | 2.41 | 0.0544 |
| MmuSTS.1706.1.S1_at | ATP binding cassette, sub-family A (ABC1), member 13 | LOC695208 | 2.41 | 0.0215 |
| MmuSTS.415.1.S1_at | — | — | 2.41 | 0.0183 |
| MmugDNA.5945.1.S1_at | CG6729-PA | LOC711172 | 2.41 | 0.0529 |
| MmugDNA.16172.1.S1_at | transmembrane protein 5 | TMEM5 | 2.41 | 0.0000 |
| MmugDNA.7215.1.S1_at | uronyl-2-sulfotransferase | LOC697355 | 2.41 | 0.0823 |
| MmugDNA.20155.1.S1_at | — | — | 2.41 | 0.0172 |
| MmugDNA.39588.1.S1_at | — | — | 2.41 | 0.0526 |
| MmugDNA.1883.1.S1_at | EGFR-coamplified and overexpressed protein | LOC716151 | 2.41 | 0.0004 |
| MmugDNA.2888.1.S1_at | HMT1 hnRNP methyltransferase-like 1 | PRMT2 | 2.41 | 0.0030 |
| MmugDNA.36209.1.S1_at | — | — | 2.40 | 0.0506 |
| MmugDNA.5649.1.S1_at | autocrine motility factor receptor | LOC699972 | 2.40 | 0.0223 |
| MmugDNA.33055.1.S1_at | hypothetical protein LOC696384 | LOC696384 | 2.40 | 0.0752 |
| MmuSTS.2026.1.S1_at | cAMP-dependent protein kinase inhibitor gamma | LOC712474 | 2.40 | 0.0094 |
| MmugDNA.14045.1.S1_at | advillin | LOC712581 | 2.40 | 0.0001 |
| MmugDNA.35277.1.S1_s_at | actin related protein 2/3 complex, subunit 5 | LOC699657 | 2.40 | 0.0138 |
| MmugDNA.30729.1.S1_s_at | golgi reassembly stacking protein 2 | LOC694170 | 2.40 | 0.0106 |
| MmugDNA.36130.1.S1_at | attractin | ATRN | 2.40 | 0.0097 |
| MmugDNA.7819.1.S1_at | mitogen-activated protein kinase 8 isoform 1 | LOC711115 | 2.39 | 0.0438 |
| MmugDNA.43615.1.S1_at | — | — | 2.39 | 0.0695 |
| MmugDNA.25611.1.S1_at | phosphodiesterase 6D, cGMP-specific, rod, delta | LOC712629 | 2.39 | 0.0100 |
| MmugDNA.27560.1.S1_at | Hypothetical protein LOC709178 | — | 2.39 | 0.0044 |
| MmugDNA.13637.1.S1_at | zinc finger protein 135 (clone pHZ-17) | LOC706617 | 2.39 | 0.0734 |
| MmugDNA.103.1.S1_at | PDZ and LIM domain 7 isoform 2 | LOC706581 | 2.39 | 0.0805 |
| MmugDNA.41605.1.S1_s_at | casein kinase II, alpha 1 polypeptide | LOC714841 | 2.39 | 0.0647 |
| MmuSTS.3945.1.S1_at | synaptotagmin I | SYT1 | 2.39 | 0.0424 |
| MmugDNA.5481.1.S1_at | — | — | 2.39 | 0.0011 |
| MmugDNA.10940.1.S1_at | — | — | 2.39 | 0.0516 |
| MmugDNA.9600.1.S1_at | regulating synaptic membrane exocytosis 2 isoform 1 | LOC694366 | 2.39 | 0.0629 |
| MmuSTS.2040.1.S1_at | hypothetical protein LOC716045 | LOC716045 | 2.38 | 0.0203 |
| MmugDNA.5934.1.S1_at | — | — | 2.38 | 0.0282 |
| MmugDNA.7962.1.S1_at | syntaphilin | SNPH | 2.38 | 0.0359 |
| MmugDNA.13339.1.S1_at | G protein-coupled receptor 178 | LOC705039 | 2.38 | 0.0053 |
| MmuSTS.1208.1.S1_at | trimethyllysine hydroxylase, epsilon | TMLHE | 2.38 | 0.0921 |
| MmugDNA.31636.1.S1_at | HMT1 hnRNP methyltransferase-like 3 | LOC701789 | 2.38 | 0.0213 |
| MmugDNA.3222.1.S1_at | — | — | 2.38 | 0.0317 |
| MmugDNA.38925.1.S1_at | CG15021-PA | LOC699097 | 2.38 | 0.0200 |
| MmugDNA.8848.1.S1_at | transmembrane protein 37 | LOC695060 | 2.38 | 0.0843 |

| Probe Set ID | Gene Title | Gene Symbol | Ratio Top verus Bottom | p value Top versus Bottom |
|---|---|---|---|---|
| MmuSTS.168.1.S1_x_at | isopentenyl-diphosphate delta isomerase | LOC710052 | 2.38 | 0.0011 |
| MmugDNA.10165.1.S1_at | Hematological and neurological expressed 1 | — | 2.38 | 0.0381 |
| MmugDNA.14296.1.S1_at | — | — | 2.37 | 0.0118 |
| MmugDNA.26530.1.S1_at | hypothetical protein LOC721032 | LOC721032 | 2.37 | 0.0873 |
| MmugDNA.42344.1.S1_at | ADP-ribosylarginine hydrolase | ADPRH | 2.37 | 0.0911 |
| MmugDNA.31196.1.S1_at | — | — | 2.37 | 0.0106 |
| MmugDNA.6107.1.S1_at | Juxtaposed with another zinc finger protein 1 | LOC697973 | 2.37 | 0.0564 |
| MmugDNA.12227.1.S1_at | — | — | 2.37 | 0.0092 |
| MmugDNA.6506.1.S1_at | — | — | 2.37 | 0.0548 |
| MmugDNA.33621.1.S1_at | zinc finger protein 528 | LOC720193 | 2.37 | 0.0807 |
| MmugDNA.5483.1.S1_at | cell death inducing protein | LOC705579 | 2.37 | 0.0183 |
| MmugDNA.4206.1.S1_at | calcium-activated potassium channel beta 4 subunit | LOC717360 | 2.37 | 0.0762 |
| MmugDNA.27722.1.S1_at | — | — | 2.37 | 0.0449 |
| MmugDNA.37306.1.S1_at | melanoma antigen family E, 1 | LOC705379 | 2.36 | 0.0431 |
| MmugDNA.38283.1.S1_at | NADPH cytochrome B5 oxidoreductase | LOC695553 | 2.36 | 0.0419 |
| MmugDNA.9872.1.S1_at | lysosomal-associated membrane protein 1 | LAMP1 | 2.36 | 0.0380 |
| MmugDNA.39305.1.S1_at | Fc fragment of IgG binding protein | LOC700539 | 2.36 | 0.0153 |
| MmugDNA.19557.1.S1_at | filamin-binding LIM protein-1 isoform a | LOC695727 | 2.36 | 0.0284 |
| Mmu.4737.1.S1_at | riboflavin kinase | LOC704540 | 2.36 | 0.0146 |
| MmugDNA.3346.1.S1_at | makorin, ring finger protein, 2 | LOC697649 | 2.36 | 0.0193 |
| MmuSTS.3988.1.S1_at | Cathepsin S precursor | LOC708080 | 2.36 | 0.0054 |
| MmugDNA.38289.1.S1_at | WD repeat domain 27 | LOC695097 | 2.36 | 0.0583 |
| MmugDNA.684.1.S1_at | alpha 2 type IX collagen | LOC694248 | 2.36 | 0.0316 |
| MmugDNA.41344.1.S1_at | solute carrier family 4 member 11 | LOC718393 | 2.36 | 0.0120 |
| MmugDNA.8324.1.S1_at | — | — | 2.35 | 0.0096 |
| MmugDNA.12588.1.S1_at | — | — | 2.35 | 0.0199 |
| MmugDNA.36202.1.S1_at | — | — | 2.35 | 0.0482 |
| MmugDNA.23185.1.S1_at | TATA element modulatory factor 1 | LOC696619 | 2.35 | 0.0108 |
| MmugDNA.12313.1.S1_at | CG2943-PA | LOC702573 | 2.35 | 0.0270 |
| MmugDNA.15670.1.S1_s_at | insulysin | IDE | 2.35 | 0.0735 |
| MmugDNA.30396.1.S1_at | Corneodesmosin precursor (S protein) | LOC714553 | 2.35 | 0.0729 |
| MmugDNA.12626.1.S1_s_at | SWI/SNF-related matrix-associated actin-dependent regulator of chromatin a4 | SMARCA4 | 2.35 | 0.0853 |
| MmugDNA.20551.1.S1_at | discoidin, CUB and LCCL domain containing 1 | DCBLD1 | 2.35 | 0.0001 |
| MmugDNA.19751.1.S1_at | ADP-ribosylhydrolase like 1 isoform 1 | LOC697842 | 2.34 | 0.0761 |
| MmugDNA.5198.1.S1_at | uncharacterized protein family UPF0227 member RGD1359682 | LOC717757 | 2.34 | 0.0500 |
| MmugDNA.28177.1.S1_s_at | hypothetical protein LOC712492 | LOC712492 | 2.34 | 0.0330 |
| MmugDNA.14571.1.S1_s_at | phosphatidylinositol glycan, class T precursor | LOC710556 | 2.34 | 0.0061 |
| Mmu.15853.1.S1_x_at | ADP-ribosylation-like factor 6 interacting protein 5 | LOC696360 | 2.34 | 0.0344 |
| MmuSTS.255.1.S1_at | non-imprinted in Prader-Willi/Angelman syndrome 1 | LOC710236 | 2.34 | 0.0619 |
| MmugDNA.10012.1.S1_at | transmembrane protein 16D | LOC695973 | 2.34 | 0.0997 |
| MmugDNA.19562.1.S1_at | zinc finger protein 406 isoform ZFAT-1 | LOC698512 | 2.34 | 0.0839 |
| MmugDNA.22652.1.S1_s_at | — | — | 2.34 | 0.0641 |
| MmugDNA.29515.1.S1_at | splicing factor, arginine/serine-rich 14 | LOC719666 | 2.34 | 0.0382 |
| MmugDNA.17884.1.S1_at | Nuclear respiratory factor 1 (NRF-1) (Alpha palindromic-binding protein) (Alpha-pal) | LOC701933 | 2.34 | 0.0353 |
| MmugDNA.32746.1.S1_at | — | — | 2.34 | 0.0282 |
| MmuSTS.1396.1.S1_s_at | zinc finger, MYND domain containing 11 | ZMYND11 | 2.34 | 0.0128 |
| MmugDNA.18506.1.S1_at | basic beta 1 syntrophin | LOC703245 | 2.33 | 0.0093 |
| MmugDNA.26826.1.S1_s_at | solute carrier family 11 (proton-coupled divalent metal ion transporters), member 1 | SLC11A1 | 2.33 | 0.0675 |
| MmugDNA.38731.1.S1_at | steroid 5 alpha-reductase 2-like | LOC696381 | 2.33 | 0.0646 |
| MmugDNA.27590.1.S1_at | — | — | 2.33 | 0.0789 |
| MmugDNA.17575.1.S1_at | — | — | 2.33 | 0.0623 |
| MmugDNA.17935.1.S1_at | — | — | 2.33 | 0.0075 |
| MmugDNA.22419.1.S1_at | — | — | 2.33 | 0.0972 |
| MmugDNA.23057.1.S1_at | — | — | 2.33 | 0.0060 |
| MmugDNA.41434.1.S1_at | gamma-glutamyl hydrolase precursor | LOC700747 | 2.33 | 0.0384 |
| MmugDNA.17895.1.S1_at | — | — | 2.33 | 0.0135 |
| MmugDNA.23827.1.S1_at | hypothetical protein LOC699699 | LOC699699 | 2.33 | 0.0944 |
| MmugDNA.10050.1.S1_at | — | — | 2.33 | 0.0710 |
| Mmu.2224.1.A1_at | — | — | 2.32 | 0.0001 |
| Mmu.12870.1.S1_at | thymic dendritic cell-derived factor 1 | TMEM59 | 2.32 | 0.0246 |
| MmugDNA.19523.1.S1_at | CD164 antigen, sialomucin | CD164 | 2.32 | 0.0019 |
| MmugDNA.22579.1.S1_at | Growth-arrest-specific protein 7 (GAS-7) | LOC717827 | 2.32 | 0.0431 |
| MmuSTS.2905.1.S1_at | Pre-B lymphocyte protein 3 precursor (VpreB3 protein) (N27C7-2) | VPREB3 | 2.32 | 0.0105 |
| MmugDNA.41669.1.S1_at | apolipoprotein B mRNA editing enzyme, catalytic polypeptide-like 4 (putative) | LOC714993 | 2.32 | 0.0081 |
| MmugDNA.11443.1.S1_at | — | — | 2.32 | 0.0432 |
| MmugDNA.18263.1.S1_at | zinc finger, DHHC domain containing 9 | ZDHHC9 | 2.32 | 0.0271 |
| MmuAffx.1008.1.S1_at | Glutathione peroxidase 3 precursor (GSHPx-3) (GPx-3) (Plasma glutathione peroxidase) (GSHPx-P) (Extracellular glutathione peroxidase) (GPx-P) | LOC713057 | 2.32 | 0.0926 |
| MmugDNA.22975.1.S1_at | hydroxysteroid dehydrogenase like 1 | LOC714962 | 2.31 | 0.0247 |

| Probe Set ID | Gene Title | Gene Symbol | Ratio Top verus Bottom | p value Top versus Bottom |
|---|---|---|---|---|
| MmugDNA.35709.1.S1_at | calsyntenin 2 | LOC715514 | 2.31 | 0.0056 |
| MmugDNA.14527.1.S1_at | F-box only protein 2 | LOC722738 | 2.31 | 0.0601 |
| MmugDNA.35626.1.S1_s_at | Ras association (RalGDS/AF-6) domain family 6 isoform a | LOC704459 | 2.31 | 0.0137 |
| MmuSTS.2492.1.S1_at | zinc finger protein 509 | LOC712422 | 2.31 | 0.0239 |
| MmuSTS.3145.1.S1_at | nodal modulator 2 isoform 2 | LOC714226 | 2.31 | 0.0001 |
| MmuSTS.3540.1.S1_at | p21-activated kinase 3 | PAK3 | 2.31 | 0.0898 |
| MmugDNA.15593.1.S1_at | lysosomal acid phosphatase 2 | ACP2 | 2.31 | 0.0605 |
| MmugDNA.18121.1.S1_at | — | — | 2.31 | 0.0029 |
| MmugDNA.39434.1.S1_at | — | — | 2.31 | 0.0976 |
| MmugDNA.25583.1.S1_at | PDZ domain containing 8 | LOC709084 | 2.31 | 0.0851 |
| MmugDNA.38757.1.S1_at | — | — | 2.31 | 0.0970 |
| MmugDNA.10667.1.S1_at | ribophorin II precursor | LOC708971 | 2.30 | 0.0244 |
| MmugDNA.22894.1.S1_at | cellular modulator of immune recognition | LOC708030 | 2.30 | 0.0097 |
| MmuSTS.4136.1.S1_at | enolase 2 | ENO2 | 2.30 | 0.0000 |
| MmunewRS.108.1.S1_at | RNA binding motif protein 18 | LOC698457 | 2.30 | 0.0318 |
| MmugDNA.13579.1.S1_at | — | — | 2.30 | 0.0823 |
| MmugDNA.13215.1.S1_at | myosin VB | MYO5B | 2.30 | 0.0008 |
| MmuSTS.3395.1.S1_at | T16G12.5 | LOC704499 | 2.30 | 0.0158 |
| MmugDNA.3907.1.S1_at | — | — | 2.30 | 0.0862 |
| MmugDNA.26180.1.S1_at | — | — | 2.29 | 0.0769 |
| MmugDNA.37638.1.S1_at | Hypothetical protein LOC721042 | — | 2.29 | 0.0189 |
| MmuSTS.4204.1.S1_at | growth arrest-specific 8 | GAS8 | 2.29 | 0.0119 |
| MmuSTS.1320.1.S1_at | Calcipressin-2 (Thyroid hormone-responsive protein ZAKI-4) (Down syndrome candidate region 1-like 1) (Myocyte-enriched calcineurin-interacting protein 2) (MCIP2) | DSCR1L1 | 2.29 | 0.0211 |
| MmuSTS.1142.1.S1_at | pleiomorphic adenoma gene-like 1 isoform 2 | LOC699985 | 2.29 | 0.0086 |
| MmuSTS.1514.1.S1_at | — | — | 2.29 | 0.0218 |
| MmuSTS.629.1.S1_at | insulin-like growth factor 2 receptor | IGF2R | 2.29 | 0.0358 |
| MmugDNA.34704.1.S1_at | pecanex homolog | LOC694094 | 2.29 | 0.0679 |
| MmuSTS.2468.1.S1_at | DHHC1 protein | ZDHHC3 | 2.29 | 0.0010 |
| MmugDNA.39065.1.S1_at | elongation factor Tu GTP binding domain containing 1 | — | 2.29 | 0.0258 |
| MmugDNA.43592.1.S1_at | — | — | 2.29 | 0.0291 |
| MmugDNA.18594.1.S1_at | DNA-directed RNA polymerases I, II, and III 7.0 kDa polypeptide (ABC10-alpha) (RPB7.0) (RPB10alpha) (RPABC4) | POLR2K | 2.29 | 0.0182 |
| MmugDNA.22717.1.S1_at | — | — | 2.29 | 0.0484 |
| MmugDNA.11519.1.S1_at | breakpoint cluster region isoform 1 | LOC709258 | 2.28 | 0.0734 |
| MmugDNA.14224.1.S1_at | hypothetical protein LOC715184 | LOC715184 | 2.28 | 0.0889 |
| MmugDNA.2963.1.S1_at | KIAA1900 | LOC709276 | 2.28 | 0.0527 |
| MmugDNA.41313.1.S1_at | Oxytocin-neurophysin 1 precursor (OT-NPI) | OXT | 2.28 | 0.0512 |
| MmugDNA.23270.1.S1_at | archaemetzincins-2 isoform 1 | LOC718462 | 2.28 | 0.0394 |
| MmugDNA.7783.1.S1_at | solute carrier organic anion transporter family, member 3A1 | SLCO3A1 | 2.28 | 0.0616 |
| MmugDNA.40350.1.S1_s_at | glutamate dehydrogenase 1 | GLUD1 | 2.28 | 0.0037 |
| MmugDNA.9234.1.S1_at | tau tubulin kinase 2 | LOC712249 | 2.27 | 0.0807 |
| MmugDNA.21304.1.S1_s_at | MAX protein isoform c | LOC708228 | 2.27 | 0.0165 |
| MmuSTS.3238.1.S1_at | raft-linking protein | RAFTLIN | 2.27 | 0.0108 |
| MmuSTS.1238.1.S1_at | serine/threonine protein phosphatase with EF-hand motifs 1 | PPEF1 | 2.27 | 0.0956 |
| MmugDNA.39116.1.S1_at | CDW92 antigen isoform 2 | LOC715816 | 2.27 | 0.0566 |
| Mmu.924.1.S1_at | anaphase promoting complex subunit 13 | LOC717294 | 2.27 | 0.0128 |
| MmugDNA.33266.1.S1_at | — | — | 2.27 | 0.0418 |
| MmuSTS.1309.1.S1_at | Doublesex- and mab-3-related transcription factor 2 (Doublesex-like 2 protein) (DSXL-2) | DMRT2 | 2.27 | 0.0682 |
| MmugDNA.34994.1.S1_s_at | — | — | 2.27 | 0.0940 |
| MmugDNA.42427.1.S1_at | — | — | 2.27 | 0.0034 |
| MmugDNA.16606.1.S1_s_at | synapse-associated protein 97 | DLG1 | 2.27 | 0.0636 |
| MmugDNA.16402.1.S1_at | cyclin M4 | LOC710164 | 2.27 | 0.0425 |
| MmugDNA.42754.1.S1_at | — | — | 2.27 | 0.0453 |
| MmugDNA.29639.1.S1_at | — | — | 2.27 | 0.0957 |
| MmugDNA.4933.1.S1_at | — | — | 2.27 | 0.0759 |
| MmugDNA.30201.1.S1_at | Transcription factor Ovo-like 2 (hOvo2) (Zinc finger protein 339) | LOC719066 | 2.27 | 0.0162 |
| MmugDNA.13664.1.S1_at | — | — | 2.26 | 0.0969 |
| MmugDNA.11714.1.S1_at | transmembrane 6 superfamily member 1 | LOC700147 | 2.26 | 0.0935 |
| MmuSTS.160.1.S1_at | cancer susceptibility candidate 1 | LOC707753 | 2.26 | 0.0756 |
| MmugDNA.32421.1.S1_at | Mediator complex subunit 4 (Mediator of RNA polymerase II transcription subunit 4) (Vitamin D3 receptor-interacting protein complex 36 kDa component) (DRIP36) (Activator-recruited cofactor 36 kDa component) (ARC36) (TRAP/SMCC/PC2 subunit . . . | LOC704644 | 2.26 | 0.0005 |
| MmugDNA.617.1.S1_at | pleckstrin homology domain containing, family H (with MyTH4 domain) member 1 | LOC713855 | 2.26 | 0.0144 |
| MmugDNA.29286.1.S1_at | hypothetical protein LOC708459 | LOC708459 | 2.26 | 0.0585 |
| MmugDNA.26513.1.S1_at | — | — | 2.26 | 0.0079 |
| MmugDNA.4207.1.S1_at | hypothetical protein LOC695219 | LOC695219 | 2.25 | 0.0404 |
| Mmu.11792.1.S1_at | syntaxin 12 | LOC716455 | 2.25 | 0.0076 |
| MmugDNA.3187.1.S1_at | midline 1 | LOC713037 | 2.25 | 0.0123 |

| Probe Set ID | Gene Title | Gene Symbol | Ratio Top verus Bottom | p value Top versus Bottom |
|---|---|---|---|---|
| MmuSTS.2358.1.S1_at | Reticulon-2 (Neuroendocrine-specific protein-like 1) (NSP-like protein 1) (NSPLI) | RTN2 | 2.25 | 0.0554 |
| MmugDNA.13865.1.S1_at | — | — | 2.25 | 0.0808 |
| MmuSTS.1169.1.S1_at | carbohydrate (chondroitin 4) sulfotransferase 12 | CHST12 | 2.25 | 0.0631 |
| MmugDNA.7568.1.S1_at | myotubularin related protein 6 | MTMR6 | 2.25 | 0.0109 |
| MmugDNA.42542.1.S1_at | — | — | 2.25 | 0.0141 |
| MmuSTS.2722.1.S1_at | homer 2 | HOMER2 | 2.25 | 0.0035 |
| MmugDNA.10742.1.S1_at | farnesyl-diphosphate farnesyltransferase 1 | FDFT1 | 2.25 | 0.0008 |
| MmugDNA.42437.1.S1_at | N-ethylmaleimide-sensitive factor attachment protein, alpha | LOC717355 | 2.25 | 0.0490 |
| MmugDNA.23264.1.S1_at | — | — | 2.25 | 0.0558 |
| MmugDNA.33445.1.S1_at | ring finger protein 180 | LOC698166 | 2.25 | 0.0840 |
| MmugDNA.31781.1.S1_at | vacuolar protein sorting 37C | LOC694898 | 2.25 | 0.0416 |
| MmugDNA.15898.1.S1_s_at | ATPase, H+ transporting, lysosomal 70 kD, V1 subunit A, isoform 1 | LOC696878 /// LOC709958 | 2.25 | 0.0009 |
| MmugDNA.29220.1.S1_at | mitogen-activated protein kinase kinase kinase 13 | LOC701085 | 2.25 | 0.0665 |
| MmugDNA.18194.1.S1_at | mitogen-activated protein kinase kinase 6 | LOC693914 | 2.25 | 0.0209 |
| Mmu.10240.1.S1_at | ubiquitin C-terminal hydrolase UCH37 | LOC712473 | 2.25 | 0.0146 |
| MmugDNA.2778.1.S1_at | WW, C2 and coiled-coil domain containing 1 | LOC720812 | 2.25 | 0.0619 |
| MmugDNA.14327.1.S1_at | lactamase, beta isoform a | LOC705365 | 2.24 | 0.0027 |
| MmugDNA.6356.1.S1_at | CG14980-PB | LOC718128 | 2.24 | 0.0083 |
| MmugDNA.41963.1.S1_s_at | calcium binding atopy-related autoantigen 1 | LOC701131 /// LOC708654 | 2.24 | 0.0120 |
| MmuSTS.357.1.S1_s_at | malin | LOC704451 | 2.24 | 0.0520 |
| MmugDNA.12984.1.S1_at | influenza virus NS1A binding protein isoform a | LOC714152 | 2.24 | 0.0122 |
| MmugDNA.36042.1.S1_at | myotubularin-related protein 2 | MTMR2 | 2.24 | 0.0122 |
| MmugDNA.32344.1.S1_at | phosphatidylinositol glycan, class K | PIGK | 2.24 | 0.0015 |
| MmuSTS.1829.1.S1_at | shroom | LOC699613 | 2.24 | 0.0312 |
| Mmu.14177.1.S1_at | unc-50 homolog | UNC50 | 2.24 | 0.0511 |
| MmugDNA.17303.1.S1_at | — | — | 2.24 | 0.0816 |
| MmuSTS.4053.1.S1_at | diacylglycerol kinase, iota | DGKI | 2.24 | 0.0540 |
| MmugDNA.31861.1.S1_at | ADP-ribosylation factor interacting protein 1 isoform 2 | LOC697533 | 2.24 | 0.0738 |
| MmugDNA.32277.1.S1_at | DNA methyltransferase 2 | DNMT2 | 2.24 | 0.0117 |
| MmugDNA.7347.1.S1_at | — | — | 2.23 | 0.0783 |
| MmuSTS.242.1.S1_x_at | hypothetical protein LOC710534 | LOC710534 | 2.23 | 0.0769 |
| MmugDNA.29827.1.S1_at | — | — | 2.23 | 0.0209 |
| MmuSTS.2213.1.S1_at | T03G11.3 | — | 2.23 | 0.0690 |
| MmugDNA.37378.1.S1_at | — | — | 2.23 | 0.0285 |
| MmuSTS.3577.1.S1_at | protocadherin beta 15 | PCDHB15 | 2.23 | 0.0039 |
| MmugDNA.39878.1.S1_at | CG15528-PA | LOC716271 | 2.23 | 0.0314 |
| MmugDNA.21179.1.S1_at | SEC22 vesicle trafficking protein homolog C isoform b | LOC716351 | 2.23 | 0.0145 |
| MmuSTS.3806.1.S1_at | ADP-ribosylation factor GTPase activating protein 3 | LOC711160 | 2.23 | 0.0530 |
| MmugDNA.31478.1.S1_at | Ras-related protein Rab-33A (Small GTP-binding protein S10) | RAB33A | 2.23 | 0.0714 |
| MmugDNA.9384.1.S1_at | — | — | 2.23 | 0.0215 |
| MmuSTS.3704.1.S1_at | protein kinase, X-linked | PRKX | 2.23 | 0.0502 |
| MmugDNA.1624.1.S1_at | F-box only protein 3 isoform 2 | LOC693281 | 2.22 | 0.0611 |
| MmugDNA.732.1.S1_at | hexosaminidase B | HEXB | 2.22 | 0.0224 |
| MmugDNA.12951.1.S1_at | zinc finger protein 77 | LOC712142 | 2.22 | 0.0290 |
| MmugDNA.24637.1.S1_at | zinc finger protein HIT-39 | LOC710861 | 2.22 | 0.0274 |
| MmuSTS.1852.1.S1_at | cell division cycle 25A isoform a | LOC710858 | 2.22 | 0.0331 |
| MmugDNA.34293.1.S1_at | UDP-Gal:betaGlcNAc beta 1,4-galactosyltransferase 5 | B4GALT5 | 2.22 | 0.0063 |
| MmuSTS.4187.1.S1_at | NAD(P)H:quinone oxidoreductase type 3, polypeptide A2 | LOC704519 | 2.22 | 0.0262 |
| MmugDNA.42423.1.S1_at | — | — | 2.22 | 0.0136 |
| MmugDNA.34057.1.S1_at | Protein C9orf46 | LOC693286 | 2.22 | 0.0134 |
| MmugDNA.35491.1.S1_at | CG13624-PC, isoform C | LOC703459 | 2.22 | 0.0168 |
| MmugDNA.22976.1.S1_s_at | CG2747-PB, isoform B | — | 2.22 | 0.0105 |
| MmuSTS.1422.1.S1_at | hypothetical protein LOC721211 | LOC721211 | 2.22 | 0.0334 |
| MmugDNA.22793.1.S1_at | tribbles homolog 2 | LOC710966 | 2.22 | 0.0901 |
| MmugDNA.40572.1.S1_at | fucosidase, alpha-L-1, tissue | FUCA1 | 2.22 | 0.0228 |
| MmugDNA.817.1.S1_at | proteasome (prosome, macropain) 26S subunit, ATPase 2 | LOC722117 | 2.21 | 0.0637 |
| MmugDNA.38292.1.S1_at | SORCS receptor 1 isoform b | LOC693969 | 2.21 | 0.0537 |
| MmugDNA.35537.1.S1_at | cathepsin L | CTSL | 2.21 | 0.0957 |
| MmugDNA.8681.1.S1_at | CG14967-PA | LOC709307 | 2.21 | 0.0675 |
| MmuSTS.3280.1.S1_at | calcium channel, voltage-dependent, alpha 2/delta subunit 2 isoform b | LOC702429 | 2.21 | 0.0789 |
| MmugDNA.38348.1.S1_at | adducin 1 (alpha) | ADD1 | 2.21 | 0.0553 |
| MmugDNA.8155.1.S1_at | — | — | 2.21 | 0.0001 |
| Mmu.394.1.S1_at | — | — | 2.21 | 0.0019 |
| Mmu.14589.1.A1_at | Secretory carrier membrane protein 1 | — | 2.21 | 0.0253 |
| MmugDNA.15428.1.S1_at | acetoacetyl-CoA synthetase | LOC707015 | 2.21 | 0.0296 |
| MmugDNA.2672.1.S1_at | — | — | 2.21 | 0.0718 |
| Mmu.7319.1.S1_at | hypothetical protein LOC698039 | LOC698039 | 2.21 | 0.0978 |
| Mmu.14167.1.S1_at | DNA topoisomerase I | LOC697300 | 2.21 | 0.0879 |
| MmugDNA.26813.1.S1_at | — | — | 2.20 | 0.0739 |
| MmugDNA.18358.1.S1_at | jumonji domain containing 2B | JMJD2B | 2.20 | 0.0264 |
| MmugDNA.30037.1.S1_at | hypothetical protein LOC700951 | LOC700951 | 2.20 | 0.0539 |

-continued

| Probe Set ID | Gene Title | Gene Symbol | Ratio Top verus Bottom | p value Top versus Bottom |
|---|---|---|---|---|
| MmugDNA.40481.1.S1_at | dynamin binding protein | LOC709334 | 2.20 | 0.0109 |
| MmugDNA.25680.1.S1_at | hypothetical protein LOC702485 | LOC702485 | 2.20 | 0.0848 |
| MmugDNA.20470.1.S1_at | — | — | 2.20 | 0.0464 |
| MmugDNA.7063.1.S1_at | — | — | 2.20 | 0.0848 |
| MmugDNA.37434.1.S1_at | karyopherin alpha 1 | KPNA1 | 2.20 | 0.0119 |
| MmuSTS.2333.1.S1_at | Peroxisome assembly factor 1 (PAF-1) (Peroxin-2) (Peroxisomal membrane protein 3) (35 kDa peroxisomal membrane protein) (RING finger protein 72) | LOC701636 | 2.20 | 0.0939 |
| MmugDNA.17606.1.S1_at | BTB (POZ) domain containing 11 isoform 3 /// hypothetical protein LOC705027 | LOC704916 /// LOC705027 | 2.20 | 0.0238 |
| MmugDNA.32862.1.S1_at | zinc finger protein 174 | ZNF174 | 2.20 | 0.0684 |
| MmugDNA.2565.1.S1_at | — | — | 2.20 | 0.0079 |
| MmugDNA.35698.1.S1_at | — | — | 2.20 | 0.0366 |
| MmugDNA.23911.1.S1_at | — | — | 2.19 | 0.0292 |
| MmugDNA.21753.1.S1_at | — | — | 2.19 | 0.0073 |
| MmugDNA.8775.1.S1_at | — | — | 2.19 | 0.0057 |
| MmugDNA.22114.1.S1_at | 5'-methylthioadenosine phosphorylase | MTAP | 2.19 | 0.0179 |
| MmuSTS.3163.1.S1_at | regulator of G-protein signalling 7 | RGS7 | 2.19 | 0.0763 |
| MmugDNA.10574.1.S1_at | amyloid beta A4 precursor protein-binding, family B, member 1 isoform delta E9 | LOC712585 | 2.19 | 0.0110 |
| MmugDNA.11741.1.S1_at | hypothetical protein LOC694910 | LOC694910 | 2.19 | 0.0055 |
| MmugDNA.25725.1.S1_at | Potassium voltage-gated channel subfamily E member 1 (IKs producing slow voltage-gated potassium channel beta subunit Mink) (Minimal potassium channel) (Delayed rectifier potassium channel subunit IsK) | KCNE1 | 2.19 | 0.0377 |
| MmugDNA.39110.1.S1_at | membrane component chromosome 11 surface marker 1 isoform 1 | LOC717473 | 2.19 | 0.0812 |
| MmugDNA.2250.1.S1_at | hypothetical protein LOC716978 | LOC716978 | 2.19 | 0.0969 |
| MmugDNA.17877.1.S1_s_at | — | — | 2.19 | 0.0717 |
| MmugDNA.24132.1.S1_at | F16A11.1 | LOC703783 | 2.19 | 0.0504 |
| MmugDNA.34793.1.S1_at | — | — | 2.19 | 0.0542 |
| MmugDNA.7971.1.S1_at | hypothetical protein LOC719652 | LOC719652 | 2.19 | 0.0475 |
| MmugDNA.96.1.S1_at | — | — | 2.18 | 0.0813 |
| MmuSTS.2238.1.S1_at | collapsin response mediator protein 1 | CRMP1 | 2.18 | 0.0048 |
| MmugDNA.17576.1.S1_at | p21-activated kinase 1 | LOC698585 | 2.18 | 0.0691 |
| MmugDNA.42599.1.S1_at | acyl-CoA synthetase long-chain family member 5 isoform a | LOC696404 | 2.18 | 0.0180 |
| MmuSTS.4809.1.S1_at | fucosyltransferase 8 | FUT8 | 2.18 | 0.0898 |
| MmugDNA.33186.1.S1_at | kelch-like 20 | LOC708546 | 2.18 | 0.0022 |
| MmugDNA.39650.1.S1_at | multiple coagulation factor deficiency 2 | LOC717900 | 2.18 | 0.0365 |
| MmugDNA.12193.1.S1_at | beta chimerin | CHN2 | 2.18 | 0.0041 |
| MmugDNA.35302.1.S1_at | sterol regulatory element-binding transcription factor 2 | LOC712307 | 2.18 | 0.0113 |
| MmugDNA.327.1.S1_at | — | — | 2.18 | 0.0722 |
| MmugDNA.38687.1.S1_at | hypothetical protein LOC698137 | LOC698137 | 2.18 | 0.0558 |
| MmugDNA.7208.1.S1_at | seizure related 6 homolog (mouse)-like 2 isoform 2 | LOC707244 | 2.18 | 0.0767 |
| MmugDNA.16529.1.S1_at | twisted gastrulation | LOC705804 | 2.18 | 0.0004 |
| Mmu.1309.1.S1_at | BCL2-associated transcription factor 1 | BCLAF1 | 2.18 | 0.0898 |
| MmugDNA.42025.1.S1_at | — | — | 2.17 | 0.0333 |
| MmugDNA.20036.1.S1_at | — | — | 2.17 | 0.0261 |
| MmugDNA.36083.1.S1_at | — | — | 2.17 | 0.0019 |
| MmuSTS.4278.1.S1_at | secretagogin precursor | LOC694072 | 2.17 | 0.0504 |
| MmuSTS.4293.1.S1_at | CEGP1 protein | LOC708152 | 2.17 | 0.0095 |
| Mmu.12751.1.S1_at | Grancalcin | GCA | 2.17 | 0.0079 |
| MmuSTS.4137.1.S1_at | ectonucleoside triphosphate diphosphohydrolase 6 | ENTPD6 | 2.17 | 0.0582 |
| MmugDNA.36157.1.S1_at | — | — | 2.17 | 0.0466 |
| MmugDNA.40937.1.S1_at | hypothetical protein LOC699965 | LOC699965 | 2.17 | 0.0264 |
| MmugDNA.41687.1.S1_at | — | — | 2.17 | 0.0243 |
| MmugDNA.32233.1.S1_s_at | Transmembrane protein 50B (HCV p7-transregulated protein 3) | TMEM50B | 2.17 | 0.0009 |
| MmugDNA.38432.1.S1_at | WD repeat and FYVE domain containing 3 isoform 1 | LOC706535 | 2.17 | 0.0583 |
| MmuSTS.2292.1.S1_at | protein phosphatase 1, regulatory (inhibitor) subunit 3F | LOC715950 | 2.17 | 0.0293 |
| MmugDNA.28838.1.S1_at | tumor necrosis factor receptor superfamily, member 25 | TNFRSF25 | 2.17 | 0.0954 |
| MmugDNA.43442.1.S1_at | — | — | 2.17 | 0.0092 |
| MmugDNA.40985.1.S1_at | — | — | 2.17 | 0.0995 |
| MmugDNA.1900.1.S1_s_at | — | — | 2.16 | 0.0135 |
| Mmu.11367.1.S1_at | developmentally regulated protein TPO1 | LOC710413 | 2.16 | 0.0661 |
| MmugDNA.11644.1.S1_at | CG5022-PA | LOC711670 | 2.16 | 0.0671 |
| MmugDNA.5070.1.S1_at | hypothetical protein LOC709015 | LOC709015 | 2.16 | 0.0456 |
| MmugDNA.34622.1.S1_at | B aggressive lymphoma gene | PARP9 | 2.16 | 0.0894 |
| MmugDNA.28503.1.S1_at | — | — | 2.16 | 0.0168 |
| MmugDNA.14771.1.S1_s_at | — | — | 2.16 | 0.0146 |
| MmugDNA.4305.1.S1_at | — | — | 2.16 | 0.0396 |
| MmugDNA.42501.1.S1_at | Dmx-like 2 | LOC693954 | 2.16 | 0.0536 |
| Mmu.828.1.S1_at | leucine rich repeat containing 40 | LOC702565 | 2.16 | 0.0103 |
| MmugDNA.26452.1.S1_at | TRIO and F-actin-binding protein (Protein Tara) (Trio-associated repeat on actin) | LOC701241 | 2.16 | 0.0659 |
| MmugDNA.14006.1.S1_at | methyltransferase 5 domain containing 1 | LOC698208 | 2.16 | 0.0220 |

-continued

| Probe Set ID | Gene Title | Gene Symbol | Ratio Top verus Bottom | p value Top versus Bottom |
|---|---|---|---|---|
| MmugDNA.16489.1.S1_at | — | — | 2.16 | 0.0929 |
| MmugDNA.33403.1.S1_at | WD repeat and SOCS box-containing protein 2 (WSB-2) (CS box-containing WD protein) | LOC695359 | 2.16 | 0.0010 |
| MmuSTS.3848.1.S1_at | Surfeit locus protein 5 | LOC714097 | 2.16 | 0.0346 |
| MmugDNA.28161.1.S1_at | AMIGO protein | AMIGO1 | 2.16 | 0.0117 |
| Mmu.1020.1.S1_s_at | cysteine-rich with EGF-like domains 1 isoform 2 | LOC699345 | 2.15 | 0.0581 |
| MmugDNA.23895.1.S1_at | — | — | 2.15 | 0.0568 |
| MmugDNA.34300.1.S1_at | — | — | 2.15 | 0.0476 |
| MmugDNA.25815.1.S1_at | — | — | 2.15 | 0.0128 |
| MmuSTS.2538.1.S1_at | Interleukin-13 receptor alpha-1 chain precursor (IL-13R-alpha-1) (IL-13RA-1) (CD213a1 antigen) | LOC710986 | 2.15 | 0.0172 |
| MmugDNA.31245.1.S1_at | butyrophilin, subfamily 2, member A2 isoform a | LOC699861 | 2.15 | 0.0979 |
| MmugDNA.36602.1.S1_at | transducin-like enhancer protein 1 | LOC707336 | 2.15 | 0.0343 |
| MmugDNA.21781.1.S1_at | Testis-specific Y-encoded-like protein 3 (TSPY-like 3) | LOC712128 | 2.15 | 0.0723 |
| Mmu.2576.1.S1_at | RING1 and YY1 binding protein | LOC694390 | 2.15 | 0.0893 |
| MmugDNA.9098.1.S1_at | SWI/SNF related, matrix associated, actin dependent regulator of chromatin, subfamily a, member 1 | SMARCA1 | 2.15 | 0.0737 |
| MmugDNA.14464.1.S1_at | ornithine decarboxylase antizyme inhibitor | LOC693581 | 2.15 | 0.0021 |
| MmugDNA.6468.1.S1_at | WD repeat domain 48 | LOC695026 | 2.15 | 0.0807 |
| MmugDNA.12543.1.S1_at | R13A5.9 | LOC710476 | 2.14 | 0.0209 |
| MmugDNA.35647.1.S1_at | BTB and kelch domain containing 3 | LOC706382 | 2.14 | 0.0185 |
| MmugDNA.18973.1.S1_at | nucleobindin 1 | LOC718380 | 2.14 | 0.0548 |
| MmugDNA.7913.1.S1_at | — | — | 2.14 | 0.0589 |
| MmugDNA.9254.1.S1_at | solute carrier family 35, member C1 | SLC35C1 | 2.14 | 0.0474 |
| MmuSTS.702.1.S1_at | inhibin, beta B (activin AB beta polypeptide) | INHBB | 2.14 | 0.0076 |
| MmugDNA.1591.1.S1_at | — | — | 2.14 | 0.0915 |
| Mmu.8048.1.S1_at | protein phosphatase 3 (formerly 2B), catalytic subunit, alpha isoform (calcineurin A alpha) | PPP3CA | 2.13 | 0.0704 |
| MmugDNA.19851.1.S1_at | — | — | 2.13 | 0.0874 |
| MmugDNA.5616.1.S1_at | serine/threonine kinase 38 | STK38 | 2.13 | 0.0148 |
| MmugDNA.4789.1.S1_at | TP53-regulating kinase (p53-related protein kinase) (Nori-2) | LOC716636 | 2.13 | 0.0179 |
| MmugDNA.38238.1.S1_at | stearoyl-CoA desaturase (delta-9-desaturase) | LOC694079 | 2.13 | 0.0088 |
| MmugDNA.14345.1.S1_s_at | — | — | 2.13 | 0.0164 |
| MmugDNA.17444.1.S1_at | nucleoplasmin 2 | LOC715448 | 2.13 | 0.0571 |
| MmuSTS.4377.1.S1_at | — | — | 2.13 | 0.0948 |
| MmugDNA.26500.1.S1_at | KIAA0564 protein | KIAA0564 | 2.13 | 0.0336 |
| MmugDNA.4249.1.S1_at | — | — | 2.13 | 0.0344 |
| MmuSTS.935.1.S1_at | talin 2 | LOC705008 | 2.13 | 0.0652 |
| MmugDNA.33197.1.S1_at | — | — | 2.13 | 0.0665 |
| MmugDNA.39459.1.S1_at | Sec23 (S. cerevisiae) homolog B | LOC698440 | 2.13 | 0.0020 |
| MmuSTS.3997.1.S1_at | — | — | 2.12 | 0.0188 |
| Mmu.9557.1.S1_at | OTU domain containing 4 protein isoform 1 | LOC701837 | 2.12 | 0.0798 |
| MmugDNA.14887.1.S1_at | Protein NipSnap1 | LOC717745 | 2.12 | 0.0225 |
| MmugDNA.25767.1.S1_at | like-glycosyltransferase | LOC717403 | 2.12 | 0.0858 |
| MmugDNA.30227.1.S1_at | nitric oxide synthase trafficking isoform 1 | LOC705063 | 2.12 | 0.0210 |
| MmugDNA.29197.1.S1_at | hypothetical protein LOC698413 | LOC698413 | 2.12 | 0.0069 |
| MmugDNA.35367.1.S1_at | — | — | 2.12 | 0.0045 |
| MmuSTS.1000.1.S1_at | myoneurin | LOC698094 | 2.12 | 0.0044 |
| MmugDNA.27645.1.S1_at | hypothetical protein LOC710801 | LOC710801 | 2.12 | 0.0193 |
| MmugDNA.32669.1.S1_at | Sur-8 CG5407-PA, isoform A | — | 2.12 | 0.0319 |
| MmugDNA.43367.1.S1_at | genetic suppressor element 1 | LOC693298 | 2.12 | 0.0210 |
| MmugDNA.41452.1.S1_at | sperm protein 17 | LOC574157 | 2.12 | 0.0436 |
| MmugDNA.37832.1.S1_at | — | — | 2.12 | 0.0135 |
| MmugDNA.33994.1.S1_at | unc-5 homolog B | LOC715786 | 2.12 | 0.0074 |
| MmugDNA.31700.1.S1_at | stromal membrane-associated protein 1-like | LOC694502 | 2.12 | 0.0138 |
| MmugDNA.12779.1.S1_at | remodeling and spacing factor 1 | LOC699078 | 2.12 | 0.0480 |
| MmugDNA.20356.1.S1_at | platelet-activating factor acetylhydrolase 2 | LOC719750 | 2.11 | 0.0689 |
| MmuSTS.1250.1.S1_at | cAMP responsive element binding protein-like 2 | LOC696952 | 2.11 | 0.0786 |
| MmugDNA.1301.1.S1_at | InaD-like protein isoform 1 | LOC694408 | 2.11 | 0.0733 |
| MmugDNA.38366.1.S1_at | Eukaryotic translation initiation factor 3 subunit 1 (eIF-3 alpha) | LOC712295 | 2.11 | 0.0343 |
| MmugDNA.15094.1.S1_at | hypothetical protein LOC699533 | LOC699533 | 2.11 | 0.0073 |
| MmugDNA.24933.1.S1_at | hypothetical protein LOC701291 | LOC701291 | 2.11 | 0.0405 |
| MmugDNA.18451.1.S1_at | Peroxiredoxin-4 (Prx-IV) (Thioredoxin peroxidase AO372) (Thioredoxin-dependent peroxide reductase A0372) (Antioxidant enzyme AOE372) (AOE37-2) | LOC697635 | 2.11 | 0.0133 |
| MmugDNA.30695.1.S1_at | — | — | 2.11 | 0.0121 |
| MmugDNA.21266.1.S1_s_at | sorcin isoform b | LOC705215 | 2.11 | 0.0255 |
| MmugDNA.41706.1.S1_at | — | — | 2.11 | 0.0059 |
| MmuSTS.2300.1.S1_at | — | — | 2.11 | 0.0732 |
| MmuSTS.2136.1.S1_at | AXIN1 up-regulated 1 | LOC694328 | 2.10 | 0.0010 |
| MmugDNA.34250.1.S1_at | hypothetical protein LOC697587 | LOC697587 | 2.10 | 0.0430 |
| MmugDNA.30761.1.S1_at | abhydrolase domain containing 10 | — | 2.10 | 0.0313 |
| MmugDNA.25568.1.S1_at | ligase III, DNA, ATP-dependent | LIG3 | 2.10 | 0.0203 |
| MmugDNA.41814.1.S1_at | Meis1 homolog | MEIS1 | 2.10 | 0.0730 |
| MmugDNA.23946.1.S1_at | — | — | 2.10 | 0.0824 |

-continued

| Probe Set ID | Gene Title | Gene Symbol | Ratio Top verus Bottom | p value Top versus Bottom |
|---|---|---|---|---|
| MmugDNA.15939.1.S1_at | — | — | 2.10 | 0.0599 |
| MmuSTS.3941.1.S1_at | cell cycle progression 1 isoform 2 | LOC698918 | 2.09 | 0.0097 |
| MmugDNA.31766.1.S1_at | — | — | 2.09 | 0.0173 |
| MmugDNA.34607.1.S1_at | THAP domain containing 7 | LOC693821 | 2.09 | 0.0838 |
| Mmu.10002.1.S1_at | methionine adenosyltransferase II, alpha | MAT2A | 2.09 | 0.0100 |
| MmugDNA.8056.1.S1_at | Uteroglobin precursor (Secretoglobin family 1A member 1) (Clara cell phospholipid-binding protein) (CCPBP) (Clara cells 10 kDa secretory protein) (CC10) (Urinary protein 1) (Urine protein 1) (UP1) | LOC718857 | 2.09 | 0.0677 |
| MmugDNA.8398.1.S1_at | odd Oz/ten-m homolog 3 | LOC700867 | 2.09 | 0.0151 |
| MmugDNA.41504.1.S1_at | SUMO1/sentrin/SMT3 specific protease 2 | SENP2 | 2.09 | 0.0168 |
| MmugDNA.25057.1.S1_s_at | WW domain containing E3 ubiquitin protein ligase 2 | WWP2 | 2.09 | 0.0899 |
| MmugDNA.30167.1.S1_at | tumor rejection antigen (gp96) 1 | HSP90B1 | 2.09 | 0.0317 |
| MmugDNA.23937.1.S1_at | — | — | 2.09 | 0.0679 |
| MmunewRS.900.1.S1_at | — | — | 2.08 | 0.0913 |
| Mmu.13707.1.S1_at | Transcribed locus, moderately XP_001163736.1 prostaglandin-D synthase [Pan troglodytes] | — | 2.08 | 0.0995 |
| MmugDNA.42106.1.S1_at | — | — | 2.08 | 0.0031 |
| MmugDNA.25377.1.S1_at | — | — | 2.08 | 0.0867 |
| MmugDNA.33263.1.S1_at | amine oxidase, copper containing 2 isoform b | LOC711900 | 2.08 | 0.0495 |
| Mmu.10780.1.S1_at | ATP-binding cassette, sub-family D, member 3 | ABCD3 | 2.08 | 0.0668 |
| MmugDNA.23614.1.S1_at | DDHD domain containing 1 | LOC694361 | 2.08 | 0.0695 |
| MmugDNA.28356.1.S1_at | hypothetical protein LOC715793 | LOC715793 | 2.08 | 0.0799 |
| MmugDNA.39375.1.S1_at | oligonucleotide/oligosaccharide-binding fold containing 1 | LOC714968 | 2.08 | 0.0397 |
| MmugDNA.17230.1.S1_at | ets homologous factor | LOC717350 | 2.08 | 0.0092 |
| MmugDNA.43483.1.S1_at | ubiquitin specific protease 47 | USP47 | 2.07 | 0.0354 |
| MmuSTS.4574.1.S1_at | Alpha-mannosidase IIx (Mannosyl-oligosaccharide 1,3-1,6-alpha-mannosidase) (MAN IIx) (Mannosidase alpha class 2A member 2) | MAN2A2 | 2.07 | 0.0066 |
| MmugDNA.42098.1.S1_at | AP-1 complex subunit sigma-2 (Adapter-related protein complex 1 sigma-1B subunit) (Sigma-adaptin 1B) (Adaptor protein complex AP-1 sigma-1B subunit) (Golgi adaptor HA1/AP1 adaptin sigma-1B subunit) (Clathrin assembly protein complex 1 si . . . | LOC713244 | 2.07 | 0.0007 |
| MmugDNA.21632.1.S1_at | KIAA0368 protein | KIAA0368 | 2.07 | 0.0077 |
| MmugDNA.8695.1.S1_at | — | — | 2.07 | 0.0027 |
| MmugDNA.3713.1.S1_at | CG14535-PA | LOC712374 | 2.07 | 0.0672 |
| MmugDNA.32882.1.S1_at | Hypothetical protein LOC718964 | — | 2.07 | 0.0156 |
| MmugDNA.39148.1.S1_at | — | — | 2.07 | 0.0379 |
| MmuSTS.2882.1.S1_at | TCDD-inducible poly(ADP-ribose) polymerase | LOC706180 | 2.07 | 0.0051 |
| MmugDNA.6389.1.S1_at | — | — | 2.07 | 0.0452 |
| MmugDNA.25050.1.S1_at | restin | RSN | 2.07 | 0.0543 |
| MmugDNA.28737.1.S1_at | CG2843-PA | LOC695474 | 2.07 | 0.0871 |
| MmugDNA.39973.1.S1_at | Jade1 protein long isoform | LOC693690 | 2.06 | 0.0012 |
| Mmu.14041.1.S1_at | ubiquitin specific protease 15 | USP15 | 2.06 | 0.0149 |
| MmugDNA.30790.1.S1_at | chromobox homolog 7 | CBX7 | 2.06 | 0.0331 |
| MmugDNA.35116.1.S1_at | kelch-like 12 | LOC694420 /// LOC694548 /// LOC705991 | 2.06 | 0.0120 |
| MmugDNA.9677.1.S1_at | — | — | 2.06 | 0.0871 |
| MmugDNA.16866.1.S1_at | Rho guanine nucleotide exchange factor (GEF) 10-like isoform 2 | LOC701164 | 2.06 | 0.0444 |
| MmugDNA.12243.1.S1_at | — | — | 2.06 | 0.0214 |
| MmuSTS.1567.1.S1_at | diphosphomevalonate decarboxylase | MVD | 2.06 | 0.0860 |
| MmuSTS.4422.1.S1_at | tripartite motif-containing 36 | TRIM36 | 2.06 | 0.0017 |
| MmuSTS.3089.1.S1_at | latrophilin 1 | LPHN1 | 2.06 | 0.0754 |
| MmugDNA.3623.1.S1_at | CG30497-PA, isoform A | LOC714457 | 2.06 | 0.0085 |
| MmuSTS.633.1.S1_at | apical protein of Xenopus-like | APXL | 2.06 | 0.0169 |
| MmuSTS.3572.1.S1_at | coronin, actin binding protein, 2B | CORO2B | 2.06 | 0.0096 |
| MmugDNA.8806.1.S1_at | — | — | 2.06 | 0.0017 |
| MmugDNA.15578.1.S1_at | — | — | 2.06 | 0.0364 |
| MmugDNA.25084.1.S1_at | baculoviral IAP repeat-containing 6 | BIRC6 | 2.05 | 0.0157 |
| MmugDNA.1057.1.S1_at | DnaJ (Hsp40) homolog, subfamily A, member 1 | DNAJA1 | 2.05 | 0.0253 |
| MmugDNA.28429.1.S1_at | hypothetical protein LOC716268 | LOC716268 | 2.05 | 0.0256 |
| MmugDNA.25034.1.S1_at | regulator of G-protein signalling 11 isoform 1 | LOC694588 | 2.05 | 0.0266 |
| MmugDNA.42945.1.S1_at | — | — | 2.05 | 0.0548 |
| MmugDNA.26306.1.S1_at | — | — | 2.05 | 0.0580 |
| MmugDNA.17707.1.S1_at | — | — | 2.05 | 0.0141 |
| MmugDNA.1190.1.S1_at | dpy-19-like 1, like | LOC699789 /// LOC707898 /// LOC709323 | 2.05 | 0.0511 |
| MmugDNA.32656.1.S1_at | axonemal dynein light chain 1 | LOC697410 | 2.05 | 0.0635 |
| MmugDNA.20986.1.S1_s_at | cytochrome P450, family 39, subfamily A, polypeptide 1 | LOC704242 | 2.05 | 0.0860 |
| MmugDNA.19048.1.S1_at | SDA1 domain containing 1 | LOC700863 | 2.05 | 0.0742 |
| MmugDNA.39253.1.S1_at | CDC42 effector protein 5 | LOC718922 | 2.05 | 0.0045 |
| MmugDNA.14544.1.S1_at | — | — | 2.05 | 0.0125 |

-continued

| Probe Set ID | Gene Title | Gene Symbol | Ratio Top verus Bottom | p value Top versus Bottom |
|---|---|---|---|---|
| MmugDNA.4740.1.S1_at | chromosome 2 open reading frame 7 | LOC706052 | 2.04 | 0.0714 |
| MmugDNA.5141.1.S1_at | hypothetical protein LOC715248 | LOC715248 | 2.04 | 0.0755 |
| MmugDNA.19626.1.S1_at | tripartite motif protein 32 (predicted) | LOC705563 | 2.04 | 0.0199 |
| Mmu.2091.3.S1_x_at | HLA class I histocompatibility antigen, A-74 alpha chain precursor (MHC class I antigen A*74) (Aw-74) (Aw-19) /// HLA class I histocompatibility antigen, B-38 alpha chain precursor (MHC class I antigen B*38) (Bw-4) /// major histocom | LOC699243 /// LOC699987 /// LOC715737 /// LOC721022 /// LOC723284 /// LOC723552 /// MAMU-A | 2.04 | 0.0896 |
| MmugDNA.40849.1.S1_at | 7-dehydrocholesterol reductase | DHCR7 | 2.04 | 0.0437 |
| MmugDNA.2414.1.S1_at | plastin 1 | PLS1 | 2.04 | 0.0023 |
| MmugDNA.19830.1.S1_at | glycoprotein hormone alpha 2 | LOC717261 | 2.04 | 0.0977 |
| MmugDNA.27493.1.S1_at | Rho-guanine nucleotide exchange factor (Rho-interacting protein 2) (RhoGEF) (RIP2) | LOC703897 | 2.04 | 0.0532 |
| Mmu.1943.1.S1_at | Tax1 (human T-cell leukemia virus type I) binding protein 1 | LOC698103 | 2.04 | 0.0133 |
| MmunewRS.977.1.S1_s_at | hypothetical protein LOC719873 | LOC719873 | 2.04 | 0.0805 |
| MmugDNA.28230.1.S1_at | intersex-like | LOC698032 | 2.04 | 0.0031 |
| MmugDNA.14009.1.S1_s_at | 5T4 oncofetal trophoblast glycoprotein | LOC693944 | 2.04 | 0.0005 |
| MmugDNA.3795.1.S1_at | dynactin 4 (p62) | DCTN4 | 2.04 | 0.0039 |
| MmugDNA.24691.1.S1_at | selenoprotein I | SELI | 2.04 | 0.0078 |
| MmugDNA.5288.1.S1_at | pyridoxine 5'-phosphate oxidase | PNPO | 2.04 | 0.0025 |
| MmuSTS.2059.1.S1_at | phospholipase C beta 4 isoform a | LOC718418 | 2.04 | 0.0043 |
| MmugDNA.10284.1.S1_at | MORC family CW-type zinc finger 2 | MORC2 | 2.04 | 0.0531 |
| MmugDNA.22142.1.S1_at | — | — | 2.04 | 0.0858 |
| MmuSTS.3730.1.S1_at | SLIT-ROBO Rho GTPase activating protein 2 | SRGAP2 | 2.04 | 0.0146 |
| MmugDNA.21501.1.S1_at | — | — | 2.03 | 0.0030 |
| MmuSTS.4228.1.S1_at | dehydrogenase/reductase (SDR family) member 8 | DHRS8 | 2.03 | 0.0360 |
| MmugDNA.14076.1.S1_s_at | tripartite motif-containing 59 | LOC704829 | 2.03 | 0.0593 |
| MmuSTS.4498.1.S1_at | LGP1 homolog | LOC709656 | 2.03 | 0.0795 |
| MmugDNA.37577.1.S1_at | MAM domain containing glycosylphosphatidylinositol anchor 1 | LOC719423 | 2.03 | 0.0884 |
| MmugDNA.3734.1.S1_at | eukaryotic translation initiation factor 5A2 | LOC695647 | 2.03 | 0.0565 |
| MmugDNA.1893.1.S1_at | RNA guanylyltransferase and 5-phosphatase | LOC721442 | 2.03 | 0.0469 |
| MmugDNA.2395.1.S1_at | — | — | 2.03 | 0.0090 |
| MmugDNA.8455.1.S1_at | tigger transposable element derived 2 | LOC706461 | 2.03 | 0.0283 |
| MmugDNA.20114.1.S1_at | translocating chain-associating membrane protein | TRAM1 | 2.03 | 0.0380 |
| MmugDNA.442.1.S1_at | UDP-Gal:betaGlcNAc beta 1,3-galactosyltransferase 4 | B3GALT4 | 2.03 | 0.0668 |
| MmugDNA.476.1.S1_s_at | programmed cell death 6 interacting protein | LOC706636 | 2.03 | 0.0387 |
| MmugDNA.39070.1.S1_at | androgen-induced 1 | LOC700988 | 2.03 | 0.0113 |
| MmugDNA.38882.1.S1_at | hypothetical protein LOC712812 | LOC712812 | 2.03 | 0.0123 |
| Mmu.6318.1.S1_at | family with sequence similarity 18, member B /// Protein FAM18B | FAM18B /// LOC719298 /// LOC723697 | 2.03 | 0.0170 |
| Mmu.2050.1.S1_s_at | HIG1 domain family member 1A (Hypoxia-inducible gene 1 protein) | HIGD1A | 2.03 | 0.0066 |
| MmugDNA.8048.1.S1_at | calcium/calmodulin-dependent protein kinase II inhibitor 1 | LOC705302 | 2.02 | 0.0005 |
| MmugDNA.10177.1.S1_at | TNF receptor-associated factor 3 | TRAF3 | 2.02 | 0.0434 |
| MmuSTS.735.1.S1_at | — | — | 2.02 | 0.0009 |
| MmugDNA.1551.1.S1_s_at | chloride channel 3 isoform c | LOC694472 | 2.02 | 0.0414 |
| Mmu.7639.1.S1_at | signal transducer and activator of transcription 1 | STAT1 | 2.02 | 0.0894 |
| MmuSTS.2418.1.S1_at | — | — | 2.02 | 0.0452 |
| MmuSTS.88.1.S1_at | — | — | 2.02 | 0.0434 |
| MmugDNA.29466.1.S1_at | phosphorylase kinase, beta | PHKB | 2.02 | 0.0634 |
| MmugDNA.21556.1.S1_at | DNA primase large subunit, 58 kDa | LOC712921 | 2.02 | 0.0187 |
| Mmu.4348.1.S1_at | membrane interacting protein of RGS16 | LOC694849 | 2.02 | 0.0243 |
| MmugDNA.2374.1.S1_at | — | — | 2.02 | 0.0321 |
| MmugDNA.20015.1.S1_at | — | — | 2.02 | 0.0683 |
| MmuSTS.1350.1.S1_at | — | — | 2.02 | 0.0712 |
| MmugDNA.15232.1.S1_at | — | — | 2.02 | 0.0376 |
| MmugDNA.7589.1.S1_at | F-box only protein 24 isoform 1 | LOC719216 | 2.02 | 0.0212 |
| MmugDNA.12745.1.S1_at | integrin, alpha 8 | ITGA8 | 2.02 | 0.0990 |
| MmugDNA.20321.1.S1_at | HIR (histone cell cycle regulation defective, S. cerevisiae) homolog A | LOC719142 | 2.02 | 0.0441 |
| MmuSTS.2829.1.S1_at | — | — | 2.02 | 0.0906 |
| MmugDNA.12571.1.S1_at | Ras-associated protein Rap1 | LOC694037 | 2.02 | 0.0243 |
| MmugDNA.34707.1.S1_at | slit and trk like 6 | LOC699338 | 2.02 | 0.0231 |
| MmugDNA.19770.1.S1_at | tumor differentially expressed 2-like | SERINC2 | 2.01 | 0.0493 |
| MmugDNA.18541.1.S1_at | RAB guanine nucleotide exchange factor (GEF) 1 | LOC695887 | 2.01 | 0.0739 |
| MmugDNA.8837.1.S1_at | karyopherin alpha 4 | KPNA4 | 2.01 | 0.0619 |
| MmugDNA.22626.1.S1_at | dihydrolipoamide S-acetyltransferase (E2 component of pyruvate dehydrogenase complex) | — | 2.01 | 0.0061 |
| MmugDNA.6899.1.S1_at | — | — | 2.01 | 0.0370 |
| MmugDNA.40422.1.S1_at | — | — | 2.01 | 0.0545 |
| MmugDNA.12060.1.S1_at | UDP-glucose:glycoprotein glucosyltransferase 2 | LOC697784 | 2.01 | 0.0461 |
| MmugDNA.23452.1.S1_at | valosin containing protein (p97)/p47 complex interacting protein 1 | LOC703582 | 2.01 | 0.0501 |

| Probe Set ID | Gene Title | Gene Symbol | Ratio Top verus Bottom | p value Top versus Bottom |
|---|---|---|---|---|
| MmugDNA.6995.1.S1_at | — | — | 2.01 | 0.0671 |
| MmugDNA.599.1.S1_at | dpy-19-like 3 | LOC700921 | 2.01 | 0.0681 |
| Mmu.2601.1.S1_at | transmembrane emp24 protein transport domain containing 4 | LOC699105 | 2.01 | 0.0032 |
| MmuSTS.4174.1.S1_at | Cathepsin F precursor (CATSF) | LOC713743 | 2.01 | 0.0025 |
| MmugDNA.26527.1.S1_at | zinc finger protein 697 | LOC715582 | 2.01 | 0.0171 |
| MmunewRS.902.1.S1_at | embigin homolog | LOC702068 | 2.01 | 0.0964 |
| MmugDNA.10114.1.S1_at | odd Oz/ten-m homolog 4 | LOC701138 | 2.01 | 0.0938 |
| MmugDNA.37121.1.S1_at | dishevelled-associated activator of morphogenesis 1 | LOC701706 | 2.01 | 0.0282 |
| MmugDNA.34099.1.S1_at | — | — | 2.00 | 0.0953 |
| MmugDNA.25664.1.S1_at | zinc finger protein 710 | LOC701358 | 2.00 | 0.0791 |
| MmugDNA.33143.1.S1_at | nuclear factor, interleukin 3 regulated | LOC704757 | 2.00 | 0.0359 |
| MmugDNA.4085.1.S1_at | cyclin E1 isoform 1 | LOC700589 | 2.00 | 0.0203 |
| MmuSTS.749.1.S1_at | LysM, putative peptidoglycan-binding, domain containing 1 | LOC709539 | 2.00 | 0.0752 |
| MmugDNA.24820.1.S1_at | casein kinase 1, gamma 3 | CSNK1G3 | 2.00 | 0.0461 |
| MmugDNA.29470.1.S1_at | — | — | 2.00 | 0.0098 |
| MmugDNA.19512.1.S1_at | tenascin C (hexabrachion) | TNC | 92.06 | 0.0005 |
| MmugDNA.6877.1.S1_at | ankyrin repeat and sterile alpha motif domain containing 1B | LOC694033 | 37.28 | 0.0256 |
| MmuSTS.2164.1.S1_s_at | BUB1 budding uninhibited by benzimidazoles 1 homolog | LOC696598 | 30.10 | 0.0998 |
| MmuSTS.355.1.S1_at | podoplanin | PDPN | 29.70 | 0.0578 |
| MmugDNA.23448.1.S1_at | Keratin, type I cytoskeletal 14 (Cytokeratin-14) (CK-14) (Keratin-14) (K14) | LOC703932 | 26.57 | 0.0038 |
| MmugDNA.1670.1.S1_at | cysteine and tyrosine-rich 1 protein precursor | LOC708008 | 25.38 | 0.0325 |
| MmuSTS.4685.1.S1_at | thymidylate synthetase | TYMS | 24.58 | 0.0475 |
| MmugDNA.2975.1.S1_at | DNA polymerase epsilon subunit 2 | LOC707526 | 24.10 | 0.0653 |
| MmugDNA.32729.1.S1_at | antigen identified by monoclonal antibody Ki-67 | MKI67 | 22.59 | 0.0758 |
| MmugDNA.33387.1.S1_at | T-LAK cell-originated protein kinase | PBK | 19.75 | 0.0623 |
| MmuSTS.3275.1.S1_at | Probable dimethyladenosine transferase (S-adenosylmethionine-6-N,N-adenosyl(rRNA) dimethyltransferase) (18S rRNA dimethylase) | — | 19.29 | 0.0213 |
| MmugDNA.13802.1.S1_at | decorin | DCN | 17.00 | 0.0183 |
| MmuSTS.4094.1.S1_at | endothelin receptor type B | EDNRB | 16.58 | 0.0867 |
| MmugDNA.17329.1.S1_at | cell division cycle associated 7 | LOC696474 | 16.22 | 0.0389 |
| MmugDNA.38956.1.S1_at | nucleolar and spindle associated protein 1 | NUSAP1 | 15.82 | 0.0583 |
| MmugDNA.24653.1.S1_at | hyaluronan-mediated motility receptor | HMMR | 14.87 | 0.0507 |
| MmugDNA.12273.1.S1_at | DNA topoisomerase II, alpha isozyme | TOP2A | 14.45 | 0.0012 |
| MmugDNA.17571.1.S1_at | Repetin | LOC712894 | 14.37 | 0.0893 |
| MmugDNA.40742.1.S1_at | cyclin B2 | LOC702184 | 14.17 | 0.0157 |
| MmugDNA.36470.1.S1_at | kinetochore associated 2 | LOC696232 | 13.85 | 0.0725 |
| MmugDNA.19272.1.S1_s_at | sperm associated antigen 5 | SPAG5 | 13.79 | 0.0181 |
| MmuSTS.844.1.S1_at | lymphocyte-specific protein 1 isoform 1 | LOC721048 | 13.75 | 0.0307 |
| MmugDNA.25384.1.S1_at | Ubiquitin-conjugating enzyme E2 C (Ubiquitin-protein ligase C) (Ubiquitin carrier protein C) (UbcH10) | UBE2C | 13.38 | 0.0002 |
| MmuSTS.2303.1.S1_s_at | discs large homolog 7 | LOC696772 | 13.04 | 0.0536 |
| MmuSTS.1203.1.S1_at | alpha 1 type XV collagen | COL15A1 | 12.52 | 0.0022 |
| MmugDNA.11364.1.S1_at | forkhead box M1 isoform 3 | LOC708805 | 12.31 | 0.0691 |
| MmugDNA.18486.1.S1_s_at | serine protease inhibitor, Kazal type 2 (acrosin-trypsin inhibitor) | LOC693946 | 12.30 | 0.0374 |
| MmuSTS.2672.1.S1_at | centromere protein F (350/400 kD) | LOC709000 | 12.11 | 0.0860 |
| MmugDNA.41909.1.S1_at | endomucin | LOC709580 | 12.02 | 0.0215 |
| MmugDNA.24707.1.S1_at | Fibroblast growth factor 19 precursor (FGF-19) | FGF19 | 11.99 | 0.0680 |
| MmugDNA.19464.1.S1_at | ubiquitin-like, containing PHD and RING finger domains, 1 | LOC695531 | 11.73 | 0.0111 |
| MmugDNA.28534.1.S1_at | interleukin 1 receptor, type II | IL1R2 | 11.11 | 0.0247 |
| MmuSTS.3846.1.S1_at | sulfotransferase, estrogen-preferring | SULT1E1 | 11.06 | 0.0880 |
| MmuSTS.1223.1.S1_at | periostin, osteoblast specific factor | POSTN | 10.97 | 0.0077 |
| MmugDNA.10977.1.S1_at | DAZ interacting protein 1 isoform 2 | LOC695529 | 10.94 | 0.0839 |
| MmugDNA.33823.1.S1_s_at | KIAA0101 | KIAA0101 | 10.89 | 0.0363 |
| MmugDNA.35172.1.S1_at | hypothetical protein LOC701037 | LOC701037 | 10.86 | 0.0896 |
| MmuSTS.1955.1.S1_at | baculoviral IAP repeat-containing protein 5 isoform 1 | LOC709565 | 10.69 | 0.0838 |
| MmugDNA.40509.1.S1_at | basonuclin 2 | BNC2 | 10.50 | 0.0020 |
| MmugDNA.33427.1.S1_at | — | — | 10.41 | 0.0428 |
| MmuSTS.3136.1.S1_at | Regulator of G-protein signaling 5 | RGS5 | 10.29 | 0.0555 |
| MmugDNA.4481.1.S1_at | EGF-containing fibulin-like extracellular matrix protein 1 precursor | LOC718984 | 10.22 | 0.0021 |
| MmuSTS.2035.1.S1_at | platelet-derived growth factor receptor alpha | PDGFRA | 10.01 | 0.0496 |
| MmuSTS.3987.1.S1_at | — | SLC27A3 | 9.99 | 0.0105 |
| MmugDNA.8100.1.S1_at | polymerase (DNA directed), epsilon | POLE | 9.87 | 0.0244 |
| MmugDNA.9037.1.S1_at | Nasopharyngeal carcinoma-associated antigen NPC-A-5 | — | 9.87 | 0.0936 |
| MmugDNA.33356.1.S1_at | development and differentiation enhancing factor 1 | LOC695681 | 9.84 | 0.0572 |
| MmugDNA.33929.1.S1_at | trophinin associated protein (tastin) | LOC709931 | 9.71 | 0.0772 |
| MmuSTS.4310.1.S1_at | histone 1, H2ai (predicted) | LOC695891 | 9.64 | 0.0566 |
| MmuSTS.2700.1.S1_at | E2F transcription factor 7 | LOC694423 | 9.61 | 0.0927 |
| MmugDNA.9851.1.S1_at | arachidonate 15-lipoxygenase | ALOX15 | 9.59 | 0.0773 |
| MmugDNA.4983.1.S1_at | collagen, type XXVII, alpha 1 | LOC708451 | 9.38 | 0.0390 |
| MmuSTS.2858.1.S1_at | SRY (sex determining region Y)-box 15 | SOX15 | 9.38 | 0.0147 |
| MmunewRS.17.1.S1_at | aurora kinase B | AURKB | 9.35 | 0.0340 |
| MmuSTS.1534.1.S1_at | — | KIF20A | 9.26 | 0.0827 |

-continued

| Probe Set ID | Gene Title | Gene Symbol | Ratio Top verus Bottom | p value Top versus Bottom |
|---|---|---|---|---|
| MmugDNA.34877.1.S1_at | melanoma-associated chondroitin sulfate proteoglycan 4 | LOC713086 | 9.25 | 0.0703 |
| MmuSTS.1125.1.S1_at | snail 2 | SNAI2 | 9.21 | 0.0089 |
| MmugDNA.37680.1.S1_at | WD repeat and HMG-box DNA binding protein 1 | WDHD1 | 9.11 | 0.0234 |
| MmugDNA.5089.1.S1_at | growth factor receptor-bound protein 10 isoform a | LOC694786 | 9.10 | 0.0634 |
| MmugDNA.40702.1.S1_at | enolase superfamily member 1 | ENOSF1 | 9.03 | 0.0552 |
| Mmu.11047.2.S1_s_at | Ig gamma-1 chain C region | LOC711303 | 8.99 | 0.0572 |
| MmuSTS.4834.1.S1_at | glioma-associated oncogene homolog 1 | GLI1 | 8.98 | 0.0230 |
| MmugDNA.32726.1.S1_at | Antigen KI-67 | LOC705021 | 8.97 | 0.0000 |
| MmugDNA.25678.1.S1_at | EGF-like-domain, multiple 9 | LOC700106 | 8.94 | 0.0026 |
| MmuSTS.3919.1.S1_s_at | regulator of G-protein signaling 10 isoform a | LOC703125 | 8.93 | 0.0254 |
| MmugDNA.23023.1.S1_at | hypothetical protein LOC702839 | LOC702839 | 8.93 | 0.0988 |
| MmugDNA.13565.1.S1_at | kinesin family member 11 | KIF11 | 8.83 | 0.0906 |
| MmuSTS.1877.1.S1_at | collagen, type XVIII, alpha 1 | COL18A1 | 8.81 | 0.0147 |
| MmugDNA.34601.1.S1_at | Ribosomal protein S6 | RPS6 | 8.79 | 0.0857 |
| MmugDNA.33493.1.S1_at | tumor protein p73-like | LOC703997 | 8.70 | 0.0516 |
| MmugDNA.13626.1.S1_at | prostaglandin I2 (prostacyclin) synthase /// prostaglandin I2 (prostacyclin) synthase | PTGIS | 8.67 | 0.0049 |
| MmugDNA.15250.1.S1_at | centromere protein A, 17 kDa | CENPA | 8.66 | 0.0498 |
| MmugDNA.32562.1.S1_s_at | Hemoglobin theta-1 subunit (Hemoglobin theta-1 chain) (Theta-1-globin) /// alpha 2 globin | HBQ1 /// LOC701930 | 8.53 | 0.0646 |
| MmugDNA.31059.1.S1_at | Securin (Pituitary tumor-transforming protein 1) (Tumor transforming protein 1) (Esp1-associated protein) (hPTTG) | PTTG1 | 8.52 | 0.0329 |
| MmugDNA.24523.1.S1_at | cell division cycle associated 2 | LOC711581 | 8.46 | 0.0921 |
| MmugDNA.33436.1.S1_at | thymosin-like 8 | LOC693501 | 8.40 | 0.0296 |
| MmugDNA.978.1.S1_at | CDNA FLJ41452 fis, clone BRSTN2010363 | — | 8.22 | 0.0795 |
| MmugDNA.21584.1.S1_s_at | — | — | 8.21 | 0.0000 |
| MmuSTS.2916.1.S1_at | iroquois homeobox protein 2 | IRX2 | 8.18 | 0.0698 |
| MmugDNA.7359.1.S1_s_at | TYRO protein tyrosine kinase binding protein | TYROBP | 8.15 | 0.0468 |
| MmugDNA.33098.1.S1_at | homeobox A3 isoform a | LOC699979 | 8.11 | 0.0577 |
| MmugDNA.18373.1.S1_at | hypothetical protein LOC697150 | LOC697150 | 8.11 | 0.0360 |
| MmugDNA.8851.1.S1_at | E2F transcription factor 2 | E2F2 | 8.10 | 0.0630 |
| MmugDNA.21962.1.S1_at | inhibin beta A | INHBA | 8.09 | 0.0493 |
| MmuSTS.1592.1.S1_at | neuritin | LOC722968 | 8.08 | 0.0300 |
| MmuSTS.4722.1.S1_at | thyroid hormone receptor interactor 13 | LOC709328 | 7.99 | 0.0914 |
| MmugDNA.16663.1.S1_at | alpha 1 type VII collagen | COL7A1 | 7.91 | 0.0603 |
| MmugDNA.5836.1.S1_at | pregnancy-associated plasma protein A, pappalysin 1 | PAPPA | 7.58 | 0.0602 |
| MmuSTS.2073.1.S1_at | peripheral myelin protein 22 | LOC693527 | 7.57 | 0.0237 |
| MmugDNA.29315.1.S1_at | DEP domain containing 1a | LOC701888 | 7.46 | 0.0609 |
| MmuSTS.4833.1.S1_at | gap junction protein, beta 5 (connexin 31.1) | LOC711078 | 7.46 | 0.0501 |
| MmugDNA.36119.1.S1_at | hypothetical protein FLJ10357 | FLJ10357 | 7.46 | 0.0549 |
| MmuSTS.4814.1.S1_at | gamma-aminobutyric acid (GABA) A receptor, epsilon | GABRE | 7.35 | 0.0325 |
| MmugDNA.29829.1.S1_at | hypothetical protein LOC718022 | LOC718022 | 7.26 | 0.0181 |
| MmugDNA.10011.1.S1_at | establishment of cohesion 1 homolog 2 | LOC713186 | 7.23 | 0.0759 |
| MmugDNA.15721.1.S1_at | DNA polymerase theta | POLQ | 7.21 | 0.0495 |
| MmugDNA.23132.1.S1_s_at | muscleblind-like 1 | LOC708735 | 7.18 | 0.0870 |
| MmugDNA.16746.1.S1_at | Transcribed locus | — | 7.13 | 0.0397 |
| MmugDNA.9813.1.S1_at | steroid-sensitive protein 1 | LOC708504 | 7.09 | 0.0041 |
| MmugDNA.42865.1.S1_at | cell division cycle 2 protein | CDC2 | 7.09 | 0.0944 |
| MmuSTS.673.1.S1_s_at | chromatin assembly factor 1, subunit A (p150) | LOC721861 | 7.08 | 0.0407 |
| MmugDNA.42327.1.S1_at | fibulin 1 | FBLN1 | 7.05 | 0.0157 |
| MmuSTS.3146.1.S1_s_at | minichromosome maintenance deficient protein 5 | MCM5 | 7.02 | 0.0229 |
| MmugDNA.9770.1.S1_at | G-2 and S-phase expressed 1 | LOC714207 | 7.02 | 0.0673 |
| MmuSTS.4144.1.S1_at | glutathione transferase A5 | — | 7.01 | 0.0016 |
| MmugDNA.1499.1.S1_at | Pigment epithelium-derived factor precursor (PEDF) (EPC-1) | LOC721262 | 6.99 | 0.0750 |
| MmuSTS.1535.1.S1_at | kinesin family member 2C | KIF2C | 6.86 | 0.0738 |
| MmuSTS.3642.1.S1_at | fibroblast growth factor receptor 2 | FGFR2 | 6.84 | 0.0157 |
| MmugDNA.3959.1.S1_at | hypothetical protein LOC701440 | LOC701440 | 6.74 | 0.0674 |
| MmugDNA.22744.1.S1_s_at | — | — | 6.73 | 0.0581 |
| MmugDNA.10643.1.S1_s_at | Apolipoprotein D precursor (Apo-D) (ApoD) | LOC709223 | 6.71 | 0.0197 |
| MmugDNA.41251.1.S1_at | hypothetical protein LOC712701 | LOC712701 | 6.69 | 0.0805 |
| MmugDNA.25121.1.S1_at | pancreatic ribonuclease | RNASE1 | 6.65 | 0.0350 |
| MmugDNA.18755.1.S1_at | hypothetical protein LOC200030 | LOC200030 | 6.64 | 0.0332 |
| MmuSTS.644.1.S1_at | citron | LOC695846 | 6.63 | 0.0190 |
| MmugDNA.35559.1.S1_at | Histone H1.2 (H1d) | LOC698238 | 6.62 | 0.0050 |
| MmugDNA.37528.1.S1_at | — | — | 6.57 | 0.0211 |
| MmugDNA.41268.1.S1_at | cyclin B1 | CCNB1 | 6.55 | 0.0927 |
| MmugDNA.40366.1.S1_at | solute carrier family 24, member 5 | SLC24A5 | 6.55 | 0.0000 |
| Mmu.5727.1.S1_at | G1/S-specific cyclin-D2 | CCND2 | 6.53 | 0.0003 |
| MmugDNA.9497.1.S1_at | kinesin family member C1 | KIFC1 | 6.44 | 0.0172 |
| MmuSTS.1904.1.S1_at | dicer1 | LOC702516 | 6.43 | 0.0387 |
| MmugDNA.25436.1.S1_at | minichromosome maintenance protein 3 | MCM3 | 6.40 | 0.0000 |
| MmuSTS.1881.1.S1_at | alpha 3 type VI collagen isoform 5 precursor | LOC694701 | 6.38 | 0.0086 |
| MmuSTS.4021.1.S1_at | cytochrome P450, family 4, subfamily B, polypeptide 1 | LOC709290 | 6.35 | 0.0285 |
| MmugDNA.35290.1.S1_at | hypothetical protein LOC696863 | LOC696863 | 6.33 | 0.0371 |
| MmugDNA.32826.1.S1_at | kallikrein 8 isoform 2 | — | 6.32 | 0.0948 |

| Probe Set ID | Gene Title | Gene Symbol | Ratio Top verus Bottom | p value Top versus Bottom |
|---|---|---|---|---|
| MmugDNA.36260.1.S1_at | EGF, latrophilin and seven transmembrane domain containing 1 | ELTD1 | 6.31 | 0.0018 |
| MmuSTS.4328.1.S1_at | plasminogen activator inhibitor type 1, member 2 | SERPINE2 | 6.28 | 0.0044 |
| MmugDNA.41228.1.S1_at | NADP-dependent leukotriene B4 12-hydroxydehydrogenase /// NADP-dependent leukotriene B4 12-hydroxydehydrogenase (15-oxoprostaglandin 13-reductase) | LTB4DH | 6.27 | 0.0527 |
| MmugDNA.31506.1.S1_at | 3-hydroxy-3-methylglutaryl-Coenzyme A synthase 2 (mitochondrial) | HMGCS2 | 6.25 | 0.0306 |
| MmuSTS.3741.1.S1_at | tyrosine phosphatase, receptor-type, Z polypeptide 1 | PTPRZ1 | 6.23 | 0.0829 |
| MmugDNA.20272.1.S1_at | cysteine-rich, angiogenic inducer, 61 | CYR61 | 6.21 | 0.0552 |
| MmugDNA.14075.1.S1_at | Restin | — | 6.21 | 0.0576 |
| MmugDNA.35622.1.S1_at | Kinesin family member 14 | KIF14 | 6.21 | 0.0036 |
| MmugDNA.19983.1.S1_s_at | testis derived transcript | CAV1 | 6.20 | 0.0330 |
| MmuSTS.1023.1.S1_at | — | SCN4B | 6.19 | 0.0994 |
| MmugDNA.42793.1.S1_at | calcium/calmodulin-dependent protein kinase kinase 1, alpha | CAMKK1 | 6.18 | 0.0467 |
| MmugDNA.23406.1.S1_at | SH3 domain containing ring finger 2 | SH3RF2 | 6.17 | 0.0135 |
| MmugDNA.19771.1.S1_at | Transcribed locus | — | 6.16 | 0.0821 |
| MmuSTS.1779.1.S1_at | NIMA (never in mitosis gene a)-related kinase 2 | NEK2 | 6.16 | 0.0886 |
| MmugDNA.7491.1.S1_at | Biliverdin reductase A | — | 6.13 | 0.0066 |
| MmugDNA.30433.1.S1_at | SHC SH2-domain binding protein 1 | LOC716009 | 6.05 | 0.0001 |
| MmugDNA.13151.1.S1_at | Probable G-protein coupled receptor 92 | GPR92 | 6.04 | 0.0268 |
| MmugDNA.39863.1.S1_at | chromosome 18 open reading frame 24 | C18orf24 | 5.99 | 0.0496 |
| MmugDNA.34856.1.S1_at | RNA binding motif protein 6 | RBM6 | 5.96 | 0.0446 |
| Mmu.16175.1.S1_at | CK230007 | — | 5.95 | 0.0684 |
| Mmu.11188.1.S1_at | caldesmon 1 isoform 4 | LOC707050 | 5.93 | 0.0513 |
| MmuSTS.2639.1.S1_at | FAT tumor suppressor 2 precursor | LOC713698 | 5.91 | 0.0047 |
| MmugDNA.22443.1.S1_at | nuclear factor I/B | NFIB | 5.88 | 0.0187 |
| MmugDNA.19397.1.S1_at | Chromosome 2 open reading frame 17 | C2orf17 | 5.88 | 0.0483 |
| MmugDNA.26212.1.S1_at | ephrin-B1 | EFNB1 | 5.88 | 0.0634 |
| MmugDNA.27687.1.S1_s_at | guanine nucleotide binding protein gamma 11 | LOC700606 | 5.87 | 0.0207 |
| MmugDNA.42502.1.S1_at | Activity-dependent neuroprotector | ADNP | 5.86 | 0.0016 |
| MmugDNA.35031.1.S1_at | Transcription factor COE1 (OE-1) (O/E-1) (Early B-cell factor) (Olfactory neuronal transcription factor) (Olf-1) | LOC694086 | 5.82 | 0.0007 |
| Mmu.1262.1.A1_at | — | MEF2C | 5.82 | 0.0164 |
| MmuSTS.2987.1.S1_at | MADS box transcription enhancer factor 2, polypeptide C (myocyte enhancer factor 2C) | LOC694992 | 5.77 | 0.0370 |
| MmugDNA.24078.1.S1_at | hypothetical protein LOC699417 | LOC699417 | 5.76 | 0.0711 |
| MmugDNA.40153.1.S1_at | olfactomedin-like 2A | OLFML2A | 5.74 | 0.0254 |
| MmugDNA.37742.1.S1_at | oncostatin M receptor | LOC693569 | 5.74 | 0.0716 |
| MmugDNA.8988.1.S1_at | hypothetical protein LOC143381 | LOC143381 | 5.70 | 0.0738 |
| MmugDNA.18189.1.S1_at | Insulin-like growth factor-binding protein 4 precursor (IGFBP-4) (IBP-4) (IGF-binding protein 4) | LOC700963 | 5.69 | 0.0440 |
| MmugDNA.8529.1.S1_at | Secretory granule proteoglycan core protein precursor (Platelet proteoglycan core protein) (P.PG) (Hematopoetic proteoglycan core protein) (Serglycin) | PRG1 | 5.63 | 0.0001 |
| MmugDNA.23178.1.S1_at | Chromobox homolog 5 (HP1 alpha homolog, Drosophila) | CBX5 | 5.59 | 0.0958 |
| MmugDNA.36354.1.S1_at | fibroblast growth factor receptor 3 | FGFR3 | 5.59 | 0.0298 |
| MmugDNA.39673.1.S1_at | SRY (sex determining region Y)-box 6 | SOX6 | 5.57 | 0.0064 |
| MmuSTS.4420.1.S1_at | TPX2, microtubule-associated protein homolog | TPX2 | 5.54 | 0.0556 |
| MmugDNA.12787.1.S1_at | tensin /// tensin | TNS | 5.54 | 0.0009 |
| MmugDNA.35052.1.S1_at | Dermatopontin precursor (Tyrosine-rich acidic matrix protein) (TRAMP) | LOC700181 | 5.51 | 0.0038 |
| MmugDNA.27071.1.S1_at | retinoic acid receptor responder (tazarotene induced) 2 | LOC704993 | 5.50 | 0.0557 |
| MmugDNA.21100.1.S1_at | laminin alpha 3 subunit isoform 1 | LOC701313 | 5.49 | 0.0087 |
| MmugDNA.37305.1.S1_at | FRA10AC1 protein | LOC700389 | 5.48 | 0.0630 |
| MmugDNA.17614.1.S1_at | T-boxs 5 | TBX5 | 5.48 | 0.0963 |
| MmugDNA.23701.1.S1_at | — | — | 5.46 | 0.0105 |
| MmugDNA.6672.1.S1_at | dystonin | DST | 5.46 | 0.0844 |
| MmugDNA.40463.1.S1_at | MRNA; cDNA DKFZp686B0610 (from clone DKFZp686B0610) | — | 5.44 | 0.0808 |
| MmuSTS.2214.1.S1_at | six transmembrane epithelial antigen of the prostate | STEAP1 | 5.44 | 0.0063 |
| MmuSTS.1928.1.S1_at | myeloblastosis proto-oncogene product isoform 2 | LOC712321 | 5.41 | 0.0003 |
| MmugDNA.35645.1.S1_s_at | Rho GTPase activating protein 9 | ARHGAP9 | 5.40 | 0.0030 |
| MmugDNA.14897.1.S1_at | AXL receptor tyrosine kinase isoform 2 | LOC706123 | 5.35 | 0.0181 |
| MmugDNA.1117.1.S1_at | Friend leukemia virus integration 1 | FLI1 | 5.35 | 0.0975 |
| MmuSTS.4424.1.S1_at | frizzled 7 | LOC703064 | 5.31 | 0.0161 |
| MmugDNA.25887.1.S1_s_at | filamin 1 (actin-binding protein-280) | FLNA | 5.29 | 0.0256 |
| MmugDNA.40242.1.S1_at | LOC441301 | — | 5.27 | 0.0914 |
| MmugDNA.21548.1.S1_s_at | anthrax toxin receptor 2 | LOC696513 | 5.26 | 0.0654 |
| MmugDNA.36181.1.S1_at | aquaporin 1 | AQP1 | 5.26 | 0.0435 |
| MmugDNA.14767.1.S1_at | FRAS1 related extracellular matrix protein 2 | FREM2 | 5.25 | 0.0835 |
| MmugDNA.33751.1.S1_at | Dexamethasone-induced Ras-related protein 1 (Activator of G-protein signaling 1) | RASD1 | 5.25 | 0.0984 |
| MmugDNA.25691.1.S1_at | solute carrier family 16 (monocarboxylic acid transporters), member 6 | SLC16A6 | 5.25 | 0.0466 |

| Probe Set ID | Gene Title | Gene Symbol | Ratio Top verus Bottom | p value Top versus Bottom |
|---|---|---|---|---|
| MmuSTS.1922.1.S1_at | v-ets erythroblastosis virus E26 oncogene homolog 1 | ETS1 | 5.23 | 0.0322 |
| MmugDNA.3558.1.S1_at | serine/threonine protein kinase 6 | AURKA | 5.22 | 0.0358 |
| MmugDNA.4124.1.S1_at | cell division cycle associated 5 | LOC721995 | 5.21 | 0.0575 |
| MmugDNA.2333.1.S1_at | synaptopodin | SYNPO | 5.21 | 0.0006 |
| MmuSTS.2701.1.S1_at | epidermal growth factor-like protein 6 precursor | LOC711280 | 5.20 | 0.0491 |
| MmugDNA.40392.1.S1_at | lumican | LUM | 5.19 | 0.0120 |
| MmugDNA.21491.1.S1_at | CDNA clone IMAGE: 6043059, partial cds | — | 5.19 | 0.0980 |
| MmugDNA.22192.1.S1_at | vitamin K-dependent protein S precursor | LOC694845 | 5.18 | 0.0750 |
| MmugDNA.28039.1.S1_at | Chromosome 10 open reading frame 18 | C10orf18 | 5.17 | 0.0535 |
| MmugDNA.23945.1.S1_at | mitochondrial ribosomal protein L54 | LOC713878 | 5.16 | 0.0885 |
| MmugDNA.28350.1.S1_at | Heparin-binding growth factor 1 precursor (HBGF-1) (Acidic fibroblast growth factor) (aFGF) (Beta-endothelial cell growth factor) (ECGF-beta) | FGF1 | 5.16 | 0.0183 |
| MmugDNA.4851.1.S1_at | angiotensin II receptor, type 1 | LOC712773 | 5.15 | 0.0653 |
| MmugDNA.34285.1.S1_at | nitric oxide synthase trafficking isoform 1 | — | 5.14 | 0.0724 |
| MmugDNA.19357.1.S1_at | Transcribed locus, strongly similar to XP_496055.1 similar to p40 [Homo sapiens] | — | 5.13 | 0.0676 |
| Mmu.14966.1.S1_at | EH domain binding protein 1 | LOC693902 | 5.12 | 0.0757 |
| MmugDNA.42808.1.S1_at | transcription factor 8 (represses interleukin 2 expression) | TCF8 | 5.11 | 0.0254 |
| MmugDNA.30007.1.S1_at | coiled-coil domain containing 102A | LOC704988 | 5.10 | 0.0846 |
| MmugDNA.5184.1.S1_s_at | beta globin | LOC715559 | 5.10 | 0.0122 |
| MmuSTS.2069.1.S1_at | Rac GTPase activating protein 1 | LOC711887 | 5.06 | 0.0587 |
| MmugDNA.15651.1.S1_at | steroid sulfatase (microsomal), arylsulfatase C, isozyme S | STS | 5.04 | 0.0307 |
| MmugDNA.19465.1.S1_at | Transcribed locus, weakly similar to NP_060190.1 signal-transducing adaptor protein-2 [Homo sapiens] | — | 5.03 | 0.0125 |
| MmugDNA.27239.1.S1_s_at | retinol-binding protein 4, plasma precursor | LOC701270 | 5.03 | 0.0423 |
| MmugDNA.43409.1.S1_at | solute carrier family 27 member 3 | LOC718424 | 5.02 | 0.0762 |
| MmugDNA.13155.1.S1_at | chondroitin sulfate proteoglycan 2 (versican) | LOC712365 | 5.00 | 0.0576 |
| MmugDNA.18099.1.S1_at | complement component 3 | C3 | 4.97 | 0.0146 |
| MmuSTS.2151.1.S1_at | branched chain aminotransferase 1, cytosolic | LOC707321 | 4.96 | 0.0031 |
| MmunewRS.412.1.S1_s_at | solute carrier family 9 (sodiumhydrogen exchanger), isoform 4 (SLC9A4), mRNA | SLC9A4 | 4.95 | 0.0130 |
| MmugDNA.9733.1.S1_at | Muscleblind-like (Drosophila) | MBNL1 | 4.95 | 0.0396 |
| MmugDNA.20784.1.S1_at | quaking homolog, KH domain RNA binding (mouse) | QKI | 4.95 | 0.0001 |
| MmuSTS.2287.1.S1_at | peroxisome proliferator-activated receptor gamma 1-b | PPARGAMMA | 4.93 | 0.0218 |
| MmuSTS.1783.1.S1_at | nuclear factor I/A | LOC694022 | 4.92 | 0.0568 |
| MmugDNA.5690.1.S1_at | septin 4 isoform 3 | LOC714724 | 4.92 | 0.0427 |
| MmugDNA.23105.1.S1_s_at | Ig lambda chain V-II region BUR /// Ig lambda chain V-II region MGC /// Immunoglobulin lambda-like polypeptide 1 precursor (Immunoglobulin-related protein 14.1) (Immunoglobulin omega polypeptide) (Ig lambda-5) (CD179b antigen) /// Ig lambda chain V-II region NIG-84 | LOC706778 /// LOC707940 /// LOC708547 /// LOC720711 | 4.91 | 0.0034 |
| MmugDNA.39956.1.S1_at | Hairless homolog (mouse) | HR | 4.90 | 0.0242 |
| MmuSTS.2029.1.S1_at | polo-like kinase | PLK1 | 4.88 | 0.0403 |
| MmuSTS.154.1.S1_x_at | — | BTN3A2 | 4.87 | 0.0977 |
| MmugDNA.35115.1.S1_at | heparan sulfate proteoglycan 2 | HSPG2 | 4.85 | 0.0002 |
| MmugDNA.964.1.S1_at | SH3-domain binding protein 1 | SH3BP1 | 4.83 | 0.0803 |
| MmugDNA.9449.1.S1_at | WD repeat domain 76 | LOC711191 | 4.83 | 0.0376 |
| MmuSTS.165.1.S1_at | inhibitor of DNA binding 3 | LOC710290 | 4.82 | 0.0001 |
| MmugDNA.43567.1.S1_at | Homo sapiens, Similar to hypothetical protein FLJ21936, clone IMAGE: 4044084, mRNA | — | 4.82 | 0.0615 |
| MmugDNA.40816.1.S1_at | tumor necrosis factor, alpha-induced protein 9 | TNFAIP9 | 4.82 | 0.0196 |
| MmugDNA.23454.1.S1_at | 15-hydroxyprostaglandin dehydrogenase [NAD+] (PGDH) (Prostaglandin dehydrogenase 1) | HPGD | 4.82 | 0.0099 |
| MmugDNA.38346.1.S1_at | phosphoserine aminotransferase isoform 1 | LOC706387 | 4.81 | 0.0646 |
| MmugDNA.28728.1.S1_at | KIAA0485 protein | KIAA0485 | 4.80 | 0.0069 |
| MmuSTS.4004.1.S1_at | thrombospondin 1 precursor | LOC705413 | 4.78 | 0.0185 |
| MmugDNA.23996.1.S1_at | alpha 2 type I collagen | LOC700359 | 4.75 | 0.0161 |
| MmugDNA.18235.1.S1_at | TGFB-induced factor 2 (TALE family homeobox) | TGIF2 | 4.72 | 0.0241 |
| MmugDNA.30842.1.S1_s_at | Transgelin (Smooth muscle protein 22-alpha) (SM22-alpha) (WS3-10) (22 kDa actin-binding protein) | TAGLN | 4.71 | 0.0509 |
| MmugDNA.822.1.S1_at | Transcribed locus, moderately similar to XP_517655.1 similar to KIAA0825 protein [Pan troglodytes] | — | 4.71 | 0.0218 |
| MmugDNA.19564.1.S1_s_at | melanoma cell adhesion molecule | LOC708449 | 4.71 | 0.0221 |
| MmugDNA.26005.1.S1_at | thyroglobulin | TG | 4.71 | 0.0150 |
| MmugDNA.9817.1.S1_at | Likely ortholog of mouse TORC2-specific protein AVO3 (S. cerevisiae) | AVO3 | 4.70 | 0.0316 |
| MmugDNA.12099.1.S1_at | transducer of ERBB2, 1 | TOB1 | 4.70 | 0.0197 |
| MmugDNA.20357.1.S1_at | interleukin 1 receptor, type I | IL1R1 | 4.69 | 0.0159 |
| MmugDNA.38818.1.S1_at | adipocyte enhancer binding protein 1 precursor | LOC699977 | 4.67 | 0.0329 |
| MmugDNA.34995.1.S1_at | collagen, type I, alpha 1 | COL1A1 | 4.66 | 0.0032 |
| MmugDNA.4218.1.S1_at | four and a half LIM domains 1 | FHL1 | 4.65 | 0.0322 |
| MmuSTS.869.1.S1_at | dysferlin | DYSF | 4.64 | 0.0604 |
| MmugDNA.31007.1.S1_s_at | fibronectin 1 | FN1 | 4.63 | 0.0000 |
| MmugDNA.21203.1.S1_x_at | amyloid beta (A4) precursor protein-binding, family B, member 1 interacting protein | LOC707383 | 4.61 | 0.0921 |

-continued

| Probe Set ID | Gene Title | Gene Symbol | Ratio Top verus Bottom | p value Top versus Bottom |
|---|---|---|---|---|
| MmugDNA.16224.1.S1_s_at | hypothetical protein LOC704308 | LOC704308 | 4.60 | 0.0117 |
| MmugDNA.22096.1.S1_at | Galectin-1 (Lectin galactoside-binding soluble 1) (Beta-galactoside-binding lectin L-14-I) (Lactose-binding lectin 1) (S-Lac lectin 1) (Galaptin) (14 kDa lectin) (HPL) (HBL) (Putative MAPK-activating protein MP12) | LGALS1 | 4.59 | 0.0571 |
| MmugDNA.26778.1.S1_at | Hypothetical protein similar to KIAA0187 gene product | LOC96610 | 4.58 | 0.0395 |
| MmugDNA.16831.1.S1_s_at | synuclein, gamma (breast cancer-specific protein 1) | LOC696535 | 4.58 | 0.0058 |
| MmugDNA.35261.1.S1_at | Fc fragment of IgG, low affinity IIa, receptor (CD32) | FCGR2A | 4.58 | 0.0713 |
| MmugDNA.31316.1.S1_at | hypothetical protein LOC702054 /// hypothetical protein LOC702584 | LOC702054 /// LOC702584 | 4.57 | 0.0204 |
| MmugDNA.30287.1.S1_at | GTPase, IMAP family member 6 isoform 1 | LOC713565 | 4.57 | 0.0897 |
| MmugDNA.5299.1.S1_at | Rho-related BTB domain containing 1 | RHOBTB1 | 4.56 | 0.0702 |
| MmugDNA.30627.1.S1_s_at | jub, ajuba homolog isoform 1 | LOC712865 | 4.55 | 0.0343 |
| MmuSTS.220.1.S1_at | SCL/TAL1 interrupting locus | LOC710099 | 4.54 | 0.0619 |
| MmugDNA.33541.1.S1_at | calpain small subunit 2 | LOC698721 | 4.54 | 0.0190 |
| MmugDNA.10511.1.S1_at | mucin 15 | LOC700194 | 4.53 | 0.0419 |
| MmuSTS.90.1.S1_at | high mobility group AT-hook 2 | HMGA2 | 4.53 | 0.0315 |
| MmugDNA.22320.1.S1_s_at | pregnancy specific beta-1-glycoprotein 4 | PSG4 | 4.52 | 0.0011 |
| MmugDNA.6347.1.S1_at | runt-related transcription factor 3 | RUNX3 | 4.51 | 0.0494 |
| MmugDNA.21974.1.S1_at | keratin 5 | KRT3 | 4.50 | 0.0002 |
| MmugDNA.21584.1.S1_at | — | — | 4.49 | 0.0045 |
| MmugDNA.19709.1.S1_x_at | growth hormone 1 | GH1 | 4.48 | 0.0372 |
| MmuSTS.4832.1.S1_at | connexin 31 | LOC710834 | 4.48 | 0.0144 |
| MmugDNA.24059.1.S1_at | Transcribed locus | — | 4.47 | 0.0651 |
| MmugDNA.32484.1.S1_s_at | tissue inhibitor of metalloproteinase 3 (Sorsby fundus dystrophy, pseudoinflammatory) | TIMP3 | 4.47 | 0.0150 |
| MmugDNA.35122.1.S1_at | Discoidin domain receptor family, member 2 | DDR2 | 4.47 | 0.0050 |
| MmugDNA.18271.1.S1_at | CDNA FLJ44429 fis, clone UTERU2015653 | — | 4.46 | 0.0001 |
| MmuSTS.2362.1.S1_at | S100-B (S100 calcium-binding protein B) (S-100 protein beta subunit) (S-100 protein beta chain) | S100B | 4.45 | 0.0185 |
| MmugDNA.41157.1.S1_at | matrix Gla protein | MGP | 4.44 | 0.0252 |
| MmuSTS.934.1.S1_at | four jointed box 1 | LOC717833 | 4.44 | 0.0328 |
| MmugDNA.30788.1.S1_at | COBL-like 1 | LOC702934 | 4.41 | 0.0521 |
| MmugDNA.1969.1.S1_at | hypothetical protein LOC714686 | LOC714686 | 4.40 | 0.0385 |
| MmuSTS.112.1.S1_at | Asporin precursor (Periodontal ligament-associated protein 1) (PLAP-1) | LOC718125 | 4.40 | 0.0318 |
| MmugDNA.13768.1.S1_at | CDNA: FLJ22256 fis, clone HRC02860 | — | 4.39 | 0.0198 |
| MmugDNA.28759.1.S1_at | — | — | 4.39 | 0.0482 |
| MmugDNA.15862.1.S1_at | CDC28 protein kinase 2 | LOC697324 | 4.39 | 0.0028 |
| MmugDNA.22453.1.S1_at | keratin 13 isoform b | LOC706830 | 4.38 | 0.0080 |
| MmugDNA.34784.1.S1_at | CDNA FLJ12091 fis, clone HEMBB1002582 | — | 4.38 | 0.0522 |
| MmugDNA.41887.1.S1_at | MYB-related protein B | MYBL2 | 4.36 | 0.0821 |
| MmugDNA.17000.1.S1_at | Activating transcription factor 7 | ATF7 | 4.36 | 0.0972 |
| MmugDNA.29263.1.S1_at | Glycoprotein hormones alpha chain precursor (Anterior pituitary glycoprotein hormones common alpha subunit) (Follitropin alpha chain) (Follicle-stimulating hormone alpha chain) (FSH-alpha) (Lutropin alpha chain) (Luteinizing hormone alph . . . | LOC697859 | 4.34 | 0.0348 |
| MmugDNA.21650.1.S1_at | Epidermal growth factor receptor (erythroblastic leukemia viral (v-erb-b) oncogene homolog, avian) | EGFR | 4.33 | 0.0164 |
| MmugDNA.24420.1.S1_at | kidney predominant protein NCU-G1 | LOC719468 | 4.33 | 0.0291 |
| MmugDNA.26915.1.S1_at | follistatin | FST | 4.32 | 0.0314 |
| MmugDNA.35764.1.S1_s_at | High affinity immunoglobulin epsilon receptor gamma-subunit precursor (FceRI gamma) (IgE Fc receptor gamma-subunit) (Fc-epsilon RI-gamma) | LOC720291 | 4.32 | 0.0456 |
| MmugDNA.23015.1.S1_at | Y43E12A.2 | LOC702083 | 4.32 | 0.0536 |
| MmuSTS.3532.1.S1_at | CD53 antigen | LOC702350 | 4.31 | 0.0013 |
| MmuSTS.1975.1.S1_at | nuclear receptor subfamily 3, group C, member 1 | NR3C1 | 4.31 | 0.0356 |
| MmugDNA.30097.1.S1_at | coronin, actin binding protein, 1C | CORO1C | 4.30 | 0.0925 |
| MmugDNA.16359.1.S1_at | deleted in liver cancer 1 | DLC1 | 4.30 | 0.0527 |
| MmugDNA.23180.1.S1_at | cartilage associated protein | CRTAP | 4.29 | 0.0637 |
| MmugDNA.11572.1.S1_at | chemokine (C—X—C motif) ligand 12 (stromal cell-derived factor 1) | CXCL12 | 4.28 | 0.0367 |
| MmuSTS.3488.1.S1_at | CD48 antigen precursor (B-lymphocyte activation marker BLAST-1) (BCM1 surface antigen) (Leucocyte antigen MEM-102) (TCT.1) | CD48 | 4.28 | 0.0930 |
| Mmu.9771.1.S1_at | osteomodulin | OMD | 4.28 | 0.0946 |
| MmugDNA.34344.1.S1_at | Neuron navigator 1 | NAV1 | 4.27 | 0.0395 |
| MmugDNA.37179.1.S1_at | CG10889-PA | LOC714837 | 4.27 | 0.0079 |
| MmugDNA.985.1.S1_at | pyruvate dehydrogenase kinase 4 | PDK4 | 4.25 | 0.0509 |
| MmugDNA.19882.1.S1_at | potassium channel tetramerisation domain containing 15 | LOC704761 | 4.25 | 0.0224 |
| MmuSTS.3690.1.S1_at | collagen, type VI, alpha 1 | COL6A1 | 4.23 | 0.0002 |
| MmuSTS.3265.1.S1_at | RGM domain family, member A | LOC712949 | 4.23 | 0.0001 |
| MmugDNA.7509.1.S1_at | hypothetical protein LOC710962 | LOC710962 | 4.22 | 0.0691 |
| MmugDNA.15267.1.S1_at | RNA binding protein with multiple splicing 2 | LOC712536 | 4.22 | 0.0002 |
| MmugDNA.15951.1.S1_at | reticulon 4 | RTN4 | 4.21 | 0.0366 |

-continued

| Probe Set ID | Gene Title | Gene Symbol | Ratio Top verus Bottom | p value Top versus Bottom |
|---|---|---|---|---|
| MmugDNA.13995.1.S1_at | — | — | 4.21 | 0.0348 |
| MmugDNA.19825.1.S1_s_at | phosducin-like 3 | LOC696369 | 4.21 | 0.0667 |
| MmugDNA.3461.1.S1_at | similar to RIKEN cDNA 1200014N16 gene | MGC14289 | 4.19 | 0.0308 |
| MmugDNA.23968.1.S1_s_at | ubiquitin specific protease 32 | LOC716857 | 4.19 | 0.0249 |
| MmuSTS.3891.1.S1_at | smoothened | LOC701334 | 4.19 | 0.0433 |
| MmuSTS.3429.1.S1_at | Collagen alpha-1(XII) chain precursor | LOC717820 | 4.19 | 0.0386 |
| MmuSTS.1967.1.S1_at | FYN binding protein (FYB-120/130) isoform 1 | LOC693951 | 4.18 | 0.0997 |
| MmugDNA.27563.1.S1_at | hypothetical protein FLJ13910 /// hypothetical protein LOC285074 | FLJ13910 /// LOC285074 | 4.16 | 0.0252 |
| MmugDNA.15700.1.S1_s_at | phosphoglycerate dehydrogenase | PHGDH | 4.15 | 0.0032 |
| MmuSTS.3850.1.S1_at | ABI gene family, member 3 (NESH) binding protein | LOC701192 | 4.14 | 0.0817 |
| MmugDNA.1158.1.S1_at | CD36 antigen (collagen type I receptor, thrombospondin receptor) | CD36 | 4.14 | 0.0397 |
| MmugDNA.34925.1.S1_at | secreted protein, acidic, cysteine-rich (osteonectin) | SPARC | 4.09 | 0.0078 |
| MmugDNA.31894.1.S1_at | thioredoxin interacting protein | LOC698683 | 4.09 | 0.0028 |
| MmugDNA.18794.1.S1_at | cell division cycle 20 | CDC20 | 4.09 | 0.0481 |
| MmuSTS.1308.1.S1_at | dystrophin (muscular dystrophy, Duchenne and Becker types) | DMD | 4.09 | 0.0098 |
| MmugDNA.27355.1.S1_at | low density lipoprotein-related protein 1 | LRP1 | 4.08 | 0.0607 |
| MmugDNA.7866.1.S1_at | DNA replication factor | LOC711530 | 4.07 | 0.0109 |
| MmugDNA.31873.1.S1_at | Fatty acid-binding protein, adipocyte (AFABP) (Adipocyte lipid-binding protein) (ALBP) (A-FABP) | FABP4 | 4.07 | 0.0130 |
| MmugDNA.36912.1.S1_at | complement factor D preproprotein | LOC721138 | 4.07 | 0.0237 |
| MmugDNA.10186.1.S1_at | AF15q14 protein | AF15Q14 | 4.06 | 0.0211 |
| MmugDNA.6192.1.S1_at | Baculoviral IAP repeat-containing 6 (apollon) | BIRC6 | 4.06 | 0.0861 |
| MmugDNA.26073.1.S1_at | RAB30, member RAS oncogene family | LOC701550 | 4.03 | 0.0735 |
| MmugDNA.21516.1.S1_at | phospholipid transfer protein | PLTP | 4.03 | 0.0251 |
| MmugDNA.36883.1.S1_at | PDZ domain containing 3 | PDZK3 | 4.02 | 0.0007 |
| MmugDNA.16991.1.S1_at | integrin alpha 7 precursor | LOC707279 | 4.02 | 0.0319 |
| MmugDNA.3447.1.S1_at | diacylglycerol O-acyltransferase homolog 2 | LOC696549 | 4.02 | 0.0054 |
| MmugDNA.17919.1.S1_at | arachidonate 15-lipoxygenase, second type | ALOX15B | 4.01 | 0.0499 |
| MmugDNA.35103.1.S1_at | actin, alpha 2, smooth muscle, aorta | ACTA2 | 4.01 | 0.0296 |
| Mmu.16433.2.S1_at | collagen, type III, alpha 1 (Ehlers-Danlos syndrome type IV, autosomal dominant) | COL3A1 | 3.99 | 0.0332 |
| MmugDNA.24230.1.S1_s_at | chemokine-like factor superfamily 3 isoform a | LOC695592 | 3.99 | 0.0604 |
| MmugDNA.16772.1.S1_at | immunoglobulin J chain | LOC706650 | 3.98 | 0.0350 |
| MmugDNA.34863.1.S1_at | hypothetical protein LOC283445 | LOC283445 | 3.98 | 0.0580 |
| MmunewRS.431.1.S1_at | tyrosine phosphatase, receptor type, S | — | 3.97 | 0.0140 |
| MmuSTS.61.1.S1_at | helicase, lymphoid-specific | LOC701598 | 3.97 | 0.0034 |
| MmugDNA.34155.1.S1_at | nidogen (enactin) | NID1 | 3.95 | 0.0965 |
| MmugDNA.9153.1.S1_s_at | angiopoietin 1 | ANGPT1 | 3.94 | 0.0482 |
| MmugDNA.36429.1.S1_at | Phosphoglycerate dehydrogenase like 1 | PHGDHL1 | 3.93 | 0.0965 |
| MmugDNA.26560.1.S1_at | Transcribed locus | — | 3.93 | 0.0251 |
| MmugDNA.36525.1.S1_at | junctional adhesion molecule 2 | JAM2 | 3.91 | 0.0727 |
| MmugDNA.43116.1.S1_at | glycoprotein (transmembrane) nmb isoform b precursor | LOC704990 | 3.91 | 0.0020 |
| MmugDNA.14973.1.S1_at | CDC45-like | LOC711800 | 3.90 | 0.0056 |
| MmuSTS.1523.1.S1_at | mannose receptor C type 1 | MRC1 | 3.90 | 0.0326 |
| MmugDNA.39378.1.S1_at | ribonuclease HI, large subunit | RNASEH2A | 3.90 | 0.0623 |
| MmugDNA.27459.1.S1_at | Transcribed locus | — | 3.89 | 0.0217 |
| MmugDNA.17136.1.S1_at | Sorbin and SH3 domain containing 1 | SORBS1 | 3.89 | 0.0146 |
| MmugDNA.15966.1.S1_at | Bromodomain adjacent to zinc finger domain, 2A | BAZ2A | 3.88 | 0.0740 |
| MmugDNA.20219.1.S1_at | myc target 1 | LOC711296 | 3.88 | 0.0363 |
| MmugDNA.43499.1.S1_at | — | — | 3.88 | 0.0557 |
| MmugDNA.10801.1.S1_s_at | — | — | 3.86 | 0.0121 |
| Mmu.6201.1.S1_at | Glycogen phosphorylase, liver | PYGL | 3.86 | 0.0383 |
| MmuSTS.4157.1.S1_at | Mitotic spindle assembly checkpoint protein MAD2A (MAD2-like 1) (HsMAD2) | LOC708574 | 3.85 | 0.0975 |
| MmugDNA.37083.1.S1_at | pleckstrin homology-like domain, family B, member 2 | LOC709353 | 3.84 | 0.0493 |
| MmugDNA.2976.1.S1_at | hypothetical protein LOC718180 | LOC718180 | 3.83 | 0.0297 |
| MmugDNA.34946.1.S1_at | — | — | 3.82 | 0.0871 |
| MmugDNA.2272.1.S1_at | CDNA FLJ34664 fis, clone LIVER2000592 | — | 3.82 | 0.0256 |
| MmugDNA.27284.1.S1_at | endothelial differentiation, lysophosphatidic acid G-protein-coupled receptor, 2 | LOC709208 | 3.81 | 0.0286 |
| MmugDNA.29523.1.S1_at | hypothetical protein LOC700994 | LOC700994 | 3.81 | 0.0180 |
| MmugDNA.33148.1.S1_at | mitochondrial glycerol 3-phosphate acyltransferase | GPAM | 3.79 | 0.0111 |
| MmugDNA.12151.1.S1_at | chromosome 18 open reading frame 54 | LOC694192 | 3.79 | 0.0342 |
| MmugDNA.11637.1.S1_s_at | nestin | LOC718562 | 3.79 | 0.0391 |
| Mmu.15601.1.S2_s_at | Intestinal alkaline phosphatase | — | 3.79 | 0.0175 |
| MmugDNA.27885.1.S1_at | excision repair cross-complementing rodent repair deficiency complementation group 6-like | LOC699138 | 3.78 | 0.0396 |
| MmugDNA.33913.1.S1_at | Calmodulin-like 4 | CALML4 | 3.77 | 0.0635 |
| MmugDNA.42756.1.S1_at | — | — | 3.77 | 0.0776 |
| MmugDNA.33637.1.S1_s_at | melanoma antigen family D, 4 isoform 1 | LOC697293 | 3.76 | 0.0236 |
| MmugDNA.32538.1.S1_at | ecotropic viral integration site 2B | LOC712972 | 3.76 | 0.0866 |
| MmugDNA.7512.1.S1_at | mediator of RNA polymerase II transcription, subunit 13 homolog | THRAP1 | 3.76 | 0.0009 |

-continued

| Probe Set ID | Gene Title | Gene Symbol | Ratio Top verus Bottom | p value Top versus Bottom |
|---|---|---|---|---|
| MmuSTS.4815.1.S1_at | gamma-aminobutyric acid (GABA) A receptor, pi | GABRP | 3.76 | 0.0213 |
| MmugDNA.42949.1.S1_at | Kinectin 1 (kinesin receptor) | KTN1 | 3.75 | 0.0642 |
| MmugDNA.9357.1.S1_at | Similar to ribosomal protein S12 | — | 3.75 | 0.0693 |
| MmuSTS.1780.1.S1_at | hypothetical protein LOC710960 | LOC710960 | 3.75 | 0.0391 |
| MmugDNA.40177.1.S1_at | HRAS-like suppressor 5 (H-rev107-like protein 5) | LOC718317 | 3.75 | 0.0439 |
| MmugDNA.41855.1.S1_at | chloride intracellular channel 4 | CLIC4 | 3.75 | 0.0477 |
| MmugDNA.39310.1.S1_at | homeo box C4 | HOXC4 | 3.75 | 0.0753 |
| MmugDNA.33364.1.S1_at | lysosomal-associated membrane protein 1 | LAMP1 | 3.75 | 0.0891 |
| MmuSTS.2956.1.S1_at | Lysosomal-associated multispanning membrane protein-5 | LAPTM5 | 3.74 | 0.0769 |
| MmugDNA.15666.1.S1_at | prostatic secretory protein (PSP-94) | MSMB | 3.74 | 0.0536 |
| MmugDNA.37771.1.S1_at | Ring finger protein 12 | RNF12 | 3.73 | 0.0118 |
| MmugDNA.25197.1.S1_at | asp (abnormal spindle)-like, microcephaly associated | LOC711153 | 3.73 | 0.0360 |
| MmugDNA.35955.1.S1_at | Ubiquitin-conjugating enzyme E2D 3 (UBC4/5 homolog, yeast) | UBE2D3 | 3.73 | 0.0666 |
| MmugDNA.39545.1.S1_at | sialyltransferase 7 | ST6GALNAC2 | 3.73 | 0.0048 |
| MmugDNA.24940.1.S1_at | SERTA domain containing 4 | SERTAD4 | 3.73 | 0.0064 |
| MmuSTS.2245.1.S1_at | phospholipase C, delta 1 | PLCD1 | 3.72 | 0.0012 |
| MmugDNA.4054.1.S1_at | solute carrier family 25 (mitochondrial carrier; Graves disease autoantigen), member 16 | SLC25A16 | 3.72 | 0.0026 |
| MmugDNA.38062.1.S1_at | Very hypothetical protein | — | 3.71 | 0.0666 |
| MmuSTS.1539.1.S1_at | lamin B1 | LMNB1 | 3.70 | 0.0425 |
| MmugDNA.29710.1.S1_at | mitogen-activated protein kinase kinase kinase 6 | LOC715911 | 3.70 | 0.0525 |
| MmugDNA.3079.1.S1_at | START domain containing 7 | STARD7 | 3.70 | 0.0054 |
| MmuSTS.3358.1.S1_at | Hematopoietic progenitor cell antigen CD34 precursor | LOC713858 | 3.70 | 0.0201 |
| MmugDNA.23709.1.S1_at | Ras-related protein Rab-13 | LOC695135 | 3.69 | 0.0042 |
| MmugDNA.13640.1.S1_at | Plunc precursor (Palate lung and nasal epithelium clone protein) (Lung-specific protein X) (Nasopharyngeal carcinoma-related protein) (Tracheal epithelium-enriched protein) (Secretory protein in upper respiratory tracts) (Von Ebn . . . | PLUNC | 3.68 | 0.0341 |
| MmugDNA.19840.1.S1_at | Flavin containing monooxygenase 2 | FMO2 | 3.67 | 0.0200 |
| MmugDNA.12797.1.S1_at | early B-cell factor 3 | LOC713536 | 3.67 | 0.0679 |
| MmugDNA.43327.1.S1_at | Alpha crystallin B chain (Alpha(B)-crystallin) (Rosenthal fiber component) (Heat-shock protein beta-5) (HspB5) (NY-REN-27 antigen) | CRYAB | 3.66 | 0.0179 |
| MmugDNA.26357.1.S1_at | CG14299-PA, isoform A | LOC700766 | 3.65 | 0.0974 |
| Mmu.16242.1.S1_at | Pallidin (Pallid protein homolog) (Syntaxin 13-interacting protein) | PLDN | 3.65 | 0.0676 |
| MmugDNA.3343.1.S1_at | suppressor of cytokine signaling 3 | SOCS3 | 3.65 | 0.0146 |
| MmunewRS.372.1.S1_at | gi: 39645656 Homo sapiens similar to Serinethreonine-protein kinase Nek1 (NimA-related protein kinase 1), mRNA (cDNA clone MGC: 75495 IMAGE: 30383658), complete cds | MGC75495 | 3.64 | 0.0005 |
| MmugDNA.4113.1.S1_at | heat shock 22 kDa protein 8 | HSPB8 | 3.64 | 0.0306 |
| MmugDNA.42494.1.S1_at | Transcribed locus | — | 3.64 | 0.0679 |
| MmuSTS.4058.1.S1_at | sushi-repeat-containing protein, X-linked | SRPX | 3.63 | 0.0619 |
| MmugDNA.17872.1.S1_at | Putative serum amyloid A-3 protein | SAA3P | 3.63 | 0.0242 |
| MmugDNA.34659.1.S1_s_at | hypothetical protein LOC705662 | LOC705662 | 3.63 | 0.0100 |
| MmugDNA.34077.1.S1_at | WD repeat and FYVE domain containing 2 | WDFY2 | 3.63 | 0.0201 |
| MmugDNA.3557.1.S1_at | WD40 repeat protein Interacting with phosphoInosities of 49 kDa | WIPI49 | 3.62 | 0.0905 |
| MmugDNA.5835.1.S1_at | hypothetical protein LOC700615 | LOC700615 | 3.62 | 0.0021 |
| MmunewRS.1055.1.S1_at | Myosin regulatory light chain 2, smooth muscle isoform (Myosin RLC) (LC20) (Myosin regulatory light chain 9) | LOC709784 | 3.61 | 0.0184 |
| MmuSTS.4533.1.S1_at | breast cancer 1, early onset isoform 1 | LOC712634 | 3.61 | 0.0225 |
| MmugDNA.37529.1.S1_at | pleckstrin homology domain containing, family H (with MyTH4 domain) member 2 | LOC713488 | 3.61 | 0.0629 |
| MmugDNA.36745.1.S1_at | tubulin, beta 8 | — | 3.61 | 0.0229 |
| MmugDNA.21536.1.S1_at | proline arginine-rich end leucine-rich repeat protein | PRELP | 3.61 | 0.0589 |
| MmugDNA.29432.1.S1_at | CDNA FLJ12246 fis, clone MAMMA1001343 | — | 3.61 | 0.0308 |
| MmuSTS.911.1.S1_at | enhancer of zeste 2 | EZH2 | 3.60 | 0.0107 |
| MmugDNA.17513.1.S1_at | LIM and cysteine-rich domains 1 | LMCD1 | 3.59 | 0.0642 |
| MmunewRS.170.1.S1_at | gi: 34535503 Homo sapiens cDNA FLJ46364 fis, clone TESTI4051015, weakly similar to Aquaporin 7 | — | 3.59 | 0.0005 |
| MmugDNA.37690.1.S1_at | zinc finger protein 208 | ZNF208 | 3.59 | 0.0722 |
| MmugDNA.14830.1.S1_at | thyroid hormone responsive (SPOT14 homolog, rat) | THRSP | 3.58 | 0.0198 |
| MmugDNA.38914.1.S1_at | Rap guanine nucleotide exchange factor (GEF)-like 1 | LOC699843 | 3.57 | 0.0737 |
| MmugDNA.15276.1.S1_at | sushi, von Willebrand factor type A, EGF and pentraxin domain containing 1 | LOC709478 | 3.57 | 0.0542 |
| MmugDNA.9453.1.S1_at | lysyl oxidase preproprotein | LOC699997 | 3.57 | 0.0512 |
| MmuSTS.417.1.S1_at | alpha-2A-adrenergic receptor | ADRA2A | 3.56 | 0.0301 |
| MmugDNA.328.1.S1_at | Nuclear protein 1 (Protein p8) (Candidate of metastasis 1) | P8 | 3.56 | 0.0178 |
| MmugDNA.34766.1.S1_at | Corticoliberin precursor (Corticotropin-releasing factor) (CRF) (Corticotropin-releasing hormone) | LOC702877 | 3.55 | 0.0843 |
| MmugDNA.7723.1.S1_at | male-specific lethal 3-like 1 (Drosophila) | MSL3L1 | 3.55 | 0.0630 |
| MmugDNA.25407.1.S1_at | carboxypeptidase M | CPM | 3.54 | 0.0593 |
| MmuSTS.1530.1.S1_at | Kv channel interacting protein 2 isoform 6 | LOC712434 | 3.54 | 0.0273 |

-continued

| Probe Set ID | Gene Title | Gene Symbol | Ratio Top verus Bottom | p value Top versus Bottom |
|---|---|---|---|---|
| MmugDNA.12610.1.S1_at | OX-2 membrane glycoprotein precursor (MRC OX-2 antigen) (CD200 antigen) | CD200 | 3.54 | 0.0915 |
| MmuSTS.835.1.S1_at | downregulated in ovarian cancer 1 isoform 2 | LOC699594 | 3.54 | 0.0876 |
| MmugDNA.21403.1.S1_at | trigger of mitotic entry 1 | LOC722088 | 3.53 | 0.0250 |
| MmugDNA.2694.1.S1_at | ZW10 interactor (ZW10-interacting protein 1) (Zwint-1) | LOC702198 | 3.52 | 0.0095 |
| MmugDNA.32957.1.S1_at | CG15105-PA, isoform A | LOC696852 | 3.51 | 0.0745 |
| MmunewRS.730.1.S1_at | cadherin 13 | CDH13 | 3.50 | 0.0291 |
| MmugDNA.28367.1.S1_at | SPARC-like 1 | SPARCL1 | 3.49 | 0.0017 |
| MmugDNA.28270.1.S1_at | Early B-cell factor | EBF | 3.48 | 0.0343 |
| MmugDNA.30316.1.S1_at | Protein inhibitor of activated STAT, 1 | PIAS1 | 3.48 | 0.0646 |
| MmuSTS.1363.1.S1_at | annexin A8 | ANXA8 | 3.48 | 0.0190 |
| MmugDNA.6544.1.S1_at | Triosephosphate isomerase (TIM) (Triose-phosphate isomerase) | TPI1 | 3.48 | 0.0290 |
| MmugDNA.15422.1.S1_at | absent in melanoma 1 | LOC697117 | 3.47 | 0.0217 |
| MmugDNA.37873.1.S1_at | kinase related protein, telokin | MYLK | 3.44 | 0.0740 |
| MmugDNA.22106.1.S1_at | sterile alpha motif domain containing 4 | SAMD4 | 3.44 | 0.0269 |
| MmugDNA.25115.1.S1_at | delta-like 1 homolog isoform 1 | LOC707595 | 3.43 | 0.0452 |
| MmugDNA.25541.1.S1_at | hypothetical protein LOC705360 | LOC705360 | 3.43 | 0.0002 |
| MmuSTS.3320.1.S1_at | cyclin E2 isoform 1 | LOC700382 | 3.43 | 0.0417 |
| MmuSTS.4488.1.S1_at | spectrin, beta, non-erythrocytic 1 | SPTBN1 | 3.43 | 0.0416 |
| MmugDNA.13714.1.S1_at | kallikrein 11 isoform 2 precursor | — | 3.43 | 0.0019 |
| MmugDNA.14368.1.S1_at | lipidosin | LOC709676 | 3.41 | 0.0245 |
| MmugDNA.7128.1.S1_at | triggering receptor expressed on myeloid cells 4 | TREM4 | 3.41 | 0.0097 |
| MmugDNA.15051.1.S1_at | A kinase (PRKA) anchor protein 2 | AKAP2 | 3.41 | 0.0145 |
| MmugDNA.39271.1.S1_at | Transcribed locus | — | 3.41 | 0.0712 |
| MmugDNA.38296.1.S1_at | KIAA1102 protein | KIAA1102 | 3.40 | 0.0636 |
| MmugDNA.12755.1.S1_s_at | bone morphogenetic protein 1 | BMP1 | 3.39 | 0.0254 |
| MmugDNA.35196.1.S1_at | Transcribed locus | — | 3.39 | 0.0878 |
| MmugDNA.7507.1.S1_at | ATP-binding cassette, sub-family A, member 9 | LOC693411 | 3.39 | 0.0736 |
| Mmu.15849.1.S1_at | transcription elongation regulator 1 isoform 1 | LOC707912 | 3.38 | 0.0370 |
| MmugDNA.25155.1.S1_at | Nuclear ubiquitous casein and cyclin-dependent kinases substrate (P1) | NUCKS1 | 3.38 | 0.0007 |
| MmuSTS.2361.1.S1_at | S100-A2 (S100 calcium-binding protein A2) (Protein S-100L) (CAN19) | LOC715264 | 3.37 | 0.0014 |
| MmuAffx.23.12.S1_at | Transcribed locus, strongly XP_001153513.1 hypothetical protein [Pan troglodytes] | — | 3.36 | 0.0459 |
| MmugDNA.13395.1.S1_at | interferon, gamma-inducible protein 16 | LOC719253 | 3.34 | 0.0180 |
| MmugDNA.34006.1.S1_at | leucine rich repeat and death domain containing protein isoform 1 | LOC700580 | 3.34 | 0.0246 |
| MmugDNA.13401.1.S1_s_at | metastasis associated lung adenocarcinoma transcript 1 (non-coding RNA) | MALAT1 | 3.34 | 0.0765 |
| MmuSTS.2405.1.S1_at | growth differentiation factor 11 | GDF11 | 3.34 | 0.0680 |
| MmugDNA.22100.1.S1_at | Baculoviral IAP repeat-containing protein 5 (Apoptosis inhibitor survivin) (Apoptosis inhibitor 4) | BIRC5 | 3.34 | 0.0120 |
| MmuSTS.2514.1.S1_at | hematopoietically expressed homeobox | LOC699012 | 3.33 | 0.0592 |
| MmugDNA.29693.1.S1_at | hypothetical protein FLJ21742 | FLJ21742 | 3.33 | 0.0066 |
| MmuSTS.1347.1.S1_at | high-mobility group box 2 | LOC697057 | 3.32 | 0.0266 |
| MmuSTS.1397.1.S1_at | Complement C1q subcomponent subunit B precursor | LOC718307 | 3.31 | 0.0198 |
| MmugDNA.42305.1.S1_at | A kinase (PRKA) anchor protein 13 | AKAP13 | 3.31 | 0.0571 |
| MmugDNA.19293.1.S1_at | Chromosome 21 open reading frame 34 | C21orf34 | 3.30 | 0.0456 |
| MmugDNA.12452.1.S1_at | hypothetical protein LOC699186 | LOC699186 | 3.30 | 0.0179 |
| MmugDNA.26596.1.S1_at | methyltransferase like 4 | LOC696353 | 3.30 | 0.0082 |
| MmuSTS.4306.1.S1_at | glycogenin 2 | LOC703955 | 3.30 | 0.0119 |
| MmuSTS.1398.1.S1_at | complement component 1, s subcomponent | C1S | 3.29 | 0.0531 |
| MmugDNA.37738.1.S1_at | GRAM domain containing 3 | LOC697870 | 3.29 | 0.0849 |
| MmugDNA.36423.1.S1_at | angiomotin like 1 | LOC698211 | 3.29 | 0.0435 |
| MmugDNA.38698.1.S1_at | complement component 1, q subcomponent, receptor 1 | C1QR1 | 3.28 | 0.0036 |
| MmugDNA.21696.1.S1_at | hypothetical protein BC007901 | LOC91461 | 3.28 | 0.0816 |
| MmugDNA.20213.1.S1_at | meningioma expressed antigens 5 (hyaluronidase) | MGEA5 | 3.27 | 0.0067 |
| MmugDNA.19007.1.S1_at | catalase | CAT | 3.26 | 0.0419 |
| MmugDNA.20699.1.S1_at | hypothetical protein LOC694371 | LOC694371 | 3.26 | 0.0587 |
| MmugDNA.6381.1.S1_at | cystatin F | LOC704850 | 3.26 | 0.0825 |
| MmugDNA.13610.1.S1_at | Full length insert cDNA clone YT94E02 | — | 3.25 | 0.0318 |
| MmuSTS.159.1.S1_at | microfibrillar-associated protein 4 | LOC709521 | 3.25 | 0.0567 |
| MmugDNA.3114.1.S1_at | Wee1-like protein kinase (WEE1hu) | WEE1 | 3.25 | 0.0474 |
| MmuSTS.2860.1.S1_at | Neuroligin 4 | — | 3.24 | 0.0013 |
| MmuSTS.3636.1.S1_at | Ets2 repressor factor | ERF | 3.24 | 0.0422 |
| MmugDNA.24307.1.S1_s_at | Sarcospan (K-ras oncogene-associated protein) (Kirsten-ras-associated protein) | SSPN | 3.24 | 0.0853 |
| MmugDNA.18122.1.S1_at | RAP2B, member of RAS oncogene family | RAP2B | 3.24 | 0.0026 |
| MmugDNA.13964.1.S1_at | trophoblast-derived noncoding RNA | TncRNA | 3.23 | 0.0115 |
| MmugDNA.7717.1.S1_at | MCM10 minichromosome maintenance deficient 10 (S. cerevisiae) | MCM10 | 3.23 | 0.0644 |
| MmugDNA.10682.1.S1_at | aquaporin 7 | AQP7 | 3.22 | 0.0409 |
| MmugDNA.9561.1.S1_at | tissue inhibitor of matrix metalloproteinase-2 | TIMP-2 | 3.22 | 0.0005 |
| MmugDNA.9052.1.S1_at | MAM domain containing 2 | LOC700333 | 3.21 | 0.0581 |
| MmugDNA.23764.1.S1_at | cyclin A | CCNA2 | 3.21 | 0.0284 |

-continued

| Probe Set ID | Gene Title | Gene Symbol | Ratio Top verus Bottom | p value Top versus Bottom |
|---|---|---|---|---|
| MmugDNA.962.1.S1_at | platelet-derived growth factor receptor beta /// hypothetical protein LOC711667 | LOC711667 /// PDGFRB | 3.20 | 0.0641 |
| MmugDNA.30376.1.S1_at | minichromosome maintenance protein 7 | MCM7 | 3.20 | 0.0000 |
| MmugDNA.40338.1.S1_s_at | Collagen alpha-1(V) chain precursor | LOC722009 | 3.20 | 0.0018 |
| MmugDNA.43126.1.S1_at | KIAA1909 protein | KIAA1909 | 3.19 | 0.0678 |
| MmugDNA.12886.1.S1_at | hypothetical protein LOC283755 /// D15F37 (pseudogene) /// MGC57820 protein | LOC283755 /// MN7 /// MGC57820 | 3.19 | 0.0143 |
| MmugDNA.33174.1.S1_at | T-cell receptor beta chain V region C5 precursor | — | 3.18 | 0.0008 |
| MmugDNA.20801.1.S1_at | Transcribed locus, moderately similar to XP_515629.1 similar to U5 snRNP-specific protein, 200 kDa; U5 snRNP-specific protein, 200 kDa (DEXH RNA helicase family) [Pan troglodytes] | — | 3.16 | 0.0121 |
| MmuSTS.249.1.S1_at | integrin, beta 2 | ITGB2 | 3.16 | 0.0580 |
| MmugDNA.18032.1.S1_at | desmoglein 3 (pemphigus vulgaris antigen) | DSG3 | 3.16 | 0.0084 |
| MmugDNA.32328.1.S1_at | lipoma HMGIC fusion partner | LOC696978 | 3.16 | 0.0243 |
| MmugDNA.3768.1.S1_at | Kruppel-like factor 8 | KLF8 | 3.16 | 0.0772 |
| MmugDNA.34645.1.S1_s_at | hypothetical protein LOC714309 | LOC714309 | 3.15 | 0.0439 |
| MmugDNA.19768.1.S1_at | proliferation associated nuclear element 1 isoform a | LOC709006 | 3.15 | 0.0103 |
| MmugDNA.19278.1.S1_at | phosphatase and actin regulator 2 | PHACTR2 | 3.15 | 0.0524 |
| MmugDNA.26562.1.S1_s_at | growth arrest-specific 5 | GAS5 | 3.14 | 0.0006 |
| MmugDNA.15046.1.S1_at | hemicentin 1 | LOC714026 | 3.14 | 0.0142 |
| MmugDNA.32563.1.S1_at | methionine sulfoxide reductase B3 isoform 2 | LOC717617 | 3.13 | 0.0827 |
| MmugDNA.3350.1.S1_at | L-3-hydroxyacyl-Coenzyme A dehydrogenase | HADHSC | 3.13 | 0.0983 |
| MmugDNA.27093.1.S1_at | alpha-2-macroglobulin | A2M | 3.13 | 0.0027 |
| MmugDNA.28905.1.S1_at | testis/prostate/placenta-expressed protein, isoform 2 isoform 1 | LOC706183 | 3.12 | 0.0596 |
| MmunewRS.723.1.S1_at | serine (or cysteine) proteinase inhibitor, clade H, member 1 | SERPINH1 | 3.12 | 0.0967 |
| MmugDNA.39240.1.S1_at | acyl-CoA synthetase long-chain family member 1 | LOC694871 | 3.12 | 0.0034 |
| MmugDNA.36848.1.S1_at | Tissue factor pathway inhibitor 2 precursor (TFPI-2) (Placental protein 5) (PP5) | TFPI2 | 3.11 | 0.0431 |
| MmugDNA.5658.1.S1_at | Bcl-2-related protein A1 (BFL-1 protein) (Hemopoietic-specific early response protein) (GRS protein) | BCL2A1 | 3.11 | 0.0888 |
| MmugDNA.25040.1.S1_at | clusterin | CLU | 3.11 | 0.0568 |
| MmugDNA.15918.1.S1_at | monocyte to macrophage differentiation-associated precursor | LOC706723 | 3.10 | 0.0191 |
| MmugDNA.5064.1.S1_at | transforming growth factor, beta-induced, 68 kDa | TGFBI | 3.10 | 0.0079 |
| MmuSTS.4112.1.S1_at | early growth response 1 | EGR1 | 3.10 | 0.0015 |
| MmuSTS.37314.1.S1_at | Zinc finger, CCHC domain containing 6 | ZCCHC6 | 3.09 | 0.0274 |
| MmugDNA.16942.1.S1_at | CDNA FLJ34374 fis, clone FEBRA2017502 | — | 3.09 | 0.0999 |
| MmugDNA.24636.1.S1_at | RAB, member of RAS oncogene family-like 2B | RABL2B | 3.09 | 0.0696 |
| MmugDNA.24841.1.S1_at | hypothetical protein LOC709979 | LOC709979 | 3.08 | 0.0018 |
| MmuSTS.4753.1.S1_at | Wnt inhibitory factor 1 | WIF1 | 3.08 | 0.0124 |
| MmugDNA.30671.1.S1_at | DEAD (Asp-Glu-Ala-Asp) box polypeptide 39 | LOC718822 | 3.08 | 0.0898 |
| MmugDNA.2069.1.S1_at | Isocitrate dehydrogenase 1 (NADP+), soluble | IDH1 | 3.08 | 0.0678 |
| MmugDNA.37149.1.S1_at | oxysterol binding protein-like 6 | OSBPL6 | 3.08 | 0.0801 |
| MmugDNA.1095.1.S1_at | Mediator of RNA polymerase II transcription, subunit 28 homolog (yeast) | MED28 | 3.07 | 0.0008 |
| MmugDNA.41794.1.S1_at | moesin | MSN | 3.07 | 0.0208 |
| MmugDNA.1253.1.S1_at | — | — | 3.07 | 0.0105 |
| MmugDNA.17781.1.S1_at | neuroepithelial cell transforming gene 1 | NET1 | 3.07 | 0.0094 |
| MmugDNA.18663.1.S1_at | Slit homolog 2 (Drosophila) | SLIT2 | 3.07 | 0.0607 |
| MmugDNA.25811.1.S1_at | Transcribed locus | — | 3.07 | 0.0033 |
| MmugDNA.18485.1.S1_at | G0-rich sequence DNA-binding factor candidate | LOC700489 | 3.07 | 0.0819 |
| MmugDNA.10654.1.S1_at | X-ray repair complementing defective repair in Chinese hamster cells 5 (double-strand-break rejoining; Ku autoantigen, 80 kDa) | XRCC5 | 3.06 | 0.0952 |
| MmugDNA.42236.1.S1_at | Ribosomal protein L10a | RPL10A | 3.05 | 0.0207 |
| MmugDNA.35088.1.S1_at | Fibroblast growth factor receptor 1 (fms-related tyrosine kinase 2, Pfeiffer syndrome) | FGFR1 | 3.05 | 0.0419 |
| MmugDNA.18922.1.S1_at | Hypothetical protein AY099107 | LOC152185 | 3.05 | 0.0748 |
| MmugDNA.31239.1.S1_at | Forkhead box O3A | FOXO3A | 3.03 | 0.0108 |
| MmugDNA.5694.1.S1_at | ADAM metallopeptidase with thrombospondin type 1 motif, 5 | ADAMTS5 | 3.03 | 0.0946 |
| MmugDNA.39840.1.S1_at | coactosin-like 1 | LOC715376 | 3.03 | 0.0023 |
| MmuSTS.2604.1.S1_at | zinc finger homeobox 1b | ZFHX1B | 3.02 | 0.0942 |
| MmugDNA.21087.1.S1_at | integrin, alpha 5 (fibronectin receptor, alpha polypeptide) | ITGA5 | 3.02 | 0.0160 |
| MmuSTS.3523.1.S1_at | B-cell CLL/lymphoma 11B isoform 1 | LOC705238 | 3.02 | 0.0082 |
| Mmu.7842.1.S1_at | alpha 1 type IV collagen | COL4A1 | 3.02 | 0.0409 |
| MmugDNA.8730.1.S1_at | Homo sapiens, clone IMAGE: 4778480, mRNA | — | 3.02 | 0.0632 |
| MmuSTS.4829.1.S1_at | growth hormone receptor | GHR | 3.02 | 0.0012 |
| MmugDNA.14593.1.S1_at | frizzled 4 | LOC704754 | 3.01 | 0.0106 |
| MmugDNA.42280.1.S1_at | — | — | 3.01 | 0.0740 |
| MmugDNA.34063.1.S1_at | lysophosphatidylglycerol acyltransferase 1 | LPGAT1 | 3.01 | 0.0644 |
| MmuSTS.124.1.S1_at | Homeobox protein Hox-A10 (Hox-1H) (Hox-1.8) (PL) | LOC704713 | 3.01 | 0.0416 |
| MmuSTS.24.1.S1_at | Glycoprotein Xg precursor (Protein PBDX) | XG | 3.01 | 0.0839 |
| MmugDNA.10983.1.S1_at | septin 10 | 10-Sep | 2.99 | 0.0257 |

| Probe Set ID | Gene Title | Gene Symbol | Ratio Top verus Bottom | p value Top versus Bottom |
|---|---|---|---|---|
| MmugDNA.10337.1.S1_at | CG9047-PA, isoform A | LOC704595 | 2.99 | 0.0300 |
| MmugDNA.15798.1.S1_s_at | HLA class II histocompatibility antigen, DQ(2) alpha chain precursor | LOC717623 | 2.99 | 0.0862 |
| MmugDNA.8592.1.S1_at | fatty acid binding protein 3, muscle and heart (mammary-derived growth inhibitor) | FABP3 | 2.99 | 0.0766 |
| MmugDNA.31542.1.S1_at | colon carcinoma related protein | LOC719328 | 2.98 | 0.0021 |
| MmuSTS.1998.1.S1_at | estrogen receptor 1 | ESR1 | 2.98 | 0.0868 |
| MmugDNA.22982.1.S1_at | hypothetical protein LOC708514 | LOC708514 | 2.98 | 0.0729 |
| MmugDNA.25545.1.S1_at | Full length insert cDNA clone ZD69D05 | — | 2.98 | 0.0295 |
| MmugDNA.8954.1.S1_at | glycerol-3-phosphate dehydrogenase 1 (soluble) | GPD1 | 2.97 | 0.0050 |
| MmuSTS.1138.1.S1_at | Phospholipase A2, membrane associated precursor (Phosphatidylcholine 2-acylhydrolase) (Group IIA phospholipase A2) (GIIC sPLA2) (Non-pancreatic secretory phospholipase A2) (NPS-PLA2) | PLA2G2A | 2.97 | 0.0880 |
| MmugDNA.10778.1.S1_at | cyclin-dependent kinase inhibitor 3 | LOC694877 | 2.97 | 0.0442 |
| MmugDNA.10040.1.S1_at | p53-regulated DDA3 isoform a | LOC698060 | 2.96 | 0.0854 |
| Mmu.2305.1.S1_at | bluestreak CG6451-PA | — | 2.96 | 0.0295 |
| MmuSTS.2278.1.S1_at | peroxidasin | LOC721654 | 2.95 | 0.0127 |
| MmugDNA.1496.1.S1_at | fatty acid desaturase 3 | LOC722337 | 2.95 | 0.0442 |
| MmugDNA.29758.1.S1_at | proline-rich cyclin A1-interacting protein | LOC709846 | 2.94 | 0.0143 |
| MmuSTS.3401.1.S1_s_at | CCAAT/enhancer-binding protein alpha (C/EBP alpha) | LOC717153 | 2.94 | 0.0015 |
| MmugDNA.2393.1.S1_at | perilipin | PLIN | 2.93 | 0.0008 |
| MmugDNA.393.1.S1_at | CDNA FLJ26120 fis, clone SYN00419 | — | 2.93 | 0.0092 |
| MmugDNA.30771.1.S1_at | spermatogenesis associated factor SPAF | LOC708640 | 2.93 | 0.0712 |
| MmugDNA.15387.1.S1_at | NEDD8 ultimate buster-1 | NYREN18 | 2.92 | 0.0520 |
| MmugDNA.5488.1.S1_at | dehydrogenase/reductase (SDR family) member 3 | LOC715548 | 2.92 | 0.0258 |
| MmugDNA.35654.1.S1_at | minichromosome maintenance protein 6 | MCM6 | 2.92 | 0.0680 |
| MmugDNA.30962.1.S1_at | advanced glycosylation end product-specific receptor isoform 1 precursor | LOC717296 | 2.92 | 0.0097 |
| MmugDNA.36279.1.S1_at | P3ECSL | LOC705660 | 2.91 | 0.0626 |
| MmugDNA.30623.1.S1_at | ephrin receptor EphA1 | EPHA1 | 2.91 | 0.0185 |
| MmugDNA.42862.1.S1_s_at | Fasciculation and elongation protein zeta 2 (Zygin-2) (Zygin II) (Zygin-related protein types I/II) | LOC708288 | 2.91 | 0.0388 |
| MmuSTS.2298.1.S1_at | deafness, autosomal dominant 5 protein | DFNA5 | 2.91 | 0.0812 |
| MmugDNA.18093.1.S1_at | FERM domain containing 6 | LOC707266 | 2.91 | 0.0939 |
| MmugDNA.34261.1.S1_at | PI-3-kinase-related kinase SMG-1 | LOC693542 | 2.90 | 0.0022 |
| MmugDNA.39398.1.S1_at | hypothetical protein LOC699173 | LOC699173 | 2.89 | 0.0182 |
| MmugDNA.6471.1.S1_at | Cerebellar degeneration-related antigen 1 (CDR34) | LOC698431 | 2.89 | 0.0015 |
| MmugDNA.38313.1.S1_at | Serum amyloid A protein precursor (SAA) /// serum amyloid A1 isoform 2 | LOC694944 /// SAA1 | 2.89 | 0.0137 |
| MmugDNA.4080.1.S1_at | peptidylprolyl isomerase F (cyclophilin F) | PPIF | 2.88 | 0.0024 |
| MmugDNA.26182.1.S1_at | heterogeneous nuclear ribonucleoprotein A1 | HNRPA1 | 2.87 | 0.0025 |
| MmugDNA.27473.1.S1_at | CASP8 and FADD-like apoptosis regulator | CFLAR | 2.87 | 0.0203 |
| MmugDNA.35112.1.S1_at | kleisin beta isoform 2 | LOC716120 | 2.87 | 0.0321 |
| MmugDNA.22473.1.S1_at | PP2135 protein | PP2135 | 2.86 | 0.0928 |
| MmugDNA.37882.1.S1_at | hypothetical protein LOC703464 /// hypothetical protein LOC705990 | LOC703464 /// LOC705990 | 2.86 | 0.0211 |
| MmuAffx.52.1.A1_at | chemokine (C-C motif) ligand 4 | CCL4 | 2.84 | 0.0361 |
| MmugDNA.31283.1.S1_at | hypothetical protein LOC693798 | LOC693798 | 2.84 | 0.0659 |
| MmuSTS.2520.1.S1_at | heterogeneous nuclear ribonucleoprotein H2 | HNRPH2 | 2.84 | 0.0827 |
| MmugDNA.28432.1.S1_at | adipocyte-specific adhesion molecule | LOC708098 | 2.84 | 0.0517 |
| MmugDNA.13083.1.S1_at | activating transcription factor 7 interacting protein | LOC698815 | 2.84 | 0.0965 |
| MmugDNA.8865.1.S1_at | Visinin-like protein 1 (VILIP) (Neural visinin-like protein 1) (NVL-1) (NVP-1) (21 kDa CABP) | LOC699459 | 2.83 | 0.0285 |
| MmuSTS.2601.1.S1_at | embryonal Fyn-associated substrate isoform 2 | LOC713838 | 2.83 | 0.0000 |
| MmugDNA.38045.1.S1_at | Transcribed locus | — | 2.82 | 0.0094 |
| MmugDNA.9654.1.S1_at | Heterogeneous nuclear ribonucleoprotein D (AU-rich element RNA binding protein 1, 37 kDa) | HNRPD | 2.82 | 0.0440 |
| MmugDNA.38313.1.S1_s_at | serum amyloid A1 isoform 2 | LOC694944 | 2.81 | 0.0253 |
| MmugDNA.24597.1.S1_at | carbonyl reductase 3 | LOC695769 | 2.81 | 0.0598 |
| MmugDNA.36863.1.S1_at | vang-like 1 | LOC709730 | 2.80 | 0.0744 |
| MmugDNA.15427.1.S1_at | sterile alpha motif and leucine zipper containing kinase AZK | ZAK | 2.80 | 0.0920 |
| MmugDNA.19311.1.S1_at | laminin, beta 2 | LAMB2 | 2.80 | 0.0012 |
| MmugDNA.22113.1.S1_at | Transcribed locus, strongly similar to XP_510155.1 similar to PAPOLA protein [Pan troglodytes] | — | 2.80 | 0.0719 |
| MmuSTS.3531.1.S1_s_at | — | CCL4L | 2.80 | 0.0516 |
| MmugDNA.21105.1.S1_at | DNA ligase I | LIG1 | 2.80 | 0.0904 |
| MmugDNA.15362.1.S1_at | HEG homolog | HEG | 2.77 | 0.0055 |
| MmugDNA.6611.1.S1_at | hypothetical protein LOC701646 | LOC701646 | 2.77 | 0.0623 |
| MmugDNA.10320.1.S1_at | nicotinamide nucleotide adenylyltransferase 3 | NMNAT3 | 2.77 | 0.0937 |
| MmugDNA.5714.1.S1_at | timeless homolog | LOC712835 | 2.77 | 0.0737 |
| MmugDNA.6879.1.S1_at | SNF1-like kinase 2 | LOC711453 | 2.77 | 0.0878 |
| MmugDNA.40900.1.S1_at | Host cell factor-binding transcription factor Zhangfei (HCF-binding transcription factor Zhangfei) (Tyrosine kinase-associated leucine zipper protein LAZip) | LOC702942 | 2.76 | 0.0186 |
| MmugDNA.5326.1.S1_at | cyclin-dependent kinase 3 | CDK3 | 2.76 | 0.0203 |

| Probe Set ID | Gene Title | Gene Symbol | Ratio Top verus Bottom | p value Top versus Bottom |
|---|---|---|---|---|
| MmugDNA.42369.1.S1_s_at | Josephin domain containing 3 | LOC696602 | 2.76 | 0.0792 |
| MmuSTS.607.1.S1_at | Heat-shock protein beta-7 (HspB7) (Cardiovascular heat shock protein) (cvHsp) | LOC696704 | 2.75 | 0.0029 |
| MmugDNA.39315.1.S1_at | Leukemia inhibitory factor receptor | LIFR | 2.75 | 0.0588 |
| MmuSTS.631.1.S1_at | angiomotin like 2 | LOC718868 | 2.74 | 0.0095 |
| MmuSTS.2866.1.S1_at | Stathmin (Phosphoprotein p19) (pp19) (Oncoprotein 18) (Op18) (Leukemia-associated phosphoprotein p18) (pp17) (Prosolin) (Metablastin) (Protein Pr22) | LOC719733 | 2.74 | 0.0870 |
| MmugDNA.41518.1.S1_s_at | vimentin | VIM | 2.74 | 0.0725 |
| MmugDNA.5148.1.S1_at | Notchless gene homolog | NLE1 | 2.74 | 0.0939 |
| MmugDNA.34796.1.S1_at | chromosome 10 open reading frame 99 | C10orf99 | 2.73 | 0.0070 |
| MmugDNA.27576.1.S1_at | — | — | 2.73 | 0.0033 |
| MmuSTS.2115.1.S1_at | — | ARHGEF6 | 2.72 | 0.0401 |
| MmugDNA.27574.1.S1_at | membrane-spanning 4-domains, subfamily A, member 6A isoform 2 | LOC697689 | 2.72 | 0.0785 |
| MmugDNA.12560.1.S1_at | enoyl Coenzyme A hydratase domain containing 3 | LOC693583 | 2.72 | 0.0499 |
| MmugDNA.35275.1.S1_at | transmembrane protease, serine 8 (intestinal) | LOC697965 | 2.72 | 0.0064 |
| MmugDNA.43094.1.S1_at | procollagen C-endopeptidase enhancer 2 | PCOLCE2 | 2.72 | 0.0769 |
| Mmu.3054.2.S1_at | upstream of NRAS | CSDE1 | 2.72 | 0.0039 |
| MmuSTS.2641.1.S1_at | ATP synthase, H+ transporting, mitochondrial F1 complex, alpha subunit | — | 2.72 | 0.0461 |
| MmugDNA.18980.1.S1_at | neuromedin B | NMB | 2.71 | 0.0546 |
| MmugDNA.23958.1.S1_at | G protein-coupled receptor 37 | GPR37 | 2.71 | 0.0888 |
| MmugDNA.43305.1.S1_at | — | — | 2.71 | 0.0499 |
| MmugDNA.31834.1.S1_at | Fanconi anemia group A protein (Protein FACA) | LOC714932 | 2.71 | 0.0205 |
| MmugDNA.36837.1.S1_at | poly(rC) binding protein 2 (predicted) /// poly(rC) binding protein 2 | LOC694744 /// LOC703175 | 2.70 | 0.0636 |
| MmugDNA.11099.1.S1_at | Catenin (cadherin-associated protein), beta 1, 88 kDa | CTNNB1 | 2.70 | 0.0381 |
| MmugDNA.37576.1.S1_at | PHD finger protein 20-like 1 isoform 1 | LOC701406 | 2.70 | 0.0015 |
| MmuSTS.541.1.S1_at | oxysterol-binding protein-like protein 8 isoform a | LOC693338 | 2.69 | 0.0396 |
| MmugDNA.16521.1.S1_at | hypothetical protein DKFZp761N09121 | DKFZP761N09121 | 2.69 | 0.0319 |
| MmugDNA.9406.1.S1_at | Ubiquitin-conjugating enzyme E2H (UBC8 homolog, yeast) | UBE2H | 2.69 | 0.0368 |
| MmuSTS.3625.1.S1_at | polycystin 2 | LOC702179 | 2.68 | 0.0079 |
| MmugDNA.41756.1.S1_at | membrane protein, palmitoylated 3 (MAGUK p55 subfamily member 3) | MPP3 | 2.68 | 0.0063 |
| MmugDNA.7204.1.S1_at | serum/glucocorticoid regulated kinase | LOC713082 | 2.67 | 0.0050 |
| MmugDNA.19300.1.S1_at | Endothelial protein C receptor precursor (Endothelial cell protein C receptor) (Activated protein C receptor) (APC receptor) (CD201 antigen) | LOC706040 | 2.67 | 0.0858 |
| MmugDNA.7974.1.S1_at | TRAF interacting protein | TRAIP | 2.67 | 0.0891 |
| MmugDNA.14150.1.S1_at | CG8745-PA | LOC702302 | 2.67 | 0.0453 |
| MmugDNA.24498.1.S1_at | replication factor C (activator 1) 4, 37 kDa | RFC4 | 2.67 | 0.0043 |
| MmugDNA.31559.1.S1_at | CTD small phosphatase-like protein (CTDSP-like) (Small C-terminal domain phosphatase 3) (Small CTD phosphatase 3) (SCP3) (Nuclear LIM interactor-interacting factor 1) (NLI-interacting factor 1) (NIF-like protein) (RBSP3) (YA22 protein) ( . . . | LOC697898 | 2.67 | 0.0039 |
| MmugDNA.27755.1.S1_at | Similar to KIAA0393 protein | MGC57820 | 2.67 | 0.0755 |
| MmuSTS.825.1.S1_x_at | degenerative spermatocyte homolog 1, lipid desaturase | LOC702128 | 2.67 | 0.0943 |
| MmugDNA.32190.1.S1_at | HRAS-like suppressor 3 | HRASLS3 | 2.66 | 0.0205 |
| MmugDNA.378.1.S1_at | Syntaxin 7 | STX7 | 2.66 | 0.0271 |
| MmugDNA.7129.1.S1_at | UDP-N-acetyl-alpha-D-galactosamine:polypeptide N-acetylgalactosaminyltransferase-like 4 | LOC701790 | 2.66 | 0.0855 |
| MmugDNA.37173.1.S1_at | methyltransferase like 7A | LOC693894 | 2.66 | 0.0812 |
| MmugDNA.15924.1.S1_at | Eukaryotic translation initiation factor 4E member 2 | EIF4E2 | 2.66 | 0.0777 |
| MmugDNA.18344.1.S1_at | Jagged 1 (Alagille syndrome) | JAG1 | 2.66 | 0.0523 |
| MmugDNA.18912.1.S1_at | inter-alpha trypsin inhibitor heavy chain precursor 5 isoform 2 | LOC722614 | 2.65 | 0.0437 |
| MmugDNA.38963.1.S1_at | inhibitor of DNA binding 1 isoform b | LOC713160 | 2.65 | 0.0167 |
| MmugDNA.38359.1.S1_at | H2A histone family, member Y | H2AFY | 2.65 | 0.0069 |
| MmuSTS.1880.1.S1_at | collagen, type IV, alpha 2 | COL4A2 | 2.65 | 0.0233 |
| MmuSTS.999.1.S1_at | myc proto-oncogene protein | MYC | 2.65 | 0.0644 |
| MmugDNA.27587.1.S1_at | *Homo sapiens*, clone IMAGE: 5170410, mRNA | — | 2.65 | 0.0784 |
| MmugDNA.20660.1.S1_at | tripartite motif-containing 33 protein | TRIM33 | 2.64 | 0.0247 |
| MmugDNA.7029.1.S1_at | Receptor activity-modifying protein 3 precursor (CRLR activity-modifying protein 3) (Calcitonin-receptor-like receptor activity-modifying protein 3) | LOC697349 | 2.64 | 0.0289 |
| MmuSTS.3328.1.S1_at | origin recognition complex, subunit 1 | LOC713271 | 2.63 | 0.0374 |
| MmugDNA.38420.1.S1_s_at | Transmembrane BAX inhibitor motif-containing protein 4 (Z-protein) (S1R protein) | TMBIM4 | 2.63 | 0.0011 |
| MmugDNA.32616.1.S1_at | XIAP associated factor-1 isoform 1 | LOC713425 | 2.63 | 0.0099 |
| MmugDNA.2794.1.S1_at | Epithelial membrane protein 1 (EMP-1) (Tumor-associated membrane protein) (CL-20) (B4B protein) | EMP1 | 2.63 | 0.0386 |
| MmugDNA.28550.1.S1_at | heat shock protein, alpha-crystallin-related, B6 | LOC710760 | 2.62 | 0.0083 |
| MmugDNA.19535.1.S1_at | desmocollin 3 | DSC3 | 2.62 | 0.0261 |
| MmugDNA.14923.1.S1_at | Adenomatosis polyposis coli 2 | APC2 | 2.62 | 0.0847 |
| MmugDNA.10555.1.S1_at | CDNA FLJ36553 fis, clone TRACH2008478 | — | 2.61 | 0.0113 |

-continued

| Probe Set ID | Gene Title | Gene Symbol | Ratio Top verus Bottom | p value Top versus Bottom |
|---|---|---|---|---|
| MmugDNA.35200.1.S1_at | hypothetical protein FLJ13305 | FLJ13305 | 2.61 | 0.0709 |
| MmugDNA.10323.1.S1_s_at | RNA binding motif protein 25 | LOC695911 | 2.60 | 0.0340 |
| MmugDNA.25448.1.S1_at | CG13745-PA | LOC699878 | 2.60 | 0.0499 |
| MmugDNA.40326.1.S1_at | MRNA; cDNA DKFZp686F1318 (from clone DKFZp686F1318) | — | 2.60 | 0.0643 |
| MmugDNA.11833.1.S1_at | Homo sapiens, clone IMAGE: 5278284, mRNA | — | 2.60 | 0.0515 |
| MmugDNA.31867.1.S1_at | golgi associated, gamma adaptin ear containing, ARF binding protein 2 | GGA2 | 2.59 | 0.0586 |
| MmugDNA.33539.1.S1_at | Ankyrin 3, node of Ranvier (ankyrin G) | ANK3 | 2.59 | 0.0204 |
| MmugDNA.37283.1.S1_at | Polypyrimidine tract binding protein 2 | PTBP2 | 2.57 | 0.0946 |
| MmugDNA.40388.1.S1_at | lactotransferrin | LOC713115 | 2.57 | 0.0012 |
| MmunewRS.711.1.S1_at | corticotropin releasing hormone binding protein | LOC707589 | 2.56 | 0.0397 |
| MmugDNA.20034.1.S1_at | Full length insert cDNA clone ZD69D05 | — | 2.55 | 0.0473 |
| MmugDNA.40606.1.S1_at | Activin A receptor type II-like 1 | ACVRL1 | 2.55 | 0.0529 |
| MmugDNA.42565.1.S1_at | H+ transporting F1 ATP synthase epsilon subunit | — | 2.55 | 0.0439 |
| MmugDNA.16683.1.S1_at | solute carrier family 24 (sodium/potassium/calcium exchanger), member 3 | SLC24A3 | 2.54 | 0.0562 |
| MmugDNA.864.1.S1_at | Chromosome 16 open reading frame 28 | C16orf28 | 2.54 | 0.0225 |
| MmugDNA.41780.1.S1_at | interleukin 6 signal transducer receptor | IL-6 | 2.53 | 0.0980 |
| MmugDNA.37515.1.S1_at | Hypothetical protein FLJ13941 | FLJ13941 | 2.53 | 0.0038 |
| MmugDNA.25797.1.S1_at | Hypothetical protein MGC10067 | MGC10067 | 2.53 | 0.0315 |
| MmugDNA.27004.1.S1_at | follistatin-like 1 | FSTL1 | 2.52 | 0.0172 |
| MmugDNA.1644.1.S1_at | eukaryotic translation initiation factor 5B | EIF5B | 2.52 | 0.0295 |
| MmugDNA.23477.1.S1_at | RAS and EF hand domain containing | RASEF | 2.52 | 0.0477 |
| MmugDNA.40191.1.S1_at | Ubiquinol-cytochrome c reductase complex 14 kDa protein (Complex III subunit VI) (QP-C) | UQCRB | 2.52 | 0.0061 |
| MmugDNA.5276.1.S1_at | two AAA domain containing protein | LOC704478 | 2.51 | 0.0788 |
| MmugDNA.9275.1.S1_at | Acetyl-Coenzyme A synthetase 2 (ADP forming) | ACAS2 | 2.51 | 0.0312 |
| MmugDNA.23637.1.S1_at | Rho GTPase activating protein 23 | ARHGAP23 | 2.51 | 0.0377 |
| MmugDNA.31862.1.S1_at | Transcribed locus, moderately similar to XP_524454.1 LOC469069 [Pan troglodytes] | — | 2.51 | 0.0338 |
| MmugDNA.39520.1.S1_at | Rho GDP-dissociation inhibitor 2 (Rho GDI 2) (Rho-GDI beta) (Ly-GDI) | ARHGDIB | 2.50 | 0.0744 |
| MmugDNA.22495.1.S1_at | choline phosphotransferase 1 | LOC696056 | 2.50 | 0.0276 |
| MmugDNA.40534.1.S1_s_at | S-phase kinase-associated protein 2 isoform 1 | LOC700617 | 2.49 | 0.0640 |
| MmugDNA.25179.1.S1_s_at | hypothetical protein LOC707276 /// Acidic leucine-rich nuclear phosphoprotein 32 family member B (PHAPI2 protein) (Silver-stainable protein SSP29) (Acidic protein rich in leucines) | ANP32B /// LOC707276 | 2.49 | 0.0301 |
| MmugDNA.20756.1.S1_at | methionine aminopeptidase 1D | MAP1D | 2.49 | 0.0157 |
| MmugDNA.10451.1.S1_at | lipoprotein lipase | LPL | 2.48 | 0.0793 |
| MmugDNA.37784.1.S1_at | Microfibrillar-associated protein 5 precursor (MFAP-5) (Microfibril-associated glycoprotein 2) (MAGP-2) (MP25) | MFAP5 | 2.48 | 0.0288 |
| MmugDNA.11410.1.S1_at | WW domain-containing adapter with a coiled-coil region isoform 1 | LOC715828 | 2.48 | 0.0246 |
| MmugDNA.16003.1.S1_at | hypothetical protein LOC713457 | LOC713457 | 2.48 | 0.0832 |
| MmugDNA.7480.1.S1_at | Glutaredoxin-1 (Thioltransferase-1) (TTase-1) | GLRX | 2.48 | 0.0177 |
| MmugDNA.41094.1.S1_at | cytochrome P450, family 2, subfamily E, polypeptide 2 homolog | LOC718303 | 2.47 | 0.0545 |
| MmuSTS.2498.1.S1_at | zinc finger protein 8 | ZNF8 | 2.47 | 0.0011 |
| MmuSTS.3305.1.S1_at | Oxysterols receptor LXR-alpha (Liver X receptor alpha) (Nuclear orphan receptor LXR-alpha) | NR1H3 | 2.47 | 0.0882 |
| MmugDNA.22116.1.S1_at | Neurotensin/neuromedin N precursor | NTS | 2.47 | 0.0663 |
| MmuSTS.1525.1.S1_at | mitochondrial ribosomal protein L35 | MRPL35 | 2.47 | 0.0431 |
| MmugDNA.14539.1.S1_at | KIAA1450 protein | KIAA1450 | 2.46 | 0.0140 |
| MmugDNA.2162.1.S1_at | C20orf111 | LOC693890 | 2.46 | 0.0194 |
| MmugDNA.14181.1.S1_at | CDNA: FLJ23006 fis, clone LNG00414 | — | 2.46 | 0.0527 |
| MmugDNA.38899.1.S1_at | alpha 2 type VI collagen isoform 2C2 precursor | LOC709493 | 2.46 | 0.0950 |
| MmugDNA.12419.1.S1_at | sno, strawberry notch homolog 1 | LOC709260 | 2.46 | 0.0741 |
| Mmu.13956.1.S1_at | mitochondrial aldehyde dehydrogenase 2 | ALDH2 | 2.46 | 0.0559 |
| MmugDNA.27955.1.S1_at | thrombospondin 3 | THBS3 | 2.45 | 0.0003 |
| Mmu.12740.1.S1_at | activating transcription factor 2 | LOC699072 | 2.45 | 0.0690 |
| MmugDNA.2942.1.S1_at | Ras-related protein Rab-15 | LOC708330 | 2.44 | 0.0561 |
| MmugDNA.42705.1.S1_at | SH3 multiple domains 1 | LOC714868 | 2.44 | 0.0830 |
| MmugDNA.2199.1.S1_at | hypothetical protein LOC706003 | LOC706003 | 2.44 | 0.0707 |
| MmugDNA.31469.1.S1_at | Mitochondrial 28S ribosomal protein S25 (S25mt) (MRP-S25) | LOC703261 | 2.44 | 0.0413 |
| MmugDNA.32362.1.S1_at | v-maf musculoaponeurotic fibrosarcoma oncogene homolog B (avian) | MAFB | 2.43 | 0.0446 |
| MmugDNA.37182.1.S1_at | C17G10.1 | LOC700219 | 2.43 | 0.0349 |
| MmugDNA.3948.1.S1_at | B-cell lymphoma 6 protein | LOC708736 | 2.43 | 0.0461 |
| MmugDNA.29568.1.S1_at | Hypothetical gene supported by BX640700 | — | 2.43 | 0.0882 |
| MmugDNA.22001.1.S1_at | mucin 7, salivary | LOC707153 | 2.43 | 0.0161 |
| MmugDNA.24814.1.S1_at | RAS protein activator like 2 | RASAL2 | 2.43 | 0.0553 |
| MmugDNA.23518.1.S1_at | Muscleblind-like 2 (Drosophila) | MBNL2 | 2.42 | 0.0661 |
| MmugDNA.10700.1.S1_at | opioid growth factor receptor-like 1 | LOC715189 | 2.42 | 0.0889 |

-continued

| Probe Set ID | Gene Title | Gene Symbol | Ratio Top verus Bottom | p value Top versus Bottom |
|---|---|---|---|---|
| MmugDNA.13067.1.S1_at | serine/threonine kinase 4 | STK4 | 2.42 | 0.0978 |
| MmugDNA.40225.1.S1_at | LIM domain containing preferred translocation partner in lipoma | LPP | 2.42 | 0.0289 |
| MmugDNA.31182.1.S1_at | centrosome spindle pole associated protein | LOC704476 | 2.42 | 0.0587 |
| MmugDNA.19553.1.S1_at | damage-specific DNA binding protein 2 (48 kD) | DDB2 | 2.41 | 0.0098 |
| MmugDNA.2267.1.S1_at | Transcribed locus | — | 2.41 | 0.0491 |
| MmugDNA.2874.1.S1_at | DNA polymerase gamma subunit 2, mitochondrial precursor (Mitochondrial DNA polymerase accessory subunit) (PolG-beta) (MtPolB) (DNA polymerase gamma accessory 55 kDa subunit) (p55) | LOC720356 | 2.41 | 0.0413 |
| Mmu.11306.1.S1_at | MYC binding protein 2 | MYCBP2 | 2.41 | 0.0484 |
| MmugDNA.27252.1.S1_at | Transcribed locus | — | 2.41 | 0.0826 |
| MmugDNA.4547.1.S1_at | aarF domain containing kinase 5 | ADCK5 | 2.41 | 0.0068 |
| MmugDNA.29817.1.S1_at | Ubiquitin-conjugating enzyme E2E 2 (UBC4/5 homolog, yeast) | UBE2E2 | 2.41 | 0.0791 |
| MmugDNA.22188.1.S1_at | Rho guanine nucleotide exchange factor (GEF) 10 | ARHGEF10 | 2.40 | 0.0882 |
| MmugDNA.3376.1.S1_at | caspase recruitment domain family, member 8 | CARD8 | 2.40 | 0.0302 |
| MmugDNA.43065.1.S1_at | pregnancy-induced growth inhibitor isoform 1 | LOC714549 | 2.40 | 0.0211 |
| MmugDNA.40500.1.S1_at | hypothetical protein LOC694075 | LOC694075 | 2.40 | 0.0409 |
| MmugDNA.11419.1.S1_at | molecule interacting with Rab13 | MICAL-L1 | 2.39 | 0.0963 |
| MmugDNA.1847.1.S1_at | tissue inhibitor of metalloproteinase 2 | TIMP2 | 2.39 | 0.0030 |
| MmugDNA.11882.1.S1_at | hypothetical protein LOC721782 | LOC721782 | 2.39 | 0.0452 |
| MmuSTS.1231.1.S1_at | copine II | LOC703557 | 2.39 | 0.0061 |
| MmugDNA.22620.1.S1_at | Galectin-7 (Gal-7) (HKL-14) (PI7) (p53-induced protein 1) | LGALS7 | 2.38 | 0.0861 |
| Mmu.15973.14.S1_at | growth hormone variant /// growth hormone 1 isoform 1 /// chorionic somatommamotropin hormone 3 /// growth hormone 1 /// chorionic somatommamotropin hormone 4 | CSH-3 /// CSH-4 /// GH1 /// LOC700885 /// LOC718116 /// LOC718474 | 2.38 | 0.0038 |
| MmugDNA.40962.1.S1_at | Patched homolog (Drosophila) | PTCH | 2.37 | 0.0228 |
| MmugDNA.11810.1.S1_at | chromatin-specific transcription elongation factor large subunit | LOC708066 | 2.37 | 0.0275 |
| MmuSTS.2967.1.S1_at | alcohol dehydrogenase, iron containing, 1 | LOC703118 | 2.37 | 0.0768 |
| MmugDNA.3168.1.S1_at | CDNA clone IMAGE: 5294683, partial cds | — | 2.37 | 0.0307 |
| MmugDNA.4900.1.S1_s_at | amylase, alpha 2A; pancreatic | AMY2A | 2.37 | 0.0873 |
| MmuSTS.1626.1.S1_at | thyroid hormone receptor interactor 10 | LOC703934 | 2.36 | 0.0148 |
| MmuSTS.3226.1.S1_at | myosin IXA | LOC701520 | 2.36 | 0.0256 |
| MmugDNA.23835.1.S1_at | RNA binding motif protein 5 | RBM5 | 2.35 | 0.0695 |
| MmuSTS.1925.1.S1_at | Tissue factor precursor (TF) (Coagulation factor III) (Thromboplastin) (CD142 antigen) | F3 | 2.35 | 0.0169 |
| MmugDNA.23256.1.S1_at | guanylate cyclase 1, soluble, alpha 3 | LOC699365 | 2.35 | 0.0208 |
| MmunewRS.334.1.S1_at | gi: 42657654 | — | 2.35 | 0.0278 |
| MmugDNA.524.1.S1_at | Full length insert cDNA clone YX74D05 | — | 2.34 | 0.0963 |
| MmuSTS.891.1.S1_at | Microfibrillar-associated protein 2 precursor (MFAP-2) (Microfibril-associated glycoprotein) (MAGP) (MAGP-1) | MFAP2 | 2.34 | 0.0609 |
| MmuSTS.4399.1.S1_at | cell division cycle associated 8 | LOC719808 | 2.34 | 0.0254 |
| MmugDNA.36.1.S1_at | Sorting nexin-10 | SNX10 | 2.33 | 0.0528 |
| MmugDNA.24165.1.S1_at | ATP synthase lipid-binding protein, mitochondrial precursor (ATP synthase proteolipid P1) (ATPase protein 9) (ATPase subunit C) | — | 2.33 | 0.0024 |
| MmugDNA.38800.1.S1_at | connexin 43 | GJA1 | 2.33 | 0.0658 |
| MmugDNA.2930.1.S1_at | Full length insert cDNA clone ZE03F06 | — | 2.33 | 0.0266 |
| MmugDNA.42198.1.S1_at | glycosyltransferase-like 1B | LOC714846 | 2.33 | 0.0727 |
| MmugDNA.782.1.S1_s_at | adenine phosphoribosyltransferase isoform b | APRT | 2.33 | 0.0978 |
| MmugDNA.40585.1.S1_at | — | — | 2.32 | 0.0884 |
| Mmu.13676.1.S1_s_at | Transcribed locus | — | 2.32 | 0.0702 |
| MmugDNA.38278.1.S1_at | Solute carrier family 1 (glutamate/neutral amino acid transporter), member 4 | SLC1A4 | 2.32 | 0.0846 |
| MmugDNA.37513.1.S1_at | Y-box-binding protein 2 (Germ cell-specific Y-box-binding protein) (FRGY2 homolog) | LOC714750 | 2.32 | 0.0853 |
| MmuSTS.699.1.S1_at | calcium activated chloride channel 2 | LOC711959 | 2.32 | 0.0311 |
| MmugDNA.35545.1.S1_at | DEAD (Asp-Glu-Ala-Asp) box polypeptide 17 | DDX17 | 2.32 | 0.0193 |
| MmuSTS.4279.1.S1_at | ephrin A4 isoform b | LOC717315 | 2.31 | 0.0921 |
| MmuSTS.4415.1.S1_at | nuclear matrix protein p84 | THOC1 | 2.31 | 0.0067 |
| MmugDNA.20377.1.S1_at | growth arrest-specific 6 | LOC716066 | 2.31 | 0.0374 |
| MmugDNA.9919.1.S1_at | solute carrier family 25, member 36 | LOC715375 | 2.30 | 0.0365 |
| MmugDNA.41865.1.S1_at | procollagen C-endopeptidase enhancer | PCOLCE | 2.30 | 0.0277 |
| Mmu.2142.1.S1_at | tripartite motif-containing 22 | TRIM22 | 2.30 | 0.0336 |
| MmugDNA.21471.1.S1_at | butyrophilin-like 9 | BTNL9 | 2.30 | 0.0203 |
| MmugDNA.33142.1.S1_at | Thyroid hormone receptor associated protein 2 | THRAP2 | 2.30 | 0.0902 |
| MmugDNA.911.1.S1_at | tRNA splicing endonuclease 54 homolog (SEN54, S. cerevisiae) | LOC702604 | 2.29 | 0.0159 |
| MmugDNA.462.1.S1_at | Chromobox homolog 3 (HP1 gamma homolog, Drosophila) | CBX3 | 2.29 | 0.0325 |
| MmugDNA.16130.1.S1_at | hypothetical protein LOC90393 | LOC90393 | 2.29 | 0.0237 |
| MmugDNA.32185.1.S1_s_at | Troponin T, fast skeletal muscle (TnTf) (Fast skeletal muscle troponin T) (fTnT) (Beta TnTF) | LOC704095 | 2.29 | 0.0954 |
| MmuSTS.268.1.S1_at | U2-associated SR140 protein | LOC716408 | 2.29 | 0.0066 |

| Probe Set ID | Gene Title | Gene Symbol | Ratio Top verus Bottom | p value Top versus Bottom |
|---|---|---|---|---|
| MmugDNA.39036.1.S1_at | Coatomer subunit zeta-2 (Zeta-2 coat protein) (Zeta-2 COP) | COPZ2 | 2.28 | 0.0507 |
| MmugDNA.21025.1.S1_at | cold inducible RNA binding protein | LOC706175 | 2.28 | 0.0249 |
| MmugDNA.40486.1.S1_s_at | Immortalization-up-regulated protein (Hepatocyte growth factor activator inhibitor type 2-related small pprotein) (HAI-2-related small protein) (H2RSP) | LOC714854 | 2.28 | 0.0153 |
| MmugDNA.26396.1.S1_at | proline rich 6 | LOC700414 | 2.28 | 0.0073 |
| MmuSTS.2009.1.S1_at | protocadherin 18 precursor | LOC698420 | 2.27 | 0.0824 |
| MmugDNA.9315.1.S1_at | kinesin light chain 3 | LOC714331 | 2.27 | 0.0027 |
| MmugDNA.31698.1.S1_at | chromosome 10 open reading frame 86 | LOC705375 | 2.27 | 0.0652 |
| MmugDNA.30174.1.S1_at | v-ets erythroblastosis virus E26 oncogene like | ERG | 2.27 | 0.0267 |
| MmuSTS.7.1.S1_at | GULP, engulfment adaptor PTB domain containing 1 | LOC708601 | 2.27 | 0.0459 |
| MmuSTS.4265.1.S1_at | glypican 4 | LOC706665 | 2.26 | 0.0874 |
| MmugDNA.14551.1.S1_at | cat eye syndrome critical region protein 1 isoform a precursor | LOC709295 | 2.26 | 0.0215 |
| MmugDNA.28933.1.S1_at | septin 11 | 11-Sep | 2.26 | 0.0320 |
| MmugDNA.24711.1.S1_at | rhomboid family 1 | LOC693423 | 2.26 | 0.0985 |
| MmugDNA.22992.1.S1_at | zinc finger protein (C2H2 type) 277 | ZNF277 | 2.26 | 0.0065 |
| MmugDNA.24410.1.S1_at | melanoma associated antigen (mutated) 1 | MUM1 | 2.26 | 0.0947 |
| MmugDNA.9906.1.S1_at | Histone H1.5 (Histone H1a) | LOC705100 | 2.26 | 0.0128 |
| MmuSTS.3965.1.S1_at | colony stimulating factor 1 receptor precursor | LOC711512 | 2.26 | 0.0542 |
| MmugDNA.1769.1.S1_at | CG4699-PA, isoform A | LOC713138 | 2.25 | 0.0713 |
| MmugDNA.43306.1.S1_at | cyclin I | — | 2.25 | 0.0498 |
| MmugDNA.42603.1.S1_at | ankyrin repeat domain 28 | LOC696592 | 2.25 | 0.0775 |
| MmugDNA.37006.1.S1_at | B-cell translocation gene 1, anti-proliferative | LOC710112 | 2.25 | 0.0352 |
| MmugDNA.7428.1.S1_at | Wolf-Hirschhorn syndrome candidate 1 protein isoform 1 | LOC712618 | 2.25 | 0.0954 |
| MmugDNA.37011.1.S1_at | CXXC finger 6 | LOC694137 | 2.25 | 0.0304 |
| MmugDNA.35449.1.S1_at | Sialyltransferase 7 ((alpha-N-acetylneuraminyl-2,3-beta-galactosyl-1,3)-N-acetyl galactosaminide alpha-2,6-sialyltransferase) B //// CDNA clone IMAGE: 3831740, partial cds | SIAT7B | 2.24 | 0.0030 |
| MmuSTS.1106.1.S1_at | platelet/endothelial cell adhesion molecule (CD31 antigen) | LOC718302 | 2.24 | 0.0231 |
| MmugDNA.12061.1.S1_at | — | — | 2.24 | 0.0089 |
| MmuSTS.4678.1.S1_at | three prime repair exonuclease 1 isoform d | LOC710035 | 2.24 | 0.0664 |
| Mmu.4786.2.S1_at | pyrophosphatase 1 | LOC716720 | 2.24 | 0.0781 |
| MmugDNA.38317.1.S1_at | Transcribed locus | — | 2.23 | 0.0610 |
| MmugDNA.26830.1.S1_at | polymerase (DNA directed), eta | LOC700772 | 2.23 | 0.0463 |
| MmugDNA.18586.1.S1_at | structural maintenance of chromosomes 2-like 1 | SMC2L1 | 2.23 | 0.0554 |
| MmugDNA.11249.1.S1_at | potassium channel tetramerisation domain containing 12 | LOC695756 | 2.23 | 0.0517 |
| MmugDNA.8879.1.S1_at | sestrin 3 | SESN3 | 2.23 | 0.0195 |
| MmugDNA.24687.1.S1_at | SLIT-ROBO Rho GTPase activating protein 1 | SRGAP1 | 2.22 | 0.0821 |
| MmugDNA.37739.1.S1_at | serine/threonine kinase 24 (STE20 homolog, yeast) | STK24 | 2.22 | 0.0258 |
| MmuSTS.1280.1.S1_at | RAB39 | LOC709951 | 2.21 | 0.0169 |
| MmugDNA.24944.1.S1_at | Cytochrome P450, family 4, subfamily F, polypeptide 3 | — | 2.21 | 0.0677 |
| MmunewRS.254.1.S1_at | putative ISG12(c) protein | IFI27 | 2.21 | 0.0683 |
| MmugDNA.34004.1.S1_s_at | secretory carrier membrane protein 2 | SCAMP2 | 2.21 | 0.0608 |
| MmugDNA.12030.1.S1_at | SEC8 protein | — | 2.20 | 0.0199 |
| MmugDNA.21255.1.S1_at | neutrophil cytosolic factor 1 | NCF1 | 2.20 | 0.0161 |
| MmugDNA.43588.1.S1_at | hypothetical protein LOC712570 | LOC712570 | 2.20 | 0.0824 |
| MmugDNA.23296.1.S1_s_at | thyroid receptor-interacting protein 6 | TRIP6 | 2.20 | 0.0513 |
| MmugDNA.14929.1.S1_at | insulin-like growth factor 2 mRNA binding protein 2 isoform b | LOC701536 | 2.20 | 0.0109 |
| MmugDNA.39168.1.S1_at | platelet-derived growth factor C precursor | LOC700236 | 2.19 | 0.0284 |
| MmuSTS.1102.1.S1_at | poly(rC) binding protein 4 isoform b | PCBP4 | 2.19 | 0.0477 |
| MmugDNA.41718.1.S1_at | CG12134-PA, isoform A | LOC706314 | 2.19 | 0.0509 |
| MmugDNA.36456.1.S1_at | C1q and tumor necrosis factor related protein 2 | LOC695783 | 2.18 | 0.0650 |
| MmuSTS.4542.1.S1_at | Glycophorin C (PAS-2) (Glycoprotein beta) (GLPC) (Glycoconnectin) (Sialoglycoprotein D) (Glycophorin D) (GPD) (CD236 antigen) | LOC712092 | 2.18 | 0.0118 |
| MmugDNA.10214.1.S1_at | KIAA0792 gene product | KIAA0792 | 2.18 | 0.0596 |
| MmugDNA.7604.1.S1_at | THO complex 2 | THOC2 | 2.18 | 0.0947 |
| MmugDNA.4607.1.S1_at | zinc finger protein 326 isoform 2 | LOC696575 | 2.18 | 0.0302 |
| MmugDNA.26241.1.S1_at | cytochrome b5 reductase | LOC714058 | 2.18 | 0.0499 |
| MmugDNA.24148.1.S1_at | trafficking protein, kinesin binding 2 | LOC701779 | 2.17 | 0.0404 |
| MmugDNA.15712.1.S1_x_at | Cathepsin B | CTSB | 2.17 | 0.0099 |
| MmugDNA.34134.1.S1_at | quaking homolog, KH domain RNA binding isoform HQK-5 | LOC712600 | 2.17 | 0.0569 |
| MmugDNA.20961.1.S1_at | abhydrolase domain containing 1 (predicted) | LOC711493 | 2.17 | 0.0641 |
| MmugDNA.11400.1.S1_at | Homo sapiens, clone IMAGE: 6152133, mRNA | — | 2.17 | 0.0985 |
| MmugDNA.32260.1.S1_at | — | — | 2.17 | 0.0854 |
| MmugDNA.3224.1.S1_at | beta adrenergic receptor kinase 2 | LOC714510 | 2.17 | 0.0824 |
| MmuSTS.144.1.S1_at | minichromosome maintenance protein 2 | LOC710888 | 2.16 | 0.0450 |
| MmugDNA.8814.1.S1_at | TBC1 domain family, member 4 | LOC696915 | 2.15 | 0.0771 |
| MmugDNA.31838.1.S1_s_at | histamine N-methyltransferase | HNMT | 2.15 | 0.0984 |
| MmuSTS.224.1.S1_at | solute carrier family 25, member 27 | SLC25A27 | 2.15 | 0.0161 |
| MmugDNA.24609.1.S1_at | hypothetical protein LOC707415 | LOC707415 | 2.14 | 0.0692 |
| MmugDNA.9218.1.S1_at | RNA binding motif protein 30 | RBM30 | 2.14 | 0.0450 |
| MmugDNA.1986.1.S1_at | type 1 tumor necrosis factor receptor shedding aminopeptidase regulator | ARTS-1 | 2.14 | 0.0959 |

| Probe Set ID | Gene Title | Gene Symbol | Ratio Top verus Bottom | p value Top versus Bottom |
|---|---|---|---|---|
| MmugDNA.21483.1.S1_at | zinc finger protein 579 | LOC701452 | 2.14 | 0.0953 |
| MmugDNA.16054.1.S1_at | TWIST neighbor | LOC707781 | 2.14 | 0.0733 |
| MmugDNA.7039.1.S1_at | — | — | 2.14 | 0.0038 |
| MmuSTS.3729.1.S1_at | fibromodulin precursor | LOC703048 | 2.14 | 0.0183 |
| MmugDNA.10834.1.S1_at | allograft inflammatory factor 1 | AIF1 | 2.14 | 0.0300 |
| MmugDNA.32311.1.S1_at | hormone-sensitive lipase | LOC707997 | 2.14 | 0.0209 |
| MmugDNA.12478.1.S1_at | pleckstrin homology domain containing, family C (with FERM domain) member 1 | LOC693958 | 2.14 | 0.0232 |
| MmugDNA.37583.1.S1_at | Protein tyrosine phosphatase, receptor type, S | PTPRS | 2.13 | 0.0946 |
| MmugDNA.19987.1.S1_s_at | hypothetical protein LOC284454 | LOC284454 | 2.13 | 0.0374 |
| MmugDNA.7038.1.S1_at | Fc fragment of IgG, low affinity IIIb, receptor (CD16b) | FCGR3B | 2.13 | 0.0550 |
| MmugDNA.32358.1.S1_at | lamin A/C | LMNA | 2.13 | 0.0347 |
| MmugDNA.16962.1.S1_at | establishment of cohesion 1 homolog 1 | LOC698845 | 2.13 | 0.0556 |
| MmugDNA.23571.1.S1_at | Epithelial stromal interaction 1 (breast) | EPSTI1 | 2.13 | 0.0778 |
| MmuSTS.2627.1.S1_at | exostoses (multiple)-like 1 | EXTL1 | 2.13 | 0.0154 |
| MmuSTS.1193.1.S1_at | phorbol-12-myristate-13-acetate-induced protein 1 | LOC702789 | 2.13 | 0.0133 |
| MmugDNA.20278.1.S1_at | Insulin-like growth factor-binding protein 7 precursor (IGFBP-7) (IBP-7) (IGF-binding protein 7) (MAC25 protein) (Prostacyclin-stimulating factor) (PGI2-stimulating factor) (IGFBP-rP1) | LOC693564 | 2.12 | 0.0219 |
| MmugDNA.22598.1.S1_at | poliovirus receptor-related 1 (herpesvirus entry mediator C; nectin) | PVRL1 | 2.12 | 0.0579 |
| MmugDNA.3092.1.S1_at | Heterogeneous nuclear ribonucleoproteins A2/B1 (hnRNP A2/hnRNP B1) | HNRPA2B1 | 2.12 | 0.0077 |
| MmuSTS.8.1.S1_at | Histone H2A.x (H2a/x) | LOC703073 | 2.12 | 0.0010 |
| MmuSTS.2363.1.S1_at | squamous cell carcinoma antigen recognized by T cells 2 | LOC716054 | 2.12 | 0.0083 |
| MmuSTS.3798.1.S1_at | scavenger receptor class A, member 3 isoform 1 | LOC718263 | 2.12 | 0.0501 |
| MmugDNA.22785.1.S1_at | — | — | 2.11 | 0.0320 |
| MmugDNA.38565.1.S1_at | v-fos FBJ murine osteosarcoma viral oncogene homolog | FOS | 2.11 | 0.0239 |
| MmugDNA.20885.1.S1_at | chromosome 10 open reading frame 6 | LOC710786 | 2.11 | 0.0526 |
| MmugDNA.11836.1.S1_at | — | — | 2.11 | 0.0069 |
| MmugDNA.16849.1.S1_at | NAD-dependent deacetylase sirtuin-4 (SIR2-like protein 4) | LOC720498 | 2.11 | 0.0416 |
| MmuSTS.4531.1.S1_at | ankyrin repeat and SOCS box-containing protein 1 | ASB1 | 2.11 | 0.0647 |
| MmugDNA.607.1.S1_at | ras-like protein TC10 | LOC717769 | 2.11 | 0.0443 |
| MmugDNA.33195.1.S1_at | hypothetical protein LOC704974 /// G-protein coupled purinergic receptor P2Y5 | LOC704974 /// LOC705081 | 2.11 | 0.0049 |
| MmugDNA.40999.1.S1_at | DAB2 interacting protein | DAB2IP | 2.10 | 0.0008 |
| MmugDNA.9833.1.S1_at | v-maf musculoaponeurotic fibrosarcoma oncogene homolog (avian) | MAF | 2.10 | 0.0082 |
| MmugDNA.21011.1.S1_at | hypothetical protein FLJ90396 | FLJ90396 | 2.10 | 0.0507 |
| MmugDNA.2101.1.S1_at | stearoyl-CoA desaturase (delta-9-desaturase) | SCD | 2.10 | 0.0023 |
| MmuSTS.822.1.S1_at | drebrin 1 | DBN1 | 2.10 | 0.0386 |
| MmugDNA.41100.1.S1_at | GPI-anchored metastasis-associated protein homolog | LOC718197 | 2.10 | 0.0588 |
| MmugDNA.38957.1.S1_at | Cleavage stimulation factor, 3' pre-RNA, subunit 2, 64 kDa, tau variant | CSTF2T | 2.10 | 0.0646 |
| MmugDNA.34474.1.S1_at | cysteine sulfinic acid decarboxylase-related protein 2 | LOC701290 | 2.08 | 0.0698 |
| MmugDNA.9802.1.S1_at | aldehyde dehydrogenase 3 family, member A1 | ALDH3A1 | 2.08 | 0.0132 |
| MmugDNA.43169.1.S1_at | CD109 antigen (Gov platelet alloantigens) | CD109 | 2.08 | 0.0492 |
| MmuSTS.698.1.S1_at | CKLF-like MARVEL transmembrane domain-containing protein 6 (Chemokine factor superfamily member 6) | CMTM6 | 2.08 | 0.0065 |
| MmugDNA.34248.1.S1_at | splicing factor, arginine/serine-rich 15 | LOC701931 | 2.08 | 0.0239 |
| MmugDNA.33686.1.S1_s_at | hypothetical protein LOC722265 | LOC722265 | 2.08 | 0.0776 |
| MmugDNA.33032.1.S1_at | K06A9.1b | LOC710668 | 2.07 | 0.0082 |
| MmugDNA.14765.1.S1_at | polymerase I and transcript release factor | PTRF | 2.07 | 0.0288 |
| MmugDNA.32283.1.S1_at | ladinin 1 | LOC707971 | 2.07 | 0.0106 |
| MmuSTS.2113.1.S1_at | — | ARHGEF19 | 2.07 | 0.0016 |
| MmugDNA.11281.1.S1_at | proline-, glutamic acid-, leucine-rich protein 1 | LOC709306 | 2.07 | 0.0128 |
| MmugDNA.21716.1.S1_at | CDNA FLJ36544 fis, clone TRACH2006378 | — | 2.07 | 0.0908 |
| MmugDNA.33042.1.S1_at | latent transforming growth factor beta binding protein 2 | LOC699435 | 2.07 | 0.0762 |
| MmugDNA.9373.1.S1_at | metastasis-associated protein 2 | — | 2.06 | 0.0100 |
| Mmu.13445.1.S1_at | calumenin precursor | LOC699730 | 2.06 | 0.0342 |
| MmuSTS.4590.1.S1_at | transglutaminase 2 | TGM2 | 2.06 | 0.0817 |
| MmugDNA.19491.1.S1_at | KIAA1219 protein | KIAA1219 | 2.06 | 0.0781 |
| MmugDNA.10100.1.S1_at | hypothetical protein LOC722637 | LOC722637 | 2.06 | 0.0099 |
| MmugDNA.16322.1.S1_at | Transcribed locus, weakly similar to NP_055301.1 neuronal thread protein AD7c-NTP [Homo sapiens] | — | 2.06 | 0.0989 |
| MmugDNA.4438.1.S1_at | transmembrane protein 39B | LOC706700 | 2.06 | 0.0916 |
| MmugDNA.35973.1.S1_at | agrin | LOC693314 | 2.06 | 0.0197 |
| MmugDNA.36549.1.S1_at | Hypothetical protein FLJ14888 | FLJ14888 | 2.06 | 0.0846 |
| MmugDNA.15963.1.S1_at | PABP1-dependent poly A-specific ribonuclease subunit PAN3 | PAN3 | 2.05 | 0.0740 |
| MmugDNA.18234.1.S1_at | runt-related transcription factor 2 isoform b | LOC703331 | 2.05 | 0.0228 |
| MmugDNA.32119.1.S1_at | cytosolic malic enzyme 1 | ME1 | 2.05 | 0.0425 |
| MmugDNA.18163.1.S1_at | gamma-aminobutyric acid (GABA) B receptor 1 isoform a precursor | LOC708987 | 2.05 | 0.0129 |
| MmugDNA.18569.1.S1_at | phospholipase A2, group IVB | LOC707262 | 2.04 | 0.0116 |

-continued

| Probe Set ID | Gene Title | Gene Symbol | Ratio Top verus Bottom | p value Top versus Bottom |
|---|---|---|---|---|
| MmugDNA.23773.1.S1_at | alpha 1 type XVIII collagen isoform 1 precursor | LOC721919 | 2.04 | 0.0444 |
| Mmu.16285.1.A1_at | — | ANP32A | 2.04 | 0.0274 |
| MmuSTS.2061.1.S1_at | phospholipase C gamma 1 isoform a | LOC697069 | 2.04 | 0.0259 |
| MmugDNA.25737.1.S1_at | Abl-interactor 1 | ABI1 | 2.04 | 0.0333 |
| MmugDNA.37418.1.S1_at | NMD3 homolog | LOC701677 | 2.04 | 0.0354 |
| MmugDNA.29644.1.S1_at | RAN binding protein 2-like 1 | RANBP2L1 | 2.04 | 0.0405 |
| MmugDNA.22841.1.S1_at | Karyopherin alpha 5 (importin alpha 6) | KPNA5 | 2.04 | 0.0159 |
| MmugDNA.40840.1.S1_at | ring finger and KH domain containing 2 | LOC719403 | 2.03 | 0.0970 |
| MmugDNA.39873.1.S1_s_at | solute carrier family 38, member 2 | LOC702253 | 2.03 | 0.0018 |
| MmugDNA.29688.1.S1_at | G-protein coupled receptor 116 | LOC704887 | 2.03 | 0.0715 |
| MmugDNA.2555.1.S1_at | CDNA FLJ37816 fis, clone BRSSN2003093 | — | 2.03 | 0.0765 |
| MmugDNA.27712.1.S1_at | golgi SNAP receptor complex member 1 | GOSR1 | 2.03 | 0.0166 |
| MmuSTS.3453.1.S1_at | PYD and CARD domain containing isoform b | LOC713563 | 2.03 | 0.0818 |
| MmugDNA.38737.1.S1_s_at | transcription factor B1, mitochondrial | LOC701830 | 2.03 | 0.0574 |
| MmugDNA.371.1.S1_at | — | — | 2.03 | 0.0252 |
| MmuSTS.2285.1.S1_at | POU domain, class 5, transcription factor 1 | POU5F1 | 2.02 | 0.0989 |
| MmugDNA.11375.1.S1_at | spartin | LOC693663 | 2.02 | 0.0884 |
| MmuSTS.3541.1.S1_at | NOD2 protein | LOC695542 | 2.02 | 0.0867 |
| MmunewRS.886.1.S1_at | gi: 51465519 | — | 2.02 | 0.0891 |
| MmugDNA.33688.1.S1_at | ribosomal protein L17 | RPL17 | 2.02 | 0.0384 |
| MmugDNA.31199.1.S1_at | ADP-ribosylation factor-like protein 4C (ADP-ribosylation factor-like 7) | ARL4C | 2.02 | 0.0154 |
| MmugDNA.32540.1.S1_at | centaurin-alpha 2 protein | CENTA2 | 2.02 | 0.0939 |
| MmugDNA.19746.1.S1_at | solute carrier family 2 (facilitated glucose transporter), member 3 | SLC2A3 | 2.02 | 0.0013 |
| MmugDNA.30247.1.S1_at | RNA-binding region containing protein 2 isoform b | LOC704198 | 2.01 | 0.0297 |
| MmugDNA.35944.1.S1_at | CDNA FLJ13136 fis, clone NT2RP3003139 | — | 2.01 | 0.0963 |
| MmugDNA.29822.1.S1_at | carbonic anhydrase IV | CA4 | 2.01 | 0.0637 |
| MmugDNA.15283.1.S1_at | Transcribed locus | — | 2.01 | 0.0424 |
| MmugDNA.9600.1.S1_at | regulating synaptic membrane exocytosis 2 | RIMS2 | 13.30 | 0.0310 |
| MmugDNA.14408.1.S1_at | chromosome 12 open reading frame 24 | C12orf24 | 12.75 | 0.1070 |
| MmugDNA.37885.1.S1_at | homer homolog 1 (*Drosophila*) | HOMER1 | 12.68 | 0.0144 |
| MmugDNA.15936.1.S1_s_at | CDNA: FLJ21874 fis, clone HEP02488 | — | 12.38 | 0.0063 |
| MmuSTS.3629.1.S1_at | EMI domain containing 1 | EMID1 | 12.26 | 0.0380 |
| MmugDNA.10412.1.S1_x_at | Hypothetical protein KIAA0187 gene product /// Immunoglobulin lambda locus | LOC96610 /// IGL@ | 12.20 | 0.2034 |
| MmugDNA.21132.1.S1_at | hypothetical locus FLJ30594 | FLJ30594 | 12.08 | 0.1018 |
| MmugDNA.16717.1.S1_s_at | seizure related 6 homolog (mouse)-like 2 /// seizure related 6 homolog (mouse)-like 2 isoform 1 | SEZ6L2 /// LOC652900 | 11.95 | 0.0313 |
| MmuSTS.721.1.S1_at | N-acetylneuraminate pyruvate lyase (dihydrodipicolinate synthase | NPL | 11.73 | 0.0624 |
| MmugDNA.23998.1.S1_at | DKFZP434B0335 protein | DKFZP434B0335 | 11.67 | 0.0140 |
| Mmu.10472.1.S1_at | acid sphingomyelinase-like phosphodiesterase 3A | LOC713696 | 11.58 | 0.0004 |
| MmugDNA.34582.1.S1_at | limbic system-associated membrane protein | LSAMP | 11.56 | 0.1465 |
| MmugDNA.27799.1.S1_at | chromosome 8 open reading frame 47 | C8orf47 | 11.54 | 0.0051 |
| MmugDNA.35367.1.S1_at | transmembrane emp24 protein transport domain containing 8 | TMED8 | 11.54 | 0.0000 |
| MmuSTS.4580.1.S1_at | heparan sulfate (glucosamine) 3-O-sulfotransferase 5 | HS3ST5 | 11.36 | 0.0340 |
| MmugDNA.14099.1.S1_at | protein disulfide isomerase family A, member 5 | PDIA5 | 11.07 | 0.0354 |
| MmunewRS.286.1.S1_at | cDNA FLJ46082 fis, clone TESTI2005153. | gi: 34536371 | 10.92 | 0.1933 |
| MmugDNA.13637.1.S1_at | hypothetical protein LOC169834 | LOC169834 | 10.91 | 0.0446 |
| MmugDNA.21508.1.S1_at | CDNA FLJ37235 fis, clone BRAMY2002525 | — | 10.58 | 0.2144 |
| MmugDNA.26503.1.S1_at | polyhomeotic-like 2 (*Drosophila*) | PHC2 | 10.50 | 0.0002 |
| MmugDNA.9977.1.S1_at | ethanolamine kinase 1 | ETNK1 | 10.43 | 0.0022 |
| MmuSTS.629.1.S1_at | insulin-like growth factor 2 receptor | IGF2R | 10.32 | 0.0115 |
| MmugDNA.42459.1.S1_at | nucleotide binding protein 1 (MinD homolog, *E. coli*) | NUBP1 | 10.13 | 0.0076 |
| MmugDNA.16304.1.S1_at | paraoxonase 2 | PON2 | 10.03 | 0.2019 |
| MmugDNA.27226.1.S1_at | chromosome 10 open reading frame 49 | C10orf49 | 10.03 | 0.1874 |
| MmugDNA.27601.1.S1_at | — | — | 10.01 | 0.0801 |
| MmugDNA.19069.1.S1_at | transient receptor potential cation channel, subfamily M, member 7 | TRPM7 | 9.84 | 0.0026 |
| MmugDNA.12483.1.S1_at | HLA complex group 27 | HCG27 | 9.82 | 0.1032 |
| MmugDNA.15012.1.S1_at | Arylformamidase | AFMID | 9.78 | 0.0546 |
| MmugDNA.689.1.S1_at | hypothetical protein LOC707842 | LOC707842 | 9.65 | 0.1426 |
| MmugDNA.1511.1.S1_at | Transcribed locus | — | 9.54 | 0.1466 |
| MmugDNA.6078.1.S1_at | Sp2 transcription factor | SP2 | 9.47 | 0.1325 |
| MmugDNA.34436.1.S1_at | Hypothetical protein LOC152485 | LOC152485 | 9.36 | 0.0053 |
| Mmu.15003.1.S1_x_at | activating signal cointegrator 1 complex subunit 3-like 1 | LOC705184 | 9.28 | 0.0157 |
| MmugDNA.24349.1.S1_at | Transcribed locus | — | 9.26 | 0.0882 |
| MmugDNA.21279.1.S1_at | Leucine-rich repeat protein SHOC-2 (Ras-binding protein Sur-8) | RP11-139H14.4 | 9.21 | 0.0670 |
| MmugDNA.13732.1.S1_at | PHD finger protein 20-like 1 | PHF20L1 | 9.20 | 0.0626 |
| MmugDNA.28092.1.S1_at | breakpoint cluster region isoform 1 | LOC644165 | 9.11 | 0.2063 |
| MmugDNA.4326.1.S1_at | Transcribed locus | — | 8.93 | 0.0080 |
| Mmu.15748.1.S1_s_at | Transcribed locus, weakly XP_933032.2 hypothetical protein [*Homo sapiens*] | — | 8.88 | 0.0874 |
| MmugDNA.17676.1.S1_at | peroxisomal biogenesis factor 5-like | PEX5L | 8.86 | 0.0737 |

-continued

| Probe Set ID | Gene Title | Gene Symbol | Ratio Top verus Bottom | p value Top versus Bottom |
|---|---|---|---|---|
| MmugDNA.38590.1.S1_at | ligand-gated ion channel, zinc activated 1 | LGICZ1 | 8.81 | 0.0142 |
| MmugDNA.33781.1.S1_at | dynein, axonemal, heavy polypeptide 10 | DNAH10 | 8.80 | 0.1157 |
| MmugDNA.43623.1.S1_s_at | disabled homolog 2, mitogen-responsive phosphoprotein (Drosophila) | DAB2 | 8.75 | 0.0103 |
| MmugDNA.20593.1.S1_at | tripeptidyl peptidase II | TPP2 | 8.68 | 0.2180 |
| MmugDNA.24454.1.S1_at | phosphatidic acid phosphatase type 2C | PPAP2C | 8.68 | 0.1046 |
| MmugDNA.4150.1.S1_at | hypothetical protein FLJ40298 | FLJ40298 | 8.67 | 0.1356 |
| MmugDNA.22927.1.S1_at | — | — | 8.66 | 0.1089 |
| MmugDNA.39321.1.S1_at | CDNA FLJ41751 fis, clone HSYRA2008154 | — | 8.65 | 0.0090 |
| MmugDNA.38636.1.S1_at | hypothetical protein FLJ39653 | FLJ39653 | 8.61 | 0.0384 |
| MmugDNA.8681.1.S1_at | KIAA0100 /// hypothetical protein FLJ22349 | KIAA0100 /// FLJ22349 | 8.61 | 0.0075 |
| MmugDNA.27488.1.S1_at | suppression of tumorigenicity 14 (colon carcinoma) | ST14 | 8.58 | 0.0576 |
| MmugDNA.29768.1.S1_at | melanocortin 2 receptor accessory protein | MRAP | 8.56 | 0.0423 |
| MmugDNA.42270.1.S1_at | gremlin 1, cysteine knot superfamily, homolog (Xenopus laevis) | GREM1 | 8.53 | 0.1415 |
| MmugDNA.30894.1.S1_at | Transcribed locus, strongly NP_067647.1 leucine-rich repeat-containing G protein-coupled receptor 7 [Homo sapiens] | — | 8.44 | 0.1092 |
| MmugDNA.37925.1.S1_at | plasma glutamate carboxypeptidase | PGCP | 8.43 | 0.0055 |
| MmugDNA.7703.1.S1_s_at | pyrroline-5-carboxylate reductase family, member 2 | PYCR2 | 8.42 | 0.0481 |
| MmugDNA.29962.1.S1_at | procollagen-proline, 2-oxoglutarate 4-dioxygenase (proline 4-hydroxylase), alpha polypeptide III | P4HA3 | 8.41 | 0.0311 |
| MmugDNA.29322.1.S1_at | chromosome 6 open reading frame 159 | C6orf159 | 8.37 | 0.1465 |
| MmugDNA.32728.1.S1_at | GLIS family zinc finger 2 | LOC708454 | 8.33 | 0.0118 |
| MmugDNA.39848.1.S1_at | DIP2 disco-interacting protein 2 homolog C (Drosophila) | DIP2C | 8.32 | 0.0054 |
| MmugDNA.9959.1.S1_at | — | — | 8.31 | 0.2016 |
| MmuSTS.2576.1.S1_at | DnaJ (Hsp40) homolog, subfamily B, member 12 | DNAJB12 | 8.25 | 0.0207 |
| MmugDNA.3860.1.S1_at | — | — | 8.16 | 0.0618 |
| Mmu.4703.1.S1_at | — | CO774986 | 8.16 | 0.0134 |
| MmugDNA.33155.1.S1_at | likely ortholog of MEF2-activating SAP transcriptional regulator | FLJ36070 | 8.15 | 0.0863 |
| MmugDNA.20631.1.S1_at | Transcribed locus, strongly XP_513258.1 LOC456687 [Pan troglodytes] | 230613_at | 8.08 | 0.2120 |
| MmugDNA.39834.1.S1_s_at | fragile histidine triad gene | FHIT | 8.00 | 0.0019 |
| MmugDNA.26008.1.S1_at | musashi homolog 2 (Drosophila) | MSI2 | 7.97 | 0.0002 |
| MmugDNA.36272.1.S1_s_at | dCMP deaminase | DCTD | 7.87 | 0.0027 |
| MmugDNA.21159.1.S1_at | hypothetical protein FLJ31846 | FLJ31846 | 7.84 | 0.1945 |
| MmugDNA.7644.1.S1_at | amyloid beta (A4) precursor-like protein 2 | APLP2 | 7.82 | 0.0540 |
| MmugDNA.26889.1.S1_at | Transcribed locus | — | 7.82 | 0.1703 |
| MmugDNA.35633.1.S1_at | Transcribed locus, strongly NP_659486.1 hypothetical protein MGC10067 [Homo sapiens] | — | 7.80 | 0.0389 |
| MmugDNA.11626.1.S1_at | dynein, cytoplasmic 2, heavy chain 1 | DYNC2H1 | 7.80 | 0.0014 |
| MmugDNA.18533.1.S1_at | phospholipase D family, member 5 | PLD5 | 7.80 | 0.0512 |
| MmugDNA.36604.1.S1_at | Transcribed locus | — | 7.77 | 0.0005 |
| MmugDNA.12098.1.S1_at | Transcribed locus | — | 7.76 | 0.0954 |
| MmugDNA.8791.1.S1_at | KIAA0586 | KIAA0586 | 7.72 | 0.0606 |
| MmugDNA.25037.1.S1_at | CDNA FLJ30090 fis, clone BNGH41000015 | — | 7.68 | 0.0828 |
| MmugDNA.30003.1.S1_at | BTB (POZ) domain containing 16 | BTBD16 | 7.66 | 0.0893 |
| MmugDNA.29464.1.S1_at | inositol monophosphatase domain containing 1 | IMPAD1 | 7.65 | 0.0204 |
| MmugDNA.29130.1.S1_at | adenylate cyclase 1 (brain) | ADCY1 | 7.64 | 0.0222 |
| MmugDNA.42065.1.S1_at | distal-less homeobox 6 | DLX6 | 7.64 | 0.2136 |
| MmugDNA.3371.1.S1_at | reticulon 1 | RTN1 | 7.63 | 0.0730 |
| MmugDNA.23995.1.S1_at | zinc finger protein 501 | ZNF501 | 7.62 | 0.1374 |
| MmugDNA.5842.1.S1_at | — | — | 7.59 | 0.1545 |
| MmugDNA.21402.1.S1_at | R3H domain and coiled-coil containing 1 | R3HCC1 | 7.58 | 0.0122 |
| MmugDNA.11091.1.S1_at | Nuclear factor I/A | NFIA | 7.58 | 0.0395 |
| MmuSTS.383.1.S1_at | lipase, gastric | LIPF | 7.56 | 0.1613 |
| MmugDNA.26814.1.S1_at | chromosome 3 open reading frame 19 | C3orf19 | 7.55 | 0.0189 |
| MmugDNA.38434.1.S1_at | WD repeat domain 5B | WDR5B | 7.50 | 0.1039 |
| MmugDNA.5186.1.S1_at | RNA binding motif protein 23 | RBM23 | 7.45 | 0.0136 |
| MmugDNA.22050.1.S1_at | EID-2-like inhibitor of differentiation-3 | EID-3 | 7.45 | 0.0340 |
| MmugDNA.40688.1.S1_at | zinc finger protein 235 | ZNF235 | 7.43 | 0.0135 |
| MmugDNA.30778.1.S1_at | growth factor, augmenter of liver regeneration (ERV1 homolog, S. cerevisiae) | GFER | 7.42 | 0.0002 |
| MmuSTS.2673.1.S1_at | calmegin | CLGN | 7.41 | 0.0581 |
| MmugDNA.9553.1.S1_at | Mannosidase, alpha, class 1A, member 1 | MAN1A1 | 7.38 | 0.0114 |
| MmugDNA.16242.1.S1_at | — | — | 7.37 | 0.0006 |
| MmugDNA.23074.1.S1_at | plexin A2 | PLXNA2 | 7.36 | 0.0096 |
| MmugDNA.31786.1.S1_at | hypothetical protein LOC158402 | LOC158402 | 7.36 | 0.0327 |
| MmugDNA.9822.1.S1_at | immunoglobulin superfamily containing leucine-rich repeat 2 | ISLR2 | 7.34 | 0.1736 |
| MmugDNA.5439.1.S1_at | catechol-O-methyltransferase | COMT | 7.32 | 0.0094 |
| MmugDNA.23942.1.S1_at | — | — | 7.26 | 0.0768 |
| MmugDNA.37455.1.S1_at | Transcribed locus | — | 7.25 | 0.0155 |
| MmugDNA.34284.1.S1_at | sodium channel, voltage-gated, type III, beta | SCN3B | 7.25 | 0.0578 |
| MmugDNA.19576.1.S1_at | zinc finger protein 547 | ZNF547 | 7.24 | 0.0782 |
| MmugDNA.34395.1.S1_at | zinc finger protein 230 | ZNF230 | 7.23 | 0.0152 |
| MmugDNA.6131.1.S1_at | chromosome 16 open reading frame 35 | C16orf35 | 7.20 | 0.1537 |

| Probe Set ID | Gene Title | Gene Symbol | Ratio Top verus Bottom | p value Top versus Bottom |
|---|---|---|---|---|
| MmugDNA.6727.1.S1_at | — | — | 7.20 | 0.0804 |
| MmugDNA.24272.1.S1_at | KIAA1922 protein | KIAA1922 | 7.19 | 0.1247 |
| MmugDNA.6286.1.S1_at | zinc finger protein 599 | ZNF599 | 7.14 | 0.0790 |
| MmuSTS.3570.1.S1_at | collagen, type IV, alpha 4 | COL4A4 | 7.14 | 0.0006 |
| MmugDNA.39056.1.S1_at | chromodomain helicase DNA binding protein 4 | CHD4 | 7.13 | 0.0047 |
| MmugDNA.34250.1.S1_at | hypothetical protein LOC645644 | FLJ42627 | 7.13 | 0.0043 |
| MmuSTS.1813.1.S1_at | sterol O-acyltransferase 2 | SOAT2 | 7.11 | 0.0279 |
| MmugDNA.24694.1.S1_at | Retinoblastoma binding protein 4 | RBBP4 | 7.10 | 0.0185 |
| MmugDNA.24480.1.S1_at | splicing factor proline/glutamine-rich (polypyrimidine tract binding protein associated) | SFPQ | 7.09 | 0.0095 |
| MmugDNA.33264.1.S1_at | TIP41, TOR signalling pathway regulator-like (S. cerevisiae) | TIPRL | 7.08 | 0.1207 |
| MmugDNA.31611.1.S1_at | PRotein Associated with TIr4 | MGC40499 | 7.01 | 0.0583 |
| MmugDNA.26071.1.S1_s_at | RAB30, member RAS oncogene family | RAB30 | 6.97 | 0.0043 |
| MmugDNA.11685.1.S1_at | poly (ADP-ribose) polymerase family, member 8 | PARP8 | 6.94 | 0.0303 |
| MmugDNA.38371.1.S1_at | hexosaminidase A (alpha polypeptide) | HEXA | 6.94 | 0.0512 |
| MmugDNA.5558.1.S1_at | tRNA phosphotransferase 1 | TRPT1 | 6.93 | 0.0013 |
| MmugDNA.34597.1.S1_at | tetraspanin 1 | TSPAN1 | 6.86 | 0.0007 |
| MmugDNA.18788.1.S1_at | Capping protein (actin filament) muscle Z-line, alpha 2 | CAPZA2 | 6.85 | 0.0915 |
| MmugDNA.28272.1.S1_at | molybdenum cofactor synthesis 1 | MOCS1 | 6.83 | 0.0681 |
| MmugDNA.14078.1.S1_at | EBNA1 binding protein 2 | EBNA1BP2 | 6.82 | 0.0463 |
| MmuSTS.2123.1.S1_at | retinal outer segment membrane protein 1 | ROM1 | 6.81 | 0.0210 |
| MmugDNA.9513.1.S1_at | exostoses (multiple)-like 2 | EXTL2 | 6.79 | 0.0112 |
| Mmu.7528.1.S1_at | Zygin 1 | ZYG1 | 6.76 | 0.0713 |
| MmugDNA.12416.1.S1_at | coiled-coil domain containing 51 | CCDC51 | 6.76 | 0.0052 |
| MmuSTS.3946.1.S1_at | T-cell activation kelch repeat protein | TA-KRP | 6.76 | 0.0172 |
| MmugDNA.12522.1.S1_at | Pyrophosphatase (inorganic) 2 | PPA2 | 6.74 | 0.0061 |
| MmugDNA.39796.1.S1_at | DIRAS family, GTP-binding RAS-like 3 | DIRAS3 | 6.72 | 0.0734 |
| MmugDNA.1685.1.S1_at | zinc finger protein 682 | ZNF682 | 6.72 | 0.0142 |
| MmuSTS.2157.1.S1_at | Scm-like with four mbt domains 1 | SFMBT1 | 6.71 | 0.0051 |
| MmugDNA.2165.1.S1_at | small nuclear ribonucleoprotein polypeptide E | SNRPE | 6.70 | 0.0389 |
| MmugDNA.2643.1.S1_at | chromosome 11 open reading frame 59 | C11orf59 | 6.69 | 0.0306 |
| MmugDNA.13192.1.S1_s_at | peptidylprolyl isomerase E (cyclophilin E) | PPIE | 6.67 | 0.0336 |
| MmugDNA.13901.1.S1_at | KIAA0194 protein | KIAA0194 | 6.65 | 0.0029 |
| MmugDNA.9677.1.S1_at | hypothetical protein MGC39606 /// hypothetical protein LOC644596 | MGC39606 /// LOC644596 | 6.64 | 0.0636 |
| MmugDNA.21296.1.S1_at | CDNA FLJ14188 fis, clone NT2RP2005980 | — | 6.64 | 0.0539 |
| MmugDNA.36977.1.S1_at | transmembrane protein 107 | TMEM107 | 6.62 | 0.0537 |
| MmuSTS.3859.1.S1_at | solute carrier family 26, member 9 | SLC26A9 | 6.62 | 0.0483 |
| MmuSTS.514.1.S1_at | ATPase, Class VI, type 11C | ATP11C | 6.62 | 0.0004 |
| MmugDNA.18137.1.S1_at | — | — | 6.60 | 0.0451 |
| MmugDNA.36662.1.S1_at | STAM binding protein-like 1 | STAMBPL1 | 6.60 | 0.0041 |
| MmugDNA.13357.1.S1_at | KDEL (Lys-Asp-Glu-Leu) endoplasmic reticulum protein retention receptor 1 | KDELR1 | 6.58 | 0.0618 |
| MmugDNA.34884.1.S1_at | CUB and zona pellucida-like domains 1 | CUZD1 | 6.58 | 0.0561 |
| MmugDNA.10426.1.S1_at | neuron navigator 3 | NAV3 | 6.56 | 0.0493 |
| MmunewRS.777.1.S1_at | This record was removed as a result of standard genome annotation poroccessing. | | 6.54 | 0.0904 |
| MmugDNA.32277.1.S1_at | DNA (cytosine-5-)-methyltransferase 2 | DNMT2 | 6.51 | 0.0001 |
| MmunewRS.654.1.S1_at | taste receptor, type 2, member 44 | TAS2R44 | 6.51 | 0.1568 |
| MmuSTS.3981.1.S1_at | SH3-domain GRB2-like 2 | SH3GL2 | 6.48 | 0.0289 |
| MmugDNA.23979.1.S1_at | tetratricopeptide repeat domain 8 | TTC8 | 6.47 | 0.0227 |
| MmugDNA.9202.1.S1_at | PRO0633 | — | 6.45 | 0.0369 |
| MmugDNA.19839.1.S1_at | metallothionein 1G | MT1G | 6.44 | 0.0115 |
| MmugDNA.11505.1.S1_at | RNA (guanine-9-) methyltransferase domain containing 3 | RG9MTD3 | 6.44 | 0.0224 |
| MmugDNA.37839.1.S1_s_at | Full length insert cDNA clone ZD82B02 | — | 6.41 | 0.0024 |
| MmugDNA.26070.1.S1_at | putatative 28 kDa protein | LOC56902 | 6.39 | 0.0219 |
| MmugDNA.4320.1.S1_at | chromosome 14 open reading frame 93 | C14orf93 | 6.39 | 0.0814 |
| MmugDNA.42430.1.S1_at | chromosome 5 open reading frame 28 | C5orf28 | 6.39 | 0.0427 |
| MmugDNA.13792.1.S1_at | spermatogenesis associated 7 | SPATA7 | 6.37 | 0.0117 |
| MmugDNA.39646.1.S1_s_at | chromosome 19 open reading frame 10 | C19orf10 | 6.36 | 0.1162 |
| MmugDNA.4241.1.S1_at | FRAS1 related extracellular matrix 3 | FREM3 | 6.34 | 0.0744 |
| MmugDNA.5102.1.S1_at | — | — | 6.33 | 0.0111 |
| MmugDNA.23567.1.S1_at | protein arginine methyltransferase 6 | PRMT6 | 6.33 | 0.0382 |
| MmugDNA.42806.1.S1_at | — | — | 6.33 | 0.0980 |
| MmugDNA.35790.1.S1_at | solute carrier family 7 (cationic amino acid transporter, y+ system), member 3 | SLC7A3 | 6.31 | 0.1159 |
| MmugDNA.11215.1.S1_at | — | — | 6.30 | 0.0526 |
| MmugDNA.9057.1.S1_at | transmembrane protein 107 /// transmembrane protein 107 | TMEM107 | 6.28 | 0.0390 |
| MmugDNA.37336.1.S1_at | stathmin-like 2 | STMN2 | 6.27 | 0.1549 |
| MmugDNA.117.1.S1_at | DPH5 homolog (S. cerevisiae) | DPH5 | 6.27 | 0.0417 |
| Mmu.15115.1.S1_at | Ribonuclease UK114 (14.5 kDa translational inhibitor protein) (p14.5) (UK114 antigen homolog) | LOC705533 | 6.25 | 0.0280 |
| MmugDNA.21121.1.S1_at | Insulin-like growth factor 1 receptor | IGF1R | 6.25 | 0.0700 |
| MmugDNA.13304.1.S1_at | Fukuyama type congenital muscular dystrophy (fukutin) | FCMD | 6.24 | 0.0342 |
| MmugDNA.40836.1.S1_at | chromosome 6 open reading frame 168 | C6orf168 | 6.23 | 0.0000 |
| MmugDNA.23421.1.S1_at | FLJ16124 protein | ELJ16124 | 6.23 | 0.1070 |

-continued

| Probe Set ID | Gene Title | Gene Symbol | Ratio Top verus Bottom | p value Top versus Bottom |
|---|---|---|---|---|
| MmugDNA.29466.1.S1_at | Transcribed locus | — | 6.22 | 0.0243 |
| MmugDNA.41017.1.S1_at | CDNA clone IMAGE: 4791585 | — | 6.20 | 0.0430 |
| MmugDNA.18662.1.S1_at | parathyroid hormone receptor 2 | PTHR2 | 6.19 | 0.1555 |
| MmugDNA.27914.1.S1_at | family with sequence similarity 55, member D | FAM55D | 6.19 | 0.1240 |
| MmugDNA.39981.1.S1_at | microtubule associated monoxygenase, calponin and LIM domain containing 2 | MICAL2 | 6.17 | 0.0214 |
| MmugDNA.33630.1.S1_at | apolipoprotein B mRNA editing enzyme, catalytic polypeptide-like 3G | APOBEC3G | 6.13 | 0.0918 |
| MmugDNA.41272.1.S1_at | KIAA0174 | KIAA0174 | 6.12 | 0.0498 |
| MmugDNA.4554.1.S1_at | membrane-associated ring finger (C3HC4) 9 | 9-Mar | 6.12 | 0.0006 |
| MmuSTS.4598.1.S1_at | hypoxia up-regulated 1 | HYOU1 | 6.11 | 0.0224 |
| MmugDNA.40815.1.S1_at | Family with sequence similarity 77, member D | FAM77D | 6.11 | 0.0370 |
| MmugDNA.10816.1.S1_at | CDNA FLJ90571 fis, clone OVARC1001725, highly Homo sapiens patched related protein TRC8 (TRC8) gene | — | 6.09 | 0.0585 |
| Mmu.15827.1.S1_at | tafazzin | TAZ | 6.09 | 0.0279 |
| MmugDNA.18337.1.S1_at | neurofilament, heavy polypeptide 200 kDa | NEFH | 6.08 | 0.0788 |
| MmuSTS.3411.1.S1_at | phosphoribosyl pyrophosphate synthetase 1 | PRPS1 | 6.08 | 0.0271 |
| MmugDNA.4215.1.S1_at | matrix-remodelling associated 8 | MXRA8 | 6.07 | 0.0277 |
| MmugDNA.2493.1.S1_at | Full-length cDNA clone CS0DI054YK19 of Placenta Cot 25-normalized of Homo sapiens (human) | — | 6.07 | 0.0954 |
| MmugDNA.29221.1.S1_at | mannosidase, alpha, class 2A, member 1 | MAN2A1 | 6.06 | 0.0356 |
| MmuSTS.2268.1.S1_at | polymerase (RNA) II (DNA directed) polypeptide C, 33 kDa | POLR2C | 6.06 | 0.0054 |
| MmugDNA.16039.1.S1_at | Transcribed locus | — | 6.05 | 0.1426 |
| MmugDNA.23370.1.S1_at | SH3 and PX domains 2A | SH3PXD2A | 6.02 | 0.1440 |
| Mmu.5073.1.S1_at | histone deacetylase 1 | LOC708441 | 6.01 | 0.0636 |
| MmugDNA.18754.1.S1_at | hypothetical protein LOC134466 | LOC134466 | 6.00 | 0.0506 |
| MmugDNA.34454.1.S1_at | — | — | 5.97 | 0.0048 |
| MmugDNA.23057.1.S1_at | hypothetical gene supported by AK125122 | FLJ13137 | 5.97 | 0.0012 |
| MmugDNA.27855.1.S1_at | — | — | 5.97 | 0.0167 |
| MmuSTS.3142.1.S1_at | methyl-CpG binding domain protein 5 | MBD5 | 5.95 | 0.0115 |
| MmugDNA.23903.1.S1_at | Protein inhibitor of activated STAT, 2 | PIAS2 | 5.94 | 0.0193 |
| MmugDNA.7631.1.S1_at | CDNA FLJ11682 fis, clone HEMBA1004880 | — | 5.94 | 0.1697 |
| MmugDNA.20356.1.S1_at | platelet-activating factor acetylhydrolase 2, 40 kDa | PAFAH2 | 5.94 | 0.0009 |
| MmugDNA.2708.1.S1_at | Son of sevenless homolog 1 (Drosophila) | SOS1 | 5.91 | 0.0461 |
| MmugDNA.10905.1.S1_at | tectonic | FLJ21127 | 5.89 | 0.0025 |
| MmugDNA.28625.1.S1_at | without children CG5965-PA | LOC707028 | 5.89 | 0.0638 |
| MmugDNA.11493.1.S1_at | eukaryotic translation initiation factor 4A, isoform 2 | EIF4A2 | 5.87 | 0.0421 |
| MmugDNA.23572.1.S1_s_at | glutamate-cysteine ligase, modifier subunit | GCLM | 5.86 | 0.0027 |
| MmuSTS.2280.1.S1_at | Dapper, antagonist of beta-catenin, homolog 1 (Xenopus laevis) | DACT1 | 5.86 | 0.0752 |
| MmugDNA.25697.1.S1_at | Ubiguitin-conjugating enzyme E2W (putative) | UBE2W | 5.85 | 0.0579 |
| MmugDNA.24422.1.S1_at | glucosidase, beta, acid 3 (cytosolic) | GBA3 | 5.84 | 0.1210 |
| MmugDNA.26055.1.S1_at | THAP domain containing 5 | THAP5 | 5.82 | 0.1799 |
| MmuSTS.1960.1.S1_at | forkhead box D1 | FOXD1 | 5.81 | 0.0736 |
| MmugDNA.35294.1.S1_at | protein tyrosine phosphatase-like A domain containing 1 | PTPLAD1 | 5.80 | 0.0213 |
| MmugDNA.15150.1.S1_at | histone deacetylase 8 | HDAC8 | 5.77 | 0.0384 |
| MmugDNA.32612.1.S1_s_at | prostaglandin D2 synthase 21 kDa (brain) /// prostaglandin D2 synthase 21 kDa (brain) | PTGDS | 5.77 | 0.1930 |
| MmuSTS.1829.1.S1_at | Shroom-related protein | ShrmL | 5.77 | 0.0060 |
| MmuSTS.3849.1.S1_at | Spectrin repeat containing, nuclear envelope 2 | SYNE2 | 5.74 | 0.0000 |
| Mmu.13961.1.S1_at | Protein NipSnap3A (NipSnap4) (Target for Salmonella secreted protein C) (TassC) | LOC716188 | 5.72 | 0.0252 |
| MmugDNA.29451.1.S1_at | Transcribed locus | 241668_s_at | 5.71 | 0.1366 |
| MmugDNA.39448.1.S1_at | Interferon regulatory factor 2 | IRF2 | 5.71 | 0.0394 |
| MmugDNA.13520.1.S1_at | cytoplasmic linker associated protein 2 | CLASP2 | 5.70 | 0.0457 |
| MmugDNA.35274.1.S1_at | Hypothetical protein FLJ30707 | FLJ30707 | 5.69 | 0.0422 |
| MmugDNA.1285.1.S1_at | zinc finger protein-like 1 | ZFPL1 | 5.67 | 0.1329 |
| MmugDNA.31491.1.S1_at | KIAA1333 | KIAA1333 | 5.66 | 0.1185 |
| MmuSTS.1032.1.S1_at | nucleoporin 133 kDa | NUP133 | 5.65 | 0.1949 |
| MmugDNA.28191.1.S1_at | Pleiotropic regulator 1 (PRL1homolog, Arabidopsis) | PLRG1 | 5.64 | 0.0702 |
| MmugDNA.42978.1.S1_at | Transcribed locus, weakly XP_530800.1 PREDICTED: hypothetical protein XP_530800 [Pan troglodytes] | — | 5.64 | 0.0280 |
| MmugDNA.11439.1.S1_at | 5'-nucleotidase domain containing 1 | NT5DC1 | 5.64 | 0.0577 |
| MmuSTS.706.1.S1_at | interleukin-1 receptor-associated kinase 4 | IRAK4 | 5.64 | 0.0778 |
| MmugDNA.37826.1.S1_at | Hypothetical protein LOC285346 | LOC285346 | 5.63 | 0.0874 |
| MmuSTS.4259.1.S1_at | dual specificity phosphatase 4 | DUSP4 | 5.63 | 0.1028 |
| MmunewRS.954.1.S1_at | zinc finger protein 484 isoform a | ZNF484 | 5.63 | 0.1344 |
| MmugDNA.24846.1.S1_at | vacuolar protein sorting 26 homolog B (S. cerevisiae) | VPS26B | 5.61 | 0.0039 |
| MmugDNA.36142.1.S1_at | chromosome 9 open reading frame 117 | C9orf117 | 5.58 | 0.0052 |
| MmugDNA.3197.1.S1_at | RNA binding motif protein 25 | RBM25 | 5.58 | 0.2066 |
| MmugDNA.30489.1.S1_at | neurolysin (metallopeptidase M3 family) | NLN | 5.56 | 0.0281 |
| MmugDNA.15190.1.S1_at | chromosome 1 open reading frame 151 | C1orf151 | 5.55 | 0.0874 |
| MmugDNA.21034.1.S1_at | UDP-N-acetyl-alpha-D-galactosamine:polypeptide N-acetylgalactosaminyltransferase 1 (GalNAc-T1) | GALNT1 | 5.54 | 0.0402 |
| MmugDNA.14671.1.S1_at | dynein, cytoplasmic 2, light intermediate chain 1 | DYNC2LI1 | 5.52 | 0.0052 |
| MmugDNA.21379.1.S1_at | SNF1-like kinase 2 | SNF1LK2 | 5.52 | 0.0281 |

| Probe Set ID | Gene Title | Gene Symbol | Ratio Top verus Bottom | p value Top versus Bottom |
|---|---|---|---|---|
| MmugDNA.5564.1.S1_at | zinc finger protein 3 | ZNF3 | 5.51 | 0.0061 |
| MmugDNA.30983.1.S1_at | Metallophosphoesterase 1 | MPPE1 | 5.50 | 0.0158 |
| MmuSTS.2242.1.S1_at | TH1-like (*Drosophila*) | TH1L | 5.49 | 0.0001 |
| MmugDNA.7470.1.S1_at | hypothetical LOC400523 | LOC400523 | 5.49 | 0.0366 |
| MmugDNA.34874.1.S1_at | casein kinase 2, alpha prime polypeptide | CSNK2A2 | 5.47 | 0.0014 |
| MmugDNA.43133.1.S1_at | non-metastatic cells 5, protein expressed in (nucleoside-diphosphate kinase) | NME5 | 5.45 | 0.0009 |
| MmuSTS.3223.1.S1_at | phospholipase D3, phophatidylcholine-specific | PLD3 | 5.44 | 0.0358 |
| Mmu.10002.1.S1_s_at | methionine adenosyltransferase II, alpha | MAT2A | 5.44 | 0.0000 |
| MmugDNA.32811.1.S1_at | Transcribed locus | — | 5.44 | 0.0954 |
| MmugDNA.284.1.S1_at | hypothetical LOC149643 | LOC149643 | 5.43 | 0.0564 |
| MmuSTS.2289.1.S1_at | protein phosphatase 1, regulatory subunit 10 | PPP1R10 | 5.43 | 0.0004 |
| MmugDNA.7541.1.S1_at | coiled-coil domain containing 88 | CCDC88 | 5.41 | 0.0296 |
| MmugDNA.1662.1.S1_at | PRP38 pre-mRNA processing factor 38 (yeast) domain containing A | PRPF38A | 5.39 | 0.0054 |
| MmuSTS.4599.1.S1_at | huntingtin interacting protein B | HYPB | 5.38 | 0.0000 |
| MmugDNA.5606.1.S1_at | 5'-nucleotidase, cytosolic III-like | NT5C3L | 5.38 | 0.0235 |
| MmugDNA.12250.1.S1_at | CDNA clone IMAGE: 3928921 | — | 5.37 | 0.0135 |
| MmugDNA.25740.1.S1_at | coenzyme Q9 homolog (*S. cerevisiae*) | COQ9 | 5.37 | 0.0000 |
| MmugDNA.34111.1.S1_s_at | heat shock 105 kDa/110 kDa protein 1 | HSPH1 | 5.37 | 0.0000 |
| MmugDNA.21848.1.S1_at | TSPY-like 1 | TSPYL1 | 5.37 | 0.0105 |
| MmugDNA.9756.1.S1_at | HERPUD family member 2 | HERPUD2 | 5.36 | 0.0453 |
| Mmu.3466.1.S1_at | — | CN648872 | 5.36 | 0.0770 |
| MmugDNA.23725.1.S1_at | stress 70 protein chaperone, microsome-associated, 60 kDa | STCH | 5.34 | 0.0144 |
| MmugDNA.38793.1.S1_at | cholecystokinin | CCK | 5.33 | 0.2072 |
| MmugDNA.41164.1.S1_at | phosphonoformate immuno-associated protein 5 | PFAAP5 | 5.32 | 0.0567 |
| MmugDNA.35343.1.S1_s_at | CDNA FLJ41946 fis, clone PLACE6019701 | — | 5.31 | 0.0490 |
| MmugDNA.26593.1.S1_at | armadillo repeat containing, X-linked 5 | ARMCX5 | 5.31 | 0.0081 |
| MmugDNA.14053.1.S1_at | — | — | 5.29 | 0.0696 |
| MmugDNA.9095.1.S1_at | zinc finger protein 396 | ZNF396 | 5.27 | 0.0141 |
| MmugDNA.25958.1.S1_at | DEAH (Asp-Glu-Ala-Asp/His) box polypeptide 57 | DHX57 | 5.27 | 0.0389 |
| MmugDNA.21062.1.S1_at | suppression of tumorigenicity 7 | ST7 | 5.27 | 0.0326 |
| MmugDNA.12969.1.S1_at | ribonuclease H2, subunit C | RNASEH2C | 5.27 | 0.0527 |
| MmugDNA.39651.1.S1_at | heparan sulfate 2-O-sulfotransferase 1 | HS2ST1 | 5.26 | 0.0062 |
| MmugDNA.26250.1.S1_at | zinc finger protein 111 | LOC388565 | 5.25 | 0.0232 |
| MmugDNA.39242.1.S1_at | melanoma inhibitory activity family, member 3 | MIA3 | 5.25 | 0.0014 |
| MmugDNA.35720.1.S1_at | zinc finger protein 306 /// zinc finger protein 306 | ZNF306 | 5.25 | 0.0552 |
| MmuSTS.4680.1.S1_at | thymic stromal lymphopoietin | TSLP | 5.25 | 0.0113 |
| MmugDNA.35830.1.S1_at | — | — | 5.24 | 0.0523 |
| MmuSTS.2253.1.S1_at | polymerase (DNA directed), iota | POLI | 5.23 | 0.0000 |
| MmugDNA.41690.1.S1_at | Fibronectin type III domain containing 3 | FNDC3 | 5.23 | 0.0908 |
| MmugDNA.16026.1.S1_at | — | — | 5.22 | 0.0871 |
| MmugDNA.12860.1.S1_at | hypothetical protein 284297 | FLJ35258 | 5.21 | 0.0605 |
| Mmu.6352.1.S1_at | F16A11.1 | LOC703783 | 5.21 | 0.0698 |
| MmugDNA.28831.1.S1_at | G protein-regulated inducer of neurite outgrowth 1 | KIAA1893 | 5.21 | 0.0138 |
| MmuSTS.4601.1.S1_at | interleukin 19 | IL19 | 5.20 | 0.0401 |
| MmugDNA.25269.1.S1_at | chitinase domain containing 1 | CHID1 | 5.20 | 0.0280 |
| MmuAffx.956.1.S1_at | dolichyl-diphosphooligosaccharide-protein glycosyltransferase | — | 5.20 | 0.0203 |
| MmugDNA.10359.1.S1_at | DEAH (Asp-Glu-Ala-His) box polypeptide 30 | DHX30 | 5.20 | 0.0654 |
| MmugDNA.32727.1.S1_at | — | — | 5.19 | 0.0109 |
| MmugDNA.37069.1.S1_at | dihydropyrimidinase | DPYS | 5.19 | 0.0266 |
| MmugDNA.30075.1.S1_at | chromosome 6 open reading frame 162 | C6orf162 | 5.18 | 0.0316 |
| MmugDNA.9073.1.S1_at | — | — | 5.18 | 0.0376 |
| MmugDNA.12316.1.S1_at | KIAA0090 | KIAA0090 | 5.18 | 0.0905 |
| MmugDNA.39259.1.S1_at | MRNA; cDNA DKFZp564E202 (from clone DKFZp564E202) /// CDNA FLJ44257 fis, clone TKIDN2015263 | — | 5.17 | 0.0284 |
| MmugDNA.38606.1.S1_at | chromosome 9 open reading frame 89 | C9orf89 | 5.16 | 0.0215 |
| MmugDNA.3686.1.S1_at | intraflagellar transport 57 homolog (*Chlamydomonas*) | IFT57 | 5.14 | 0.0000 |
| MmugDNA.29286.1.S1_at | zinc finger protein 320 /// hypothetical protein FLJ38482 | ZNF320 /// FLJ38482 | 5.14 | 0.0252 |
| MmugDNA.31720.1.S1_at | CUE domain containing 1 | CUEDC1 | 5.14 | 0.0362 |
| MmugDNA.22403.1.S1_at | receptor accessory protein 5 | REEP5 | 5.14 | 0.0303 |
| MmugDNA.1116.1.S1_at | Transcribed locus | — | 5.12 | 0.0056 |
| MmugDNA.8918.1.S1_at | WNT1 inducible signaling pathway protein 2 | WISP2 | 5.12 | 0.1048 |
| MmugDNA.17764.1.S1_at | RCC1 domain containing 1 | RCCD1 | 5.11 | 0.0040 |
| MmugDNA.31260.1.S1_at | chromosome 11 open reading frame 63 | C11orf63 | 5.11 | 0.0246 |
| Mmu.6716.1.S1_at | Cathepsin S precursor | LOC708080 | 5.09 | 0.0754 |
| MmuSTS.299.1.S1_at | potassium intermediate/small conductance calcium-activated chann,, subfamily N, member 2 | KCNN2 | 5.09 | 0.0055 |
| MmugDNA.31161.1.S1_at | *Homo sapiens*, clone IMAGE: 4095671, mRNA | — | 5.09 | 0.0722 |
| MmugDNA.34930.1.S1_at | — | — | 5.08 | 0.1327 |
| MmugDNA.19331.1.S1_at | Full-length cDNA clone CS0DK012YA15 of HeLa cells Cot 25-normalized of *Homo sapiens* (human) | — | 5.07 | 0.0161 |
| MmugDNA.36727.1.S1_at | zinc finger, MYM-type 4 | ZMYM4 | 5.07 | 0.0456 |
| MmugDNA.42518.1.S1_at | nudE nuclear distribution gene E homolog like 1 (*A. nidulans*) | NDEL1 | 5.05 | 0.0746 |

| Probe Set ID | Gene Title | Gene Symbol | Ratio Top verus Bottom | p value Top versus Bottom |
|---|---|---|---|---|
| MmugDNA.14355.1.S1_at | chromosome 21 open reading frame 6 | C21orf6 | 5.05 | 0.0047 |
| MmugDNA.4328.1.S1_at | zinc finger protein 480 | ZNF480 | 5.03 | 0.0101 |
| MmuSTS.2927.1.S1_at | potassium voltage-gated channel, subfamily H (eag-related), memb, 3 | KCNH3 | 5.00 | 0.0509 |
| MmuSTS.4230.1.S1_at | discs, large (Drosophila) homolog-associated protein 4 | DLGAP 4 | 5.00 | 0.0584 |
| MmugDNA.27648.1.S1_at | — | — | 4.98 | 0.0573 |
| MmugDNA.41452.1.S1_at | sperm autoantigenic protein 17 | SPA17 | 4.98 | 0.0031 |
| MmuSTS.3254.1.S1_at | sema domain, immunoglobulin domain (Ig), short basic domain, sec ted, (semaphorin) 3A | SEMA3A | 4.98 | 0.0854 |
| MmugDNA.3708.1.S1_at | Full length insert cDNA clone YX81F03 | — | 4.97 | 0.0024 |
| MmugDNA.3643.1.S1_at | hypothetical protein LOC643749 | LOC643749 | 4.97 | 0.0165 |
| MmugDNA.7067.1.S1_at | RNA binding motif protein 18 | LOC698457 | 4.97 | 0.0025 |
| MmugDNA.10033.1.S1_at | poliovirus receptor | PVR | 4.96 | 0.0778 |
| MmugDNA.16402.1.S1_at | cyclin M4 | CNNM4 | 4.96 | 0.0001 |
| MmugDNA.42450.1.S1_at | — | — | 4.96 | 0.1236 |
| MmugDNA.7713.1.S1_at | chromosome 4 open reading frame 17 | C4orf17 | 4.96 | 0.0059 |
| MmugDNA.11708.1.S1_at | chloride channel CLIC-like 1 | CLCC1 | 4.95 | 0.0038 |
| MmugDNA.19659.1.S1_at | Interleukin 17 receptor D | IL17RD | 4.95 | 0.0034 |
| MmugDNA.11406.1.S1_at | protein tyrosine phosphatase, receptor type, G | PTPRG | 4.95 | 0.0002 |
| MmugDNA.3737.1.S1_at | chromosome 13 open reading frame 23 | C13orf23 | 4.95 | 0.0133 |
| MmugDNA.1748.1.S1_at | transmembrane protein 27 | TMEM27 | 4.94 | 0.0726 |
| MmugDNA.30715.1.S1_at | armadillo repeat containing 8 | ARMC8 | 4.94 | 0.0096 |
| MmugDNA.31956.1.S1_at | Transcribed locus | — | 4.94 | 0.0633 |
| MmugDNA.2511.1.S1_at | CDNA FLJ40061 fis, clone TESOP2000083 | — | 4.94 | 0.1619 |
| MmugDNA.20090.1.S1_at | TDP-glucose 4,6-dehydratase | TGDS | 4.93 | 0.0336 |
| MmugDNA.17318.1.S1_at | Transcribed locus | — | 4.91 | 0.1084 |
| MmugDNA.22124.1.S1_at | transmembrane protein 138 | TMEM138 | 4.90 | 0.1081 |
| Mmu.6994.1.S1_at | basic fibroblast growth factor mRNA, partial cds. | AF251270 | 4.89 | 0.0539 |
| MmugDNA.25717.1.S1_s_at | retinoblastoma-like 2 (p130) | RBL2 | 4.89 | 0.1029 |
| MmugDNA.32584.1.S1_at | zinc finger protein 571 | ZNF571 | 4.88 | 0.0004 |
| MmuSTS.32.1.S1_at | zinc finger protein 32 | ZNF32 | 4.87 | 0.0000 |
| MmugDNA.30643.1.S1_at | B9 protein | EPPB9 | 4.86 | 0.1011 |
| MmugDNA.14909.1.S1_at | N-acetyltransferase 1 (arylamine N-acetyltransferase) | NAT1 | 4.86 | 0.0099 |
| MmuSTS.2239.1.S1_at | testis expressed sequence 264 | TEX264 | 4.85 | 0.0109 |
| MmugDNA.28738.1.S1_at | zinc finger protein 354C | LOC713468 | 4.85 | 0.0244 |
| MmuSTS.773.1.S1_at | core 1 UDP-galactose:N-acetylgalactosamine-alpha-R beta 1,3-gala, osyltransferase 2 | C1GALT2 | 4.85 | 0.0022 |
| MmugDNA.7405.1.S1_at | multiple substrate lipid kinase | MULK | 4.84 | 0.0000 |
| MmugDNA.8329.1.S1_at | chromosome 10 open reading frame 72 | C10orf72 | 4.83 | 0.1341 |
| MmugDNA.33312.1.S1_at | zinc finger, CCHC domain containing 9 | ZCCHC9 | 4.83 | 0.0024 |
| Mmu.11141.1.S1_at | catenin (cadherin-associated protein), alpha 1, 102 kDa | CTNNA1 | 4.83 | 0.0647 |
| MmugDNA.3844.1.S1_at | — | — | 4.82 | 0.0000 |
| MmuSTS.1873.1.S1_at | cornichon homolog | CNIH | 4.82 | 0.0001 |
| Mmu.1020.1.S1_s_at | cysteine-rich with EGF-like domains 1 isoform 2 | LOC699345 | 4.82 | 0.0586 |
| MmugDNA.24075.1.S1_at | CG15828-PA | 244889_at | 4.81 | 0.0948 |
| MmugDNA.30042.1.S1_at | chromosome X open reading frame 6 | CXorf6 | 4.81 | 0.0517 |
| MmuSTS.351.1.S1_at | synaptophysin | SYP | 4.81 | 0.0485 |
| MmugDNA.38488.1.S1_s_at | LSM10, U7 small nuclear RNA associated | LSM10 | 4.80 | 0.0004 |
| MmugDNA.1625.1.S1_at | protein kinase, AMP-activated, alpha 1 catalytic subunit | PRKAA1 | 4.80 | 0.0425 |
| MmugDNA.25564.1.S1_at | MRNA; cDNA DKFZp564G1162 (from clone DKFZp564G1162) | — | 4.79 | 0.0079 |
| MmugDNA.29139.1.S1_at | chromosome 14 open reading frame 50 | C14orf50 | 4.79 | 0.1206 |
| MmuSTS.1491.1.S1_at | zinc finger protein 281 | ZNF281 | 4.78 | 0.0190 |
| MmugDNA.5201.1.S1_at | chromosome 14 open reading frame 130 | C14orf130 | 4.78 | 0.0074 |
| MmunewRS.875.1.S1_at | neuroligin 4, Y-linked | NLGN4Y | 4.78 | 0.0000 |
| MmugDNA.6389.1.S1_at | zinc finger, CCHC domain containing 12 | ZCCHC12 | 4.76 | 0.0124 |
| MmugDNA.12224.1.S1_at | CDNA clone IMAGE: 4821804 | — | 4.76 | 0.0779 |
| MmunewRS.335.1.S1_at | full length insert cDNA clone YZ18B05. | gi: 3483412 | 4.75 | 0.0715 |
| MmugDNA.21758.1.S1_at | DNA cross-link repair 1C (PSO2 homolog, S. cerevisiae) | DCLRE1C | 4.75 | 0.1520 |
| MmugDNA.4778.1.S1_at | KIAA1505 protein | KIAA1505 | 4.75 | 0.1070 |
| MmugDNA.133.1.S1_at | zinc finger protein 223 | LOC711740 | 4.74 | 0.1432 |
| MmugDNA.7270.1.S1_at | zinc finger protein 641 | ZNF641 | 4.74 | 0.0002 |
| MmugDNA.20328.1.S1_s_at | N-acetylglucosamine-1-phosphate transferase, gamma subunit | GNPTG | 4.74 | 0.0000 |
| MmugDNA.40786.1.S1_at | arylsulfatase family, member K | ARSK | 4.74 | 0.0631 |
| Mmu.11997.1.S1_at | calmodulin 1 | LOC698552 | 4.73 | 0.0030 |
| MmugDNA.1667.1.S1_at | immunoglobulin superfamily, member 4D | IGSF4D | 4.73 | 0.1791 |
| MmugDNA.20342.1.S1_at | spindlin family, member 2 /// spindlin family, member 2 /// spindlin-like protein 2 /// spindlin-like protein 2 | SPIN2 /// SPIN-2 | 4.72 | 0.0223 |
| MmugDNA.3891.1.S1_at | chromosome 2 open reading frame 15 | C2orf15 | 4.72 | 0.0163 |
| MmugDNA.32461.1.S1_at | — | — | 4.72 | 0.0094 |
| MmugDNA.14567.1.S1_at | KIAA0859 | KIAA0859 | 4.72 | 0.1058 |
| MmugDNA.43246.1.S1_at | neutral sphingomyelinase (N-SMase) activation associated factor | NSMAF | 4.72 | 0.0053 |
| MmugDNA.2324.1.S1_at | KIAA0895 protein | KIAA0895 | 4.71 | 0.0648 |
| MmugDNA.1640.1.S1_at | Transcribed locus | — | 4.71 | 0.1101 |

-continued

| Probe Set ID | Gene Title | Gene Symbol | Ratio Top verus Bottom | p value Top versus Bottom |
|---|---|---|---|---|
| MmugDNA.42549.1.S1_at | galanin | GAL | 4.71 | 0.0951 |
| MmugDNA.3017.1.S1_at | LQK1 hypothetical protein short isoform | LQK1 | 4.70 | 0.0226 |
| MmugDNA.28661.1.S1_at | coiled-coil domain containing 28B | CCDC28B | 4.69 | 0.1325 |
| MmuSTS.4364.1.S1_at | sterol O-acyltransferase 1 | SOAT1 | 4.69 | 0.0729 |
| MmugDNA.2668.1.S1_at | mannose receptor-like | LOC709768 | 4.69 | 0.0118 |
| MmugDNA.8460.1.S1_at | LAG1 longevity assurance homolog 6 (*S. cerevisiae*) | LASS6 | 4.68 | 0.0041 |
| MmugDNA.30211.1.S1_at | ATPase, Ca++ transporting, type 2C, member 1 | ATP2C1 | 4.67 | 0.0624 |
| MmugDNA.22541.1.S1_at | chromosome 1 open reading frame 89 /// chromosome 1 open reading frame 89 | C1orf89 | 4.66 | 0.0231 |
| MmugDNA.23541.1.S1_at | coiled-coil domain containing 50 | CCDC50 | 4.65 | 0.0487 |
| MmugDNA.38008.1.S1_at | asparaginase-like 1 protein | LOC718871 | 4.65 | 0.0005 |
| MmugDNA.34690.1.S1_at | MAWD binding protein | MAWBP | 4.65 | 0.0787 |
| MmugDNA.31478.1.S1_at | RAB33A, member RAS oncogene family | RAB33A | 4.64 | 0.0430 |
| MmugDNA.28356.1.S1_at | hypothetical protein LOC715793 | LOC715793 | 4.64 | 0.1301 |
| MmugDNA.35760.1.S1_at | receptor transporter protein 4 | RTP4 | 4.63 | 0.1847 |
| MmugDNA.1257.1.S1_at | peptidylprolyl isomerase (cyclophilin)-like 1 | PPIL1 | 4.63 | 0.0032 |
| MmugDNA.38638.1.S1_at | inhibitor of kappa light polypeptide gene enhancer in B-cells, kinase beta /// nicastrin | IKBKB /// NCSTN | 4.61 | 0.0019 |
| MmugDNA.31887.1.S1_at | hypothetical LOC402617 | LOC402617 | 4.60 | 0.1114 |
| MmugDNA.18767.1.S1_at | MRNA full length insert cDNA clone EUROIMAGE 110216 | — | 4.57 | 0.1233 |
| MmugDNA.40451.1.S1_at | polycomb group ring finger 1 | PCGF1 | 4.56 | 0.0175 |
| MmugDNA.18456.1.S1_at | CDNA FLJ33400 fis, clone BRACE2009828 | — | 4.55 | 0.1261 |
| MmugDNA.31245.1.S1_at | butyrophilin, subfamily 2, member A2 | BTN2A2 | 4.55 | 0.0552 |
| MmugDNA.43078.1.S1_at | KIAA1838 | KIAA1838 | 4.55 | 0.0050 |
| MmugDNA.39763.1.S1_at | ubiquitin specific peptidase 36 | USP36 | 4.54 | 0.0836 |
| MmugDNA.12921.1.S1_at | hypothetical protein FLJ36208 | FLJ36208 | 4.54 | 0.1669 |
| MmugDNA.3000.1.S1_at | signal sequence receptor, gamma (translocon-associated protein gamma) | SSR3 | 4.54 | 0.0185 |
| MmugDNA.31177.1.S1_at | zinc finger protein 582 | ZNF582 | 4.54 | 0.0129 |
| MmuSTS.2548.1.S1_at | thioredoxin domain containing 12 (endoplasmic reticulum) | TXNDC12 | 4.54 | 0.0231 |
| MmugDNA.32746.1.S1_at | inositol 1,4,5-triphosphate receptor, type 2 | ITPR2 | 4.54 | 0.0394 |
| MmugDNA.14882.1.S1_s_at | Huntingtin interacting protein K | HYPK | 4.53 | 0.0411 |
| MmugDNA.2875.1.S1_at | Protein-O-mannosyltransferase 1 | POMT1 | 4.53 | 0.0018 |
| MmugDNA.13007.1.S1_at | hypothetical protein LOC284669 | LOC284669 | 4.52 | 0.0142 |
| Mmu.3693.1.S1_at | splicing factor p54 | LOC702698 | 4.52 | 0.0572 |
| MmugDNA.20453.1.S1_at | heterogeneous nuclear ribonucleoprotein L | HNRPL | 4.51 | 0.0000 |
| MmugDNA.14296.1.S1_at | hypothetical protein FLJ37201 | FLJ37201 | 4.51 | 0.0035 |
| MmugDNA.9174.1.S1_at | coiled-coil domain containing 129 | CCDC129 | 4.51 | 0.0743 |
| MmugDNA.17031.1.S1_at | DTW domain containing 1 | DTWD1 | 4.50 | 0.0000 |
| MmugDNA.10168.1.S1_at | trafficking protein particle complex 4 | TRAPPC4 | 4.50 | 0.0069 |
| MmugDNA.33621.1.S1_at | zinc finger-like | LOC400713 | 4.49 | 0.0368 |
| MmugDNA.28329.1.S1_at | Zinc finger protein 250 | ZNF250 | 4.49 | 0.0001 |
| MmugDNA.3693.1.S1_at | DEAD (Asp-Glu-Ala-Asp) box polypeptide 17 | DDX17 | 4.49 | 0.0217 |
| MmugDNA.5788.1.S1_s_at | transmembrane 4 L six family member 5 | TM4SF5 | 4.48 | 0.1028 |
| MmugDNA.3666.1.S1_at | glucose 6 phosphatase, catalytic, 3 | G6PC3 | 4.47 | 0.0353 |
| MmugDNA.4300.1.S1_at | CDNA clone IMAGE: 4812643 | — | 4.47 | 0.0315 |
| MmugDNA.13717.1.S1_at | Type 1 tumor necrosis factor receptor shedding aminopeptidase regulator | ARTS-1 | 4.46 | 0.0839 |
| MmugDNA.31311.1.S1_at | methyltransferase like 5 | METTL5 | 4.46 | 0.0001 |
| MmugDNA.19122.1.S1_at | N-deacetylase/N-sulfotransferase (heparan glucosaminyl) 2 | NDST2 | 4.46 | 0.1122 |
| MmugDNA.17470.1.S1_at | translocase of inner mitochondrial membrane 9 homolog (yeast) | TIMM9 | 4.45 | 0.0749 |
| MmugDNA.36689.1.S1_at | dihydroxyacetone kinase 2 homolog (*S. cerevisiae*) | DAK | 4.45 | 0.2128 |
| MmugDNA.32341.1.S1_at | UDP-N-acetyl-alpha-D-galactosamine:polypeptide N-acetylgalactosaminyltransferase 5 (GalNAc-T5) | GALNT5 | 4.45 | 0.0515 |
| MmugDNA.29495.1.S1_at | ankyrin and armadillo repeat containing | ANKAR | 4.45 | 0.0616 |
| MmugDNA.9999.1.S1_at | cytochrome b5 domain containing 2 | CYB5D2 | 4.45 | 0.0104 |
| MmugDNA.28421.1.S1_at | Discs, large (*Drosophila*) homolog-associated protein 1 | DLGAP1 | 4.45 | 0.0793 |
| MmugDNA.38681.1.S1_at | — | — | 4.44 | 0.1501 |
| MmugDNA.28495.1.S1_at | integrin beta 1 binding protein 1 | ITGB1BP1 | 4.44 | 0.0060 |
| MmugDNA.42735.1.S1_at | hypothetical protein LOC144874 | LOC144874 | 4.44 | 0.1195 |
| MmugDNA.6818.1.S1_at | armadillo repeat containing 2 | ARMC2 | 4.43 | 0.0802 |
| MmugDNA.40576.1.S1_at | — | — | 4.43 | 0.1762 |
| MmugDNA.8518.1.S1_at | Hypothetical protein LOC645323 | LOC645323 | 4.42 | 0.1298 |
| MmugDNA.16049.1.S1_at | Ubiquitin specific peptidase 30 | USP30 | 4.42 | 0.0000 |
| MmuSTS.4469.1.S1_s_at | vasodilator-stimulated phosphoprotein | VASP | 4.42 | 0.0468 |
| MmugDNA.38086.1.S1_at | chromosome 10 open reading frame 137 | C10orf137 | 4.41 | 0.0223 |
| MmugDNA.31273.1.S1_at | bobby sox homolog (*Drosophila*) | BBX | 4.41 | 0.0269 |
| MmugDNA.39436.1.S1_at | Transcribed locus | — | 4.41 | 0.0107 |
| MmuSTS.2675.1.S1_s_at | ATP-binding cassette, sub-family B (MDR/TAP), member 10 | ABCB10 | 4.41 | 0.0156 |
| Mmu.2243.1.S1_at | eukaryotic translation initiation factor 3, subunit 2 beta, 36 kDa | EIF3S2 | 4.40 | 0.0204 |
| MmugDNA.14154.1.S1_at | ceroid-lipofuscinosis, neuronal 5 | CLN5 | 4.40 | 0.0271 |
| MmugDNA.8714.1.S1_s_at | inosine triphosphatase (nucleoside triphosphate pyrophosphatase) | ITPA | 4.40 | 0.0380 |
| Mmu.15592.2.S1_at | phosphatidylinositol glycan, class F isoform 1 | LOC714844 | 4.39 | 0.0098 |

-continued

| Probe Set ID | Gene Title | Gene Symbol | Ratio Top verus Bottom | p value Top versus Bottom |
|---|---|---|---|---|
| MmugDNA.19980.1.S1_at | tripartite motif-containing 5 | TRIM5 | 4.39 | 0.1642 |
| MmugDNA.3645.1.S1_at | serine/threonine kinase receptor associated protein | STRAP | 4.39 | 0.0135 |
| MmugDNA.29562.1.S1_at | prohibitin | PHB | 4.37 | 0.0035 |
| MmugDNA.2122.1.S1_at | stomatin | STOM | 4.37 | 0.0263 |
| MmugDNA.20601.1.S1_s_at | prolyl endopeptidase-like | PREPL | 4.37 | 0.0512 |
| MmugDNA.26227.1.S1_at | RFT1 homolog (S. cerevisiae) | RFT1 | 4.37 | 0.1974 |
| MmugDNA.119.1.S1_at | zinc finger protein 542 | ZNF542 | 4.36 | 0.1250 |
| MmugDNA.38257.1.S1_at | chromosome 3 open reading frame 18 | C3orf18 | 4.36 | 0.0391 |
| MmugDNA.38303.1.S1_at | TAF4b RNA polymerase II, TATA box binding protein (TBP)-associated factor, 105 kDa | TAF4B | 4.35 | 0.0954 |
| Mmu.13799.1.S1_at | hypothetical protein LOC696762 | LOC696762 | 4.35 | 0.0294 |
| MmugDNA.24015.1.S1_at | LanC lantibiotic synthetase component C-like 2 (bacterial) | LANCL2 | 4.35 | 0.0403 |
| MmugDNA.38882.1.S1_at | zinc finger protein 775 | ZNF775 | 4.35 | 0.0238 |
| MmugDNA.11471.1.S1_at | ATPase family, AAA domain containing 1 | ATAD1 | 4.35 | 0.0077 |
| MmugDNA.6735.1.S1_at | zinc finger protein 642 | ZNF642 | 4.33 | 0.0727 |
| MmugDNA.18469.1.S1_at | zinc finger protein 588 | ZNF588 | 4.33 | 0.1354 |
| MmugDNA.11216.1.S1_at | cancer susceptibility candidate 4 | CASC4 | 4.33 | 0.0008 |
| MmugDNA.28842.1.S1_at | CKLF-like MARVEL transmembrane domain containing 7 | CMTM7 | 4.32 | 0.0168 |
| MmugDNA.19883.1.S1_at | SECIS binding protein 2 | SECISBP2 | 4.32 | 0.0191 |
| MmugDNA.18544.1.S1_at | renal tumor antigen | RAGE | 4.32 | 0.0365 |
| MmugDNA.31414.1.S1_at | SMT3 suppressor of mif two 3 homolog 1 (S. cerevisiae) | SUMO1 | 4.32 | 0.0298 |
| MmugDNA.30985.1.S1_at | glucosidase, beta (bile acid) 2 | GBA2 | 4.32 | 0.0080 |
| MmugDNA.33696.1.S1_at | hyaluronan binding protein 4 | HABP4 | 4.32 | 0.0433 |
| MmugDNA.24247.1.S1_at | chromosome 10 open reading frame 11 | C10orf11 | 4.31 | 0.1241 |
| Mmu.11729.1.S1_s_at | Translocon-associated protein beta subunit precursor (TRAP-beta) (Signal sequence receptor beta subunit) (SSR-beta) | LOC719383 | 4.31 | 0.0536 |
| MmugDNA.33158.1.S1_at | coiled-coil domain containing 22 | CCDC22 | 4.30 | 0.0689 |
| MmugDNA.10111.1.S1_at | chromosome 1 open reading frame 131 | C1orf131 | 4.29 | 0.0196 |
| MmugDNA.43034.1.S1_at | HLA-B associated transcript 5 | BAT5 | 4.29 | 0.0313 |
| MmugDNA.10771.1.S1_at | ligase IV, DNA, ATP-dependent | LIG4 | 4.29 | 0.0048 |
| MmugDNA.39663.1.S1_at | Bernardinelli-Seip congenital lipodystrophy 2 (seipin) /// heterogeneous nuclear ribonucleoprotein U-like 2 | BSCL2 /// HNRPUL2 | 4.28 | 0.0093 |
| MmugDNA.36927.1.S1_at | DNA (cytosine-5-)-methyltransferase 3 alpha | DNMT3A | 4.28 | 0.0096 |
| MmugDNA.24861.1.S1_s_at | neuroguidin, EIF4E binding protein | NGDN | 4.27 | 0.0007 |
| MmugDNA.24533.1.S1_at | cathepsin S | CTSS | 4.27 | 0.0031 |
| MmuSTS.1546.1.S1_at | musashi homolog 2 | MSI2 | 4.27 | 0.0014 |
| MmugDNA.831.1.S1_at | Chromosome 14 open reading frame 161 | C14orf161 | 4.26 | 0.0165 |
| MmugDNA.10644.1.S1_at | Muscleblind-like 2 (Drosophila) | MBNL2 | 4.25 | 0.0000 |
| MmugDNA.33695.1.S1_at | zinc finger protein 34 | ZNF34 | 4.25 | 0.0030 |
| MmugDNA.23792.1.S1_at | thrombospondin, type I, domain containing 3 | THSD3 | 4.24 | 0.1178 |
| MmugDNA.12396.1.S1_at | chromosome 3 open reading frame 41 | C3orf41 | 4.24 | 0.0202 |
| MmugDNA.21184.1.S1_at | hypoxia inducible factor 3, alpha subunit | HIF3A | 4.24 | 0.1766 |
| MmugDNA.6866.1.S1_at | STEAP family member 3 | STEAP3 | 4.24 | 0.1494 |
| MmugDNA.15710.1.S1_at | vacuolar protein sorting 39 (yeast) | VPS39 | 4.23 | 0.0007 |
| Mmu.586.1.S1_at | Protein KIAA0143 | LOC696036 | 4.23 | 0.0432 |
| MmuSTS.2503.1.S1_at | zinc finger, SWIM domain containing 5 | ZSWIM5 | 4.23 | 0.0370 |
| MmugDNA.21399.1.S1_at | Transcribed locus | — | 4.22 | 0.0664 |
| MmuSTS.2401.1.S1_s_at | replication protein A1, 70 kDa | RPA1 | 4.22 | 0.0162 |
| Mmu.5491.1.S1_at | prosaposin | LOC709510 | 4.22 | 0.1033 |
| MmugDNA.15874.1.S1_at | Mitochondrial fission regulator 1 | MTFR1 | 4.21 | 0.0570 |
| MmugDNA.32637.1.S1_at | nucleosomal binding protein 1 | NSBP1 | 4.21 | 0.0038 |
| MmugDNA.10551.1.S1_at | mannosyl (alpha-1,6-)-glycoprotein beta-1,2-N-acetylglucosaminyltransferase /// mannosyl (alpha-1,6-)-glycoprotein beta-1,2-N-acetylglucosaminyltransferase | MGAT2 | 4.21 | 0.0530 |
| MmugDNA.41398.1.S1_at | chromosome 3 open reading frame 31 | C3orf31 | 4.21 | 0.0943 |
| MmugDNA.17617.1.S1_s_at | trophinin /// trophinin | TRO | 4.21 | 0.0108 |
| MmugDNA.39122.1.S1_at | chromosome 3 open reading frame 1 | C3orf1 | 4.21 | 0.0262 |
| MmugDNA.18454.1.S1_at | Transcribed locus | — | 4.20 | 0.0989 |
| MmugDNA.39611.1.S1_at | Dedicator of cytokinesis 2 | DOCK2 | 4.19 | 0.1153 |
| MmuSTS.2075.1.S1_at | POU domain, class 2, transcription factor 3 | POU2F3 | 4.19 | 0.0002 |
| MmugDNA.28348.1.S1_s_at | chaperonin containing TCP1, subunit 2 (beta) | CCT2 | 4.18 | 0.0291 |
| MmugDNA.26826.1.S1_s_at | solute carrier family 11 (proton-coupled divalent metal ion transporters), member 1 | SLC11A1 | 4.17 | 0.0308 |
| Mmu.9862.2.S1_at | F-box only protein 4 isoform 2 | LOC697007 | 4.17 | 0.2109 |
| Mmu.303.1.S1_at | crystallin, zeta | LOC704403 | 4.17 | 0.0292 |
| MmugDNA.19380.1.S1_at | chromosome 1 open reading frame 19 | C1orf19 | 4.16 | 0.0000 |
| MmugDNA.11030.1.S1_s_at | chromosome 3 open reading frame 15 | C3orf15 | 4.16 | 0.0146 |
| MmugDNA.732.1.S1_at | hexosaminidase B (beta polypeptide) | HEXB | 4.16 | 0.0013 |
| MmugDNA.43014.1.S1_at | hypothetical LOC389172 | LOC389172 | 4.16 | 0.0052 |
| MmugDNA.14429.1.S1_at | chromosome X open reading frame 58 | CXorf58 | 4.15 | 0.0672 |
| MmugDNA.33820.1.S1_at | KIAA0100 | KIAA0100 | 4.15 | 0.0184 |
| MmugDNA.1154.1.S1_at | SNF1-like kinase /// SNF1-like kinase | SNF1LK | 4.15 | 0.0142 |
| MmugDNA.9493.1.S1_at | phosphodiesterase 4D, cAMP-specific (phosphodiesterase E3 dunce homolog, Drosophila) | PDE4D | 4.15 | 0.0016 |
| MmugDNA.38138.1.S1_at | zinc finger protein 267 | ZNF267 | 4.14 | 0.0014 |

| Probe Set ID | Gene Title | Gene Symbol | Ratio Top verus Bottom | p value Top versus Bottom |
|---|---|---|---|---|
| MmugDNA.37212.1.S1_at | zinc finger, ZZ-type containing 3 | ZZZ3 | 4.14 | 0.0098 |
| MmugDNA.41461.1.S1_at | zinc finger protein 333 | ZNF333 | 4.14 | 0.1972 |
| MmugDNA.19606.1.S1_at | pseudouridylate synthase 7 homolog (S. cerevisiae)-like /// pseudouridylate synthase 7 homolog (S. cerevisiae)-like | PUS7L | 4.13 | 0.0653 |
| MmugDNA.11456.1.S1_at | ligatin | LGTN | 4.13 | 0.0557 |
| MmugDNA.36143.1.S1_s_at | choline dehydrogenase | CHDH | 4.13 | 0.2015 |
| MmugDNA.7248.1.S1_s_at | CCR4-NOT transcription complex, subunit 2 | CNOT2 | 4.13 | 0.0005 |
| MmugDNA.5833.1.S1_at | phosphoinositide-3-kinase, regulatory subunit 4, p150 | PIK3R4 | 4.13 | 0.0029 |
| MmugDNA.39422.1.S1_at | UDP-GlcNAc: betaGal beta-1,3-N-acetylglucosaminyltransferase 1 | B3GNT1 | 4.12 | 0.0370 |
| MmugDNA.1591.1.S1_at | Homo sapiens, clone IMAGE: 3352913, mRNA | — | 4.12 | 0.0569 |
| MmugDNA.34328.1.S1_at | dyslexia susceptibility 1 candidate 1 | DYX1C1 | 4.12 | 0.0834 |
| MmugDNA.111.1.S1_at | zinc finger protein 180 | ZNF180 | 4.11 | 0.1267 |
| MmugDNA.5762.1.S1_at | vacuolar protein sorting 25 homolog (S. cerevisiae) | VPS25 | 4.10 | 0.0377 |
| MmugDNA.16868.1.S1_at | hypothetical protein FLJ36665 | FLJ36665 | 4.09 | 0.1171 |
| MmugDNA.6114.1.S1_s_at | DEAD (Asp-Glu-Ala-Asp) box polypeptide 18 | DDX18 | 4.09 | 0.0159 |
| MmugDNA.33106.1.S1_at | — | — | 4.09 | 0.0272 |
| MmugDNA.24857.1.S1_at | RAP2A, member of RAS oncogene family /// RAP2B, member of RAS oncogene family | RAP2A /// RAP2B | 4.07 | 0.1231 |
| MmunewRS.1035.1.S1_s_at | cDNA FLJ31653 fis, clone NT2RI2004190. | gi: 16551556 | 4.06 | 0.0241 |
| MmugDNA.6270.1.S1_at | synaptogyrin 1 | SYNGR1 | 4.06 | 0.0066 |
| MmugDNA.42267.1.S1_at | Transcribed locus | — | 4.06 | 0.1725 |
| MmugDNA.1721.1.S1_at | zinc finger protein 442 /// zinc finger protein 442 | ZNF442 | 4.06 | 0.0870 |
| MmugDNA.1190.1.S1_at | dpy-19-like 2 (C. elegans) | DPY19L2 | 4.06 | 0.0340 |
| MmugDNA.10350.1.S1_at | DEAH (Asp-Glu-Ala-His) box polypeptide 16 | DHX16 | 4.05 | 0.0105 |
| MmuSTS.2597.1.S1_at | eukaryotic translation elongation factor 1 epsilon 1 | EEF1E1 | 4.05 | 0.0005 |
| MmugDNA.13760.1.S1_at | AHA1, activator of heat shock 90 kDa protein ATPase homolog 1 (yeast) | AHSA1 | 4.05 | 0.0000 |
| MmugDNA.27617.1.S1_at | tektin 2 (testicular) | TEKT2 | 4.04 | 0.0469 |
| MmugDNA.29808.1.S1_at | mannosidase, alpha, class 2C, member 1 | MAN2C1 | 4.04 | 0.0015 |
| MmugDNA.29621.1.S1_at | bone morphogenetic protein 6 | BMP6 | 4.04 | 0.0815 |
| MmugDNA.26069.1.S1_at | — | — | 4.04 | 0.0531 |
| MmuSTS.3237.1.S1_at | RAD54 homolog B (S. cerevisiae) | RAD54B | 4.04 | 0.0748 |
| Mmu.9266.1.S1_x_at | alpha-defensin 4 precursor, mRNA, complete cds. | AY859406 | 4.02 | 0.0972 |
| MmugDNA.35254.1.S1_at | nudix (nucleoside diphosphate linked moiety X)-type motif 16 pseudogene | NUDT16P | 4.01 | 0.1650 |
| MmugDNA.40333.1.S1_at | low density lipoprotein receptor-related protein associated protein 1 | LRPAP1 | 4.01 | 0.0177 |
| Mmu.4677.1.S1_s_at | rabconnectin-3 beta isoform 2 | LOC695302 | 4.01 | 0.0167 |
| MmugDNA.15059.1.S1_at | zinc finger protein 780B | ZNF780B | 4.01 | 0.1768 |
| MmugDNA.2321.1.S1_at | ELL associated factor 2 | EAF2 | 4.00 | 0.0663 |
| Mmu.14167.1.S1_at | DNA topoisomerase I | LOC697300 | 4.00 | 0.1952 |
| MmugDNA.3213.1.S1_at | single stranded DNA binding protein 4 | SSBP4 | 4.00 | 0.0429 |
| MmugDNA.42484.1.S1_at | ARP6 actin-related protein 6 homolog (yeast) | ACTR6 | 4.00 | 0.0252 |
| MmugDNA.7865.1.S1_at | PPAR binding protein | PPARBP | 4.00 | 0.0589 |
| MmugDNA.18330.1.S1_at | chromosome 18 open reading frame 10 | C18orf10 | 4.00 | 0.0013 |
| MmugDNA.40541.1.S1_at | zinc finger protein 555 | ZNF555 | 4.00 | 0.0028 |
| MmugDNA.6772.1.S1_at | ER degradation enhancer, mannosidase alpha-like 2 | EDEM2 | 3.99 | 0.0411 |
| MmugDNA.24353.1.S1_at | retinoic acid receptor responder (tazarotene induced) 1 | RARRES1 | 3.99 | 0.1529 |
| MmugDNA.34452.1.S1_s_at | — | — | 3.98 | 0.0067 |
| MmugDNA.9814.1.S1_at | Transcribed locus | — | 3.98 | 0.0111 |
| MmugDNA.27740.1.S1_at | U2-associated SR140 protein | SR140 | 3.98 | 0.0286 |
| MmuSTS.3952.1.S1_at | SEC22 vesicle trafficking protein homolog C (S. cerevisiae) | SEC22C | 3.98 | 0.0001 |
| MmugDNA.36936.1.S1_at | deoxyguanosine kinase | DGUOK | 3.97 | 0.0061 |
| MmugDNA.16551.1.S1_at | hypothetical protein FLJ25770 | FLJ25770 | 3.97 | 0.0789 |
| MmugDNA.32988.1.S1_at | ring finger protein 123 | RNF123 | 3.97 | 0.0078 |
| MmugDNA.40932.1.S1_at | zinc finger protein 691 | ZNF691 | 3.97 | 0.0191 |
| MmugDNA.42528.1.S1_at | cytochrome P450, family 4, subfamily F, polypeptide 2 | CYP4F2 | 3.96 | 0.1843 |
| MmugDNA.38754.1.S1_at | Galactokinase 2 | GALK2 | 3.96 | 0.0572 |
| MmuSTS.2536.1.S1_at | Interferon tau-1 | IFNT1 | 3.96 | 0.1884 |
| MmugDNA.21837.1.S1_at | CDNA FLJ40810 fis, clone TRACH2009743 | — | 3.95 | 0.0554 |
| Mmu.10030.1.S1_at | syntenin isoform 3 | LOC698381 | 3.95 | 0.0001 |
| Mmu.5329.1.S1_at | Phospholipid hydroperoxide glutathione peroxidase, mitochondrial precursor (PHGPx) (GPX-4) | GPX4 | 3.95 | 0.1220 |
| MmugDNA.36752.1.S1_at | lymphocyte antigen 6 complex, locus G5C | LY6G5C | 3.93 | 0.1998 |
| MmuSTS.897.1.S1_at | sema domain, seven thrombospondin repeats (type 1 and type 1-lik,, transmembrane domain (TM) and short cytoplasmic domain, (semaphorin) 5B | SEMA5B | 3.93 | 0.0637 |
| MmugDNA.40072.1.S1_at | hypothetical protein DKFZp313A2432 | DKFZp313A2432 | 3.93 | 0.1059 |
| MmugDNA.19577.1.S1_at | phosphatidylinositol glycan anchor biosynthesis, class M | PIGM | 3.93 | 0.2113 |
| MmugDNA.11968.1.S1_at | UBX domain containing 7 | UBXD7 | 3.93 | 0.0163 |
| MmugDNA.19665.1.S1_at | hypothetical protein LOC196394 | LOC196394 | 3.93 | 0.0165 |
| MmugDNA.23833.1.S1_at | chromosome 21 open reading frame 58 | C21orf58 | 3.93 | 0.1718 |
| MmugDNA.27456.1.S1_at | polymerase (RNA) I polypeptide D, 16 kDa | POLR1D | 3.92 | 0.0000 |
| MmugDNA.30349.1.S1_at | Transcribed locus | — | 3.92 | 0.0066 |
| MmugDNA.7253.1.S1_at | — | — | 3.92 | 0.1111 |

| Probe Set ID | Gene Title | Gene Symbol | Ratio Top verus Bottom | p value Top versus Bottom |
|---|---|---|---|---|
| MmugDNA.14931.1.S1_at | t-SNARE domain containing 1 | TSNARE1 | 3.91 | 0.0947 |
| MmugDNA.30795.1.S1_at | chromosome 10 open reading frame 81 | C10orf81 | 3.91 | 0.0955 |
| MmugDNA.17018.1.S1_s_at | butyrophilin, subfamily 2, member A1 | BTN2A1 | 3.91 | 0.0004 |
| MmugDNA.26488.1.S1_at | nischarin | NISCH | 3.90 | 0.0435 |
| MmugDNA.1076.1.S1_at | WD repeat domain 61 | WDR61 | 3.89 | 0.0001 |
| MmugDNA.19511.1.S1_at | death inducer-obliterator 1 | DIDO1 | 3.89 | 0.0638 |
| MmugDNA.5147.1.S1_s_at | kelch repeat and BTB (POZ) domain containing 4 | KBTBD4 | 3.89 | 0.0043 |
| MmugDNA.26429.1.S1_at | AP2 associated kinase 1 | AAK1 | 3.89 | 0.1855 |
| MmugDNA.36463.1.S1_s_at | tyrosine kinase, non-receptor, 1 | TNK1 | 3.89 | 0.0001 |
| MmuSTS.1060.1.S1_at | Solute carrier family 25, member 29 | SLC25A29 | 3.89 | 0.0804 |
| MmugDNA.12692.1.S1_at | quinolinate phosphoribosyltransferase (nicotinate-nucleotide pyrophosphorylase (carboxylating)) | QPRT | 3.88 | 0.0444 |
| MmugDNA.19435.1.S1_s_at | DnaJ (Hsp40) homolog, subfamily A, member 1 | DNAJA1 | 3.88 | 0.0014 |
| MmugDNA.1963.1.S1_at | CDNA clone IMAGE: 5278089 | — | 3.88 | 0.1079 |
| MmugDNA.40985.1.S1_at | CDNA clone IMAGE: 4825288 | — | 3.88 | 0.0338 |
| MmuSTS.3495.1.S1_at | A kinase (PRKA) anchor protein 3 | AKAP3 | 3.87 | 0.0508 |
| MmuSTS.3737.1.S1_at | protein tyrosine phosphatase, receptor type, C | PTPRC | 3.87 | 0.0186 |
| MmugDNA.31476.1.S1_at | RAB28, member RAS oncogene family | RAB28 | 3.87 | 0.0939 |
| MmugDNA.30719.1.S1_at | dom-3 homolog Z (C. elegans) | DOM3Z | 3.87 | 0.0007 |
| MmugDNA.3113.1.S1_at | transient receptor potential cation channel, subfamily C, member 2 | TRPC2 | 3.87 | 0.0121 |
| MmuSTS.4117.1.S1_at | transmembrane protein 15 | TMEM15 | 3.87 | 0.0145 |
| MmugDNA.41463.1.S1_at | Vac14 homolog (S. cerevisiae) | VAC14 | 3.86 | 0.0546 |
| MmugDNA.26499.1.S1_at | leupaxin | LPXN | 3.86 | 0.0090 |
| MmugDNA.37595.1.S1_at | mortality factor 4 like 1 | MORF4L1 | 3.85 | 0.0059 |
| MmugDNA.22504.1.S1_at | — | — | 3.84 | 0.0508 |
| MmugDNA.20249.1.S1_at | RNA binding motif protein 26 | RBM26 | 3.84 | 0.0198 |
| MmugDNA.13483.1.S1_at | — | — | 3.84 | 0.0604 |
| MmugDNA.16424.1.S1_at | gelsolin (amyloidosis, Finnish type) | GSN | 3.84 | 0.0118 |
| MmugDNA.16896.1.S1_at | stromal antigen 3 | STAG3 | 3.82 | 0.0959 |
| MmuSTS.2334.1.S1_at | peroxisomal membrane protein 4, 24 kDa | PXMP4 | 3.81 | 0.0013 |
| MmugDNA.28442.1.S1_s_at | chromosome 20 open reading frame 74 | C20orf74 | 3.81 | 0.0043 |
| MmugDNA.6811.1.S1_at | smu-1 suppressor of mec-8 and unc-52 homolog (C. elegans) | SMU1 | 3.80 | 0.0001 |
| MmugDNA.13860.1.S1_at | — | — | 3.79 | 0.0387 |
| MmugDNA.13463.1.S1_at | COP9 constitutive photomorphogenic homolog subunit 6 (Arabidopsis) | COPS6 | 3.79 | 0.0192 |
| MmugDNA.4402.1.S1_s_at | mago-nashi homolog | FLJ10292 | 3.78 | 0.0492 |
| MmugDNA.18844.1.S1_at | cholinergic receptor, nicotinic, alpha 1 (muscle) | CHRNA1 | 3.77 | 0.1879 |
| MmugDNA.40143.1.S1_at | transmembrane protein 67 | TMEM67 | 3.77 | 0.0848 |
| MmuSTS.2481.1.S1_at | zinc finger protein 294 | ZNF294 | 3.77 | 0.0304 |
| MmugDNA.30140.1.S1_at | thioredoxin-like 4B | TXNL4B | 3.77 | 0.0239 |
| MmugDNA.38654.1.S1_at | MORN repeat containing 2 | MORN2 | 3.77 | 0.0047 |
| MmuSTS.2773.1.S1_at | solute carrier family 1 (neutral amino acid transporter), member | SLC1A5 | 3.76 | 0.0113 |
| MmugDNA.31203.1.S1_at | THAP domain containing, apoptosis associated protein 2 | THAP2 | 3.76 | 0.0136 |
| MmugDNA.13298.1.S1_at | zinc finger protein 473 | ZNF473 | 3.76 | 0.0210 |
| MmugDNA.19431.1.S1_at | ZXD family zinc finger C | ZXDC | 3.76 | 0.1070 |
| MmugDNA.33573.1.S1_s_at | serine/threonine kinase 16 | STK16 | 3.76 | 0.0507 |
| MmugDNA.24286.1.S1_at | coagulation factor II (thrombin) receptor-like 1 | F2RL1 | 3.76 | 0.0055 |
| MmugDNA.41306.1.S1_at | zinc finger protein 650 | ZNF650 | 3.76 | 0.0002 |
| MmugDNA.8919.1.S1_at | Transcribed locus | — | 3.75 | 0.0786 |
| MmugDNA.4185.1.S1_at | nicolin 1 | NICN1 | 3.75 | 0.1272 |
| MmugDNA.21236.1.S1_at | arginine/serine-rich coiled-coil 1 | LOC704232 | 3.75 | 0.0445 |
| MmugDNA.32661.1.S1_at | dihydropyrimidine dehydrogenase | DPYD | 3.75 | 0.0062 |
| MmugDNA.20872.1.S1_at | docking protein 1, 62 kDa (downstream of tyrosine kinase 1) | DOK1 | 3.75 | 0.0846 |
| MmugDNA.34300.1.S1_at | nicotinamide nucleotide adenylyltransferase 1 | NMNAT1 | 3.75 | 0.0851 |
| MmugSTS.3697.1.S1_at | COP9 constitutive photomorphogenic homolog subunit 4 | COPS4 | 3.74 | 0.0000 |
| MmuSTS.3649.1.S1_at | chloride channel 4 | CLCN4 | 3.74 | 0.1113 |
| MmugDNA.40690.1.S1_at | zinc finger protein 197 | ZNF197 | 3.74 | 0.0025 |
| MmugDNA.41072.1.S1_at | chromosome X and Y open reading frame 10 | CXYorf10 | 3.73 | 0.0146 |
| MmugDNA.26793.1.S1_at | hypothetical protein MGC40579 | MGC40579 | 3.73 | 0.0030 |
| MmugDNA.7453.1.S1_at | integrator complex subunit 9 | RC74 | 3.73 | 0.0020 |
| MmugDNA.42873.1.S1_at | KIAA1429 | KIAA1429 | 3.72 | 0.0204 |
| MmugDNA.13884.1.S1_at | nuclear transcription factor, X-box binding 1 | NFX1 | 3.72 | 0.1160 |
| MmugDNA.6002.1.S1_at | TNFAIP3 interacting protein 2 | TNIP2 | 3.72 | 0.0166 |
| MmugDNA.28839.1.S1_at | apolipoprotein A-I binding protein | APOA1BP | 3.72 | 0.0046 |
| MmugDNA.11009.1.S1_at | Hypothetical protein LOC150384 | LOC150384 | 3.72 | 0.0243 |
| MmuSTS.2811.1.S1_s_at | elongation factor Tu GTP binding domain containing 1 | EFTUD1 | 3.72 | 0.0006 |
| MmugDNA.11298.1.S1_at | solute carrier family 39 (zinc transporter), member 7 | SLC39A7 | 3.72 | 0.1074 |
| MmugDNA.38831.1.S1_at | RNA binding motif protein 12B | RBM12B | 3.72 | 0.1376 |
| MmuSTS.1121.1.S1_at | transient receptor potential cation channel, subfamily C, member 4 associated protein | TRPC4AP | 3.71 | 0.0751 |
| MmuSTS.1121.1.S1_at | single-strand-selective monofunctional uracil-DNA glycosylase 1 | SMUG1 | 3.71 | 0.1049 |

-continued

| Probe Set ID | Gene Title | Gene Symbol | Ratio Top verus Bottom | p value Top versus Bottom |
|---|---|---|---|---|
| MmugDNA.23627.1.S1_at | caspase 2, apoptosis-related cysteine peptidase (neural precursor cell expressed, developmentally down-regulated 2) | CASP2 | 3.71 | 0.1012 |
| Mmu.14962.1.S1_at | glycosyltransferase 8 domain containing 1 | LOC695999 | 3.71 | 0.0060 |
| MmugDNA.13631.1.S1_s_at | CD320 molecule | CD320 | 3.71 | 0.0663 |
| MmugDNA.23982.1.S1_at | phosphoprotein associated with glycosphingolipid microdomains 1 /// phosphoprotein associated with glycosphingolipid microdomains 1 | PAG1 /// LOC653745 | 3.71 | 0.0018 |
| MmuSTS.2557.1.S1_at | tumor necrosis factor (ligand) superfamily, member 19 | TNFSF4 | 3.70 | 0.0375 |
| MmugDNA.9215.1.S1_s_at | REX2, RNA exonuclease 2 homolog (*S. cerevisiae*) | REXO2 | 3.70 | 0.0235 |
| MmugDNA.14634.1.S1_at | alcohol dehydrogenase IB (class I), beta polypeptide | ADH1B | 3.70 | 0.2072 |
| MmuSTS.2989.1.S1_at | met proto-oncogene | MET | 3.69 | 0.0006 |
| MmugDNA.6796.1.S1_at | F-box and WD-40 domain protein 8 | FBXW8 | 3.69 | 0.0022 |
| MmugDNA.35611.1.S1_at | — | — | 3.69 | 0.0476 |
| MmunewRS.1092.1.S1_at | F-box and WD-40 domain protein 12 | FBXW12 | 3.69 | 0.1972 |
| MmugDNA.37110.1.S1_at | chromosome 1 open reading frame 34 | C1orf34 | 3.69 | 0.0005 |
| MmugDNA.8905.1.S1_at | Transcribed locus, strongly XP_376888.2 PREDICTED: Laminin receptor 1 [*Homo sapiens*] | — | 3.69 | 0.0321 |
| MmugDNA.24188.1.S1_s_at | deleted in a mouse model of primary ciliary dyskinesia | RP11-529I10.4 | 3.68 | 0.0323 |
| MmugDNA.36794.1.S1_at | zinc finger protein 593 | ZNF593 | 3.68 | 0.0540 |
| MmuSTS.4394.1.S1_at | DENN/MADD domain containing 4A | DENND4A | 3.67 | 0.0345 |
| MmugDNA.4893.1.S1_at | hypothetical protein MGC16385 | MGC16385 | 3.67 | 0.0054 |
| MmunewRS.474.1.S1_at | ras homolog gene family, member C | RHOC | 3.67 | 0.1242 |
| MmugDNA.29861.1.S1_at | carbonic anhydrase XI | CA11 | 3.67 | 0.0227 |
| MmugDNA.3791.1.S1_at | sphingosine-1-phosphate phosphatase 1 | SGPP1 | 3.67 | 0.0007 |
| MmugDNA.10595.1.S1_at | — | — | 3.67 | 0.1276 |
| MmugDNA.34611.1.S1_at | Hypothetical protein LOC643011 | LOC643011 | 3.67 | 0.0005 |
| MmugDNA.38962.1.S1_at | acid phosphatase 6, lysophosphatidic | ACP6 | 3.66 | 0.0113 |
| MmugDNA.3351.1.S1_at | DNA segment on chromosome 4 (unique) 234 expressed sequence | D4S234E | 3.66 | 0.0658 |
| MmugDNA.2806.1.S1_s_at | mitogen-activated protein kinase kinase kinase kinase 1 | MAP4K1 | 3.66 | 0.0540 |
| MmugDNA.1419.1.S1_at | CDNA: FLJ23065 fis, clone LNG04894 | — | 3.65 | 0.1255 |
| MmugDNA.24776.1.S1_at | protein phosphatase 1, regulatory subunit 7 | PPP1R7 | 3.65 | 0.0367 |
| MmugDNA.35069.1.S1_at | RAB6B, member RAS oncogene family | RAB6B | 3.65 | 0.0351 |
| MmugDNA.29893.1.S1_at | ankyrin repeat domain 28 | ANKRD28 | 3.64 | 0.0027 |
| MmugDNA.2018.1.S1_at | RNA binding protein S1, serine-rich domain /// RNA binding protein S1, serine-rich domain | RNPS1 | 3.64 | 0.0026 |
| MmugDNA.31080.1.S1_at | phosphatidylinositol glycan anchor biosynthesis, class O | PIGO | 3.64 | 0.0464 |
| MmugDNA.24890.1.S1_at | transmembrane and tetratricopeptide repeat containing 2 | TMTC2 | 3.64 | 0.0230 |
| MmugDNA.5735.1.S1_at | — | — | 3.64 | 0.0557 |
| MmugDNA.26841.1.S1_at | estrogen-related receptor alpha | ESRRA | 3.63 | 0.0274 |
| MmugDNA.27441.1.S1_at | protein phosphatase 2 (formerly 2A), regulatory subunit A (PR 65), beta isoform | PPP2R1B | 3.63 | 0.0345 |
| MmuSTS.1040.1.S1_at | ST8 alpha-N-acetyl-neuraminide alpha-2,8-sialyltransferase 5 | ST8SIA5 | 3.63 | 0.0623 |
| MmugDNA.7493.1.S1_at | intraflagellar transport 122 homolog (*Chlamydomonas*) | IFT122 | 3.63 | 0.0020 |
| MmuSTS.3957.1.S1_at | splicing factor, arginine/serine-rich 6 | SFRS6 | 3.62 | 0.0000 |
| MmugDNA.29820.1.S1_at | calcium and integrin binding 1 (calmyrin) | CIB1 | 3.62 | 0.0323 |
| MmugDNA.16149.1.S1_at | Full-length cDNA clone CS0DC025YP03 of Neuroblastoma Cot 25-normalized of *Homo sapiens* (human) | — | 3.62 | 0.0491 |
| MmugDNA.6842.1.S1_at | proteasome maturation protein | POMP | 3.62 | 0.0204 |
| MmuSTS.1527.1.S1_at | mitochondrial ribosomal protein L49 | MRPL49 | 3.62 | 0.0034 |
| MmugDNA.19557.1.S1_at | filamin binding LIM protein 1 | FBLIM1 | 3.61 | 0.0016 |
| MmugDNA.32221.1.S1_at | family with sequence similarity 3, member C | FAM3C | 3.61 | 0.0022 |
| MmuSTS.1501.1.S1_at | membrane cofactor protein | MCP | 3.60 | 0.0015 |
| MmugDNA.38325.1.S1_s_at | chromosome 15 open reading frame 17 | C15orf17 | 3.60 | 0.0580 |
| MmugDNA.3200.1.S1_at | *Homo sapiens*, clone IMAGE: 5768746, mRNA | — | 3.60 | 0.1685 |
| MmugDNA.2659.1.S1_at | coiled-coil domain containing 32 | CCDC32 | 3.60 | 0.0505 |
| MmugDNA.19268.1.S1_at | mitochondrial ribosomal protein L2 | MRPL2 | 3.60 | 0.0018 |
| MmugDNA.24173.1.S1_at | Mastermind-like 2 (*Drosophila*) | MAML2 | 3.59 | 0.0493 |
| MmugDNA.24843.1.S1_at | zinc finger protein 226 | ZNF226 | 3.59 | 0.0000 |
| MmugDNA.35062.1.S1_s_at | aconitase 2, mitochondrial | ACO2 | 3.59 | 0.0031 |
| MmugDNA.17481.1.S1_at | tripartite motif-containing 36 | TRIM36 | 3.58 | 0.0010 |
| MmugDNA.3106.1.S1_at | protective protein for beta-galactosidase (galactosialidosis) | PPGB | 3.58 | 0.0000 |
| MmugDNA.38210.1.S1_at | Full-length cDNA clone CS0DF025YA01 of Fetal brain of *Homo sapiens* (human) | — | 3.58 | 0.0127 |
| MmugDNA.15726.1.S1_at | corin, serine peptidase | CORIN | 3.58 | 0.2106 |
| MmugDNA.24500.1.S1_at | CGI-09 protein | CGI-09 | 3.57 | 0.0000 |
| MmugDNA.16131.1.S1_at | penta-EF-hand domain containing 1 | PEF1 | 3.57 | 0.0794 |
| MmugDNA.9872.1.S1_at | lysosomal-associated membrane protein 1 | LAMP1 | 3.56 | 0.0236 |
| Mmu.4348.1.S1_at | membrane interacting protein of RGS16 | LOC694849 | 3.56 | 0.0006 |
| MmugDNA.5941.1.S1_at | BTB (POZ) domain containing 9 | BTBD9 | 3.56 | 0.1375 |
| MmugDNA.10425.1.S1_at | chondroitin polymerizing factor | CHPF | 3.56 | 0.0133 |
| MmugDNA.845.1.S1_at | aspartylglucosaminidase | AGA | 3.56 | 0.0019 |
| MmugDNA.3137.1.S1_at | protein phosphatase 1G (formerly 2C), magnesium-dependent, gamma isoform | PPM1G | 3.56 | 0.0107 |
| MmugDNA.35064.1.S1_at | acyl-Coenzyme A oxidase 2, branched chain | ACOX2 | 3.55 | 0.0374 |

-continued

| Probe Set ID | Gene Title | Gene Symbol | Ratio Top verus Bottom | p value Top versus Bottom |
|---|---|---|---|---|
| MmugDNA.33241.1.S1_at | Impact homolog (mouse) | IMPACT | 3.55 | 0.0052 |
| MmugDNA.18757.1.S1_at | chromosome 3 open reading frame 39 | C3orf39 | 3.55 | 0.0763 |
| MmugDNA.4130.1.S1_at | mitochondrial ribosomal protein L14 | MRPL14 | 3.55 | 0.0210 |
| MmugDNA.7996.1.S1_at | zinc finger protein 536 | ZNF536 | 3.55 | 0.1304 |
| MmugDNA.34470.1.S1_s_at | Hypothetical protein FLJ20309 | FLJ20309 | 3.55 | 0.0078 |
| MmugDNA.722.1.S1_at | — | — | 3.54 | 0.0027 |
| MmugDNA.26101.1.S1_at | chromosome 10 open reading frame 25 | C10orf25 | 3.54 | 0.1140 |
| MmugDNA.10676.1.S1_s_at | Dmx-like 1 | DMXL1 | 3.54 | 0.0303 |
| MmugDNA.16755.1.S1_at | ureidopropionase, beta | UPB1 | 3.54 | 0.1655 |
| MmugDNA.22341.1.S1_at | CDNA FLJ31513 fis, clone NT2RI1000127 | — | 3.54 | 0.0101 |
| MmuSTS.4756.1.S1_at | Fanconi anemia, complementation group A | FANCA | 3.54 | 0.0421 |
| MmuSTS.149.1.S1_at | MAM domain containing glycosylphosphatidylinositol anchor 1 | MDGA1 | 3.54 | 0.0991 |
| Mmu.9020.1.S1_at | — | CN802973 | 3.53 | 0.0706 |
| MmugDNA.14464.1.S1_at | antizyme inhibitor 1 | AZIN1 | 3.53 | 0.0000 |
| MmugDNA.3591.1.S1_at | hematopoietic signal peptide-containing | LOC284361 | 3.52 | 0.0013 |
| MmugDNA.2520.1.S1_at | gamma-aminobutyric acid (GABA) A receptor, beta 3 | GABRB3 | 3.52 | 0.1177 |
| MmugDNA.9838.1.S1_x_at | protein disulfide isomerase family A, member 4 /// protein disulfide isomerase family A, member 4 | PDIA4 | 3.52 | 0.0436 |
| MmugDNA.961.1.S1_at | hypothetical protein BC009862 | LOC90113 | 3.52 | 0.0115 |
| MmugDNA.11411.1.S1_at | — | — | 3.52 | 0.0264 |
| MmuSTS.3925.1.S1_at | sal-like 2 (Drosophila) | SALL2 | 3.51 | 0.0042 |
| MmugDNA.32205.1.S1_s_at | cytochrome b5 type A (microsomal) | CYB5A | 3.51 | 0.0112 |
| MmugDNA.32647.1.S1_at | KIAA0409 | KIAA0409 | 3.51 | 0.0080 |
| MmugDNA.11293.1.S1_at | F-box protein 4 | FBXO4 | 3.51 | 0.0376 |
| MmugDNA.4391.1.S1_at | secernin 2 | SCRN2 | 3.51 | 0.0570 |
| MmugDNA.15005.1.S1_at | glutaminase | GLS | 3.50 | 0.1533 |
| MmugDNA.28947.1.S1_at | lactamase, beta 2 | LACTB2 | 3.50 | 0.0364 |
| MmugDNA.16632.1.S1_at | Coenzyme Q10 homolog B (S. cerevisiae) | COQ10B | 3.50 | 0.0485 |
| MmugDNA.8992.1.S1_at | cytoplasmic beta-actin | LOC709469 | 3.50 | 0.1131 |
| MmugDNA.36746.1.S1_at | FYVE, RhoGEF and PH domain containing 6 | FGD6 | 3.50 | 0.0657 |
| MmugDNA.24282.1.S1_at | RIKEN cDNA 4921524J17 | LOC388272 | 3.50 | 0.0156 |
| MmugDNA.6398.1.S1_at | 1-acylglycerol-3-phosphate O-acyltransferase 7 (lysophosphatidic acid acyltransferase, eta) | AGPAT7 | 3.50 | 0.0454 |
| MmugDNA.8757.1.S1_at | chromosome 21 open reading frame 108 | C21orf108 | 3.49 | 0.0797 |
| MmugDNA.26500.1.S1_at | KIAA0564 protein | RP11-125A7.3 | 3.49 | 0.0000 |
| MmugDNA.34273.1.S1_at | Mitochondrial transcription termination factor | MTERF | 3.49 | 0.0856 |
| MmuSTS.2708.1.S1_at | a disintegrin and metalloproteinase domain 10 | ADAM10 | 3.49 | 0.0131 |
| MmugDNA.41055.1.S1_at | chromosome 3 open reading frame 62 | C3orf62 | 3.49 | 0.0726 |
| MmugDNA.29251.1.S1_at | guanine nucleotide binding protein (G protein), alpha transducing activity polypeptide 2 | GNAT2 | 3.49 | 0.0400 |
| MmugDNA.26180.1.S1_at | Chromosome 9 open reading frame 42 | C9orf42 | 3.49 | 0.0292 |
| MmuSTS.1660.1.S1_at | leucyl-tRNA synthetase 2, mitochondrial | LARS2 | 3.49 | 0.0460 |
| MmugDNA.43332.1.S1_at | Transcribed locus | — | 3.49 | 0.0334 |
| MmugDNA.20126.1.S1_at | 5,10-methenyltetrahydrofolate synthetase (5-formyltetrahydrofolate cyclo-ligase) | MTHFS | 3.48 | 0.0071 |
| MmuSTS.1987.1.S1_at | death-associated protein | DAP | 3.48 | 0.0005 |
| MmugDNA.40683.1.S1_at | heterogeneous nuclear ribonucleoprotein K | HNRPK | 3.48 | 0.0301 |
| MmugDNA.22114.1.S1_at | methylthioadenosine phosphorylase | MTAP | 3.47 | 0.0264 |
| MmugDNA.40281.1.S1_at | Transcribed locus | 237420_at | 3.47 | 0.0200 |
| MmugDNA.9668.1.S1_at | PWP1 homolog (S. cerevisiae) | PWP1 | 3.47 | 0.0124 |
| MmugDNA.3432.1.S1_at | plexin C1 | PLXNC1 | 3.47 | 0.0162 |
| MmugDNA.11221.1.S1_s_at | catenin (cadherin-associated protein), beta 1, 88 kDa | CTNNB1 | 3.47 | 0.0447 |
| MmugDNA.32959.1.S1_at | CDNA FLJ38419 fis, clone FEBRA2009846 | — | 3.47 | 0.1735 |
| MmugDNA.19660.1.S1_s_at | epoxide hydrolase 1, microsomal (xenobiotic) | EPHX1 | 3.46 | 0.0000 |
| MmuSTS.4149.1.S1_at | lipoic acid synthetase | LIAS | 3.45 | 0.0166 |
| MmugDNA.27400.1.S1_at | mannosyl (alpha-1,3-)-glycoprotein beta-1,4-N-acetylglucosaminyltransferase, isozyme A | MGAT4A | 3.45 | 0.0004 |
| MmugDNA.3969.1.S1_at | Transcribed locus, strongly XP_372416.1 PREDICTED: leucine rich repeat containing 10 [Homo sapiens] | — | 3.45 | 0.1619 |
| MmunewRS.977.1.S1_s_at | chromosome 10 open reading frame 125 | C10orf125 | 3.45 | 0.0268 |
| MmugDNA.336.1.S1_s_at | SH3 and multiple ankyrin repeat domains 2 | SHANK2 | 3.44 | 0.0424 |
| MmugDNA.10656.1.S1_at | GPI-anchored membrane protein 1 | GPIAP1 | 3.44 | 0.0012 |
| MmugDNA.38403.1.S1_at | — | — | 3.44 | 0.0927 |
| MmugDNA.28792.1.S1_at | metallo-beta-lactamase superfamily protein | LOC153364 | 3.43 | 0.0467 |
| MmugDNA.15913.1.S1_at | NudC domain containing 2 | NUDCD2 | 3.43 | 0.0000 |
| MmugDNA.10398.1.S1_s_at | G protein-coupled receptor 172A | GPR172A | 3.43 | 0.0559 |
| MmugDNA.15.1.S1_at | Hypothetical protein FLJ30655 | FLJ30655 | 3.43 | 0.0037 |
| MmugDNA.39070.1.S1_at | androgen-induced 1 | AIG1 | 3.43 | 0.0025 |
| MmugDNA.2721.1.S1_s_at | Transcribed locus, weakly XP_864747.1 PREDICTED: hypothetical protein XP_859654 [Canis familiaris] | — | 3.43 | 0.0094 |
| Mmu.12027.3.S1_at | heterogeneous nuclear ribonucleoprotein K isoform a | LOC709112 | 3.43 | 0.0681 |
| MmugDNA.38984.1.S1_at | uracil-DNA glycosylase 2 | UNG2 | 3.43 | 0.0995 |
| MmuSTS.4179.1.S1_at | cathepsin O | CTSO | 3.43 | 0.0144 |
| MmugDNA.26924.1.S1_at | hypothetical protein LOC720691 | LOC720691 | 3.42 | 0.1571 |

| Probe Set ID | Gene Title | Gene Symbol | Ratio Top verus Bottom | p value Top versus Bottom |
|---|---|---|---|---|
| Mmu.1137.1.S1_at | clone 2.32 T-cell receptor gamma chain mRNA, complete cds. | AY190025 | 3.42 | 0.0301 |
| MmuSTS.3149.1.S1_at | nuclear receptor subfamily 2, group F, member 6 | NR2F6 | 3.42 | 0.0585 |
| MmugDNA.3922.1.S1_at | CDNA clone IMAGE: 5266242 | — | 3.42 | 0.0051 |
| MmugDNA.8473.1.S1_at | KIAA1875 | KIAA1875 | 3.42 | 0.0943 |
| MmugDNA.38687.1.S1_at | family with sequence similarity 121B /// NODAL modulator 3 | FAM121B /// NOMO3 | 3.42 | 0.1139 |
| MmugDNA.21376.1.S1_s_at | SMAD, mothers against DPP homolog 3 (Drosophila) /// uroporphyrinogen decarboxylase | SMAD3 /// UROD | 3.42 | 0.0101 |
| MmugDNA.17400.1.S1_at | UDP-N-acetyl-alpha-D-galactosamine:polypeptide N-acetylgalactosaminyltransferase 7 (GalNAc-T7) | GALNT7 | 3.42 | 0.0000 |
| Mmu.4958.1.S1_at | Rhesus monkey apolipoprotein(a) mRNA, 3 end. | J04635 | 3.42 | 0.0785 |
| MmugDNA.9546.1.S1_s_at | succinate dehydrogenase complex, subunit B, iron sulfur (Ip) | SDHB | 3.41 | 0.0242 |
| MmugDNA.8291.1.S1_at | spectrin, beta, erythrocytic (includes spherocytosis, clinical type I) /// spectrin, beta, erythrocytic (includes spherocytosis, clinical type I) | SPTB /// LOC653716 | 3.41 | 0.1210 |
| MmugDNA.5881.1.S1_at | IQ motif containing C | IQCC | 3.40 | 0.0207 |
| MmugDNA.2675.1.S1_at | trimethyllysine hydroxylase, epsilon | TMLHE | 3.40 | 0.1204 |
| MmugDNA.36751.1.S1_at | ret finger protein 2 | RFP2 | 3.40 | 0.0005 |
| MmugDNA.32977.1.S1_at | osmosis responsive factor | OSRF | 3.40 | 0.0100 |
| MmugDNA.20463.1.S1_at | EST from clone 27306, 5' end | — | 3.40 | 0.0005 |
| MmugDNA.14340.1.S1_s_at | SEH1-like (S. cerevisiae) | SEH1L | 3.39 | 0.0258 |
| MmugDNA.34005.1.S1_at | CG8580-PA, isoform A | LOC718520 | 3.39 | 0.0005 |
| MmugDNA.767.1.S1_at | hypothetical protein BC015395 | LOC130940 | 3.39 | 0.1357 |
| MmugDNA.10620.1.S1_at | Rho GTPase activating protein 18 | ARHGAP18 | 3.39 | 0.0000 |
| Mmu.11667.1.S1_at | Calcyclin-binding protein (CacyBP) (hCacyBP) (Siah-interacting protein) (S100A6-binding protein) | CACYBP /// LOC709343 | 3.39 | 0.0000 |
| MmugDNA.8892.1.S1_at | hypothetical protein LOC646482 | LOC646482 | 3.38 | 0.1081 |
| MmugDNA.26367.1.S1_at | acyl-CoA synthetase short-chain family member 1 | ACSS1 | 3.38 | 0.0380 |
| MmugDNA.2176.1.S1_at | interferon stimulated exonuclease gene 20 kDa | ISG20 | 3.38 | 0.0000 |
| MmugDNA.29483.1.S1_at | UDP-N-acetyl-alpha-D-galactosamine:polypeptide N-acetylgalactosaminyltransferase 13 (GalNAc-T13) | GALNT13 | 3.38 | 0.0534 |
| MmuSTS.3944.1.S1_at | succinate-CoA ligase, GDP-forming, beta subunit | SUCLG2 | 3.37 | 0.0043 |
| MmugDNA.2878.1.S1_at | IQ motif containing E | IQCE | 3.37 | 0.0575 |
| MmugDNA.24079.1.S1_s_at | coiled-coil domain containing 115 | CCDC115 | 3.37 | 0.0018 |
| MmugDNA.646.1.S1_at | zinc finger protein 420 | ZNF420 | 3.37 | 0.0215 |
| MmuSTS.2567.1.S1_s_at | Ubiquitin-like 4 | UBL4 | 3.37 | 0.0006 |
| MmunewRS.414.1.S1_at | transcription elongation factor A (SII)-like 1 | TCEAL1 | 3.37 | 0.0002 |
| MmugDNA.18382.1.S1_at | potassium channel tetramerisation domain containing 18 | KCTD18 | 3.37 | 0.0036 |
| MmugDNA.36367.1.S1_at | replication factor C (activator 1) 1, 145 kDa | RFC1 | 3.36 | 0.0093 |
| MmuSTS.2408.1.S1_s_at | splicing factor, arginine/serine-rich 15 | SFRS15 | 3.36 | 0.0084 |
| MmugDNA.38549.1.S1_at | elongation protein 4 homolog (S. cerevisiae) | ELP4 | 3.36 | 0.0279 |
| MmugDNA.27232.1.S1_at | RNA binding motif and ELMO/CED-12 domain 1 | RBED1 | 3.36 | 0.0628 |
| MmugDNA.30570.1.S1_at | flightless I homolog (Drosophila) | FLII | 3.36 | 0.0522 |
| MmugDNA.22711.1.S1_at | arginyl-tRNA synthetase-like | RARSL | 3.36 | 0.0078 |
| MmugDNA.40118.1.S1_at | vitelliform macular dystrophy 2-like 2 | VMD2L2 | 3.35 | 0.0953 |
| MmuSTS.3727.1.S1_at | protein tyrosine phosphatase, non-receptor type substrate 1 | PTPNS1 | 3.35 | 0.0115 |
| MmugDNA.16151.1.S1_at | zinc finger protein 567 | ZNF567 | 3.35 | 0.0104 |
| MmugDNA.34207.1.S1_at | Transcribed locus | — | 3.35 | 0.1488 |
| MmugDNA.3005.1.S1_at | polymerase (RNA) II (DNA directed) polypeptide B, 140 kDa | POLR2B | 3.34 | 0.0033 |
| MmugDNA.26951.1.S1_at | zinc finger protein 174 | ZNF174 | 3.34 | 0.0446 |
| MmugDNA.25836.1.S1_at | SWI/SNF related, matrix associated, actin dependent regulator of chromatin, subfamily a, member 4 | SMARCA4 | 3.34 | 0.0394 |
| MmugDNA.40790.1.S1_at | matrin 3 | MATR3 | 3.34 | 0.0880 |
| MmugDNA.15859.1.S1_s_at | FAST kinase domains 2 | FASTKD2 | 3.33 | 0.0003 |
| MmugDNA.26707.1.S1_at | aarF domain containing kinase 4 | ADCK4 | 3.33 | 0.0000 |
| MmuSTS.1553.1.S1_at | Mitogen-activated protein kinase kinase kinase 7 interacting protein 1 | MAP3K7IP1 | 3.33 | 0.0067 |
| MmugDNA.27387.1.S1_s_at | mannosidase, alpha, class 2B, member 1 | MAN2B1 | 3.32 | 0.0175 |
| MmugDNA.23626.1.S1_at | — | — | 3.32 | 0.0842 |
| MmugDNA.27590.1.S1_at | — | — | 3.32 | 0.1370 |
| MmugDNA.13842.1.S1_at | ADP-ribosylation-like factor 6 interacting protein 4 | ARL6IP4 | 3.31 | 0.0687 |
| MmugDNA.36711.1.S1_at | bolA-like 1 (E. coli) | BOLA1 | 3.31 | 0.0000 |
| MmugDNA.35351.1.S1_at | round spermatid basic protein 1 | RSBN1 | 3.31 | 0.0414 |
| MmunewRS.884.1.S1_at | zinc finger protein 29 | MGC75360 | 3.31 | 0.1372 |
| MmugDNA.21146.1.S1_at | STT3, subunit of the oligosaccharyltransferase complex, homolog A (S. cerevisiae) | STT3A | 3.29 | 0.0106 |
| MmugDNA.14126.1.S1_at | chromosome 1 open reading frame 176 | C1orf176 | 3.29 | 0.0492 |
| MmugDNA.3522.1.S1_at | KRIT1, ankyrin repeat containing | KRIT1 | 3.29 | 0.0900 |
| MmugDNA.1835.1.S1_at | zinc finger protein 786 | ZNF786 | 3.29 | 0.0065 |
| MmugDNA.30488.1.S1_at | isocitrate dehydrogenase 2 (NADP+), mitochondrial | IDH2 | 3.29 | 0.0771 |
| MmugDNA.35876.1.S1_at | ST8 alpha-N-acetyl-neuraminide alpha-2,8-sialyltransferase 2 | ST8SIA2 | 3.28 | 0.0593 |
| MmugDNA.29769.1.S1_at | Proteasome (prosome, macropain) subunit, beta type, 7 | PSMB7 | 3.28 | 0.1130 |
| MmuSTS.3141.1.S1_at | methionine adenosyltransferase I, alpha | MAT1A | 3.28 | 0.0685 |
| MmugDNA.28691.1.S1_at | chromosome 4 open reading frame 30 | C4orf30 | 3.28 | 0.0289 |

-continued

| Probe Set ID | Gene Title | Gene Symbol | Ratio Top verus Bottom | p value Top versus Bottom |
| --- | --- | --- | --- | --- |
| MmugDNA.27041.1.S1_at | solute carrier family 25 (mitochondrial carrier; phosphate carrier), member 23 | SLC25A23 | 3.27 | 0.0245 |
| MmugDNA.1453.1.S1_at | dysbindin (dystrobrevin binding protein 1) domain containing 2 | DBNDD2 | 3.27 | 0.0046 |
| MmuSTS.2928.1.S1_at | potassium voltage-gated channel, subfamily H (eag-related), memb, 7 | KCNH7 | 3.27 | 0.1254 |
| Mmu.1184.1.S1_at | endomembrane protein emp70 precursor isolog | TM9SF3 | 3.27 | 0.1019 |
| MmugDNA.17590.1.S1_at | hypothetical gene supported by BC036588 | LOC400657 | 3.27 | 0.0882 |
| MmugDNA.4941.1.S1_at | ring finger protein 14 | RNF14 | 3.27 | 0.1095 |
| MmugDNA.15613.1.S1_at | glucosamine (N-acetyl)-6-sulfatase (Sanfilippo disease IIID) | GNS | 3.27 | 0.0730 |
| MmugDNA.15594.1.S1_at | gonadotropin-releasing hormone 2 | GNRH2 | 3.27 | 0.0389 |
| MmuSTS.1234.1.S1_at | carnitine palmitoyltransferase II | CPT2 | 3.26 | 0.0017 |
| MmugDNA.1780.1.S1_at | — | — | 3.26 | 0.0226 |
| MmugDNA.36001.1.S1_at | septin 3 | 3-Sep | 3.26 | 0.1383 |
| MmugDNA.18459.1.S1_at | protease, serine, 15 | PRSS15 | 3.26 | 0.1011 |
| MmugDNA.31437.1.S1_at | Glycosylphosphatidylinositol specific phospholipase D1 | GPLD1 | 3.26 | 0.0097 |
| MmugDNA.736.1.S1_at | Full-length cDNA clone CS0DJ002YF02 of T cells (Jurkat cell line) Cot 10-normalized of *Homo sapiens* (human) | — | 3.25 | 0.0015 |
| MmugDNA.27420.1.S1_at | — | — | 3.25 | 0.0258 |
| MmugDNA.16170.1.S1_s_at | transmembrane protein 4 | TMEM4 | 3.25 | 0.0005 |
| MmugDNA.37197.1.S1_at | cytochrome b5 domain containing 1 | CYB5D1 | 3.25 | 0.0905 |
| MmugDNA.3346.1.S1_at | makorin, ring finger protein, 2 | MKRN2 | 3.25 | 0.0000 |
| MmugDNA.8231.1.S1_at | triple functional domain (PTPRF interacting) | TRIO | 3.25 | 0.2126 |
| MmugDNA.32917.1.S1_at | G protein-coupled receptor 56 | GPR56 | 3.24 | 0.0001 |
| MmugDNA.34839.1.S1_at | unc-5 homolog A (*C. elegans*) | UNC5A | 3.24 | 0.0215 |
| MmugDNA.35448.1.S1_at | phosphohistidine phosphatase 1 | PHPT1 | 3.24 | 0.0749 |
| MmugDNA.8574.1.S1_at | tetraspanin 32 | TSPAN32 | 3.24 | 0.0871 |
| MmugDNA.33908.1.S1_at | KIAA0141 | KIAA0141 | 3.24 | 0.0050 |
| MmuSTS.4810.1.S1_at | follicular lymphoma variant translocation 1 | FVT1 | 3.23 | 0.0006 |
| MmugDNA.17221.1.S1_at | chromosome 11 open reading frame 11 | C11orf11 | 3.23 | 0.0529 |
| MmugDNA.15445.1.S1_at | chromosome 14 open reading frame 132 | C14orf132 | 3.23 | 0.0629 |
| MmugDNA.37901.1.S1_at | COX4 neighbor | COX4NB | 3.23 | 0.0005 |
| MmugDNA.9762.1.S1_at | Hypothetical protein LOC643382 | LOC643382 | 3.23 | 0.0376 |
| MmuSTS.2544.1.S1_at | translocase of inner mitochondrial membrane 23 homolog (yeast) | TIMM23 | 3.22 | 0.0000 |
| MmuSTS.3926.1.S1_at | tetraspanin 31 | TSPAN31 | 3.22 | 0.0303 |
| MmugDNA.23914.1.S1_at | hypothetical gene supported by AF064843; AK025716 /// hypothetical protein LOC642361 /// hypothetical protein LOC646509 | LOC439994 /// LOC642361 /// LOC646509 | 3.21 | 0.1319 |
| MmugDNA.25504.1.S1_at | tubulin, gamma complex associated protein 5 | TUBGCP5 | 3.21 | 0.0027 |
| MmugDNA.19562.1.S1_at | zinc finger protein 406 /// Zinc finger protein 406 | ZNF406 /// LOC654252 | 3.21 | 0.0468 |
| MmugDNA.11799.1.S1_at | CAS1 domain containing 1 | CASD1 | 3.21 | 0.0679 |
| MmugDNA.22745.1.S1_at | oxidoreductase NAD-binding domain containing 1 | OXNAD1 | 3.21 | 0.0025 |
| MmugDNA.29698.1.S1_at | transmembrane protein 128 | TMEM128 | 3.21 | 0.0063 |
| MmugDNA.21404.1.S1_at | high-mobility group 20B | HMG20B | 3.20 | 0.0295 |
| MmugDNA.37311.1.S1_at | F-box and leucine-rich repeat protein 20 | FBXL20 | 3.20 | 0.1599 |
| MmugDNA.26098.1.S1_at | Yip1 domain family, member 4 | YIPF4 | 3.20 | 0.0937 |
| MmunewRS.416.1.S1_at | ATPase, H+ transporting, lysosomal 5658 kDa, V1 subunit B, isoform 1 (Renal tubular acidosis with deafness), mRNA (cDNA clone MGC: 74733 IMAGE: 5208385), complete cds. /GEN = ATP6V1B1 /PROD = ATPase, H+ transporting, lysosomal 5658 kD, V1subunit B, isoform 1 | gi: 39645818 | 3.20 | 0.0716 |
| MmugDNA.24420.1.S1_s_at | Chromosome 1 open reading frame 85 | C1orf85 | 3.19 | 0.0399 |
| MmugDNA.1438.1.S1_at | mitochondrial ribosomal protein 63 | MRP63 | 3.19 | 0.0838 |
| MmugDNA.25245.1.S1_at | cSH-PTP2 | LOC441868 | 3.18 | 0.0771 |
| MmugDNA.20570.1.S1_at | WW domain binding protein 1 | WBP1 | 3.18 | 0.0001 |
| MmugDNA.37020.1.S1_at | dedicator of cytokinesis 1 | DOCK1 | 3.18 | 0.0728 |
| MmuSTS.1407.1.S1_at | potassium channel, subfamily K, member 3 | KCNK3 | 3.18 | 0.0806 |
| MmugDNA.11054.1.S1_at | transmembrane protein 53 | TMEM53 | 3.18 | 0.1004 |
| MmugDNA.25885.1.S1_at | ATP/GTP binding protein-like 3 | AGBL3 | 3.18 | 0.0755 |
| MmugDNA.38701.1.S1_at | glucosidase, alpha; acid (Pompe disease, glycogen storage disease type II) | GAA | 3.18 | 0.0184 |
| MmugDNA.43423.1.S1_s_at | Nuclear respiratory factor 1 | NRF1 | 3.18 | 0.0933 |
| MmugDNA.3251.1.S1_at | KIAA1183 protein | KIAA1183 | 3.18 | 0.2092 |
| MmugDNA.30199.1.S1_at | transmembrane protein 70 | TMEM70 | 3.18 | 0.0021 |
| MmugDNA.15760.1.S1_at | peroxiredoxin 5 | PRDX5 | 3.17 | 0.1334 |
| MmugDNA.30636.1.S1_at | eukaryotic translation initiation factor 2-alpha kinase 3 | EIF2AK3 | 3.17 | 0.0171 |
| MmugDNA.36645.1.S1_at | isochorismatase domain containing 1 | ISOC1 | 3.17 | 0.0099 |
| Mmu.3814.1.S1_at | MGC15407-like | LOC677698 | 3.17 | 0.0744 |
| MmugDNA.16486.1.S1_at | coiled-coil domain containing 66 | CCDC66 | 3.16 | 0.0054 |
| MmugDNA.12087.1.S1_at | peptidyl-tRNA hydrolase 1 homolog (*S. cerevisiae*) | PTRH1 | 3.16 | 0.0024 |
| MmugDNA.33464.1.S1_at | PHD finger protein 6 /// PHD finger protein 6 | PHF6 | 3.16 | 0.0667 |
| MmuSTS.238.1.S1_at | 3-hydroxymethyl-3-methylglutaryl-Coenzyme A lyase (hydroxymethyl, utaricaciduria) | HMGCL | 3.16 | 0.0027 |
| MmunewRS.64.1.S1_at | mitochondrial ribosomal protein L13 | MRPL13 | 3.16 | 0.0003 |

| Probe Set ID | Gene Title | Gene Symbol | Ratio Top verus Bottom | p value Top versus Bottom |
|---|---|---|---|---|
| MmugDNA.15050.1.S1_x_at | chromosome 5 open reading frame 31 | C5orf31 | 3.16 | 0.0390 |
| Mmu.3280.1.S1_at | retinoblastoma-associated protein 140 | LOC722528 | 3.16 | 0.0136 |
| MmugDNA.28942.1.S1_at | — | — | 3.16 | 0.0067 |
| MmugDNA.43211.1.S1_at | IBR domain containing 1 | IBRDC1 | 3.15 | 0.0006 |
| MmuSTS.1528.1.S1_at | mitochondrial ribosomal protein L50 | MRPL50 | 3.15 | 0.0206 |
| MmuSTS.3308.1.S1_at | SATB family member 1 | SATB1 | 3.15 | 0.0007 |
| MmugDNA.8392.1.S1_s_at | SWI/SNF related, matrix associated, actin dependent regulator of chromatin, subfamily a, member 5 | SMARCA5 | 3.15 | 0.0053 |
| MmugDNA.11966.1.S1_at | ribonuclease T2 | RNASET2 | 3.15 | 0.0025 |
| MmugDNA.19079.1.S1_s_at | karyopherin alpha 1 (importin alpha 5) | KPNA1 | 3.14 | 0.0136 |
| MmuSTS.2957.1.S1_at | LIM domain binding 1 | LDB1 | 3.14 | 0.0697 |
| MmuSTS.1291.1.S1_at | de-etiolated 1 | DET1 | 3.14 | 0.0395 |
| MmugDNA.9689.1.S1_at | chromosome 20 open reading frame 82 | C20orf82 | 3.14 | 0.0503 |
| MmugDNA.4538.1.S1_at | dynein, light chain, roadblock-type 2 | DYNLRB2 | 3.14 | 0.0037 |
| MmugDNA.10006.1.S1_at | activating signal cointegrator 1 complex subunit 3-like 1 /// activating signal cointegrator 1 complex subunit 3-like 1 | ASCC3L1 | 3.14 | 0.0043 |
| MmugDNA.35020.1.S1_at | PHD finger protein 20 | PHF20 | 3.14 | 0.0000 |
| MmugDNA.18760.1.S1_at | integrin alpha FG-GAP repeat containing 3 | ITFG3 | 3.14 | 0.0000 |
| MmuSTS.4243.1.S1_s_at | protein phosphatase 1F (PP2C domain containing) | PPM1F | 3.14 | 0.0303 |
| MmugDNA.21710.1.S1_at | CDNA FLJ38498 fis, clone FELNG2000241 | — | 3.14 | 0.0038 |
| MmugDNA.18438.1.S1_at | Rho guanine nucleotide exchange factor (GEF) 12 | ARHGEF12 | 3.13 | 0.1368 |
| MmugDNA.27794.1.S1_at | Transcribed locus, strongly NP_079090.1 Cas-Br-M (murine) ecotropic retroviral transforming sequence-like 1; E-cadherin binding protein E7 [Homo sapiens] | — | 3.13 | 0.0004 |
| MmugDNA.36386.1.S1_at | hypothetical protein LOC283680 | LOC283680 | 3.13 | 0.0048 |
| MmugDNA.13015.1.S1_at | echinoderm microtubule associated protein like 4 | EML4 | 3.13 | 0.0093 |
| MmugDNA.7282.1.S1_at | hypothetical protein MGC5242 | MGC5242 | 3.13 | 0.0008 |
| MmugDNA.36432.1.S1_at | smoothelin | SMTN | 3.13 | 0.0273 |
| MmugDNA.21419.1.S1_at | hypothetical protein LOC644096 | LOC644096 | 3.13 | 0.0006 |
| Mmu.2231.1.S1_at | F-actin capping protein alpha-1 subunit | CAPZA1 | 3.13 | 0.1124 |
| MmugDNA.30086.1.S1_at | CG13876-PA | LOC693668 | 3.13 | 0.0672 |
| MmugDNA.8672.1.S1_at | syndecan 3 (N-syndecan) | SDC3 | 3.13 | 0.0201 |
| MmugDNA.1837.1.S1_at | radial spokehead-like 1 /// radial spokehead-like 1 | RSHL1 | 3.13 | 0.2159 |
| MmugDNA.40109.1.S1_at | ubiquitin-like 7 (bone marrow stromal cell-derived) | UBL7 | 3.13 | 0.0040 |
| MmuSTS.3145.1.S1_at | NODAL modulator 1 | NOMO1 | 3.12 | 0.0003 |
| MmugDNA.1608.1.S1_at | F-box and leucine-rich repeat protein 2 | FBXL2 | 3.12 | 0.0301 |
| MmugDNA.7343.1.S1_at | CDNA clone IMAGE: 4797878 | — | 3.12 | 0.1962 |
| MmugDNA.20535.1.S1_at | chromosome 1 open reading frame 50 | C1orf50 | 3.12 | 0.0081 |
| MmuSTS.2562.1.S1_s_at | tumor suppressing subtransferable candidate 1 | TSSC1 | 3.12 | 0.0010 |
| MmugDNA.19650.1.S1_at | deoxyhypusine hydroxylase/monooxygenase /// deoxyhypusine hydroxylase/monooxygenase | DOHH | 3.12 | 0.0831 |
| MmugDNA.3700.1.S1_at | transmembrane protein 39A | TMEM39A | 3.12 | 0.0384 |
| MmugDNA.41216.1.S1_at | AF034176 Human mRNA (Tripodis and Ragoussis) Homo sapiens cDNA clone ntcon5 contig | — | 3.11 | 0.1344 |
| MmugDNA.24685.1.S1_at | retinitis pigmentosa 2 (X-linked recessive) | RP2 | 3.11 | 0.0605 |
| MmuSTS.507.1.S1_s_at | N-acylsphingosine amidohydrolase 3-like | ASAH3L | 3.11 | 0.0119 |
| MmugDNA.988.1.S1_at | 3-phosphoinositide dependent protein kinase-1 | PDPK1 | 3.11 | 0.0509 |
| MmugDNA.3400.1.S1_at | Doublecortin domain-containing protein 2 | LOC642926 | 3.11 | 0.0189 |
| MmugDNA.15806.1.S1_at | CDNA clone IMAGE: 4813920 | — | 3.11 | 0.1892 |
| MmugDNA.41923.1.S1_at | eukaryotic translation initiation factor 2 alpha kinase 4 | EIF2AK4 | 3.11 | 0.0696 |
| MmugDNA.7995.1.S1_at | cysteine-rich PAK1inhibitor | CRIPAK | 3.11 | 0.1785 |
| MmugDNA.5163.1.S1_at | Transcribed locus | — | 3.10 | 0.0566 |
| MmugDNA.23909.1.S1_at | acyl-Coenzyme A dehydrogenase family, member 8 | ACAD8 | 3.10 | 0.1817 |
| MmugDNA.28412.1.S1_at | KIAA1370 | KIAA1370 | 3.10 | 0.0000 |
| MmugDNA.11861.1.S1_at | salvador homolog 1 (Drosophila) | SAV1 | 3.10 | 0.0059 |
| MmugDNA.7288.1.S1_s_at | KIAA0280 | KIAA0280 | 3.09 | 0.0105 |
| MmugDNA.15715.1.S1_at | HCLS1 associated protein X-1 | HAX1 | 3.09 | 0.0106 |
| MmugDNA.38581.1.S1_at | excision repair cross-complementing rodent repair deficiency, complementation group 1 (includes overlapping antisense sequence) | ERCC1 | 3.09 | 0.0102 |
| MmugDNA.9603.1.S1_at | KIAA0753 | KIAA0753 | 3.09 | 0.0595 |
| MmugDNA.22362.1.S1_at | proteasome (prosome, macropain) subunit, beta type, 1 | PSMB1 | 3.09 | 0.0108 |
| MmugDNA.6764.1.S1_at | ATPase type 13A1 | ATP13A1 | 3.08 | 0.0244 |
| MmunewRS.184.1.S1_at | hypothetical protein LOC701867 | LOC701867 | 3.08 | 0.1983 |
| MmugDNA.23270.1.S1_at | hypothetical protein FLJ32065 | FLJ32065 | 3.08 | 0.0304 |
| MmugDNA.41792.1.S1_at | keratinocyte associated protein 3 | KRTCAP3 | 3.08 | 0.0277 |
| MmugDNA.28683.1.S1_at | chromosome 9 open reading frame 39 | C9orf39 | 3.08 | 0.0154 |
| MmuSTS.4748.1.S1_at | ubiquitin specific protease 18 | USP18 | 3.08 | 0.1155 |
| MmugDNA.13548.1.S1_at | cytochrome c oxidase subunit Va | COX5A | 3.07 | 0.0790 |
| MmugDNA.30189.1.S1_at | hypothetical protein LOC283481 | LOC283481 | 3.07 | 0.2062 |
| MmugDNA.35491.1.S1_at | adult retina protein | LOC153222 | 3.07 | 0.0001 |
| MmugDNA.37253.1.S1_s_at | heterogeneous nuclear ribonucleoprotein D-like | HNRPDL | 3.07 | 0.0577 |
| MmugDNA.31553.1.S1_at | cofactor of BRCA1 | COBRA1 | 3.07 | 0.0232 |
| MmugDNA.25401.1.S1_at | abhydrolase domain containing 14B | ABHD14B | 3.07 | 0.0170 |
| MmuSTS.4318.1.S1_at | solute carrier family 36 (proton/amino acid symporter), member 4 | SLC36A4 | 3.07 | 0.1274 |

-continued

| Probe Set ID | Gene Title | Gene Symbol | Ratio Top verus Bottom | p value Top versus Bottom |
|---|---|---|---|---|
| MmuSTS.4037.1.S1_at | solute carrier family 41, member 2 | SLC41A2 | 3.07 | 0.1483 |
| MmugDNA.41507.1.S1_at | ATP-binding cassette, sub-family B (MDR/TAP), member 6 | ABCB6 | 3.06 | 0.0126 |
| MmugDNA.14233.1.S1_at | sperm specific antigen 2 | SSFA2 | 3.06 | 0.0120 |
| MmugDNA.34695.1.S1_at | Leucine rich repeat neuronal 6C | LRRN6C | 3.06 | 0.1945 |
| MmugDNA.39744.1.S1_at | zinc finger protein 609 | ZNF609 | 3.06 | 0.0160 |
| MmugDNA.4156.1.S1_at | ATPase, H+ transporting V0 subunit E2-like (rat) | ATP6V0E2L | 3.06 | 0.0340 |
| MmugDNA.29456.1.S1_at | Breakpoint cluster region protein, uterine leiomyoma, 2 | WDR22 | 3.06 | 0.0131 |
| MmugDNA.4944.1.S1_at | tau tubulin kinase 1 | TTBK1 | 3.05 | 0.0548 |
| MmugDNA.22968.1.S1_at | — | — | 3.05 | 0.0531 |
| MmugDNA.42434.1.S1_at | N-acetylglucosaminidase, alpha-(Sanfilippo disease IIIB) | NAGLU | 3.05 | 0.0982 |
| MmugDNA.42291.1.S1_at | G protein-coupled receptor kinase 6 | GRK6 | 3.05 | 0.0293 |
| MmugDNA.121.1.S1_at | golgi SNAP receptor complex member 2 | GOSR2 | 3.05 | 0.0435 |
| MmugDNA.17630.1.S1_at | cell division cycle 40 homolog (S. cerevisiae) | CDC40 | 3.05 | 0.0398 |
| MmugDNA.30084.1.S1_at | — | — | 3.05 | 0.0012 |
| MmugDNA.33923.1.S1_at | chromosome 1 open reading frame 79 | C1orf79 | 3.05 | 0.0664 |
| MmugDNA.37503.1.S1_at | ets variant gene 7 (TEL2 oncogene) | ETV7 | 3.05 | 0.0228 |
| MmugDNA.15871.1.S1_at | BSD domain containing 1 | BSDC1 | 3.04 | 0.0107 |
| MmugDNA.32390.1.S1_at | dipeptidyl-peptidase 7 | DPP7 | 3.04 | 0.1328 |
| MmugDNA.41073.1.S1_at | Transcribed locus | — | 3.04 | 0.0000 |
| MmuSTS.2834.1.S1_at | solute carrier family 8 (sodium/calcium exchanger), member 3 | SLC8A3 | 3.04 | 0.0879 |
| MmugDNA.20734.1.S1_at | zinc finger and BTB domain containing 11 | ZBTB11 | 3.04 | 0.0326 |
| MmuSTS.247.1.S1_at | inositol polyphosphate-1-phosphatase | INPP1 | 3.04 | 0.0049 |
| MmugDNA.22134.1.S1_at | SIN3 homolog A, transcription regulator (yeast) | SIN3A | 3.04 | 0.0000 |
| MmugDNA.17708.1.S1_at | torsin A interacting protein 1 | TOR1AIP1 | 3.03 | 0.0001 |
| MmugDNA.42050.1.S1_at | — | — | 3.03 | 0.0980 |
| MmugDNA.30213.1.S1_at | zinc finger, MYM-type 5 | ZMYM5 | 3.03 | 0.0036 |
| MmugDNA.43311.1.S1_at | LDLR-FUT fusion protein (LDLR-FUT) | — | 3.02 | 0.1029 |
| MmugDNA.26409.1.S1_at | hypothetical protein LOC644242 /// hypothetical protein LOC650429 /// hypothetical protein LOC650446 | LOC644242 /// LOC650429 /// LOC650446 | 3.02 | 0.0510 |
| MmuSTS.59.1.S1_at | histone deacetylase 5 | HDAC5 | 3.02 | 0.0063 |
| MmugDNA.34663.1.S1_at | flavin containing monooxygenase 3 | FMO3 | 3.02 | 0.1292 |
| MmugDNA.40441.1.S1_at | CDNA clone IMAGE: 5270500 | — | 3.02 | 0.1493 |
| MmuSTS.1202.1.S1_at | component of oligomeric golgi complex 7 | COG7 | 3.01 | 0.0056 |
| MmugDNA.33076.1.S1_at | Transcribed locus | — | 3.01 | 0.0492 |
| MmuSTS.658.1.S1_at | putative T1/ST2 receptor binding protein | IL1RL1LG | 3.01 | 0.0153 |
| MmugDNA.26960.1.S1_at | WD repeats and SOF1 domain containing | WDSOF1 | 3.01 | 0.0000 |
| MmugDNA.24887.1.S1_at | tripartite motif-containing 2 | TRIM2 | 3.01 | 0.0073 |
| MmugDNA.26072.1.S1_at | active BCR-related gene | ABR | 3.01 | 0.0038 |
| MmugDNA.28188.1.S1_at | hypothetical gene supported by AK124342 | FLJ42351 | 3.01 | 0.0975 |
| MmugDNA.40888.1.S1_at | taurine upregulated gene 1 | TUG1 | 3.00 | 0.0221 |
| MmugDNA.39101.1.S1_at | — | — | 3.00 | 0.1428 |
| MmuSTS.4591.1.S1_at | thyroid hormone receptor, alpha | THRA | 3.00 | 0.0270 |
| MmugDNA.16168.1.S1_s_at | structural maintenance of chromosomes 3 | SMC3 | 3.00 | 0.0000 |
| MmugDNA.40670.1.S1_at | 3'(2'), 5'-bisphosphate nucleotidase 1 | BPNT1 | 3.00 | 0.0221 |
| MmuSTS.1100.1.S1_at | PAX transcription activation domain interacting protein 1 like | PAXIP1L | 3.00 | 0.0160 |
| MmugDNA.4318.1.S1_at | FLJ12716 protein | FLJ12716 | 3.00 | 0.0565 |
| MmugDNA.28833.1.S1_at | CDNA FLJ41690 fis, clone HCASM2009405 | — | 2.99 | 0.0293 |
| MmugDNA.28320.1.S1_at | CDNA clone IMAGE: 5259419 | — | 2.99 | 0.2149 |
| MmugDNA.19977.1.S1_at | KIAA1217 | KIAA1217 | 2.99 | 0.0595 |
| MmunewRS.283.1.S1_at | NAD(P) dependent steroid dehydrogenase-like | HSPC105 | 2.99 | 0.1709 |
| MmuSTS.4337.1.S1_at | F-box only protein 25 | FBXO25 | 2.99 | 0.0969 |
| MmugDNA.42396.1.S1_at | germ cell-less | LOC701545 | 2.99 | 0.0783 |
| MmugDNA.23292.1.S1_at | Ras suppressor protein 1 | RSU1 | 2.99 | 0.0016 |
| MmugDNA.17188.1.S1_at | acyl-Coenzyme A dehydrogenase, C-2 to C-3 short chain | ACADS | 2.99 | 0.0453 |
| MmugDNA.8639.1.S1_at | DEAD (Asp-Glu-Ala-Asp) box polypeptide 21 | DDX21 | 2.99 | 0.0027 |
| MmugDNA.6559.1.S1_at | chromosome 9 open reading frame 119 | C9orf119 | 2.99 | 0.0393 |
| MmugDNA.41506.1.S1_at | ankyrin repeat and SOCS box-containing 6 | ASB6 | 2.99 | 0.0077 |
| MmugDNA.13579.1.S1_at | KIAA1712 | KIAA1712 | 2.99 | 0.0879 |
| MmugDNA.19830.1.S1_at | glycoprotein hormone alpha 2 | GPHA2 | 2.99 | 0.0280 |
| Mmu.3556.1.S1_s_at | family with sequence similarity 96, member A isoform a | LOC714217 | 2.98 | 0.0000 |
| MmugDNA.10102.1.S1_s_at | heat shock 70 kDa protein 8 | HSPA8 | 2.98 | 0.0043 |
| MmugDNA.4343.1.S1_at | hypothetical protein FLJ10241 | FLJ10241 | 2.98 | 0.0015 |
| MmugDNA.6426.1.S1_at | CD151 molecule (Raph blood group) | CD151 | 2.98 | 0.0338 |
| MmugDNA.27731.1.S1_at | MRNA from chromosome 5q21-22, clone: 843Ex | — | 2.98 | 0.0000 |
| MmugDNA.33252.1.S1_at | protease, serine, 16 (thymus) | PRSS16 | 2.98 | 0.0020 |
| MmugDNA.20450.1.S1_at | chromosome 19 open reading frame 2 | C19orf2 | 2.97 | 0.0001 |
| MmuSTS.3421.1.S1_at | claudin 3 | CLDN3 | 2.97 | 0.0204 |
| MmugDNA.26818.1.S1_at | methyltransferase like 4 | METTL4 | 2.97 | 0.0076 |
| MmugDNA.33099.1.S1_at | KIAA0423 | KIAA0423 | 2.97 | 0.0005 |
| MmuAffx.1252.1.A1_at | protocadherin alpha (PCDH) mRNA, 3 prime UTR. | AY598414 | 2.96 | 0.1373 |
| MmugDNA.9975.1.S1_at | zinc finger protein 331 | ZNF331 | 2.95 | 0.0596 |
| MmugDNA.41468.1.S1_at | necdin-like 2 | NDNL2 | 2.95 | 0.0006 |
| MmugDNA.17362.1.S1_at | PTD016 protein | LOC51136 | 2.95 | 0.0267 |
| MmugDNA.43033.1.S1_at | HemK methyltransferase family member 2 | HEMK2 | 2.95 | 0.1934 |
| MmugDNA.29141.1.S1_at | UDP-glucose ceramide glucosyltransferase-like 1 | UGCGL1 | 2.95 | 0.0396 |

-continued

| Probe Set ID | Gene Title | Gene Symbol | Ratio Top verus Bottom | p value Top versus Bottom |
|---|---|---|---|---|
| MmugDNA.13178.1.S1_at | CDC14 cell division cycle 14 homolog B (S. cerevisiae) | CDC14B | 2.95 | 0.0382 |
| MmugDNA.26142.1.S1_at | coiled-coil domain containing 95 | CCDC95 | 2.95 | 0.0654 |
| MmugDNA.2882.1.S1_at | zinc finger CCCH-type containing 7B | ZC3H7B | 2.95 | 0.0351 |
| MmugDNA.22445.1.S1_at | Ubiquitin-conjugating enzyme E2I (UBC9 homolog, yeast) | UBE2I | 2.95 | 0.0079 |
| MmugDNA.5279.1.S1_at | transmembrane protein 33 | TMEM33 | 2.95 | 0.0097 |
| Mmu.1276.1.S1_at | serine protease inhibitor, Kunitz type, 2 | LOC714755 | 2.94 | 0.0663 |
| MmugDNA.43012.1.S1_at | chromosome 17 open reading frame 28 | C17orf28 | 2.94 | 0.0440 |
| MmuSTS.1982.1.S1_at | CD14 antigen | CD14 | 2.94 | 0.0049 |
| MmugDNA.41964.1.S1_at | hypothetical protein LOC646870 | LOC646870 | 2.94 | 0.0728 |
| MmugDNA.37306.1.S1_at | melanoma antigen family E, 1 | MAGEE1 | 2.94 | 0.0035 |
| MmugDNA.36805.1.S1_at | CDNA clone IMAGE: 5265020 | — | 2.93 | 0.0047 |
| MmugDNA.23752.1.S1_at | Hypothetical gene supported by AK126569 | 230404_at | 2.93 | 0.0014 |
| MmugDNA.7176.1.S1_at | zinc finger protein 508 | ZNF508 | 2.93 | 0.1404 |
| MmugDNA.15639.1.S1_s_at | nuclear distribution gene C homolog (A. nidulans) | NUDC | 2.93 | 0.1171 |
| MmugDNA.23645.1.S1_at | kinase insert domain receptor (a type III receptor tyrosine kinase) | KDR | 2.93 | 0.0526 |
| MmugDNA.28242.1.S1_at | G protein-coupled receptor 82 | GPR82 | 2.92 | 0.0520 |
| MmugDNA.26896.1.S1_at | hypothetical protein LOC285847 | LOC285847 | 2.92 | 0.1348 |
| MmugDNA.33291.1.S1_at | E74-like factor 2 (ets domain transcription factor) | ELF2 | 2.92 | 0.0090 |
| MmugDNA.1352.1.S1_at | 3-hydroxyisobutyryl-Coenzyme A hydrolase | HIBCH | 2.92 | 0.0317 |
| Mmu.14583.1.S1_at | Transcribed locus | — | 2.92 | 0.0000 |
| MmugDNA.23757.1.S1_at | high-mobility group protein 2-like 1 | HMG2L1 | 2.92 | 0.0821 |
| MmugDNA.3973.1.S1_at | TBP-interacting protein | TIP120A | 2.92 | 0.0295 |
| MmugDNA.20292.1.S1_at | breast cancer metastasis suppressor 1 | BRMS1 | 2.92 | 0.0411 |
| MmugDNA.28666.1.S1_at | palmdelphin | PALMD | 2.91 | 0.0451 |
| MmuSTS.2571.1.S1_at | ubiquitin specific peptidase 20 | USP20 | 2.91 | 0.0475 |
| MmugDNA.26331.1.S1_at | Mitogen-activated protein kinase kinase kinase 13 | MAP3K13 | 2.91 | 0.0470 |
| MmugDNA.10238.1.S1_at | testis expressed sequence 9 | TEX9 | 2.91 | 0.1328 |
| MmunewRS.102.1.S1_at | mRNA for KIAA1979 protein. | gi: 18916872 | 2.90 | 0.1195 |
| MmuSTS.3241.1.S1_at | BCL2/adenovirus E1B 19 kDa interacting protein 1 | BNIP1 | 2.90 | 0.0091 |
| MmugDNA.1167.1.S1_at | pyrophosphatase (inorganic) 2 /// ring finger protein 36 | PPA2 /// RNF36 | 2.90 | 0.0008 |
| MmugDNA.2679.1.S1_at | small nuclear ribonucleoprotein polypeptide A' | SNRPA1 | 2.90 | 0.0215 |
| MmugDNA.29871.1.S1_at | NADH dehydrogenase (ubiquinone) Fe-S protein 2, 49 kDa (NADH-coenzyme Q reductase) | NDUFS2 | 2.89 | 0.0192 |
| Mmu.4717.1.S1_at | ankyrin repeat and BTB (POZ) domain containing 1 isoform 2 | LOC710603 | 2.89 | 0.0439 |
| MmugDNA.20718.1.S1_at | heterogeneous nuclear ribonucleoprotein A3 pseudogene 1 /// heterogeneous nuclear ribonucleoprotein A3 | HNRPA3P1 /// HNRPA3 | 2.89 | 0.0013 |
| MmugDNA.28284.1.S1_at | GA binding protein transcription factor, alpha subunit 60 kDa | GABPA | 2.89 | 0.0000 |
| MmuSTS.4752.1.S1_at | vacuolar protein sorting 45 homolog (S. cerevisiae) | VPS45 | 2.89 | 0.0020 |
| MmugDNA.7814.1.S1_at | family with sequence similarity 120A | FAM120A | 2.89 | 0.0377 |
| MmugDNA.43320.1.S1_at | UDP-Gal:betaGlcNAc beta 1,3-galactosyltransferase, polypeptide 4 | B3GALT4 | 2.89 | 0.0379 |
| MmugDNA.38533.1.S1_at | CDNA FLJ11692 fis, clone HEMBA1004983 | — | 2.89 | 0.1672 |
| MmugDNA.37108.1.S1_at | Ribosomal protein L7-like 1 | RPL7L1 | 2.89 | 0.0294 |
| MmugDNA.43087.1.S1_at | choroideremia (Rab escort protein 1) /// hypothetical protein LOC642090 | CHM /// LOC642090 | 2.89 | 0.0003 |
| MmugDNA.37619.1.S1_at | serine/threonine/tyrosine interacting protein /// serine/threonine/tyrosine interacting protein | STYX /// LOC653890 | 2.89 | 0.0039 |
| MmugDNA.6995.1.S1_at | Heterogeneous nuclear ribonucleoprotein A0 | HNRPA0 | 2.89 | 0.0419 |
| MmugDNA.33286.1.S1_at | centrosomal protein 57 kDa | CEP57 | 2.88 | 0.0039 |
| MmugDNA.7613.1.S1_at | vitelliform macular dystrophy 2 (Best disease, bestrophin) | VMD2 | 2.88 | 0.0211 |
| MmugDNA.41643.1.S1_at | TPTE and PTEN homologous inositol lipid phosphatase pseudogene /// TPTE and PTEN homologous inositol lipid phosphatase isoform gamma /// TPTE and PTEN homologous inositol lipid phosphatase isoform gamma | LOC374491 /// LOC642904 /// LOC649370 | 2.88 | 0.1625 |
| MmugDNA.17851.1.S1_at | NADH dehydrogenase (ubiquinone) 1, alpha/beta subcomplex, 1, 8 kDa | NDUFAB1 | 2.88 | 0.0718 |
| MmugDNA.35659.1.S1_at | chromosome 9 open reading frame 84 | C9orf84 | 2.88 | 0.1866 |
| MmuSTS.1608.1.S1_at | kelch-like 7 (Drosophila) | KLHL7 | 2.88 | 0.0008 |
| MmuSTS.20882.1.S1_at | hypothetical protein MGC61571 | MGC61571 | 2.88 | 0.0025 |
| MmugDNA.7201.1.S1_at | carboxypeptidase D | CPD | 2.87 | 0.0239 |
| MmugDNA.22156.1.S1_at | LOC166075 | LOC401097 | 2.87 | 0.0185 |
| MmugDNA.18421.1.S1_at | Keratin associated protein 5-11 | KRTAP5-11 | 2.87 | 0.0621 |
| MmugDNA.10502.1.S1_at | dehydrogenase/reductase (SDR family) member 13 | DHRS13 | 2.87 | 0.0613 |
| MmuSTS.2492.1.S1_at | zinc finger protein 509 | ZNF509 | 2.87 | 0.0312 |
| MmugDNA.33371.1.S1_at | chymotrypsin-like | CTRL | 2.87 | 0.0277 |
| MmugDNA.24978.1.S1_at | neuronal PAS domain protein 1 | NPAS1 | 2.87 | 0.1278 |
| MmugDNA.37408.1.S1_at | tyrosyl-tRNA synthetase 2 (mitochondrial) | YARS2 | 2.86 | 0.0023 |
| MmugDNA.27947.1.S1_at | FLJ45244 protein | FLJ45244 | 2.86 | 0.2182 |
| MmugDNA.38426.1.S1_at | KIAA0892 | KIAA0892 | 2.86 | 0.0020 |
| Mmu.12307.1.S1_at | KIAA1008 | KIAA1008 | 2.86 | 0.1271 |
| MmuSTS.534.1.S1_at | UDP-Gal:betaGlcNAc beta 1,4-galactosyltransferase, polypeptide | B4GALT2 | 2.86 | 0.1428 |
| MmugDNA.21102.1.S1_at | hypothetical protein LOC651803 | LOC651803 | 2.86 | 0.0893 |
| MmugDNA.25674.1.S1_at | potassium channel tetramerisation domain containing 14 | KCTD14 | 2.86 | 0.0286 |
| MmugDNA.11321.1.S1_at | FUN14 domain containing 1 | FUNDC1 | 2.86 | 0.0497 |

| Probe Set ID | Gene Title | Gene Symbol | Ratio Top verus Bottom | p value Top versus Bottom |
|---|---|---|---|---|
| MmugDNA.27909.1.S1_at | hypothetical protein FLJ20125 | FLJ20125 | 2.86 | 0.0288 |
| MmugDNA.41621.1.S1_at | tetratricopeptide repeat domain 30B | TTC30B | 2.85 | 0.0837 |
| MmugDNA.22964.1 S1_at | Transcribed locus | — | 2.85 | 0.1242 |
| MmugDNA.32172.1.S1_at | haloacid dehalogenase-like hydrolase domain containing 2 | HDHD2 | 2.85 | 0.0025 |
| MmugDNA.33685.1.S1_at | chromosome X open reading frame 26 | CXorf26 | 2.85 | 0.0000 |
| MmuSTS.2187.1.S1_at | solute carrier family 41, member 3 | SLC41A3 | 2.85 | 0.0794 |
| MmuSTS.3436.1.S1_at | alpha-methylacyl-CoA racemase | AMACR | 2.85 | 0.0891 |
| MmuSTS.1512.1.S1_at | isoprenylcysteine carboxyl methyltransferase | ICMT | 2.84 | 0.0002 |
| MmuSTS.234.1.S1_at | chromosome 15 open reading frame 40 | C15orf40 | 2.84 | 0.0002 |
| MmunewRS.872.1.S1_at | otopetrin 1 | OTOP1 | 2.84 | 0.0322 |
| MmugDNA.28434.1.S1_at | TROVE domain family, member 2 | TROVE2 | 2.84 | 0.0136 |
| MmugDNA.18405.1.S1_s_at | Suppression of tumorigenicity 7 like | ST7L | 2.84 | 0.0768 |
| MmugDNA.32265.1.S1_at | chromosome 19 open reading frame 52 | C19orf52 | 2.84 | 0.0659 |
| MmugDNA.11590.1.S1_at | chromosome 1 open reading frame 165 | C1orf165 | 2.83 | 0.0087 |
| MmugDNA.12017.1.S1_at | fibronectin type III and ankyrin repeat domains 1 | FANK1 | 2.82 | 0.0001 |
| MmugDNA.8492.1.S1_at | chromosome 6 open reading frame 153 | C6orf153 | 2.82 | 0.0193 |
| MmugDNA.22105.1.S1_at | dynein, axonemal, light intermediate polypeptide 1 | DNALI1 | 2.82 | 0.0264 |
| Mmu.16365.1.S1_at | PRP4 pre-mRNA processing factor 4 homolog B (yeast) (predicted) | LOC709497 /// LOC710193 | 2.82 | 0.0238 |
| MmugDNA.42362.1.S1_at | ornithine decarboxylase antizyme 2 | OAZ2 | 2.82 | 0.0858 |
| MmugDNA.2230.1.S1_at | phosphatidylinositol 4-kinase, catalytic, alpha polypeptide | PIK4CA | 2.82 | 0.0002 |
| MmugDNA.23113.1.S1_at | Midline 2 | MID2 | 2.81 | 0.0018 |
| MmugDNA.9055.1.S1_at | multiple C2 domains, transmembrane 2 | MCTP2 | 2.81 | 0.1229 |
| MmugDNA.28806.1.S1_at | Zinc finger protein 284 | ZNF284 | 2.81 | 0.0754 |
| MmugDNA.6963.1.S1_at | tweety homolog 2 (*Drosophila*) | TTYH2 | 2.81 | 0.0997 |
| MmugDNA.24592.1.S1_at | CTD (carboxy-terminal domain, RNA polymerase II, polypeptide A) small phosphatase 2 | CTDSP2 | 2.81 | 0.1065 |
| MmugDNA.18857.1.S1_at | KIAA0467 | KIAA0467 | 2.81 | 0.0008 |
| MmugDNA.40098.1.S1_at | hypothetical protein LOC144363 | LOC144363 | 2.81 | 0.1331 |
| MmugDNA.23612.1.S1_at | Transcribed locus | — | 2.81 | 0.0728 |
| MmuSTS.1461.1.S1_at | mitogen-activated protein kinase kinase kinase kinase 3 | MAP4K3 | 2.81 | 0.0000 |
| MmuSTS.2022.1.S1_at | prostaglandin D2 synthase, hematopoietic | PGDS | 2.80 | 0.1324 |
| MmugDNA.21008.1.S1_at | ubiquitin specific peptidase 14 (tRNA-guanine transglycosylase) | USP14 | 2.80 | 0.0026 |
| MmugDNA.5481.1.S1_at | Full-length cDNA clone CS0DF012YD09 of Fetal brain of *Homo sapiens* (human) | — | 2.80 | 0.0074 |
| MmuSTS.4011.1.S1_at | solute carrier family 35, member B3 | SLC35B3 | 2.80 | 0.0186 |
| MmugDNA.12978.1.S1_at | phosphoinositide-3-kinase, class 2, alpha polypeptide | PIK3C2A | 2.80 | 0.0138 |
| MmugDNA.25990.1.S1_at | coiled-coil domain containing 123 | CCDC123 | 2.79 | 0.1079 |
| MmugDNA.21323.1.S1_at | CDNA FLJ14181 fis, clone NT2RP2004300 | — | 2.79 | 0.1179 |
| MmugDNA.34194.1.S1_at | chromosome 6 open reading frame 120 | C6orf120 | 2.79 | 0.1196 |
| MmugDNA.1311.1.S1_at | hypothetical protein MGC26733 | MGC26733 | 2.79 | 0.0076 |
| MmugDNA.10629.1.S1_at | translocase of inner mitochondrial membrane 17 homolog A (yeast) | TIMM17A | 2.79 | 0.0004 |
| MmugDNA.33991.1.S1_at | CDNA: FLJ22539 fis, clone HRC13227 | — | 2.78 | 0.0066 |
| MmugDNA.20536.1.S1_at | transmembrane and tetratricopeptide repeat containing 3 | TMTC3 | 2.78 | 0.0230 |
| MmugDNA.6356.1.S1_at | chromosome 7 open reading frame 28A /// chromosome 7 open reading frame 28B | C7orf28A /// C7orf28B | 2.78 | 0.0024 |
| MmugDNA.6519.1.S1_at | WD repeat domain 39 | WDR39 | 2.78 | 0.0098 |
| MmugDNA.36685.1.S1_at | SET domain, bifurcated 2 | SETDB2 | 2.78 | 0.0199 |
| MmugDNA.22793.1.S1_s_at | tribbles homolog 2 (*Drosophila*) | TRIB2 | 2.78 | 0.1659 |
| MmugDNA.2623.1.S1_at | prefoldin subunit 4 | PFDN4 | 2.77 | 0.0015 |
| MmuSTS.421.1.S1_at | ORM1-like 3 (*S. cerevisiae*) | ORMDL3 | 2.77 | 0.0697 |
| MmugDNA.36435.1 S1_s_at | histidyl-tRNA synthetase | HARS | 2.77 | 0.0220 |
| MmugDNA.39696.1.S1_at | UTP15, U3 small nucleolar ribonucleoprotein, homolog (*S. cerevisiae*) | UTP15 | 2.77 | 0.1158 |
| MmugDNA.13739.1.S1_at | sorting nexin 14 | SNX14 | 2.77 | 0.0059 |
| MmuSTS.1965.1.S1_at | frequently rearranged in advanced T-cell lymphomas 2 | FRAT2 | 2.77 | 0.0258 |
| MmugDNA.18514.1.S1_at | RNA (guanine-9-) methyltransferase domain containing 2 | RG9MTD2 | 2.77 | 0.0616 |
| MmugDNA.26813.1.S1_at | MRNA; cDNA DKFZp762M127 (from clone DKFZp762M127) | — | 2.77 | 0.0023 |
| MmunewRS.1000.1.S1_s_at | zinc finger protein 432 | ZNF432 | 2.76 | 0.1958 |
| MmugDNA.22282.1.S1_at | WD repeat and FYVE domain containing 1 | WDFY1 | 2.76 | 0.1120 |
| MmuSTS.4631.1.S1_at | vascular endothelial growth factor B | VEGFB | 2.76 | 0.0010 |
| MmugDNA.14574.1.S1_at | dedicator of cytokinesis 5 | DOCK5 | 2.76 | 0.0832 |
| MmugDNA.32208.1.S1_at | katanin p80 (WD repeat containing) subunit B 1 | KATNB1 | 2.76 | 0.0202 |
| MmugDNA.7187.1.S1_at | splicing factor, arginine/serine-rich 4 | SFRS4 | 2.76 | 0.0061 |
| MmuSTS.1088.1.S1_at | Solute carrier family 43, member 2 | SLC43A1 | 2.76 | 0.0585 |
| MmugDNA.4698.1.S1_at | calcium binding and coiled-coil domain 2 | CALCOCO2 | 2.76 | 0.0099 |
| MmugDNA.11372.1.S1_at | Cysteine rich BMP regulator 2 (chordin-like) | CRIM2 | 2.76 | 0.1851 |
| MmugDNA.18070.1.S1_at | Kruppel-like factor 9 | KLF9 | 2.76 | 0.0804 |
| MmugDNA.14499.1.S1_at | zinc finger protein 596 | ZNF596 | 2.76 | 0.0833 |
| MmugDNA.40758.1.S1_at | galactokinase 2 /// retinoblastoma binding protein 8 | GALK2 /// RBBP8 | 2.76 | 0.0046 |
| MmugDNA.33141.1.S1_at | nitrilase 1 | NIT1 | 2.75 | 0.0000 |
| MmugDNA.42186.1.S1_at | hippocampus abundant transcript 1 | HIAT1 | 2.75 | 0.0086 |
| MmugDNA.4834.1.S1_at | aarF domain containing kinase 2 | ADCK2 | 2.75 | 0.0220 |

| Probe Set ID | Gene Title | Gene Symbol | Ratio Top verus Bottom | p value Top versus Bottom |
|---|---|---|---|---|
| MmugDNA.26458.1.S1_at | Activating transcription factor 6 | ATF6 | 2.74 | 0.0017 |
| MmugDNA.2646.1 S1_at | atrophin 1 | ATN1 | 2.74 | 0.0001 |
| MmugDNA.40233.1.S1_at | X-ray repair complementing defective repair in Chinese hamster cells 1 | XRCC1 | 2.74 | 0.1076 |
| MmugDNA.20861.1.S1_at | spermatogenesis associated 13 | LOC721468 | 2.74 | 0.0177 |
| MmugDNA.12752.1.S1_s_at | spastic paraplegia 20, spartin (Troyer syndrome) | SPG20 | 2.74 | 0.0000 |
| MmugDNA.41135.1.S1_at | Colorectal cancer-related mRNA sequence | — | 2.74 | 0.1356 |
| MmuSTS.4719.1.S1_at | tripartite motif-containing 6 | TRIM6 | 2.74 | 0.0029 |
| MmugDNA.4017.1.S1_at | — | — | 2.74 | 0.1313 |
| MmugDNA.27784.1.S1_at | — | — | 2.74 | 0.1942 |
| MmuSTS.4614.1.S1_at | tripartite motif-containing 4 | TRIM4 | 2.74 | 0.0305 |
| MmugDNA.8727.1.S1_at | t-complex 1 | TCP1 | 2.74 | 0.0457 |
| MmugDNA.638.1.S1_at | cytoskeleton associated protein 1 | CKAP1 | 2.74 | 0.1205 |
| MmugDNA.6338.1.S1_at | hypothetical protein FLJ20152 | FLJ20152 | 2.73 | 0.0006 |
| MmuSTS.2636.1.S1_at | family with sequence similarity 3, member A | FAM3A | 2.73 | 0.0019 |
| MmugDNA.33300.1.S1_at | WWC family member 3 | WWC3 | 2.73 | 0.1279 |
| MmugDNA.18996.1.S1_at | elongation factor Tu GTP binding domain containing 2 | EFTUD2 | 2.73 | 0.0230 |
| MmugDNA.24045.1.S1_s_at | zinc finger protein 292 | ZNF292 | 2.73 | 0.1182 |
| MmugDNA.1299.1.S1_at | CLPTM1-like | CLPTM1L | 2.73 | 0.0121 |
| MmugDNA.22429.1.S1_at | family with sequence similarity 120B | FAM120B | 2.73 | 0.0002 |
| MmugDNA.13037.1.S1_at | chromosome 21 open reading frame 119 | C21orf119 | 2.72 | 0.0357 |
| MmugDNA.20321.1.S1_at | HIR histone cell cycle regulation defective homolog A (S. cerevisiae) | HIRA | 2.72 | 0.0018 |
| MmugDNA.42547.1.S1_at | histidyl-tRNA synthetase-like | HARSL | 2.72 | 0.0116 |
| MmugDNA.1760.1.S1_s_at | COP9 constitutive photomorphogenic homolog subunit 8 (Arabidopsis) | COPS8 | 2.72 | 0.0761 |
| MmugDNA.13758.1.S1_at | COMM domain containing 3 | COMMD3 | 2.72 | 0.0140 |
| MmuSTS.304.1.S1_at | single stranded DNA binding protein 3 | SSBP3 | 2.71 | 0.0862 |
| MmuSTS.2591.1.S1_at | Xenotropic and polytropic retrovirus receptor | XPR1 | 2.71 | 0.0029 |
| MmugDNA.33009.1.S1_at | zinc finger protein 700 | ZNF700 | 2.71 | 0.0451 |
| MmugDNA.1463.1.S1_s_at | proline rich 14 | PRR14 | 2.71 | 0.0339 |
| MmugDNA.35741.1.S1_at | coiled-coil-helix-coiled-coil-helix domain containing 6 /// coiled-coil-helix-coiled-coil-helix domain containing 6 | CHCHD6 | 2.71 | 0.0482 |
| MmugDNA.4692.1.S1_at | zinc finger RNA binding protein | ZFR | 2.71 | 0.0332 |
| MmugDNA.36934.1.S1_at | zinc finger protein 643 | ZNF643 | 2.71 | 0.1950 |
| MmugDNA.16923.1.S1_at | tumor necrosis factor receptor superfamily, member 13B | TNFRSF13B | 2.71 | 0.1291 |
| MmugDNA.15223.1.S1_at | hypothetical protein FLJ39061 | FLJ39061 | 2.70 | 0.0031 |
| MmuSTS.350.1.S1_at | spectrin repeat containing, nuclear envelope 1 | SYNE1 | 2.70 | 0.1061 |
| MmuSTS.246.1.S1_at | leucine rich repeat containing 42 | LRRC42 | 2.70 | 0.0007 |
| MmuSTS.2186.1.S1_at | zinc finger protein 354B | ZNF354B | 2.70 | 0.0677 |
| Mmu.12802.2.S1_at | chaperonin containing TCP1, subunit 2 | LOC717182 | 2.70 | 0.1220 |
| MmugDNA.6418.1.S1_at | zinc finger protein 83 | ZNF83 | 2.70 | 0.0013 |
| MmuSTS.528.1.S1_at | ATPase, Cu++ transporting, beta polypeptide (Wilson disease) | ATP7B | 2.70 | 0.0280 |
| MmuSTS.727.1.S1_at | cyclin M2 | CNNM2 | 2.70 | 0.1167 |
| MmugDNA.15549.1.S1_s_at | GDP-mannose 4,6-dehydratase | GMDS | 2.70 | 0.0006 |
| MmugDNA.8210.1.S1_at | PR domain containing 16 | PRDM16 | 2.70 | 0.1783 |
| MmuSTS.3743.1.S1_at | RAB26, member RAS onocogene family | RAB26 | 2.69 | 0.0289 |
| MmugDNA.6865.1.S1_at | Transcribed locus, moderately NP_689672.2 hypothetical protein MGC45438 [Homo sapiens] | — | 2.69 | 0.0231 |
| MmuSTS.2292.1.S1_at | protein phosphatase 1, regulatory (inhibitor) subunit 3F | PPP1R3F | 2.69 | 0.0001 |
| MmugDNA.34280.1.S1_at | KIAA0683 gene product | KIAA0683 | 2.69 | 0.0352 |
| MmugDNA.13838.1.S1_at | zinc finger protein 502 | ZNF502 | 2.69 | 0.0750 |
| MmuSTS.1404.1.S1_at | potassium inwardly-rectifying channel, subfamily J, member 6 | KCNJ6 | 2.69 | 0.1718 |
| MmugDNA.19168.1.S1_at | enhancer of mRNA decapping 4 | EDC4 | 2.69 | 0.0220 |
| MmugDNA.34757.1.S1_s_at | dynactin 6 | DCTN6 | 2.69 | 0.0000 |
| MmugDNA.8435.1.S1_at | proline synthetase co-transcribed homolog (bacterial) | PROSC | 2.69 | 0.0000 |
| MmugDNA.6197.1.S1_at | chromosome 4 open reading frame 24 | C4orf24 | 2.69 | 0.2130 |
| MmugDNA.3702.1.S1_at | CDNA FLJ46388 fis, clone UTERU3015647, moderately Embigin precursor | — | 2.69 | 0.0653 |
| MmugDNA.12591.1.S1_s_at | dendritic cell-derived ubiquitin-like protein | DC-UbP | 2.68 | 0.0503 |
| MmugDNA.11985.1.S1_at | asparagine-linked glycosylation 2 homolog (S. cerevisiae, alpha-1,3-mannosyltransferase) | ALG2 | 2.68 | 0.0105 |
| MmugDNA.25835.1.S1_at | Homo sapiens, clone IMAGE: 4133122, mRNA | — | 2.68 | 0.0342 |
| MmuSTS.3979.1.S1_at | serum/glucocorticoid regulated kinase family, member 3 | SGK3 | 2.68 | 0.0238 |
| MmugDNA.9043.1.S1_at | ADP-ribosylation factor-like 6 interacting protein 2 | ARL6IP2 | 2.68 | 0.0814 |
| Mmu.7150.1.S1_at | Heterogeneous nuclear ribonucleoproteins A2/B1 (hnRNP A2/hnRNP B1) | HNRPA2B1 | 2.68 | 0.0223 |
| MmugDNA.33865.1.S1_s_at | chromosome 20 open reading frame 7 /// chromosome 20 open reading frame 7 /// transmembrane protein 14B /// transmembrane protein 14B | C20orf7 /// TMEM14B | 2.67 | 0.0426 |
| MmugDNA.3820.1.S1_at | clathrin, light polypeptide (Lcb) | CLTB | 2.67 | 0.2188 |
| MmugDNA.30567.1.S1_at | hypothetical protein BC014011 | LOC116349 | 2.67 | 0.0466 |
| MmugDNA.40707.1.S1_at | zinc finger, X-linked, duplicated B | ZXDB | 2.66 | 0.0300 |
| MmugDNA.43058.1.S1_at | kinesin family member 13A | KIF13A | 2.66 | 0.1629 |
| MmuSTS.4168.1.S1_at | M-phase phosphoprotein 6 | MPHOSPH9 | 2.66 | 0.0283 |
| MmugDNA.3585.1.S1_at | — | — | 2.66 | 0.1649 |

-continued

| Probe Set ID | Gene Title | Gene Symbol | Ratio Top verus Bottom | p value Top versus Bottom |
|---|---|---|---|---|
| MmugDNA.37285.1.S1_at | mitochondrial GTPase 1 homolog (*S. cerevisiae*) | MTG1 | 2.66 | 0.0492 |
| MmugDNA.25292.1.S1_at | jagunal homolog 1 (*Drosophila*) | JAGN1 | 2.66 | 0.0199 |
| MmugDNA.9421.1.S1_at | mannose-6-phosphate receptor (cation dependent) | M6PR | 2.66 | 0.0305 |
| MmugDNA.18308.1.S1_at | poliovirus receptor-related 2 (herpesvirus entry mediator B) | PVRL2 | 2.65 | 0.1122 |
| MmugDNA.20905.1.S1_at | Chromosome 13 open reading frame 10 | C13orf10 | 2.65 | 0.0168 |
| MmugDNA.34704.1.S1_at | pecanex homolog (*Drosophila*) | PCNX | 2.65 | 0.1063 |
| MmugDNA.12760.1.S1_at | Fibroblast growth factor 14 | FGF14 | 2.65 | 0.0872 |
| MmugDNA.43498.1.S1_at | NmrA-like family domain containing 1 | NMRAL1 | 2.65 | 0.0479 |
| MmugDNA.21653.1.S1_at | hypothetical protein FLJ30596 | FLJ30596 | 2.65 | 0.0681 |
| MmugDNA.14752.1.S1_at | MRNA; cDNA DKFZp547E193 (from clone DKFZp547E193) | — | 2.65 | 0.1773 |
| MmuSTS.4276.1.S1_at | SREBF chaperone | SCAP | 2.64 | 0.0005 |
| MmugDNA.8363.1.S1_at | tyrosyl-DNA phosphodiesterase 1 | TDP1 | 2.64 | 0.1058 |
| MmugDNA.34065.1.S1_at | uncharacterized hematopoietic stem/progenitor cells protein MDS032 | MDS032 | 2.64 | 0.0254 |
| MmunewRS.641.1.S1_at | selenoprotein S | SELS | 2.64 | 0.0693 |
| MmugDNA.7596.1.S1_at | — | — | 2.64 | 0.2105 |
| MmugDNA.3465.1.S1_at | Full-length cDNA clone CS0DI027YJ20 of Placenta Cot 25-normalized of *Homo sapiens* (human) | — | 2.64 | 0.1052 |
| MmugDNA.13992.1.S1_at | Leo1, Paf1/RNA polymerase II complex component, homolog (*S. cerevisiae*) | LEO1 | 2.64 | 0.0000 |
| MmugDNA.14603.1.S1_at | bicaudal D homolog 1 (*Drosophila*) | BICD1 | 2.64 | 0.0314 |
| Mmu.2724.1.S1_at | glutamate dehydrogenase 1 | GLUD1 | 2.63 | 0.0345 |
| MmugDNA.26006.1.S1_at | hypothetical protein MGC16169 | MGC16169 | 2.63 | 0.1844 |
| MmugDNA.34293.1.S1_at | UDP-Gal:betaGlcNAc beta 1,4-galactosyltransferase, polypeptide 5 | B4GALT5 | 2.63 | 0.0018 |
| MmugDNA.5213.1.S1_at | Spleen tyrosine kinase | SYK | 2.63 | 0.0169 |
| MmugDNA.26186.1.S1_at | ankyrin repeat and IBR domain containing 1 | ANKIB1 | 2.63 | 0.0499 |
| MmugDNA.30722.1.S1_at | tetratricopeptide repeat domain 12 | TTC12 | 2.63 | 0.1383 |
| MmugDNA.20572.1.S1_at | trafficking protein particle complex 6A | TRAPPC6A | 2.63 | 0.1754 |
| MmuSTS.645.1.S1_at | Charcot-Marie-Tooth neuropathy 4B2 (autosomal recessive, with my, in outfolding) | CMT4B2 | 2.63 | 0.0754 |
| MmugDNA.12020.1.S1_at | YTH domain family, member 3 | YTHDF3 | 2.63 | 0.1578 |
| MmugDNA.23364.1.S1_at | Transcribed locus, strongly XP_515572.1 PREDICTED: hypothetical protein XP_515572 [*Pan troglodytes*] | — | 2.63 | 0.1417 |
| MmugDNA.3150.1.S1_s_at | Cdc42 guanine nucleotide exchange factor (GEF) 9 | ARHGEF9 | 2.63 | 0.0380 |
| MmugDNA.26131.1.S1_at | Nuclear transcription factor, X-box binding-like 1 | NFXL1 | 2.62 | 0.0005 |
| MmugDNA.23082.1.S1_at | nudix (nucleoside diphosphate linked moiety X)-type motif 14 | NUDT14 | 2.62 | 0.0487 |
| MmugDNA.33074.1.S1_at | Transcribed locus, strongly XP_068632.2 PREDICTED: hypothetical protein XP_068632 [*Homo sapiens*] | — | 2.62 | 0.0003 |
| MmugDNA.30447.1.S1_at | Hermansky-Pudlak syndrome 6 | HPS6 | 2.62 | 0.0431 |
| MmugDNA.37520.1.S1_at | chromosome 1 open reading frame 66 | C1orf66 | 2.62 | 0.0280 |
| MmuSTS.4696.1.S1_at | alanyl-tRNA synthetase | AARS | 2.62 | 0.0110 |
| Mmu.1900.1.S1_s_at | H3 histone, family 3B | LOC693887 /// LOC693939 /// LOC694152 /// LOC695663 /// LOC699443 /// LOC702881 /// LOC707040 /// LOC708847 /// LOC708899 /// LOC709296 /// LOC710748 /// LOC718673 | 2.62 | 0.0092 |
| MmugDNA.3450.1.S1_at | signal recognition particle receptor ('docking protein') | SRPR | 2.62 | 0.0000 |
| MmugDNA.20613.1.S1_at | CSL-type zinc finger-containing protein 2 (DelGEF-interacting protein 1) (DelGIP1) | ZCSL2 | 2.61 | 0.0000 |
| MmugDNA.26173.1.S1_at | LOC440133 | LOC440133 | 2.61 | 0.1688 |
| MmugDNA.15693.1.S1_at | acyl-Coenzyme A dehydrogenase family, member 11 | ACAD11 | 2.61 | 0.1017 |
| Mmu.14509.2.S1_at | cytosolic malate dehydrogenase | MDH1 | 2.61 | 0.0408 |
| Mmu.967.1.S1_s_at | N-acetylated alpha-linked acidic dipeptidase 2 | — | 2.61 | 0.0338 |
| MmugDNA.33096.1.S1_s_at | coiled-coil domain containing 47 | CCDC47 | 2.61 | 0.0002 |
| MmugDNA.43345.1.S1_at | Family with sequence similarity 98, member B | FAM98B | 2.61 | 0.0000 |
| MmugDNA.20494.1.S1_at | Ewing sarcoma breakpoint region 1 | EWSR1 | 2.61 | 0.0040 |
| MmugDNA.901.1.S1_at | — | — | 2.61 | 0.1627 |
| MmugDNA.18015.1.S1_at | major histocompatibility complex, class II, DM beta /// major histocompatibility complex, class II, DM beta | HLA-DMB | 2.61 | 0.1120 |
| MmugDNA.18688.1.S1_at | FLJ32363 protein | FLJ32363 | 2.61 | 0.1221 |
| MmugDNA.40426.1.S1_at | chromosome 20 open reading frame 42 | C20orf42 | 2.61 | 0.0017 |
| MmugDNA.17109.1.S1_at | zinc finger protein 570 | ZNF570 | 2.61 | 0.0031 |
| MmuSTS.448.1.S1_at | piggyBac transposable element derived 2 | PGBD2 | 2.60 | 0.0847 |
| MmuSTS.2213.1.S1_at | lysosomal trafficking regulator | LYST | 2.60 | 0.0532 |
| MmugDNA.41077.1.S1_at | chromosome 11 open reading frame 10 | C11orf10 | 2.60 | 0.0723 |

-continued

| Probe Set ID | Gene Title | Gene Symbol | Ratio Top verus Bottom | p value Top versus Bottom |
|---|---|---|---|---|
| MmugDNA.7760.1.S1_at | Transcribed locus, strongly XP_498525.1 PREDICTED: hypothetical protein XP_498525 [*Homo sapiens*] | — | 2.60 | 0.0044 |
| MmuDNA.14575.1.S1_at | hypothetical protein FLJ32810 | FLJ32810 | 2.60 | 0.0347 |

The invention claimed is:

1. An in vitro method for identifying a compound that modulates the activity of a human or non-human gene putatively encoding a polypeptide involved in salty taste perception in a human or primate comprising: (i) identifying a set of human or primate genes which are expressed in human or non-human primate fungiform taste cells but which are not expressed in lingual cells (ii) of the genes identified in (i) identifying a set of genes which are not expressed in taste cells which express umami, sweet, bitter, or sour taste receptors or markers of these cells (T1Rs or T2Rs, TRPM5, and PKD2L1/PKD1L3); (iii) determining which of said identified taste specific genes in (ii) is expressed at higher levels in cells comprised in the top half of the taste bud than in cells in the bottom of the taste bud and based on this outcome selecting the identified taste specific gene which are expressed more in the top half of the taste bud cells for further analysis as a potential salty taste receptor encoding gene; (iv) reviewing the list of genes identified in step (iii) and selecting from these genes those of which encode sodium permeable ion channels and selecting from these genes a set of genes which is contained in Table 3 for further testing as a putative salty taste gene, (v) expressing in a test cell at least one of said genes identified in (iv) and contacting the test cell with at least one compound and identifying the compound as a putative salty taste blocker or enhancer if it affects sodium conductance or sodium transport by the ion channel encoded by said at least one gene.

2. The method of claim 1 wherein the identified putative salty taste enhancer or blocker modulates TRPML3 activity.

3. The method of claim 1 wherein the identified compound is assayed in a taste test for its effect on salty taste perception.

4. The method of claim 2 wherein the identified compound is assayed in a taste test for its effect on salty taste perception.

* * * * *